US011612625B2

(12) United States Patent
Finer et al.

(10) Patent No.: US 11,612,625 B2
(45) Date of Patent: Mar. 28, 2023

(54) ONCOLYTIC VIRAL VECTORS AND USES THEREOF

(71) Applicant: ONCORUS, INC., Cambridge, MA (US)

(72) Inventors: Mitchell H. Finer, Cambridge, MA (US); Lorena Lerner, Cambridge, MA (US); Christophe Quéva, Cambridge, MA (US); Edward Kennedy, Cambridge, MA (US)

(73) Assignee: Oncorus, Inc., Andover, MA (US)

( * ) Notice: Subject to any disclaimer, the term of this patent is extended or adjusted under 35 U.S.C. 154(b) by 540 days.

(21) Appl. No.: 16/633,653

(22) PCT Filed: Jul. 26, 2018

(86) PCT No.: PCT/US2018/043938
§ 371 (c)(1),
(2) Date: Jan. 24, 2020

(87) PCT Pub. No.: WO2019/023483
PCT Pub. Date: Jan. 31, 2019

(65) Prior Publication Data

US 2020/0206285 A1 Jul. 2, 2020

Related U.S. Application Data

(60) Provisional application No. 62/686,802, filed on Jun. 19, 2018, provisional application No. 62/537,359, filed on Jul. 26, 2017.

(51) Int. Cl.

| | |
|---|---|
| ***A61K 35/763*** | (2015.01) |
| ***C12N 7/00*** | (2006.01) |
| ***C12N 15/86*** | (2006.01) |

(52) U.S. Cl.
CPC .............. *A61K 35/763* (2013.01); *C12N 7/00* (2013.01); *C12N 15/86* (2013.01); *C12N 2710/16632* (2013.01); *C12N 2710/16643* (2013.01)

(58) Field of Classification Search
CPC ........ A61K 35/763; C12N 7/00; C12N 15/86; C12N 2710/16632; C12N 2710/16643; C12N 2710/16645; C12N 2710/16671; C12N 2710/16761; C12N 9/22; A61P 35/00
See application file for complete search history.

(56) References Cited

U.S. PATENT DOCUMENTS

| | | | |
|---|---|---|---|
| 5,059,538 | A | 10/1991 | Nozaki et al. |
| 5,399,363 | A | 3/1995 | Liversidge et al. |
| 5,466,468 | A | 11/1995 | Schneider et al. |
| 5,543,158 | A | 8/1996 | Gref et al. |
| 5,641,515 | A | 6/1997 | Ramtoola |
| 5,658,724 | A | 8/1997 | DeLuca |
| 5,780,045 | A | 1/1998 | McQuinn et al. |
| 5,725,871 | A | 3/1998 | Illum |
| 5,756,353 | A | 5/1998 | Debs |
| 5,759,814 | A | 6/1998 | Burke et al. |
| 5,804,212 | A | 9/1998 | Illum |
| 5,804,413 | A | 9/1998 | DeLuca |
| 5,837,532 | A | 11/1998 | Preston et al. |
| 5,849,571 | A | 12/1998 | Glorioso et al. |
| 5,849,572 | A | 12/1998 | Glorioso et al. |
| 5,879,934 | A | 3/1999 | DeLuca |
| 5,998,174 | A | 12/1999 | Glorioso et al. |
| 6,071,742 | A | 6/2000 | Tracy et al. |
| 6,261,552 | B1 | 7/2001 | DeLuca |
| 6,469,155 | B1 | 10/2002 | Fiume et al. |
| 6,653,447 | B1 | 11/2003 | Cosman et al. |
| 7,078,029 | B2 | 7/2006 | DeLuca |
| 7,473,418 | B2 | 1/2009 | Yu et al. |
| 7,514,252 | B2 | 4/2009 | Chiocca et al. |
| 7,531,167 | B2 | 5/2009 | Glorioso, III et al. |
| 8,129,167 | B2 | 3/2012 | Cosman |
| 8,546,553 | B2 | 10/2013 | Terns et al. |
| 8,957,036 | B2 | 2/2015 | Cascio et al. |
| 8,980,246 | B2 | 3/2015 | Kirn |
| 9,157,071 | B2 | 10/2015 | Capmadelli et al. |
| 9,226,977 | B2 | 1/2016 | Kirn |
| 9,593,347 | B2 | 3/2017 | Glorioso, III et al. |
| 9,919,062 | B2 | 3/2018 | Kirn |
| 10,000,757 | B2 * | 6/2018 | Naldini .................. A61P 15/00 |
| 10,172,893 | B2 | 1/2019 | Uchida et al. |

(Continued)

FOREIGN PATENT DOCUMENTS

| | | |
|---|---|---|
| AU | 2012322999 B2 | 8/2017 |
| AU | 2017206231 B2 | 2/2019 |

(Continued)

OTHER PUBLICATIONS

Extended European Search Report for European Application No. 20184441.2, dated Jan. 12, 2021, 7 pages.
Baertsch et al., "MicroRNA-mediated multi-tissue detargeting of oncolytic measles virus," Cancer Gene Therapy (2014) 21, 373-380.
Henke et al., "microRNA-122 stimulates translation of hepatitis C virus RNA," EMBO J. (2008) 27:3300-3310.
U.S. Patent Office, International Search Report in International Patent Application No. PCT/US2017/037531, 4 pp. (dated Sep. 29, 2017) .
U.S. Patent Office, Written Opinion in International Patent Application No. PCT/US2017/037531, 4 pp. (dated Sep. 29, 2017).
Jenkins et al., "Deletion of the Herpes simplex 1 internal repeat sequences affects pathogenicity in the mouse," Frontiers in Bioscience, Oct. 1996, 1:a59-68.

(Continued)

*Primary Examiner* — Rachel B Gill
(74) *Attorney, Agent, or Firm* — Cooley LLP

(57) ABSTRACT

Oncolytic viral vectors that incorporate one or more of the following features: viral replication restriction by insertion of microRNA (miRNA) target sequences into the viral genome; disruption of oncogenic miRNA function; cancer microenvironment remodeling; and cancer cell targeting by incorporation of protease-activated antibodies into the viral particle. Such viral vectors can be used for the treatment and prevention of cancer.

26 Claims, 57 Drawing Sheets

Specification includes a Sequence Listing.

(56) References Cited

U.S. PATENT DOCUMENTS

| | | | | |
|---|---|---|---|---|
| 10,188,686 | B2 | 1/2019 | Uchida et al. | |
| 10,201,575 | B2 | 2/2019 | Uchida et al. | |
| 10,210,575 | B1 | 2/2019 | Engelhorn | |
| 10,391,132 | B2 * | 8/2019 | Greenberg | A61K 35/763 |
| 10,576,115 | B2 | 3/2020 | Uchida et al. | |
| 11,452,750 | B2 | 9/2022 | Greenberg et al. | |
| 2002/0037575 | A1 | 3/2002 | Speck | |
| 2002/0187126 | A1 | 12/2002 | Blaho et al. | |
| 2007/0161110 | A1 | 7/2007 | Iida et al. | |
| 2008/0008686 | A1 | 1/2008 | Yao | |
| 2008/0289058 | A1 | 11/2008 | Cascio et al. | |
| 2009/0136452 | A1 | 5/2009 | Zhou et al. | |
| 2010/0041737 | A1 | 2/2010 | Naldini et al. | |
| 2010/0076057 | A1 | 3/2010 | Sontheimer et al. | |
| 2010/0093617 | A1 | 4/2010 | Barrangou et al. | |
| 2010/0104578 | A1 | 4/2010 | Shafren | |
| 2010/0233141 | A1 | 9/2010 | Polach et al. | |
| 2010/0257638 | A1 | 10/2010 | Cai et al. | |
| 2011/0213017 | A1 | 9/2011 | Cascio et al. | |
| 2011/0217739 | A1 | 9/2011 | Terns et al. | |
| 2011/0300538 | A1 | 12/2011 | Barrangou et al. | |
| 2012/0277120 | A1 | 11/2012 | Serber et al. | |
| 2013/0011828 | A1 | 1/2013 | Barrangou et al. | |
| 2013/0071430 | A1 | 3/2013 | Nakamura et al. | |
| 2013/0096186 | A1 | 4/2013 | Glorioso, III et al. | |
| 2013/0156808 | A1 | 6/2013 | Jonjic | |
| 2013/0288251 | A1 | 10/2013 | Horvath et al. | |
| 2014/0255313 | A1 | 9/2014 | Vasiljeva et al. | |
| 2014/0363469 | A1 * | 12/2014 | Meyers | A61K 39/245 435/236 |
| 2015/0017121 | A1 | 1/2015 | Becher et al. | |
| 2016/0153000 | A1 | 6/2016 | Glorioso et al. | |
| 2016/0175462 | A1 | 6/2016 | Zhang et al. | |
| 2016/0250267 | A1 | 9/2016 | Evnin | |
| 2017/0000832 | A1 | 1/2017 | Shafren et al. | |
| 2017/0035819 | A1 | 2/2017 | Uchida et al. | |
| 2017/0036819 | A1 | 2/2017 | Aguero-Hernandez et al. | |
| 2017/0042995 | A1 * | 2/2017 | Ali | A61K 39/001192 |
| 2017/0081384 | A1 | 3/2017 | Cascio et al. | |
| 2017/0107537 | A1 | 4/2017 | Glorioso, III et al. | |
| 2017/0157188 | A1 | 6/2017 | Silvestre et al. | |
| 2017/0189514 | A1 | 7/2017 | Uchida et al. | |
| 2017/0274025 | A1 | 9/2017 | Cascio et al. | |
| 2017/0274057 | A1 | 9/2017 | Jonjic | |
| 2018/0169241 | A1 | 6/2018 | Cantwell | |
| 2018/0169271 | A1 | 6/2018 | Cantwell et al. | |
| 2018/0215794 | A1 | 8/2018 | Russell et al. | |
| 2018/0318365 | A1 | 11/2018 | Yeung et al. | |
| 2018/0339004 | A1 | 11/2018 | Greenberg et al. | |
| 2019/0048082 | A1 * | 2/2019 | Evnin | C07K 14/70503 |
| 2019/0070233 | A1 | 3/2019 | Yeung et al. | |
| 2019/0201493 | A1 | 7/2019 | Becher et al. | |
| 2019/0026241 | A1 | 8/2019 | Uchida et al. | |
| 2020/0147156 | A1 * | 5/2020 | Greenberg | C12N 15/1133 |
| 2020/0405792 | A1 | 12/2020 | Zhou et al. | |
| 2021/0138007 | A1 | 5/2021 | Uchida et al. | |

FOREIGN PATENT DOCUMENTS

| | | | | |
|---|---|---|---|---|
| CA | 2850575 | A1 | 4/2013 | |
| EP | 2591796 | A1 | 5/2013 | |
| EP | 2766035 | B1 | 3/2018 | |
| EP | 3351261 | A1 | 7/2018 | |
| EP | 3441084 | A1 | 2/2019 | |
| JP | 2001-508294 | | 6/2001 | |
| JP | 2003-518080 | | 6/2003 | |
| JP | 2009-060907 | A | 3/2009 | |
| KR | 2003-0047667 | A | 6/2003 | |
| WO | WO 91/02788 | A1 | 3/1991 | |
| WO | WO 96/04394 | A1 | 2/1996 | |
| WO | WO 98/15637 | A1 | 4/1998 | |
| WO | WO 99/06583 | A1 | 2/1999 | |
| WO | WO-9960142 | A2 | 11/1999 | |
| WO | WO-2005092374 | A2 | 10/2005 | |
| WO | WO 2006/017914 | A1 | 2/2006 | |
| WO | WO 2007/025097 | A2 | 3/2007 | |
| WO | WO 2008/021207 | A2 | 2/2008 | |
| WO | WO 2008/141151 | A2 | 11/2008 | |
| WO | WO 2008/143875 | A1 | 11/2008 | |
| WO | WO 2009/111892 | A1 | 9/2009 | |
| WO | WO-2009130479 | A2 | 10/2009 | |
| WO | WO 2009/144755 | A1 | 12/2009 | |
| WO | WO 2009/148488 | A2 | 12/2009 | |
| WO | WO 2009/150431 | A1 | 12/2009 | |
| WO | WO 2010/011961 | A2 | 1/2010 | |
| WO | WO 2010/054108 | A2 | 5/2010 | |
| WO | WO 2010/054154 | A2 | 5/2010 | |
| WO | WO 2010/135242 | A1 | 11/2010 | |
| WO | WO 2011/125469 | A1 | 10/2011 | |
| WO | WO 2011/130749 | A2 | 10/2011 | |
| WO | WO 2012/006181 | A2 | 1/2012 | |
| WO | WO 2012/054726 | A1 | 4/2012 | |
| WO | WO 2012/149470 | A1 | 11/2012 | |
| WO | WO 2012/164565 | A1 | 12/2012 | |
| WO | WO-2013004396 | A2 | 1/2013 | |
| WO | WO 2013/053775 | A1 | 4/2013 | |
| WO | WO 2013/098244 | A1 | 7/2013 | |
| WO | WO 2013/109604 | A1 | 7/2013 | |
| WO | WO 2013/126794 | A1 | 8/2013 | |
| WO | WO 2013/141680 | A1 | 9/2013 | |
| WO | WO 2013/142578 | A1 | 9/2013 | |
| WO | WO 2015/009952 | A1 | 1/2015 | |
| WO | WO 2015/066042 | A1 | 5/2015 | |
| WO | WO 2016/141320 | A2 | 9/2016 | |
| WO | WO-2017096201 | A1 | 6/2017 | |
| WO | WO-2017103291 | A1 * | 6/2017 | A61K 35/761 |
| WO | WO 2017/118864 | A1 | 7/2017 | |
| WO | WO 2017/118865 | A1 | 7/2017 | |
| WO | WO 2017/118866 | A1 | 7/2017 | |
| WO | WO 2017/118867 | A1 | 7/2017 | |
| WO | WO 2017/132552 | A1 | 8/2017 | |
| WO | WO 2017/156349 | A1 | 9/2017 | |
| WO | WO 2018/026872 | A1 | 2/2018 | |
| WO | WO 2018/027316 | A1 | 2/2018 | |
| WO | WO 2018/049248 | A1 | 3/2018 | |
| WO | WO 2018/049261 | A1 | 3/2018 | |
| WO | WO 2018/085461 | A1 | 5/2018 | |
| WO | WO 2018/118819 | A2 | 6/2018 | |
| WO | WO 2018/118967 | A1 | 6/2018 | |
| WO | WO 2018/127713 | A1 | 7/2018 | |
| WO | WO 2019/023483 | A1 | 1/2019 | |
| WO | WO-2019014623 | A1 | 1/2019 | |
| WO | WO-2020186355 | A1 | 9/2020 | |
| WO | WO-2020186356 | A1 | 9/2020 | |
| WO | WO-2021072310 | A1 | 4/2021 | |

OTHER PUBLICATIONS

Junejo et al., "Deletions and Duplication in Internal Inverted Repeat Sequence of Long Region/Unique Sequence of Long Region (IRL/UL) of Herpes Simplex Virus Type-i (HSV-i) Genome are not Evidently Associated with Intracranial and Foot-Pad Pathogenicity in Mouse Model," J. Pak. Med. Assoc., 45(4), pp. 95-98, 1995.

Wollman et al., "Oncolytic Virus Therapy for Glioblastoma Multiforme: Concepts and Candidates," Cancer J., Jan.-Feb. 2012;18(1):69-81.

Cherenkova et al., "Generation of recombinant adenoviruses and lentiviruses expressing angiogenic and neuroprotective factors using Gateway cloning technology," Cell Transplantology and Tissue Engineering, 2012, vol. 7, No. 3, 164-168 (with English abstract).

Stamenkovic et al., "Extracellular matrix remodelling: the role of matrix metalloproteinases," Journal of Pathology, 2003, 200: 448-464.

Tocchi et al., "Functional interactions between matrix metalloproteinases and glycosaminoglycans," FEBS Journal (2013) 280:2332-2341.

U.S. Appl. No. 60/917,752, filed May 14, 2007, Cascio et al.

U.S. Appl. No. 61/325,137, filed Apr. 16, 2010, Glorioso et al.

U.S. Appl. No. 61/562,738, filed Nov. 22, 2011, Jonjic.

U.S. Appl. No. 61/847,405, filed Jul. 17, 2013, Glorioso et al.

(56) References Cited

OTHER PUBLICATIONS

Adamiak et al., "Herpes Simplex Virus Type 2 Glycoprotein G is Targeted by the Sulfated Oligo—and Polysaccharide Inhibitors of Virus Attachment to Cells," Journal of Virology, 81(24), 13424-13434 (2007).
Aghi et al., "Oncolytic herpes virus with defective ICP6 specifically replicates in quiescent cells with homozygous genetic mutations in p16.," Oncogene, 27: 4249-4254 (2008).
Akimoto et al., "A new delivery system for 5-fluorouracil using prodrug and converting enzyme," J. Ophthalmol., 86(5): 581-586 (2002).
Amelio et al., "A Chromatin Insulator-Like Element in the Herpes Simplex Virus Type 1 Latency-Associated Transcript Region Binds CCCTC-Binding Factor and Displays Enhancer-Blocking and Silencing Activities," J. of Virology, 80(5): 2358-2368 (Mar. 2006).
Anderson et al., "Pseudotyping of Glycoprotein D-Deficient Herpes Simplex Virus Type 1 with Vesicular Stomatitis Virus Glycoprotein G Enable Mutant Virus Attachment and Entrv," Journal of Virology, 74(5): 2481-2487 (Mar. 2000).
Asano et al., "Humanization of the Bispecific Epidermal Growth Factor Receptor X CD3 Diabody and Its Efficacy as a Potential Clinical Reagent," Clin. Cancer Res., 12(13): 4036-4042 (Jul. 1, 2006).
Assi et al., "Gene Therapy for Brain Tumors: Basic Developments and Clinical Implementation," Neurosci. Lett. 527(2): 71-77 (2012).
Baek et al., "Bispecific Adapter-Mediated Retargeting of a Receptor-Restricted HSV-1 Vector to CEA-Bearing Tumor Cells," Molecular Therapy, 19(3): 507-514 (Mar. 2011).
Barrangou et al., "CRISPR Provides Acquired Resistance Against Viruses in Prokaryotes," Science 315, 1709 (2007).
Bennett et al., "Comparison of safety, delivery, and efficacy of oncolytic herpes viruses (G207 and NV1020) for peritoneal cancer," Cancer Gene Therapy, 9: 935-945 (2002).
Broberg et al., "Immune Response to Herpes Simplex Virus and γ134.5 Deleted HSV Vectors," Current Gene Therapy, 5: 523-530 (2005).
Brouns et al., "Small CRISPR RNAs Guide Antiviral Defense in Prokaryotes," Science, Aug. 15, 2008; 321(5891): 960-964.
Bzik et al., "Nucleotide Sequence of a Region of the Herpes Simplex Virus Type 1 gB Glycoprotein Gene: Mutations Affecting Rate of Virus Entry and Cell Fusion," Virology, 37: 185-190 (1984).
Cai et al., "Linker-Insertion Nonsense and Restriction-Site Deletion Mutations of the gB Glycoprotein Gene of Herpes Simplex Virus Type 1," Journal of Virology, 61(3): 714-721 (Mar. 1987).
Camacho et al., "Phase 1 clinical trial of anti-CTLA4 human monoclonal antibody CP-675,206 in patients (pts) with advanced solid malignancies," J. Clin. Oncol., 22(145): Abstract No. 2505 (2004) (antibody CP- 675206), 4 pages.
Campadelli-Fiume et al., "Rethinking herpes simplex virus: the way to oncolytic agents," Rev. Med. Viral., 21: 213-226 (2011).
Cao et al., "A functional study of miR-124 in the developing neural tube," Genes & Development, 21: 531-536 (2007).
Cattaneo et al., "Reprogrammed viruses as cancer therapeutics: targeted, armed and shielded" Nature Reviews. Microbiology, 6(7): 529-540 (2008).
Cawood et al., "Use of Tissue-Specific MicroRNA to Control Pathology of Wild—Type Adenovirus without Attenuation of Its Ability to Kill Cancer Cells," PloS Pathogens, 5(5): 1-10 (May 2009).
Cheadle et al., "Cloning and expression of the variable regions of mouse myeloma protein MOPC315 in *E. coli*: recovery of active FV fragments.," Mol Immunol (1992) 29(1): 21-30.
Cocchi et al., "The Ectodomain of a Novel Member of the Immunoglobulin Subfamily Related to the Poliovirus Receptor Has the Attributes of a Bona Fide Receptor for Herpes Simplex Virus Types 1 and 2 in Human Cells," Journal of Virology, 72(12): 9992-10002 (Dec. 1998).
Cocchi et al., "The Herpes Simplex Virus JMP Mutant Enters Receptor-Negative J Cells through a Novel Pathway Independent of the Known Receptors nectin1, HveA, and nectin2," Journal of Virology, 78(9): 4720-4729 (May 2004).
Cong et al., "Multiplex Genome Engineering Using CRISPR/Cas Systems," Science, Feb. 15, 2013; 339(6121): 819-823.
Conner et al., "A strategy for systemic delivery of the oncolytic herpes virus HSV1716: redirected tropism by antibody-binding sites incorporated on the virion surface as a glycoprotein D fusion protein," Gene Therapy, 15: 1579-1592 (2008).
Connolly et al., "Potential Nectin-1 Binding Site on Herpes Simplex Virus Glycoprotein D," Journal of Virology, 79(2): 1282-1295 (Jan. 2005).
Connolly et al., Structure-Based Analysis of the Herpes Simplex Virus Glycoprotein D Binding Site Present on Herpevirus Entry Mediator HveA (HVEM), Journal of Virology 76(21):10894-10904 (Nov. 2002).
Currier et al., "Efficacy and Safety of the Oncolytic Herpes Simplex Virus rRp450 Alone and Combined With Cyclophosphamide," Molecular Therapy, 16(5): 879-885 (2008).
Deltcheva et al., "CRISPR RNA maturation by trans-encoded small RNA and hostfactor RNase III," Nature, Mar. 31, 2011; 471(7340): 602-607.
Deluca et al., "Nucleotide Sequences of Herpes Simplex Virus Type 1 (HSV-1) Affecting Virus Entry, Cell Fusion, and Production of Glycoprotein gB (VP7)," Virology, 122:411-423 (1982).
Delwar et al., "Tumour-specific triple-regulated oncolytic herpes virus to target glioma," Oncotarget, 2016, vol. 7, No. 19, pp. 28658-28669.
Desai et al., "Incorporation of the Green Fluorescent Protein into the Herpes Simplex Virus Type 1 Capsid," Journal of Virology, 72(9): 7563-7568 (Sep. 1998).
Dmitrieva et al., "Chondroitinase ABC I-mediated spread and antitumor efficacy," Clin. Cancer Res., 17(6): 1362-1372 (2011).
Doronina et al.,"Site-specific release of nascent chains from ribosomes at a sense codon.," Molecular and Cellular Biology, 28(13): 4227-4239 (2008).
Edge et al., "A let-7 MicroRNA-sensitive Vesicular Stomatitis Virus Demonstrates Tumor-specific Replication," Molecular Therapy, 16(8): 1437-1443 (Aug. 2008).
Eisenring et al., "IL-12 initiates tumor rejection via lymphoid tissue-inducer cells bearing the natural cytotoxicity receptor NKp46," Nat Immunol., 2010;11(11):1030-8.
Esko et al., "Animal Cell Mutants Defective in Glycosaminoglycan biosynthesis," Proc. Natl. Acad. Sci. USA, 82: 3197-3201 (May 1985).
European Patent Office, European Search Report in European Patent Application No. 17155129 (dated May 30, 2017), 8 pages.
Fecci et al., "Systemic CTLA-4 Blockade Ameliorates Glioma-Induced Changes to the CD4+ T Cell Compartment without Affecting Regulatory T-Cell Function," Clin Cancer Res., 2007;13(7):2158-2167.
Frampton et al., "Equine Herpesvirus 1 Enters Cells by Two Different Pathways, and Infection Requires the Activation of the Cellular Kinase ROCK1," Journal of Virology, 81(20): 10879-10889 (2007).
Friedman et al., "Herpes Simplex Virus Oncolytic Therapy for Pediatric Malignancies," Molecular Therapy, 17(7): 1125-1135 (2009).
Fu et al., "Construction of an oncolytic herpes simplex virus that precisely targets hepatocellular carcinoma cells," Mol. Ther 20:339-46 (2012).
Fujioka et al., "Interleukin-18 protects mice against acute herpes simplex virus type 1 infection," Journal of Virology, 73(3): 2401-2409 (1999).
Fuller et al., "Anti-glycoprotein D Antibodies That Permit Adsorption but Block Infection by Herpes Simplex Virus 1 Prevent Virion-cell Fusion at the Cell Surface," Proc. Natl. Acad. Sci. USA, 84: 5454-5458 (Aug. 1987).
Fuller et al., "Neutralizing Antibodies Specific for Glycoprotein H of Herpes Simplex Virus Permit Viral Attachment to Cells but Prevent Penetration," Journal of Virology, 63(8): 3435-3443 (Aug. 1989).
Garneau et al., "The CRISPR/Cas bacterial immune system cleaves bacteriophage and plasmid DNA," Nature, vol. 468, Nov. 4, 2010, pp. 67-72.

(56) References Cited

OTHER PUBLICATIONS

Gasiunas et al., "Cas9-crRNA ribonucleoprotein complex mediates specific DNA cleavage for adaptive immunity in bacteria," PNAS, Sep. 25, 2012, vol. 109, No. 39, pp. 15539-15540.
Gaur et al., "Characterization of microRNA expression levels and their biological correlates in human cancer cell lines," Cancer Res., 67(6): 2456-2468 (2007).
Geraghty et al., "Entry of Alphaherpesviruses Mediated by Poliovirus Receptor-Related Protein 1 and Poliovirus Receptor," Science, 280: 1618-1620 (Jun. 5, 1998).
Gibson et al., "Enzymatic assembly of DNA molecules up to several hundred kilobases," Nature Methods 2009;6(5):343-345.
Gierasch et al., "Construction and Characterization of Bacterial Artificial Chromosomes Containing HSV-1 Strains 17 and KOS," Journal of Virological Methods, 135: 197-206 (2006).
Grandi et al., Design and application of oncolytic HSV vectors for glioblastoma therapy, Golemis; Protein-Protein Interactions: A Molecular Cloning Manual; Cold Spring Harbor Laboratory Press, 2002 Expert Rev. Neurother., 9(4): 505-517 (2009).
Grossman et al., "Survival of Patients with Newly Diagnosed Glioblastoma Treated with Radiation and Temozolomide in Research Studies in the United States," Clinical Cancer Research, 16: 2443-2449 (2010).
Gubanova et al., "Oncolytic viruses in the therapy of gliomas," Mol Biol (Mosk), 46(6), pp. 874-886 (Nov.-Dec. 2012), ISSN: 0026-8984 (English abstract).
Hale et al., "RNA-Guided RNA Cleavage by a CRISPR RNA-Cas Protein Complex," Cell 139, 945-956, Nov. 25, 2009.
He et al., "Targeting Glioblastoma Stem Cells: Cell Surface Markers," Current Medicinal Chemistry, 19: 6050-6055 (2012).
Highlander et al., "Identification of mar Mutations in Herpes Simplex Virus Type 1 Glycoprotein B Which Alter Antigenic Structure and Function in Virus Penetration," Journal of Virology, 63(2): 730-738 (Feb. 1989).
Hodi et al., "Improved Survival with Ipilimumab in Patients with Metastatic Melanoma," The New England Journal of Medicine, 363(8): 711-723 (2010).
Hong et al. "Ectopic matrix metalloproteinase 9 expression in human brain tumor cells enhances oncolytic HSV vector infection," Gene Therapy 17:1200-1205 (2010).
Iorio et al., "microRNA involvement in human cancer," Carcinogenesis, 33(6): 1126-1133 (2012).
Ishida et al., "Enhanced cytotoxicity with a novel system combining the paclitaxel-2'-ethylcarbonate prodrug and an HSV amplicon with an attenuated replication-competent virus, HF10 as a helper virus," Cancer Letters, 288: 17-27 (2010).
Jackson et al., "Crystal structure of the CRISPR RNA-guided surveillance complex from *Escherichia coli*," Science, Sep. 19, 2014; 345(6203): 1473-1479.
Jackson et al., "Insertion Mutations in Herpes Simplex Virus 1 Glycoprotein H Reduce Cell Surface Expression, Slow the Rate of Cell Fusion, or Abrogate Functions in Cell Fusion and Viral Entry," Journal of Virology, 84(4): 2038-2046 (Feb. 2010).
Jinek et al., "A Programmable Dual-RNA-Guided DNA Endonuclease in Adaptive Bacterial Immunity," Science Aug. 17, 2012: vol. 337, Issue 6096, pp. 816-821.
Jinek et al., "RNA-programmed genome editing in human cells," eLife 2013;2:e00471, 9 pages.
Kaji et al., "Virus-free induction of pluripotency and subsequent excision of reprogramming factors," Nature, 458(7239): 771-775 (2009).
Kambara et al., "An oncolytic HSV-1 mutant expressing ICP34.5 under control of a nestin promoter increases survival of animals even when symptomatic from a brain tumor," Cancer Res., 65(7): 2832-2839 (2005).
Karpowicz et al., "E-Cadherin Regulates Neural Stem Cell Self-Renewal," The Journal of Neuroscience, 29(12): 3885-3896 (2009).
Karsy et al., "Current Progress on Understanding MicroRNAs in Glioblastoma Multiforme," Genes & Cancer, 3(1): 3-15 (2012).
Katoh et al., "Hedgehog signaling, epithelial-to-mesenchymal transition and miRNA (review)," International Journal of Molecular Medicine, 22: 271-275 (2008).
Kaur et al., "Oncolytic HSV-1 Virotherapy: Clinical Experience and Opportunities for Progress," Curr Pharm Biotechnol., Jul. 2012; 13(9): 1842-1851.
Kelly et al., "Attenuation of Vesicular Stomatitis Virus Encephalitis through MicroRNA Targeting," Journal of Virology, Feb. 2010, vol. 84, No. 3, pp. 1550-1562.
Kelly et al., "Engineering microRNA responsiveness to decrease virus pathogenicity," Nature Medicine, Nov. 2008, vol. 14, No. 11, pp. 1277-1283.
Kosovsky et al., "Herpes Simplex Virus 1 (HSV-1) Strain HSZP Glycoprotein B Gene: Comparison of Mutations among Strains Differing in Virulence," Virus Genes, 20(1): 27-33 (2000).
Krisky et al., "Rapid method for construction of recombinant HSV gene transfer vectors," Gene Therapy, 4: 1120-1125 (1997).
Krisky et al., "Deletion of multiple immediate-early genes from herpes simplex virus reduces cytotoxicity and permits long-term gene expression in neurons," Gene Therapy 5:1593-1603 (1998).
Krummenacher et al., "Effects of Herpes Simplex Virus on Structure and Function of Nectin-1/HveC," Journal of Virology, 76(5): 2424-2433 (Mar. 2002).
Kuan et al., "Increased Binding Affinity Enhances Targeting of Glioma Xenografts by EGFRVIII-Specific scFv," Int. J. Cancer, 88: 962-969 (2000).
Kumar et al., "Impaired microRNA processing enhances cellular transformation and tumorigenesis," Nature Genetics, 39(5): 673-677 (2007).
Kwon et al., "Soluble V Domain of Nectin-1/HveC Enables Entry of Herpes Simplex Virus Type 1 (HSV-1) into HSY-Resistant Cells by Binding to Viral Glycoprotein D," Journal of Virology, 80(1): 138-148 (Jan. 2006).
Lavon et al., "Gliomas display a microRNA expression profile reminiscent of neural precursor cells," Neuro-Oncology, 12(5): 422-433 (2010).
Lee et al., "MicroRNA Regulation of Oncolytic Herpes Simplex Virus-1 for Selective Killing of Prostate Cancer Cells," Clin. Cancer Res., 15(16): 5126-5135 (2009).
Lee et al., "Transcriptional and Translational Dual-regulated Oncolytic Herpes Simplex Virus Type 1 for Targeting Prostate Tumors," Molecular Therapy, 2010; 18(5):929-935.
Li et al., "Identification of Functional Domains in Herpes Simplex Virus 2 Glycoprotein B," Journal of Virology, 3792-3800 (Apr. 2006).
Li et al., "MicroRNA-145 regulates oncolytic herpes simplex virus-1 for selective killing of human non-small cell lung cancer cells", Virology Journal 10(1): 241 (2013), 9 pages.
Ligas et al., "A Herpes Simplex Virus Mutant in Which Glycoprotein D Sequences are Replaced by 13-Galactosidase Sequences Binds to but is Unable to Penetrate into Cells," Journal of Virology, 62(5): 1486-1494 (May 1988).
Lilley et al., "Multiple Immediate-Early Gene-Deficient Herpes Simplex Virus Vectors Allowing Efficient Gene Delivery to Neurons in Culture and Widespread Gene Delivery to the Central Nervous System In Vivo," J. of Virology, 75:9: 4343-4356 (May 2001).
Loakes et al., "5-Nitroindole as an universal base analogue," Nucleic Acids Research, 1994, 22(20): 4039-4043.
López-Otin et al., "Emerging roles of proteases in tumour suppression," Nat Rev Cancer, 2007, 7(10):800-808.
Ma et al., "A novel HBV antisense RNA gene delivery system targeting hepatocellular carcinoma," World J Gastroenterol 9:463-467 (2003).
MacDonald et al., "Genome Sequence of Herpes Simplex Virus 1 Strain KOS," Journal of Virology, 86(11): 6371-6372 (Jun. 2012).
Mali et al., "RNA-Guided Human Genome Engineering via Cas9," Science, Feb. 15, 2013; 339(6121): 823-826.
Mammoto et al., "Role of Collagen Matrix in Tumor Angiogenesis and Glioblastoma Multiforme Progression," The American Journal of Pathology, 183(4): 1293-1305 (2013).
Manickan et al., "Genetic immunization against herpes simplex virus. Protection is mediated by CD4+ T lymphocytes.," The Journal of Immunology, 155: 259-265 (1995).

(56) References Cited

OTHER PUBLICATIONS

Markert et al., "Conditionally replicating herpes simplex virus mutant, G207 for the treatment of malignant glioma: results of a phase I trial.," Gene Therapy, 7: 867-874 (2000).
Marraffini and Sontheimer, "CRISPR Interference Limits Horizontal Gene Transfer in Staphylococci by Targeting DNA," Science, Dec. 19, 2008; 322(5909): 1843-1845.
Mazzacurati et al., "Use of miRNA response sequences to block off-target replication and increase the safety of an unattenuated, glioblastoma-targeted oncolytic HSV.," Molecular Therapy, 23(1): 99-107 (2015).
McGeoch et al., "The Complete DNA Sequence of the Long Unique Region in the Genome of Herpes Simplex Virus Type 1," J. Gen. Virol. (1988), 69, 1531-1574.
McKee et al., "Degradation of fibrillar collagen in a human melanoma xenograft improves the efficacy of an oncolytic herpes simplex virus vector."Cancer Research, 66(5): 2509-2513 (2006).
Menotti et al., "Construction of a Fully Retargeted Herpes Simplex Virus 1 Recombinant Capable of Entering Cells Solely via Human Epidermal Growth Factor Receptor 2," Journal of Virology, 82(20): 10153-10161 (Oct. 2008).
Menotti, L., et al., "Inhibition of human tumor growth in mice by an oncolytic herpes simplex virus designed to target solely HER-2-positive cells," PNAS 106:9039-9044 (2009).
Metz et al., "Bispecific antibody derivatives with restricted binding functionalities that are activated by proteolytic processing," Protein Engineering, Design & Selection vol. 25 No. 10 pp. 571-580, 2012.
Miao et al., "EphA2 promotes infiltrative invasion of glioma stem cells in vivo through cross-talk with Akt and regulates stem cell properties," Oncogene, 34(5): 558-567 (2015).
Miest et al., "New viruses for cancer therapy: meeting clinical needs," Nature Reviews. Microbiology, 12(1): 23-34 (2014).
Miller et al., "Development of a Syngenic Murine 816 Cell Line-Derived Melanoma Susceptible to Destruction by Neuroattenuated HSV-1," Molecular Therapy, 3(2): 160-168 (Feb. 2001).
Milne et al., "Glycoprotein D Receptor-Dependent, Low-pH-Independent Endocytic Entry of Herpes Simplex Virus Type 1," Journal of Virology, 79(11): 6655-6663 (Jun. 2005).
Mohyeldin et al., "Gene and viral therapy for glioblastoma: a review of clinical trials and future directions," The Cancer Journal, 18(1): 82-88 (2012).
Mok et al., "Matrix Metalloproteinases-1 and -8 Improve the Distribution and Efficacy of an Oncolytic Virus," Cancer Res., 67(22): 10664-10668 (2007).
Montgomery et al., "Herpes Simplex Virus-1 Entry into Cells Mediated by a Novel Member of the TNF/NGF Receptor Family," Cell 87:427-436 (1996).
Muggeridge, "Characterization of Cell-cell Fusion Mediated by Herpes Simplex Virus 2 glycoproteins gB, gD, gH and gL in Transfected Cells," Journal of General Virology, 81: 2017-2027 (2000).
Mullokandov et al., "High-throughput assessment of microRNA activity and function using microRNA sensor and decoy libraries," Nature methods 9:840-846 (2012).
Mulepati et al., "Crystal structure of a CRISPR RNA-guided surveillance complex bound to a ssDNA target," Science, Sep. 19, 2014; 345(6203): 1479-1484.
Nakano et al., "Mechanism of HSV infection through soluble adapter-mediated virus bridging to the EGF receptor," Virology, 413: 12-18 (2011).
Navaratnarajah et al., "Targeted Entry of Enveloped Viruses: Measles and Herpes Simplex Virus," Curr. Opin. Viral., 2(1): 43-49 (2012).
NCBI, "Chain A, Glycoprotein B From Herpes Simplex Virus Type 1" Database Entrez-Nucleotide, Accession No. 4L1R_A (Jun. 26, 2013). Retrieved on Mar. 5, 2018, 5 pages.
NCBI, "glycoprotein B [Human herpesvirus 1]," Database Entrez-Nucleotide, Accession No. AAA91805 (Mar. 8, 1996). Retrieved on Mar. 5, 2018, 1 page.
NCBI, "glycoprotein B [Human herpesvirus 1]," Database Entrez-Nucleotide, Accession No. AAF70301 (May 16, 2000). Retrieved on Mar. 5, 2018, 1 page.
NCBI, "glycoprotein B [Human herpesvirus 2]," Database Entrez-Nucleotide, Accession No. ABU45427 (Nov. 29, 2007). Retrieved on Mar. 5, 2018, 2 pages.
NCBI, "Herpes Simplex Virus Type 1 Gene for Glycoprotein gH," Database GenBank Accession No. X03896 (Apr. 18, 2005). Retrieved on Mar. 5, 2018, 3 pages.
NCBI, "Human Herpesvirus 1 Complete Genome," Database GenBank Accession No. X14112 (Oct. 23, 2008). Retrieved on Mar. 5, 2018, 70 pages.
NCBI, "Human Herpesvirus 1 Strain KOS Glycoprotein B Gene," Database GenBank Accession No. AF311740 (Jan. 24, 2001). Retrieved on Mar. 5, 2018, 2 pages.
NCBI Reference Sequence: NC_001806.2, Human herpesvirus 1 strain 17, complete genome, Aug. 13, 2018, 62 pages.
Nduom et al., "Glioblastoma Cancer Stem-like Cells13 Implications for Pathogenesis and Treatment," Cancer., 18(1): 100-106 (2012).
Nichols et al., "A universal nucleoside for use at ambiguous sites in DNA primers," Nature, Jun. 1994, vol. 369, pp. 492-493.
Nicola and Strauss., "Cellular and Viral Requirements for Rapid Endocytic Entry of Herpes Simplex Virus," Journal of Virology, 78(14): 7508-7517 (Jul. 2004).
Nicola et al., "Roles for Endocytosis and Low pH in Herpes Simplex Virus Entry into HeLa and Chinese Hamster Ovary Cells," Journal of Virology, 77(9): 5324-5332 (May 2003).
O'Day et al., "Efficacy and safety of ipilimumab monotherapy in patients with pretreated advanced melanoma: a multicenter single-arm phase II study," Annals of Oncology, 2010 21:1712-1717.
Ocana et al., "A new regulatory loop in cancer-cell invasion," Molecular Biology Organization, 9(6): 521-522 (2008).
Omidfar et al., "Production of a Novel Camel Single-Domain Antibody Specific for the Type III Mutant EGFR," Tumor Biology, 25: 296-305 (2004).
Omidfar et al., "Production and Characterization of a New Antibody Specific for the Mutant EGF Receptor, EGFRvIII, in Camelus bactrianus," Tumor Biology, 25:179-187 (2004).
Opalinska et al., "Nucleic-Acid Therapeutics: Basic Principles and Recent Applications," Nature Reviews, 1: 503-514 (2002).
Parker et al., "Oncolytic viral therapy of malignant glioma," Neurotherapeutics: The Journal of the American Society for Experimental NeuroTherapeutics, 6: 558-569 (2009).
Patriarca et al., "Epithelial cell adhesion molecule expression (CD326) in cancer: a short review," Cancer Treatment Reviews, 38: 68-75 (2012).
Payne et al., "The pathobiology of collagens in glioma," Mol. Cancer Res., 11: 1129-1140 (2013).
Pertel et al., "Cell Fusion Induced by Herpes Simplex Virus Glycoproteins gB, gD, and gH-gL Requires a gD Receptor but Not Necessarily Heparan Sulfate," Virology, 279: 313-324 (2001).
Peters et al., "Designing herpes viruses as oncolytics," Molecular Therapy—Oncoiytics (2015) 2, 15010, 14 pages.
Qi et al., "Repurposing CRISPR as an RNA-Guided Platform for Sequence-Specific Control of Gene Expression," Cell 152, 1173-1183, Feb. 28, 2013.
Raag and Whitlow, "Single-chain Fvs.," FASEB (1995) 9(1):73-80.
Ran et al., "Genome engineering using the CRISPR-Cas9 system," Nature Protocols Nov. 2013;8(11):2281-2308.
Rauch et al., "Mutations in Herpes Simplex Virus Glycoprotein D Distinguish Entry of Free Virus from Cell-Cell Spread," Journal of Virology, 74(24): 11437-11446 (Dec. 2000).
Richard et al., "The pUL37 tegument protein guides alpha-herpesvirus retrograde axonal transport to promote neuroinvasion," PLoS Pathogens, 2017, 13(12), e1006741, 32 pages.
Riddick et al., "Integration and analysis of genome-scale data from gliomas," Nature Reviews—Neurology, 7: 439-450 (2011).
Saharkhiz-Langroodi and Holland, Identification of the Fusion-from-without Determinants of Herpes Simplex Virus Type 1 Glycoprotein B, VIROLOGY 227, 153-159 (1997).
Sapranauskas et al., "The *Streptococcus thermophilus* CRISPR/Cas system provides immunity in *Escherichia coli*," Nucleic Acids Research, 2011, vol. 39, No. 21, pp. 9275-9282.

(56) References Cited

OTHER PUBLICATIONS

Schaffer et al., "Temperature-Sensitive Mutants of Herpes Simplex Virus Type 1: Isolation, Complementation and Partial Characterization," Virology, 52: 57-71 (1973).
Segal, "Bacteria herald a new era of gene editing," eLife 2013;2:e00563, 3 pages.
Sethi et al., "Protection of Mice from Fatal Herpes Simplex Virus Type 1 Infection by Adoptive Transfer of Cloned Virus-specific and H-2-restricted Cytotoxic T Lymphocytes," J. Gen. Viral., 64: 443-447 (1983).
Shi et al., "hsa-mir-181 a and hsa-mir-181b function as tumor suppressors in human glioma cells," Brain Research, 1236: 185-193 (2008).
Shogan et al., "Virucidal Activity of a GT-Rich Oligonucleotide against Herpes Simplex Virus Mediated by Glycoprotein B," Journal of Virology, 80(10): 4740-4747 (May 2006).
Silber et al., "miR-124 and miR-137 inhibit proliferation of glioblastoma multiforme cells and induce differentiation of brain tumor stem cells," BMC Medicine, 6(14): 1-17 (2008).
Simmons et al., "Local secretion of anti-CTLA-4 enhances the therapeutic efficacy of a cancer immunotherapy with reduced evidence of systemic autoimmunity," Cancer Immunol Immunother., 2008;57(8):1263-1270.
Sinkunas et al., "In vitro reconstitution of Cascade-mediated CRISPR immunity in *Streptococcus thermophilus*," The EMBO Journal (2013) 32, 385-394.
Slavuljica et al., "Recombinant mouse cytomegalovirus expressing a ligand for the NKG2d receptor is attenuated and has improved vaccine properties," J. Clin. Invest., 120(12): 4532-4545 (Dec. 2010).
Smith, "Relationship Between the Envelope and the Infectivity of Herpes Simplex Virus," Herpes Virus Envelopes, 814-816 (1964).
Struyf et al., "Mutations in the N-Terminal Domains of Nectin-1 and Nectin-2 Reveal Differences in Requirements for Entry of Various Alphaherpesviruses and for Nectin-Nectin Interactions," Journal of Virology, 76(24): 12940-12950 (Dec. 2002).
Szymczak et al., "Development of 2A peptide-based strategies in the design of multicistronic vectors," Expert Opin. Biol. Ther., 5(5): 627-638 (2005).
Takenaga et al., "Microparticle resins as a potential nasal drug delivery system for insulin," Journal of Controlled Release, Mar. 1998, vol. 52, Issues 1-2, pp. 81-87.
Thomas et al., "Equine Herpesvirus 1 Gene 12 Can Substitute for vmw65 in the Growth of Herpes Simplex Virus (HSV) Type 1, Allowing the Generation of Optimized Cell Lines for the Propagation of HSV Vectors with Multiple Immediate-Early Gene Defects," J. of Virology, 73(9): 7399-7 409 (Sep. 1999).
Tischer et al., "Two-step red-mediated recombination for versatile high-efficiency markerless DNA manipulation in *Escherichia coli.*," BioTechniques, 40(2): 191-196 (2006).
Todo, "Oncolytic Virus Therapy Using Genetically Engineered Herpes Simplex Viruses," Cell, 15(3): 151-159 (2002).
Topalian et al., "Safety, Activity, and Immune Correlates of Anti-PD-1 Antibody in Cancer," The New England Journal of Medicine, 366(26): 2443-2454 (2012).
Trriozzi et al., "Phase I Study of the Intratumoral Administration of Recombinant Canarypox Viruses Expressing B7.1 and Interleukin 12 in Patients with Metastatic Melanoma," Clin Cancer Res 2005;11(11):4168-4175.
Tsvitov et al., "Characterization of Soluble Glycoprotein D-mediated Herpes Simplex Virus Type 1 Infection," Virology, 360: 477-491 (2007).
Turner et al., "Glycoproteins gB, gD, and gHgL of Herpes Simplex Virus Type 1 are Necessary and Sufficient to Mediate Membrane Fusion in a Cos Cell Transfection System," Journal of Virology, 72(1): 873-875 (Jan. 1998).
Uchida et al., "A Double Mutation in Glycoprotein gB Compensates for Ineffective gD-Dependent initiation of Herpes Simplex Virus Type 1 Infection," Journal of Virology, 84(23): 12200-12209 (Dec. 2010).
Uchida et al., "Co-engineering of HSV-1 gB and gD Enables Efficient Retargeted Infection," 29th Annual Meeting of the American Society for Virology, slides of oral presentation, 38 pages, Bozeman, MT (Jul. 17-21, 2010).
Uchida et al., "Co-engineering of HSV-1 Glycoproteins B and D Enables Highly Efficient Retargeted Infection," 29th Annual Meeting of the American Society for Virology, abstract, 1 page, Bozeman, MT (Jul. 17-21, 2010).
Uchida et al., "Effective Treatment of an Orthotopic Xenograft Model of Human Glioblastoma Using an EGFR-retargeted Oncolytic Herpes Simplex Virus," Molecular Therapy 21(3):561-569 (2012).
Uchida et al., "Fully Retargeted HSV-1 Infection Directed by Re-Engineered Glycoprotein D (gD) is Augmented by Hyperactive gB Mutations," Molecular Therapy, 18(Supp. 1): S249, Abstract 640 (May 2010).
Uchida et al., "Generation of Herpes virus Entry Mediator (HVEM)-Restricted Herpes Simplex Virus Type 1 Mutant Viruses: Resistance of HVEM-Expressing Cells and Identification of Mutations That Rescue Nectin-1 Recognition," Journal of Virology, 83(7): 2951-2961 (Apr. 2009).
Uchida et al., "Hyperactive gB Mutations Augment Fully Retargeted HSV Infection," 13' Annual Meeting of the American Society of Gene & Cell Therapy, slides of oral presentation, 34 pages, Washington, DC (May 19-22, 2010).
Uchida et al., "Hyperactive gB Mutations Augment Fully Retargeted HSV Infection," 35th Annual International Herpes Virus Workshop, poster presentation, 1 page, Salt Lake City, UT (Jul. 24-29, 2010).
Uchida et al., "Hyperactive Glycoprotein B (gB) Mutations Augment Fully Retargeted Herpes Simplex Virus (HSV) Infection," 101st Annual Meeting of the American Association for Cancer Research, poster presentation, 1 page, Washington, DC (Apr. 18, 2010).
Uchida et al., "Hyperactive Glycoprotein B Mutations Augment Fully Retargeted HSV Infection," 35th Annual International Herpes Virus Workshop, abstract, 1 page, Salt Lake City, UT (Jul. 24-29, 2010).
Uchida et al., "Identification of Mutations in HSV-1 Envelope Glycoprotein B That Enhance Retargeted Infection," Proceedings of the American Association for Cancer Research, 51: 139, Abstract 584 (Apr. 2010).
Uchida et al., "Novel Mutations in gB and gH Circumvent the Requirement for Known gD Receptors in Herpes Simplex Virus 1 Entry and Cell-to-Cell Spread," Journal of Virology, 87(3): 1430-1442 (Feb. 2013).
Ushijima et al., "Determination and Analysis of the DNA Sequence of Highly Attenuated Herpes Simplex Virus Type 1 Mutant HF10, a Potential Oncolylic Virus," Microbes and Infection, 9: 142-149 (2007).
Varghese et al., "Oncolytic herpes simplex virus vectors for cancer virotherapy," Cancer Gene Therapy, 9(12): 967-978 (2002).
Verhaak et al., "An integrated genomic analysis identifies clinically relevant subtypes of glioblastoma characterized by abnormalities in PDGFRA, IDH1, EGFR and NF1," Cancer Cell, 17: 98-110 (2010).
Visvanathan et al., "The microRNA miR-124 antagonizes the anti-neural REST/SCP1 pathway during embryonic CNS development," Genes & Development, 21: 744-749 (2007).
Voeks et al., "Gene therapy for prostate cancer delivered by ovine adenovirus and mediated by purine nucleoside phosphorylase and fludarabine in mouse models," Gene Therapy, 9(12): 759-768 (2002).
Wahid et al., "MicroRNAs: Synthesis, mechanism, function, and recent clinical trials," Biochimica et Biophysica Acta, 2010, 1803: 1231-1243.
Wakimoto et al., "Effects of innate immunity on herpes simplex virus and its ability to kill tumor cells," Gene Therapy, 10: 983-990 (2003).
Warner et al., "A Cell Surface Protein with Herpesvirus Entry Activity (HveB) Confers Susceptibility to Infection by Mutants of Herpes Simplex Virus Type 1, Herpes Simples Virus Type 2, and Pseudorabies Virus," Virology, 246: 179-189 (1998).

(56) References Cited

OTHER PUBLICATIONS

Watkins, Jr. and Santalucia, Jr., "Nearest-neighbor thermodynamics of deoxyinosine pairs in DNA duplexes," Nucleic Acids Research, 2005, 33(19): 6258-6267.
Wikstrand et al., "Monoclonal Antibodies against EGFRvIII Are Tumor Specific and React with Breast and Lung Carcinomas and Malignant Gliomas," Cancer Research, 55: 3140-3148 (Jul. 15, 1995).
Wong et al., "Targeted oncolytic herpes simplex viruses for aggressive cancers," Current Pharmaceutical Biotechnology, 13: 1786-1794 (2012).
Xia et al., "Loss of Brain-enriched miR-124 MicroRNA Enhances Stem-like Traits and Invasiveness of Glioma Cells," The Journal of Biological Chemistry, 287(13): 9962-9971 (2012).
Yan et al. "Effective small RNA destruction by the expression of a short tandem target mimic in Arabidopsis," The Plant Cell 24:415-427 (2012).
Yin et al., "The treatment of glioblastomas: A systematic update on clinical Phase III trials," Critical Reviews in Oncology/Hematology, 87: 265-282 (2013).
Yun, "Overcoming the extracellular matrix barrier to improve intratumoral spread and therapeutic potential of oncolytic virotherapy," Current Opinion in Molecular Therapeutics, 10(4): 356-361 (2008).
Zaharoff et al., "Intratumoral Immunotherapy of Established Solid Tumors with Chitosan/IL-12," J Immunother. 2010;33(7):697-705.
Zetsche et al., "Cpf1 is a Single RNA-Guided Endonuclease of a Class 2 CRISPR-Cas System," Cell 163, 759-771, Oct. 22, 2015.
Zhang et al., "Abstract 3669: IDH mutant glial cell resistance to natural killer cell cytotoxicity," Cancer Research, 74, 3669 (Oct. 1, 2014).
Zhang et al., "MicroRNA-128 inhibits glioma cells proliferation by targeting transcription factor E2F3a," J. Mol Med., 87: 43-51 (2009).
Zhong et al., "Induction, Selection and Expansion of Acute Myeloid Leukemia Reactive Autologous T Cells for Adoptive Immunotherapy," Blood, Nov. 2005, 106(11):1061.
Zhou and Roizman, "Construction and properties of a herpes simplex virus 1 designed to enter cells solely via the IL-13α2 receptor," PNAS 103(14):5508-5513 (2006).
Extended European Search Report issued by the European Patent Office for Application No. 14859119.1, dated Apr. 19, 2017, 10 pages.
International Preliminary Report on Patentability issued by the International Searching Authority for Application No. PCT/US2011/032923, dated Oct. 16, 2012, 8 pages.
International Search Report and Written Opinion issued by the International Searching Authority for Application No. PCT/US2011/032923, dated Mar. 28, 2012 12 pages.
International Preliminary Report on Patentability issued by the International Searching Authority for Application No. PCT/US2014/062676, dated May 3, 2016, 5 pages.
International Search Report and Written Opinion issued by the International Searching Authority for Application No. PCT/US2014/062676, dated Dec. 23, 2014, 9 pages.
International Search Report and Written Opinion of the International Searching Authority for International Application No. PCT/US2018/43938, dated Dec. 14, 2018, 16 pages.
Aurelian, L. et al., "Oncolytic viruses as immunotherapy: progress and remaining challenges," OncoTargets and Therapy, 9, pp. 2627-2637 (May 2016).
Ausländer, S. et al., "A ligand-dependent hammerhead ribozyme switch for controlling mammalian gene expression," Molecular BioSystems, 6, pp. 807-814, DOI: 10.1039/b923076a (2010).
Beilstein, K. et al., "Conditional Control of Mammalian Gene Expression by Tetracycline-Dependent Hammerhead Ribozymes," ACS Synthetic Biology, 4, pp. 526-534, dx.doi.org/10.1021/sb500270h (2015).
Brown, S. M. et al., "ICP 34.5 influences herpes simplex virus type 1 maturation and egress from infected cells in vitro," Journal of General Virology, 75, 3679-3686 (1994).
Burton, E. A., et al., "Use of the Herpes Simplex Viral Genome to Construct Gene Therapy Vectors," Methods in Molecular Medicine, Humana Press, vol. 76, pp. 1-31 (Jan. 2003).
Chou, J. et al., "Mapping of Herpes Simplex Virus-1 Neurovirulence to γ134.5, a Gene Nonessential for Growth in Culture," Science, vol. 250, Issue 4985, pp. 1262-1266, doi: 10.1126/science.2173860 (Nov. 1990).
Chumakov, P. M., Oncolytic viruses, Institute of Molecular Biology. V.A. Engelgard RAS, 10th Zilber lecture, Nov. 19, 2015.
El-Andaloussi, N., et al., "Generation of an Adenovirus-Parvovirus Chimera with Enhanced Oncolytic Potential", Journal of Virology, The American Society for Microbiology, vol. 86, No. 19, p. 10418-10431 (Oct. 2012).
GenBank Reference No. D00627.1, Human coxsackievirus A9 genomic RNA, complete genome, strain: Griggs, Dec. 14, 2007 (online) (retrieved on Jul. 21, 2022) Retrieved from https://www.ncbi.nlm.nih.gov/nuccore/221214 (4 total pages).
GenBank Reference No. KT161266.1, Coxsackievirus A21 isolate JN12377/SD/CHN/2012/CVA21, complete genome, Dec. 15, 2015 (online) (retrieved on Jul. 21, 2022) Retrieved from https://www.ncbi.nlm.nih.gov/nuccore/930578064 (4 total pages).
GenBank Reference No. M33854.1, Coxsackievirus B3 (CVB3) complete genome, Jun. 29, 1999 (online) (retrieved on Jul. 21, 2022) Retrieved from https://www.ncbi.nlm.nih.gov/nuccore/323419 (4 total pages).
Gossen, M. and Bujard, H., "Tight control of gene expression in mammalian cells by tetracycline-responsive promoters," PNAS, vol. 89, pp. 5547-5551 (Jun. 1992).
Ikeda, K. et al., Oncolytic virus therapy of multiple tumors in the brain requires suppression of innate and elicited antiviral responses, Nature Medicine, vol. 5, No. 8, pp. 881-887 (Aug. 1999).
International Search Report and Written Opinion, dated May 19, 2017, for International Application No. PCT/US2017/015417 (15 total pages).
International Search Report and Written Opinion, dated Mar. 26, 2021, for International Application No. PCT/US202/055133 (24 total pages).
Invitation to Pay Additional Fees, and, Where Applicable, Protest Fee, mailed Feb. 5, 2021, for International Application No. PCT/US2020/055133 (20 total pages).
Kennedy et al., "Design of an Interferon-Resistant Oncolytic HSV-1 Incorporating Redundant Safety Modalities for Improved Tolerability," Molecular Therapy: Oncolytics, vol. 18, pp. 476-490 (Sep. 2020).
Ketzer, Patrick, et al., "Artificial riboswitches for gene expression and replication control of DNA and RNA viruses," PNAS, www.pnas.org/cgi/doi/10.1073/pnas.1318563111, E554-E562 (Jan. 2014).
Liu B.L., et al., "ICP34.5 Deleted Herpes Simplex Virus with Enhanced Oncolytic, Immune Stimulating, and Anti-Tumour Properties," Gene Therophy, 2003, pp. 292-303.
MacLean, A. R. et al., "Herpes simplex virus type 1 deletion variants 1714 and 1716 pinpoint neurovirulence-related sequences in Glasgow strain 17+ between immediate early gene 1 and the 'a' sequence," Journal of General Virology, 72, 631-639 (1991).
Martin, N. T., et al., "Oncolytic Virus Combination Therapy: Killing One Bird with Two Stones", Molecular Therapy, vol. 26, No. 6, pp. 1414-1422 (Jun. 2018).
Mou, H., et al., Conditional Regulation of Gene Expression by Ligand-Induced Occlusion of a MicroRNA Target Sequence, Molecular Therapy, vol. 26, No. 5, pp. 1277-1286 (May 2018).
Nomura, Y. et al., "Synthetic mammalian riboswitches based on guanine aptazyme," Chem. Commun., 48, 7215-7217, DOI: 10.1039/c2cc33140c (2012).
Power, A. T., et al., "Taming the Trojan horse: optimizing dynamic carrier cell/oncolytic virus systems for cancer biotherapy," Gene Therapy, vol. 15, No. 10, pp. 772-779 (Mar. 2008).
Robertson, Lesley M. et al., "Peripheral replication and latency reactivation kinetics of the non-neurovirulent herpes simplex virus type 1 variant 1716," Journal of General Virology, vol. 73, pp. 967-970 (1992).
Supplementary Partial European Search Report for European Application No. 18837388.0, dated Aug. 3, 2021, 9 pages.

(56) References Cited

OTHER PUBLICATIONS

Tarasova M.V., et al., "Oncolytic viruses in the treatment of gliomas, study guide," Novosibirsk, 2015, 30 pages (with partial English translation).
Turan, S., et al., Recombinase-mediated cassette exchange (RMCE)—A rapidly-expanding toolbox for targeted genomic modifications, GENE, vol. 515, No. 1, pp. 1-27 (Feb. 2013).
Whittman, A. and Suess, B., "Selection of tetracycline inducible self-cleaving ribozymes as synthetic devices for gene regulation in yeast," Molecular Biosystems, 7, pp. 2419-2427 (2011).
Win, M. N. and Smolke, C. D., "A modular and extensible RNA-based gene-regulatory platform for engineering cellular function," PNAS, vol. 104, No. 36, pp. 14283-14288 (Sep. 2007).
Xiao, H. et al., "Structural Basis for Specific, High-Affinity Tetracycline Binding by an In Vitro Evolved Aptamer and Artificial Riboswitch," Chemistry & Biology, vol. 15, Issue 10, pp. 1125-1137 (Oct. 2008).
Zhang et al., "Intravesical treatment of advanced urothelial bladder cancers with oncolytic HSV-1 co-regulated by differentially expressed microRNAs," Gene Therapy, vol. 23, No. 5, pp. 460-468, doi: 10.1038/gt.2016.18 (2016).
Zhong, G. et al., "Rational design of aptazyme riboswitches for efficient control of gene expression in mammalian cells", eLIFE,5:e18858, doi: 10.7554/eLife.18858 (Nov. 2016) (17 total pages).
Extended European Search Report for Application EP22161034.8, dated Oct. 17, 2022, 7 pages.

* cited by examiner

All non-Schwannoma = non-cancerous tissue
BM = non-cancerous bone marrow

| | | | | | | | | | |
|---|---|---|---|---|---|---|---|---|---|
| 122 | - | + | - | - | - | + | + | + | - |
| 184 | - | - | + | - | - | - | - | + | - |
| 34a | - | - | - | + | - | - | + | - | - |
| Let7a | - | - | - | - | + | + | + | + | - |

*Fig. 25*
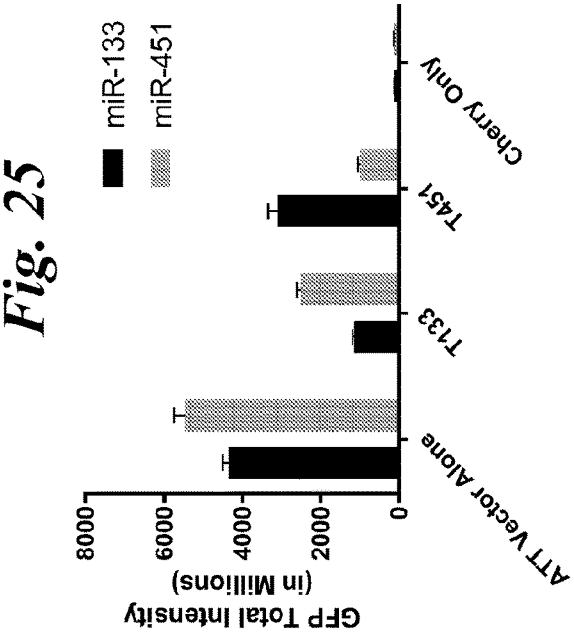
*Fig. 24*
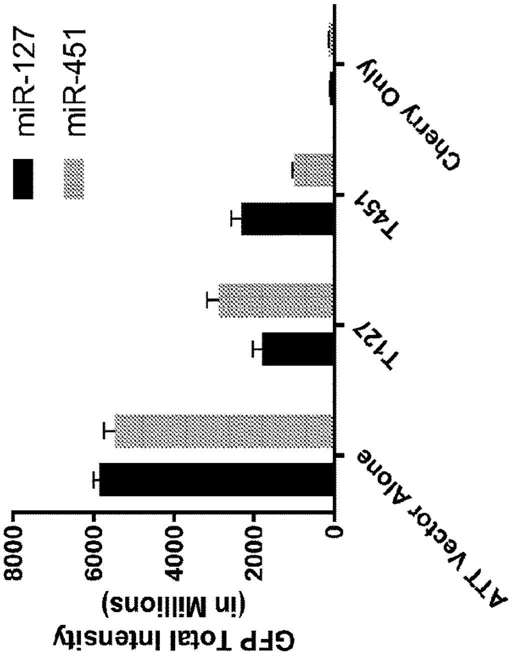
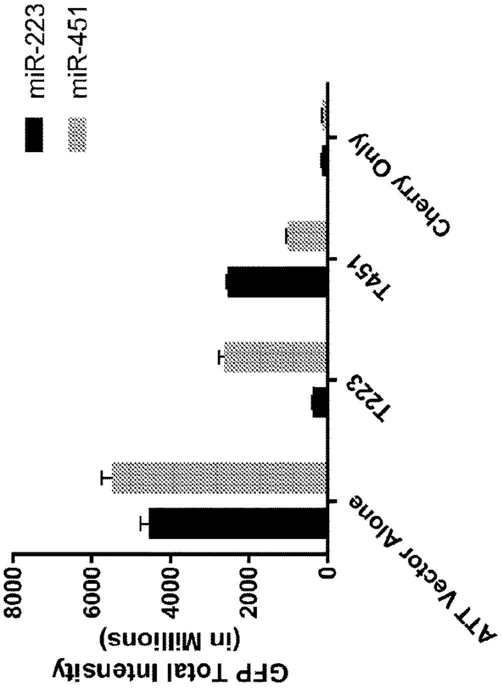
*Fig. 26*

| | Injected | | Non-injected | |
|---|---|---|---|---|
| | %TGI | p | %TGI | p |
| ONCR-133 | 71 | <0.0001 | 42 | 0.005 |

| | Injected | | | Non-injected | | |
|---|---|---|---|---|---|---|
| | CR | %TGI | p | CR | %TGI | p |
| ONCR-2 + ONCR-133 | 1/8 | 66 | <0.0001 | 0/8 | 35 | 0.005 |
| ONCR-7 + ONCR-133 | 0/8 | 57 | <0.0001 | 0/8 | 35 | 0.01 |

| | Injected | | | Non-injected | | |
|---|---|---|---|---|---|---|
| | CR | %TGI | p | CR | %TGI | p |
| ONCR-106 + ONCR-113 | 3/8 | 75 | <0.0001 | 0/8 | 47 | 0.001 |
| ONCR-031 + ONCR-113 | 3/8 | 79 | <0.0001 | 1/8 | 57 | 0.001 |

ONCOLYTIC VIRAL VECTORS AND USES THEREOF

REFERENCE TO RELATED APPLICATIONS

This application is a national phase filing under 35 U.S.C. § 371 of International Patent Application No. PCT/US2018/043938, filed Jul. 26, 2018, which claims the benefit of priority to U.S. Provisional Application No. 62/537,359, filed Jul. 26, 2017; and U.S. Provisional Application No. 62/686,802, filed Jun. 19, 2018, the disclosures of which are each incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ONCR_010_02WO_SubSeqList_ST25.txt. The text file is 502 KB, created on Aug. 21, 2018, and is being submitted electronically via EFS-Web.

FIELD

The present disclosure relates to recombinant viral vectors for the treatment and prevention of cancer. In particular, the disclosure relates to oncolytic viral vectors.

BACKGROUND

Current targeted cancer therapeutics are efficacious in only a narrow range of cancers due to the heterogeneity of tumor protein expression profiles. Furthermore, many cancer treatments, including existing viral vectors, chemotherapy, radiation, and surgery lack the specificity to selectively treat cancerous cells, while maintaining the health and viability of normal, non-cancerous cells and can produce undesirable off-target effects. As such, there is a need in the art for cancer therapies that are broadly efficacious in multiple cancers and are capable of selectively eliminating cancerous cells.

Oncolytic viruses are viruses that preferentially infect cancer cells and have been used in multiple pre-clinical and clinical studies for cancer treatment. Use of oncolytic viruses carries the risk of non-specific viral infection of healthy cells, leading to the death of non-cancerous cells and tissues. However, genetic manipulation of the viruses to exploit pathways, proteins, and genes that are differentially expressed in normal vs. cancerous tissue can increase the specificity of these viruses and limit off-target infection and cell death.

MicroRNAs (miRNAs or miRs) are small non-coding endogenous RNAs that regulate gene expression by directing their target messenger RNAs for degradation or translational repression. miRs are intimately associated with normal cellular processes and therefore, deregulation of miRNAs contributes to a wide array of diseases including cancer. Many miR genes are located in cancer associated genomic regions, or in fragile sites, further strengthening the evidence that miRs play a pivotal role in cancer. miRs are differentially expressed in cancer tissues compared to normal tissues and can have a causative relationship to tumorigenesis. By exploiting this differential miR expression in diverse tumor types, the cancer therapeutics described herein possess a broad spectrum safety and efficacy profile, wherein oncolytic viral replication is regulated based on the expression of a particular miR or group of miRs. Further, the oncolytic viruses described herein may also express proteins that facilitate viral spread throughout a tumor, such as those altering the expression of genes and proteins that regulate the extracellular matrix, thereby increasing their therapeutic efficacy.

There remains a need in the art for improved oncolytic viral vectors. The present disclosure provides such improved oncolytic viral vectors, and more.

SUMMARY

The present disclosure provides oncolytic viral vectors that exhibit improved technical effects compared to the prior art. The present inventors have designed various oncolytic viral vectors and performed extensive experiments, described herein, to identify oncolytic viral vectors with superior properties for clinical use in treatment of cancer.

The invention relates to recombinant viral vectors that are useful for the treatment and prevention of cancer. The oncolytic viral vectors described herein are capable of restricting viral vector replication to cancer or tumor cells by virtue of microRNA (miR) target sequences that are inserted into the viral genome. In particular embodiments described herein, the viral vectors comprise two, three, four or more copies of a miR target sequence incorporated into one or more essential viral genes. In further embodiments, the viral vectors comprise incorporation of one or more polynucleotide sequences into the viral genome whose product(s) disrupt the function of an oncogenic miR and/or alter the extracellular matrix. In further embodiments, the viral vectors comprise protease-activated antibodies incorporated into the viral particle, thereby allowing for highly selective targeting of the vectors to cancer/tumor cells. Compositions of the viral vectors and methods of use in killing of cancerous cells and the treatment of cancer are further provided herein.

In an embodiment, the present disclosure provides a recombinant oncolytic herpes simplex virus (HSV) comprising at least two micro-RNA (miRNA) target sequence inserted into a locus of one or more essential viral genes, wherein the one or more viral genes are selected from the group consisting of ICP4, ICP27, ICP8, ICP22, ICP34.5, UL5, UL8, UL9, UL30, UL39/40, and UL42. In an embodiment, the replication of the recombinant HSV is reduced in a non-cancerous cell compared to the replication of the the recombinant HSV in a cancerous cell of the same cell type. In an embodiment, the one or more viral genes are selected from the group consisting of ICP8, ICP22, ICP34.5, UL5, UL8, UL9, UL30, UL39/40, and UL42. In an embodiment, the one or more viral genes are selected from the group consisting of UL8, ICP8, and UL30. In an embodiment, the one or more viral genes are selected from the group consisting of ICP27 and ICP4. In an embodiment, the one or more viral genes are selected from the group consisting of ICP4, ICP27, UL8, UL42, and ICP34.5.

In an embodiment, the cell is selected from the group consisting of a neuronal cell, a cardiac cell, a muscle cell, and a liver cell. In an embodiment, the neuronal cell is a a central nervous system cell, a peripheral nervous system cell, a brain cell, or a spinal cord cell. In an embodiment, the muscle cell is a striated muscle cell or a smooth muscle cell. In an embodiment, the non-cancerous cell and the cancerous cell are brain cells, and the at least two miRNA target sequences are target sequences for an miRNA selected from the group consisting of miR-137, miR-219a, miR-124, miR- 9, miR-487b, and miR-128. In an embodiment, the at least two miRNA target sequences are target sequences for an miRNA selected from the group consisting of miR-137, miR-219a, miR-124, and miR-128 In an embodiment, the non-cancerous cell and the cancerous cell are cardiac or striated muscle cells, and the at least two miRNA target sequences are target sequences for an miRNA selected from the group consisting of miR-208b, miR-1, miR-208a, miR-133a, miR-4284, miR-499a, miR-126, miR-30e, miR-378i, miR-30b, and miR-378. In an embodiment, the at least two miRNA target sequences are target sequences for an miRNA selected from the group consisting of miR-208b, miR-1, and miR-208a In an embodiment, the non-cancerous cell and the cancerous cell are spinal cord cells, and the at least two miRNA target sequences are target sequences for an miRNA selected from the group consisting of miR-219a, miR-9, miR-204, miR-577, miR-99a, miR-100, miR-132, and miR-135. In an embodiment, the at least two miRNA target sequences are target sequences for an miRNA selected from the group consisting of miR-219a, miR-9, and miR-204. In an embodiment, the non-cancerous cell and the cancerous cell are peripheral nervous system cells, and the at least two miRNA target sequences are target sequences for an miRNA selected from the group consisting of miR-204, miR-1, miR-206, miR-9, miR-99a, miR-199b, miR-145, miR-100, miR-574. In an embodiment, the non-cancerous cell and the cancerous cell are liver cells, and the at least two miRNA target sequences are target sequences for an miRNA selected from the group consisting of miR-122 and miR-126. In an embodiment, the non-cancerous cell and the cancerous cell are smooth muscle cells, and the at least two miRNA target sequences are target sequences for an miRNA selected from the group consisting of miR-143 and miR-145.

In an embodiment, the two or more miR target sequences are incorporated into a miR-T cassette that is inserted in the 5' untranslated region (UTR) or 3' UTR of the one or more essential viral genes. In an embodiment, the miR-T cassette comprises a length of less than 1000 nucleotides. In an embodiment, the miR-T cassette comprises a length of between about 25 and about 500 nucleotides. In an embodiment, the miR-T cassette comprises a length of between about 100 and about 500 nucleotides.

In an embodiment, the present disclosure provides a recombinant oncolytic herpes simplex virus (HSV) comprising: (i) a first microRNA (miRNA) target sequence cassette (miR-TS cassette) inserted into a first viral gene and comprising at least 2 target sequences for each of miR-124, miR-1, and miR-143; (ii) a second miR-TS cassette inserted into a second viral gene and comprising at least 2 target sequences for each of miR-128, miR-219a, and miR-122; and (iii) a third miR-TS cassette inserted into a third viral gene and comprising at least 2 target sequences for each of miR-219a, miR-204, and miR-128. In an embodiment, the recombinant HSV further comprises a fourth miR-TS cassette inserted into a fourth viral gene, wherein the fourth miR-TS cassette comprises: (a) at least 2 target sequences for each of miR-137, miR-208b-3p, and miR-126; or (b) at least 2 target sequences for each of miR-137, miR-217, and miR-126.

In an embodiment, each of the miR-TS cassettes comprises 4 target sequences for each of the respectively miRNAs. In an embodiment, the first viral gene is ICP4. In an embodiment, the second viral gene is ICP27. In an embodiment, the third viral gene is ICP34.5. In an embodiment, the fourth viral gene is UL8. In an embodiment, the replication of the recombinant HSV is reduced in a non-cancerous cell compared to the replication of the the recombinant HSV in a cancerous cell of the same cell type, wherein the cell is selected from the group consisting of a neuronal cell, a cardiac cell, a muscle cell, and a liver cell.

In an embodiment, the first miR-TS cassette comprises a nucleic acid sequence that is at least 95% identical to SEQ ID NO: 852. In an embodiment, the first miR-TS cassette comprises or consists of the nucleic acid sequence of SEQ ID NO: 852. In an embodiment, the second miR-TS cassette comprises a nucleic acid sequence that is at least 95% identical to SEQ ID NO: 853. In an embodiment, the second miR-TS cassette comprises or consists of the nucleic acid sequence of SEQ ID NO: 853. In an embodiment, the third miR-TS cassette comprises a nucleic acid sequence that is at least 95% identical to SEQ ID NO: 854. In an embodiment, the third miR-TS cassette comprises or consists of the nucleic acid sequence of SEQ ID NO: 854. In an embodiment, the fourth miR-TS cassette comprises a nucleic acid sequence that is at least 95% identical to SEQ ID NO: 855. In an embodiment, the fourth miR-TS cassette comprises or consists of the nucleic acid sequence of SEQ ID NO: 855.

In an embodiment, the recombinant HSV further comprises a heterologous polynucleotide sequence encoding one or more payload molecules. In an embodiment, the heterologous polynucleotide sequence encodes a payload selected from the group consisting of IL-12, CCL4, and CXCL10. In an embodiment, the heterologous polynucleotide sequence encodes two or more payloads selected from the group consisting of IL-12, CCL4, and CXCL10. In an embodiment, the heterologous polynucleotide sequence encodes three payloads comprising IL-12, CCL4, and CXCL10.

In an embodiment, the present disclosure provides a recombinant oncolytic virus comprising one or more microRNA (miR) target sequences inserted into a locus of one or more viral genes required for viral replication, wherein the virus is herpes simplex virus (HSV), and wherein the one or more viral genes are selected from the group consisting of UL8, ICP34.5, UL42, UL19, ICP4, and ICP27. In an embodiment, the one or more miR target sequences is incorporated into the 5' untranslated region (UTR) or 3' UTR of the one or more viral genes required for viral replication. In an embodiment, the miR target sequence is a target sequence for a miR selected from the group consisting of miR-122, miR-184, miR-34a, let7a, miR-145-5p, miR-199a-5p, miR-451a, miR-125a, miR-125a-5p, miR-126-3p, miR-233-3p, miR-143-3p, miR-1-3p, miR-133a-3p, miR-127a-3p, miR-133b, miR-134-3p, miR-124, miR-101, miR-125b, miR-145, miR-559, miR-213, miR-31-5p, and miR-205p.

In an embodiment, one or more copies of the one or more miR target sequences are inserted into a locus of one or more viral genes. In an embodiment, two, three, four, or more copies of the one or more miR target sequences are inserted into a locus of one or more viral genes. In an embodiment, replication of the virus is reduced or attenuated in a first cell compared to replication of the virus in a second cell, wherein the first cell has an increased expression of a miR capable of binding to the one or more miR target sequences compared to the expression of the miR in the second cell. In an embodiment, the expression level of the miR in the first cell is at least 5% greater than the expression level of the miR in the second cell. In an embodiment, the first cell is a non-cancerous cell. In an embodiment, the second cell has a reduced expression of a miR capable of binding to the one or more miR target sequences compared to the expression of the miR in the first cell. In an embodiment, the expression level of the miR in the second cell is at least 5% less than the expression level of the miR in the first cell. In an embodiment, the second cell is a cancerous cell.

In an embodiment, one copy of a miR-122 target sequence is inserted into the locus of one or more viral genes required for viral replication. In an embodiment, four copies of the miR-122 target sequence are inserted into the locus of one or more viral genes required for viral replication. In an embodiment, the one or more viral genes is ICP27. In an embodiment, one copy of a miR-125a target sequence inserted into the locus of one or more viral genes required for viral replication. In an embodiment, four copies of the miR-125a target sequence are inserted into the locus of one or more viral genes required for viral replication. In an embodiment, the one or more viral genes is UL42. In an embodiment, four copies of a miR-122 target sequence are inserted into the locus of ICP27 and one copy of a miR-125a target sequence is inserted into the locus of UL42. In an embodiment, one copy of a miR-122 target sequence is inserted into the locus of ICP27 and one copy of a miR-125a target sequence is inserted into the locus of UL42. In an embodiment, one copy of a miR-122 target sequence is inserted into the locus of ICP27 and three copies of a miR-125a target sequence are inserted into the locus of UL42. In an embodiment, four copies of a miR-122 target sequence are inserted into the locus of ICP27 and four copies of a miR-125a target sequence are inserted into the locus of UL42.

In an embodiment, the present disclosure provides a recombinant oncolytic virus comprising: (a) one or more micro-RNA (miR) target sequences inserted into a locus of one or more viral genes required for viral replication; and (b) one or more polynucleotides encoding (i) one or more proteins or oligonucleotides, wherein the proteins or oligonucleotides reduce the expression or inhibit the function of a miR, a gene, or a tissue inhibitor of metalloproteinases (TIMP); or (ii) a protease-activated antibody; wherein the virus is an HSV, wherein the one or more viral genes are selected from the group consisting of UL42, UL19, ICP4, and ICP27. In an embodiment, the miR is an oncogenic miR or a microenvironment remodeling miR. In an embodiment, oncogenic miR is selected from the miRs listed in Table 4. In an embodiment, the gene is an oncogenic gene. In an embodiment, the oncogenic gene is selected from the genes listed in Table 7. In an embodiment, the microenvironment remodeling miR is selected from the miRs listed in Table 5. In an embodiment, the one or more miR target sequences is incorporated into the 5' untranslated region (UTR) or 3' UTR of the one or more viral genes required for viral replication. In an embodiment, the miR target sequence is a target sequence for a miR selected from the group consisting of miR-122, miR-184, miR-34a, let7a, miR-145-5p, miR-199a-5p, miR-451a, miR-125a, miR-125a-5p, miR-126-3p, miR-233-3p, miR-143-3p, miR-1-3p, miR-133a-3p, miR-127a-3p, miR-133b, miR-134-3p, miR-124, miR-101, miR-125b, miR-145, miR-559, miR-213, miR-31-5p, and miR-205p.

In an embodiment, one or more copies of the one or more miR target sequences are inserted into a locus of one or more viral genes. In an embodiment, two, three, four, or more copies of the one or more miR target sequences are inserted into a locus of one or more viral genes. In an embodiment, one copy of a miR-122 target sequence is inserted into the locus of one or more viral genes required for viral replication. In an embodiment, four copies of the miR-122 target sequence are inserted into the locus of one or more viral genes required for viral replication. In an embodiment, the one or more viral genes is ICP27. In an embodiment, one copy of a miR-125a target sequence is inserted into the locus of one or more viral genes required for viral replication. In an embodiment, four copies of the miR-125a target sequence are inserted into the locus of one or more viral genes required for viral replication. In an embodiment, the one or more viral genes is UL42. In an embodiment, four copies of a miR-122 target sequence are inserted into the locus of ICP27 and one copy of a miR-125a target sequence is inserted into the locus of UL42. In an embodiment, one copy of a miR-122 target sequence is inserted into the locus of ICP27 and one copy of a miR-125a target sequence is inserted into the locus of UL42. In an embodiment, one copy of a miR-122 target sequence is inserted into the locus of ICP27 and three copies of a miR-125a target sequence are inserted into the locus of UL42. In an embodiment, four copies of a miR-122 target sequence are inserted into the locus of ICP27 and four copies of a miR-125a target sequence are inserted into the locus of UL42.

In an embodiment, the TIMP is selected from TIMP1, TIMP2, TIMP3 and TIMP4. In an embodiment, the oligonucleotide is an shRNA or a decoy oligonucleotide. In an embodiment, the protein is a nuclease, a bispecific T-cell engager (BiTE), an anti-immunosuppressive protein, or an immunogenic antigen. In an embodiment, the nuclease is selected from a Clustered Regulatory Interspaced Short Palindromic Repeats (CRISPR)-associated endonuclease, a zinc-finger nuclease (ZFN) or a transcription activator-like effector nuclease (TALEN). In an embodiment, the CRISPR-associated endonuclease is selected from SpCas9, SpCas9-HF1, SpCas9-HF2, SpCas9-HF3, SpCas9-HF4, SaCas9, FnCpf, FnCas9, eSpCas9, C2C1, C2C3, Cpf1, Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. In an embodiment, the recombinant virus further comprises a heterologous polynucleotide encoding an tracr-RNA (trRNA) and a crispr-RNA (crRNA), wherein the crRNA is targeted to a genomic DNA sequence encoding a miR or a TIMP and wherein the trRNA facilitates binding and activation of a CRISPR-associated endonuclease.

In an embodiment, the anti-immunosuppressive protein is an anti-regulatory T-cell (Treg) protein or an anti-myeloid-derived suppressor cell (MDSC) protein. In an embodiment, the anti-immunosuppressive protein is a VHH-derived blocker or a VHH-derived BiTE. In an embodiment, the protein induces an anti-tumor immune response. In an embodiment, the protein binds to an antigen expressed on a cell surface, wherein the antigen is selected from the group consisting of EpCAM, CTLA-4, PD1, FGF2, FGFR/FGFR2b, endothelin B Receptor, and SEMA4D. In an embodiment, the protein is selected from, folate, IFNβ, A2A, CCL5, CD137, CD200, CD38, CD44, CSF-1R, CXCL10, CXCL13, IL-12, IL-15, IL-2, IL-21, IL-35, ISRE7, LFA-1, NG2 (also known as SPEG4), a SMAD protein, STING, TGFβ, and VCAM1. In an embodiment, the at least one protease-activated antibody is incorporated into a viral glycoprotein envelope. In an embodiment, the protease-activated antibody is activated by a protease selected from a cysteine cathepsin, an aspartic cathepsin, a kallikrein (hK), a serine protease, a caspase, a matrix metalloproteinase (MMP), and a disintegrin metalloproteinase (ADAM). In an embodiment, the protease is selected from cathepsin K, cathepsin B, cathepsin L, cathepsin E, cathepsin D, hK1, PSA (hK3), hK10, hK15, uPA, uPAR, MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-23A, MMP-23B, MMP-24, MMP-25, MMP-26, MMP-27, MMP-28, or a protease listed in Table 6. In an embodiment, the protease-activated antibody binds to a protein expressed more highly by a cancer cell or in a cancer microenvironment than by a non-cancer cell or in a non-cancer microenvironment. In an embodiment, the protease-activated antibody binds NKG2D, c-met, HGFR, CD8, heparan sulfate, VSPG4 (also known as NG2), EGFR, EGFRvIII, CD133, CXCR4, carcinoembryonic antigen (CEA), CLC-3, annexin II, human transferrin receptor, or EpCAM.

In an embodiment, one or more polynucleotides are inserted into a gene locus of the viral genome, or inserted between two gene loci of the viral genome. In an embodiment, the viral gene loci are selected from the group consisting of the internal repeat joint region (comprising one copy each of the diploid genes ICP0, ICP34.5, LAT, ICP4, and the ICP47 promoter), ICP0, LAT, UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, US8, US9, US10, US11, and US12.

In an embodiment, the present disclosure provides a nucleic acid molecule encoding an oncolytic virus described herein. In an embodiment, the present disclosure provides a viral stock comprising an oncolytic virus described herein. In an embodiment, the present disclosure provides a composition comprising an oncolytic virus described herein and a pharmaceutically-acceptable carrier.

In an embodiment, the present disclosure provides a method of killing a cancerous cell, comprising exposing the cancerous cell to an oncolytic virus described herein or compositions thereof under conditions sufficient for the oncolytic virus to infect and replicate within said cancerous cell, and wherein replication of the oncolytic virus within the cancerous cell results in cell death. In an embodiment, the cancerous cell has a reduced expression of a miR capable of binding to the one or more miR-target sequences compared to the expression of the miR in a non-cancerous cell. In an embodiment, the expression level of the miR in the cancerous cell is at least 5% less than the expression level the miR in the non-cancerous cell. In an embodiment, replication of the oncolytic virus is increased or maintained in cancerous cells with a reduced expression of the miR capable of binding to the one or more miR-target sequences. In an embodiment, the viral replication is at least 5% greater in the cancerous cells compared to the viral replication in the non-cancerous cell. In an embodiment, the cell is in vivo. In an embodiment, the cell is within a tumor.

In an embodiment, the present disclosure provides a method of treating cancer in a subject in need thereof, comprising administering an oncolytic virus described herein or compositions thereof to a subject in need thereof. In an embodiment, the subject is a mouse, a rat, a rabbit, a cat, a dog, a horse, a non-human primate, or a human. In an embodiment, the oncolytic virus or compositions thereof are administered intravenously, subcutaneously, intratumorally, intramuscularly, or intranasally. In an embodiment, the cancer is selected from lung cancer, breast cancer, ovarian cancer, cervical cancer, prostate cancer, testicular cancer, colorectal cancer, colon cancer, pancreatic cancer, liver cancer, gastric cancer, head and neck cancer, thyroid cancer, malignant glioma, glioblastoma, melanoma, B-cell chronic lymphocytic leukemia, diffuse large B-cell lymphoma (DLBCL), and marginal zone lymphoma (MZL). In an embodiment, the lung cancer is small cell lung cancer or non-small cell lung cancer. In an embodiment, the liver cancer is hepatocellular carcinoma (HCC).

In an embodiment, a recombinant oncolytic virus described herein further comprises a payload molecule, wherein the payload molecule or protein is an anti-FAP/anti-CD3 bispecific T cell engager. In an embodiment, a recombinant oncolytic virus described herein further comprises a payload molecule, wherein the payload molecule or protein is an anti-PD1-Fc-41BBL protein.

BRIEF DESCRIPTION OF THE DRAWINGS

FIG. 10A shows a schematic of a pTetR tet repressor plasmid that induces expression of an miRNA expression plasmid. FIG. 10B shows a schematic of a pTF-002 miRNA expression plasmid containing a tet-inducible mCherry and miRNA expression cassette. FIG. 10C shows a schematic of a pTF-004 miRNA attenuation reporter enabling the readout of destabilized GFP (dsGFP).

FIG. 24 shows quantitation of miR-127 and miR-451-attenuated GFP fluorescence.

FIG. 25 shows quantitation of miR-133 and miR-451-attenuated GFP fluorescence.

FIG. 26 shows quantitation of miR-223 and miR-451-attenuated GFP fluorescence.

FIG. 27A shows fluorescence-based quantitation of HSV attenuation in post-mitotic lung cells. FIG. 27B shows fluorescence-based quantitation of HSV attenuation in A253 cells. FIG. 27C shows qPCR-based quantitation of HSV attenuation in post-mitotic lung cells. FIG. 27D shows qPCR-based quantitation of HSV attenuation in A253 cells.

FIG. 31 shows a Western blot illustrating reduced viral spread and protein expression after infection with miR-T122 and/or miR-T125a containing HSV in cells expressing miR-122 and miR-125a.

FIG. 32A-FIG. 32B shows increased intracellular expression of miR-125a and mir-122 after transfection with a miR-125a mimic (FIG. 32A) or a miR-122 mimic (FIG. 32B). FIG. 32C shows attenuation of replication of oncolytic HSV vectors with cognate miR target sequences at distinct genetic loci shown by fluorescence images and quantification of GFP fluorescence (FIG. 32D).

CRISPR associated endonuclease (e.g. SpCas9, SaCas9, FnCpf1, FnCas9, etc.); Poly(A): polyadenylation signal (e.g. bGH); gRNA: Single crRNA-trRNA fusion (DR-crRNA-DR-trRNA); crRNA targeted to oncogenic microRNA (e.g. miR-17, miR-21, miR-155); Pol III promoter: E.g. U6, H1, 7SK.

Figure 40:
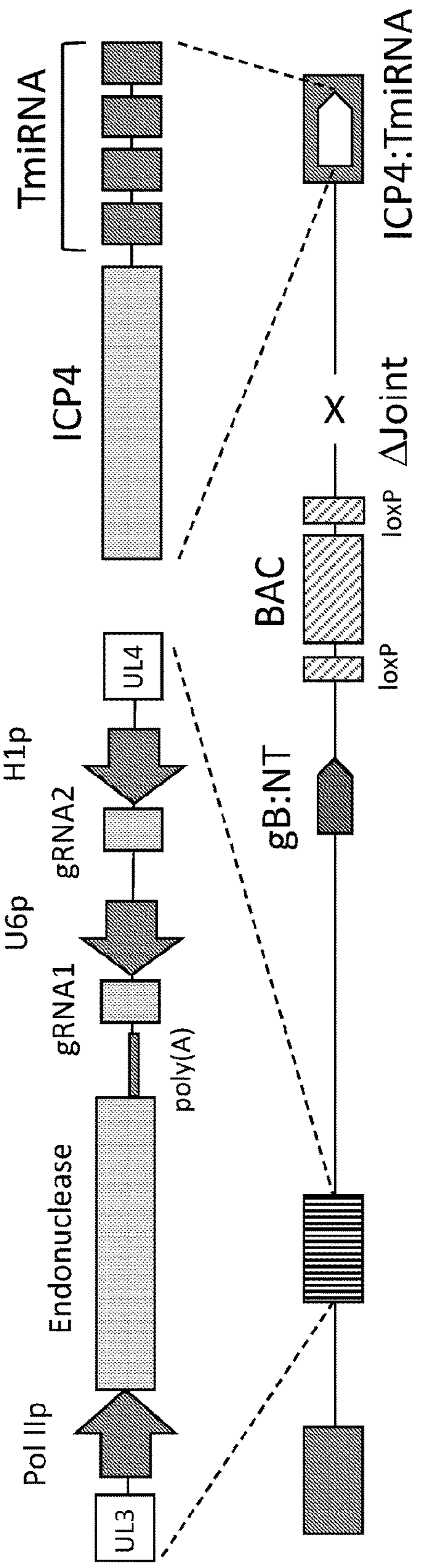

FIG. 40 shows a schematic of an ICP4-TmiRNA-attenuated, genome-editing, microenvironment-remodeling HSV vector for the treatment of cancer. gB:NT: virus entry-enhancing double mutation in gB gene; BAC: loxP-flanked choramphenicol-resistance and lacZ sequences; Δjoint: deletion of the complete internal repeat region including one copy of the ICP4 gene; ICP4:TmiRNA: insertion of miRNA target sequences (e.g. let-7, miR-34a, miR-101, miR-125b, miR-145) into the 3' UTR of the remaining ICP4 gene (also may be placed in 5' UTR); Pol II promoter: Constitutive (CAG, UbC, EF1a, PGK) or cell-specific (e.g. TRPV1, Nav1.7, hSYN); Endonuclease: CRISPR associated endonuclease (e.g. SpCas9, SaCas9, FnCpf1, FnCas9, etc.); Poly(A): polyadenylation signal (e.g. bGH); gRNA2: crRNA targeted to microenvironment remodeling miRNA (e.g. miR-143, miR-218) or TIMP (e.g. TIMP1, TIMP2); Pol III promoter: E.g. U6, H1, 7SK.

Figure 41:
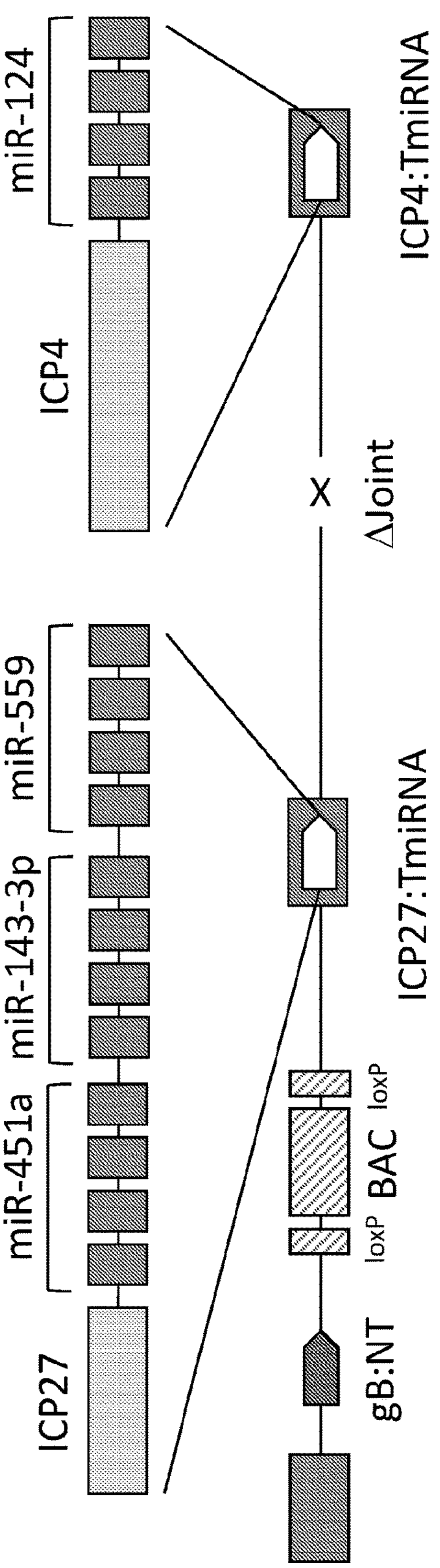

FIG. 41 shows a schematic of an ICP4-TmiRNA and ICP27-TmiRNA-attenuated HSV vector for the treatment of pancreatic, lung, and colon cancer. gB:NT: virus entry-enhancing double mutation in gB gene; BAC: loxP-flanked choramphenicol-resistance and lacZ sequences; Δjoint: deletion of the complete internal repeat region including one copy of the ICP4 gene; ICP4:TmiRNA: insertion of miR-124 target sequence cassette into the 3' UTR of the remaining ICP4 gene (also may be placed in 5' UTR); ICP27: TmiRNA: insertion of miR-451a, miR-143-3p, and miR-559 target sequence cassettes into the 3' UTR of the ICP-27 gene (also may be placed in 5' UTR).

Figure 42:
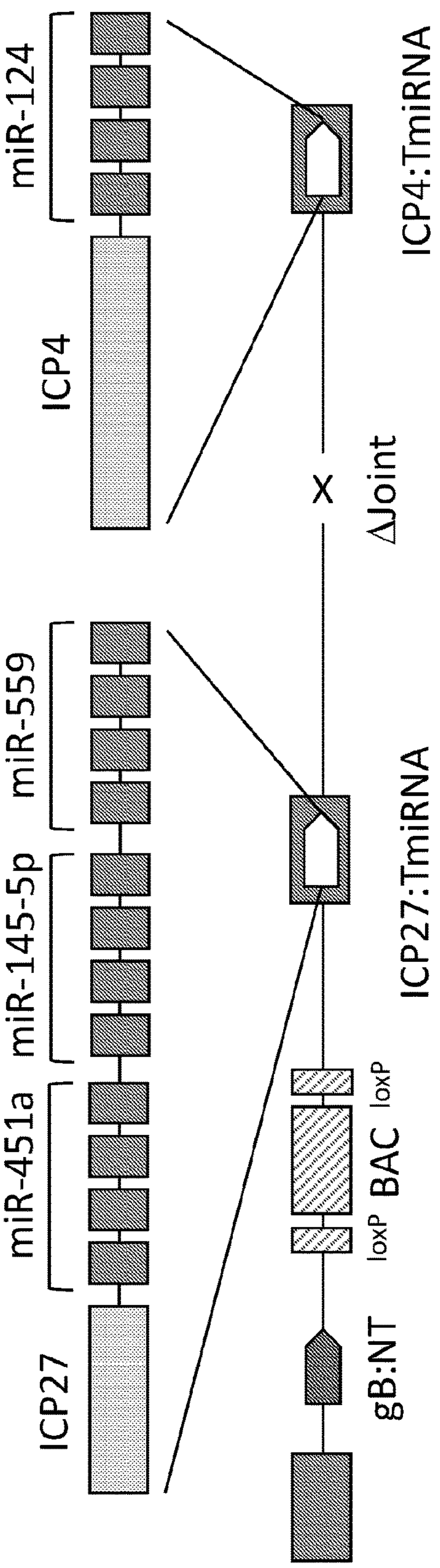

FIG. 42 shows a schematic of an ICP4-TmiRNA and ICP27-TmiRNA-attenuated HSV vector for the treatment of multiple cancer types. gB:NT: virus entry-enhancing double mutation in gB gene; BAC: loxP-flanked choramphenicol-resistance and lacZ sequences; Δjoint: deletion of the complete internal repeat region including one copy of the ICP4 gene; ICP4:TmiRNA: insertion of miR-124 target sequence cassette into the 3' UTR of the remaining ICP4 gene (also may be placed in 5' UTR); ICP27:TmiRNA: insertion of miR-451a, miR-145-5p, and miR-559 target sequence cassettes into the 3' UTR of the ICP-27 gene (also may be placed in 5' UTR).

Figure 43:
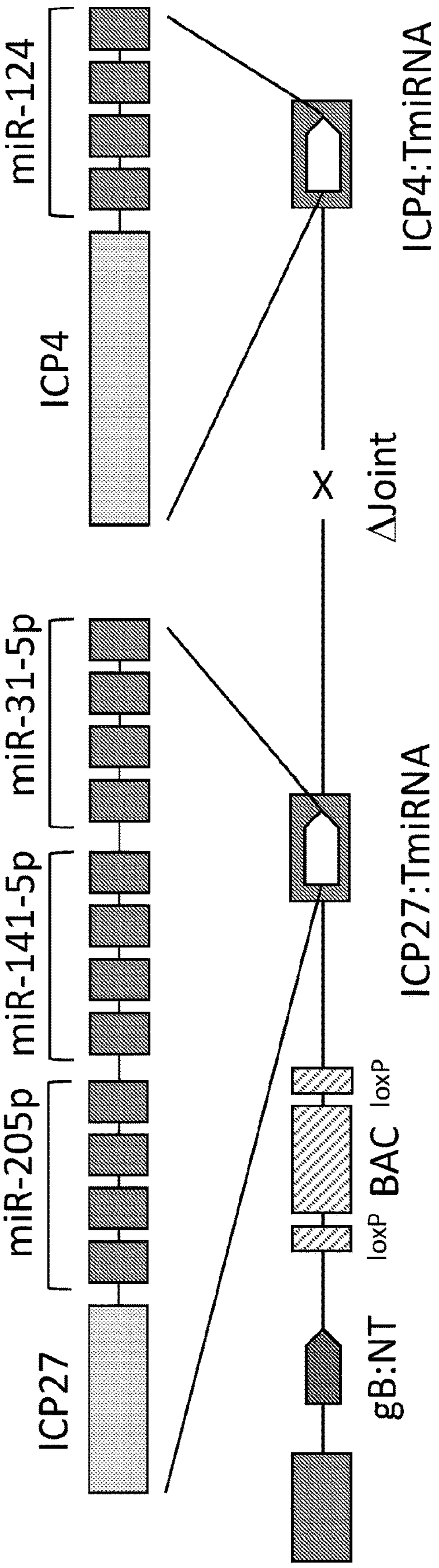

FIG. 43 shows a schematic of an ICP4-TmiRNA and ICP27-TmiRNA-attenuated HSV vector for the treatment of schwannoma. gB:NT: virus entry-enhancing double mutation in gB gene; BAC: loxP-flanked choramphenicol-resistance and lacZ sequences; Δjoint: deletion of the complete internal repeat region including one copy of the ICP4 gene; ICP4:TmiRNA: insertion of miR-124 target sequence cassette into the 3' UTR of the remaining ICP4 gene (also may be placed in 5' UTR); ICP27:TmiRNA: insertion of miR-205p, miR-141-5p, and miR-31-5p target sequence cassettes into the 3' UTR of the ICP-27 gene (also may be placed in 5' UTR).

Figure 44:
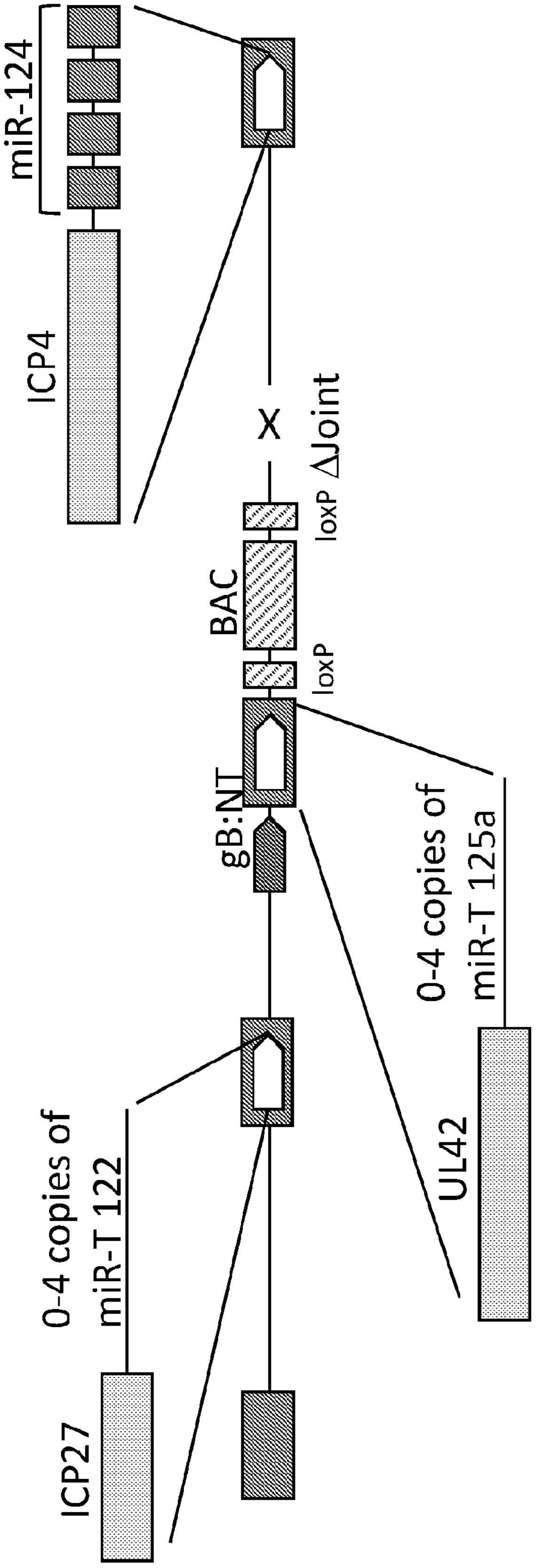

FIG. 44 shows a schematic of a miR-attenuated HSV virus, wherein multiple copies of miR-122, miR-125a, and/or miR-124 target sites are inserted into ICP27, UL42 and/or ICP4.

Figure 45:
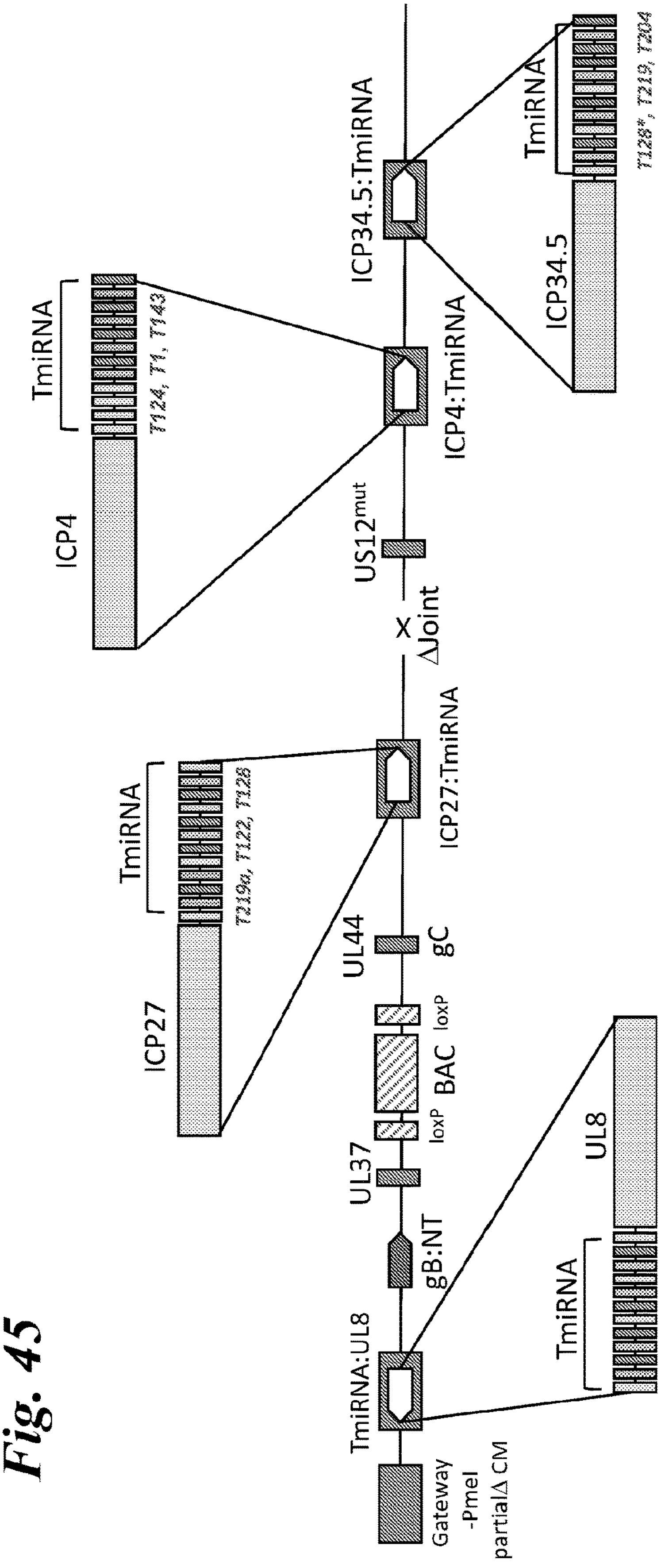

FIG. 45 shows a schematic of a miR-attenuated HSV virus (ONCR-157), wherein miR target site cassettes are inserted into UL8, ICP12, ICP4, and ICP34.5

Figure 46:
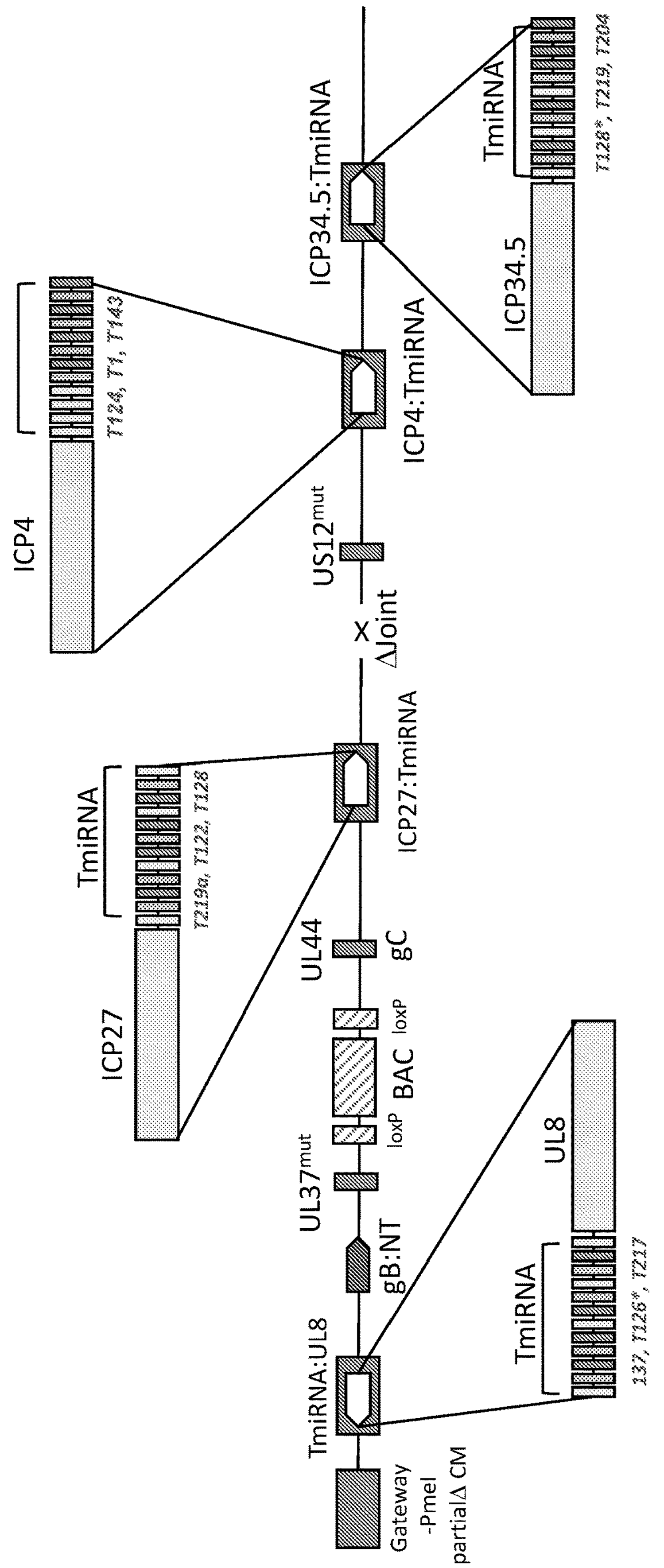

FIG. 46 shows a schematic of a miR-attenuated HSV virus (ONCR-159), wherein miR target site cassettes are inserted into UL8, ICP12, ICP4, and ICP34.5.

Figure 47B:
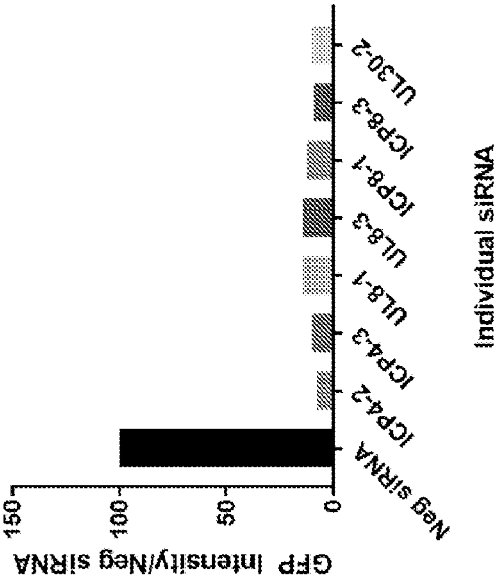
Figure 47A:
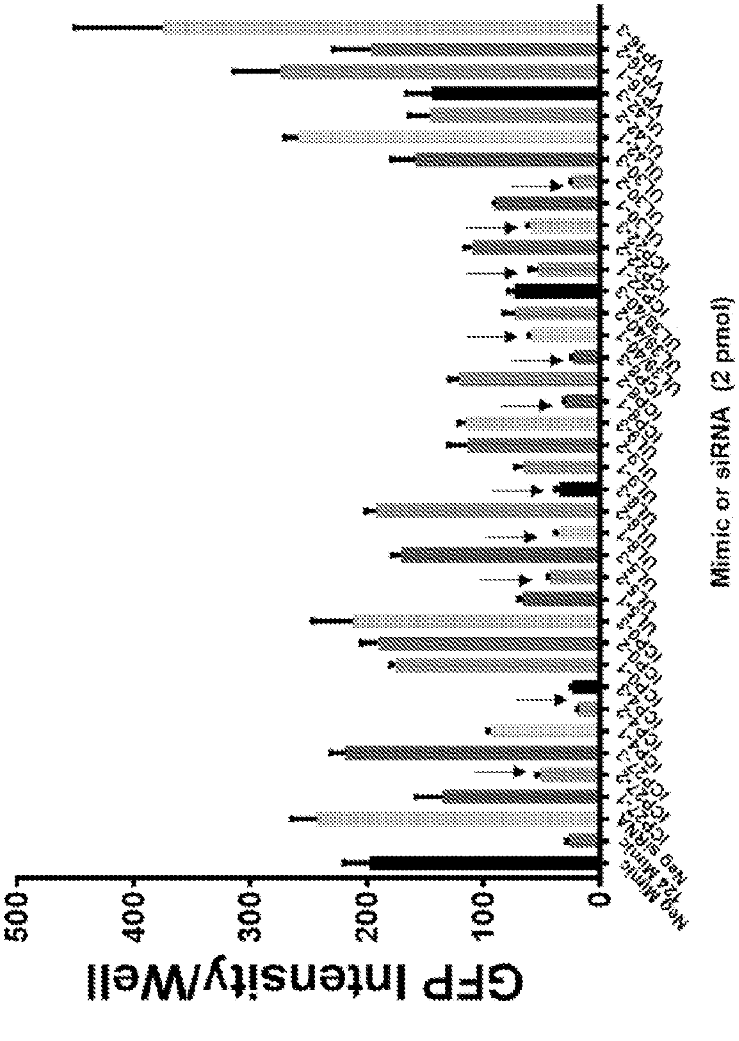

FIG. 47A shows GFP intensity generated by a reporter virus engineered to expression GFP in cells treated with pooled siRNAs against various viral genes. FIG. 47B shows results in the same assay for individual siRNAs.

Figure 48A:
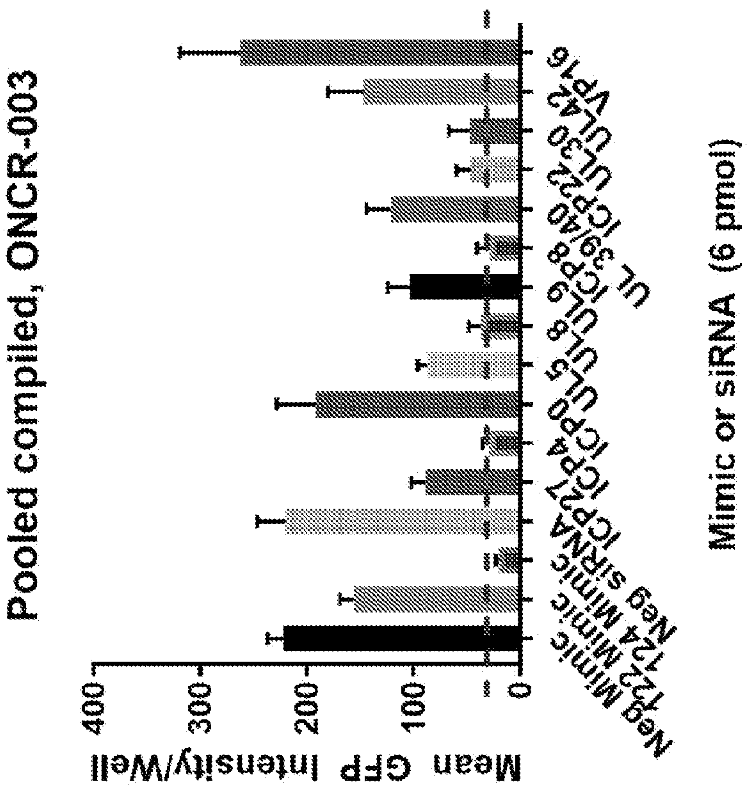
Figure 48B:
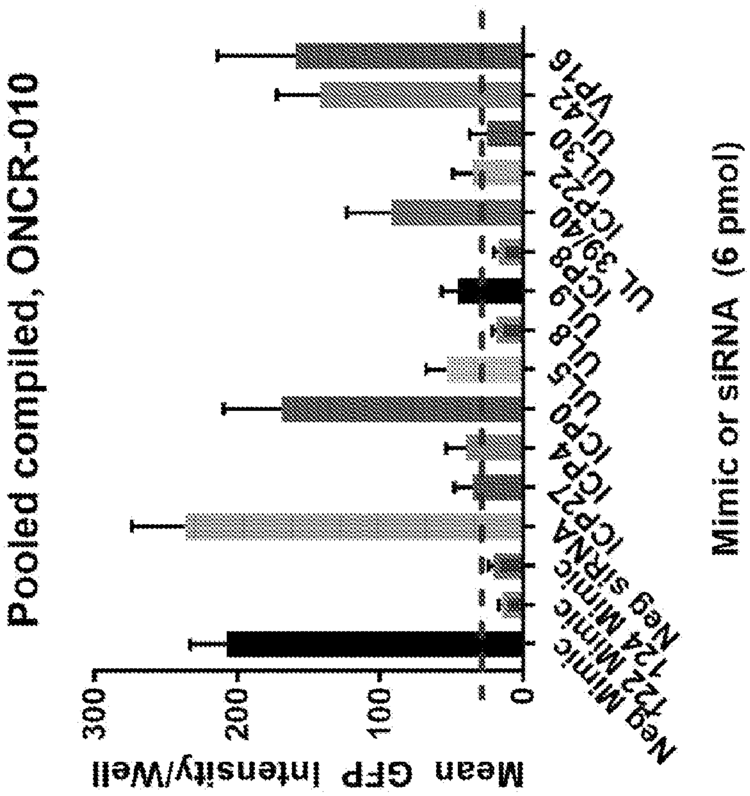

FIGS. 48A and 48B shows GFP intensity generated by a reporter virus engineered to expression GFP in cells treated with pooled siRNAs against various viral genes using the HSV vector ONCR-003 (left) or ONCR-010 (right).

Figure 49:
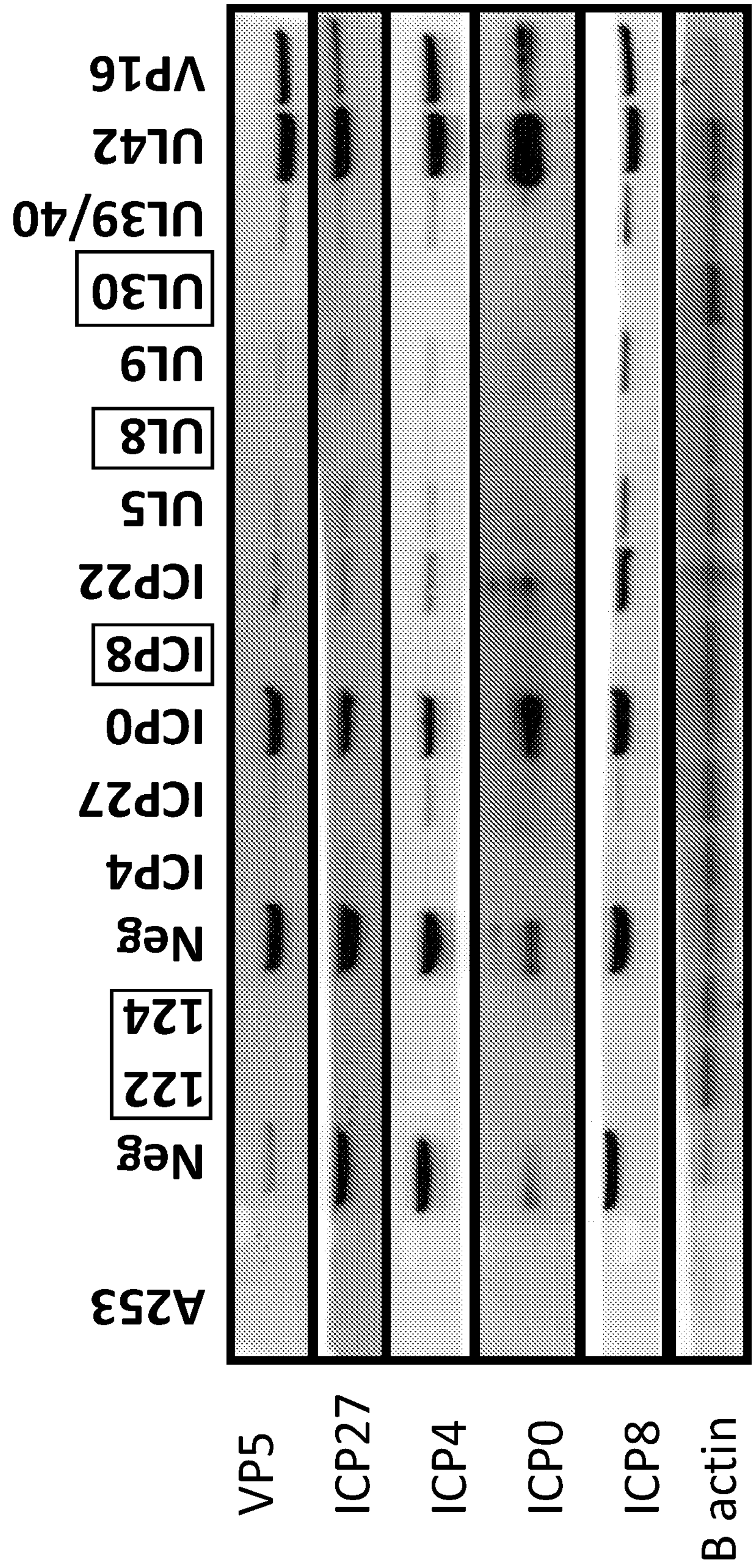

FIG. 49 shows a Western blot to detect expression of viral proteins in cells infected with HSV vector and treated with siRNA against viral genes as indicated. Beta-actin is a positive control for the Western blot.

Figure 50B:
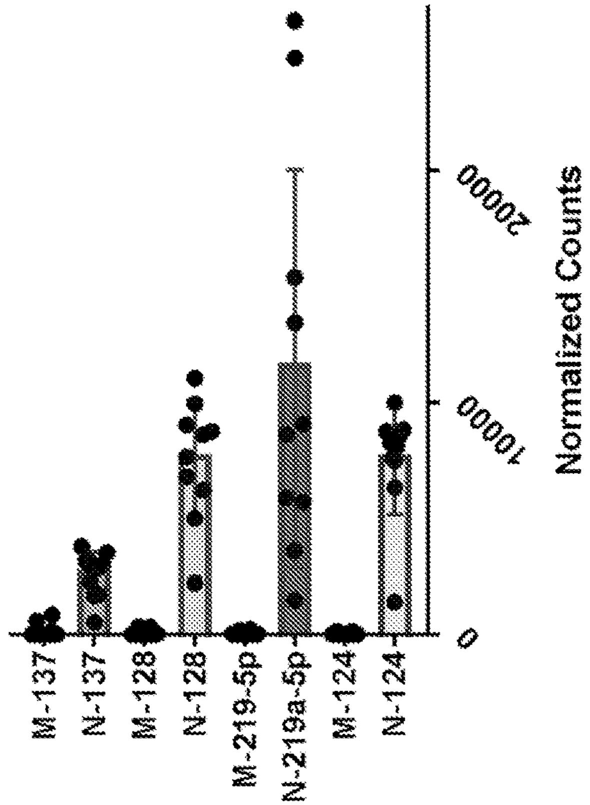

FIGS. 50A and 50B show Nanostring assay data for normal brain tissue compared to malignant tissue as ratio of miRNA expression (FIG. 50A) and normalized counts (FIG. 50B).

Figure 51B:
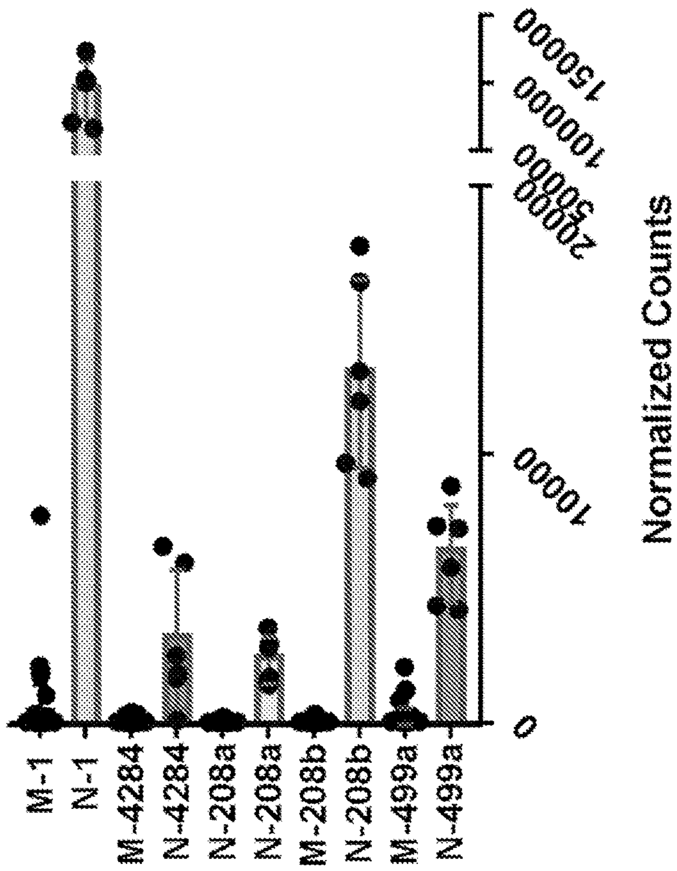
Figure 51A:
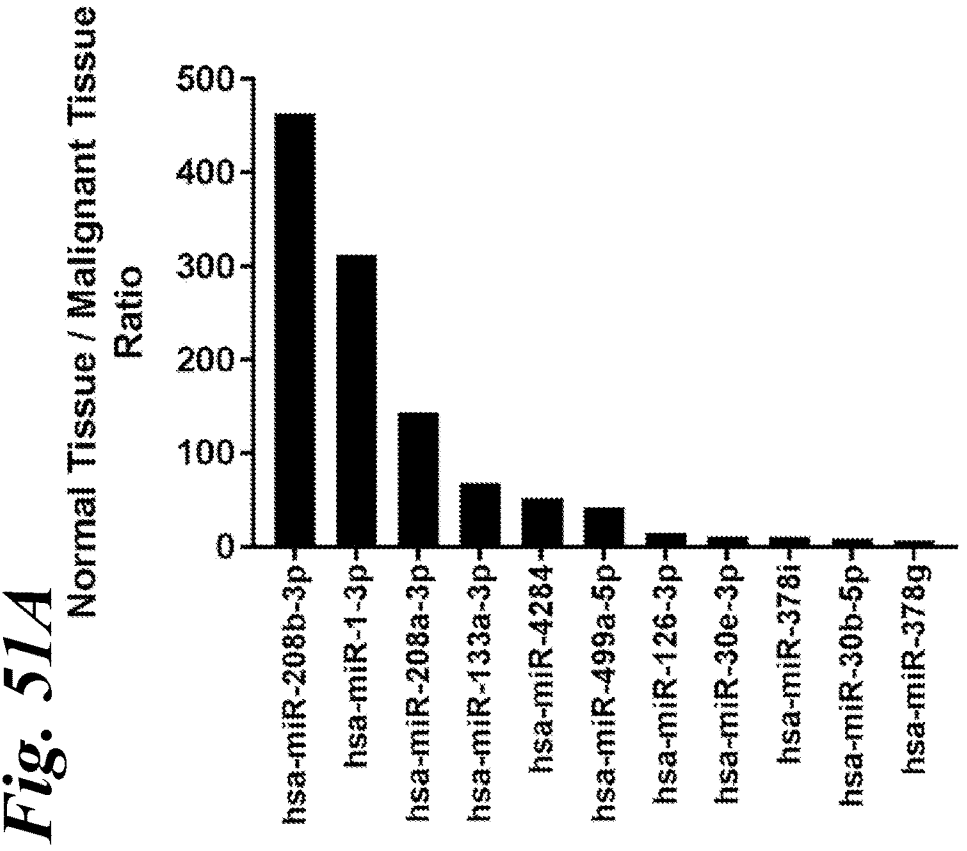

FIGS. 51A and 51B show Nanostring assay data for normal heart tissue compared to malignant tissue as ratio of miRNA expression (FIG. 51A) and normalized counts (FIG. 51B).

Figure 52B:
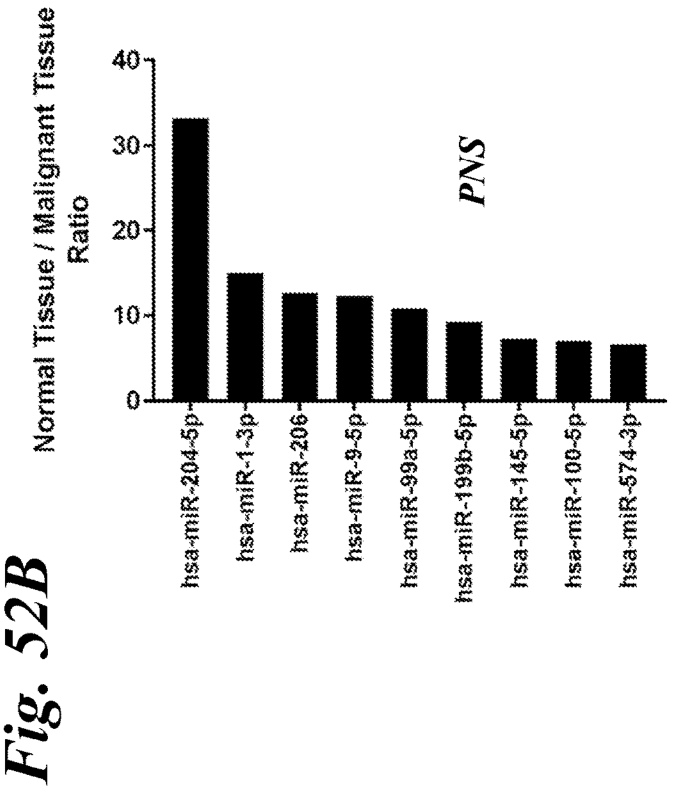
Figure 52A:
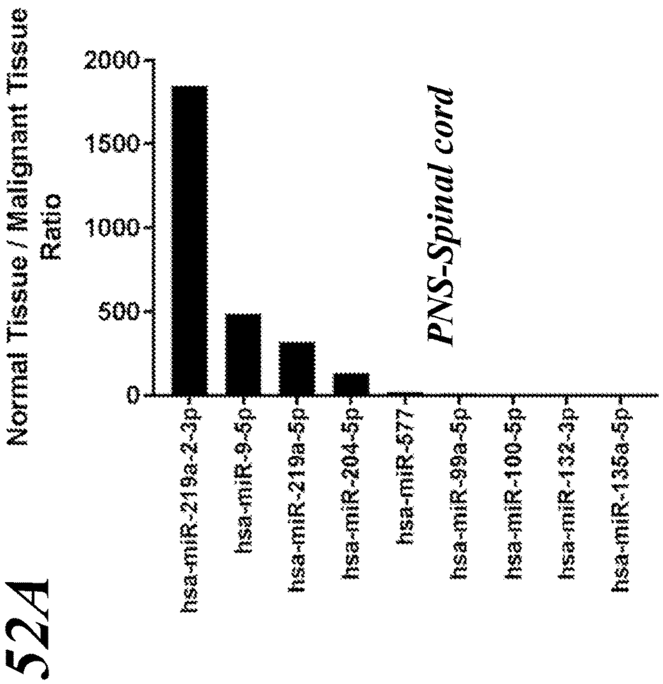
Figure 52C:
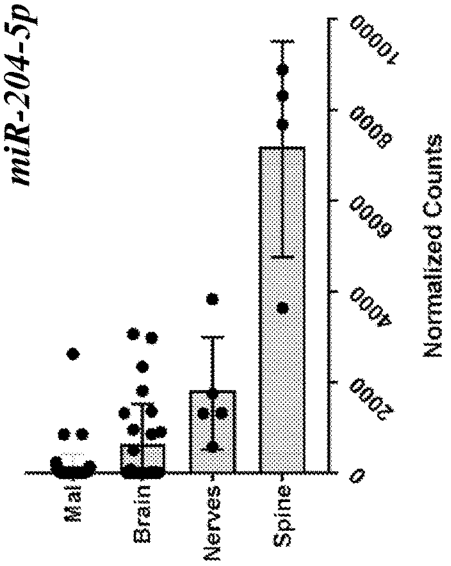

FIG. 52A shows Nanostring assay data for normal spinal-cord tissue compared to malignant tissue as ratio of miRNA expression. FIGS. 52A and 52B show Nanostring assay data for normal nerve or ganglion tissue compared to malignant tissue as ratio of miRNA expression (FIG. 52A) and normalized counts (FIG. 52C).

Figure 53A:
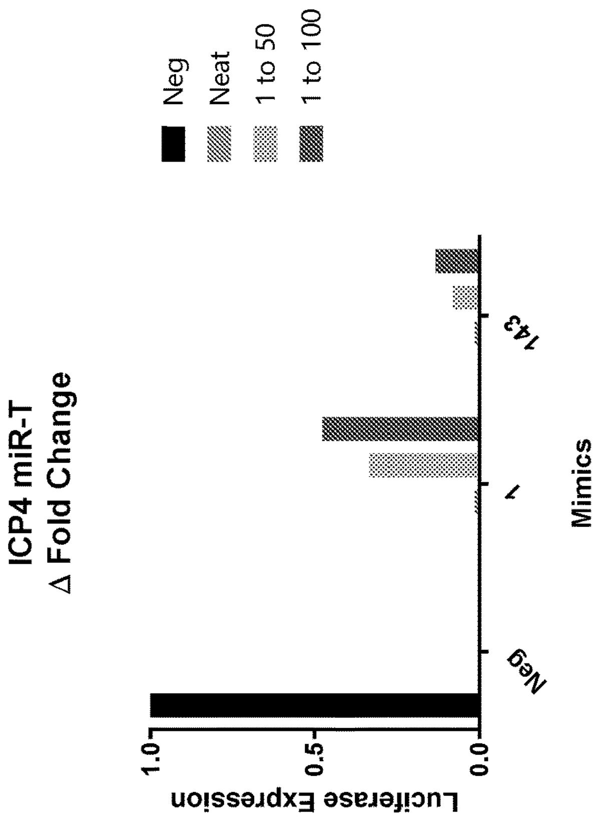
Figure 53B:
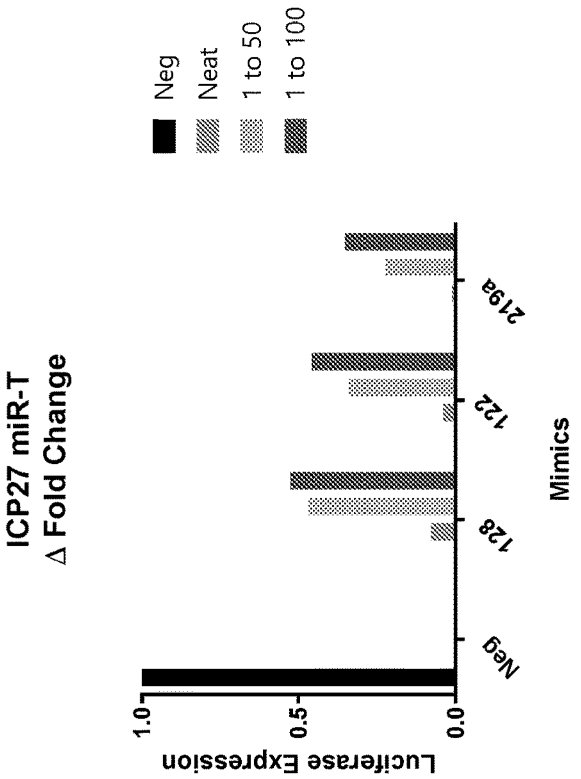

FIGS. 53A and 53B show luciferase assay testing of miR-TS cassettes for cassette 1 (FIG. 53A) or cassette 2 (FIG. 53B)

Figure 54A:
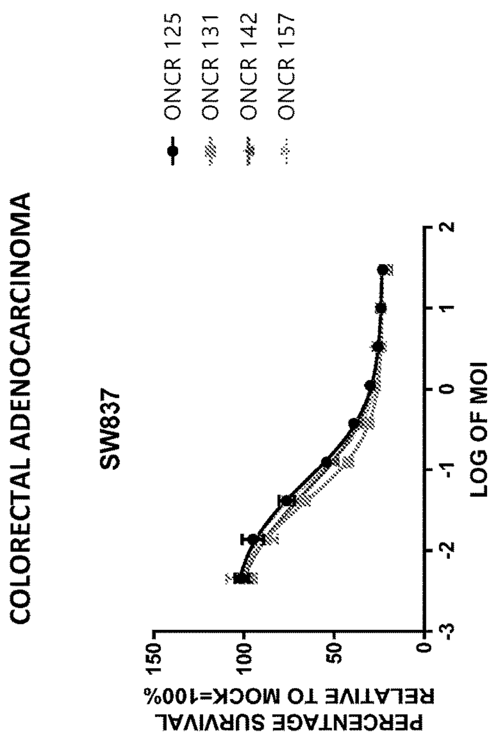
Figure 54B:
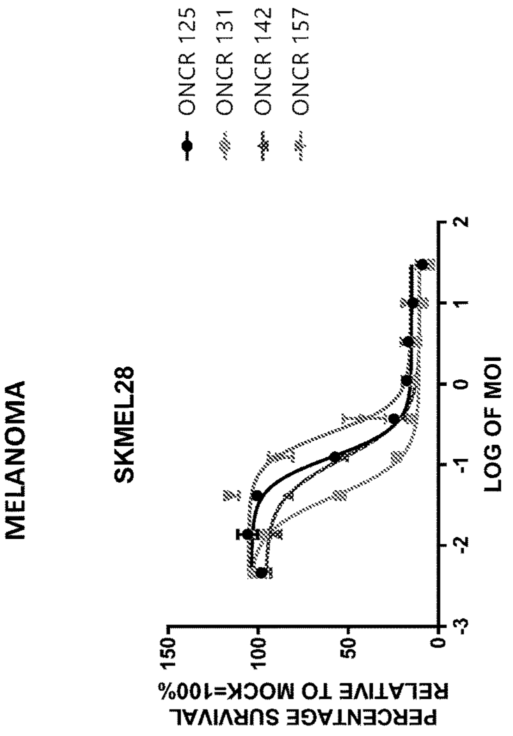
Figure 54C:
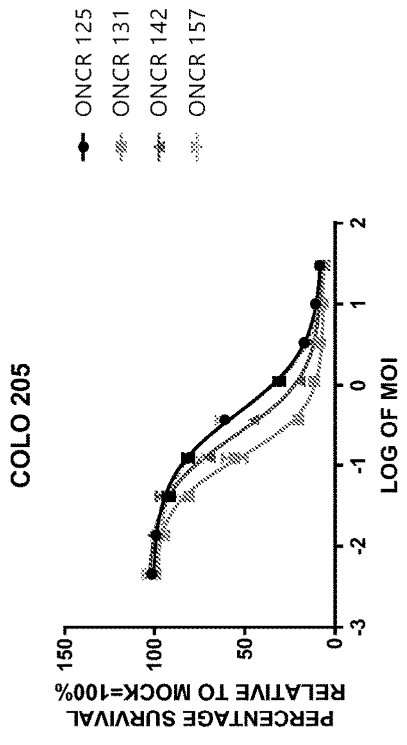
Figure 54D:
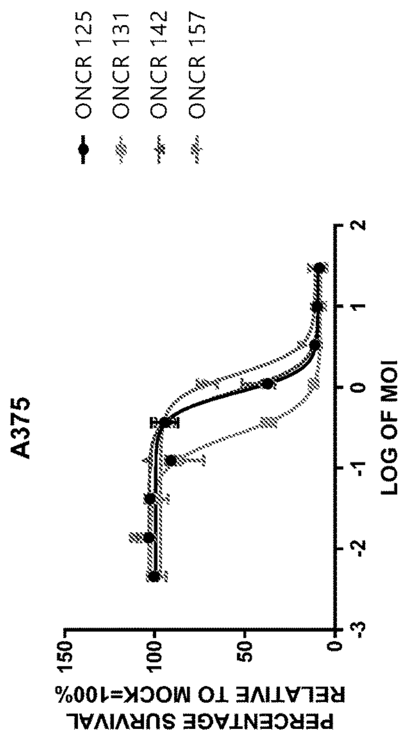
Figure 54E:
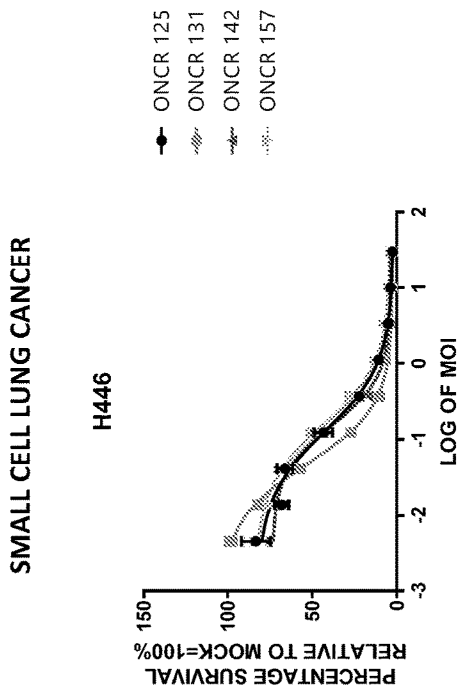
Figure 54F:
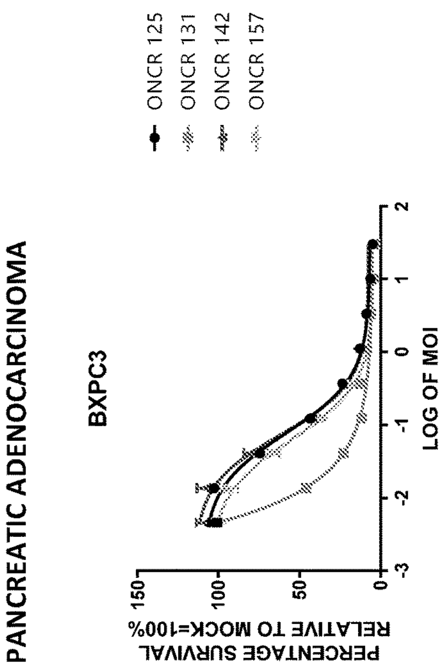
Figure 54G:
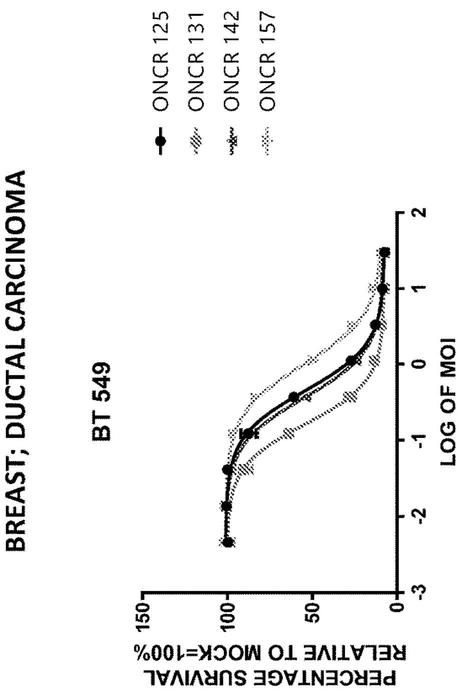

FIG. 54A-FIG. 54G show cytotoxicity of oncolytic HSV viral vectors ONCR-125, ONCR-131, ONCR-142, and ONCR-157 in cancer cell lies SW837 (FIG. 54A), SKMEL28 (FIG. 54B), COLO 205 (FIG. 54C), A375 (FIG. 54D), H446 (FIG. 54E), BXPC3 (FIG. 54F), and BT549 (FIG. 54G).

Figure 55:
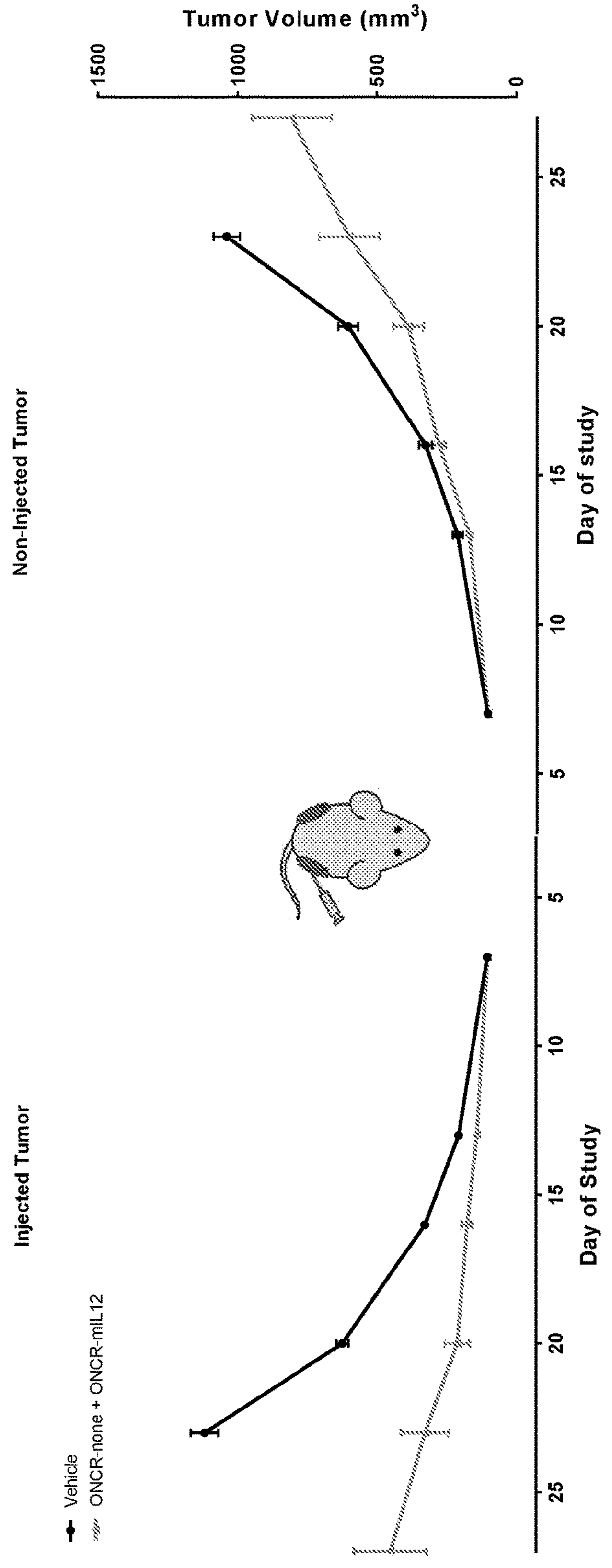

FIG. 55 shows tumor growth inhibitor effect of vehicle compared to virus (as indicated in legend) in a mouse xenograph experiment. The increase in tumor volume of the injected tumor is compared to the increase in tumor volume of the non-injected tumor. ONCR-133 significantly inhibited tumor growth of injected tumors compared to vehicle treated controls ($p<0.0001$). ONCR-133 treatment also significantly inhibited tumor growth of non-injected tumors ($p<0.005$), indicating an enhanced abscopal effect.

Figure 56:
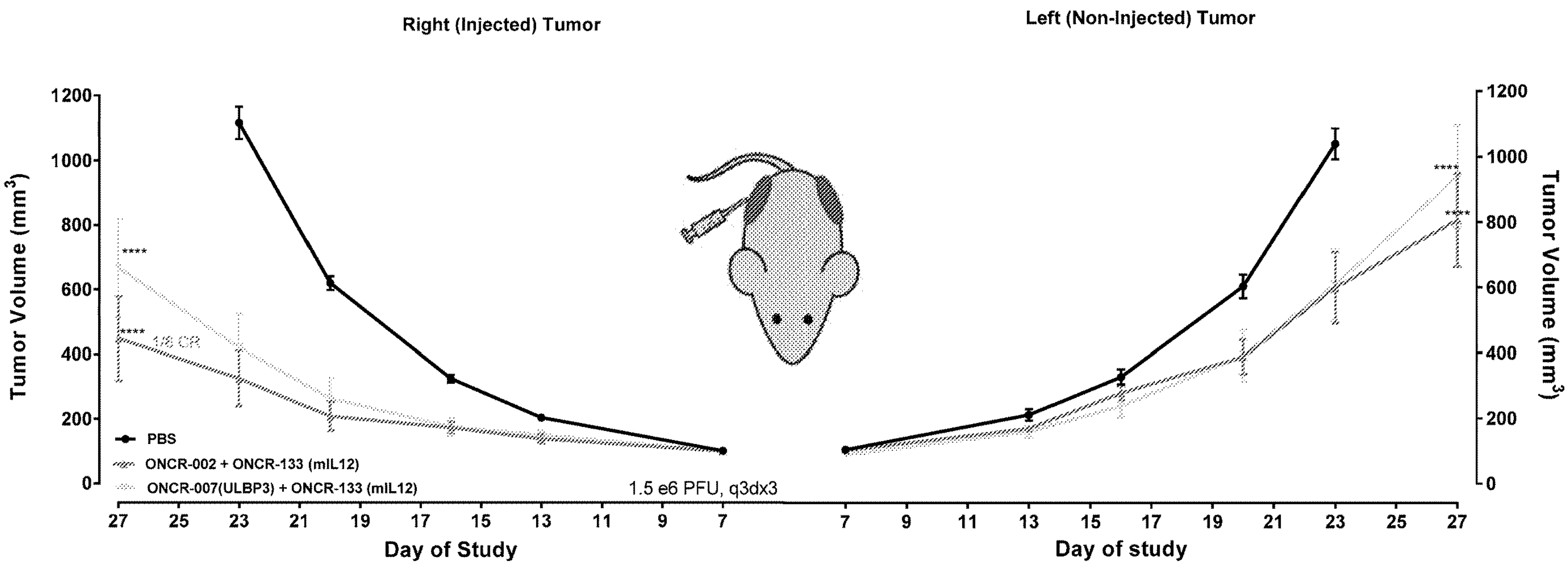

FIG. 56 shows tumor growth inhibitor effect of vehicle compared to virus (as indicated in legend) in a mouse xenograph experiment. The increase in tumor volume of the injected tumor is compared to the increase in tumor volume of the non-injected tumor. Mice treated with ONCR-133+ONCR-007 (an HSV construct expressing UL8P3) or ONCR-133+ONCR-002 (an HSV construct that does not express any additional payload molecules) both demonstrated a significant inhibition of tumor growth compared to vehicle treated controls.

Figure 57:
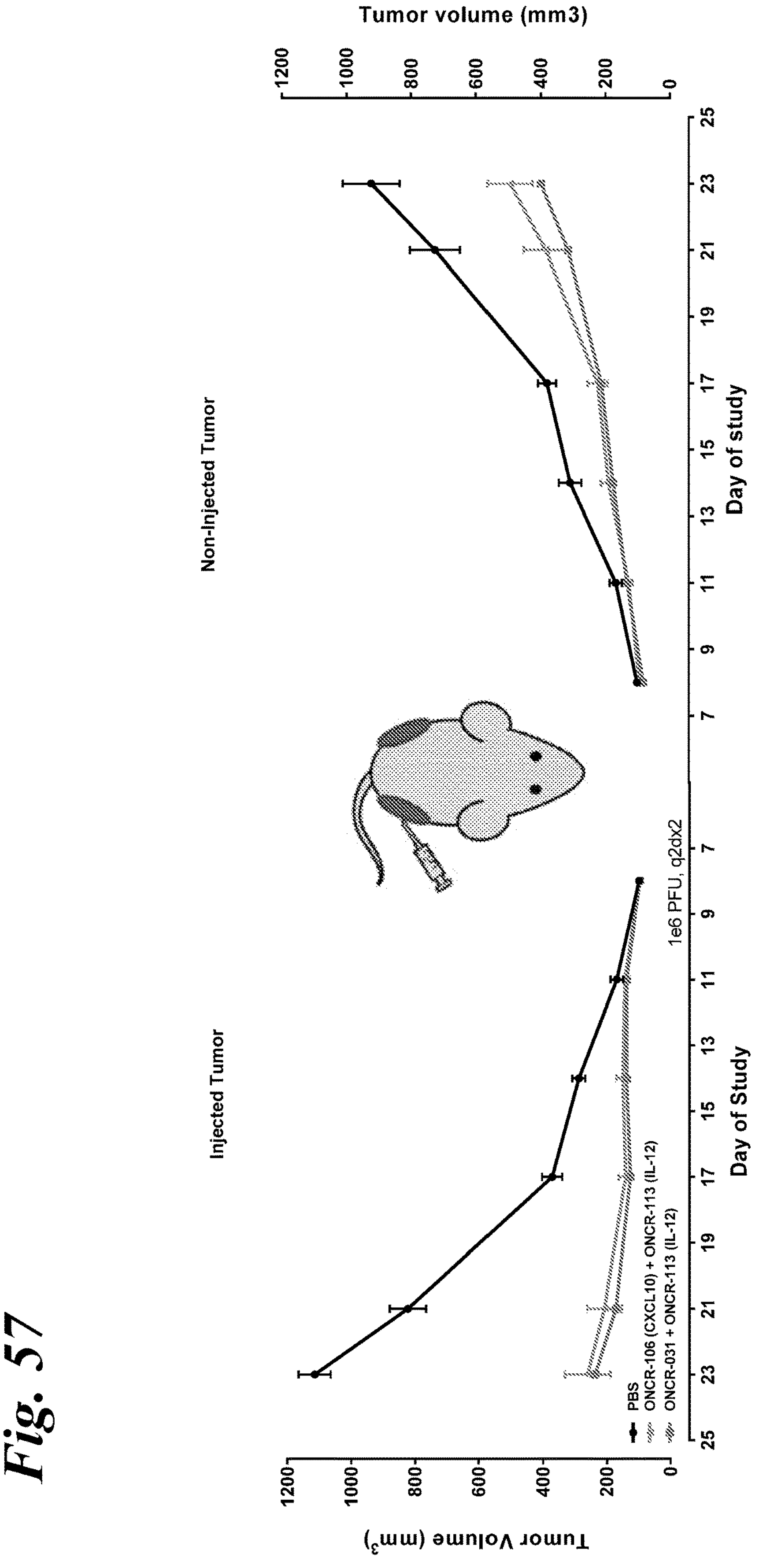

FIG. 57 shows tumor growth inhibitor effect of vehicle compared to virus (as indicated in legend) in a mouse xenograph experiment. The increase in tumor volume of the injected tumor is compared to the increase in tumor volume of the non-injected tumor. The additional expression of CXCL10 in the ONCR-106+ONCR-113 treated group did not enhance the inhibition of tumor growth in either injected or non-injected tumors compared to mice treated with ONCR-031+ONCR-113.

Figure 58:
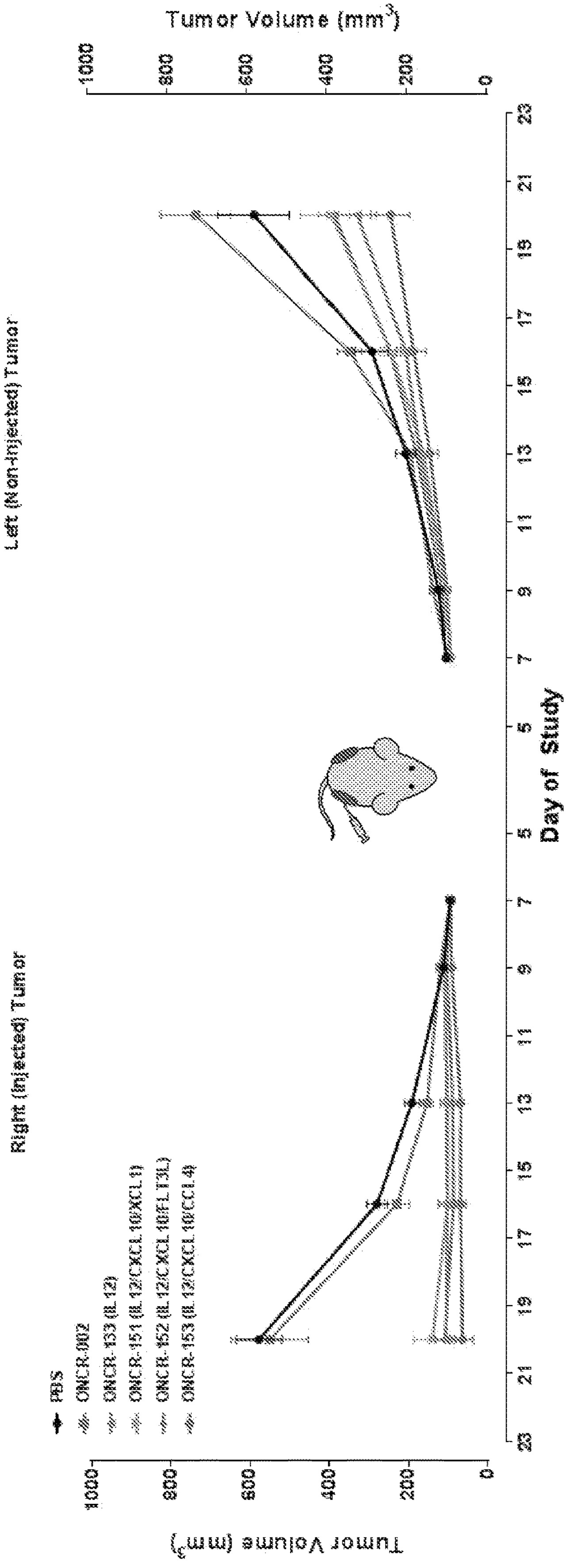

FIG. 58 shows tumor growth inhibitor effect of vehicle compared to virus (as indicated in legend) in a mouse xenograph experiment. The increase in tumor volume of the injected tumor is compared to the increase in tumor volume of the non-injected tumor. the additional expression of CXCL10 in the ONCR-106+ONCR-113 treated group did not enhance the inhibition of tumor growth in either injected or non-injected tumors compared to mice treated with ONCR-031+ONCR-113.

Figure 59A:
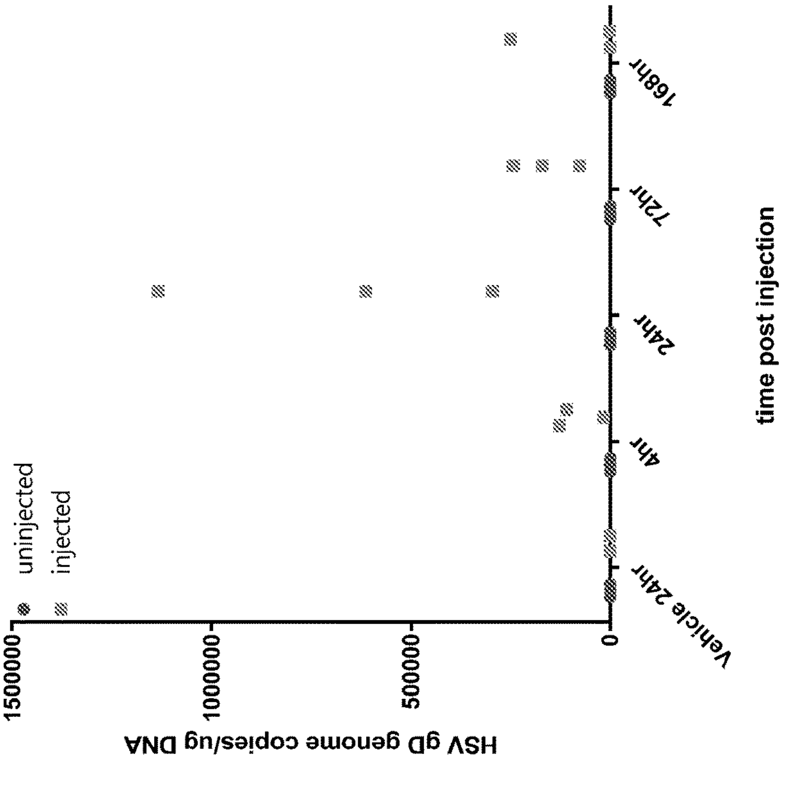
Figure 59B:
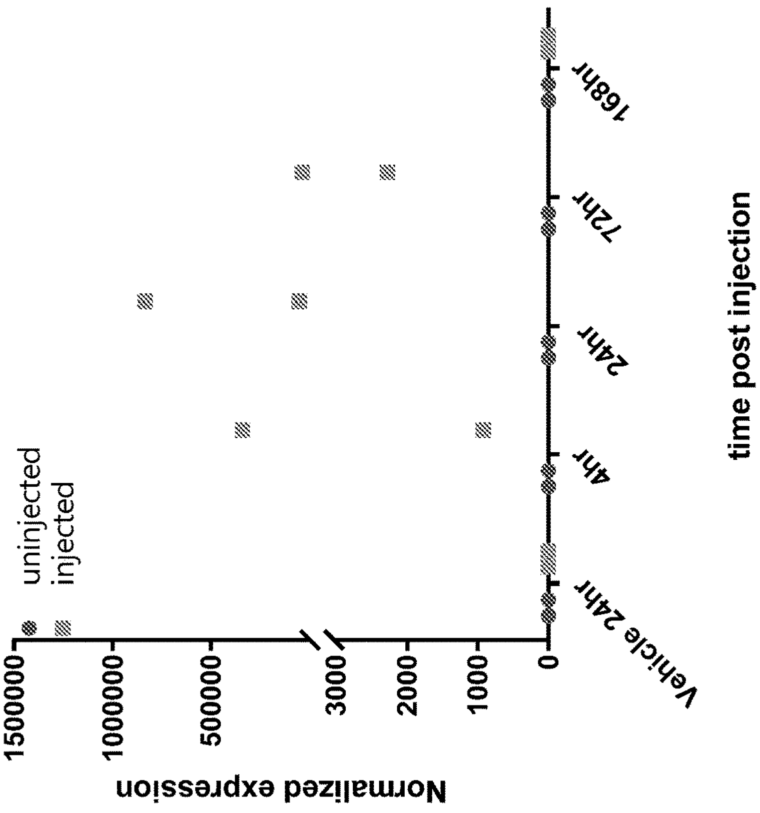

FIG. 59A-FIG. 59B show replication of injected virus occurs only in the injected tumor, not in the non-injected tumor, suggesting that the anti-tumor effect observed in the non-injected tumor is immune-mediated. Data is plotted as raw genome copies per microgram DNA (FIG. 59A) or as normalized expression (FIG. 59B). HSV was detected in the injected tumors, but not in the non-injected tumors, indicating that the tumor growth inhibition observed in the non-injected tumors was not due to viral spread, but rather the abscopal effects of virus administration.

Figure 60B:
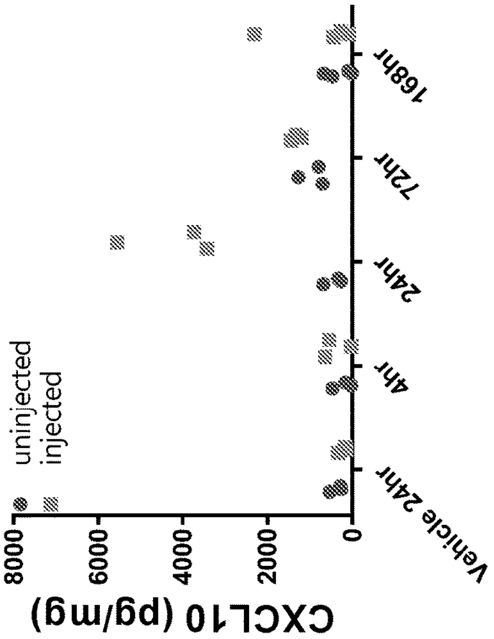
Figure 60A:
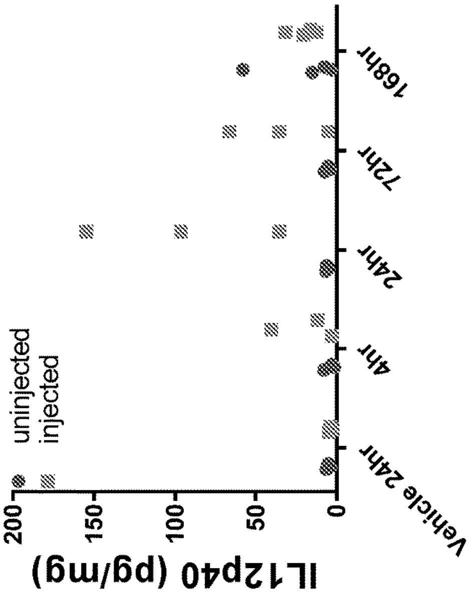
Figure 60C:
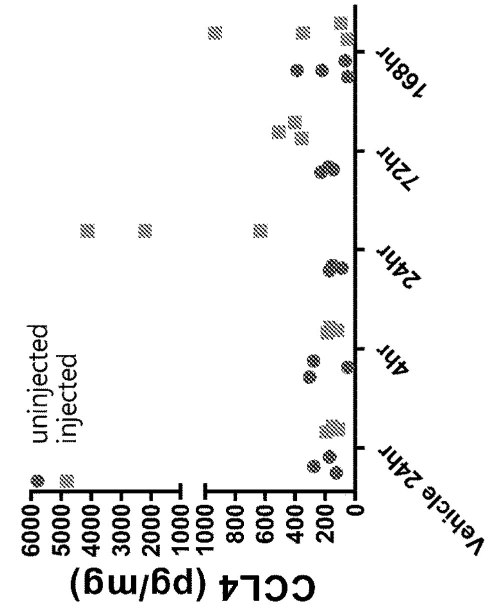

FIG. 60A-FIG. 60C show payload expression peaked in the injected tumors at 24-hours post-treatment and decreased thereafter.

Figure 61B:
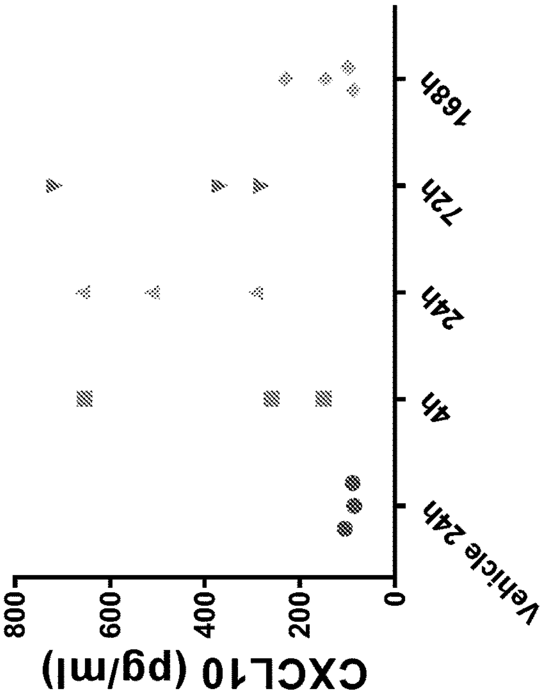
Figure 61A:
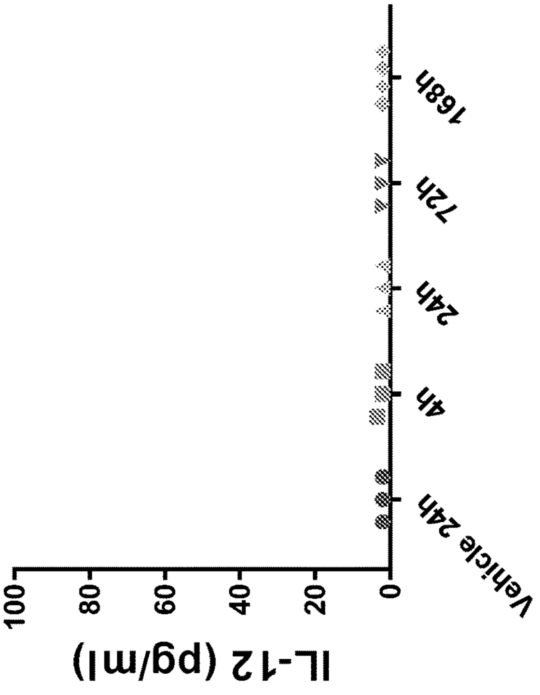
Figure 61C:
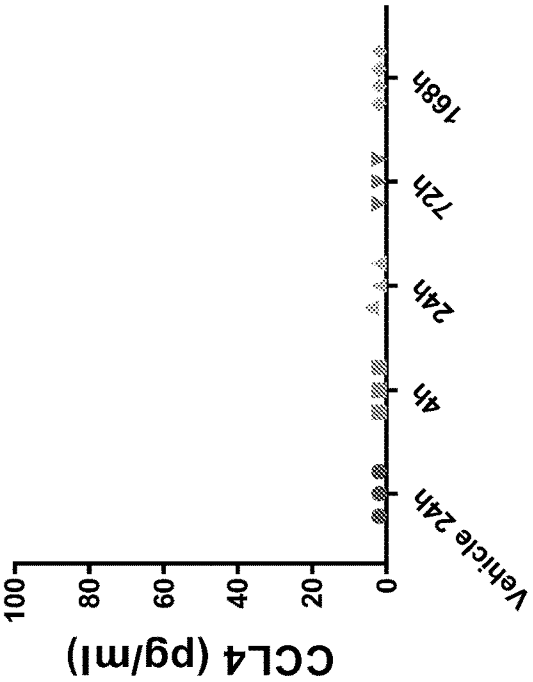

FIG. 61A-FIG. 61C shows levels of the payloads in the serum of mice treated with ONCR-153, where only CXCL10 expression was observed.

Figure 62B:
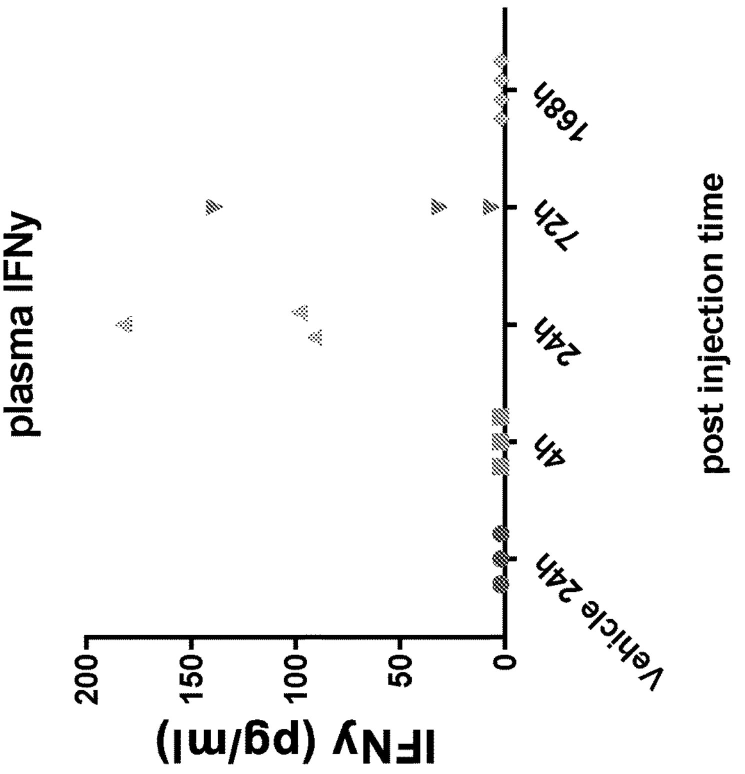
Figure 62A:
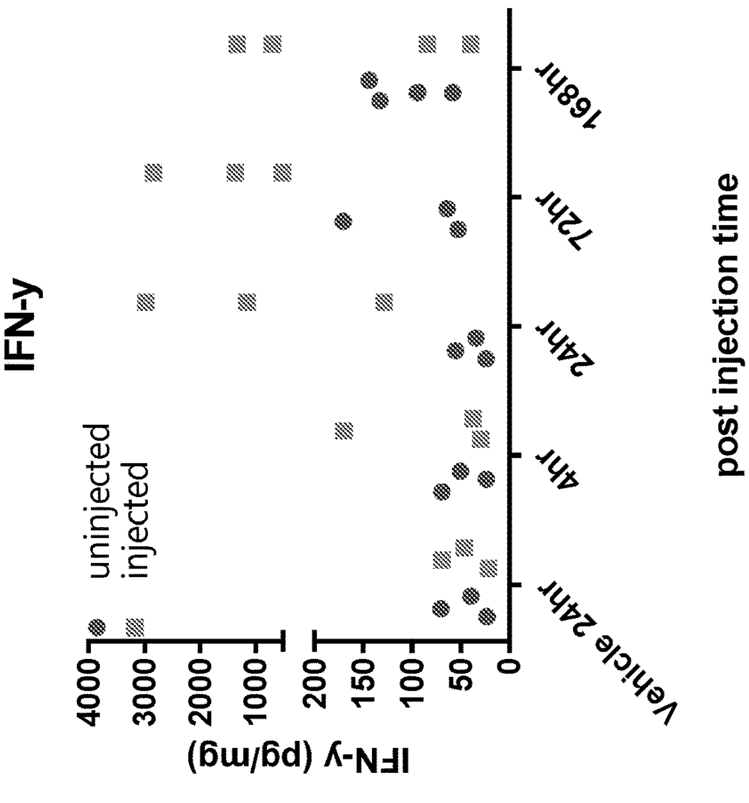

FIG. 62A shows the expression level of interferon gamma in the injected and non-injected tumors. Treatment of mice with ONCR-153 induced an intra-tumoral IFNγ response in both injected and non-injected tumors. FIG. 62B shows the expression level of interferon gamma in the plasma of the host animal.

Figure 63:
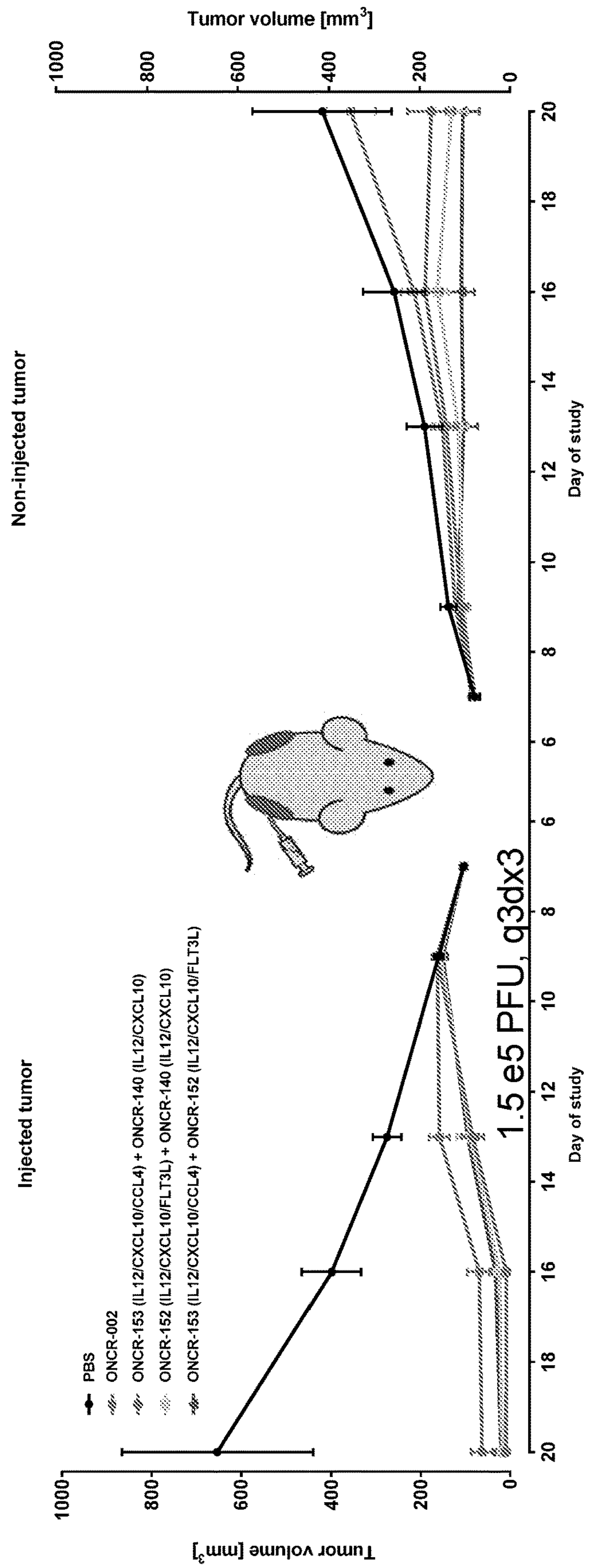

FIG. 63 shows tumor growth inhibitor effect of vehicle compared to virus (as indicated in legend) in a mouse xenograph experiment. The increase in tumor volume of the injected tumor is compared to the increase in tumor volume of the non-injected tumor.

Figure 64:
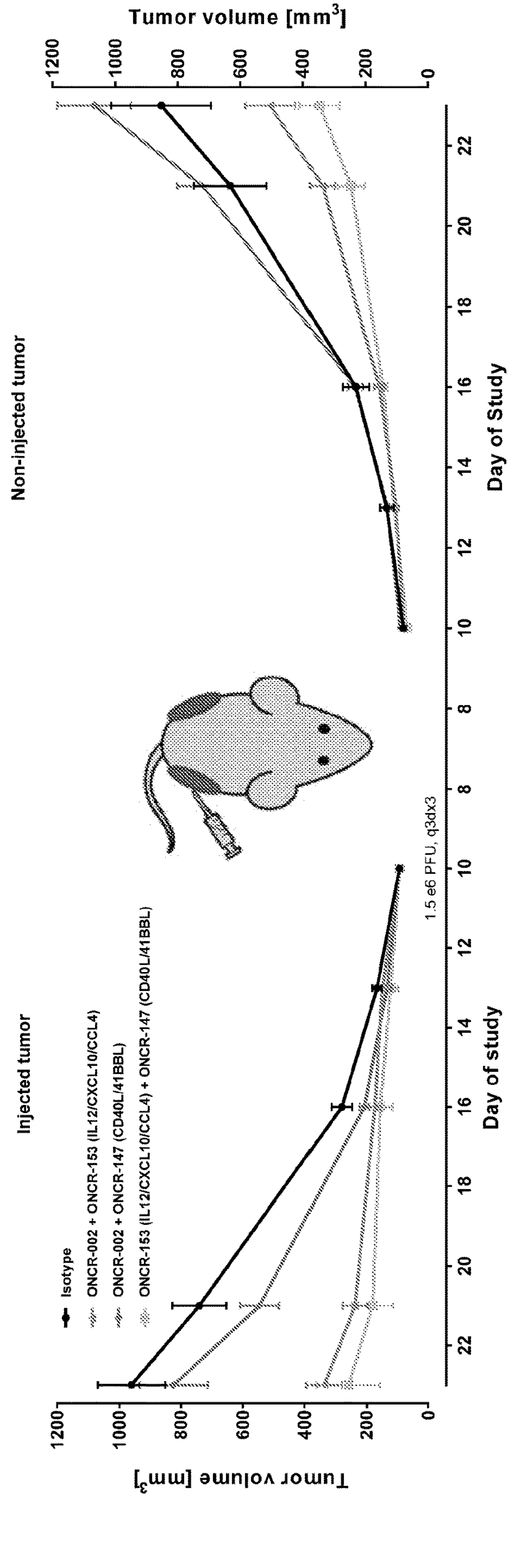

FIG. 64 shows tumor growth inhibitor effect of vehicle compared to virus (as indicated in legend) in a mouse xenograph experiment. The increase in tumor volume of the injected tumor is compared to the increase in tumor volume of the non-injected tumor.

Figure 65:
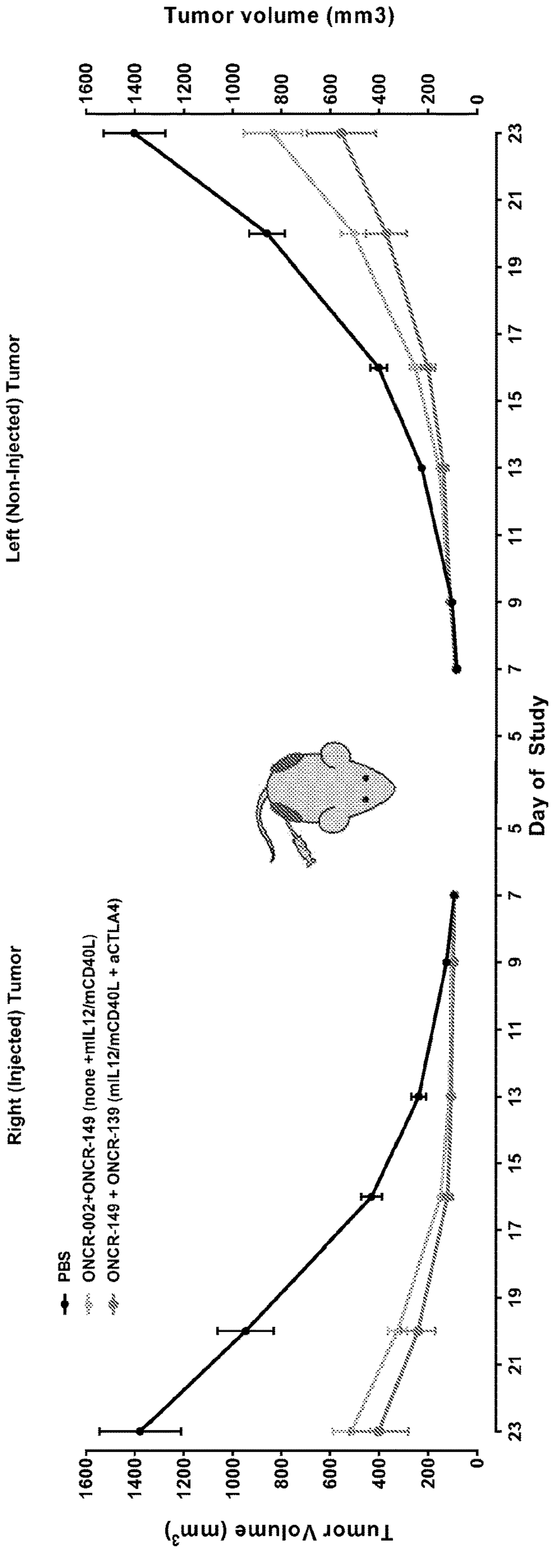

FIG. 65 shows tumor growth inhibitor effect of vehicle compared to virus (as indicated in legend) in a mouse xenograph experiment. The increase in tumor volume of the injected tumor is compared to the increase in tumor volume of the non-injected tumor.

Figure 66A:
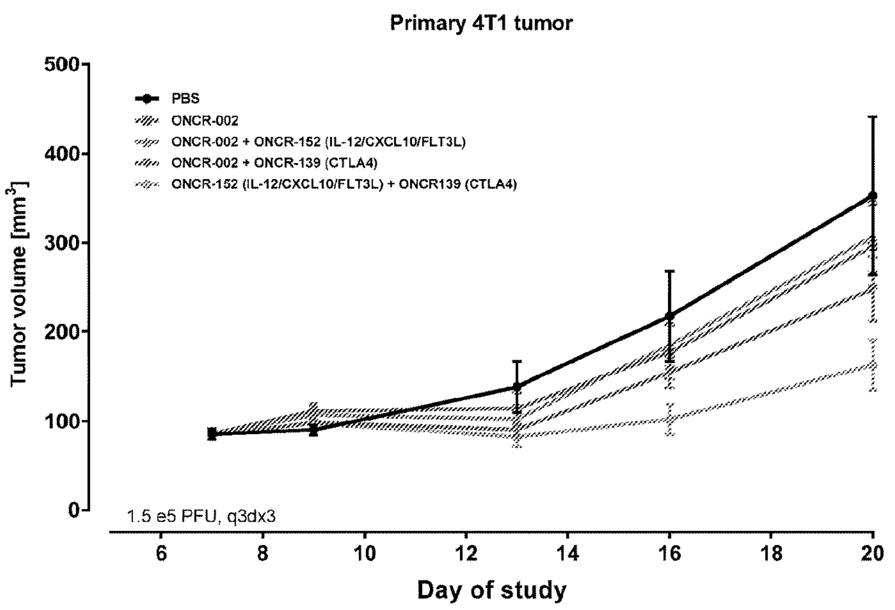
Figure 66B:
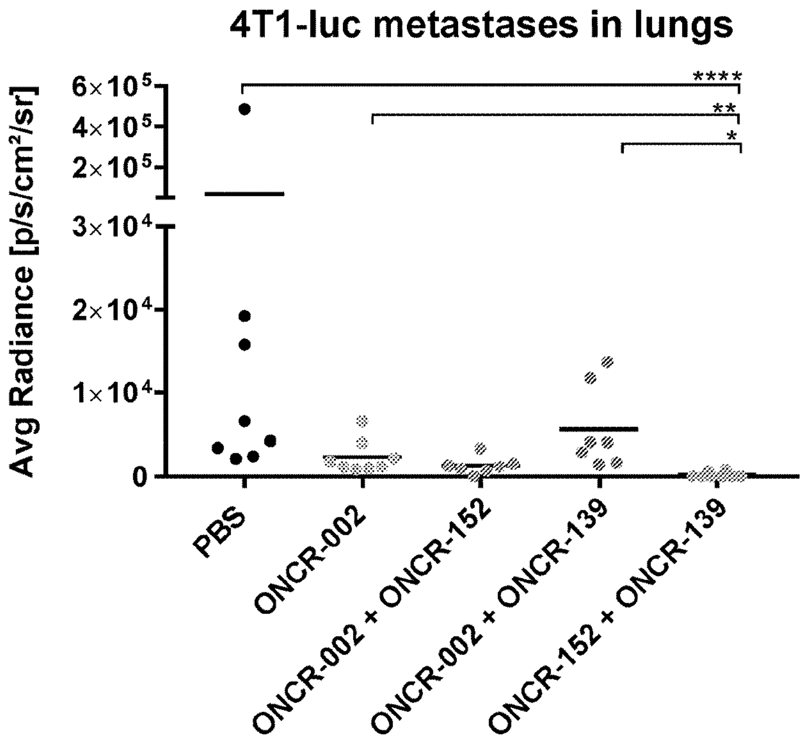
Figure 66C:
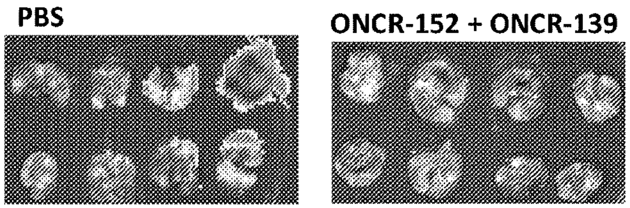

FIG. 66A shows tumor growth inhibitor effect of vehicle compared to virus (as indicated in legend) in a mouse xenograph experiment. FIG. 66B shows decreased incident of metasteses to the lung. FIG. 66C shows images of lung tissue from vehicle (PBS) control or vector-treated animals.

Figure 67:
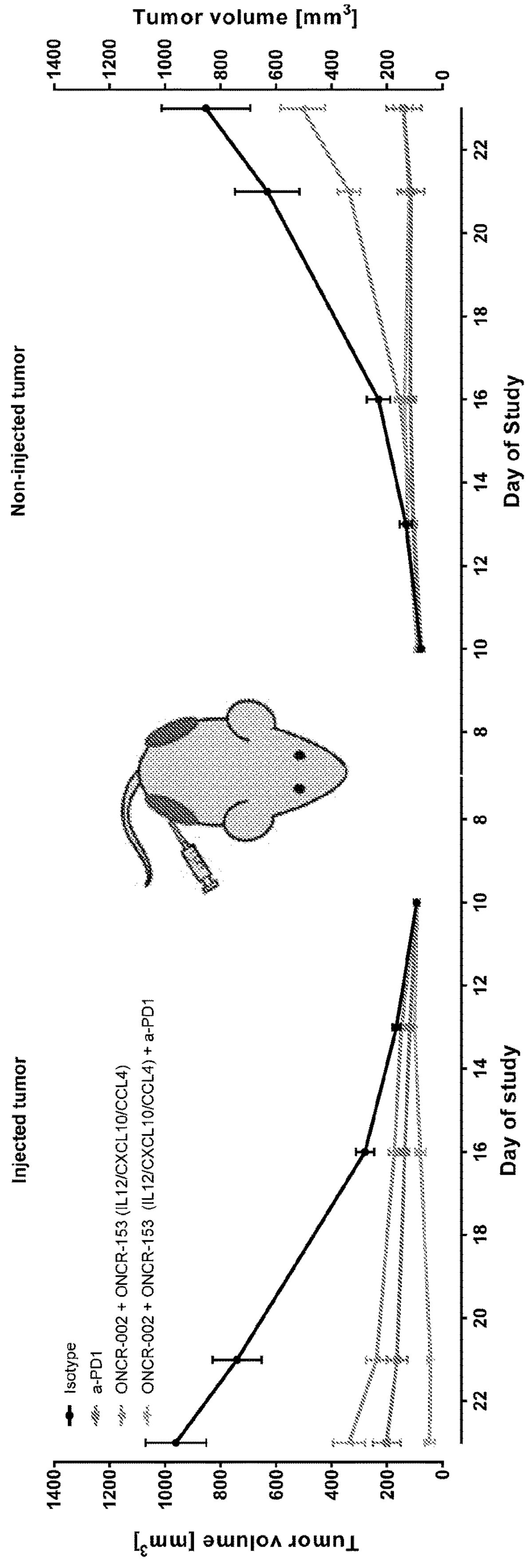

FIG. 67 shows tumor growth inhibitor effect of vehicle compared to virus (as indicated in legend) in a mouse xenograph experiment. The increase in tumor volume of the injected tumor is compared to the increase in tumor volume of the non-injected tumor. Treatment with ONCR-152 and -139 demonstrated an enhanced effect in tumor growth inhibition compared to treatment with ONCR-139 alone.

DETAILED DESCRIPTION

In some aspects, the present invention utilizes differential miR expression profiles to effectively restrict viral vector replication to tumor cells by incorporating miR target sequences into one or more genes required for viral replication. In particular embodiments, the viral vectors described herein comprise two, three, four or more copies of a miR target sequence incorporated into one or more viral genes. In some embodiments, the viral vectors described herein also disrupt the expression of specific miRNAs for reduced tumor proliferation, metastasis, and/or remodeling of the tumor microenvironment to enable enhanced viral spread. In some embodiments, the viral vectors described herein encompass the use of surface molecules on viral vectors to facilitate targeting to tumor cells. These aspects can be applied individually or in combination to develop viral vectors potentially capable of treating a wide array of cancer types with a single viral vector. As such, the invention further encompasses recombinant oncolytic viral vectors for use in the treatment and prevention of diseases and disorders (e.g., cancer). In some embodiments, this invention utilizes endogenous microRNA (miR) expression to enable a safe and efficacious recombinant viral vector suitable to treat a broad array of cancers.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

Definitions

In the present description, any concentration range, percentage range, ratio range, or integer range is to be understood to include the value of any integer within the recited range and, when appropriate, fractions thereof (such as one tenth and one hundredth of an integer), unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously. As used herein, "plurality" may refer to one or more components (e.g., one or more miRNA target sequences).

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Decrease" or "reduce" refers to a decrease or a reduction in a particular value of at least 5%, for example, 5, 6, 7, 8, 9, 10, 15, 20, 25, 30, 35, 40, 45, 50, 55, 60, 65, 70, 75, 80, 85, 90, 95, 99 or 100% as compared to a reference value. A decrease or reduction in a particular value may also be represented as a fold-change in the value compared to a reference value, for example, at least 1, 2, 3, 4, 5, 6, 7, 8, 9, 10, 15, 20, 30, 40, 50, 60, 70, 80, 90, 100, 200, 500, 1000-fold, or more, decrease as compared to a reference value.

"Increase" refers to an increase in a particular value of at least 5%, for example, 5, 6, 7, 8, 9, 10, 15, 20, 25, 30, 35, 40, 45, 50, 55, 60, 65, 70, 75, 80, 85, 90, 95, 99, 100, 200, 300, 400, 500% or more as compared to a reference value. An increase in a particular value may also be represented as a fold-change in the value compared to a reference value, for example, at least 1-fold, 2, 3, 4, 5, 6, 7, 8, 9, 10, 15, 20, 30, 40, 50, 60, 70, 80, 90, 100, 200, 500, 1000-fold or more, increase as compared to the level of a reference value.

The term "sequence identity" refers to the percentage of bases or amino acids between two polynucleotide or polypeptide sequences that are the same, and in the same relative position. As such one polynucleotide or polypeptide sequence has a certain percentage of sequence identity compared to another polynucleotide or polypeptide sequence. For sequence comparison, typically one sequence acts as a reference sequence, to which test sequences are compared. The term "reference sequence" refers to a molecule to which a test sequence is compared.

"Complementary" refers to the capacity for pairing, through base stacking and specific hydrogen bonding, between two sequences comprising naturally or non-naturally occurring (e.g., modified as described above) bases (nucleosides) or analogs thereof. For example, if a base at one position of a nucleic acid is capable of hydrogen bonding with a base at the corresponding position of a target, then the bases are considered to be complementary to each other at that position. Nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and SantaLucia, Nucl. Acids Research, 2005; 33 (19): 6258-6267.

"Operably linked" refers to a juxtaposition wherein the components so described are in a relationship permitting them to function in their intended manner. For instance, a promoter is operably linked to a polynucleotide sequence if the promoter affects the transcription or expression of the polynucleotide sequence.

The term "subject" includes animals, such as e.g. mammals. In some embodiments, the mammal is a primate. In some embodiments, the mammal is a human. In some embodiments, subjects are livestock such as cattle, sheep, goats, cows, swine, and the like; or domesticated animals such as dogs and cats. In some embodiments (e.g., particularly in research contexts) subjects are rodents (e.g., mice, rats, hamsters), rabbits, primates, or swine such as inbred pigs and the like. The terms "subject" and "patient" are used interchangeably herein.

The term "effective amount" refers to the minimum amount of an agent or composition required to result in a particular physiological effect (e.g., an amount required to increase, activate, and/or enhance a particular physiological effect). The effective amount of a particular agent may be represented in a variety of ways based on the nature of the agent, such as mass/volume, #of cells/volume, particles/volume, (mass of the agent)/(mass of the subject), #of cells/(mass of subject), or particles/(mass of subject). The effective amount of a particular agent may also be expressed as the half-maximal effective concentration ($EC_{50}$), which refers to the concentration of an agent that results in a magnitude of a particular physiological response that is half-way between a reference level and a maximum response level.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, and/or emulsifier which has been approved by the United States Food and Drug Administration as being acceptable for use in humans and/or domestic animals.

As used herein, the term "oncolytic virus" refers to a virus that has been modified to, or naturally, preferentially infect cancer cells.

The terms "microRNA," "miRNA," and "miR" are used interchangeably herein and refer to small non-coding endogenous RNAs of about 21-25 nucleotides in length that regulate gene expression by directing their target messenger RNAs (mRNA) for degradation or translational repression.

"Essential viral gene" as used herein refers to a viral gene that is required for one or more essential viral function, such as viral replication, viral packaging, or viral infectivity.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Oncolytic Viruses

In some embodiments, the present invention provides for recombinant oncolytic viruses, wherein one or more copies of one or more micro-RNA (miRNA) target sequences are inserted into a locus of one or more essential viral genes required for viral replication. Examples of oncolytic viruses are known in the art including, but not limited to, herpes simplex virus (HSV), an adenovirus, a polio virus, a vaccinia virus, a measles virus, a vesicular stomatitis virus, an orthomyxovirus, a parvovirus, a maraba virus or a coxsackievirus. In some embodiments, the oncolytic viruses described herein are referred to as recombinant viral vectors or oncolytic vectors.

In certain embodiments, an oncolytic virus described herein is a herpesvirus (for example, herpes simplex virus (e.g., HSV-1 or HSV-2)), an adenovirus, a polio virus, a vaccinia virus, a measles virus, a vesicular stomatitis virus, an orthomyxovirus, a parvovirus, a maraba virus or a coxsackievirus. In particular embodiments, the recombinant viral vector is an HSV capable of tumor-selective vector replication as described in International PCT Publication No. WO 2015/066042, which is incorporated by reference in its entirety.

HSV-based vectors and methods for their construction are described in, for example, U.S. Pat. Nos. 7,078,029, 6,261,552, 5,998,174, 5,879,934, 5,849,572, 5,849,571, 5,837,532, 5,804,413, and 5,658,724, and International Patent Applications WO 91/02788, WO 96/04394, WO 98/15637, and WO 99/06583, which are incorporated herein by reference in their entireties. The sequence of HSV is published (NCBI Accession No. NC_001806; see also McGoech et al., J. Gen. Virol, 69 (PT 7), 1531-1574 (1988)), which may facilitate designing HSV-based vectors of the invention. In some cases, the oncolytic virus of the invention is a herpes simplex virus (HSV) and comprises a deletion of the internal repeat (joint) region comprising one copy each of the diploid genes ICP0, ICP34.5, LAT, and ICP4 along with the promoter for the ICP47 gene.

In certain embodiments, the recombinant viral vector of the invention is an HSV that exhibits enhanced entry into cells, either through direct infection and/or lateral spread. In one aspect, HSV vectors of the present invention can directly infect cells through interaction with cell proteins other than typical mediators of HSV infection (e.g., other than nectin-1, HVEM, or heparan sulfate/chondroitin sulfate proteoglycans). In certain embodiments, the recombinant viral vector of the invention is an HSV and further comprises a mutation of the gB or gH gene that facilitates vector entry through non-canonical receptors. In another aspect, the invention provides an HSV vector further comprising mutant gH glycoproteins that exhibit lateral spread in cells typically resistant to HSV lateral spread, such as cells lacking gD receptors. In some embodiments, an HSV vector of the invention comprises one or more of the mutant gB or gH proteins as described in U.S. Patent Publication No. 2013/0096186, which is incorporated herein by reference in its entirety. In certain aspects, the mutant entry protein within an HSV vector is a glycoprotein involved with viral entry, such as gB, gH, and the mutant HSV vector can comprise mutated versions of both. However, the mutant entry protein can be any protein effecting entry of the HSV vector into cells. In certain embodiments, the mutant entry protein is other than gD, although the HSV vector can additionally comprise a mutant gD, such as containing a ligand or other desired mutation. Non-limiting mutations of gB or gH glycoprotein for use in the inventive HSV vector occur at one or more of the following residues: gB:D285, gB:A549, gB:S668, gH:N753, and gH:A778. In some embodiments, the inventive HSV vector comprises mutations at both gB:D285 and gB:A549, at both gH:N753 and gH:A778, and/or at each of gB:S668, gH:N753, and gH:A778. In certain embodiments, the HSV vector contains two or more of such mutations (e.g., 3 or more, 4 or more), and the HSV vector can comprise mutations in all five of these residues. In one embodiment, an HSV vector has mutations at gB:285, gB;549, gH:753, and gH: 778. The mutations are referred to herein relative to the codon (amino acid) numbering of the gD, gB, and gH genes of the HSV-1 strain KOS derivative K26GFP. The sequences for gB and gH of K26GFP differ from the sequences for gB as disclosed in GenBank (#AF311740 (incorporated herein by reference)) and for gH (GenBank # X03896 (incorporated herein by reference)) as reflected in Table 9 below.

TABLE 9

| | Amino acid position | AF311740 | K26GFP | Nucleotide position(s) | AF311740 | K26GFP |
|---|---|---|---|---|---|---|
| gB | 313 | T | S | 938-939 | ACG | AGC |
| | 315 | A | T | 943 | GCC | ACC |
| | 515 | H | R | 1,544 | CAC | CGC |
| | | X03896 | | | X03896 | |
| gH | 12 | I | L | 1,011 | ATT | CTT |
| | 110 | P | S | 1,305 | CCG | TCG |
| | 127 | T | I | 1,357 | ACC | ATC |
| | 138 | S | A | 1,389 | TCG | GCG |
| | 150 | A | T | 1,425 | GCC | ACC |
| | 532 | A | A | 2,573 | GCT | GCG |
| | 633 | R | R | 2,876 | CGT | CGC |

However, K26GFP may contain additional differences in the region of the gene corresponding to nucleotides 2,079-2,102 of GenBank X03896. Thus, it will be understood that the sequence of either KOS derivative K26GFP or GenBank Accession No. AF311740 can serve as a reference sequence for the gB mutations discussed herein. Also, the sequence of either KOS derivative K26GFP or GenBank Accession No. X03896 can serve as a reference sequence for the gH mutations discussed herein. However, HSV vectors of the invention may include homologous mutations in gB and gH of any HSV strain.

In some aspects, the mutation of the entry protein for inclusion in an HSV vector is a substitution mutation; however, mutations are not limited to substitution mutants. In certain embodiments, mutant gB or gH glycoproteins for use in an HSV vector are selected from the group of substitution mutations consisting of gB:D285N, gB:A549T, gB:S668N, gH:N753K, gH:A778V. In certain aspects, an HSV vector includes combinations of these substitutions (such as two or more of such substitutions (e.g., 3 or more, 4 or more, or all)), with the gB:D285N/gB:A549T double mutant, the gH:N753K/gH:A778V double mutant, and the gB:S668N/gH:N753K/gH:A778V triple mutant being examples of embodiments. In one embodiment, an HSV vector comprises gB:D285N/gB:A549T/gH:N753K/gH:A778V.

In certain aspects, an HSV vector comprises a mutant gB and/or a mutant gH glycoprotein, wherein the mutations in the glycoproteins are substitution mutations in at least two residues, wherein, when the vector is HSV-1 K26GFP, the at least two residues are selected from the group consisting of gB:D285, gB:A549, gB:S668, gH:N753, and gH:A778, or wherein when the vector is a homologous HSV, the at least two residues are selected from amino acids that correlate to gB:D285, gB:A549, gB:S668, gH:N753, and gH:A778 wherein the gB:D285 residue correlates to X in VYPYXEFVL (SEQ ID NO: 838), the gB:A549 residue correlates to X in KLNPNXIAS (SEQ ID NO: 839), the gB:S668 residue correlates to X in ITTVXTFID (SEQ ID NO: 840) the gH:N753 residue correlates to X in VDTDXTQQQ (SEQ ID NO: 841), and the gH:A778 residue correlates to X in VPSTXLLLF (SEQ ID NO: 842); and wherein the HSV vector is an HSV-1 or HSV-2 vector.

In some embodiments, the oncolytic HSV viruses described herein comprise one or more mutations in the UL37 gene that reduce HSV infection of neuronal cells, such as those described in International PCT Publication No. WO 2016/141320 and Richard et al., Plos Pathogens, 2017, 13(12), e1006741.

miRNA-Attenuated Oncolytic Viruses miRs are differentially expressed in a broad array of disease states, including multiple types of cancer. Importantly, miRNAs are differentially expressed in cancer tissues compared to normal tissues, enabling them to serve as a targeting mechanism in a broad variety of cancers. miRNAs that are associated (either positively or negatively) with carcinogenesis, malignant transformation, or metastasis are known as "oncomiRs".

In some aspects, the expression level of a particular oncomiR is positively associated with the development or maintenance of a particular cancer. Such miRs are referred to herein as "oncogenic miRs." In some embodiments, the expression of an oncogenic miR is increased in cancerous cells or tissues compared to the expression level observed in non-cancerous controls cells (i.e., normal or healthy controls) or is increased compared to the expression level observed in cancerous cells derived from a different cancer type. In some embodiments, the expression of an oncogenic miR is increased by at least 5%, 10%, 15%, 20%, 25%, 30%, 35%, 40%, 45%, 50%, 60%, 70%, 80%, 90%, 100%, 150%, 200%, 300%, 400%, 500%, 1000% or more compared to the expression of the oncogenic miR in a non-cancerous control cell or a cancerous cell derived from a different cancer type. In some aspects, a cancerous cell or tissue may express an oncogenic miR that is not expressed in non-cancerous control cells or tissues. Examples of oncogenic miRNAs that are frequently over-expressed in cancer tissues include, but are not limited to, miR-21, miR-155 and miR-17-92. Additional examples of oncogenic miRs are listed in Table 4.

In some embodiments, the expression of a particular oncomiR is negatively associated with the development or maintenance of a particular cancer and/or metastasis. Such oncomiRs are referred to herein as "tumor-suppressor miRs" or "tumor-suppressive miRs," as their expression prevents or suppresses the development of cancer. In some embodiments, the expression of a tumor-suppressor miRNA is decreased in cancerous cells or tissues compared to the expression level observed in non-cancerous control cells (i.e., normal or healthy controls), or is decreased compared to the expression level of the tumor-suppressor miRNA observed in cancerous cells derived from a different cancer type. For example, the expression of a tumor-suppressor miRNA in a cancerous cell may be decreased by at least 5%, 10%, 15%, 20%, 25%, 30%, 35%, 40%, 45%, 50%, 60%, 70%, 80%, 90%, or 100% compared to the expression of the tumor-suppressor miRNA in a non-cancerous control cell or a cancerous cell derived from a different cancer type. In some aspects, a non-cancerous control cell may express a tumor-suppressor miRNA that is not expressed in cancerous cells. Examples of tumor-suppressive miRNAs include, but are not limited to, miR-122, miR-184, miR-34a, let7a, miR-145-5p, miR-199a-5p, miR-451a, miR-125a, miR-125a-5p, miR-126-3p, miR-233-3p, miR-143-3p, miR-1-3p, miR-133a-3p, miR-127a-3p, miR-133b, miR-134-3p, miR-124, miR-101, miR-125b, miR-145, miR-559, miR-213, miR-31-5p, miR-205p, miR-15a, miR-16-1, miR-34, as well as miRNAs of the let-7 family. Additional examples of tumor-suppressive miRs are listed in Table 3 and Table 8.

Cancer pathogenesis is a heterogeneous and multigenic process. As such, activation of particular pathways and the expression of particular genes may lead to cancer development in one context, and result in distinct or opposing results when activated or expressed in a different context. Therefore, the characterization of a particular gene or miR as an "oncogene" or "oncogenic miR" or as a "tumor-suppressor" or "tumor-suppressive miR" is not a binary distinction and will vary according to the type of cancer. For example, the expression of one miRNA may be increased in a particular cancer and associated with the development of that cancer, while the expression of the same miRNA may be decreased in a different cancer and associated with prevention of the development of that cancer. However, some miRNAs may function as oncogenic miRNAs independent of the type of cancer. For example, some miRNAs target mRNA transcripts of tumor suppressor genes for degradation, thereby reducing expression of the tumor suppressor protein. For example, miR-152b functions as an oncogenic miR in the vast majority of hematologic malignancies, but functions as a tumor-suppressive miR in many solid tumors. Further, a particular miR may be highly expressed in both cancerous and non-cancerous cells. For example, miR-155 is highly expressed in normal cells, playing an essential role in macrophage polarization, and is also highly expressed in cancer cells. As such, the development of the miR-attenuated, genome-editing, and microenvironment-remodeling oncolytic viruses described herein is based on the differential expression of a particular miR or group of miRs in one cell population or tissue compared to another cell population or tissue. One of skill in the art will understand that the term tumor-suppressive miR generally refers to a miR that is more highly expressed in a non-cancerous cell or tissue compared to a cancerous cell or tissue, and that the term oncogenic miR generally refers to a miR that is more highly expressed in a cancerous cell or tissue compared to a non-cancerous cell or tissue. One of skill in the art will further understand that a miR characterized as a tumor-suppressive miR in one type of cancer may or more may not function as a tumor-suppressive miR in a different type of cancer, and that a miR characterized as an oncogenic miR in one type of cancer may or more may not function as an oncogenic miR in a different type of cancer.

Table 1 shows the relationship between 12 select oncomiRs (9 tumor suppressors and 3 oncogenic miRNAs) and numerous cancers. A list of 3,410 oncomiR-cancer relationships is shown in Table 2. miRNAs regulate many transcripts of proteins that are involved in the control of cellular proliferation and apoptosis. Regulated proteins include conventional proto-oncoproteins and tumor suppressors such as Ras, Myc, Bcl2, PTEN and p53. Aberrant expression of miRNAs therefore often is involved in development of cancer and can therapeutically be corrected by either inhibiting oncogenic miRNAs or replacing the depleted tumor suppressor miRNA. Further, the differential expression of particular oncomiRs in cancerous vs. non-cancerous cells can be exploited as a means to target cancer therapeutics specifically to cancer cells. As such, in some embodiments, the oncolytic viral vectors described herein can comprise the following properties individually or in combination: insertion of miRNA target sequences into the viral genome, thereby restricting viral vector replication to cancer or tumor cells; one or more polynucleotides incorporated into the viral genome whose product(s) disrupt the function of an oncogenic miRNA, modulate the cancer extracellular matrix, and/or enhance or activate an anti-cancer immune response; and/or protease-activated antibodies incorporated into the viral particle in order to selectively target the vectors to cancer and/or tumor cells.

One aspect of the invention comprises a recombinant oncolytic virus (or viral vector) comprising a plurality of copies of one or more miRNA target sequences inserted into a locus of one or more essential viral genes. In certain embodiments, a recombinant oncolytic virus may comprise miRNA target sequences inserted into a locus of at least one, at least two, at least three, at least four, at least five, at least six, at least seven, at least eight, at least nine, or at least ten essential viral genes. miRNAs expressed in normal (non-cancerous) cells can bind to such target sequences and suppress expression of the viral gene containing the miRNA target sequence, thereby limiting viral replication in healthy, non-cancerous cells. Such recombinant oncolytic viruses are referred to herein as "miR-attenuated" or "replication-restricted" as they demonstrate reduced or attenuated viral replication in cells that express one or more miRNAs capable of binding to the incorporated miR target sequences compared to cells that do not express, or have reduced expression of, the miR. By incorporating miRNA target sequences into key genes required for viral replication, viral replication can be conditionally suppressed in normal diploid cells expressing the miRNAs and can proceed normally in cells that do not express themiRNAs. In such embodiments, healthy, non-cancerous cells are protected from the normal cells from lytic effects of infection by the recombinant viral vector.

In certain embodiments, the one or more miRNA target sequences is incorporated into the 5' untranslated region (UTR) and/or 3' UTR of one or more essential viral genes. In some embodiments, the oncolytic virus is a herpes simplex virus (HSV), and the viral genes required for viral replication include any of UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP34.5, ICP47, gamma-34.5, US3, US4, US5, US6, US7, US8, US9, US10, US11, and/or US12. In certain embodiments, the oncolytic virus is HSV and comprises one or more miRNA target sequences incorporated into the 5' or 3' UTR of one or more essential viral genes. In some embodiments, the oncolytic virus is HSV, and the one or more miRNA target sequences is incorporated into one or more of ICP4, ICP27, UL8, UL42, UL19, and ICP34.5. In some embodiments, the oncolytic virus is HSV, and the one or more miRNA target sequences is incorporated into the 5' or 3' UTR of one or more of ICP4, ICP27, UL8, UL42, UL19, and ICP34.5 miRNA Target Sequence Cassettes

In animals, genes for miRNAs are transcribed to a primary miRNA (pri-miRNA), which is then processed in the nucleus by Drosha, a class 2 RNase III enzyme, to form a precursor miRNA (pre-miRNA) hairpin. The pre-miRNA hairpin are transported to the cytoplasm, where they are cleaved by the RNase III enzyme Dicer. This endoribonuclease interacts with 5' and 3' ends of the hairpin and cuts away the loop joining the 3' and 5' arms, yielding a duplex RNA molecule about 22 nucleotides in length. Although either strand of the duplex may potentially act as a functional miRNA, typically one strand of the miRNA is degraded and only one strand is loaded onto the Argonaute (Ago) protein to produce the effector RNA-induced silencing complex (RISC) where the miRNA and its mRNA target interact (Wahid et al., 1803:11, 2010, 1231-1243).

Herein, the gene encoding a particular miRNA is referenced as "MIR" followed by the miRNA number. The intermediate hairpin pre-miRNA molecules are referenced as "mir-" followed by the miRNA number, while the mature single-stranded miRNA molecule is referenced as "miR-" followed by the miRNA numer. For example, "MIR122" refers to the gene encoding a hairpin mir-122 pre-miRNA molecule, which is then processed into a mature miR-122 molecule. Due to the hairpin structure of the pre-miRNA, it is possible that two mature microRNAs can originate from opposite arms of the same pre-miRNA. In some instances, expression data clearly indentify one strand as the predominantly expressed miRNA and the other as the minor product. In such instances, the mature miRNA sequences are assigned names of the form miR-## (the predominant product) and miR-##*(minor product from the opposite arm of the precursor). For example, the major and minor products of mir-56 are denoted as miR-56 and miR-56*, respectively. When the existing data are not sufficient to determine which sequence is the predominant one, or when they are found in roughly similar amounts, the two mature miRNA products are denoted as miR-##-5p (from the 5' arm of the pre-miRNA hairpin) and miR-##-3p (from the 3' arm of the pre-miRNA hairpin). For example, the two mature miRNA products of mir-142 are denoted as miR-142-5p and miR-142-3p. Because they originate from opposite ends of the pre-miRNA hairpin, the -3p and -5p products of a particular miRNA will comprise different RNA sequences and will therefore recognize different target sequences.

Herein, miRNA target sequences are inserted into the locus of one or more essential viral genes in the form of a "miR target sequence cassette" or "miR-TS cassette." A miR-TS cassette which refers to a polynucleotide sequence comprising one or more miRNA target sequences and capable of being inserted into a specific locus of a viral gene. When transcribed, the mRNA transcripts of a viral gene comprising a miR-TS cassette will comprise one or more miRNA target sequences. In some embodiments, the miR-TS cassettes described herein comprise at least one miRNA target sequence. In some embodiments, the miR-TS cassettes described herein comprise a plurality of miRNA target sequences. For example, in some embodiments, the miR-TS cassettes described herein comprise 2, 3, 4, 5, 6, 7, 8, 9, 10, 11, 12, 13, 14, 15, 16, 17, 18, 19, 20, or more miRNA target sequences. In such embodiments, wherein the miR-TS cassettes comprise two or more miRNA target sequences, the two or more target sequences are arranged such that the total length of the miR-TS cassette (m) is less than or equal to the average length of the miRNA target sequences (n) multiplied by the total number of miRNA target sequences in the cassette (y) plus the average length of a linker sequence (l) multiplied by the total number of miRNA target sequences in the cassette plus 1 (y+1). Thus, the length of a miR-TS cassette (m) can be represented by the formula: $m \leq (n^*+(l^*(y+1))$, wherein n=the average length of the miRNA target sequences, l=the average length of the linker sequences, and y=the total number of target sequences in the miR-TS cassette). As an illustrative example, if a miR-TS cassettes comprises 4 miRNA target sequences (y) with an average length of 21 nt (n), and the average length of the linker sequences is between 4 and 25 nt (l), the length of the miR-TS cassette (m) is between about 104 nt and about 205 nt.

As used herein, the "length" of a miR-TS cassette is defined as the total number of nucleotides (basepairs for double-stranded polynucleotides) from the 5' nucleotide of the first miR-TS to the 3' nucleotide of the last miR-TS in the polynucleotide, inclusive of any intervening sequences. For non-overlapping miR-TSs, the minimum length of a miR-TS cassette will be the sum of the lengths of the miR-TSs. Spacers increase the length. The choice of spacer length determines the number of additional nucleotides in the cassette. Longer spacers increase the length of the cassette more than shorter spacers. By recognizing that shorter spacers (as short as 0, 1, 2, 3, 4, 5, or 6 nt) can be used when miR-TSs are interleaved (minimizing the number of mi-TSs for the same miRNA that are adjacent to one another)—the interleaved miR-TSs serving to increase the space between the other miR-TSs—the present inventors have determined that it is possible to generate shorter miR-TS cassettes than is possible in miR-TS cassettes in which miR-TSs for the same miRNA are arrayed in tandem, e.g. four of one type followed by four of the next type. In some embodiments, the the length of the miR-TS cassette is less than 1000 nt. In some embodiments, the length of the miR-TS cassette is less than 900 nt, less than 800 nt, less than 700 nt, less than 600 nt, less than 500 nt, less than 400 nt, less than 300 nt, less than 200 nt, less than 100 nt, or less than 50 nt. In some embodiments, the length of the miR-TS cassette is less than 26, 27, 28, 29, or 30 nt times the number of miR-TS sites, less than about 30 nt times the number of miR-TS sites, less than about 35 nt times the number of miR-TS sites, or less than about 40 nt times the number of miR-TS sites.

In some embodiments, the miR-TS cassettes comprise a plurality miRNA target sequences, wherein each miRNA target sequence in the plurality is a target sequence for the same miRNA. For example, the miR-TS cassettes may comprise 2, 3, 4, 5, 6, 7, 8, 9, 10 or more copies of the same miR target sequence. In some embodiments, the miR-TS cassettes comprise between 2 to 6 copies of the same miR target sequence. In some embodiments, the miR-TS cassettes comprise 3 copies of the same miR target sequence. In some embodiments, the miR-TS cassettes comprise 4 copies of the same miR target sequence.

In some embodiments, the miR-TS cassettes described herein comprise a plurality of miRNA target sequences, wherein the plurality comprises at least two different miRNA target sequences. In some embodiments, the miR-TS cassettes described herein comprise 2, 3, 4, 5, 6, 7, 8, 9, or 10 different miRNA target sequences. For example, in some embodiments, the miR-TS cassette may one or more copies of a first miRNA target sequence and one or more copies of a second miRNA target sequence. In some embodiments, the miR-TS cassette comprises at least 2, 3, 4, 5, 6, 7, 8, 9, 10, or more copies of a first miR target sequence and at least 2, 3, 4, 5, 6, 7, 8, 9, 10, or more copies of a second miR target sequence. In some embodiments, the miR-TS cassette comprises 3 or 4 copies of a first miR target sequence and 3 or 4 copies of a second miR target sequence. In some embodiments, the plurality of miRNA target sequences comprises at least 3 different miRNA target sequences. For example, in some embodiments, the miR-TS cassette comprises one or more copies of a first miR target sequence, one or more copies of a second miR target sequence, and one or more copies of a third miR target sequence. In some embodiments, the miR-TS cassette comprises at least 2, 3, 4, 5, 6, 7, 8, 9, 10, or more copies of a first miR target sequence, at least 2, 3, 4, 5, 6, 7, 8, 9, 10, or more copies of a second miR target sequence, and at least 2, 3, 4, 5, 6, 7, 8, 9, 10, or more copies of a third miR target sequence. In some embodiments, the miR-TS cassette comprises 3 or 4 copies of a first miR target sequence, 3 or 4 copies of a second miR target sequence, and 3 or 4 copies of a third miR target sequence. In some embodiments, the plurality of miRNA target sequences comprises at least 4 different miRNA target sequences. For example, in some embodiments, the miR-TS cassette comprises one or more copies of a first miR target sequence, one or more copies of a second miR target sequence, one or more copies of a third miR target sequence, and one or more copies of a fourth miR target sequence. In some embodiments, the miR-TS cassette comprises at least 2, 3, 4, 5, 6, 7, 8, 9, 10, or more copies of a first miR target sequence, at least 2, 3, 4, 5, 6, 7, 8, 9, 10, or more copies of a second miR target sequence, at least 2, 3, 4, 5, 6, 7, 8, 9, 10, or more copies of a third miR target sequence, and at least 2, 3, 4, 5, 6, 7, 8, 9, 10, or more copies of a fourth miR target sequence. In some embodiments, the miR-TS cassette comprises 3 or 4 copies of a first miR target sequence, 3 or 4 copies of a second miR target sequence, 3 or 4 copies of a third miR target sequence, and 3 or 4 copies of a fourth miR target sequence. In some embodiments, the miR-TS cassettes described herein comprise a plurality of miRNA target sequences, wherein In some aspects, wherein the miR-TS cassettes comprise a plurality of miRNA target sequences, the plurality of miRNA target sequences may arranged in tandem, without any intervening nucleic acid sequences. In some aspects, the plurality of miRNA target sequences may be separated by a linker sequence. In some embodiments, the linker sequence comprises 2, 3, 4, 5, 6, 7, 8, 9, 10, 15, 20, 25, or more nucleotides. In some embodiments, the linker sequence comprises about 4 to about 20 nucleotides. In further embodiments, the linker sequence comprises about 4 to about 16 nucleotides. As an illustrative embodiment, a miR-TS cassette may comprise 1, 2, 3, 4, 5, 6, 7, 8, 9, 10, or more of the following subunits: (a) a first miRNA target sequence-linker-a second miRNA target sequence, wherein adjacent subunits are separated by an additional linker sequence. In some embodiments, the first and the second miRNA target sequence are targets of the same miRNA. In some embodiments, the first and the second miRNA target sequence are targets of different miRNAs.

In some embodiments, miR-TS cassettes described herein comprise a miRNA target sequence that is at least 95%, at least 96%, at least 97%, at least 98%, or at least 99% identical to the reverse complement of a sequence selected from SEQ ID NOs: 1-803. In some embodiments, miR-TS cassettes described herein comprise a miRNA target sequence that comprises or consists of the reverse complement of a sequence selected from SEQ ID NOs: 1-803.

In some embodiments, the miR-TS cassettes described herein comprise at least 1, at least 2, at least 3, or at least 4 miR-122-5p target sequences. In some embodiments, the miR-122-5p target sequences are at least 95%, at least 96%, at least 97%, at least 98%, or at least 99% identical to SEQ ID NO: 804. In some embodiments, the miR-122-5p target sequences comprise or consist of SEQ ID NO: 804. In some embodiments, the miR-TS cassettes described herein comprise at least 1, at least 2, at least 3, or at least 4 miR-124-3p target sequences. In some embodiments, the miR-124-3p target sequences are at least 95%, at least 96%, at least 97%, at least 98%, or at least 99% identical to SEQ ID NO: 805. In some embodiments, the miR-124-3p target sequences comprise or consist of SEQ ID NO: 805. In some embodiments, the miR-TS cassettes described herein comprise at least 1, at least 2, at least 3, or at least 4 miR-125a-5p target sequences. In some embodiments, the miR-125a-5p target sequences are at least 95%, at least 96%, at least 97%, at least 98%, or at least 99% identical to SEQ ID NO: 806. In some embodiments, the miR-125a-5p target sequences comprise or consist of SEQ ID NO: 806.

In some embodiments, the miR-TS cassettes described herein comprise at least 1, at least 2, at least 3, or at least 4 miR-126-3p target sequences. In some embodiments, the miR-126-3p target sequences are at least 95%, at least 96%, at least 97%, at least 98%, or at least 99% identical to SEQ ID NO: 807 or SEQ ID NO: 808. In some embodiments, the miR-126-3p target sequences comprise or consist of SEQ ID NO: 807 or SEQ ID NO: 808. In some embodiments, the miR-TS cassettes described herein comprise at least 1, at least 2, at least 3, or at least 4 miR-127a-3p target sequences. In some embodiments, the miR-127a-3p target sequences are at least 95%, at least 96%, at least 97%, at least 98%, or at least 99% identical to SEQ ID NO: 809. In some embodiments, the miR-127a-3p target sequences comprise or consist of SEQ ID NO: 809.

In some embodiments, the miR-TS cassettes described herein comprise at least 1, at least 2, at least 3, or at least 4 miR-128-3p target sequences. In some embodiments, the miR-128-3p target sequences are at least 95%, at least 96%, at least 97%, at least 98%, or at least 99% identical to SEQ ID NO: 810 or SEQ ID NO: 811. In some embodiments, the miR-128-3p target sequences comprise or consist of SEQ ID NO: 810 or SEQ ID NO: 811. In some embodiments, the miR-TS cassettes described herein comprise at least 1, at least 2, at least 3, or at least 4 miR-129-3p target sequences. In some embodiments, the miR-129-3p target sequences are at least 95%, at least 96%, at least 97%, at least 98%, or at least 99% identical to SEQ ID NO: 812. In some embodiments, the miR-129-3p target sequences comprise or consist of SEQ ID NO: 812.

In some embodiments, the miR-TS cassettes described herein comprise at least 1, at least 2, at least 3, or at least 4 miR-129-5p target sequences. In some embodiments, the miR-129-5p target sequences are at least 95%, at least 96%, at least 97%, at least 98%, or at least 99% identical to SEQ ID NO: 813. In some embodiments, the miR-129-5p target sequences comprise or consist of SEQ ID NO: 813. In some embodiments, the miR-TS cassettes described herein comprise at least 1, at least 2, at least 3, or at least 4 miR-130b-3p target sequences. In some embodiments, the miR-130b-3p target sequences are at least 95%, at least 96%, at least 97%, at least 98%, or at least 99% identical to SEQ ID NO: 814. In some embodiments, the miR-130b-3p target sequences comprise or consist of SEQ ID NO: 814. In some embodiments, the miR-TS cassettes described herein comprise at least 1, at least 2, at least 3, or at least 4 miR-130b-5p target sequences. In some embodiments, the miR-130b-5p target sequences are at least 95%, at least 96%, at least 97%, at least 98%, or at least 99% identical to SEQ ID NO: 815. In some embodiments, the miR-130b-5p target sequences comprise or consist of SEQ ID NO: 815.

In some embodiments, the miR-TS cassettes described herein comprise at least 1, at least 2, at least 3, or at least 4 miR-133a-3p target sequences. In some embodiments, the miR-133a-3p target sequences are at least 95%, at least 96%, at least 97%, at least 98%, or at least 99% identical to SEQ ID NO: 816. In some embodiments, the miR-133a-3p target sequences comprise or consist of SEQ ID NO: 816. In some embodiments, the miR-TS cassettes described herein comprise at least 1, at least 2, at least 3, or at least 4 miR-133b-3p target sequences. In some embodiments, the miR-133b-3p target sequences are at least 95%, at least 96%, at least 97%, at least 98%, or at least 99% identical to SEQ ID NO: 817. In some embodiments, the miR-133b-3p target sequences comprise or consist of SEQ ID NO: 817. In some embodiments, the miR-TS cassettes described herein comprise at least 1, at least 2, at least 3, or at least 4 miR-134-3p target sequences. In some embodiments, the miR-134-3p target sequences are at least 95%, at least 96%, at least 97%, at least 98%, or at least 99% identical to SEQ ID NO: 818. In some embodiments, the miR-134-3p target sequences comprise or consist of SEQ ID NO: 818.

In some embodiments, the miR-TS cassettes described herein comprise at least 1, at least 2, at least 3, or at least 4 miR-137-3p target sequences. In some embodiments, the miR-137-3p target sequences are at least 95%, at least 96%, at least 97%, at least 98%, or at least 99% identical to SEQ ID NO: 819. In some embodiments, the miR-137-3p target sequences comprise or consist of SEQ ID NO: 819. In some embodiments, the miR-TS cassettes described herein comprise at least 1, at least 2, at least 3, or at least 4 miR-1-3p target sequences. In some embodiments, the miR-1-3p target sequences are at least 95%, at least 96%, at least 97%, at least 98%, or at least 99% identical to SEQ ID NO: 820. In some embodiments, the miR-1-3p target sequences comprise or consist of SEQ ID NO: 820. In some embodiments, the miR-TS cassettes described herein comprise at least 1, at least 2, at least 3, or at least 4 miR-143-3p target sequences. In some embodiments, the miR-143-3p target sequences are at least 95%, at least 96%, at least 97%, at least 98%, or at least 99% identical to SEQ ID NO: 821. In some embodiments, miR-143-3p target sequences comprise or consist of SEQ ID NO: 821.

In some embodiments, the miR-TS cassettes described herein comprise at least 1, at least 2, at least 3, or at least 4 miR-145-3p target sequences. In some embodiments, the miR-145-3p target sequences are at least 95%, at least 96%, at least 97%, at least 98%, or at least 99% identical to SEQ ID NO: 822. In some embodiments, the miR-145-3p target sequences comprise or consist of SEQ ID NO: 822. In some embodiments, the miR-TS cassettes described herein comprise at least 1, at least 2, at least 3, or at least 4 miR-145-5p target sequences. In some embodiments, the miR-145-5p target sequences are at least 95%, at least 96%, at least 97%, at least 98%, or at least 99% identical to SEQ ID NO: 823. In some embodiments, the miR-145-5p target sequences comprise or consist of SEQ ID NO: 823. In some embodiments, the miR-TS cassettes described herein comprise at least 1, at least 2, at least 3, or at least 4 miR-184-3p target sequences. In some embodiments, the miR-184-3p target sequences are at least 95%, at least 96%, at least 97%, at least 98%, or at least 99% identical to SEQ ID NO: 824. In some embodiments, the miR-184-3p target sequences comprise or consist of SEQ ID NO: 824.

In some embodiments, the miR-TS cassettes described herein comprise at least 1, at least 2, at least 3, or at least 4 miR-199a-3p target sequences. In some embodiments, the miR-199a-3p target sequences are at least 95%, at least 96%, at least 97%, at least 98%, or at least 99% identical to SEQ ID NO: 825. In some embodiments, the miR-199a-3p target sequences comprise or consist of SEQ ID NO: 825. In some embodiments, the miR-TS cassettes described herein comprise at least 1, at least 2, at least 3, or at least 4 miR-199a-5p target sequences. In some embodiments, the miR-199a-5p target sequences are at least 95%, at least 96%, at least 97%, at least 98%, or at least 99% identical to SEQ ID NO: 826. In some embodiments, the miR-199a-5p target sequences comprise or consist of SEQ ID NO: 826. In some embodiments, the miR-TS cassettes described herein comprise at least 1, at least 2, at least 3, or at least 4 miR-204-5p target sequences. In some embodiments, the miR-204-5p target sequences are at least 95%, at least 96%, at least 97%, at least 98%, or at least 99% identical to SEQ ID NO: 827. In some embodiments, the miR-204-5p target sequences comprise or consist of SEQ ID NO: 827.

In some embodiments, the miR-TS cassettes described herein comprise at least 1, at least 2, at least 3, or at least 4 miR-208b-3p target sequences. In some embodiments, the miR-208b-3p target sequences are at least 95%, at least 96%, at least 97%, at least 98%, or at least 99% identical to SEQ ID NO: 828. In some embodiments, the miR-208b-3p target sequences comprise or consist of SEQ ID NO: 828. In some embodiments, the miR-TS cassettes described herein comprise at least 1, at least 2, at least 3, or at least 4 miR-214-3p target sequences. In some embodiments, the miR-214-3p target sequences are at least 95%, at least 96%, at least 97%, at least 98%, or at least 99% identical to SEQ ID NO: 829. In some embodiments, the miR-214-3p target sequences comprise or consist of SEQ ID NO: 829. In some embodiments, the miR-TS cassettes described herein comprise at least 1, at least 2, at least 3, or at least 4 miR-217-5p target sequences. In some embodiments, the miR-217-5p target sequences are at least 95%, at least 96%, at least 97%, at least 98%, or at least 99% identical to SEQ ID NO: 830. In some embodiments, the miR-217-5p target sequences comprise or consist of SEQ ID NO: 830.

In some embodiments, the miR-TS cassettes described herein comprise at least 1, at least 2, at least 3, or at least 4 miR-219a-5p target sequences. In some embodiments, the miR-219a-5p target sequences are at least 95%, at least 96%, at least 97%, at least 98%, or at least 99% identical to SEQ ID NO: 831. In some embodiments, the miR-219a-5p target sequences comprise or consist of SEQ ID NO: 831. In some embodiments, the miR-TS cassettes described herein comprise at least 1, at least 2, at least 3, or at least 4 miR-223-3p target sequences. In some embodiments, the miR-223-3p target sequences are at least 95%, at least 96%, at least 97%, at least 98%, or at least 99% identical to SEQ ID NO: 832. In some embodiments, the miR-223-3p target sequences comprise or consist of SEQ ID NO: 832. In some embodiments, the miR-TS cassettes described herein comprise at least 1, at least 2, at least 3, or at least 4 miR-34a-5p target sequences. In some embodiments, the miR-34a-5p target sequences are at least 95%, at least 96%, at least 97%, at least 98%, or at least 99% identical to SEQ ID NO: 833. In some embodiments, the miR-34a-5p target sequences comprise or consist of SEQ ID NO: 833.

In some embodiments, the miR-TS cassettes described herein comprise at least 1, at least 2, at least 3, or at least 4 miR-451a target sequences. In some embodiments, the miR-451a target sequences are at least 95%, at least 96%, at least 97%, at least 98%, or at least 99% identical to SEQ ID NO: 834. In some embodiments, the miR-451a target sequences comprise or consist of SEQ ID NO: 834. In some embodiments, the miR-TS cassettes described herein comprise at least 1, at least 2, at least 3, or at least 4 miR-559-5p target sequences. In some embodiments, the miR-559-5p target sequences are at least 95%, at least 96%, at least 97%, at least 98%, or at least 99% identical to SEQ ID NO: 835. In some embodiments, the miR-559-5p target sequences comprise or consist of SEQ ID NO: 835. In some embodiments, the miR-TS cassettes described herein comprise at least 1, at least 2, at least 3, or at least 4 miR-Let-7a-5p target sequences. In some embodiments, the miR-Let-7a-5p target sequences are at least 95%, at least 96%, at least 97%, at least 98%, or at least 99% identical to SEQ ID NO: 836. In some embodiments, the miR-Let-7a-5p target sequences comprise or consist of SEQ ID NO: 836. In some embodiments, the miR-TS cassettes described herein comprise at least 1, at least 2, at least 3, or at least 4 miR-9-5p target sequences. In some embodiments, the miR-9-5p target sequences are at least 95%, at least 96%, at least 97%, at least 98%, or at least 99% identical to SEQ ID NO: 837. In some embodiments, the miR-9-5p target sequences comprise or consist of SEQ ID NO: 837.

Table 10 below provides sequences of exemplary miRNAs that can bind to the miRNA target sequences in the oncolytic viruses described herein. Additional miRNA sequences are provided in SEQ ID NOs: 33-803.

TABLE 10

Exemplary miRNAs and Target Sequences

| miRNA | miRNA Sequence | SEQ ID: | miR-TS | SEQ ID: |
|---|---|---|---|---|
| 122-5p | uggagugugacaaugguguuug | 1 | caaacaccattgtcacactcca | 804 |
| 124-3p | uaaggcacgcggugaaugcc | 2 | ggcattcaccgcgtgcctta | 805 |
| 125a-5p | ucccugagacccuuuaaccuguga | 3 | tcacaggttaaagggtctcaggga | 806 |
| 126-3p | ucguaccgugaguaauaaugcg | 4 | cgcattattactcacggtacga<br>cacattattactcacggtacga | 807<br>808 |
| 127a-3p | ucggauccgucugagcuuggcu | 5 | agccaagctcagacggatccga | 809 |
| 128-3p | ucacagugaaccggucucuuu | 6 | aaagagaccggttcactgtga<br>aaagagaccggttcactgtgg | 810<br>811 |
| 129-3p | aagcccuuaccccaaaaaguau | 7 | atactttttggggtaagggctt | 812 |
| 129-5p | cuuuuugcggucugggcuugc | 8 | gcaagcccagaccgcaaaaag | 813 |
| 130b-3p | cagugcaaugaugaaagggcau | 9 | atgccctttcatcattgcactg | 814 |
| 130b-5p | acucuuucccuguugcacuac | 10 | gtagtgcaacagggaaagagt | 815 |
| 133a-3p | uuuggucccuucaaccagcug | 11 | cagctggttgaaggggaccaaa | 816 |
| 133b-3p | uuugguccccuucaaccagcua | 12 | tagctggttgaaggggaccaaa | 817 |
| 134-3p | ccugugggccaccuagucaccaa | 13 | ttggtgactaggtggcccacagg | 818 |

TABLE 10 -continued

Exemplary miRNAs and Target Sequences

| miRNA | miRNA Sequence | SEQ ID: | miR-TS | SEQ ID: |
|---|---|---|---|---|
| 137_3p | uuauugcuuaagaauacgcguag | 14 | ctacgcgtattcttaagcaataa | 819 |
| 1-3p | uggaauguaaagaaguauguau | 15 | atacatacttctttacattcca | 820 |
| 143-3p | ugagaugaagcacuguagcuc | 16 | gagctacagtgcttcatctca | 821 |
| 145-3p | ggauuccuggaaauacuguucu | 17 | agaacagtatttccaggaatcc | 822 |
| 145-5p | guccaguuuucccaggaaucccu | 18 | agggattcctgggaaaactggac | 823 |
| 184-3p | uggacggagaacugauaagggu | 19 | acccttatcagttctccgtcca | 824 |
| 199a-3p | acaguagucugcacauugguua | 20 | taaccaatgtgcagactactgt | 825 |
| 199a-5p | cccaguguucagacuaccuguuc | 21 | gaacaggtagtctgaacactggg | 826 |
| 204-5p | uucccuuugucauccuaugccu | 22 | aggcataggatgacaaagggaa | 827 |
| 208b-3p | auaagacgaacaaaagguuugu | 23 | acaaaccttttgttcgtcttat | 828 |
| 214-3p | acagcaggcacagacaggcagu | 24 | actgcctgtctgtgcctgctgt | 829 |
| 217-5p | uacugcaucaggaacugauugga | 25 | tccaatcagttcctgatgcagta | 830 |
| 219a-5p | ugauuguccaaacgcaauucu | 26 | agaattgcgtttggacaatca | 831 |
| 223-3p | ugucaguuugucaaauacccca | 27 | tggggtatttgacaaactgaca | 832 |
| 34a-5p | uggcagugucuuagcugguugu | 28 | acaaccagctaagacactgcca | 833 |
| 451a | aaaccguuaccauuacugaguu | 29 | aactcagtaatggtaacggttt | 834 |
| 559-5p | uaaaguaaauaugcaccaaaa | 30 | ttttggtgcatatttacttta | 835 |
| Let7a-5p | ugagguaguagguuguauaguu | 31 | aactatacaacctactacctca | 836 |
| 9-5p | ucuuugguuaucuagcuguauga | 32 | tcatacagctagataaccaaaga | 837 |

In some embodiments, the miR-TS cassettes comprise one or more additional polynucleotide sequences that enable the cassette to be inserted into the locus of a viral gene. For example, a miR-TS cassette may further comprise short polynucleotide sequence on the 5' and 3' ends that are complementary to a nucleic acid sequence at a desired location in the viral genome. Such sequences are referred to herein as “homology arms” and facilitate the insertion of a miR-TS cassette into a specific location in the viral genome.

In some embodiments, the miR-TS cassettes disclosed comprise two or more pluralities of miR-TSs each corresponding to a different miRNA and the miR-TSs are selected to protect diverse cell types or organs from an oncolytic virus. In some embodiments, the pluralities of miR-TSs are interleaved rather than in tandem to one another. In some embodiments, the miR-TS cassettes have short (e.g., 4-15 nt in length) spacers, resulting in a more compact cassette. In some embodiments, the miR-TS cassettes are free from (or have reduced) RNA secondary structures that inhibit activity of the miR-TSs. In some embodiments, the miR-TS cassettes are free from (or have reduced) seed sequences for miRNAs associated with carcinogenesis, malignant transformation, or metastasis (i.e., “oncomiRs”). In some embodiments, the miR-TS cassettes are free from (or have reduced) polyadenylation sites.

Oncolytic Viruses Comprising miR-TS Cassettes

In some embodiments, a recombinant oncolytic virus may comprise one miR-TS cassette incorporated into a locus of one essential viral gene, wherein the miR-TS cassette comprises a plurality of miRNA target sequences, such that the recombinant oncolytic virus comprises a plurality of miRNA target sequences incorporated into a locus of one essential viral gene. In some aspects, the miR-TS cassette may comprise a plurality of miRNA target sequences, wherein each miRNA target sequence of the plurality is a target for the same miRNA, such that the recombinant oncolytic virus comprises a plurality (e.g., 2, 3, 4, 5, 6, 7, 8, 9, 10 or more) copies of the same miRNA target sequence incorporated into a locus of an essential viral gene. For example, in some embodiments, a recombinant oncolytic HSV may comprise a miR-TS cassette comprising 2, 3, 4, 5, 6 or more target sequences inserted into one of ICP4, ICP27, ICP8, ICP22, ICP34.5, UL5, UL8, UL9, UL30, UL39/40, or UL42. In some embodiments, a recombinant oncolytic HSV may comprise a miR-TS cassette comprising 2, 3, 4, or more target sequences inserted into one of ICP8, ICP22, ICP34.5, UL5, UL8, UL9, UL30, UL39/40, or UL42. In some embodiments, a recombinant oncolytic HSV may comprise a miR-TS cassette comprising 2, 3, 4, 5, 6 or more target sequence inserted into one of ICP4, ICP27, ICP34.5, UL8, or UL9.

In some aspects, the plurality of miRNA target sequences comprises at least two different miRNA target sequences, at least three different miRNA target sequences, or at least four different miRNA target sequences, such that the recombinant oncolytic virus comprises one or more copies of at least 2, 3, or 4 different miRNA target sequence incorporated into a locus of an essential viral gene. For example, in some embodiments, a recombinant oncolytic HSV may comprise a miR-TS cassette comprising one or more target sequences for miR-122-5p, miR-34a-5p, and miR-Let-7a-5p inserted into one of ICP4, ICP27, ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-122-5p, miR-34a-5p, and miR-Let-7a-5p inserted into one of ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-122-5p, miR-34a-5p, and miR-Let-7a-5p inserted into one of ICP4, ICP27, ICP34.5, UL8, or UL9. In some embodiments, a recombinant oncolytic HSV may comprise a miR-TS cassette comprising one or more target sequences for miR-122-5p, miR-184-3p, and miR-Let-7a-5p inserted into one of ICP4, ICP27, ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-122-5p, miR-184-3p, and miR-Let-7a-5p inserted into one of ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-122-5p, miR-184-3p, and miR-Let-7a-5p inserted into one of ICP4, ICP27, ICP34.5, UL8, or UL9.

In some embodiments, a recombinant oncolytic HSV may comprise a miR-TS cassette comprising one or more target sequences for miR-122-5p and miR-Let-7a-5p inserted into one of ICP4, ICP27, ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-122-5p and miR-Let-7a-5p inserted into one of ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-122-5p and miR-Let-7a-5p inserted into one of ICP4, ICP27, ICP34.5, UL8, or UL9. In some embodiments, a recombinant oncolytic HSV may comprise a miR-TS cassette comprising one or more target sequences for miR-145-5p, miR-199a-5p, and miR-599-5p inserted into one of ICP4, ICP27, ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-145-5p, miR-199a-5p, and miR-599-5p inserted into one of ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-145-5p, miR-199a-5p, and miR-599-5p inserted into one of ICP4, ICP27, ICP34.5, UL8, or UL9.

In some embodiments, a recombinant oncolytic HSV may comprise a miR-TS cassette comprising one or more target sequences for miR-124-3p, miR-1-3p, and miR-124-3p inserted into one of ICP4, ICP27, ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-124-3p, miR-1-3p, and miR-124-3p inserted into one of ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-124-3p, miR-1-3p, and miR-124-3p inserted into one of ICP4, ICP27, ICP34.5, UL8, or UL9. In some embodiments, a recombinant oncolytic HSV may comprise a miR-TS cassette comprising one or more target sequences for miR-219a-5p, miR-122-5p, and miR-128-3p inserted into one of ICP4, ICP27, ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-219a-5p, miR-122-5p, and miR-128-3p inserted into one of ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-219a-5p, miR-122-5p, and miR-128-3p inserted into one of ICP4, ICP27, ICP34.5, UL8, or UL9.

In some embodiments, a recombinant oncolytic HSV may comprise a miR-TS cassette comprising one or more target sequences for miR-137-3p, miR-208b-3p, and miR-126-3p inserted into one of ICP4, ICP27, ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-137-3p, miR-208b-3p, and miR-126-3p inserted into one of ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-137-3p, miR-208b-3p, and miR-126-3p inserted into one of ICP4, ICP27, ICP34.5, UL8, or UL9. In some embodiments, a recombinant oncolytic HSV may comprise a miR-TS cassette comprising one or more target sequences for miR-137-3p, miR-217-3p, and miR-126-3p inserted into one of ICP4, ICP27, ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-137-3p, miR-217-3p, and miR-126-3p inserted into one of ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-137-3p, miR-217-3p, and miR-126-3p inserted into one of ICP4, ICP27, ICP34.5, UL8, or UL9.

In some embodiments, a recombinant oncolytic HSV may comprise a miR-TS cassette comprising one or more target sequences for miR-128-3p, miR-204-5p, and miR-219-5p inserted into one of ICP4, ICP27, ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-128-3p, miR-204-5p, and miR-219-5p inserted into one of ICP8, ICP22, ICP34.5, UL5, UL8, UL9, UL30, UL39/40, or UL42. In some embodiments, a recombinant oncolytic HSV may comprise a miR-TS cassette comprising one or more target sequences for miR-128-3p, miR-204-5p, and miR-219-5p inserted into one of ICP4, ICP27, ICP34.5, UL8, or UL9.

In some embodiments, a recombinant oncolytic virus may comprise one miR-TS cassette incorporated into the 3' or 5' untranslated region (UTR) of the viral genome. In such embodiments, the miR-TS cassette may comprise one copy of a miRNA target sequence, such that the recombinant oncolytic virus comprises one copy of a miRNA target sequence incorporated into the 3' or 5' UTR of the viral genome. For example, in some embodiments, a recombinant polio virus, SVV, or Coxsackievirus may comprise a miR-TS cassette comprising a miRNA target sequence shown in Table 10 inserted into the 3' or 5' UTR of the viral genome. In some embodiments, a recombinant oncolytic virus may comprise one miR-TS cassette incorporated into the 3' or 5' UTR of the viral genome, wherein the miR-TS cassette comprises a plurality of miRNA target sequences shown in Table 10, such that the recombinant oncolytic virus comprises a plurality of miRNA target sequences incorporated into the 3' or 5' UTR of the viral genome.

In some aspects, the plurality of miRNA target sequences comprises at least two different miRNA target sequences, at least three different miRNA target sequences, or at least four different miRNA target sequences, such that the recombinant oncolytic virus comprises one or more copies of at least 2, 3, or 4 different miRNA target sequence incorporated into the 3' or 5' UTR of the viral genome. For example, in some embodiments, a recombinant polio virus, SVV, or Coxsackievirus may comprise a miR-TS cassette comprising one or more copies of at least 2, 3, or 4 different miRNA target sequences selected from Table 10 inserted into the 3' or 5' UTR of the viral genome.

In some embodiments, a recombinant oncolytic virus may comprise a miR-TS cassette incorporated into a locus of two or more essential viral genes. In some embodiments, the recombinant oncolytic virus is an HSV virus and the two or more essential viral genes are selected from the group consisting of ICP4, ICP27, ICP8, ICP22, ICP34.5, UL5, UL8, UL9, UL30, UL39/40, or UL42. In some embodiments, the recombinant oncolytic virus is an HSV virus and the two or more essential viral genes are selected from the group consisting of ICP8, ICP22, ICP34.5, UL5, UL8, UL9, UL30, UL39/40, or UL42. In some embodiments, the recombinant oncolytic virus is an HSV virus and the two or more essential viral genes are selected from the group consisting of ICP4, ICP27, ICP34.5, UL8, or UL9. In some embodiments, the recombinant oncolytic virus is an HSV virus and the two or more essential viral genes are selected from the group consisting of ICP27, ICP4, ICP34.5, UL8, and UL42.

In some embodiments, the recombinant oncolytic virus is an HSV virus comprising (i) a first miR-TS cassette comprising a plurality of miRNA target sequences inserted into a locus of ICP4 and a second miR-TS cassette comprising a plurality of miRNA target sequences into a locus of ICP27. In some embodiments, the first miR-TS cassette is inserted into a locus of ICP4 and comprises 1, 2, 3, or 4 copies of a target sequence for miR-124. In some embodiments, the first miR-TS cassette is inserted into a locus of ICP4 and comprises 1, 2, 3, or 4 copies of a target sequence for miR-124; 1, 2, 3, or 4 copies of a target sequence for miR-1-3p; and 1, 2, 3, or 4 copies of a target sequence for miR-143-3p. In some embodiments, the plurality of miRNA target sequences in the first miR-TS cassettes are arranged as follows:

(a) (124-3p)-(124-3p)-(124-3p)-(124-3p);

(b) (124-3p)-(124-3p)-(124-3p)-(124-3p)-(1-3p)-(143-3p)-(1-3p)-(143-3p)-(1-3p)-(143-3p)-(1-3p)-(143-3p).

In some embodiments, the second miR-TS cassette is inserted into a locus of ICP27 and comprises 1, 2, 3, or 4 copies of a target sequence for miR-1-3p; 1, 2, 3, or 4 copies of a target sequence for miR-145-5p; 1, 2, 3, or 4 copies of a target sequence for miR-199-5p; and 1, 2, 3, or 4 copies of a target sequence for miR-559. In some embodiments, the second miR-TS cassette is inserted into a locus of ICP27 and comprises 1, 2, 3, or 4 copies of a target sequence for miR-219a-5p; 1, 2, 3, or 4 copies of a target sequence for miR-122-5p; and 1, 2, 3, or 4 copies of a target sequence for miR-128.

In some embodiments, the first miR-TS cassette comprises 4 copies of a target sequence for miR-124 and the second miR-TS cassette comprises 2, 3, or more copies of a target sequence for each of 1-3p, 145-5p, 199a-5p, and 559. In some embodiments, the first miR-TS cassette comprises 4 copies of a target sequence for miR-124 and the second miR-TS cassette comprises 4 copies of a target sequence for each of 219a-5p, 122-5p, 128T.

In some embodiments, the recombinant oncolytic virus is an HSV virus comprising (i) a first miR-TS cassette comprising a plurality of miRNA target sequences inserted into a locus of ICP4; and (ii) a second miR-TS cassette comprising a plurality of miRNA target sequences inserted into a locus of UL42. In some embodiments, the first miR-TS cassette is inserted into a locus of ICP4 and comprises 1, 2, 3, or 4 copies of a target sequence for miR-124. In some embodiments, the plurality of miRNA target sequences in the second miR-TS cassettes are arranged as follows:

(a) (124-3p)-(124-3p)-(124-3p)-(124-3p).

In some embodiments, the second miR-TS cassette is inserted into a locus of UL42 comprises 1, 2, 3, or 4 copies of a target sequence for miR-122-5p. In some embodiments, the plurality of miRNA target sequences in the second miR-TS cassettes are arranged as follows:

(a) (122-5p)-(122-5p)-(122-5p).

In some embodiments, the recombinant oncolytic virus is an HSV virus comprising (i) a first miR-TS cassette comprising 4 copies of a target sequence for miR-124 inserted into a locus of ICP4; and (ii) a second miR-TS cassette comprising 3 copies of a target sequence for miR-122-5p inserted into a locus of UL42.

In some embodiments, the recombinant oncolytic virus is an HSV virus comprising (i) a first miR-TS cassette comprising a plurality of miRNA target sequences inserted into a locus of ICP4; (ii) a second miR-TS cassette comprising a plurality of miRNA target sequences inserted into a locus of ICP27; and (iii) a third miR-TS cassette comprising a plurality of miRNA target sequences is inserted into a locus of UL42. In some embodiments, the first miR-TS cassette is inserted into a locus of ICP4 and comprises 1, 2, 3, or 4 copies of a target sequence for miR-124. In some embodiments, the plurality of miRNA target sequences in the second miR-TS cassettes are arranged as follows:

(a) (124-3p)-(124-3p)-(124-3p)-(124-3p).

In some embodiments, the second miR-TS cassette is inserted into a locus of ICP27 and comprises 1, 2, 3, or 4 copies of a target sequence for miR-122. In some embodiments, the plurality of miRNA target sequences in the second miR-TS cassettes are arranged according to one of the following:

(a) (122-5p);

(b) (122-5p)-(122-5p)-(122-5p)-(122-5p);

(c) (122-5p)-(122-5p)-(122-5p).

In some embodiments, the third miR-TS cassette is inserted into a locus of UL42 and comprises 1, 2, 3, or 4 copies of a target sequence for miR-125-5p. In some embodiments, the plurality of miRNA target sequences in the third miR-TS cassettes are arranged according to one of the following:

(a) (122-5p);

(b) (122-5p)-(122-5p)-(122-5p)-(122-5p);

(c) (122-5p)-(122-5p)-(122-5p).

In some embodiments, the recombinant oncolytic virus is an HSV virus comprising (i) a first miR-TS cassette inserted into a locus of ICP4 and comprising 4 copies of a target sequence for miRNA-124-3p; (ii) a second miR-TS cassette inserted into a locus of ICP27 and comprising 1, 2, 3, or 4 copies of a target sequence for miR-122-5p; and (iii) a third miR-TS cassette inserted into a locus of UL42 and comprising 4 copies of a target sequence for miR-125-5p. In some embodiments, the recombinant oncolytic virus is an HSV virus comprising (i) a first miR-TS cassette inserted into a locus of ICP4 and comprising 4 copies of a target sequence for miRNA-124; (ii) a second miR-TS cassette inserted into a locus of ICP27 and comprising 4 copies of a target sequence for miR-122; and (iii) a third miR-TS cassette inserted into a locus of UL42 and comprising 1, 2, 3, or 4 copies of a target sequence for miR-125-5p. In some embodiments, the recombinant oncolytic virus is an HSV virus comprising (i) a first miR-TS cassette inserted into a locus of ICP4 and comprising 4 copies of a target sequence for miRNA-124; (ii) a second miR-TS cassette inserted into a locus of ICP27 and comprising 4 copies of a target sequence for miR-122-3p; and (iii) a third miR-TS cassette inserted into a locus of UL42 and comprising 4 copies of a target sequence for miR-125-5p. In some embodiments, the recombinant oncolytic virus is an HSV virus comprising (i) a first miR-TS cassette inserted into a locus of ICP4 and comprising 4 copies of a target sequence for miRNA-124-3p; (ii) a second miR-TS cassette inserted into a locus of ICP27 and comprising 3 copies of a target sequence for miR-122-3p; and (iii) a third miR-TS cassette inserted into a locus of UL42 and comprising 4 copies of a target sequence for miR-125-5p.

In some embodiments, the recombinant oncolytic virus is an HSV virus comprising (i) a first miR-TS cassette comprising a plurality of miRNA target sequences inserted into a locus of ICP4; (ii) a second miR-TS cassette a plurality of miRNA target sequences inserted into a locus of UL8. In some embodiments, the first miR-TS cassette is inserted into a locus of ICP4 and comprises 1, 2, 3, or 4 copies of a target sequence for miR-124. In some embodiments, the plurality of miRNA target sequences in the second miR-TS cassettes are arranged as follows:

(a) (124-3p)-(124-3p)-(124-3p)-(124-3p).

In some embodiments, the second miR-TS cassette is inserted into a locus of UL8 and comprises 1, 2, 3, or 4 copies of a target sequence for each of miR-137, miR-208b-3p, and miR-126. In some embodiments, the plurality of miRNA target sequences in the second miR-TS cassettes are arranged as follows:

(a) (208b-3p)-(126-3p)-(137-3p)-(208b-3p)-(137-3p)-(126-3p)-(208b-3p)-(137-3p)-(126-3p)-(137-3p)-(126-3p)-(208b-3p).

In some embodiments, the recombinant oncolytic virus is an HSV virus comprising (i) a first miR-TS cassette inserted into a locus of ICP4 and comprising 4 copies of a target sequence for miR-124; (ii) a second miR-TS cassette inserted into a locus of UL8 and comprising 4 copies of a miR-137 target sequence, 4 copies of a miR-208b-3p target sequence, and 4 copies of a miR-126-3p target sequence.

In some embodiments, the recombinant oncolytic virus is an HSV virus comprising (i) a first miR-TS cassette comprising a plurality of miRNA target sequences inserted into a locus of ICP4; (ii) a second miR-TS cassette comprising a plurality of miRNA target sequences inserted into a locus of ICP27; and (iii) a third miR-TS cassette comprising a plurality of miRNA target sequences inserted into a locus of UL8. In some embodiments, the first miR-TS cassette is inserted into a locus of ICP4 and comprises 1, 2, 3, or 4 copies of a target sequence for each of miR-124, miR-1-3p, and miR-143-3p. In some embodiments, the plurality of miRNA target sequences in the first miR-TS cassette are arranged as follows:

(a) (124-3p)-(124-3p)-(124-3p)-(124-3p)-(1-3p)-(143-3p)-(1-3p)-(143-3p)-(1-3p)-(143-3p)-(1-3p)-(143-3p).

In some embodiments, the second miR-TS cassette is inserted into a locus of ICP27 and comprises 1, 2, 3, or 4 copies of a target sequence for each of miR-219a-5p, miR-122-5p, and miR-128. In some embodiments, the plurality of miRNA target sequences in the second miR-TS cassette are arranged as follows:

(a) (219a-5p)-(122-5p)-(128-3p)-(122-5p)-(219a-5p)-(128-3p)-(122-5p)-(128-3p)-(219a-5p)-(128-3p)-(122-5p)-(219a-5p).

In some embodiments, the third miR-TS cassette is inserted into a locus of UL8 and comprises 1, 2, 3, or 4 copies of a target sequence for each of miR-137, miR-208a, and miR-126. In some embodiments, the plurality of miRNA target sequences in the third miR-TS cassette are arranged as follows:

(a) (208b-3p)-(126-3p)-(137-3p)-(208b-3p)-(137-3p)-(126-3p)-(208b-3p)-(137-3p)-(126-3p)-(137-3p)-(126-3p)-(208b-3p).

In some embodiments, the recombinant oncolytic virus is an HSV virus comprising (i) a first miR-TS cassette inserted into a locus of ICP4 and comprising 4 copies of a target sequence for each of miR-124, miR-1-3p, and miR-143-3p; (ii) a second miR-TS cassette inserted into a locus of ICP27 and comprising 4 copies of a target sequence for miR-219a-5p, 4 copies of a target sequence for miR-122-5p, and 4 copies of a target sequence for miR-128; and (iii) a third miR-TS cassette inserted into a locus of UL8 and comprising 4 copies of a target sequence for miR-137, 4 copies of a target sequence for miR-208a, and 4 copies of a target sequence for miR-126.

In some embodiments, the recombinant oncolytic virus is an HSV virus comprising (i) a first miR-TS cassette comprising a plurality of miRNA target sequences inserted into a locus of ICP4; (ii) a second miR-TS cassette comprising a plurality of miRNA target sequences inserted into a locus of ICP27; (iii) a third miR-TS cassette comprising a plurality of miRNA target sequences inserted into a locus of UL8; and (iv) a fourth miR-TS cassette comprising a plurality of miRNA target sequences inserted into a locus of ICP34.5. In some embodiments, the first miR-TS cassette is inserted into a locus of ICP4 and comprises 1, 2, 3, or 4 copies of a target sequence for each of miR-124, miR-1-3p, and miR-143-3p. In some embodiments, the plurality of miRNA target sequences in the first miR-TS cassette are arranged as follows:

(a) (124-3p)-(124-3p)-(124-3p)-(124-3p)-(1-3p)-(143-3p)-(1-3p)-(143-3p)-(1-3p)-(143-3p)-(1-3p)-(143-3p).

In some embodiments, the second miR-TS cassette is inserted into a locus of ICP27 and comprises 1, 2, 3, or 4 copies of a target sequence for each of miRNA 219a-5p, miRNA 122-5p, and miRNA 128. In some embodiments, the plurality of miRNA target sequences in the second miR-TS cassette are arranged as follows:

(a) (219a-5p)-(122-5p)-(128-3p)-(122-5p)-(219a-5p)-(128-3p)-(122-5p)-(128-3p)-(219a-5p)-(128-3p)-(122-5p)-(219a-5p).

In some embodiments, the third miR-TS cassette is inserted into a locus of UL8 and comprises 1, 2, 3, or 4 copies of a target sequence for each of miR-137, miR-208a, and miR-126. In some embodiments, the plurality of miRNA target sequences in the third miR-TS cassette are arranged as follows:

(a) (208b-3p)-(126-3p)-(137-3p)-(208b-3p)-(137-3p)-(126-3p)-(208b-3p)-(137-3p)-(126-3p)-(137-3p)-(126-3p)-(208b-3p).

In some embodiments, the third miR-TS cassette is inserted into a locus of UL8 and comprises 1, 2, 3, or 4 copies of a target sequence for each of miR137, miR-217-5p, and miR-126. In some embodiments, the plurality of miRNA target sequences in the third miR-TS cassette are arranged as follows:

(a) (137-3p)-(126-3p)-(217-5p)-(126-3p)-(217-5p)-(137-3p)-(217-5p)-(126-3p)-(137-3p)-(126-3p)-(217-5p)-(137-3p).

In some embodiments, the third miR-TS cassette is inserted into a locus of UL8 and comprises 1, 2, 3, or 4 copies of a target sequence for each of miR-137, miR-217-5p, and miR-127. In some embodiments, the plurality of miRNA target sequences in the third miR-TS cassette are arranged as follows:

(a) (137-3p)-(127-3p)-(217-5p)-(127-3p)-(217-5p)-(137-3p)-(217-5p)-(127-3p)-(137-3p)-(127-3p)-(217-5p)-(137-3p).

In some embodiments, the third miR-TS cassette is inserted into a locus of UL8 and comprises 1, 2, 3, or 4 copies of a target sequence for each of miR-137, miR-217-5p, and miR-128. In some embodiments, the plurality of miRNA target sequences in the third miR-TS cassette are arranged as follows:

(a) (137-3p)-(128-3p)-(217-5p)-(128-3p)-(217-5p)-(137-3p)-(217-5p)-(128-3p)-(137-3p)-(128-3p)-(217-5p)-(137-3p).

In some embodiments, the third miR-TS cassette is inserted into a locus of UL8 and comprises 1, 2, 3, or 4 copies of a target sequence for each of miR-137, miR-217-5p, and miR-129. In some embodiments, the plurality of miRNA target sequences in the third miR-TS cassette are arranged as follows:

(a) (137-3p)-(129-3p)-(217-5p)-(129-3p)-(217-5p)-(137-3p)-(217-5p)-(129-3p)-(137-3p)-(129-3p)-(219-5p)-(137-3p).

In some embodiments, the third miR-TS cassette is inserted into a locus of UL8 and comprises 1, 2, 3, or 4 copies of a target sequence for each of miR-137, miR-217-5p, and miR-130. In some embodiments, the plurality of miRNA target sequences in the third miR-TS cassette are arranged as follows:

(a) (137-3p)-(130-3p)-(217-5p)-(130-3p)-(217-5p)-(130-3p)-(217-5p)-(127-3p)-(137-3p)-(130-3p)-(217-5p)-(137-3p).

In some embodiments, the fourth miR-TS cassette is inserted into a locus of ICP34.5 and comprises 1, 2, 3, or 4 copies of a target sequence for each of miRNA 128M, miRNA 204, and miRNA 219-3p. In some embodiments, the plurality of miRNA target sequences in the fourth miR-TS cassette are arranged as follows:

(a) (128-3p)-(219a-5p)-(204-5p)-(128-3p)-(219a-5p)-(204-5p)-(128-3p)-(219a-5p)-(204-5p)-(128-3p)-(219a-5p)-(204-5p).

In some embodiments, the recombinant oncolytic virus is an HSV virus comprising (i) a first miR-TS cassette inserted into a locus of ICP4 and comprising four copies of a target sequence for each of miR-124, miR-1-3p, and miR-14; (ii) a second miR-TS cassette inserted into a locus of ICP27 and comprising 4 of a target sequence for each of miR-219a-5p, miR-122-5p, and miR-128; (iii) a third miR-TS cassette inserted into a locus of UL8 and comprising 4 of a target sequence for each of miR-137, miR-208b-3p, and miR-126; and (iv) a fourth miR-TS cassette inserted into a locus of ICP34.5 and comprising 4 of a target sequence for miR-128, 4 copies of a target sequence for miR-204, and 4 copies of a target sequence for miR-219-3p. In some embodiments, the recombinant oncolytic virus is an HSV virus comprising (i) a first miR-TS cassette inserted into a locus of ICP4 and comprising four copies of a target sequence for each of miR-124, miR-1-3p, and miR-14; (ii) a second miR-TS cassette inserted into a locus of ICP27 and comprising 40f a target sequence for each of miR-219a-5p, miR-122-5p, and miR-128; and (iii) a third miR-TS cassette inserted into a locus of UL8 and comprising 4 of a target sequence for each of miR-137, miR-208a, and miR-126.

In some embodiments, the recombinant oncolytic virus is an HSV virus comprising (i) a first miR-TS cassette inserted into a locus of ICP4 and comprising four copies of a target sequence for each of miR-124, miR-1-3p, and miR-14; (ii) a second miR-TS cassette inserted into a locus of ICP27 and comprising 4 of a target sequence for each of miR-219a-5p, miR-122-5p, and miR-128; (iii) a third miR-TS cassette inserted into a locus of UL8 and comprising 4 of a target sequence for miR-137-3p, 4 of a target sequence for miR-217-5p, and 4 of a target sequence for miR-126-3p; and (iv) a fourth miR-TS cassette inserted into a locus of ICP34.5 and comprising 4 of a target sequence for miR-128, 4 copies of a target sequence for miR-204, and 4 copies of a target sequence for miR-219-3p.

In some embodiments, the recombinant oncolytic virus is an HSV virus comprising (i) a first miR-TS cassette inserted into a locus of ICP4 and comprising four copies of a target sequence for each of miR-124, miR-1-3p, and miR-14; (ii) a second miR-TS cassette inserted into a locus of ICP27 and comprising 4 of a target sequence for each of miR-219a-5p, miR-122-5p, and miR-128; (iii) a third miR-TS cassette inserted into a locus of UL8 and comprising 4 of a target sequence for miR-137-3p, 4 of a target sequence for miR-217-5p, and 4 of a target sequence for miR-127; and (iv) a fourth miR-TS cassette inserted into a locus of ICP34.5 and comprising 4 of a target sequence for miR-128, 3 copies of a target sequence for miR-204, and 3 copies of a target sequence for miR-219-5p.

In some embodiments, the recombinant oncolytic virus is an HSV virus comprising (i) a first miR-TS cassette inserted into a locus of ICP4 and comprising four copies of a target sequence for each of miR-124, miR-1-3p, and miR-14; (ii) a second miR-TS cassette inserted into a locus of ICP27 and comprising 4 of a target sequence for each of miR-219a-5p, miR-122-5p, and miR-128; (iii) a third miR-TS cassette inserted into a locus of UL8 and comprising 4 of a target sequence for miR-137-3p, 4 of a target sequence for miR-217-5p, and 4 of a target sequence for miR-128; and (iv) a fourth miR-TS cassette inserted into a locus of ICP34.5 and comprising 4 of a target sequence for miR-128, 3 copies of a target sequence for miR-204, and 3 copies of a target sequence for miR-219-5p. In some embodiments, the recombinant oncolytic virus is an HSV virus comprising (i) a first miR-TS cassette inserted into a locus of ICP4 and comprising four copies of a target sequence for each of miR-124, miR-1-3p, and miR-14; (ii) a second miR-TS cassette inserted into a locus of ICP27 and comprising 4 of a target sequence for each of miR-219a-5p, miR-122-5p, and miR-128; (iii) a third miR-TS cassette inserted into a locus of UL8 and comprising 4 of a target sequence for miR-137-3p, 4 of a target sequence for miR-217-5p, and 4 of a target sequence for miR-129; and (iv) a fourth miR-TS cassette inserted into a locus of ICP34.5 and comprising 4 of a target sequence for miR-128, 3 copies of a target sequence for miR-204, and 3 copies of a target sequence for miR-219-5p In some embodiments, the recombinant oncolytic virus is an HSV virus comprising (i) a first miR-TS cassette inserted into a locus of ICP4 and comprising four copies of a target sequence for each of miR-124, miR-1-3p, and miR-14; (ii) a second miR-TS cassette inserted into a locus of ICP27 and comprising 4 of a target sequence for each of miR-219a-5p, miR-122-5p, and miR-128; (iii) a third miR-TS cassette inserted into a locus of UL8 and comprising 4 of a target sequence for miR-137-3p, 4 of a target sequence for miR-217-5p, and 4 of a target sequence for miR-130; and (iv) a fourth miR-TS cassette inserted into a locus of ICP34.5 and comprising 4 of a target sequence for miR-128, 3 copies of a target sequence for miR-204, and 3 copies of a target sequence for miR-219-5p.

In some embodiments, the viral vectors described herein comprise one copy of a miR-125a target sequence incorporated into one essential viral gene. In some embodiments, the viral vectors described herein comprise one copy of a miR-125a target sequence incorporated into the UL42 locus. In some embodiments, the viral vectors described herein comprise one copy of a miR-122 target sequence incorporated into one essential viral gene. In some embodiments, the viral vectors described herein comprise one copy of a miR-122 target sequence incorporated into the ICP27 locus (e.g., ONCR-036).

In further embodiments, the viral vectors described herein comprise 3 copies of a miR-125a target sequence incorporated a viral gene required for viral replication. In further embodiments, the viral vectors described herein may comprise 3 copies of a miR-125a target sequence incorporated into the UL42 locus. In some embodiments, 4 copies of a miR target sequence are incorporated into the 3' UTR of an essential viral gene. In further embodiments, the viral vectors described herein may comprise 4 copies of a miR-125a target sequence incorporated into an essential viral gene. In further embodiments, the viral vectors described herein may comprise 4 copies of a miR-125a target sequence incorporated into the UL42 locus. In some embodiments, the viral vectors described herein may comprise 4 copies of a miR-122 target sequence incorporated into an essential viral gene. In further embodiments, the viral vectors described herein may comprise 4 copies of a miR-122 target sequence incorporated into the ICP27 locus (e.g., ONCR-063).

In some embodiments, 1 copy of a miR-122 target sequence is incorporated into the 3' UTR of a first essential viral gene, and 1 copy of a miR-125a target sequence is incorporated into the 3' UTR of a second essential viral gene. In some embodiments, 1 copy of a miR-122 target sequence is incorporated into the 3' UTR of the ICP27 locus, and 1 copy of a miR-125a target sequence is incorporated into the 3' UTR of the UL42 locus (e.g., ONCR-094).

In some embodiments, 1 copy of a miR-122 target sequence is incorporated into the 3' UTR of a first essential viral gene, and 3 copies of a miR-125a target sequence are incorporated into the 3' UTR of a second essential viral gene. In some embodiments, 1 copy of a miR-122 target sequence is incorporated into the 3' UTR of the ICP27 locus, and 3 copies of a miR-125a target sequence are incorporated into the 3' UTR of the UL42 locus (e.g., ONCR-095).

In some embodiments, 4 copies of a first miR target sequence are incorporated into the 3' UTR of a first essential viral gene, and 1 copy of a second miR target sequence is incorporated into the 3' UTR of a second essential viral gene. In some embodiments, 4 copies of a miR-122 target sequence are incorporated into the 3' UTR of a first essential viral gene, and 1 copy of a miR-125a target sequence is incorporated into the 3' UTR of a second essential viral gene. In some embodiments, 4 copies of a miR-122 target sequence are incorporated into the 3' UTR of the ICP27 locus, and 1 copy of a miR-125a target sequence is incorporated into the 3' UTR of the UL42 locus (e.g., ONCR-093).

In some embodiments, 4 copies of a first miR target sequence are incorporated into the 3' UTR of a first essential viral gene, and 4 copies of a second miR target sequence are incorporated into the 3' UTR of a second essential viral gene. In some embodiments, 4 copies of a miR-122 target sequence are incorporated into the 3' UTR of a first essential viral gene, and 4 copies of a miR-125a target sequence are incorporated into the 3' UTR of a second essential viral gene. In some embodiments, 4 copies of a miR-122 target sequence are incorporated into the 3' UTR of the ICP27 locus, and 4 copies of a miR-125a target sequence is incorporated into the 3' UTR of the UL42 locus (e.g., ONCR-096).

In some embodiments, the miR-attenuated oncolytic viruses described herein result in reduced viral replication in a cell that expresses a miR capable of binding to one or more of the incorporated miR-target sequences. "Viral replication" refers to the total number of viral replication cycles that occur in a particular cell or population of cells during a given amount of time. In some embodiments, viral replication can be measured directly by assessing the total viral titer present over the course of the given amount of time, or by assessing the number of viral genome copies present (e.g., by sequencing). In some embodiments, the viral vector may additionally comprise a detectable label, such as a fluorescent reporter. In such embodiments, viral replication may be assessed by measuring the fluorescence intensity of the reporter, or the number of cells that express the reporter. In some embodiments, viral replication can be measured indirectly by assessing the number of viable cells over the course of the given amount of time. For example, the level of viral replication would be expected to inversely correlate with the number of viable cells over time.

"Reduced viral replication" as used herein, refers to a level of viral replication that is lower in a first cell or first population of cells compared to a second cell or a second population of cells. In some embodiments, the level of viral replication in the first cell or first population of cells is reduced by at least 5% compared to the level of viral replication in the second cell or population of cells. In some embodiments, the level of viral replication in the first cell or first population of cells is reduced by at least 5%, 6%, 7%, 8%, 9%, 10%, 15%, 20%, 25%, 30%, 35%, 40%, 50%, 60%, 70%, 80%, 90% or more compared to the level of viral replication in the second cell or population of cells. In some embodiments, viral replication in the first cell or first population of cells is completely inhibited compared to the viral replication in the second cell or population of cells.

In some embodiments, the reduced viral replication in the first cell or first population of cells correlates with the expression of a miR capable of binding to the one or more miR-target sequences incorporated into one or more viral genes required for replication. In some embodiments, expression of a miR corresponding to the incorporated miR-target sequence therefore inhibits or reduces the expression of the replication gene, thereby inhibiting or reducing viral replication. In some embodiments, the second cell or second population of cells does not express, or has a reduced expression level, of the t miR. In some embodiments, absent or reduced expression of a miR (e.g., in a cancer cell) corresponding to the incorporated miR-target sequence allows for viral replication to proceed. In some embodiments, the expression level of the miR in the second cell or population of cells is at least 5% lower than the expression level of the miR in the first cell or population. In some embodiments, the expression level of the miR in the second cell or population of cells is reduced at least 5%, 6%, 7%, 8%, 9%, 10%, 15%, 20%, 25%, 30%, 35%, 40%, 50%, 60%, 70%, 80%, 90% or more compared to the expression level of the miR in the first cell or population. In some embodiments, the second cell does not express the miR. In particular embodiments, the first cell is a non-cancerous cell and the second cell is a cancerous cell.

In some embodiments, a replication-restricted viral vector (e.g., a miR-attenuated viral vector) comprises at least one let-7 target sequence and is used to treat lung cancer. In some embodiments, a replication-restricted viral vector comprises at least one miR-15a and/or at least one miR-16A target sequences and is used to treat B-cell chronic lymphocytic leukemia. In some embodiments, a replication-restricted viral vector comprises at least one miR-125b, at least one miR-145, at least one miR-21, and/or at least one miR-155 target sequences and is used to treat breast cancer. In other embodiments, a replication-restricted viral vector comprises at least one miR-143 and/or at least one miR-145 target sequences and is used to treat colorectal cancer. In certain embodiments, a replication-restricted viral vector comprises at least one miR-181a, at least one miR-181b, and/or at least one miR-181c target sequences and is used to treat glioblastoma. In some embodiments, a replication-restricted viral vector comprises at least one miR-199a*, at least one miR-195, at least one miR-199a, at least one miR-200a, and/or at least one miR-125a target sequences and is used to treat liver cancer (e.g., hepatocellular carcinoma).

In particular embodiments, a replication-restricted viral vector comprises at least one miR-451a target sequence, at least one miR-143-3p target sequence, at least one miR-559 target sequence, and at least one miR-124 target sequence and is used for the treatment of pancreatic, lung, and/or colon cancer. In such embodiments, the target sequences for miR-451a, miR-143-3p, miR-559, and miR-124 are incorporated into two or more genes required for viral replication (e.g., ICP4 and ICP27). In further particular embodiments, a replication-restricted viral vector comprises at least one miR-451a target sequence, at least one miR-145-5p target sequence, at least one miR-559 target sequence, and at least one miR-124 target sequence and is used for the treatment of any type of cancer described herein. In such embodiments, the target sequences for miR-451a, miR-145-5p, miR-559, and miR-124 are incorporated into two or more genes required for viral replication (e.g., ICP4 and ICP27). In further particular embodiments, a replication-restricted viral vector comprises at least one miR-205p target sequence, at least one miR-141-5p target sequence, at least one miR-31-5p target sequence, and at least one miR-124 target sequence and is used for the treatment of schwannoma. In such embodiments, the target sequences for miR-205p, miR-141-5p, miR-31-5p, and miR-124 are incorporated into two or more genes required for viral replication (e.g., ICP4 and ICP27).

In some embodiments, a recombinant oncolytic virus comprises a plurality of copies of one or more miRNA target sequences for miR-136-3p, miR-432-5p, miR-1-3p, miR-127-3p, miR-379-5p, miR-493-5p, miR-223-5p, miR-223-5p, miR-136-5p, miR-451a, miR-487b-3p, miR-370-3p, miR-410-3p, miR-431-3p, miR-4485-3p, miR-4485-5p, miR-127-5p, miR-409-3p, miR-338-3p, miR-559, miR-411-5p, miR-133a-5p, miR-143-3p, miR-376b-3p, miR-758-3p, miR-1, miR-101, miR-1180, miR-1236, miR-124-3p, miR-125b, miR-126, miR-1280, miR-133a, miR-133b, miR-141, miR-143, miR-144, miR-145, miR-155, miR-16, miR-18a, miR-192, miR-195, miR-200a, miR-200b, miR-200c, miR-203, miR-205, miR-214, miR-218, miR-23b, miR-26a, miR-29c, miR-320c, miR-34a, miR-370, miR-409-3p, miR-429, miR-451, miR-490-5p, miR-493, miR-576-3p, and/or miR-99a inserted into the 5' UTR or 3' UTR of one or more viral genes required for viral replication. This oncolytic virus may be used in methods and compositions for treating bladder cancer.

In some embodiments, a recombinant oncolytic virus comprises a plurality of copies of one or more miRNA target sequences for miR-1251-5p, miR-219a-5p, miR-219a-2-3p, miR-124-3p, miR-448, miR-138-2-3p, miR-490-5p, miR-129-1-3p, miR-1264, miR-3943, miR-490-3p, miR-383-5p, miR-133b, miR-129-2-3p, miR-128-2-5p, miR-133a-3p, miR-129-5p, miR-1-3p, miR-885-3p, miR-124-5p, miR-759, miR-7158-3p, miR-770-5p, miR-135a-5p, miR-885-5p, let-7g-5p, miR-100, miR-101, miR-106a, miR-124, miR-124a, miR-125a, miR-125a-5p, miR-125b, miR-127-3p, miR-128, miR-129, miR-136, miR-137, miR-139-5p, miR-142-3p, miR-143, miR-145, miR-146b-5p, miR-149, miR-152, miR-153, miR-195, miR-21, miR-212-3p, miR-219-5p, miR-222, miR-29b, miR-31, miR-3189-3p, miR-320, miR-320a, miR-326, miR-330, miR-331-3p, miR-340, miR-342, miR-34a, miR-376a, miR-449a, miR-483-5p, miR-503, miR-577, miR-663, miR-7, miR-7-5p, miR-873, let-7a, let-7f, miR-107, miR-122, miR-124-5p, miR-139, miR-146a, miR-146b, miR-15b, miR-16, miR-181a, miR-181a-1, miR-181a-2, miR-181b, miR-181b-1, miR-181b-2, miR-181c, miR-181d, miR-184, miR-185, miR-199a-3p, miR-200a, miR-200b, miR-203, miR-204, miR-205, miR-218, miR-23b, miR-26b, miR-27a, miR-29c, miR-328, miR-34c-3p, miR-34c-5p, miR-375, miR-383, miR-451, miR-452, miR-495, miR-584, miR-622, miR-656, miR-98, miR-124-3p, miR-181b-5p, miR-200b, and/or miR-3189-3p inserted into the 5 UTR or 3' UTR of one or more viral genes required for viral replication. This oncolytic virus may be used in methods and compositions for treating brain cancer. In certain embodiments, the brain cancer is astrocytoma, glioblastoma, or glioma.

In some embodiments, a recombinant oncolytic virus comprises a plurality of copies of one or more miRNA target sequences for miR-10b-5p, miR-126-3p, miR-145-3p, miR-451a, miR-199b-5p, miR-5683, miR-3195, miR-3182, miR-1271-5p, miR-204-5p, miR-409-5p, miR-136-5p, miR-514a-5p, miR-559, miR-483-3p, miR-1-3p, miR-6080, miR-144-3p, miR-10b-3p, miR-6130, miR-6089, miR-203b-5p, miR-4266, miR-4327, miR-5694, miR-193b, let-7a, let-7a-1, let-7a-2, let-7a-3, let-7b, let-7c, let-7d, let-7e, let-7f-1, let-7f-2, let-7g, let-7i, miR-100, miR-107, miR-10a, miR-10b, miR-122, miR-124, miR-1258, miR-125a-5p, miR-125b, miR-126, miR-127, miR-129, miR-130a, miR-132, miR-133a, miR-143, miR-145, miR-146a, miR-146b, miR-147, miR-148a, miR-149, miR-152, miR-153, miR-15a, miR-16, miR-17-5p, miR-181a, miR-1826, miR-183, miR-185, miR-191, miR-193a-3p, miR-195, miR-199b-5p, miR-19a-3p, miR-200a, miR-200b, miR-200c, miR-205, miR-206, miR-211, miR-216b, miR-218, miR-22, miR-26a, miR-26b, miR-300, miR-30a, miR-31, miR-335, miR-339-5p, miR-33b, miR-34a, miR-34b, miR-34c, miR-374a, miR-379, miR-381, miR-383, miR-425, miR-429, miR-450b-3p, miR-494, miR-495, miR-497, miR-502-5p, miR-517a, miR-574-3p, miR-638, miR-7, miR-720, miR-873, miR-874, miR-92a, miR-98, miR-99a, mmu-miR-290-3p, and/or mmu-miR-290-5p inserted into the 5' UTR or 3' UTR of one or more viral genes required for viral replication. This oncolytic virus may be used in methods and compositions for treating breast cancer.

In some embodiments, a recombinant oncolytic virus comprises a plurality of copies of one or more miRNA target sequences for miR-143, miR-145, miR-17-5p, miR-203, miR-214, miR-218, miR-335, miR-342-3p, miR-372, miR-424, miR-491-5p, miR-497, miR-7, miR-99a, miR-99b, miR-100, miR-101, miR-15a, miR-16, miR-34a, miR-886-5p, miR-106a, miR-124, miR-148a, miR-29a, and/or miR-375 inserted into the 5' UTR or 3' UTR of one or more viral genes required for viral replication. This oncolytic virus may be used in methods and compositions for treating cervical cancer.

In some embodiments, a recombinant oncolytic virus comprises a plurality of copies of one or more miRNA target sequences for miR-133a-5p, miR-490-5p, miR-124-3p, miR-137, miR-655-3p, miR-376c-3p, miR-369-5p, miR-490-3p, miR-432-5p, miR-487b-3p, miR-342-3p, miR-223-3p, miR-136-3p, miR-136-3p, miR-143-5p, miR-1-3p, miR-214-3p, miR-143-3p, miR-199a-3p, miR-199b-3p, miR-451a, miR-127-3p, miR-133a-3p, miR-145-5p, miR-145-3p, miR-199a-5p, let-7a-1, let-7a-2, let-7a-3, let-7b, let-7c, let-7d, let-7e, let-7f-1, let-7f-2, let-7g, let-7i, miR-100, miR-101, miR-126, miR-142-3p, miR-143, miR-145, miR-192, miR-200c, miR-21, miR-214, miR-215, miR-22, miR-25, miR-302a, miR-320, miR-320a, miR-34a, miR-34c, miR-365, miR-373, miR-424, miR-429, miR-455, miR-484, miR-502, miR-503, miR-93, miR-98, miR-186, miR-30a-5p, miR-627, let-7a, miR-1, miR-124, miR-125a, miR-129, miR-1295b-3p, miR-1307, miR-130b, miR-132, miR-133a, miR-133b, miR-137, miR-138, miR-139, miR-139-5p, miR-140-5p, miR-148a, miR-148b, miR-149, miR-150-5p, miR-154, miR-15a, miR-15b, miR-16, miR-18a, miR-191, miR-193a-5p, miR-194, miR-195, miR-196a, miR-198, miR-199a-5p, miR-203, miR-204-5p, miR-206, miR-212, miR-218, miR-224, miR-24-3p, miR-26b, miR-27a, miR-28-3p, miR-28-5p, miR-29b, miR-30a-3p, miR-30b, miR-328, miR-338-3p, miR-342, miR-345, miR-34a-5p, miR-361-5p, miR-375, miR-378, miR-378a-3p, miR-378a-5p, miR-409-3p, miR-422a, miR-4487, miR-483, miR-497, miR-498, miR-518a-3p, miR-551a, miR-574-5p, miR-625, miR-638, miR-7, miR-96-5p, miR-202-3p, miR-30a, and/or miR-451 inserted into the 5' UTR or 3' UTR of one or more viral genes required for viral replication. This oncolytic virus may be used in methods and compositions for treating colon or colorectal cancer.

In some embodiments, a recombinant oncolytic virus comprises a plurality of copies of one or more miRNA target sequences for miR-101, miR-130a, miR-130b, miR-134, miR-143, miR-145, miR-152, miR-205, miR-223, miR-301a, miR-301b, miR-30c, miR-34a, miR-34c, miR-424, miR-449a, miR-543, and/or miR-34b inserted into the 5' UTR or 3' UTR of one or more viral genes required for viral replication. This oncolytic virus may be used in methods and compositions for treating endometrial cancer.

In some embodiments, a recombinant oncolytic virus comprises a plurality of copies of one or more miRNA target sequences for miR-125b, miR-138, miR-15a, miR-15b, miR-16, miR-16-1, miR-16-1-3p, miR-16-2, miR-181a, miR-181b, miR-195, miR-223, miR-29b, miR-34b, miR-34c, miR-424, miR-10a, miR-146a, miR-150, miR-151, miR-155, miR-2278, miR-26a, miR-30e, miR-31, miR-326, miR-564, miR-27a, let-7b, miR-124a, miR-142-3p, let-7c, miR-17, miR-20a, miR-29a, miR-30c, miR-720, miR-107, miR-342, miR-34a, miR-202, miR-142-5p, miR-29c, miR-145, miR-193b, miR-199a, miR-214, miR-22, miR-137, and/or miR-197 inserted into the 5' UTR or 3' UTR of one or more viral genes required for viral replication. This oncolytic virus may be used in methods and compositions for treating hematologic cancer. In some embodiments, the hematologic cancer is leukemia, lymphoma, or myeloma.

In some embodiments, a recombinant oncolytic virus comprises a plurality of copies of one or more miRNA target sequences for miR-1, miR-145, miR-1826, miR-199a, miR-199a-3p, miR-203, miR-205, miR-497, miR-508-3p, miR-509-3p, let-7a, let-7d, miR-106a*, miR-126, miR-1285, miR-129-3p, miR-1291, miR-133a, miR-135a, miR-138, miR-141, miR-143, miR-182-5p, miR-200a, miR-218, miR-28-5p, miR-30a, miR-30c, miR-30d, miR-34a, miR-378, miR-429, miR-509-5p, miR-646, miR-133b, let-7b, let-7c, miR-200c, miR-204, miR-335, miR-377, and/or miR-506 inserted into the 5' UTR or 3' UTR of one or more viral genes required for viral replication. This oncolytic virus may be used in methods and compositions for treating kidney cancer.

In some embodiments, a recombinant oncolytic virus comprises a plurality of copies of one or more miRNA target sequences for let-7a-1, let-7a-2, let-7a-3, let-7b, let-7c, let-7d, let-7e, let-7f, let-7f-1, let-7f-2, let-7g, let-7i, miR-1, miR-100, miR-101, miR-105, miR-122, miR-122a, miR-1236, miR-124, miR-125b, miR-126, miR-127, miR-1271, miR-128-3p, miR-129-5p, miR-130a, miR-130b, miR-133a, miR-134, miR-137, miR-138, miR-139, miR-139-5p, miR-140-5p, miR-141, miR-142-3p, miR-143, miR-144, miR-145, miR-146a, miR-148a, miR-148b, miR-150-5p, miR-15b, miR-16, miR-181a-5p, miR-185, miR-188-5p, miR-193b, miR-195, miR-195-5p, miR-197, miR-198, miR-199a, miR-199a-5p, miR-199b, miR-199b-5p, miR-200a, miR-200b, miR-200c, miR-202, miR-203, miR-204-3p, miR-205, miR-206, miR-20a, miR-21, miR-21-3p, miR-211, miR-212, miR-214, miR-217, miR-218, miR-219-5p, miR-22, miR-223, miR-26a, miR-26b, miR-29a, miR-29b-1, miR-29b-2, miR-29c, miR-302b, miR-302c, miR-30a, miR-30a-3p, miR-335, miR-338-3p, miR-33a, miR-34a, miR-34b, miR-365, miR-370, miR-372, miR-375, miR-376a, miR-377, miR-422a, miR-424, miR-424-5p, miR-433, miR-4458, miR-448, miR-450a, miR-451, miR-485-5p, miR-486-5p, miR-497, miR-503, miR-506, miR-519d, miR-520a, miR-520b, miR-520c-3p, miR-582-5p, miR-590-5p, miR-610, miR-612, miR-625, miR-637, miR-675, miR-7, miR-877, miR-940, miR-941, miR-98, miR-99a, miR-132, and/or miR-31 inserted into the 5' UTR or 3' UTR of one or more viral genes required for viral replication. This oncolytic virus may be used in methods and compositions for treating liver cancer. In some embodiments, the liver cancer is hepatocellular carcinoma.

In some embodiments, a recombinant oncolytic virus comprises a plurality of copies of one or more miRNA target sequences for miR-143-3p, miR-126-3p, miR-126-5p, miR-1266-3p, miR-6130, miR-6080, miR-511-5p, miR-143-5p, miR-223-5p, miR-199b-5p, miR-199a-3p, miR-199b-3p, miR-451a, miR-142-5p, miR-144, miR-150-5p, miR-142-3p, miR-214-3p, miR-214-5p, miR-199a-5p, miR-145-3p, miR-145-5p, miR-1297, miR-141, miR-145, miR-16, miR-200a, miR-200b, miR-200c, miR-29b, miR-381, miR-409-3p, miR-429, miR-451, miR-511, miR-99a, let-7a-1, let-7a-2, let-7a-3, let-7b, let-7c, let-7d, let-7e, let-7f-1, let-7f-2, let-7g, let-7i, miR-1, miR-101, miR-133b, miR-138, miR-142-5p, miR-144, miR-1469, miR-146a, miR-153, miR-15a, miR-15b, miR-16-1, miR-16-2, miR-182, miR-192, miR-193a-3p, miR-194, miR-195, miR-198, miR-203, miR-217, miR-218, miR-22, miR-223, miR-26a, miR-26b, miR-29c, miR-33a, miR-34a, miR-34b, miR-34c, miR-365, miR-449a, miR-449b, miR-486-5p, miR-545, miR-610, miR-614, miR-630, miR-660, miR-7515, miR-9500, miR-98, miR-99b, miR-133a, let-7a, miR-100, miR-106a, miR-107, miR-124, miR-125a-3p, miR-125a-5p, miR-126, miR-126*, miR-129, miR-137, miR-140, miR-143, miR-146b, miR-148a, miR-148b, miR-149, miR-152, miR-154, miR-155, miR-17-5p, miR-181a-1, miR-181a-2, miR-181b, miR-181b-1, miR-181b-2, miR-181c, miR-181d, miR-184, miR-186, miR-193b, miR-199a, miR-204, miR-212, miR-221, miR-224, miR-27a, miR-27b, miR-29a, miR-30a, miR-30b, miR-30c, miR-30d, miR-30d-5p, miR-30e-5p, miR-32, miR-335, miR-338-3p, miR-340, miR-342-3p, miR-361-3p, miR-373, miR-375, miR-4500, miR-4782-3p, miR-497, miR-503, miR-512-3p, miR-520a-3p, miR-526b, miR-625*, and/or miR-96 inserted into the 5' UTR or 3' UTR of one or more viral genes required for viral replication. This oncolytic virus may be used in methods and compositions for treating lung cancer.

In some embodiments, a recombinant oncolytic virus comprises a plurality of copies of one or more miRNA target sequences for let-7b, miR-101, miR-125b, miR-1280, miR-143, miR-146a, miR-146b, miR-155, miR-17, miR-184, miR-185, miR-18b, miR-193b, miR-200c, miR-203, miR-204, miR-205, miR-206, miR-20a, miR-211, miR-218, miR-26a, miR-31, miR-33a, miR-34a, miR-34c, miR-376a, miR-376c, miR-573, miR-7-5p, miR-9, and/or miR-98 inserted into the 5' UTR or 3' UTR of one or more viral genes required for viral replication. This oncolytic virus may be used in methods and compositions for treating melanoma.

In some embodiments, a recombinant oncolytic virus comprises a plurality of copies of one or more miRNA target sequences for let-7d, miR-218, miR-34a, miR-375, miR-494, miR-100, miR-124, miR-1250, miR-125b, miR-126, miR-1271, miR-136, miR-138, miR-145, miR-147, miR-148a, miR-181a, miR-206, miR-220a, miR-26a, miR-26b, miR-29a, miR-32, miR-323-5p, miR-329, miR-338, miR-370, miR-410, miR-429, miR-433, miR-499a-5p, miR-503, miR-506, miR-632, miR-646, miR-668, miR-877, and/or miR-9 inserted into the 5' UTR or 3' UTR of one or more viral genes required for viral replication. This oncolytic virus may be used in methods and compositions for treating oral cancer.

In some embodiments, a recombinant oncolytic virus comprises a plurality of copies of one or more miRNA target sequences for let-7i, miR-100, miR-124, miR-125b, miR-129-5p, miR-130b, miR-133a, miR-137, miR-138, miR-141, miR-145, miR-148a, miR-152, miR-153, miR-155, miR-199a, miR-200a, miR-200b, miR-200c, miR-212, miR-335, miR-34a, miR-34b, miR-34c, miR-409-3p, miR-411, miR-429, miR-432, miR-449a, miR-494, miR-497, miR-498, miR-519d, miR-655, miR-9, miR-98, miR-101, miR-532-5p, miR-124a, miR-192, miR-193a, and/or miR-7 inserted into the 5' UTR or 3' UTR of one or more viral genes required for viral replication. This oncolytic virus may be used in methods and compositions for treating ovarian cancer.

In some embodiments, a recombinant oncolytic virus comprises a plurality of copies of one or more miRNA target sequences for miR-216a-5p, miR-802, miR-217, miR-145-3p, miR-143-3p, miR-451a, miR-375, miR-214-3p, miR-216b-3p, miR-432-5p, miR-216a-3p, miR-199b-5p, miR-199a-5p, miR-136-3p, miR-216b-5p, miR-136-5p, miR-145-5p, miR-127-3p, miR-199a-3p, miR-199b-3p, miR-559, miR-129-2-3p, miR-4507, miR-1-3p, miR-148a-3p, miR-101, miR-1181, miR-124, miR-1247, miR-133a, miR-141, miR-145, miR-146a, miR-148a, miR-148b, miR-150*, miR-150-5p, miR-152, miR-15a, miR-198, miR-203, miR-214, miR-216a, miR-29c, miR-335, miR-34a, miR-34b, miR-34c, miR-373, miR-375, miR-410, miR-497, miR-615-5p, miR-630, miR-96, miR-132, let-7a, let-7a-1, let-7a-2, let-7a-3, let-7b, let-7c, let-7d, let-7e, let-7f-1, let-7f-2, let-7g, let-7i, miR-126, miR-135a, miR-143, miR-144, miR-150, miR-16, miR-200a, miR-200b, miR-200c, miR-217, miR-218, miR-337, miR-494, and/or miR-98 inserted into the 5' UTR or 3' UTR of one or more viral genes required for viral replication. This oncolytic virus may be used in methods and compositions for treating pancreatic cancer.

In some embodiments, a recombinant oncolytic virus comprises a plurality of copies of one or more miRNA target sequences for let-7a-3p, let-7c, miR-100, miR-101, miR-105, miR-124, miR-128, miR-1296, miR-130b, miR-133a-1, miR-133a-2, miR-133b, miR-135a, miR-143, miR-145, miR-146a, miR-154, miR-15a, miR-187, miR-188-5p, miR-199b, miR-200b, miR-203, miR-205, miR-212, miR-218, miR-221, miR-224, miR-23a, miR-23b, miR-25, miR-26a, miR-26b, miR-29b, miR-302a, miR-30a, miR-30b, miR-30c-1, miR-30c-2, miR-30d, miR-30e, miR-31, miR-330, miR-331-3p, miR-34a, miR-34b, miR-34c, miR-374b, miR-449a, miR-4723-5p, miR-497, miR-628-5p, miR-642a-5p, miR-765, and/or miR-940 inserted into the 5' UTR or 3' UTR of one or more viral genes required for viral replication. This oncolytic virus may be used in methods and compositions for treating prostate cancer.

In some embodiments, a recombinant oncolytic virus comprises a plurality of copies of one or more miRNA target sequences for miR-101, miR-183, miR-204, miR-34a, miR-365b-3p, miR-486-3p, and/or miR-532-5p inserted into the 5' UTR or 3' UTR of one or more viral genes required for viral replication. This oncolytic virus may be used in methods and compositions for treating retinoblastoma.

In some embodiments, an oncolytic virus described herein is a herpes simplex virus and wherein the one or more viral genes required for viral replication is selected from the group consisting of UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, USB, US9, US10, US11, and US12.

Payload Molecules

In some embodiments, the oncolytic viruses described herein comprise a nucleic acid sequence encoding a payload molecule. As used herein, a "payload molecule" refers to a molecule capable of further enhancing the therapeutic efficacy of a virus. Payload molecules suitable for use in the present disclosure include antigen-binding molecules such as antibodies or antigen binding fragments thereof, cytokines, chemokines, soluble receptors, cell-surface receptor ligands, bipartite peptides, enzymes, and nucleic acids (e.g., shRNAs, siRNAs, antisense RNAs, antagomirs, ribozymes, apatamers, a decoy oligonucleotide, or an antagomir). The nature of the payload molecule will vary with the disease type and desired therapeutic outcome. In some embodiments, one or more miRNA target sequences is incorporated in to the 3' or 5' UTR of a polynucleotide sequence encoding a payload molecule. In such embodiments, translation and subsequent expression of the payload does not occur, or is substantially reduced, in cells where the corresponding miRNA is expressed. In some embodiments, one or more miRNA target sequences are inserted into the 3' and/or 5' UTR of the polynucleotide sequence encoding the therapeutic polypeptide.

In some embodiments, the recombinant oncolytic viruses described herein comprise at least one polynucleotide encoding a payload molecule that that reduces the expression or inhibits the function of an endogenous miRNA, a gene, or a tissue inhibitor of metalloproteinases (TIMP). Such recombinant oncolytic viruses are referred to herein as "genome-editing" or "microenvironment-remodeling" viruses or vectors. The encoded protein or oligonucleotide may reduce expression or inhibit the function of a miRNA, gene, or TIMP in any number of ways including targeting the protein (e.g., a TIMP) for degradation (e.g., by ubiquitination and proteosomal degradation or targeting for lysosomal degradation), blocking interactions with cognate receptors (e.g., blocking antibodies or antigen binding fragments thereof or peptide inhibitors), degrading messenger RNA transcripts (e.g., a short interfering RNA or short hairpin RNA), and/or altering the genomic DNA sequence encoding the specific miRNA, gene, or protein (e.g., by an endonuclease).

In particular embodiments, the protein or oligonucleotide reduces the expression of a miR or a gene involved in carcinogenesis or metastasis (e.g., an oncogenic miR or an oncogene). In some embodiments, a recombinant oncolytic virus comprises at least one polynucleotide encoding a payload molecule that reduces the expression or function of a miRNA that is an oncogenic miRNA (e.g., one or more of the miRNAs listed in Table 4). In some embodiments, the recombinant oncolytic virus comprises at least 1, 2, 3, 4, 5, 6, 7, 8, 9, 10 or more polynucleotides encoding for a protein or oligonucleotide that reduces the expression or function of an oncogenic miRNA. In some embodiments, the recombinant oncolytic virus comprises at least 1, 2, 3, 4, 5, 6, 7, 8, 9, 10 or more polynucleotides encoding for a plurality of proteins or oligonucleotides that reduce the expression or function of a plurality of oncogenic miRNAs. In some embodiments, the protein or oligonucleotide reduces the expression of miR-17-92 and is used to treat lung cancer (e.g., small-cell lung cancer). In other embodiments, the protein or oligonucleotide reduces the expression of miR-221 and/or miR-21 and is used to treat glioblastoma. In certain embodiments, the protein or oligonucleotide reduces the expression of miR-155 and/or miR-17-92 and is used to treat lymphoma (e.g., Burkitt's lymphoma, diffuse large B cell lymphoma, marginal zone lymphoma, or chronic lymphocytic leukemia). In some embodiments, the protein or oligonucleotide reduces the expression of miR-221, miR-222, and/or miR-146 and is used to treat thyroid cancer. In some embodiments, the protein or oligonucleotide reduces the expression of miR-372 and/or miR-373 and is used to treat testicular cancer (e.g., testicular germ cell tumors). In some embodiments, the protein or oligonucleotide reduces the expression of miR-18 and/or miR-224 and is used to treat liver cancer (e.g., hepatocellular carcinoma).

In some embodiments, a recombinant viral vectors described herein comprise a polynucleotide encoding a payload molecule that degrades the tumor extracellular matrix (ECM), which in some aspects leads to enhanced viral spread. Matrix metalloproteinases (MMPs) are zinc-dependent proteases that are classified, based on their activity, into collagenases, gelatinases, stromelysins and matrilysins. These proteases are generally secreted as pro-enzymes (zymogens) and are activated by proteolytic removal of the pro-peptide pro-domain. The primary role that MMPs play in cancer is in the degradation of the ECM, which facilitates tumor invasion and metastasis. MMPs are also involved in tumor progression, epithelial to mesenchymal transition (EMT), and angiogenesis. MMPs are regulated by miRs as well as TIMPs, which comprise a family of four protease inhibitors (TIMP1, TIMP2, TIMP3, and TIMP4). A broad array of tumor microenvironments can be degraded by disrupting miRNAs or TIMPs that negatively regulate the MMP family with the recombinant viral vectors of the invention. Examples of miR/MMP interactions are shown in Table 5. Many of these interactions show that multiple MMPs are regulated by a single miRNA: e.g. let-7 regulates MMP-2, MMP-9, and MMP-14; miR-143 regulates MMP-2, MMP-9, and MMP-13; miR-218 regulates MMP-2, MMP-7, and MMP-9. Furthermore, the vast majority of MMPs may be regulated by a single TIMP master switch: e.g. TIMP1 is known to inhibit most all of the known MMPs and also promotes cell proliferation in a wide range of cell types; TIMP2 interacts with MMP-14 and MMP-2.

In some embodiments, the recombinant oncolytic viruses described herein comprise at least one polynucleotide encoding a protein or an oligonucleotide that reduces the expression or function of a miRNA that is capable of altering the extracellular matrix or capable of modulating a pathway that alters the extracellular matrix, particularly in a tumor microenvironment (e.g., one or more of the miRNAs listed in Table 5). A microenvironment remodeling miR, as used herein, refers to a miR. In some embodiments, the protein or oligonucleotide reduces the expression or function of one microenvironment remodeling miR. In some embodiments, the protein or oligonucleotide reduces the expression or function of at least 2, 3, 4, 5, 6, 7, 8, 9, or 10 or more microenvironment remodeling miRs. In some embodiments, the recombinant oncolytic virus comprises a plurality of polynucleotides encoding a plurality of protein or oligonucleotides that reduce the expression or function of a plurality of microenvironment remodeling miRs. In some embodiments, strategies described herein may be utilized by recombinant viral vectors of the present invention to knockdown or disrupt expression or function of miRs or TIMPs which negatively regulate MMPs. In some embodiments, a recombinant oncolytic virus reduces the expression of a TIMP selected from TIMP1, TIMP2, TIMP3 and TIMP4.

In some embodiments, the recombinant oncolytic viruses described herein comprise at least one polynucleotide encoding a protein or an oligonucleotide that reduces the expression or function of a gene in the host cell genome. In some aspects, the gene is an oncogenic gene (e.g., a gene selected from the genes listed in Table 7). In some aspects, the gene encodes an oncogenic miR (e.g., a miRNA listed in Table 4), a microenvironment remodeling miR (e.g., a miRNA listed in Table 5), or a negative regulator of ECM-degradation (e.g., a TIMP). Reduction of gene expression and/or function may be accomplished by at the level of transcription (e.g., mutating, deleting, or silencing the genomic DNA sequence) or at the level of translation (e.g., by inhibiting the production of the gene product through mRNA degradation). In some embodiments, the recombinant oncolytic viruses described herein comprise one or more polynucleotides that encode for nucleases that reduce the expression or function of a gene by enabling the mutation, deletion, or repression of transcription of a gene sequence. In specific embodiments, the nuclease is selected from a Clustered Regulatory Interspaced Short Palindromic Repeats (CRISPR)-associated endonuclease, a zinc-finger nuclease (ZFN) or a Transcription activator-like effector nuclease (TALEN). In non-limiting examples, a CRISPR-associated endonuclease is selected from SpCas9, SpCas9-HF1, SpCas9-HF2, SpCas9-HF3, SpCas9-HF4, SaCas9, FnCpf, FnCas9, eSpCas9, C2C1, C2C3, Cpf1, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

Recombinant viral vectors of the invention may utilize the CRISPR (Clustered Regularly Interspaced Short Palindromic Repeats)/Cas (CRISPR Associated) nuclease system, which is an engineered nuclease system based on a bacterial system that can be used for mammalian genome engineering. Generally, the system comprises a Cas nuclease and a guide RNA (gRNA). The gRNA is comprised of two parts; a crispr-RNA (crRNA) that is specific for a target genomic DNA sequence, and a tracr RNA (trRNA) that facilitates Cas binding. The crRNA and trRNA may be present as separate RNA oligonucleotides, or may be present in the same RNA oligonucleotide, referred to as a single guide-RNA (sgRNA). As used herein, the term "guide RNA" or "gRNA" refers to either the combination of an individual trRNA and an individual crRNA or an sgRNA. See, e.g., Jinek et al. (2012) *Science* 337:816-821; Cong et al. (2013) *Science* 339:819-823; Mali et al. (2013) *Science* 339:823-826; Qi et al. (2013) Cell 152:1173-1183; Jinek et al. (2013), *eLife* 2:e00471; David Segal (2013) *eLife* 2:e00563; Ran et al. (2013) *Nature Protocols* 8(11):2281-2308; Zetsche et al. (2015) Cell 163 (3):759-771; PCT Publication Nos. WO 2007/025097, WO 2008/021207, WO 2010/011961, WO 2010/054108, WO 2010/054154, WO 2012/054726, WO 2012/149470, WO 2012/164565, WO 2013/098244, WO 2013/126794, WO 2013/141680, and WO 2013/142578; U.S. Patent Publication Nos. 2010-0093617, 2013-0011828, 2010-0257638, 2010-0076057, 2011-0217739, 2011-0300538, 2013-0288251, and 2012-0277120; and U.S. Pat. No. 8,546,553, each of which is incorporated herein by reference in its entirety.

Multiple class 1 CRISPR-Cas systems, which include the type I and type III systems, have been identified and functionally characterized in detail, revealing the complex architecture and dynamics of the effector complexes (Brouns et al., 2008, Marraffini and Sontheimer, 2008, Hale et al., 2009, Sinkunas et al., 2013, Jackson et al., 2014, Mulepati et al., 2014). In addition, several class 2-type II CRISPR-Cas systems that employ homologous RNA-guided endonucleases of the Cas9 family as effectors have also been identified and experimentally characterized (Barrangou et al., 2007, Garneau et al., 2010, Deltcheva et al., 2011, Sapranauskas et al., 2011, Jinek et al., 2012, Gasiunas et al., 2012). A second, putative class 2-type V CRISPR-Cas system has been recently identified in several bacterial genomes. The putative type V CRISPR-Cas systems contain a large, ~1,300 amino acid protein called Cpf1 (CRISPR from *Prevotella* and *Francisella* 1).

Figure 39:
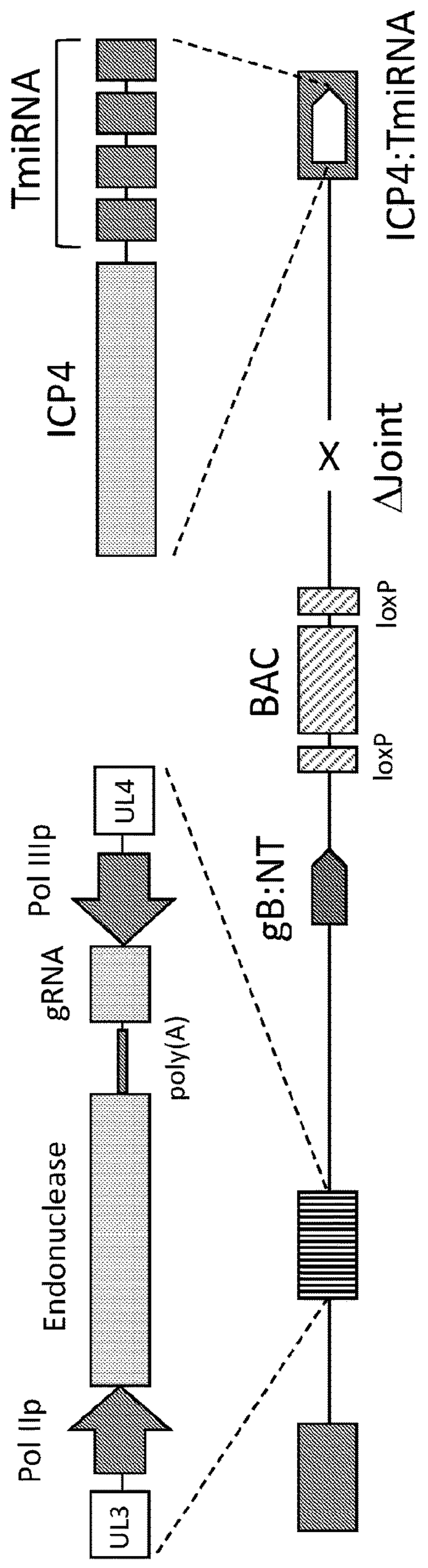
FIG. 39 shows a schematic of an ICP4-TmiRNA-attenuated, genome-editing HSV vector for the treatment of cancer. gB:NT: virus entry-enhancing double mutation in gB gene; BAC: loxP-flanked choramphenicol-resistance and lacZ sequences; Δjoint: deletion of the complete internal repeat region including one copy of the ICP4 gene; ICP4: TmiRNA: insertion of miRNA target sequences (e.g. let-7, miR-34a, miR-101, miR-125b, miR-145) into the 3' UTR of the remaining ICP4 gene (also may be placed in 5' UTR); Pol II promoter: Constitutive (CAG, UbC, EF1a, PGK) or cell-specific (e.g. TRPV1, Nav1.7, hSYN); Endonuclease.

In some embodiments, an oncolytic virus described herein further comprises at least one polynucleotide encoding a trRNA and crRNA targeted to the miRNA or the TIMP. In some cases, the at least one polynucleotide encoding a trRNA and crRNA is inserted into a locus on the viral genome. In some embodiments, the polynucleotide is an insulated sequence comprising a synthetic insulator or a native viral (e.g., HSV) insulator. In certain embodiments, an oncolytic virus is a herpes simplex virus and the at least one polynucleotide encoding an RNA binding site is inserted into or between one or more loci including the internal repeat joint region (comprising one copy each of the diploid genes ICP0, ICP34.5, LAT, ICP4, and the ICP47 promoter), ICP0, LAT, UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, USB, US9, US10, US11, and US12. In one embodiment, an oncolytic virus is a herpes simplex virus (HSV) and the at least one polynucleotide encoding an RNA binding site is inserted into a locus between the UL3 and the UL4 open reading frames (e.g., FIG. 39 and FIG. 40).

In some embodiments, the recombinant oncolytic virus comprises at least one polynucleotide encoding a payload molecule that activate or enhances an anti-tumor immune response. In some embodiments, the payload molecule is a cytokine, a chemokine, an antibody or antigen binding fragment thereof, a bispecific T-cell engager (BiTE). For example, in some embodiments, the payload molecule is an antibody or antigen binding fragments thereof that bind to and inhibit immune checkpoint receptors (e.g. CTLA4, LAG3, PD1, PDL1, and others). In some embodiments, the payload molecule is an anti-PD1 antibody or antigen-binding fragment thereof, an anti-PDL1 antibody or antigen-binding fragment thereof, or an anti-CTLA4 antibody or antigen-binding fragment thereof.

In some embodiments, the payload molecule is a protein that binds to and activates a cell-surface receptor. For example, in some embodiments, payload molecule comprises an endogenous cell-surface ligand, such as the extracellular domain of 41BBL, the extracellular domain of CD40L, FLT3L. In some embodiments, the payload molecule is a cytokine (e.g., IFNγ, IFNα, IFNβ, TNFα, IL-12, IL-2, IL-6, IL-8, IL-15, GM-CSF, IL-21, IL-35, TGFβ, and others) or chemokine (e.g., CCL4, CXCL10, CCL5, CXCL13, or XCL1).

In some embodiments, the payload molecule is a protein that binding to and activate an activating receptor (e.g., FcγRI, FcγIIa, FcγIIIa, costimulatory receptors, and others). In particular embodiments, the protein is selected from EpCAM, folate, A2A, anti-FGF2, anti-FGFR/FGFR2b, anti-SEMA4D, CD137, CD200, CD38, CD44, CSF-1R, endothelin B Receptor, ISRE7, LFA-1, NG2 (also known as SPEG4), SMADs, STING, and VCAM1.

In certain embodiments, a polynucleotide encoding a protein or an oligonucleotide targeted to reduce expression of an miRNA, a gene, or a TIMP is inserted into a locus on the viral genome of a recombinant oncolytic virus. In some embodiments, the polynucleotide is an insulated sequence comprising a synthetic insulator or a native viral (e.g., HSV) insulator. In certain embodiments, the oncolytic virus is a herpes simplex virus and the at least one polynucleotide encoding an RNA binding site is inserted into or between one or more loci including the internal repeat joint region (comprising one copy each of the diploid genes ICP0, ICP34.5, LAT, ICP4, and the ICP47 promoter), ICP0, LAT, UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, US8, US9, US10, US11, and US12. In one embodiment, the virus is a herpes simplex virus (HSV) and the at least one polynucleotide is inserted into a locus between the UL3 and the UL4 open reading frames (see, e.g., FIG. 39 and FIG. 40).

In some embodiments, the recombinant oncolytic virus comprises at least one protease-activated antibody. Protease-activated antibodies, such as those described by Metz et al. (Protein Eng Des Sel, 25(10):571-80, 2012) are activated and bind only to targets following protease cleavage of a protective cap. In some instances, tumor microenvironments possess an array of proteases that are well differentiated from surrounding healthy tissues. For example, the protease cathepsin B is overexpressed in numerous cancers, including breast, cervix, colon, colorectal, gastric, head and neck, liver, lung, melanoma, ovarian, pancreatic, prostate, and thyroid cancer. The human degradome, comprised of a complete list of proteases synthesized by human cells, is made up of at least 569 proteases that are distributed into five broad classes (in order from greatest to least number): metalloproteinases (MMPs), serine, cysteine, threonine, and aspartic proteases (Lopez-Otin et al., Nat Rev Cancer, 7(10):800-8, 2007). In particular, protease antibodies specifically cleaved by MMPs can serve as an excellent means of targeting the recombinant viral vectors described herein to the tumor microenvironment, as MMPs are found in the extracellular and pericellular areas of the cell. Table 6 summarizes proteases that are overexpressed in cancers which can be exploited to enable specific binding of recombinant viral vectors pseudotyped with protease-activated antibodies.

In certain embodiments, the protease-activated antibody is incorporated into the viral glycoprotein envelope. Protease-activated antibodies can be incorporated into the glycoprotein envelope of a recombinant viral vector of the invention (e.g., an HSV vector) to increase the therapeutic index and reduce off-target infection. In the case of an HSV vector, in some embodiments, the glycoprotein may be gC or gD. In some embodiments, the recombinant oncolytic viruses described herein comprise at least one polynucleotide encoding a protease-activated antibody. In certain embodiments, a protease-activated antibody is activated by a protease selected from a cysteine cathepsin, an aspartic cathepsin, a kallikrein (hK), a serine protease, a caspase, a matrix metalloproteinase (MMP), and a disintegrin and metalloproteinase (ADAM). In some embodiments, a protease is selected from cathepsin K, cathepsin B, cathepsin L, cathepsin E, cathepsin D, hK1, PSA (hK3), hK10, hK15, uPA, uPAR, MMP-1, MMP-2, MMP-3, MMP-7, MMP-8, MMP-9, MMP-10, MMP-11, MMP-12, MMP-13, MMP-14, MMP-15, MMP-16, MMP-17, MMP-18, MMP-19, MMP-20, MMP-21, MMP-23A, MMP-23B, MMP-24, MMP-25, MMP-26, MMP-27, MMP-28, or a protease listed in Table 6.

In some embodiments, the protease-activated antibody binds a protein expressed more highly by cancer cells or in cancer microenvironments than by non-cancer cells or in non-cancer microenvironments. In certain aspects, a protease-activated antibody binds NKG2D, c-met, HGFR, CD8, heparan sulfate, VSPG4 (also known as NG2), EGFR, EGFRvIII, CD133, CXCR4, carcinoembryonic antigen (CEA), CLC-3, annexin II, human transferrin receptor, or EpCAM. In certain instances, multiple protease activated antibodies may be incorporated into a single viral vector particle to ensure that diverse tumor histotypes are targeted. For example, at least 1, 2, 3, 4, 6, 7, 8, 9, 10, or more protease activated antibodies may be incorporated into the viral glycoprotein envelope. In some embodiments, the recombinant oncolytic virus comprises at least 1, 2, 3, 4, 5, 6, 7, 8, 9, 10, or more polynucleotides that encodes for at least 1, 2, 3, 4, 5, 6, 7, 8, 9, 10, or more protease activated antibodies. In some embodiments, an oncolytic virus comprises a first protease-activated antibody that binds a first protein expressed more highly by cancer cells or in cancer microenvironments than by non-cancer cells or in non-cancer microenvironments, and a second protease-activated antibody that binds a second protein expressed more highly by cancer cells or in cancer microenvironments than by non-cancer cells or in non-cancer microenvironments. In further embodiments, an oncolytic virus comprises a plurality of protease-activated antibodies binding a plurality of protein expressed more highly by cancer cells or in cancer microenvironments than by non-cancer cells or in non-cancer microenvironments. An oncolytic virus comprises, for example, a protease-activated antibody that is a human antibody, a humanized antibody or a chimeric antibody. In some embodiments, an oncolytic virus comprises an antibody that is a full-length immunoglobulin, an scFv, a Fab, a Fab', an F(ab')2, an Fv, a diabody, a triabody, a minibody, a single-domain antibody, or a multispecific antibody.

In some embodiments, a recombinant oncolytic virus comprises one or more of: one or more micro-RNA (miR) target sequences inserted into a locus of one or more viral genes required for viral replication; one or more polynucleotides encoding one or more proteins or oligonucleotides, wherein the proteins or oligonucleotides reduce the expression or inhibit the function of a miR, a gene, or a TIMP; at least one protease-activated antibody; and/or a polynucleotide encoding at least one protease activated antibody. In some embodiments, a recombinant oncolytic virus comprises: a plurality of copies of one or more miRNA target sequences inserted into a locus of a viral gene required for viral replication in non-cancerous cells; and/or a first polynucleotide encoding a protein or an oligonucleotide targeted to reduce expression of an oncogenic miRNA or an oncogenic gene; and/or a second polynucleotide encoding a protein or an oligonucleotide targeted to reduce expression of a microenvironment remodeling miRNA or a TIMP. In some embodiments, a recombinant oncolytic virus comprises: a plurality of copies of one or more miRNA target sequences inserted into a locus of a viral gene required for viral replication in non-cancerous cells; and/or a polynucleotide encoding a protein or an oligonucleotide targeted to reduce expression of an oncogenic miRNA or an oncogenic gene; and/or at least one protease-activated antibody. In further embodiments, a recombinant oncolytic virus comprises a plurality of copies of one or more miRNA target sequences inserted into a locus of a viral gene required for viral replication in non-cancerous cells; and/or a polynucleotide encoding a protein or an oligonucleotide targeted to reduce expression of a microenvironment remodeling miRNA or a TIMP; and/or at least one protease-activated antibody. In one embodiment, a recombinant oncolytic virus comprises a plurality of copies of one or more miRNA target sequences inserted into a locus of a viral gene required for viral replication in non-cancerous cells; and/or a first polynucleotide encoding a protein or an oligonucleotide targeted to reduce expression of an oncogenic miRNA or an oncogenic gene; and/or a second polynucleotide encoding a protein or an oligonucleotide targeted to reduce expression of a microenvironment remodeling miRNA or a TIMP; and/or at least one protease-activated antibody. In some specific embodiments, an oncolytic virus described in this paragraph is a herpes simplex virus and the viral gene required for viral replication in non-cancerous cells is UL1, UL5, UL6, UL7, UL8, UL9, UL11, UL12, UL14, UL15, UL17, UL18, UL19, UL20, UL22, UL25, UL26, UL26.5, UL27, UL28, UL29, UL30, UL31, UL32, UL33, UL34, UL35, UL36, UL37, UL38, UL39, UL40, UL42, UL48, UL49, UL52, UL53, UL54, ICP0, ICP4, ICP22, ICP27, ICP47, gamma-34.5, US3, US4, US5, US6, US7, USB, US9, US10, US11, and US12.

In certain aspects, the invention relates to a recombinant oncolytic virus comprising a first polynucleotide encoding a protein or an oligonucleotide targeted to reduce expression of an oncogenic miRNA or an oncogenic gene; and a second polynucleotide encoding a protein or an oligonucleotide targeted to reduce expression of a microenvironment remodeling miRNA or a TIMP. In other embodiments, a recombinant oncolytic virus comprises a polynucleotide encoding a protein or an oligonucleotide targeted to reduce expression of an oncogenic miRNA or an oncogenic gene; and at least one protease-activated antibody. In some embodiments, a recombinant oncolytic virus comprises a polynucleotide encoding a protein or an oligonucleotide targeted to reduce expression of a microenvironment remodeling miRNA or a TIMP; and at least one protease-activated antibody. In one embodiment, a recombinant oncolytic virus comprises a first polynucleotide encoding a protein or an oligonucleotide targeted to reduce expression of an oncogenic miRNA or an oncogenic gene; and/or a second polynucleotide encoding a protein or an oligonucleotide targeted to reduce expression of a microenvironment remodeling miRNA or a TIMP; and/or at least one protease-activated antibody.

In some embodiments, the oncolytic virus is an HSV virus comprising a first miR-TS cassette inserted into the 3' UTR of ICP4 comprising 4 target sequences for each of miR-124-3p, miR-1-3p, and miR-143-3p; a second miR-TS cassette inserted into the 3' UTR of ICP27 comprising 4 target sequences for each of miR-219a-5p, miR-122-5p, and miR128-3p; and a third miR-TS cassette inserted into the 3' UTR of UL8 comprising 4 target sequences for each of miR-137-3p, miR-208b-3p, and miR-126-3p. In some embodiments, the oncolytic virus further comprises a polynucleotide sequence encoding IL-12. In some embodiments, the oncolytic virus further comprises a polynucleotide sequence encoding IL-12 and MMP9. In some embodiments, the oncolytic virus further comprises a polynucleotide sequence encoding CXCL10. In some embodiments, the oncolytic virus further comprises a polynucleotide sequence encoding IL-12 and CXCL10. In some embodiments, the oncolytic virus further comprises a polynucleotide sequence encoding CXCL10 and MMP9. In some embodiments, the oncolytic virus further comprises a polynucleotide sequence encoding IL-12, CXCL10, and XCL1. In some embodiments, the oncolytic virus further comprises a polynucleotide sequence encoding IL-12, CXCL10, and CCL4. In some embodiments, the oncolytic virus further comprises a polynucleotide sequence encoding IL-12, CXCL10, and FLT3L. In some embodiments, the oncolytic virus further comprises a polynucleotide sequence encoding IL-12 and 41BBL. In some embodiments, the oncolytic virus further comprises a polynucleotide sequence encoding IL-12 and CD40L. In some embodiments, the oncolytic virus further comprises a polynucleotide sequence encoding 41BBL and CD40L. In some embodiments, the oncolytic virus further comprises a polynucleotide sequence encoding an anti-CTLA4 antibody or antigen binding fragment thereof. In some embodiments, the oncolytic virus further comprises a polynucleotide sequence encoding an anti-PD1 or anti-PDL1 antibody or antigen binding fragment thereof. In some embodiments, the oncolytic virus comprises a nucleic acid sequence that is at least 95%, 96%, 97%, 98%, or 99% identical to one of SEQ ID NOs: 843, 844, 847, or 848. In some embodiments, the the oncolytic virus comprises or consists of the nucleic acid sequence of one of SEQ ID NOs: 843, 844, 847, or 848.

In some embodiments, the oncolytic virus is an HSV virus comprising a first miR-TS cassette inserted into the 3' UTR of ICP4 comprising 4 target sequences for each of miR-124-3p, miR-1-3p, and miR-143-3p; a second miR-TS cassette inserted into the 3' UTR of ICP27 comprising 4 target sequences for each of miR-219a-5p, miR-122-5p, and miR128-3p; a third miR-TS cassette inserted into the 3' UTR of UL8 comprising 4 target sequences for each of miR-137-3p, miR-208b-3p, and miR-126-3p. In some embodiments, the oncolytic virus further comprises a polynucleotide sequence encoding IL-12. In some embodiments, the oncolytic virus further comprises a polynucleotide sequence encoding IL-12. In some embodiments, the oncolytic virus further comprises a polynucleotide sequence encoding IL-12 and MMP9. In some embodiments, the oncolytic virus further comprises a polynucleotide sequence encoding CXCL10. In some embodiments, the oncolytic virus further comprises a polynucleotide sequence encoding IL-12 and CXCL10. In some embodiments, the oncolytic virus further comprises a polynucleotide sequence encoding CXCL10 and MMP9. In some embodiments, the oncolytic virus further comprises a polynucleotide sequence encoding IL-12, CXCL10, and XCL1. In some embodiments, the oncolytic virus further comprises a polynucleotide sequence encoding IL-12, CXCL10, and CCL4. In some embodiments, the oncolytic virus further comprises a polynucleotide sequence encoding IL-12, CXCL10, and FLT3L. In some embodiments, the oncolytic virus further comprises a polynucleotide sequence encoding IL-12 and 41BBL. In some embodiments, the oncolytic virus further comprises a polynucleotide sequence encoding IL-12 and CD40L. In some embodiments, the oncolytic virus further comprises a polynucleotide sequence encoding 41BBL and CD40L. In some embodiments, the oncolytic virus further comprises a polynucleotide sequence encoding an anti-CTLA4 antibody or antigen binding fragment thereof. In some embodiments, the oncolytic virus further comprises a polynucleotide sequence encoding an anti-PD1 or anti-PDL1 antibody or antigen binding fragment thereof. In some embodiments, the oncolytic virus comprises a nucleic acid sequence that is at least 95%, 96%, 97%, 98%, or 99% identical to SEQ ID NO: 845 or 846. In some embodiments, the the oncolytic virus comprises or consists of the nucleic acid sequence of one of SEQ ID NOs: 845 or 846.

In some embodiments, the oncolytic virus is an HSV virus comprising a first miR-TS cassette inserted into the 3' UTR of ICP4 comprising 4 target sequences for each of miR-124-3p, miR-1-3p, and miR-143-3p; a second miR-TS cassette inserted into the 3' UTR of ICP27 comprising 4 target sequences for each of miR-219a-5p, miR-122-5p, and miR128-3p; a third miR-TS cassette inserted into the 3' UTR of UL8 comprising 4 target sequences for each of miR-137-3p, miR-208b-3p, and miR-126-3p; and a fourth miR-TS cassette inserted into the 3' UTR of ICP34.5 comprising 4 target sequences for each of miR-128-3p, miR-204-5p, and miR-219a-5p. In some embodiments, the oncolytic virus further comprises a polynucleotide sequence encoding IL-12. In some embodiments, the oncolytic virus further comprises a polynucleotide sequence encoding IL-12. In some embodiments, the oncolytic virus further comprises a polynucleotide sequence encoding IL-12 and MMP9. In some embodiments, the oncolytic virus further comprises a polynucleotide sequence encoding CXCL10. In some embodiments, the oncolytic virus further comprises a polynucleotide sequence encoding IL-12 and CXCL10. In some embodiments, the oncolytic virus further comprises a polynucleotide sequence encoding CXCL10 and MMP9. In some embodiments, the oncolytic virus further comprises a polynucleotide sequence encoding IL-12, CXCL10, and XCL1. In some embodiments, the oncolytic virus further comprises a polynucleotide sequence encoding IL-12, CXCL10, and CCL4. In some embodiments, the oncolytic virus further comprises a polynucleotide sequence encoding IL-12, CXCL10, and FLT3L. In some embodiments, the oncolytic virus further comprises a polynucleotide sequence encoding IL-12 and 41BBL. In some embodiments, the oncolytic virus further comprises a polynucleotide sequence encoding IL-12 and CD40L. In some embodiments, the oncolytic virus further comprises a polynucleotide sequence encoding 41BBL and CD40L. In some embodiments, the oncolytic virus further comprises a polynucleotide sequence encoding an anti-CTLA4 antibody or antigen binding fragment thereof. In some embodiments, the oncolytic virus further comprises a polynucleotide sequence encoding an anti-PD1 or anti-PDL1 antibody or antigen binding fragment thereof. In some embodiments, the oncolytic virus comprises a nucleic acid sequence that is at least 95%, 96%, 97%, 98%, or 99% identical to SEQ ID NO: 850. In some embodiments, the the oncolytic virus comprises or consists of the nucleic acid sequence of SEQ ID NO: 850.

In some embodiments, the oncolytic virus is an HSV virus comprising a first miR-TS cassette inserted into the 3' UTR of ICP4 comprising 4 target sequences for each of miR-124-3p, miR-1-3p, and miR-143-3p; a second miR-TS cassette inserted into the 3' UTR of ICP27 comprising 4 target sequences for each of miR-219a-5p, miR-122-5p, and miR128-3p; a third miR-TS cassette inserted into the 3' UTR of UL8 comprising 4 target sequences for each of miR-137-3p, miR-217-5p, and miR-126-3p; and a fourth miR-TS cassette inserted into the 3' UTR of ICP34.5 comprising 4 target sequences for each of miR-128-3p, miR-204-5p, and miR-219a-5p. In some embodiments, the oncolytic virus further comprises a polynucleotide sequence encoding IL-12. In some embodiments, the oncolytic virus further comprises a polynucleotide sequence encoding IL-12. In some embodiments, the oncolytic virus further comprises a polynucleotide sequence encoding IL-12 and MMP9. In some embodiments, the oncolytic virus further comprises a polynucleotide sequence encoding CXCL10. In some embodiments, the oncolytic virus further comprises a polynucleotide sequence encoding IL-12 and CXCL10. In some embodiments, the oncolytic virus further comprises a polynucleotide sequence encoding CXCL10 and MMP9. In some embodiments, the oncolytic virus further comprises a polynucleotide sequence encoding IL-12, CXCL10, and XCL1. In some embodiments, the oncolytic virus further comprises a polynucleotide sequence encoding IL-12, CXCL10, and CCL4. In some embodiments, the oncolytic virus further comprises a polynucleotide sequence encoding IL-12, CXCL10, and FLT3L. In some embodiments, the oncolytic virus further comprises a polynucleotide sequence encoding IL-12 and 41BBL. In some embodiments, the oncolytic virus further comprises a polynucleotide sequence encoding IL-12 and CD40L. In some embodiments, the oncolytic virus further comprises a polynucleotide sequence encoding 41BBL and CD40L. In some embodiments, the oncolytic virus further comprises a polynucleotide sequence encoding an anti-CTLA4 antibody or antigen binding fragment thereof. In some embodiments, the oncolytic virus further comprises a polynucleotide sequence encoding an anti-PD1 or anti-PDL1 antibody or antigen binding fragment thereof. In some embodiments, the oncolytic virus comprises a nucleic acid sequence that is at least 95%, 96%, 97%, 98%, or 99% identical to SEQ ID NO: 849. In some embodiments, the the oncolytic virus comprises or consists of the nucleic acid sequence of SEQ ID NO: 849.

In some embodiments, the oncolytic virus is an HSV virus comprising a first miR-TS cassette inserted into the 3' UTR of ICP4 comprising 4 target sequences for each of miR-124-3p, miR-1-3p, and miR-143-3p; a second miR-TS cassette inserted into the 3' UTR of ICP27 comprising 4 target sequences for each of miR-219a-5p, miR-122-5p, and miR128-3p; a third miR-TS cassette inserted into the 3' UTR of UL8 comprising 4 target sequences for each of miR-137-3p, miR-217-5p, and miR-126-3p; and a fourth miR-TS cassette inserted into the 3' UTR of ICP34.5 comprising 4 target sequences for each of miR-128-3p, miR-204-5p, and miR-219a-5p. In some embodiments, the oncolytic virus further comprises a polynucleotide sequence encoding IL-12. In some embodiments, the oncolytic virus further comprises a polynucleotide sequence encoding IL-12. In some embodiments, the oncolytic virus further comprises a polynucleotide sequence encoding IL-12 and MMP9. In some embodiments, the oncolytic virus further comprises a polynucleotide sequence encoding CXCL10. In some embodiments, the oncolytic virus further comprises a polynucleotide sequence encoding IL-12 and CXCL10. In some embodiments, the oncolytic virus further comprises a polynucleotide sequence encoding CXCL10 and MMP9. In some embodiments, the oncolytic virus further comprises a polynucleotide sequence encoding IL-12, CXCL10, and XCL1. In some embodiments, the oncolytic virus further comprises a polynucleotide sequence encoding IL-12, CXCL10, and CCL4. In some embodiments, the oncolytic virus further comprises a polynucleotide sequence encoding IL-12, CXCL10, and FLT3L. In some embodiments, the oncolytic virus further comprises a polynucleotide sequence encoding IL-12 and 41BBL. In some embodiments, the oncolytic virus further comprises a polynucleotide sequence encoding IL-12 and CD40L. In some embodiments, the oncolytic virus further comprises a polynucleotide sequence encoding 41BBL and CD40L. In some embodiments, the oncolytic virus further comprises a polynucleotide sequence encoding an anti-CTLA4 antibody or antigen binding fragment thereof. In some embodiments, the oncolytic virus further comprises a polynucleotide sequence encoding an anti-PD1 or anti-PDL1 antibody or antigen binding fragment thereof. In some embodiments, the oncolytic virus comprises a nucleic acid sequence that is at least 95%, 96%, 97%, 98%, or 99% identical to SEQ ID NO: 851. In some embodiments, the the oncolytic virus comprises or consists of the nucleic acid sequence of SEQ ID NO: 851.

The invention also encompasses a nucleic acid molecule encoding an oncolytic virus described herein.

Compositions and Methods of Use

Certain aspects of the invention relate to stocks and compositions comprising the oncolytic viruses described herein. In some aspects, the invention relates to a viral stock comprising an oncolytic virus described herein. In some embodiments, a viral stock is a homogeneous stock. The preparation and analysis of viral stocks is well known in the art. For example, a viral stock can be manufactured in roller bottles containing cells transduced with the viral vector. The viral stock can then be purified on a continuous nycodenze gradient, and aliquotted and stored until needed. Viral stocks vary considerably in titer, depending largely on viral genotype and the protocol and cell lines used to prepare them.

In particular embodiments, the titer of a viral stock (e.g., an HSV-based vector viral stock) contemplated herein is at least about $10^5$ plaque-forming units (pfu), such as at least about $10^6$ pfu or even more preferably at least about 1 pfu. In certain embodiments, the titer can be at least about $10^8$ pfu, or at least about $10^9$ pfu, and high titer stocks of at least about $10^{10}$ pfu or at least about $10^{11}$ pfu are most preferred.

The invention further contemplates a composition comprising an oncolytic virus or a nucleic acid molecule described herein and a pharmaceutically acceptable carrier. The phrase "pharmaceutically-acceptable" refers to molecular entities and compositions that do not produce an allergic or similar untoward reaction when administered to a subject (e.g., a human). The term "composition" as used herein refers to a formulation of one or more oncolytic virus or a nucleic acid molecules described herein that is capable of being administered or delivered to a subject and/or a cell. Typically, formulations include all physiologically acceptable compositions including derivatives and/or prodrugs, solvates, stereoisomers, racemates, or tautomers thereof with any physiologically acceptable carriers, diluents, and/or excipients. A "therapeutic composition" or "pharmaceutical composition" (used interchangeably herein) is a composition of one or more agents capable of being administered or delivered to a patient and/or subject and/or cell for the treatment of a particular disease or disorder.

The compositions disclosed herein may be formulated in a neutral or salt form. "Pharmaceutically acceptable salt" includes both acid and base addition salts. Pharmaceutically-acceptable salts include the acid addition salts (formed with the free amino groups of the protein) and which are formed with inorganic acids such as, for example, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, ptoluenesulfonic acid, trifluoroacetic acid, undecylenic acid, and the like. Salts formed with the free carboxyl groups can also be derived from inorganic bases such as, for example, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

As used herein "pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, dispersion media, coatings, antibacterial and antifungal agents, isotonic and absorption delaying agents, and the like that are physiologically compatible, including pharmaceutically acceptable cell culture media and/or emulsifier which has been approved by the United States Food and Drug Administration as being acceptable for use in humans and/or domestic animals. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations. Except insofar as any conventional media and/or agent is incompatible with the agents of the present disclosure, its use in therapeutic compositions is contemplated. Supplementary active ingredients also can be incorporated into the compositions.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In one embodiment, a composition comprising a carrier is suitable for parenteral administration, e.g., intravascular (intravenous or intraarterial), intraperitoneal or intramuscular administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with a viral vector or nucleic acid molecule, use thereof in the pharmaceutical compositions of the invention is contemplated.

The compositions of the invention may comprise one or more polypeptides, polynucleotides, vectors comprising same, infected cells, etc., as described herein, formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., cytokines, growth factors, hormones, small molecules or various pharmaceutically-active agents. There is virtually no limit to other components that may also be included in the compositions, provided that the additional agents do not adversely affect the ability of the composition to deliver the intended therapy.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens. Upon formulation, solutions are administered in a manner compatible with the dosage formulation and in such amount as is therapeutically effective to result in an improvement or remediation of the symptoms. The formulations are easily administered in a variety of dosage forms such as ingestible solutions, drug release capsules and the like. Some variation in dosage can occur depending on the condition of the subject being treated. The person responsible for administration can, in any event, determine the appropriate dose for the individual subject. Moreover, for human administration, preparations meet sterility, general safety and purity standards as required by FDA Center for Biologics Evaluation and Research standards. The route of administration will vary, naturally, with the location and nature of the disease being treated, and may include, for example intradermal, transdermal, subdermal, parenteral, nasal, intravenous, intramuscular, intranasal, subcutaneous, percutaneous, intratracheal, intraperitoneal, intratumoral, perfusion, lavage, direct injection, and oral administration.

In certain circumstances it will be desirable to deliver the compositions, recombinant viral vectors, and nucleic acid molecules disclosed herein parenterally, intravenously, intramuscularly, or even intraperitoneally as described, for example, in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabenes, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington: The *Science* and Practice of Pharmacy, 20th Edition. Baltimore, Md.: Lippincott Williams & Wilkins, 2000). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain embodiments, the compositions may be delivered by intranasal sprays, inhalation, and/or other aerosol delivery vehicles. Methods for delivering polynucleotides and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, optionally mixing with CPP polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques. The formulations and compositions of the invention may comprise one or more polypeptides, polynucleotides, and small molecules, as described herein, formulated in pharmaceutically-acceptable or physiologically-acceptable solutions (e.g., culture medium) for administration to a cell or an animal, either alone, or in combination with one or more other modalities of therapy. It will also be understood that, if desired, the compositions of the invention may be administered in combination with other agents as well, such as, e.g., cells, other proteins or polypeptides or various pharmaceutically-active agents.

In a particular embodiment, a formulation or composition according to the present invention comprises a cell contacted with a combination of any number of polynucleotides or viral vectors, as contemplated herein.

In certain aspects, the present invention provides formulations or compositions suitable for the delivery of viral vector systems.

Exemplary formulations for ex vivo delivery may also include the use of various transfection agents known in the art, such as calcium phosphate, electroporation, heat shock and various liposome formulations (i.e., lipid-mediated transfection). Liposomes are lipid bilayers entrapping a fraction of aqueous fluid. DNA spontaneously associates to the external surface of cationic liposomes (by virtue of its charge) and these liposomes will interact with the cell membrane.

Particular embodiments of the invention may comprise other formulations, such as those that are well known in the pharmaceutical art, and are described, for example, in Remington: The Science and Practice of Pharmacy, 20th Edition. Baltimore, Md.: Lippincott Williams & Wilkins, 2000.

In certain aspects, the present invention provides pharmaceutically acceptable compositions which comprise a therapeutically effective amount of one or more viral vectors or polynucleotides, as described herein, formulated together with one or more pharmaceutically acceptable carriers (additives) and/or diluents (e.g., pharmaceutically acceptable cell culture medium). As used herein, a “therapeutically effective amount” refers to the amount of a composition or recombinant virus described herein required to achieve a desired physiologic and/or biological outcome. A “therapeutically effective amount” of a virus, a viral stock, or a composition may vary according to factors such as the disease state, age, sex, and weight of the individual, and the ability of the stem and progenitor cells to elicit a desired response in the individual. A therapeutically effective amount is also one in which any toxic or detrimental effects of the virus or transduced therapeutic cells are outweighed by the therapeutically beneficial effects. The term “therapeutically effective amount” includes an amount that is effective to “treat” a subject (e.g., a patient). The therapeutically effective amount may be quantified by the total number of plaque forming units (pfu) (e.g. at least $1e^1$ to at least $1e^{20}$, particularly about $1e^4$ to about $1e^{15}$, more particularly about $1e^6$ to about $1e^{12}$ pfu), or number of viral genomes (e.g. at least $1e^1$ to at least $1e^{20}$, particularly about $1e^4$ to about $1e^{15}$, more particularly about $1e^6$ to about $1e^{12}$ viral genomes). One of skill in the art will understand that the therapeutically effective amount will vary based on the type of virus being administered, nature of the formulation, route of administration, nature and/or severity of the disease to be treated, and/or general health and well-being of the subject.

Some aspects of the invention encompass a method of killing a cancerous cell, comprising exposing the cancerous cell to an oncolytic virus described herein or compositions thereof under conditions sufficient for the oncolytic virus to infect and replicate within said cancerous cell, and wherein replication of the oncolytic virus within the cancerous cell results in cell death. In certain embodiments, the cancerous cell has a reduced expression of a miR compared to a non-cancerous cell. In some embodiments, a cancerous cell killed by this method is in vivo. In certain embodiments, a cancerous cell killed by this method is within a tumor.

The invention relates to a method of treating cancer in a subject in need thereof, comprising administering a prophylactically effective amount or a therapeutically effective amount of an oncolytic virus, a viral stock, or a composition as described herein to the subject. A “subject,” as used herein, includes any animal that exhibits a symptom of a disease, disorder, or condition that can be treated with the recombinant viral vectors, compositions, and methods disclosed herein. Suitable subjects (e.g., patients) include laboratory animals (such as mouse, rat, rabbit, or guinea pig), farm animals (such as horse or cow), and domestic animals or pets (such as cat or dog). Non-human primates and, preferably, human patients, are included.

“Administration” refers herein to introducing an oncolytic virus, a viral stock, or a composition thereof into a subject or contacting an oncolytic virus, a viral stock, or a composition thereof with a cell and/or tissue. Administration can occur by injection, irrigation, inhalation, consumption, electro-osmosis, hemodialysis, iontophoresis, and other methods known in the art. The route of administration will vary, naturally, with the location and nature of the disease being treated, and may include, for example auricular, buccal, conjunctival, cutaneous, dental, endocervical, endosinusial, endotracheal, enteral, epidural, interstitial, intra-articular, intraarterial, intra-abdominal, intraauricular, intrabiliary, intrabronchial, intrabursal, intracavernous, intracerebral, intracisternal, intracorneal, intracronal, intracoronary, intracranial, intradermal, intradiscal, intraductal, intraduodenal, intraduodenal, intradural, intraepicardial, intraepidermal, intraesophageal, intragastric, intragingival, intrahepatic, intraileal, intralesional, intralingual, intraluminal, intralymphatic, intramammary, intramedulleray, intrameningeal, instramuscular, intranasal, intranodal, intraocular, intraomentum, intraovarian, intraperitoneal, intrapericardial, intrapleural, intraprostatic, intrapulmonary, intraruminal, intrasinal, intraspinal, intrasynovial, intratendinous, intratesticular, intratracheal, intrathecal, intrathoracic, intratubular, intratumoral, intratympanic, intrauterine, intraperitoneal, intravascular, intraventricular, intravesical, intravestibular, intravenous, intravitreal, larangeal, nasal, nasogastric, oral, ophthalmic, oropharyngeal, parenteral, percutaneous, periarticular, peridural, perineural, periodontal, respiratory, retrotubular, rectal, spinal, subarachnoid, subconjunctival, subcutaneous, subdermal, subgingival, sublingual, submucosal, subretinal, topical, transdermal, transendocardial, transmucosal, transplacental, trantracheal, transtympanic, ureteral, urethral, and/or vaginal perfusion, lavage, direct injection, and oral administration.

The term "treating" and "treatment" as used herein refers to administering to a subject a therapeutically effective amount of a recombinant virus or composition thereof as described herein so that the subject has an improvement in a disease or condition, or a symptom of the disease or condition. The improvement is any improvement or remediation of the disease or condition, or symptom of the disease or condition. The improvement is an observable or measurable improvement, or may be an improvement in the general feeling of well-being of the subject. Thus, one of skill in the art realizes that a treatment may improve the disease condition, but may not be a complete cure for the disease. A "prophylactically effective amount" refers to an amount of a virus, a viral stock, or a composition effective to achieve the desired prophylactic result. As used herein, "prophylaxis" can mean complete prevention of the symptoms of a disease, a delay in onset of the symptoms of a disease, or a lessening in the severity of subsequently developed disease symptoms. Typically, but not necessarily, since a prophylactic dose is used in subjects prior to or at an earlier stage of disease, the prophylactically effective amount is less than the therapeutically effective amount.

"Cancer" herein refers to or describes the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, leiomyosarcoma, chordoma, lymphangio sarcoma, lymphangioendotheliosarcoma, rhabdomyosarcoma, fibro sarcoma, myxosarcoma, chondrosarcoma), neuroendocrine tumors, mesothelioma, synovioma, schwannoma, meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwannoma, and other carcinomas, as well as head and neck cancer.

In certain embodiments, an oncolytic virus (e.g., an HSV), a viral stock, or a composition as described herein are used to treat a cancer selected from lung cancer (e.g., small cell lung cancer or non-small cell lung cancer), breast cancer, ovarian cancer, cervical cancer, prostate cancer, testicular cancer, colorectal cancer, colon cancer, pancreatic cancer, liver cancer (e.g., hepatocellular carcinoma (HCC)), gastric cancer, head and neck cancer, thyroid cancer, malignant glioma, glioblastoma, melanoma, B-cell chronic lymphocytic leukemia, diffuse large B-cell lymphoma (DLBCL), and marginal zone lymphoma (MZL).

In certain aspects, the invention relates to an oncolytic viral vector as shown in any one of the figures or embodiments disclosed herein.

EXAMPLES

The following examples for the purpose of illustrating various embodiments of the invention and are not meant to limit the present invention in any fashion. The present examples, along with the methods described herein, are exemplary, and are not intended as limitations on the scope of the invention. Alterations, modifications, and other changes to the described embodiments which are encompassed within the spirit of the invention as defined by the scope of the claims are specifically contemplated.

Example 1—miR Sequence Analysis of Normal and Malignant Cells

Differential miR expression is a hallmark of many cancers (Lu et al, Nature, 2005). Experiments were performed to determine the miRs that were mostly highly differentially expressed in eight different cancer cells lines. Differential expression was determined by comparisons to non-cancerous control tissues. In total, 108 samples were sequenced. Sample details are provided in Table 11.

TABLE 11

| Cancer Type | # of Cancer Cell Lines | # of Control Tissue Samples |
|---|---|---|
| Bladder | 8 | 4 |
| Colon | 8 | 3 |
| Breast | 12 | 4 |
| Pancreatic | 7 | 3 |
| Lung | 8 | 5 |
| Head and Neck | 6 | 6 |
| Schwannoma | 7 | 4* |
| Glioblastoma | 14 | 4* |
| Additional Controls | | |
| Normal Liver | 3 | |
| Normal Bone Marrow | 3 | |

*Same control samples used for both Schwannoma and glioblastoma analysis

To facilitate the identification of appropriate miRNA target sequences suitable for HSV attenuation in select cell types, miRNA sequence profiling of cancer lines and non-cancer control tissue was performed. Sequencing libraries of dicer-processed RNAs were generated for cancer and non-cancer cells, including bladder, colon, breast, pancreas, lung, head and neck, schwannoma, glioblastoma, brain, liver, and bone marrow. These miRNA sequencing libraries were normalized to total RNA, and sequenced using a HiSeq 2500 ultra-high throughput sequencing system with HiSeq V4 chemistry reagents for sequencing reads up to $3e^8$ reads/run (Illumina). FASTQ files from sequencing runs were analyzed using the miRNAs Analysis tool in Basespace (Illumina). Rankings were made by calculating the mean of normal, the mean of cancer and sorting the ratio of normal/cancer from high to low. Heat maps were generated with natural logarithmic values with zero and negative values converted to zero (scale: black is high, white is low expression). Normalized data across samples were expressed as normalized miRNA read counts in a given sample. Normalization is related to total number of reads in a given sample relative to other samples in the comparison.

Figure 1:
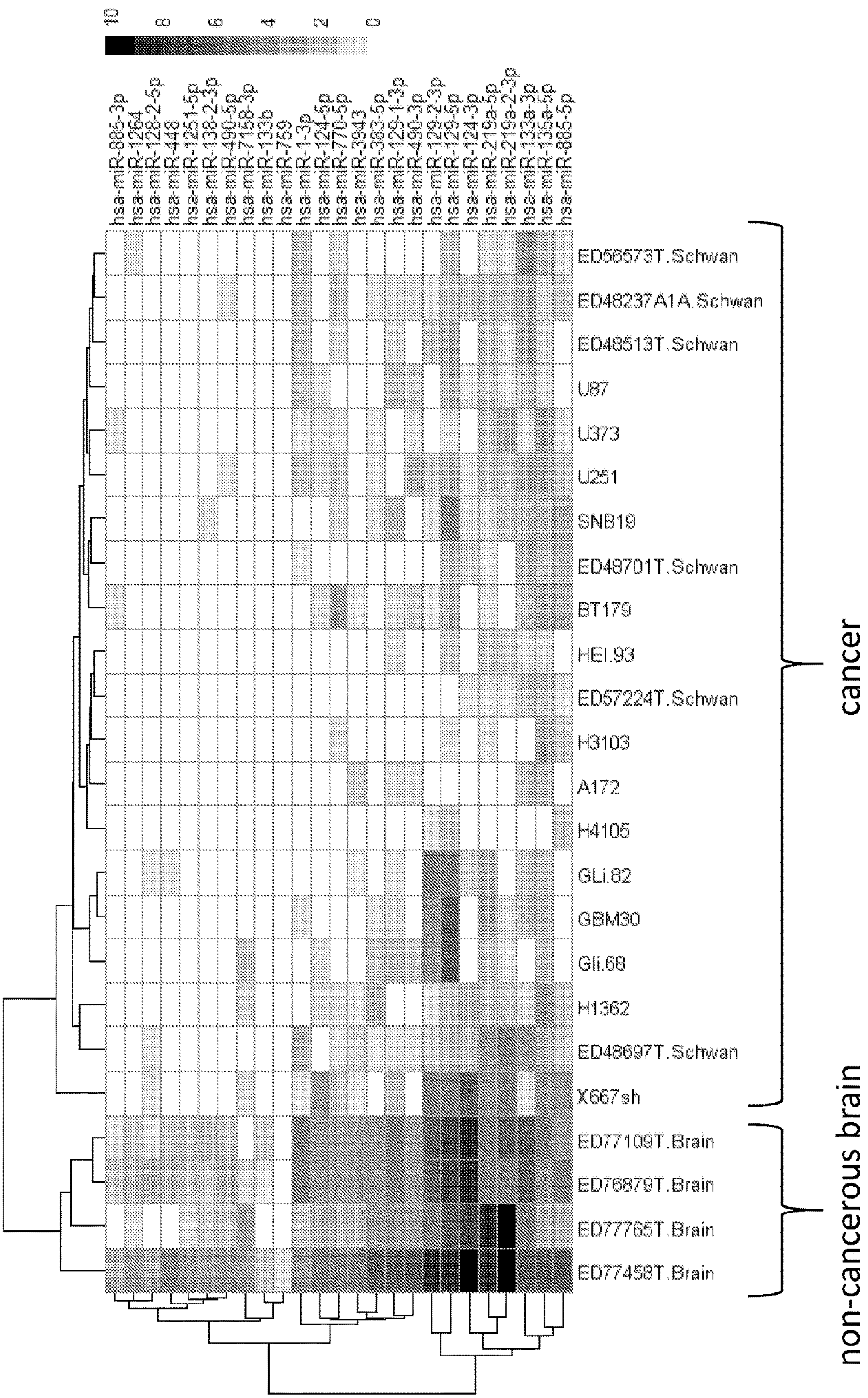
FIG. 1 illustrates a heat map of an miRNA expression profile in cancerous and non-cancerous brain tissue corresponding to 25 selected miRNAs.
Figure 2:
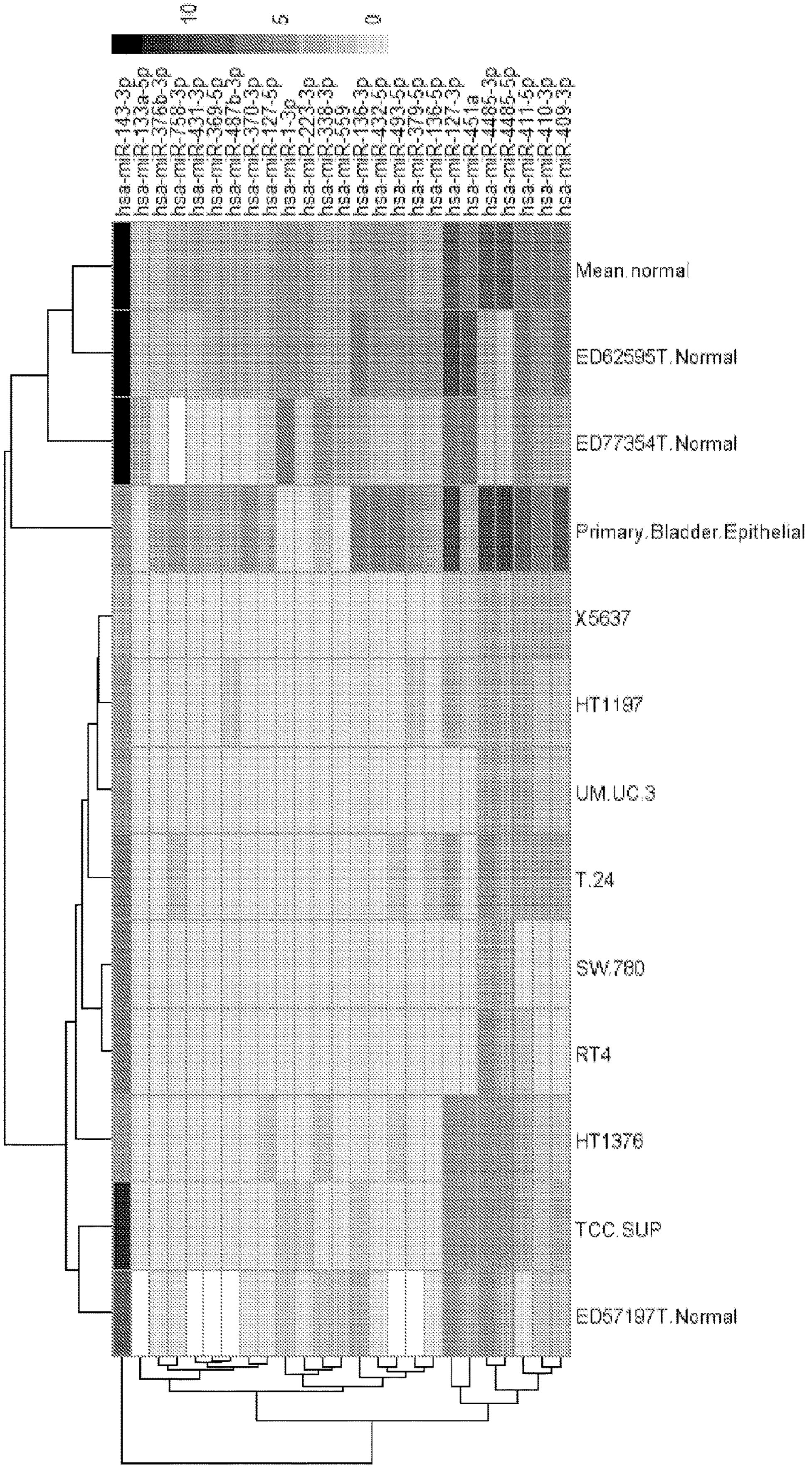
FIG. 2 illustrates a heat map of an miRNA expression profile in cancerous and non-cancerous bladder tissue corresponding to 25 selected miRNAs.
Figure 3:
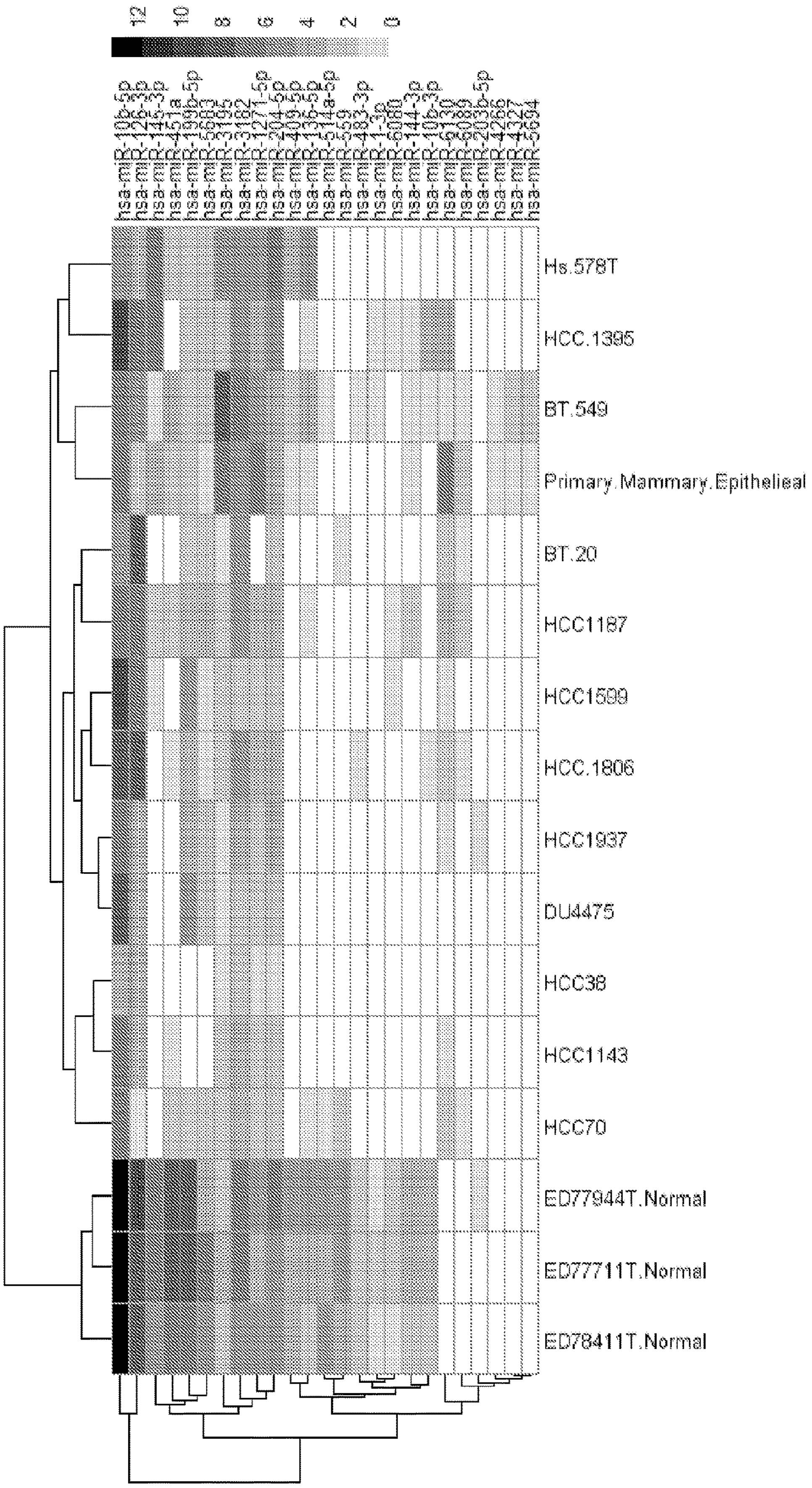
FIG. 3 illustrates a heat map of an miRNA expression profile in cancerous and non-cancerous breast tissue corresponding to 25 selected miRNAs.
Figure 4:
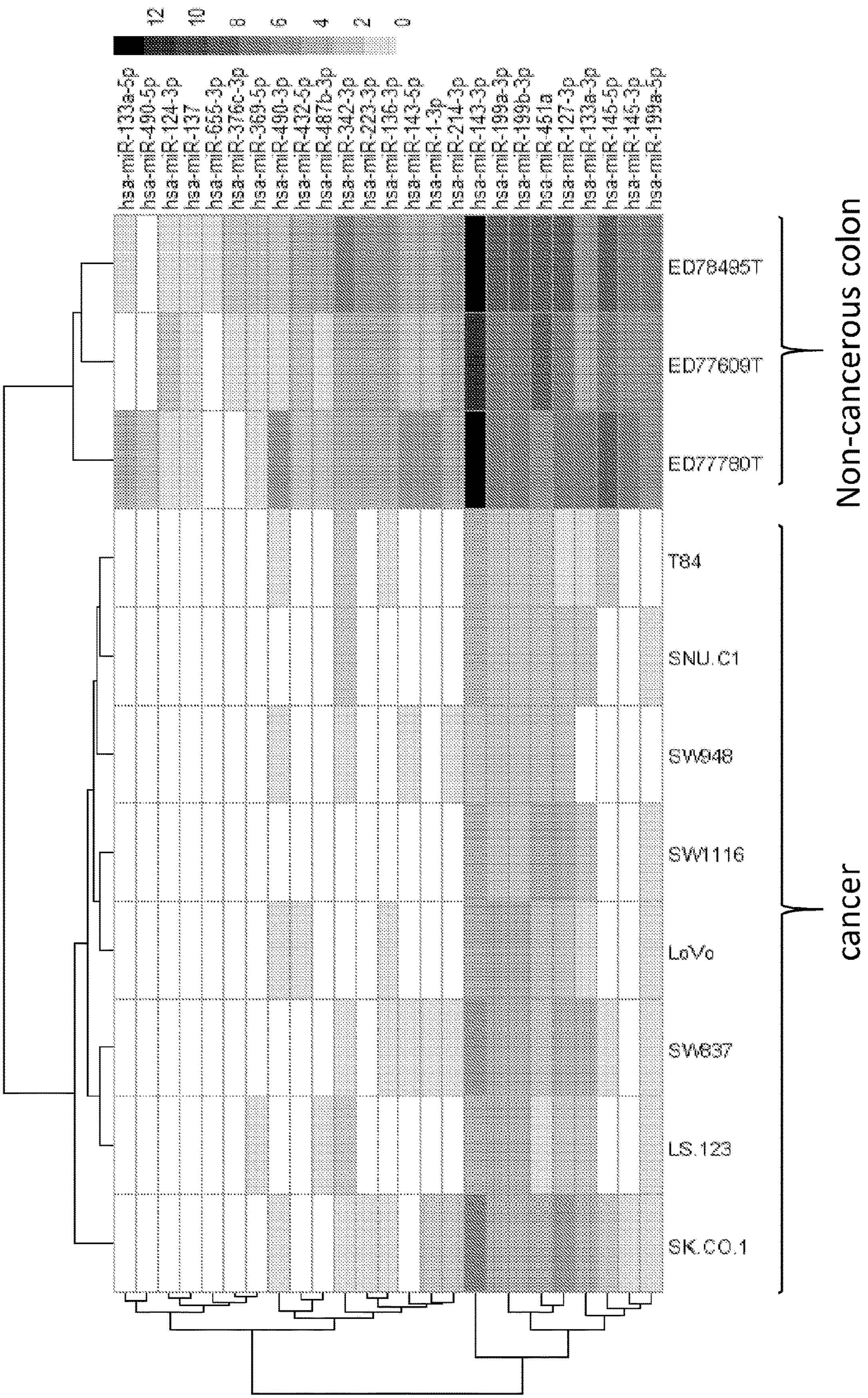
FIG. 4 illustrates a heat map of an miRNA expression profile in cancerous and non-cancerous colon tissue corresponding to 25 selected miRNAs.
Figure 5:
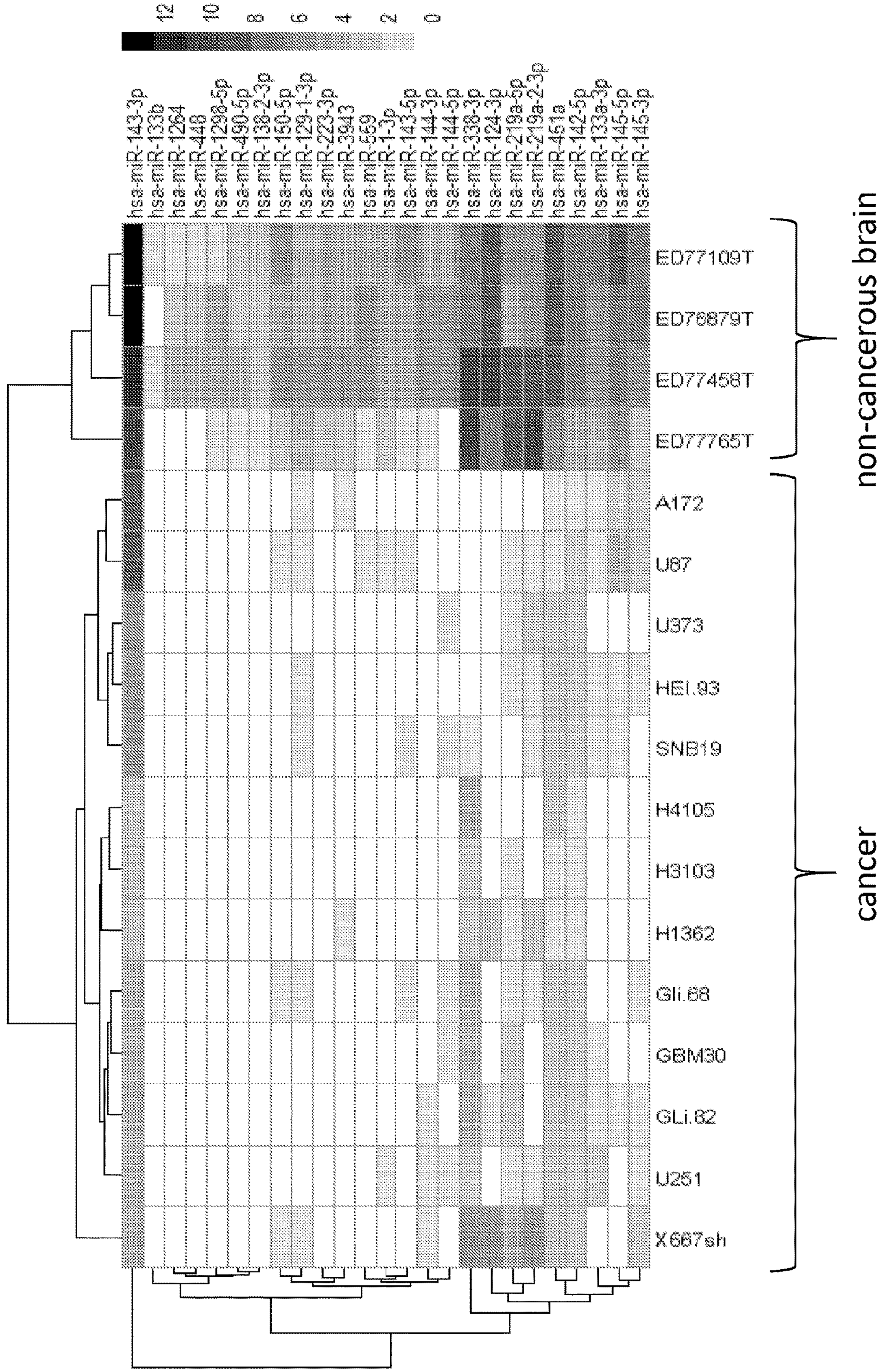
FIG. 5 illustrates a heat map of an miRNA expression profile in glioblastoma and non-cancerous brain tissue corresponding to 25 selected miRNAs.
Figure 6:
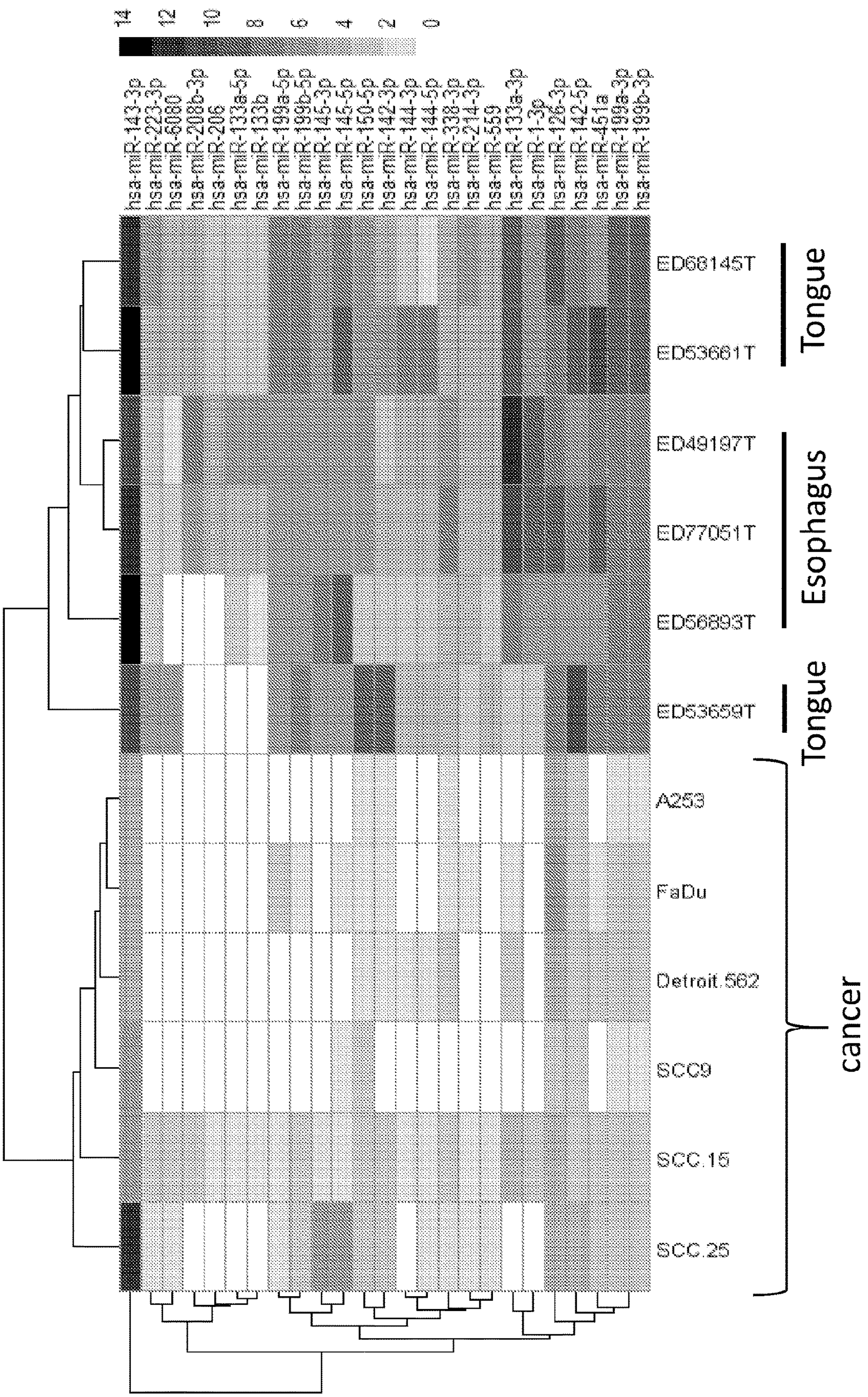
FIG. 6 illustrates a heat map of an miRNA expression profile in cancerous and non-cancerous head and neck tissue corresponding to 25 selected miRNAs.
Figure 7:
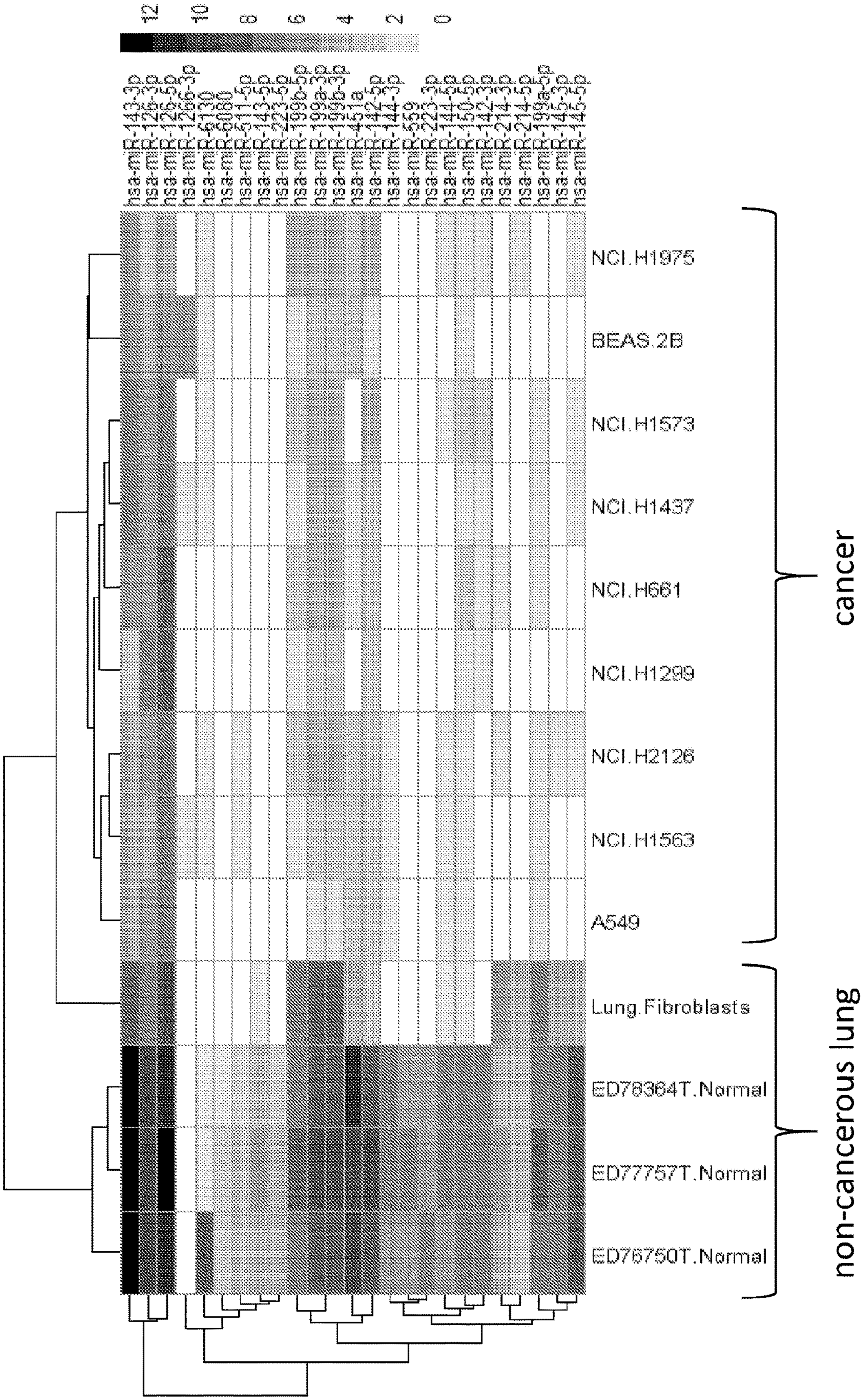
FIG. 7 illustrates a heat map of an miRNA expression profile in cancerous and non-cancerous lung tissue corresponding to 25 selected miRNAs.
Figure 8:
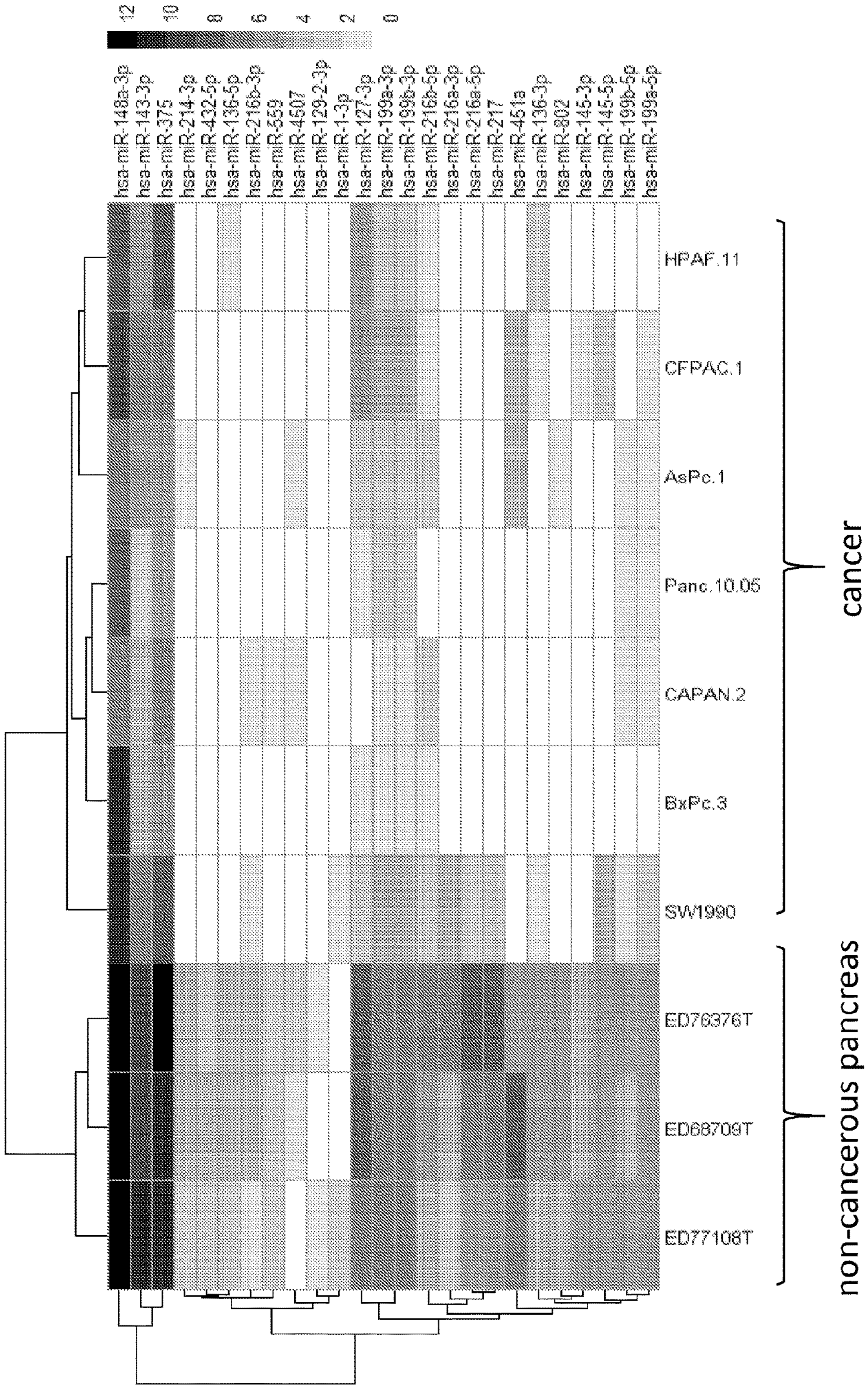
FIG. 8 illustrates a heat map of an miRNA expression profile in cancerous and non-cancerous pancreatic tissue corresponding to 25 selected miRNAs.
Figure 9:
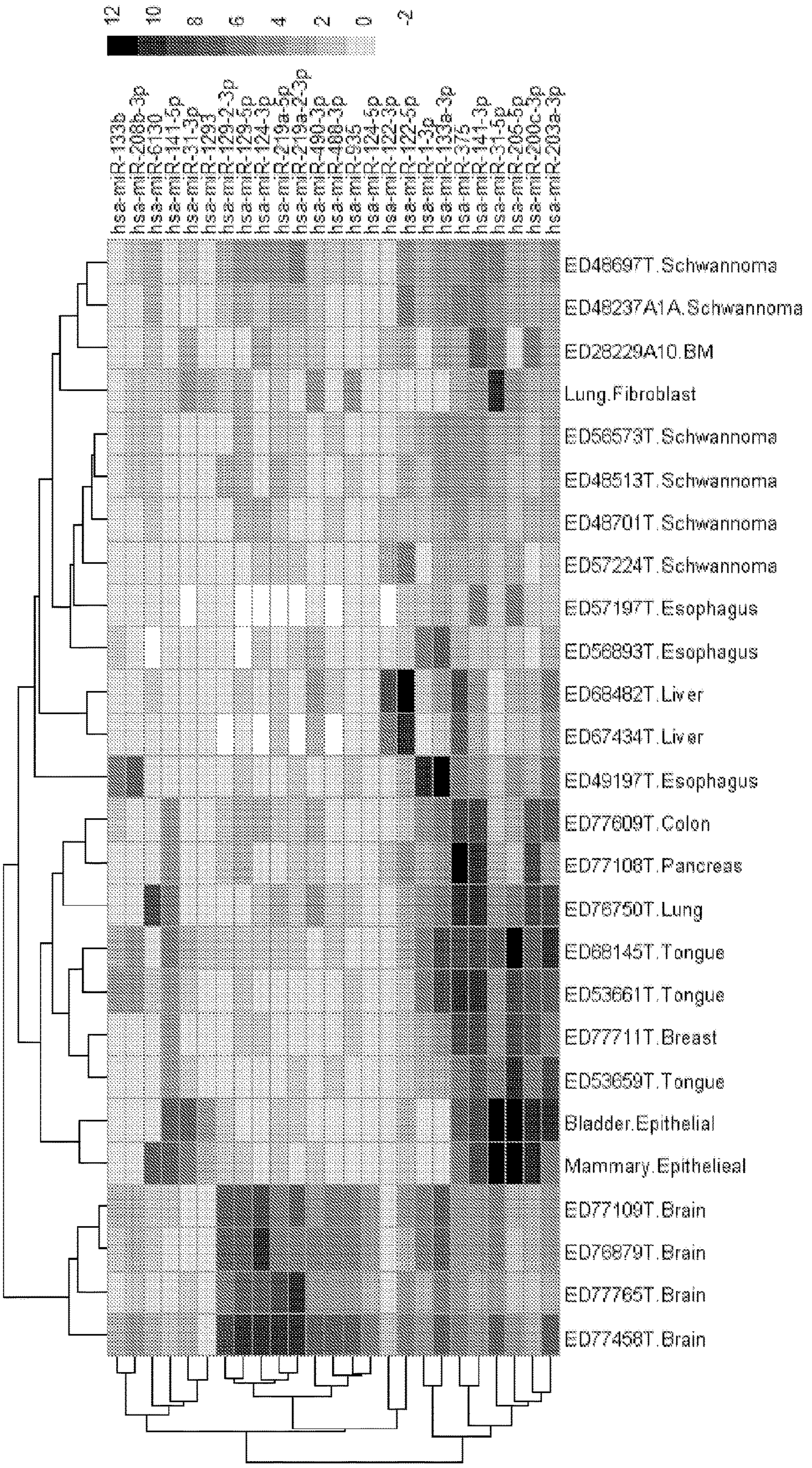
FIG. 9 illustrates a heat map of an miRNA expression profile in schwannoma and non-schwannoma tissue corresponding to 25 selected miRNAs.

FIG. 1 exemplifies the miRNA expression profile heat map in non-cancerous and cancerous brain tissue of twenty-five miRNAs. Additional examples of miRNA expression profile heat maps are shown for non-cancerous and cancerous bladder (FIG. 2), breast (FIG. 3), colon (FIG. 4), brain (FIG. 5), head and neck (FIG. 6), lung (FIG. 7), pancreas (FIG. 8), and schwannoma (FIG. 9) tissue corresponding to twenty-five miRNAs in each example. Table 12 shows a summary of the expression levels of particular miRs between cancerous and non-cancerous tissue. As shown, miR-451a levels are down regulated in all tumor types compared to non-cancerous tissue, representing a potential pan-tumor suppressor miRNA. miR-1-3p is down-regulated in all tumor types tested, present at moderate levels in non-cancerous tissue, and present at high levels in head and neck tissue. miR-559 is down-regulated in all tumor types tested, present generally at low levels in non-cancerous tissue, and present at high levels in non-cancerous lung tissue. miR-145-5p is down-regulated in all tumor types tested and present generally at high levels in the majority of non-cancerous tissue types tested. miR-143-3p is down-regulated in colon, lung, and pancreatic tumors, and is present at high levels in all normal tissue types and some breast tumor lines. miRNA data analysis revealed at least eleven miRNAs that represent novel and unexpected miRNA expression profiles not previously identified in the literature.

of broadly treating a variety of cancer types. Although the mean expression for miR-451a, miR-559, miR-1-3p, miR-145-3p, and miR143-3p was lower in cancer cell lines compared to normal controls, the decreased expression was not fully penetrant across all cancer cell lines. For example, ⅔ of the normal bladder samples tested showed increased expression of miR-145-3p, while expression in the remaining sample was substantially similar to the average observed in the cancer cell lines. Similar results were observed in breast cancer cell lines. Although the average read count for all breast cancer samples was 106, 5/12 samples had a normalized read count of >1000 counts, 2 of which were >40,000 counts.

These data indicate the potential to generate a single miR-attenuated oncolytic virus capable of targeting a broad array of tumor types. For example, a construct comprising target sequences for miR-124, miR-451a, miR-559, miR-1, and miR-145-3p may be used in the treatment of all the tumor types tested (e.g., bladder, colon, breast, pancreatic, lung, head and neck, Schwannoma, and glioblastoma). The variability in expression levels of miRs in different cancer types indicates the potential need to stratify patients by miR expression or through the use of an additional biomarker.

Figure 50:
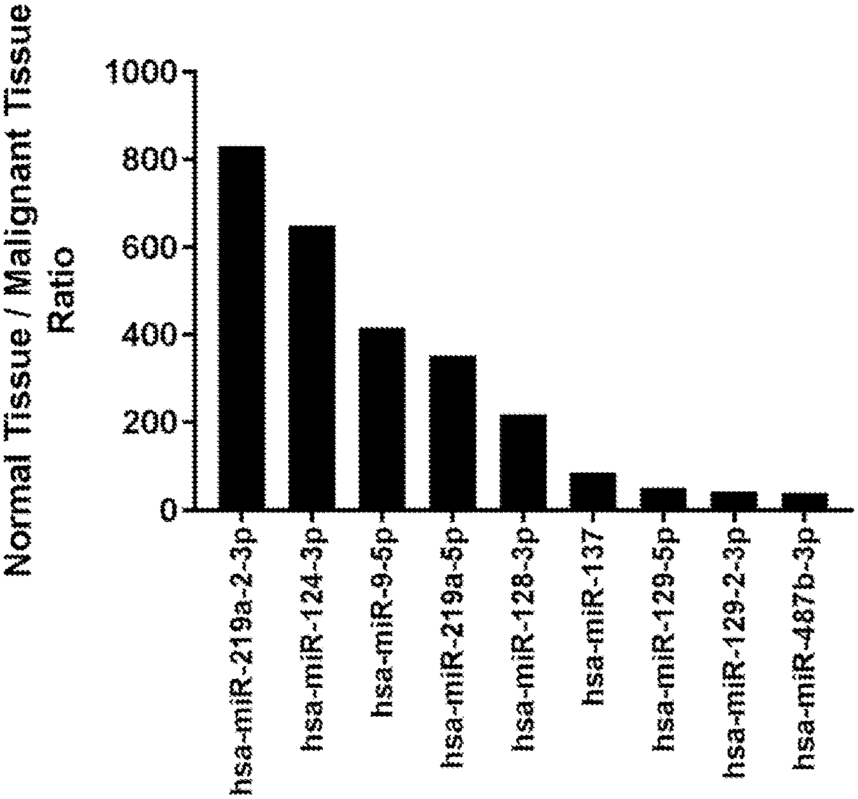

Additional miRNA profiling between cancerous and non-cancerous tissues was performed using a quantitative expression assay from Nanostring. The results of these experiments are shown for brain samples (FIG. 50), and demonstrate the identification of additional miRNAs that exhibit differential expression in cancerous and non-cancerous brain tissue that were not previously identified by the earlier studies outlined above, namely miR-9-5p, miR-128-3p, miR-137, miR-129-2-3p, and miR-487b-3p. Additional results are shown for heart samples (FIG. 51), demonstrating differential expression of miR-208b-3p, miR-1-3p, miR-208a-3p, miR133-3p, miR-4284, and miR-499a-5p between cancerous and non-cancerous heart tissue. Additional results are shown for peripheral nervous system samples (FIG. 52A-B), demonstrating differential expression of miR-204-5p, miR-1-3p, miR-206, miR-9-5p, miR-199b-5p, miR-145-5p, miR-100-5p, miR-574-3p. Specifically, miR-219a-2-3p, miR-9-5, miR-219a-5p, and miR-204-5p are differentially expressed in the spinal cord.

TABLE 12

| | miR-451a | | miR-1-3p | | miR-559 | | miR-145-5p | | miR-143-3p | |
|---|---|---|---|---|---|---|---|---|---|---|
| Tissue | Norm | Can | Norm | Can | Norm | Can | Norm | Can | Norm | Can |
| Bladder | 1402.9 | 21.1 | 175 | 0.8 | 14 | 0.4 | 971.5 | 39.8 | 489028.8 | 14904.6 |
| Breast | 2262.1 | 3.9 | 3 | 0.3 | 88.4 | 0.9 | 406.1 | 106.6 | 125943.9 | 91543.1 |
| Colon | 3606.9 | 22 | 149.3 | 1.6 | 40.8 | 2.1 | 1177.3 | 0.5 | 809955.6 | 193.9 |
| Glioma | 4269.7 | 16.7 | 75.2 | 1 | 162.7 | 0.4 | 2399.2 | 7.2 | 514114.8 | 1248.6 |
| Head & Neck | 11919.8 | 10.3 | 2846.6 | 2.6 | 71.2 | 2.2 | 690.9 | 30.4 | 331034.2 | 20706.2 |
| Lung | 31442 | 10.5 | 73.3 | 1.4 | 548.3 | 0.1 | 1547.5 | 1 | 436136.8 | 390.9 |
| Pancreatic | 1035.8 | 13.3 | 4.1 | 0.4 | 13.3 | 0.5 | 81.7 | 0.5 | 25557 | 269.8 |

Many of these identified miRNAs are pan- or multi-tumor specific. For example, expression of miR-451a, miR-559, miR-1-3p, miR-145-3p, and miR143-3p were generally down-regulated across all cancer cell lines tested compared to control tissues. This was particularly notable for miR-451a, which was highly expressed in all normal tissue type and substantially down-regulated in all cancer types, thus representing a pan-specific tumor-suppressive miRNA. The expression of miR-559 was lower in normal tissue types, except for normal lung tissue, and expression of miR-1-3p and mir-145-3p in normal tissue was variable. Despite the variability in the magnitude of differences and absolute expression levels, mean expression of each miR in cancer cells lines was substantially lower compared to levels in the corresponding normal tissues. These miRNAs are candidates for generating pan-tumor HSV virions that are capable

Example 2—Identification of Viral Genes for miR-T Attenuation siRNA screens were performed to test the attenuation phenotype HSV genes. An siRNA screen is the ideal modality to test RISC attenuation phenotype of immediate early genes, and select early genes. siRNAs targeting the HSV genes ICP27, ICP4, ICP0, UL5, UL8, UL9, ICP8, ULC39/40, ICP22, UL30, UL42, and VP19 were transfected individually and in pools into A253 cells. 24 hours after siRNA transfection, cells were infected with ONCR-003 or ONCR-010 (described below in Table 13), each of which comprise a GFP cassette. Viral spread was measured 48 hours post-infection by quantifying GFP intensity. HSV genes identified as potential hits were validated by Western blots, viral titer measurements, and RT-PCR.

The results of these screen are shown in FIGS. 47A and 47B. Individual siRNAs mediating >75% knockdown of the corresponding HSV gene are indicated by arrows in FIG. 47A and GFP intensity for a select subset of the siRNAs are shown in FIG. 47B. As shown in FIG. 48, siRNA-mediated knockdown of ICP4, UL5, UL8, ICP8, ICP22, and UL30 substantially reduced viral replication of ONCR-003 as indicated by a reduction in GFP intensity. Further, siRNA-mediated knockdown of ICP27, ICP4, UL5, UL8, UL9, ICP8, ICP22, and ICP30 substantially reduced viral replication of ONCR-010 as indicated by a reduction in GFP intensity. Cells infected with ONCR-010 were further analyzed by Western blot for expression of particular viral proteins. As shown in FIG. 49, significant reduction in these HSV genes was also observed at the protein level.

Figure 10A:
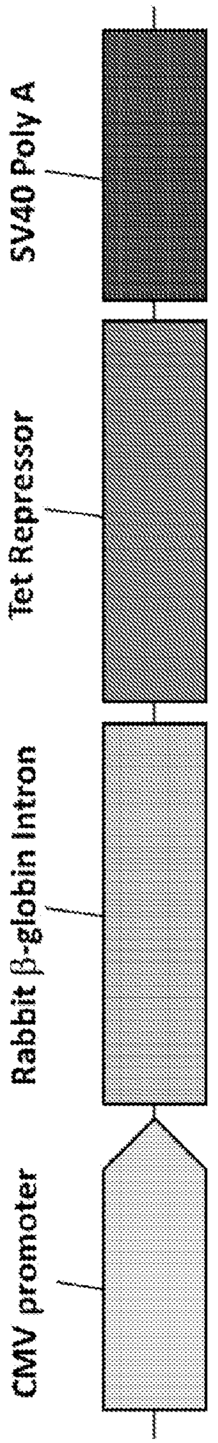
FIG. 10A-FIG. 10C illustrate an miRNA expression and attenuation reporter gene system described in Example 2.
Figure 10B:
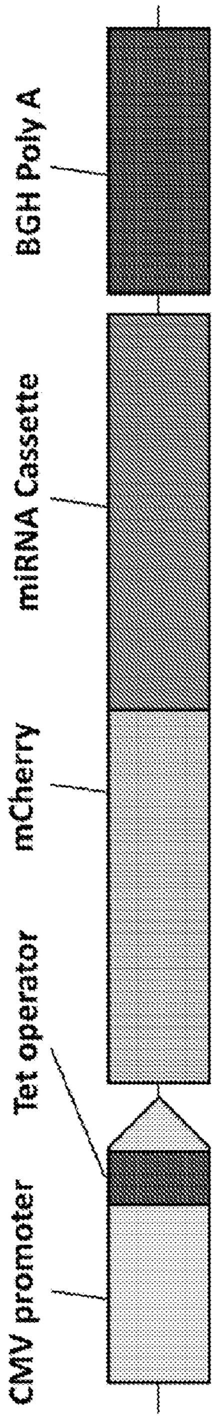
Figure 10C:
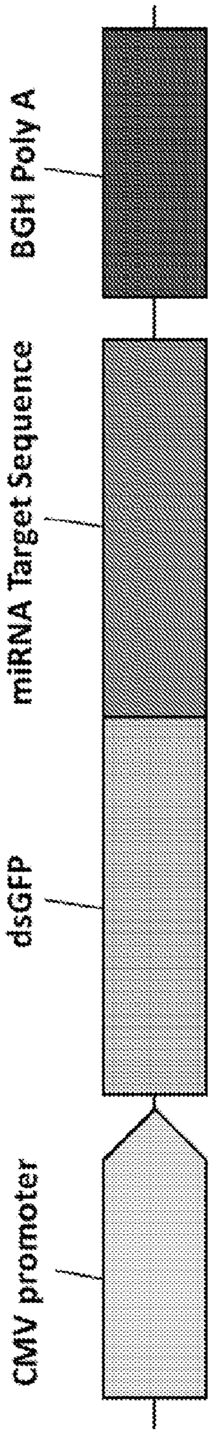

Example 3—Construction and Use of a Reporter System to Rapidly Assay miRNA-Based Gene Attenuation A reporter system was developed to assess miRNA-based gene attenuation using virtually any miRNA target sequence and cognate miRNA. In this system (shown in FIG. 10), the target sequence recognized by miRNAs (i.e. hsa-miR-122) was inserted into the 3' UTR of de-stabilized green fluorescent protein (dsGFP). The cognate miRNA was then expressed via a tetracycline (tet) inducible promoter using mCherry as a control for miRNA expression. All expression vectors were cloned into a tet repressible vector pcDNA5 Frt/To that also expresses mCherry (pTF002). All miRNAs for expression generated by gene synthesis from human genomic DNA and were cloned into pTF002. To generate attenuation reporter vectors, dsGFP was cloned into cDNA3.1+, generating vector pTF004. Attenuation vectors contain four tandem repeats of the reverse complement of the miRNA sequence of interest separated by 8-16 nucleotides. Plasmids were constructed by insertion of synthetically generated oligonucleotides into the 3'UTR of the dsGFP gene of pTF004 using standard molecular biology techniques. On day one, HEK293TetR cells were transfected with the miRNA attenuation and reporter expression plasmids (0.15 μg each, for a total of 0.3 μg of CMV promotor-containing plasmid) using Lipofectamine 2000 per manufacturers protocol (Invitrogen). On day two, cells were treated with Tetracycline at 5 ng/ml and allowed to incubate for up to 72 hours. After incubation, GFP and mCherry fluorescence signals were detected daily using a SpectraMax® i3x Minimax multi-mode microplate reader (Molecular Devices) and analyzed using Softmax Pro or Metamorph imaging software (Molecular Devices). Phase images were acquired with an exposure of 5-6 ms. Fluorescence images were acquired with a GFP (541 nm channel) exposure of 10 ms, and an mCherry (713 nm channel) of 200-1500 ms.

Figure 11:
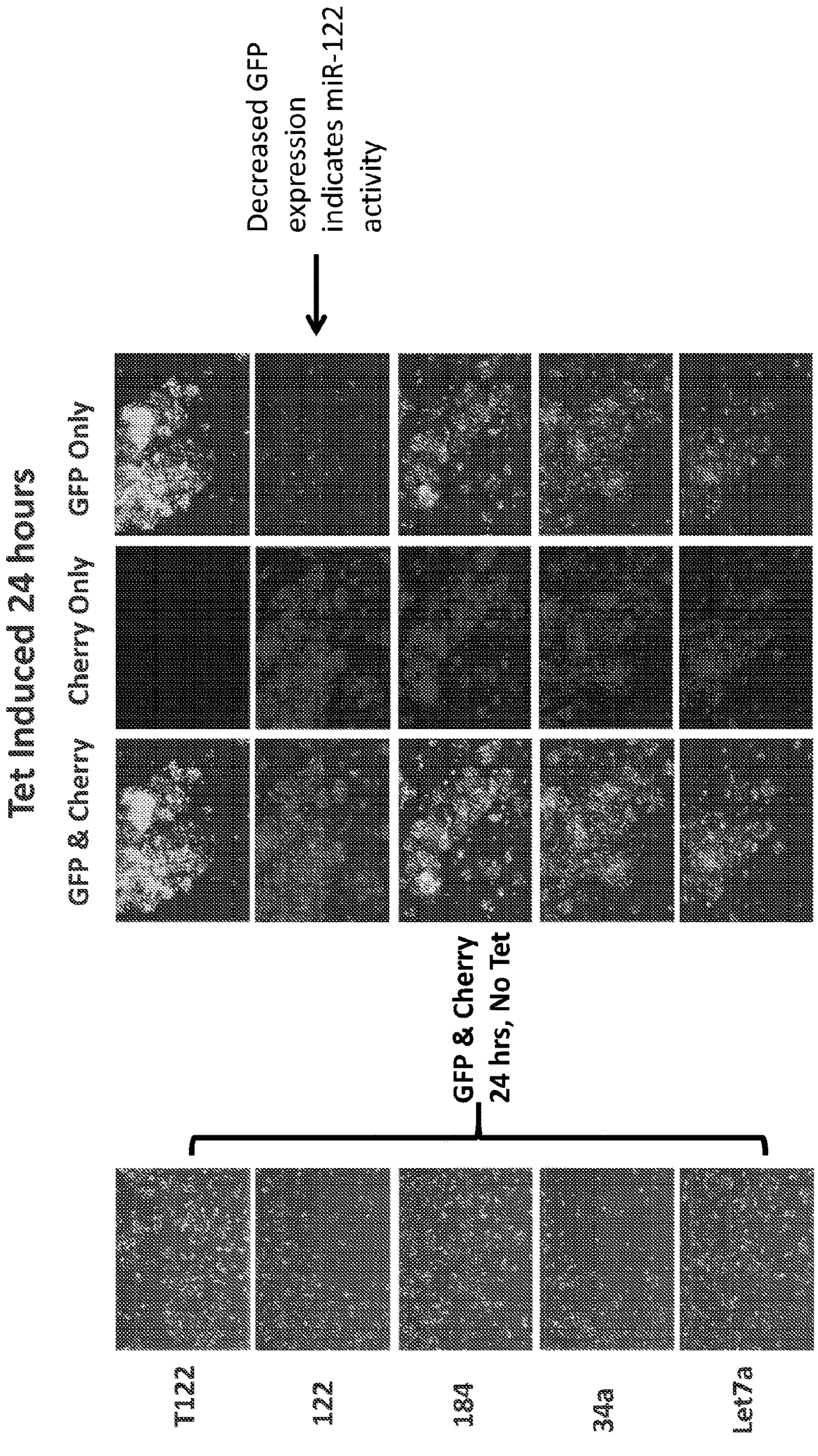
FIG. 11 illustrates miR-122 expression and attenuation using the reporter system shown in FIG. 10 and described in Example 2.
Figure 12:
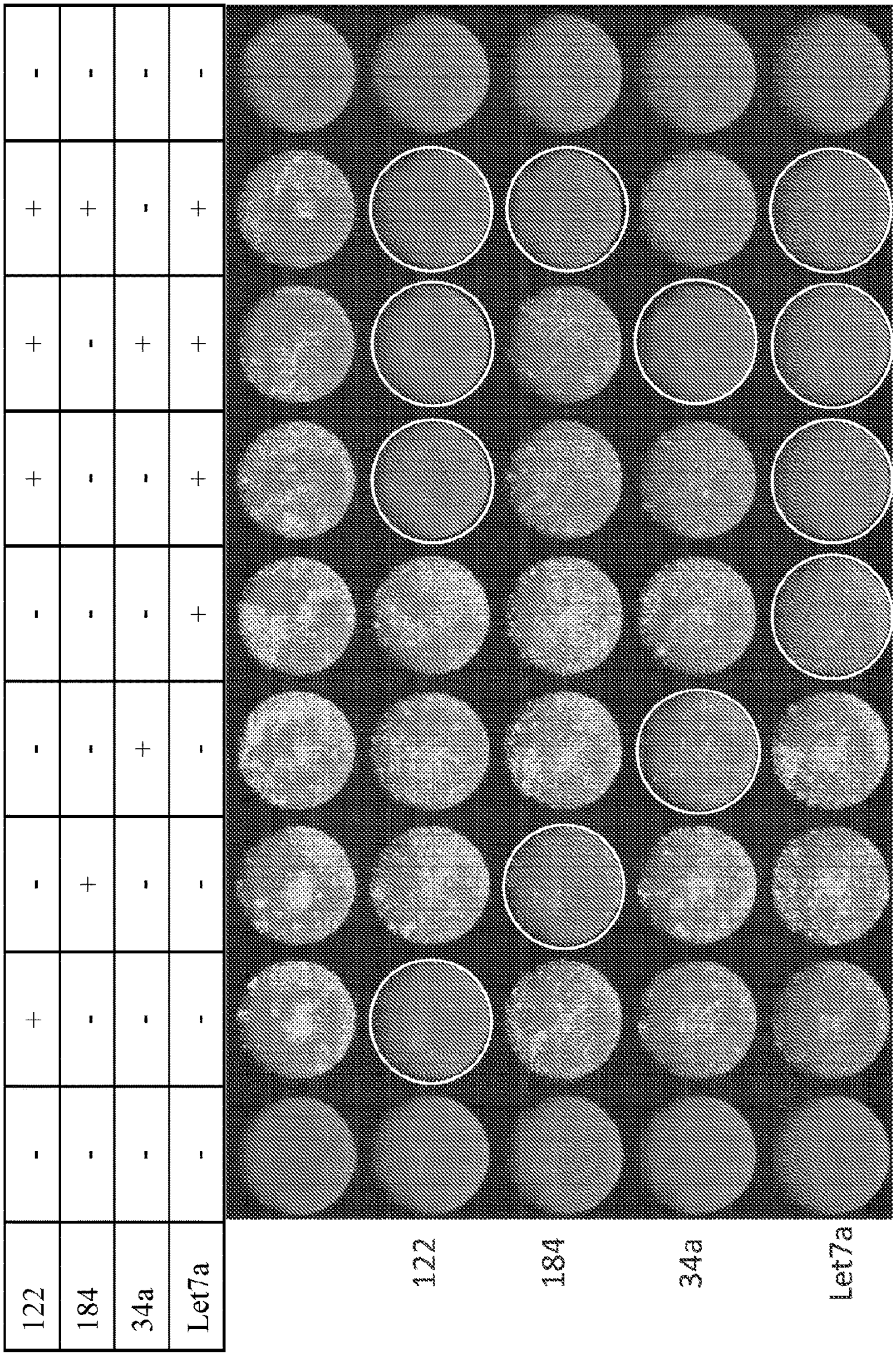
FIG. 12 illustrates miR-122, miR-184, miR-34a, and Let7a-mediated GFP attenuation using the reporter system shown in FIG. 10 and described in Example 2. Circled wells indicate reduced GFP expression levels.
Figure 13:
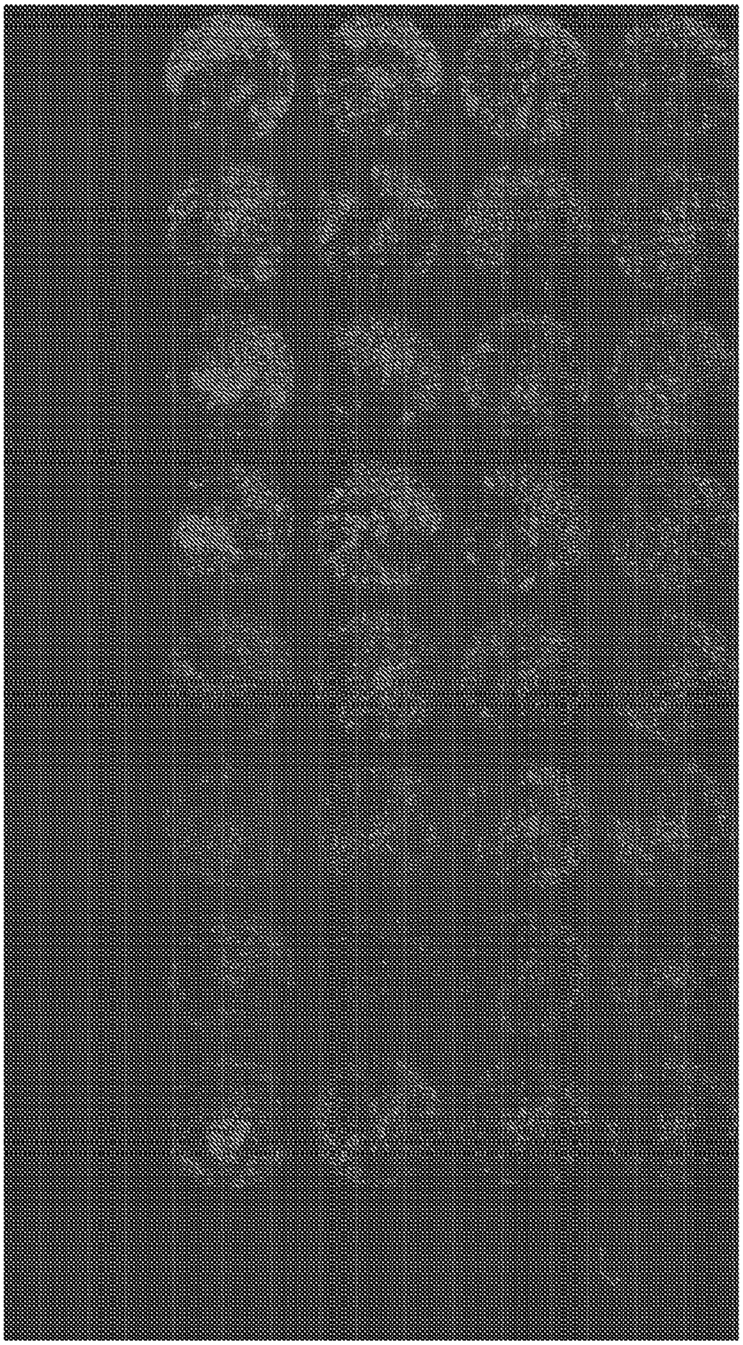
FIG. 13 illustrates expression of miR-122, miR-184, miR-34a, and Let7a, indicated by mCherry expression, using the reporter system shown in FIG. 10 and described in Example 2.
Figure 14:
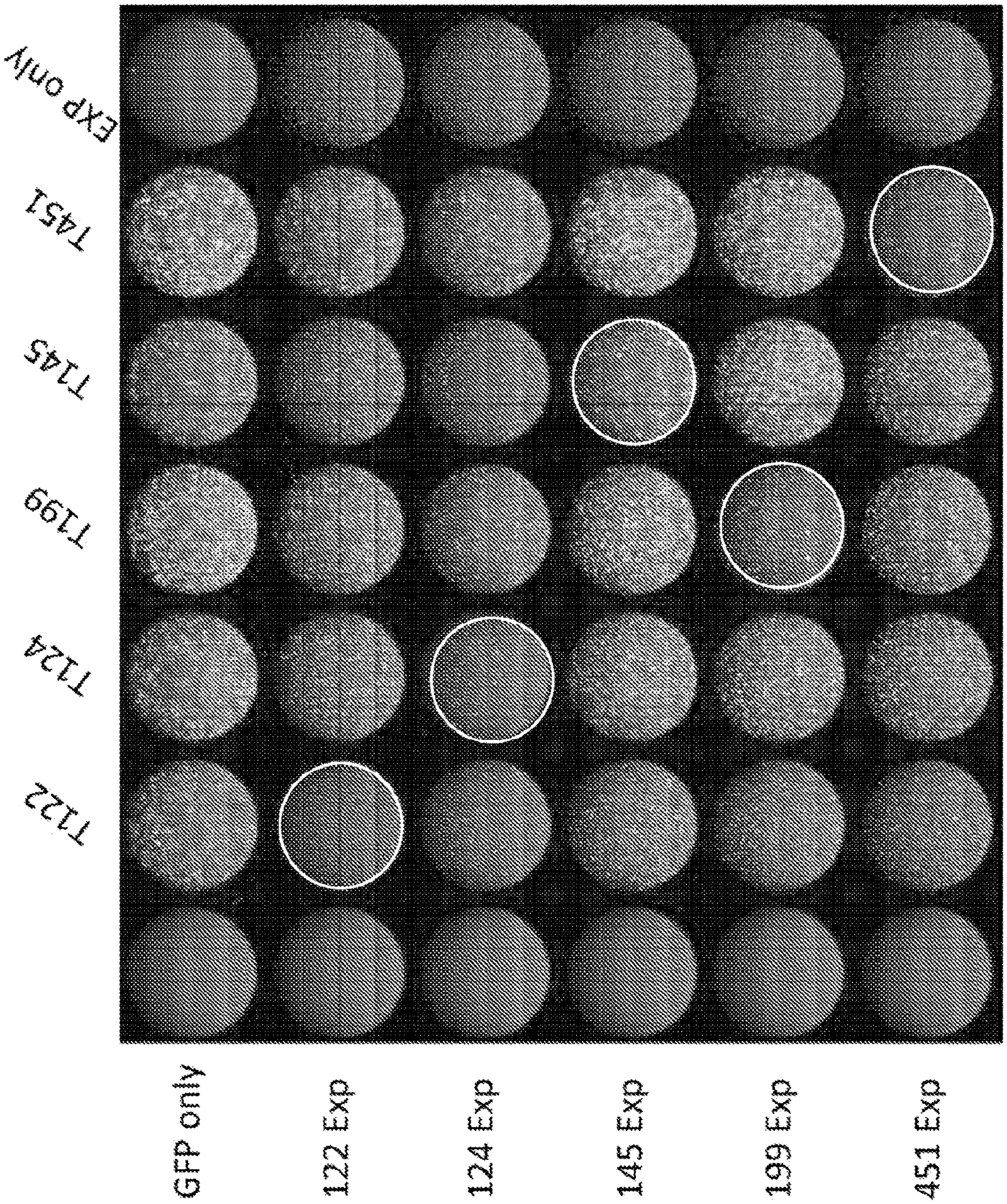
FIG. 14 illustrates miR-122, miR-124, miR-145, miR-199, and miR-451-mediated GFP attenuation using the reporter system shown in FIG. 10 and described in Example 2. Circled wells indicate reduced GFP expression levels.
Figure 15:
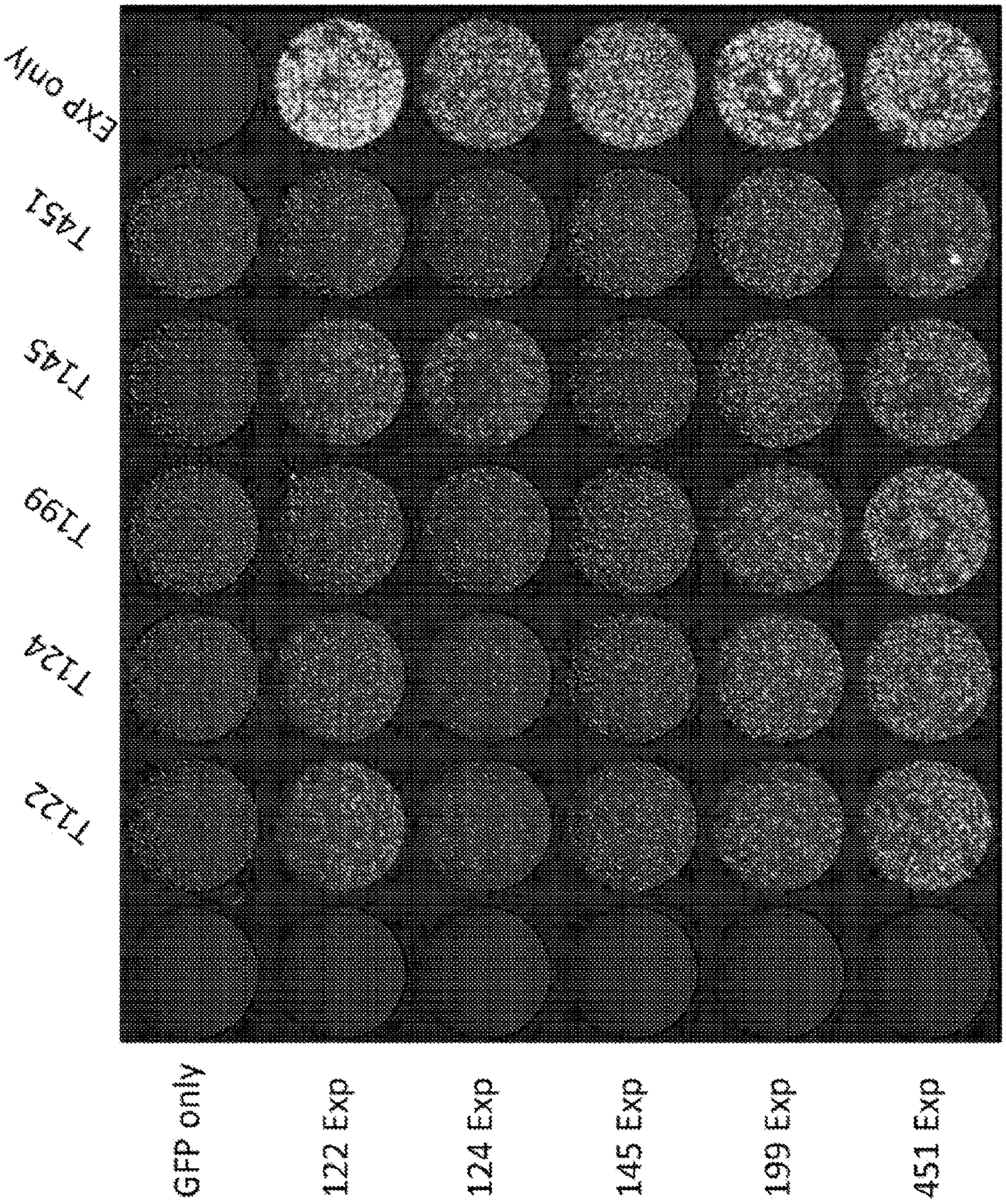
FIG. 15 illustrates expression of miR-122, miR-124, miR-145, miR-199, and miR-451, indicated by mCherry expression, using the reporter system shown in FIG. 10 and described in Example 2.
Figure 17:
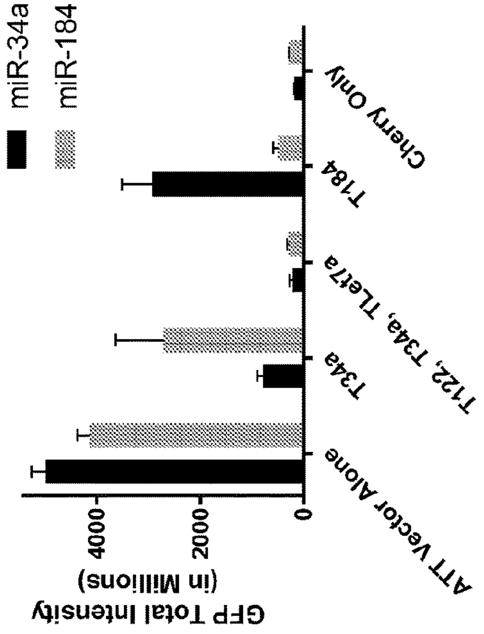
FIG. 17 shows quantitation of miR-34a and miR-184-attenuated GFP fluorescence.
Figure 16:
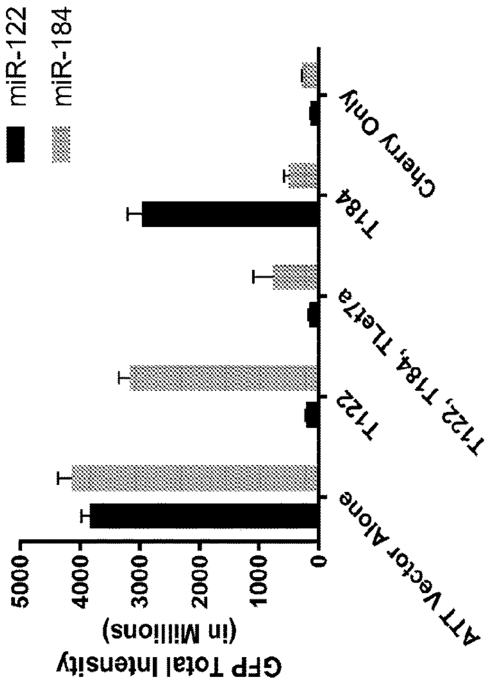
FIG. 16 shows quantitation of miR-122 and miR-184-attenuated GFP fluorescence.
Figure 18:
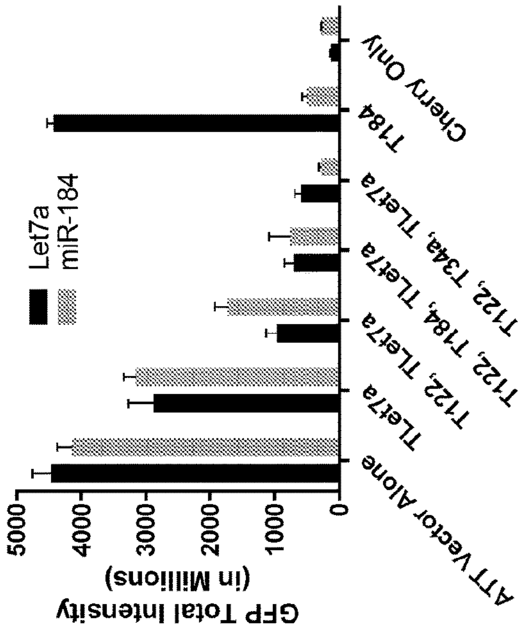
FIG. 18 shows quantitation of Let7a and miR-184-attenuated GFP fluorescence.
Figure 20:
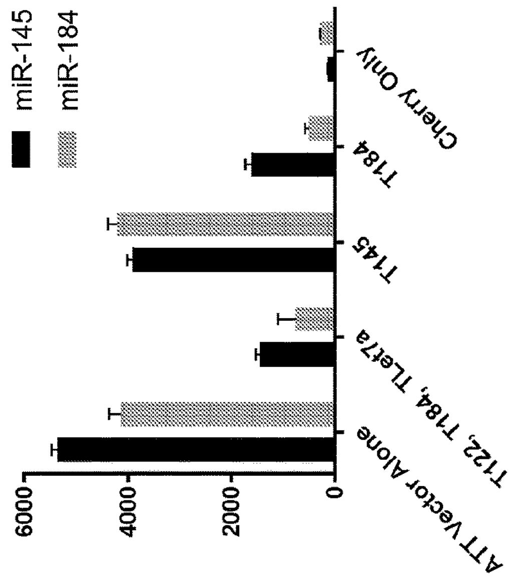
FIG. 20 shows quantitation of miR-145 and miR-184-attenuated GFP fluorescence.
Figure 19:
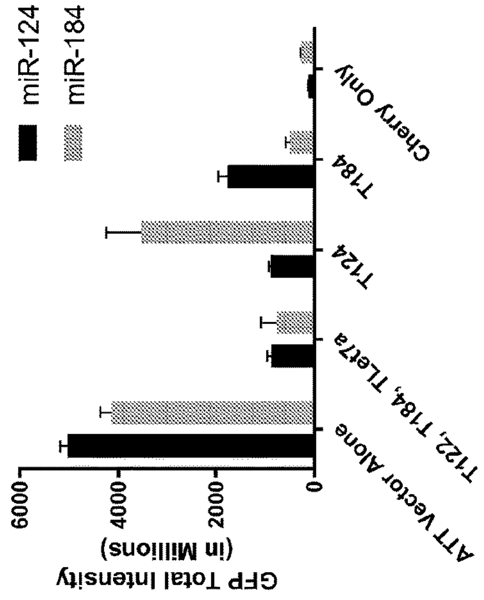
FIG. 19 shows quantitation of miR-124 and miR-184-attenuated GFP fluorescence.
Figure 21:
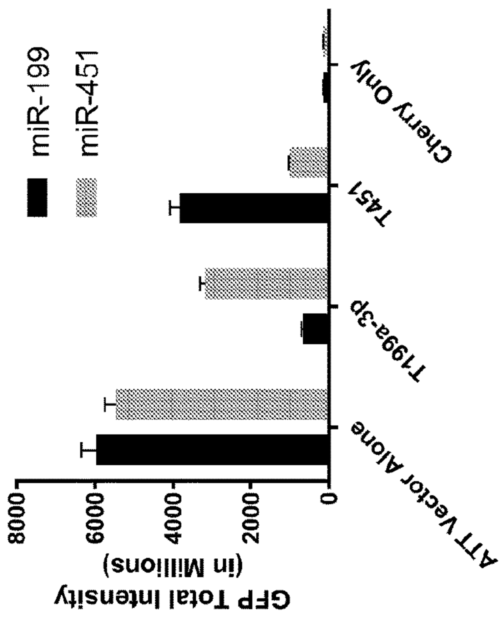
FIG. 21 shows quantitation of miR-199 and miR-451-attenuated GFP fluorescence.
Figure 23:
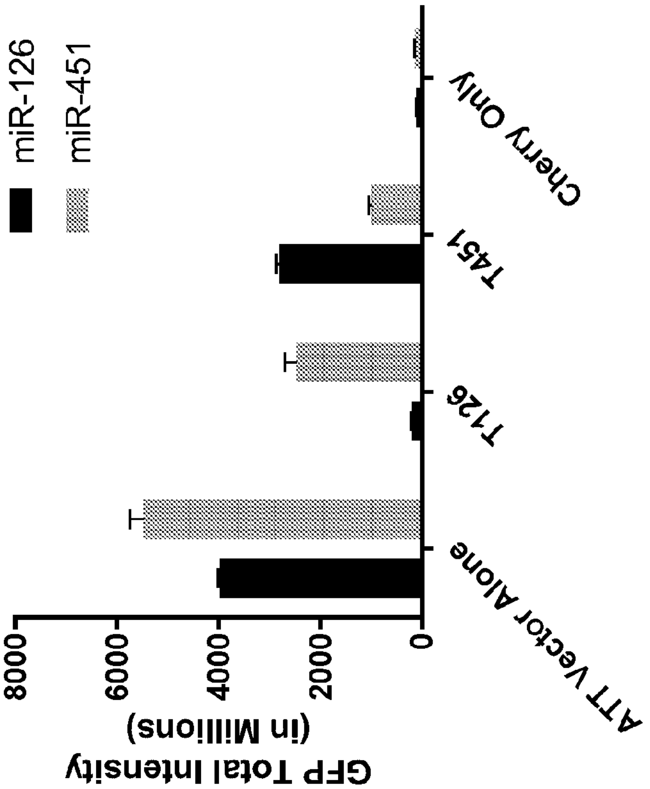
FIG. 23 shows quantitation of miR-126 and miR-451-attenuated GFP fluorescence.
Figure 22:
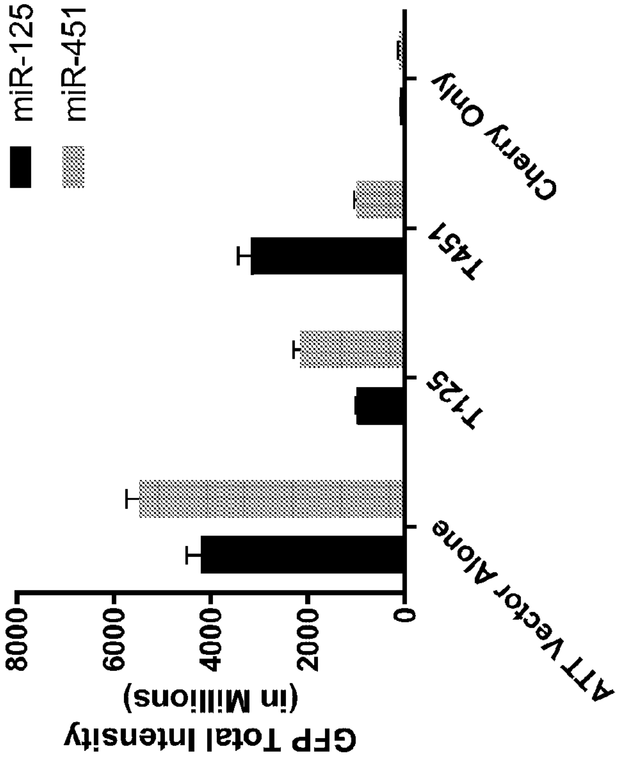
FIG. 22 shows quantitation of miR-125 and miR-451-attenuated GFP fluorescence.

FIG. 11 exemplifies miR-122 mediated attenuation of GFP expression upon induction of miR-122 expression via tet at 24 hours. The control miRNA mimics, miR-184, miR-34a, and Let7a, do not attenuate GFP levels, nor is GFP attenuation observed in the absence of tet. FIG. 12 shows the effect of miR-122, miR-184, miR-34a, and Let7a mimics on attenuation of GFP cassettes with miR-TS cassettes comprising each miR target sequence individually and in cassette combinations of miR-122/Let7a, miR-122/Let7a/miR-34a, or miR-122/Let7a/miR-184. Decreased GFP is only observed when the appropriate miR and cognate target sequence are present together (circled wells). FIG. 13 serves as a non-attenuated control and shows mCherry expression as a measure of the expression of the miR-122, miR-184, miR-34a, and Let7a mimics. FIG. 14 shows the effects of miR-122, miR-124, miR-145, miR-199, and miR-451 mimic expression on attenuated-GFP cassettes with miR-TS cassettes comprising each miR target sequence individually (circled wells). Non-attenuated controls are shown in FIG. 15 and show miR-122, miR-124, miR-145, miR-199, and miR-451 expression and mCherry expression using each target sequence individually.

The ability of additional combinations of miR target sequence to attenuate GFP expression in the presence of cognate miR mimics are shown in FIG. 16-FIG. 26. In each figure, GFP fluorescence is measured at 72 hours post-transfection. In each instance, insertion of the indicated miR target sequences resulted in attenuated GFP expression when the cognate miRs were also expression. The effects of insertion of miR-122 and miR-184 target sequences (FIG. 16), miR-34a and miR-184 target sequences (FIG. 17), Let-7a and miR-184 target sequences (FIG. 18), miR-124 and miR-184 target sequences (FIG. 19), miR-145 and miR-184 target sequences (FIG. 20), miR-199 and miR-451 target sequences (FIG. 21), miR-125 and miR-451 target sequences (FIG. 22), miR-126 and miR-451 target sequences (FIG. 23), miR-127 and miR-451 target sequences (FIG. 24), miR-133 and miR-451 target sequences (FIG. 25), and miR-223 and miR-451 target sequences (FIG. 26) are each shown.

As such, these data indicate that miR expression can result in the specific attenuation of genes expressing the cognate miR target sequence.

Example 4—Generation of miRNA-Attenuated HSV

Following reporter gene-based validation of miRNA target sequences and cognate miRNA pairs, HSV-based viruses comprising miR-TS cassettes were generated. A series of modifications were made in KOS-37 BAC, a full-length genomic clone of the KOS strain of HSV-1 on a bacterial artificial chromosome (BAC) as described (Mazzacurati et al., Mol Ther., 2015). The product, $KG^{BAC}$, was deleted for the internal repeat (joint) region containing one copy each of the diploid genes ICP0, ICP34.5, LAT and ICP4 along with the promoter for the ICP47 gene. This deletion facilitates manipulation of the remaining copies of the 4 deleted genes, provides abundant space for the potential incorporation of transgenes that enhance the oncolytic activity of the virus, and increases tumor specificity by reducing expression of the neurovirulence factor ICP34.5; elimination of ICP47 expression benefits immune recognition of infected cancer cells by virus-specific T cells. $KG^{BAC}$ also contains the GFP open reading frame (ORF) fused to the glycoprotein C (gC) ORF via a 2A peptide sequence to allow monitoring of late (post-replication) viral gene expression. Lastly, $KG^{BAC}$ contains a pair of mutations in the gB gene shown to enhance HSV entry through non-canonical receptors (See e.g., International PCT Publication No. WO 2011/130749). A miR-TS cassette comprising 4 repeats of a target sequence for miR-124-3p were recombined into the 3' UTR of ICP4 to generate the 2A5B vector See e.g., International PCT Publication No. WO 2015/066042), and an expression cassette for MMP9 was inserted into the intergenic region between the UL3 and UL4 genes to generate the 2A5B-MMP9 vector (ONCR-003). Additional miRNA target sequence cassettes were recombined into the 3' UTR of the ICP4, ICP27, UL8, UL42, and/or ICP34.5 genes of ONCR-003 to generate the constructs shown in Table 13 below. All BAC constructs were converted to virus particles with simultaneous removal of the BAC sequences located between loxP sites by transfection of Vero-Cre cells. Following plaque purification, virus stocks were prepared and titered on Vero cells.

TABLE 13

Exemplary miRNA-attenuated HSV constructs

| Construct | ICP27 | UL8 | ICP34.5 | ICP4 | UL42 |
|---|---|---|---|---|---|
| ONCR-003 | None | X | X | 124-3p (4x) | X |
| ONCR-010 | 122-5p<br>34a-5p<br>Let-7a-5p | X | X | 124-3p (4x) | X |
| ONCR-011 | 125a-5p (1x) | X | X | 124-3p (4x) | X |
| ONCR-012 | 143-3p (1x) | X | X | 124-3p (4x) | X |
| ONCR-013 | 145-5p (1x) | X | X | 124-3p (4x) | X |
| ONCR-014 | 199a-5p (1x) | X | X | 124-3p (4x) | X |
| ONCR-015 | 1-3p (1x) | X | X | 124-3p (4x) | X |
| ONCR-016 | 133a-3p (1x) | X | X | 124-3p (4x) | X |
| ONCR-017 | 223-3p (1x) | X | X | 124-3p (4x) | X |
| ONCR-018 | 451a[#] (1x) | X | X | 124-3p (4x) | X |
| ONCR-019 | 126-3p (1x) | X | X | 124-3p (4x) | X |
| ONCR-020 | 127a-3p (1x) | X | X | 124-3p (4x) | X |
| ONCR-021 | 133b-3p (1x) | X | X | 124-3p (4x) | X |
| ONCR-022 | 134-3p (1x) | X | X | 124-3p (4x) | X |
| ONCR-030 | 199a-3p (1x) | X | X | 124-3p (4x) | X |
| ONCR-035 | 214-3p (1x) | X | X | 124-3p (4x) | X |
| ONCR-036 | 122-5p (1x) | X | X | 124-3p (4x) | X |
| ONCR-039 | 122-5p (2x) | X | X | 124-3p (4x) | X |
| ONCR-040 | 122-5p (3x) | X | X | 124-3p (4x) | X |
| ONCR-043 | 137-3p | X | X | 124-3p (4x) | X |
| ONCR-047 | 34a-5p | X | X | 124-3p (4x) | X |
| ONCR-048 | 184-3p | X | X | 124-3p (4x) | X |
| ONCR-053 | Let7a-5p | X | X | 124-3p (4x) | X |
| ONCR-054 | 122-5p<br>184-3p<br>Let-7a-5p | X | X | 124-3p (4x) | X |
| ONCR-055 | 145-3p | X | X | 124-3p (4x) | X |
| ONCR-062 | 559-5p | X | X | 124-3p (4x) | X |
| ONCR-063 | 122-5p | X | X | 124-3p (4x) | X |
| ONCR-064 | 122-5p<br>Let-7a-5p | X | X | 124-3p (4x) | X |
| ONCR-081 | X | X | X | 124-3p (4x) | 125a-5p (1x) |
| ONCR-082 | X | X | X | 124-3p (4x) | 125a-5p (2x) |
| ONCR-083 | X | X | X | 124-3p (4x) | 125a-5p (3x) |
| ONCR-084 | X | X | X | 124-3p (4x) | 125a-5p (4x) |
| ONCR-092 | 122-5p (1x) | X | X | 124-3p (4x) | 125a-5p (4x) |
| ONCR-093 | 122-5p (4x) | X | X | 124-3p (4x) | 125a-5p (1x) |
| ONCR-094 | 122-5p (1x) | X | X | 124-3p (4x) | 125a-5p (1x) |
| ONCR-095 | 122-5p (1x) | X | X | 124-3p (4x) | 125a-5p (3x) |
| ONCR-096 | 122-5p (4x) | X | X | 124-3p (4x) | 125a-5p (4x) |
| ONCR-098<br>ONCR-099 | 1-3p<br>145-5p<br>199a-5p<br>559-5p | X | X | 124-3p (4x) | X |
| ONCR-100 | X | X | X | 124-3p (4x) | 122-5p (3x) |
| ONCR-103 | 122-5p (3x) | X | X | 124-3p (4x) | 125a-5p (1x) |
| ONCR-104 | 122-5p (3x) | X | X | 124-3p (4x) | 125a-5p (4x) |
| ONCR-129<br>ONCR-144 | 219a-5p (4x)<br>122-5p (4x)<br>128-3p (4x) | X | X | 124-3p (4x),<br>1-3p (4x),<br>143-3p (4x) | X |
| ONCR-130 | 219a-5p (4x)<br>122-5p (4x)<br>128-3p (4x) | X | X | 124-3p (4x) | X |
| ONCR-131<br>ONCR-136<br>ONCR-155 | 219a-5p (4x)<br>122-5p (4x)<br>128-3p (4x) | 137-3p (4x)<br>208b-3p (4x)<br>126-3p (4x) | X | 124-3p (4x),<br>1-3p (4x),<br>143-3p (4x) | X |
| ONCR-132 | X | 137-3p (4x)<br>208b-3p (4x)<br>126-3p (4x) | X | 124-3p (4x) | X |

[#]miR-451a is non-canonically processed by Ago2 and does not have -3p and -5p arms

Example 5—Viral Infectivity Assay Using miRNA-Attenuated HSV

To assay for viral infectivity and replication in normal and cancerous cells, miRNA-attenuated HSV particles were tested in the following in vitro assay. On day one, for each cell type infected, HSV particles were introduced to achieve a multiplicity of infection (moi) of 0.01. On days two through five, viral infectivity was assayed by GFP detection using a SpectraMax® i3x Minimax multi-mode microplate reader (Molecular Devices) and analyzed using Softmax Pro or Metamorph imaging software (Molecular Devices). Phase images were acquired with an exposure of 5-6 ms. Fluorescence images were acquired with a GFP (541 nm channel) exposure of 10 ms and an mCherry (713 nm channel) exposure of 200-1500 ms to evaluated any potential non-specific autofluorescence signal.

Figure 27A:
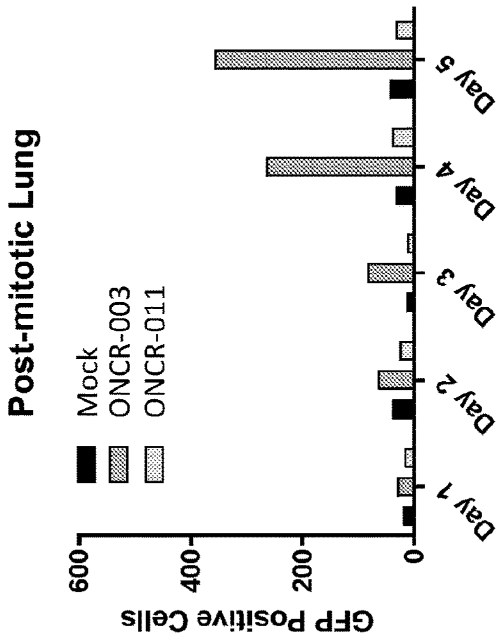
FIG. 27A-FIG. 27D illustrate fluorescence-based quantitation of HSV attenuation by miR-125 in non-cancerous post-mitotic lung cells and cancerous A253 cells.
Figure 27B:
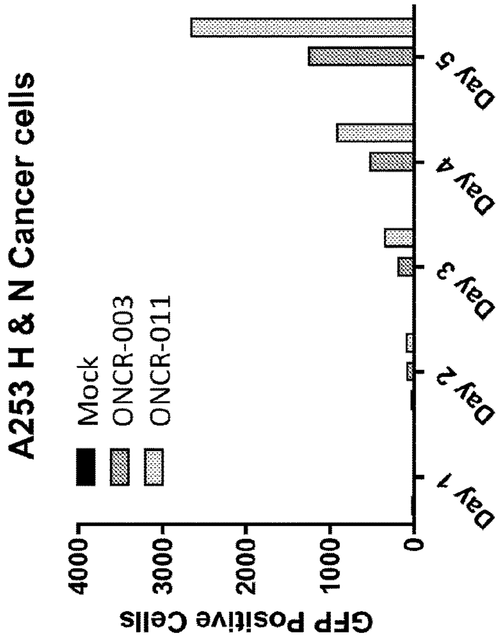
Figure 27C:
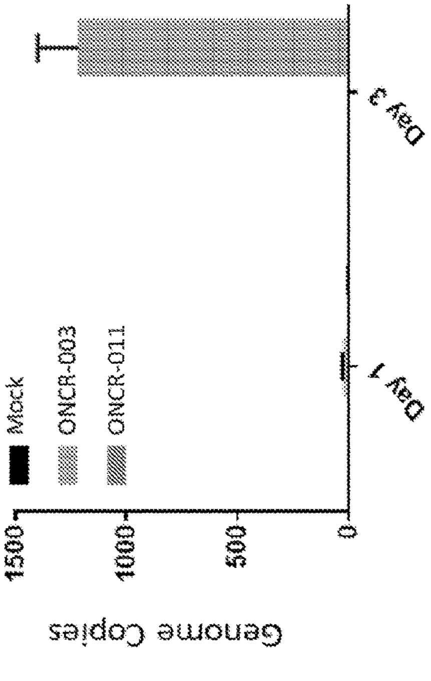
Figure 27D:
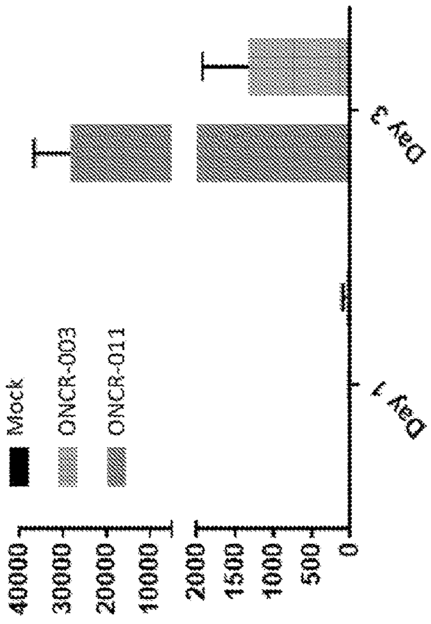

ONCR-011 replication was significantly attenuated in post-mitotic lung tissue due to the presence of the miR-T125 cassette in the ICP27 gene and high levels of miR-125a (>3000 counts, Table 14 below) in these cells, as shown in FIG. 27A (read out by GFP positive cell quantitation) and FIG. 27C (read out by quantitative PCR). Although ONCR-011 and the control virus, ONCR-003, contain miR-124 target sequences in the ICP4 gene, miR-124 is present at low levels (<100 counts, Table 14 below) which were insufficient to attenuate viral replication (FIG. 27B and FIG. 27D). Both ONCR-011 and ONCR-003 replicated freely in head and neck cancer cells (A253) because these cells contain low levels of both miR-125a and miR-124 (<100 counts) (Table 14).

TABLE 14 miR-125a and miR-124 counts in post-mitotic lung and A253 cells

| Cell | miRNA 125a counts | miRNA 124 counts |
|---|---|---|
| PM-lung | >3000 | <100 |
| H&N CA | <100 | <100 |

Figure 28B:
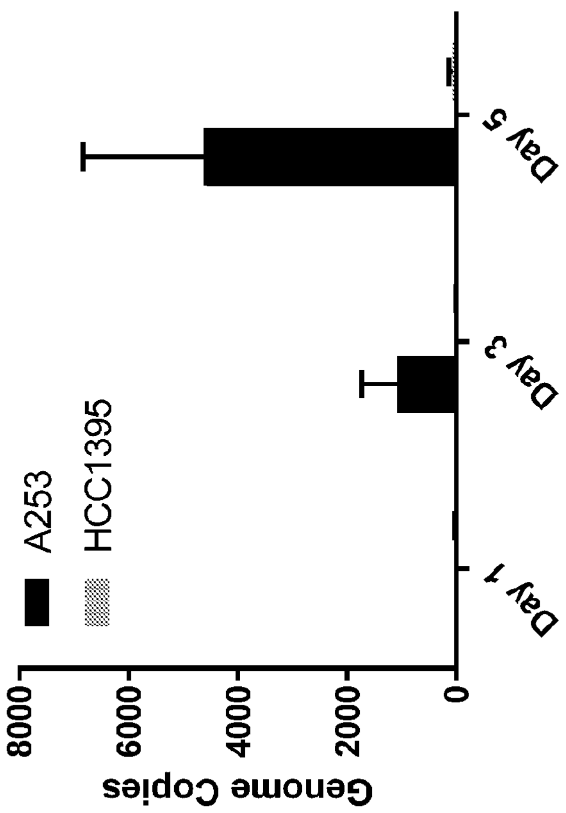
FIG. 28A-FIG. 28B illustrate fluorescence-based (FIG. 28A) and qPCR-based (FIG. 28B) quantitation of HSV attenuation by miR-145 in HCC1395 vs. A253 cells.
Figure 28A:
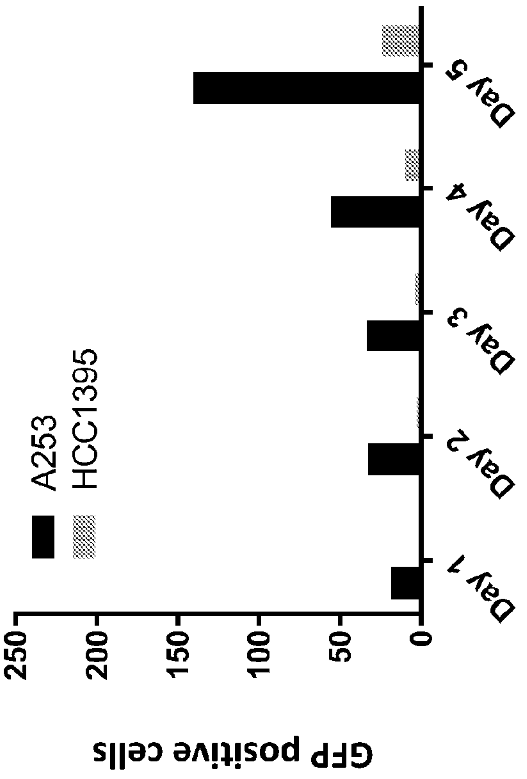

FIG. 28 shows replication of a miR-145 attenuated construct, ONCR-013, in HCC1395 and A253 cells. As shown in FIG. 28A (read out by GFP positive cell quantitation) and FIG. 28B (read out by quantitative PCR), replication of ONCR-013 was significantly attenuated in HCC1395 cells, but not in A253 cells due to the high expression of miR-145 in A253 and absence of expression in HCC1395 cells (Table 15).

TABLE 15 miR-145 counts in A253 and HCC1395 cells

| Cell | miRNA 145 counts |
|---|---|
| A253 | 0 |
| HCC1395 | 4487 |

Figure 29B:
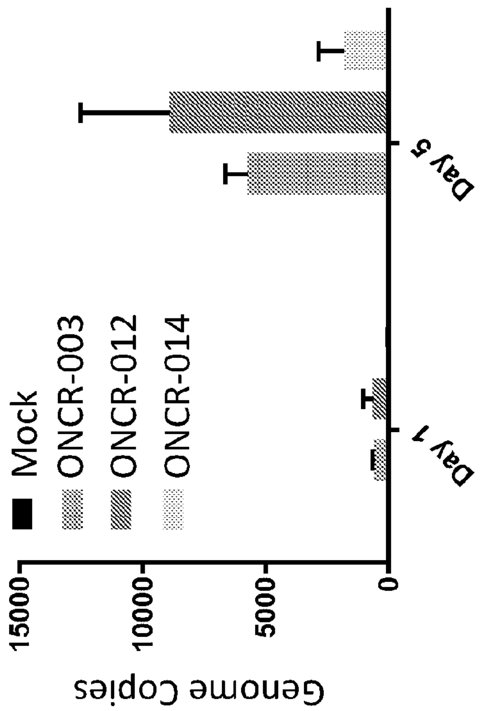
FIG. 29A-FIG. 29B illustrates fluorescence-based (FIG. 29A) and qPCR-based (FIG. 29B) quantitation of HSV attenuation by miR-199a-5p vs. miR-143-3p in normal lung cells.
Figure 29A:
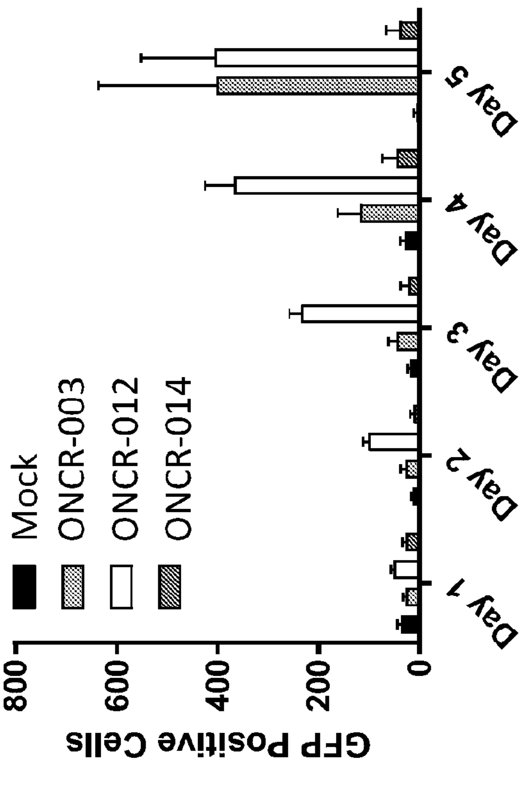

FIG. 29 shows attenuation of a miR-143-3p attenuated construct (ONCR-012) and a miR-199a-5p attenuated construct (ONCR-014) in normal BEAS-2B lung cells. As shown, replication of ONCR-014 was significantly attenuated in non-cancerous lung tissue (FIG. 29A, read out by GFP positive cell quantitation and FIG. 29B, read out by quantitative PCR), indicating that miR-199a-5p target sequences can attenuate viral replication in normal lung cells.

Example 6—Attenuated Replication of oHSV Comprising Multiple miRNA Target Sequences in Multiple Gene Loci Viral infectivity and replication of constructs comprising miR-TS cassettes in multiple genetic loci was assessed in A253, Hep3B, and Huh7 cells. Results for ONCR-036, ONCR-063, ONCR-093, ONCR-094, ONCR-095, and ONCR-096 miR-attenuated HSV constructs are provided herein. Each of these viruses comprised one or more miR-124 target sequences, one or more miR-122 target sequences, and/or one or more miR-125a target sequences inserted into the ICP4, ICP27 and/or UL42 loci. Expression of miR-122 and miR-125a in each of the cell lines was assessed by a TaqMan assay. Briefly, total RNA, including the small RNA fraction, were isolated from growing cells with miRNeasy columns. The RNA was then used as the substrate for miR-122 and miR-125 specific TaqMan assays, and a parallel TaqMan assay for the U6 snRNA was performed to normalize expression levels per cell type per the ΔΔCT method. The data are represented as a fold change relative to lowest cell line in question in each assay (A253 cells, FIG. 30A; Hep3B, FIG. 30B). As shown, A253 cells do not express miR-122 or miR-125a. Hep3B cells express high levels of miR-125 and low levels of miR-122, and Huh7 cells express miR-125a and high levels of miR-122.

Figure 30C:
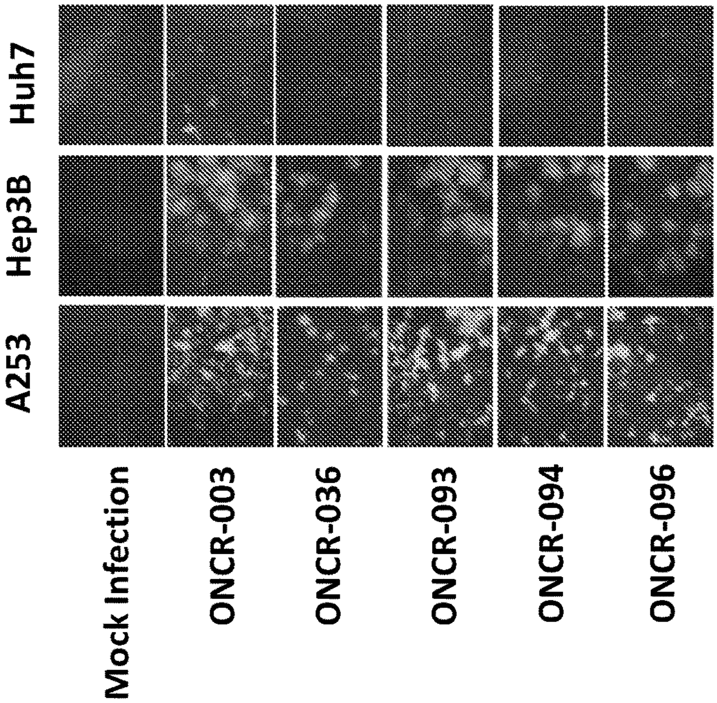
FIG. 30A-FIG. 30C illustrate miRNA-125a (FIG. 30A) and miRNA-122 (FIG. 30B) expression and effect on viral replication (FIG. 30C) in A253, Huh7, and Hep3B cell lines.
Figure 30A:
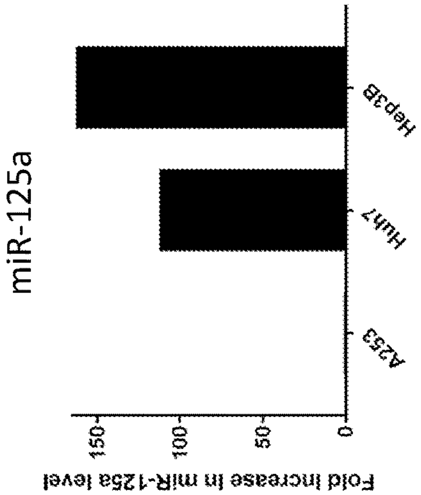
Figure 30B:
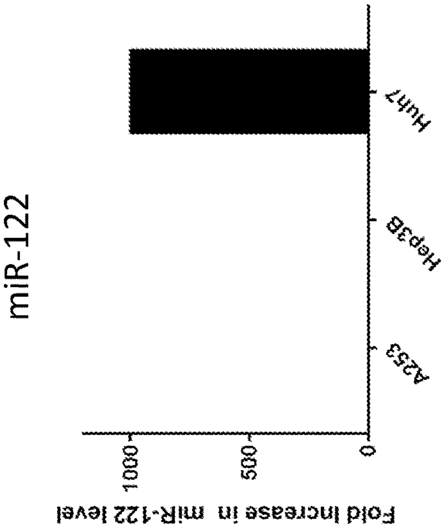

Viral infectivity and replication was assessed in an in vitro assay. Briefly, cells were plated at 45,000 cells/well in a 48-well dish and cultured overnight. On day one HSV particles were introduced into each cell type to achieve a multiplicity of infection (moi) of 0.01. 48 hours post-infection, viral infectivity was assessed by fluorescence microscopy. The results of this experiment are shown in FIG. 30C, and viral replication is indicated by eGFP levels. These data demonstrate enhanced attenuation of viral replication in cells that express intermediate to high levels of both miR-122 and miR-125a (Huh7 cells) compared to the attenuation observed in cells that express only one of the cognate miRs (Hep3B, expressing high levels of miR-125a) or compared to cells that express neither cognate miR (A253 cell, expressing neither miR-125a nor miR-122).

Figure 31:
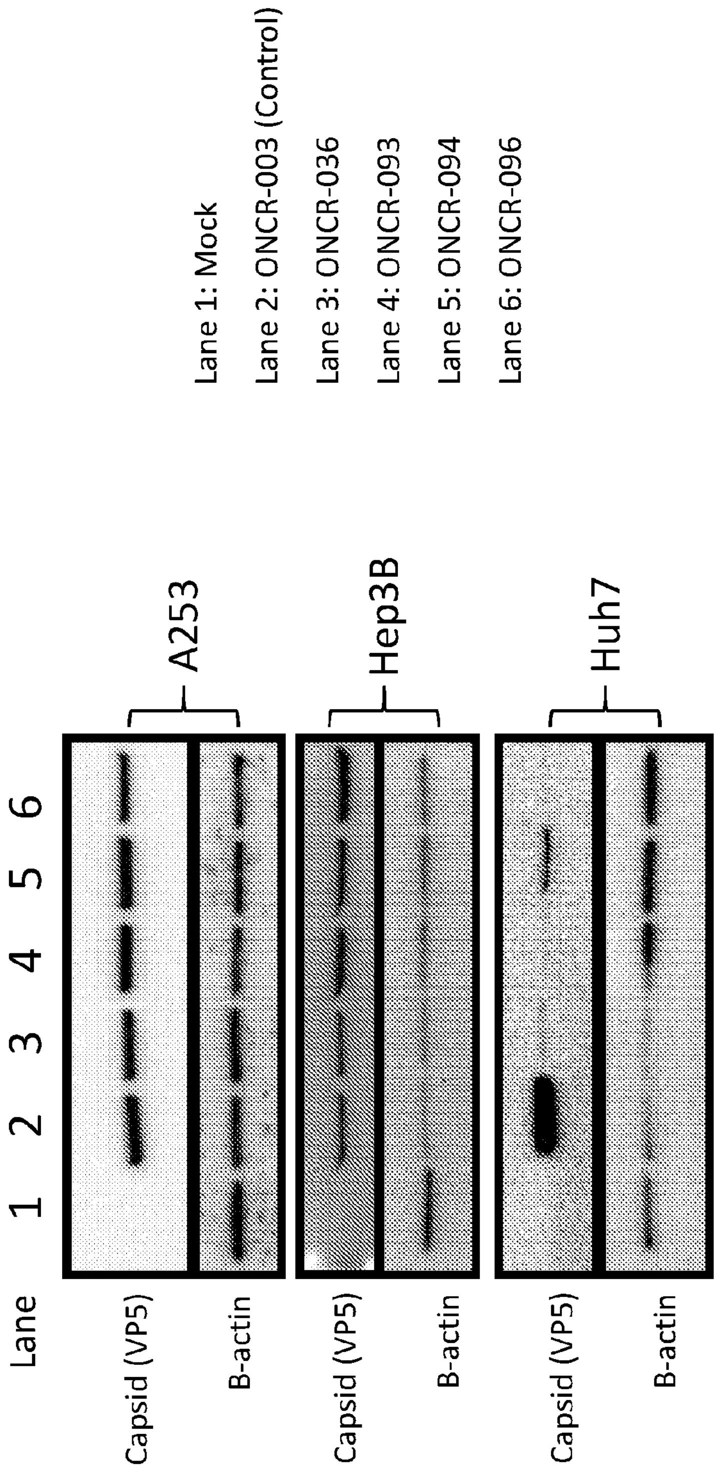

Viral spread and protein expression were also assessed. Briefly, cell lysates were harvested 72 hours post-infection and subjected to PAGE and Western blot analysis. An anti-HSV1 capsid (VP5) antibody was used to monitor viral spread/protein expression and B-actin antibody was used as a loading control. In A253 cells, where there is no miR-125a or miR-122 expression, a level of high viral replication was observed in all of the miR-attenuated viruses (FIG. 31, lanes 3-6) as compared to the non-attenuated control (FIG. 31, ONCR-003 as non-attenuated control). However, viral replication was reduced in Huh7 cells, which express both cognate miRNAs and especially high levels of miR-122. These data exemplify viral attenuation by specific miRs relative to control virus.

Figure 32A:
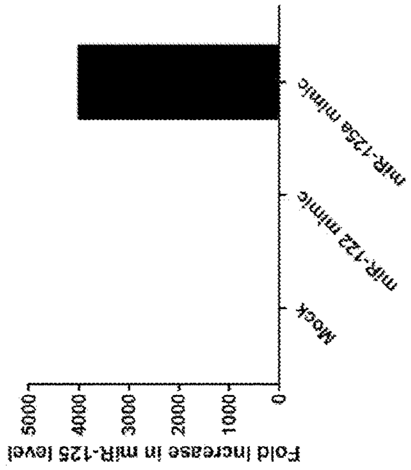
FIG. 32A-FIG. 32D illustrate effects of miRNA expression on miR-attenuated HSV replication.
Figure 32B:
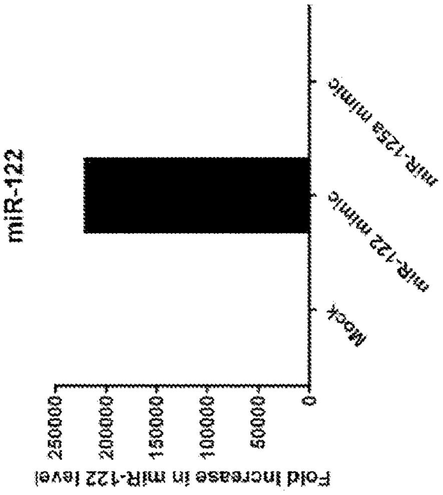

To further confirm that reduced viral replication of miR-attenuated HSV viruses was mediated by expression of specific miRs, A253 cells, which do not express endogenous miR-122 or miR-125a, were transfected with miR-122 and miR-125a mimics. Briefly, A253 cells were plated at 35,000 cells/well in a 48 well dish and cultured overnight. The cells were then transfected with Ambion miRNA mimics at 2.5 pM/well with Lipofectamine RNAiMAX. Total RNA, including the small RNA fraction, were isolated from growing cells with miRNeasy columns. These RNA samples were used as the substrate for miR-122 and miR-125 specific TaqMan assays, and a parallel TaqMan assay for the U6 snRNA was performed to normalize expression levels per cell type per the ΔΔCT method. The results are shown in FIG. 32. As shown in FIG. 32A and FIG. 32B, miR-122 and miR-125 mimics specifically increased intracellular miR-122 and miR-125 expression levels in A253 cells by orders of magnitude.

Figure 32C:
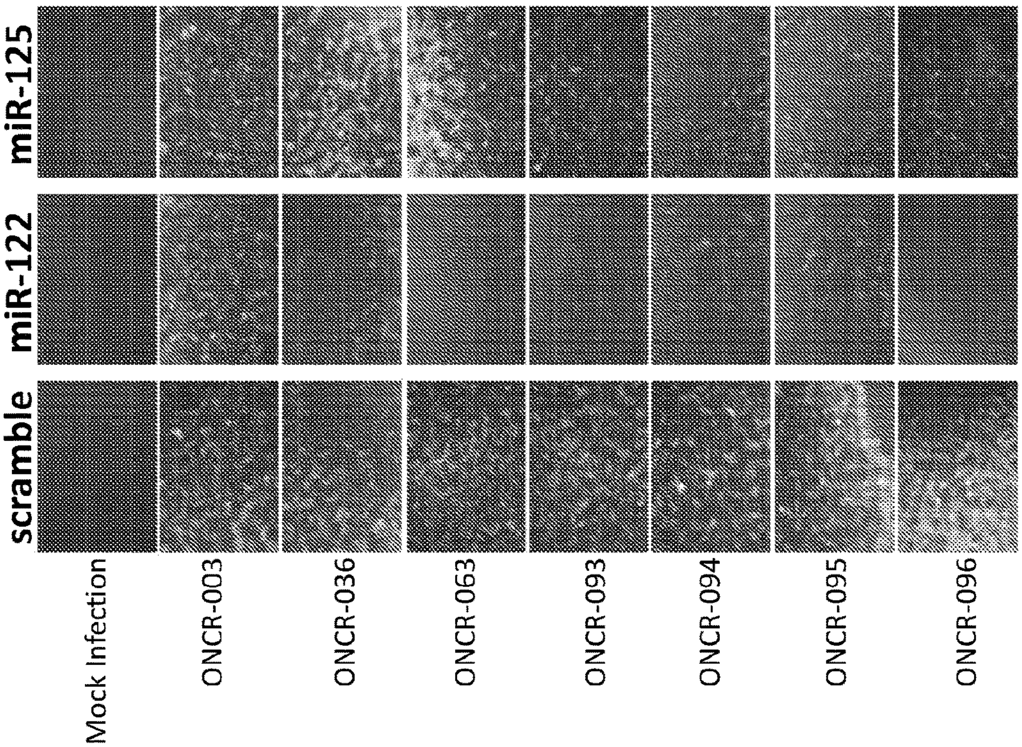
Figure 32D:
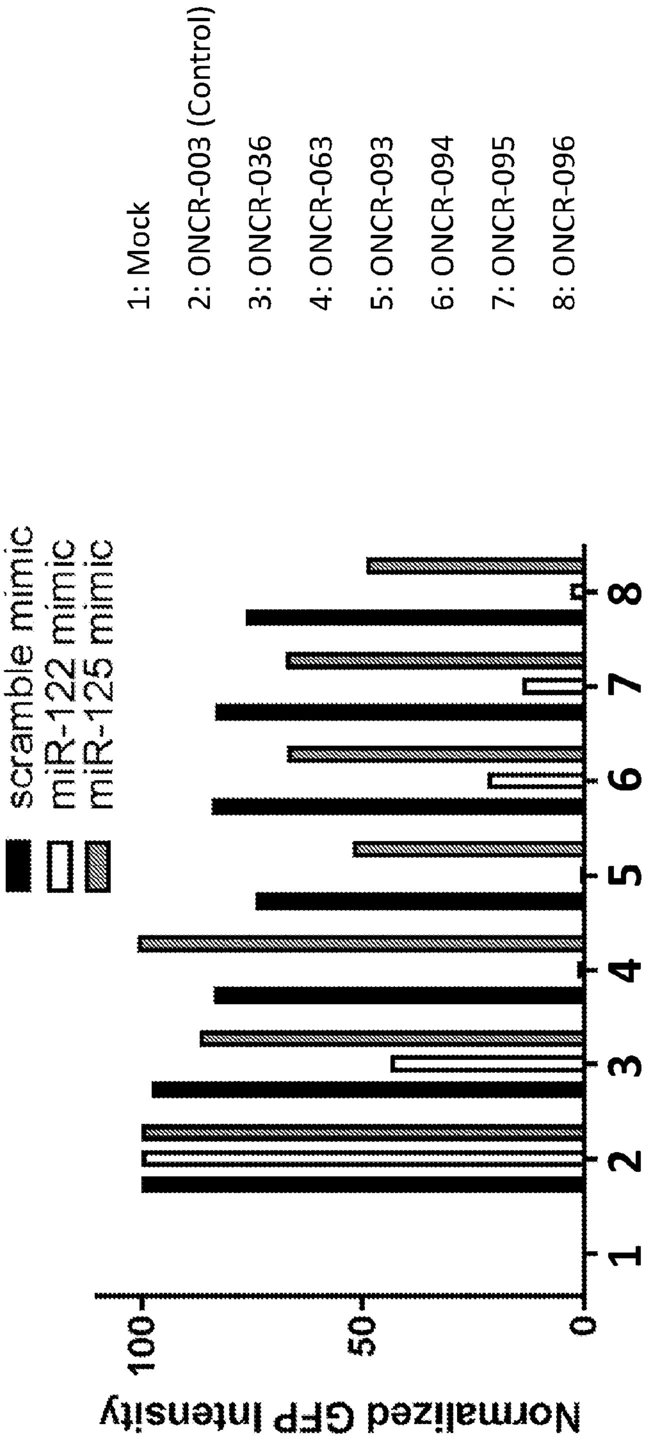
Figure 33:
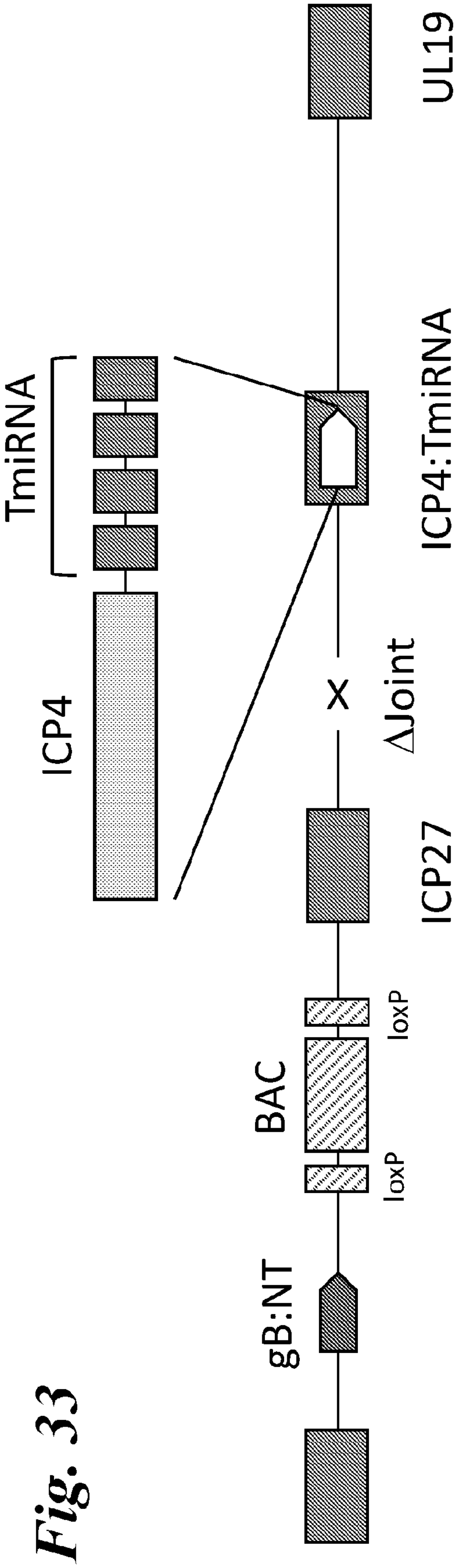
FIG. 33 illustrates a schematic of an ICP4-TmiRNA-attenuated HSV vector for the treatment of cancer or benign hyper-proliferative disorders. gB:NT: virus entry-enhancing double mutation in gB gene; BAC: loxP-flanked choramphenicol-resistance and lacZ sequences; Δjoint: deletion of the complete internal repeat region including one copy of the ICP4 gene; ICP4:TmiRNA: insertion of miRNA target sequences (e.g. let-7, miR-34a, miR-101, miR-125b, miR-145, etc.) into the 3' UTR of the remaining ICP4 gene (also may be placed in 5' UTR)
Figure 34:
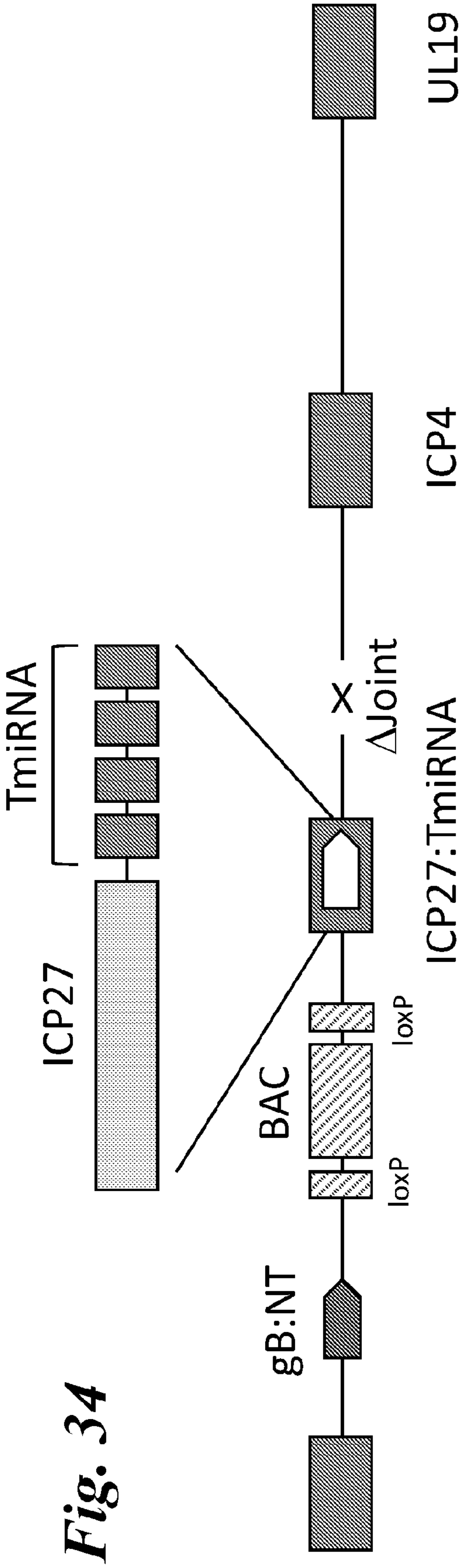
FIG. 34 shows a schematic of an ICP27-TmiRNA-attenuated HSV vector for the treatment of cancer or benign hyper-proliferative disorders. gB:NT: virus entry-enhancing double mutation in gB gene; BAC: loxP-flanked choramphenicol-resistance and lacZ sequences; Δjoint: deletion of the complete internal repeat region including one copy of the ICP4 gene; ICP27:TmiRNA: insertion of miRNA target sequences (e.g. let-7, miR-34a, miR-101, miR-125b, miR-145, etc.) into the 3' UTR of the ICP27 gene (also may be placed in 5' UTR)
Figure 35:
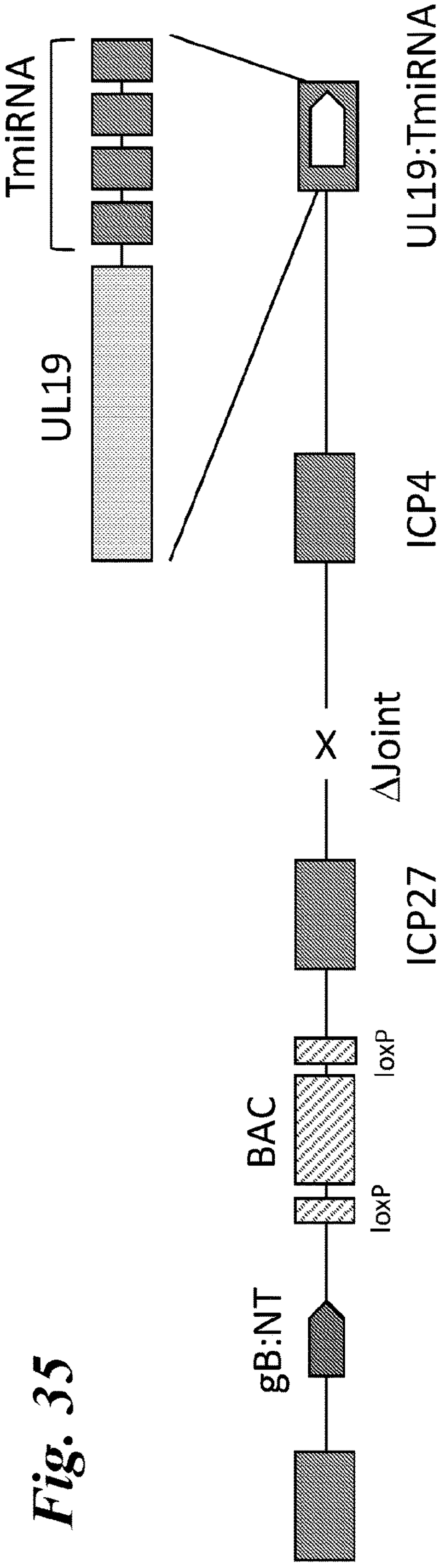
FIG. 35 shows a schematic of a UL19-TmiRNA-attenuated HSV vector for the treatment of cancer or benign hyper-proliferative disorders. gB:NT: virus entry-enhancing double mutation in gB gene; BAC: loxP-flanked choramphenicol-resistance and lacZ sequences; Δjoint: deletion of the complete internal repeat region including one copy of the ICP4 gene; UL19:TmiRNA: insertion of miRNA target sequences (e.g. let-7, miR-34a, miR-101, miR-125b, miR-145, etc.) into the 3' UTR of the UL19 gene (also may be placed in 5' UTR).
Figure 36:
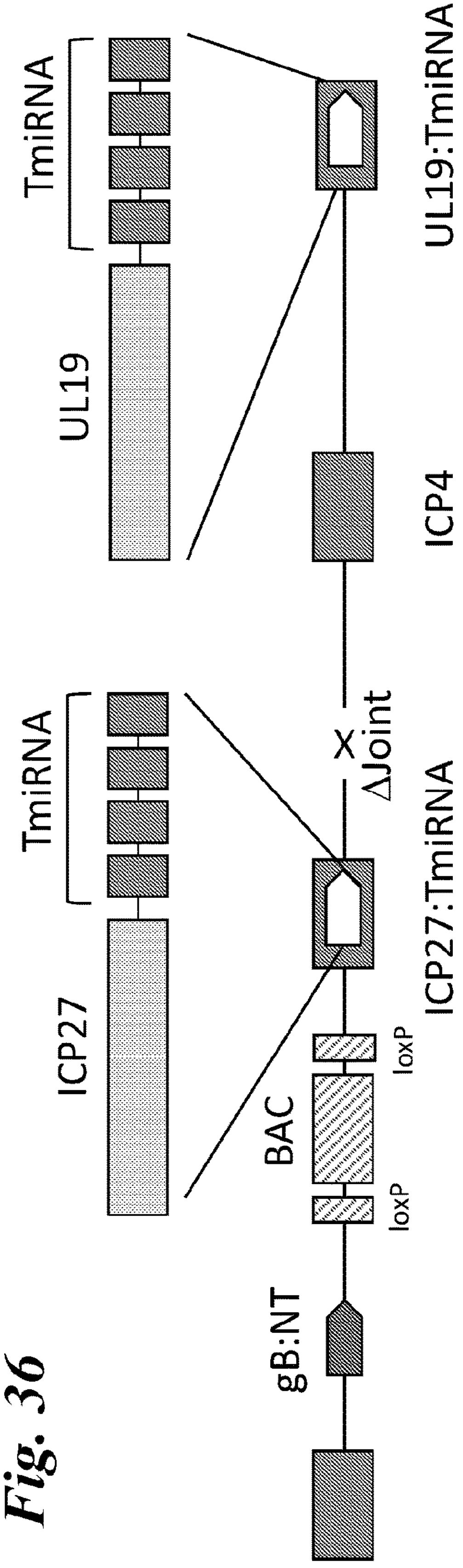
FIG. 36 shows a schematic of an UL19-TmiRNA and ICP27-TmiRNA-attenuated HSV vector for the treatment of cancer or benign hyper-proliferative disorders. gB:NT: virus entry-enhancing double mutation in gB gene; BAC: loxP-flanked choramphenicol-resistance and lacZ sequences; Δjoint: deletion of the complete internal repeat region including one copy of the ICP4 gene; UL19:TmiRNA & ICP27:TmiRNA: insertion of miRNA target sequences (e.g. let-7, miR-34a, miR-101, miR-125b, miR-145, etc.) into the 3' UTR of the UL19 and ICP27 genes (also may be placed in 5' UTR)
Figure 37:
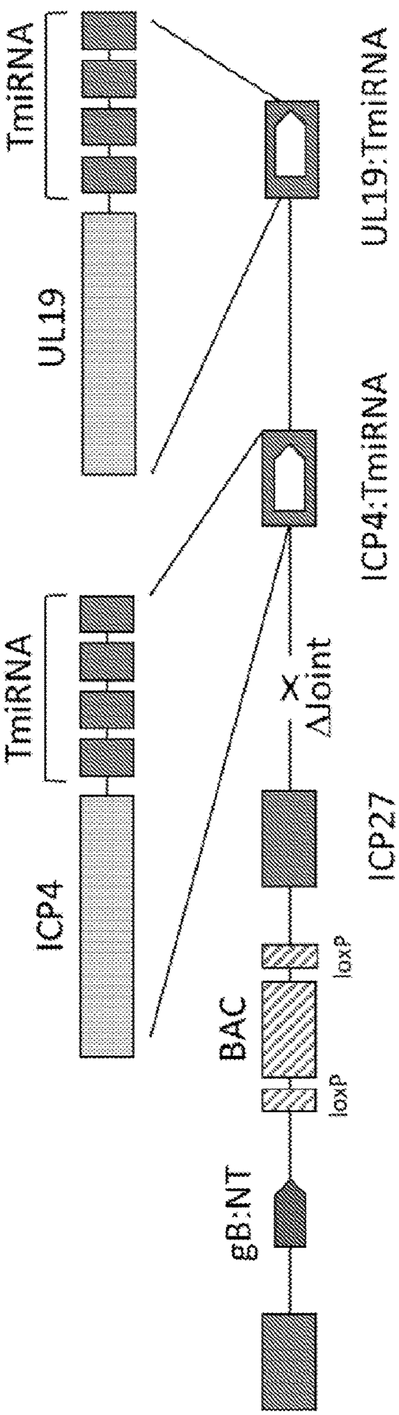
FIG. 37 shows a schematic of an UL19-TmiRNA and ICP4-TmiRNA-attenuated HSV vector for the treatment of cancer or benign hyper-proliferative disorders. gB:NT: virus entry-enhancing double mutation in gB gene; BAC: loxP-flanked choramphenicol-resistance and lacZ sequences; Δjoint: deletion of the complete internal repeat region including one copy of the ICP4 gene; UL19:TmiRNA & ICP4:TmiRNA: insertion of miRNA target sequences (e.g. let-7, miR-34a, miR-101, miR-125b, miR-145, etc.) into the 3' UTR of the UL19 and ICP4 genes (also may be placed in 5' UTR).
Figure 38:
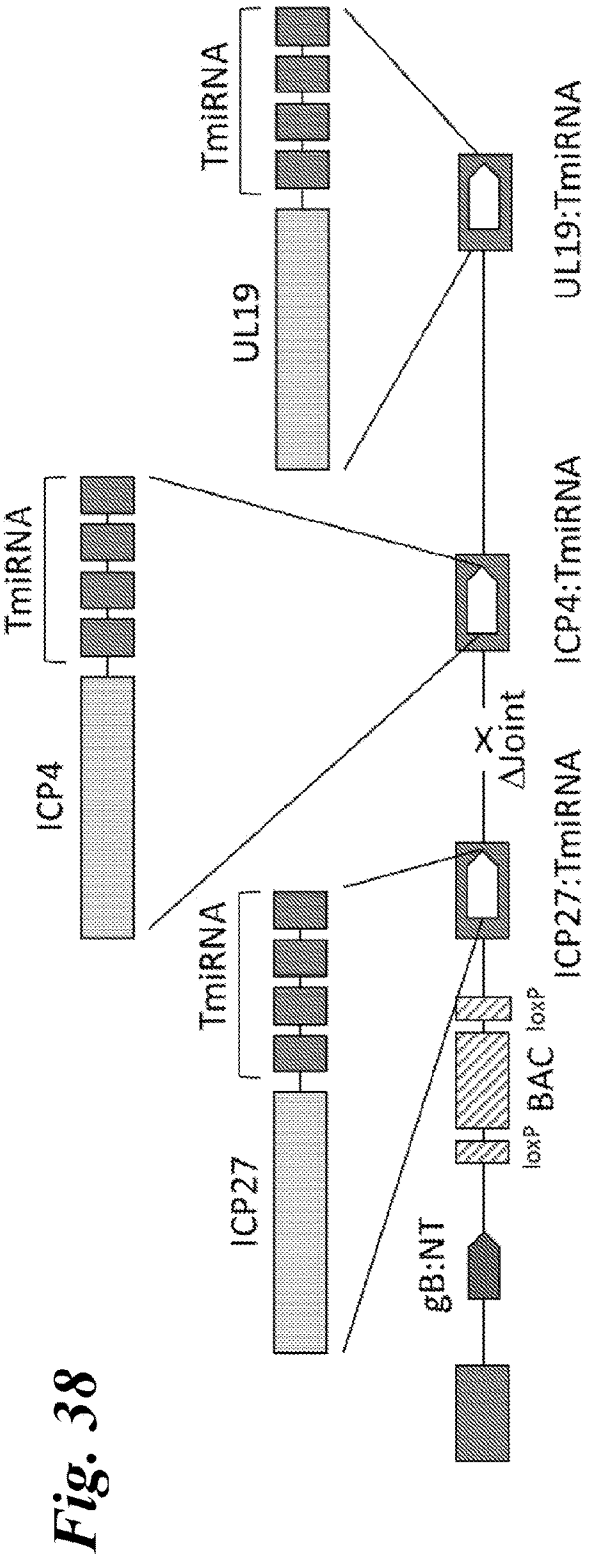
FIG. 38 shows a schematic of an UL19-TmiRNA, ICP27-TmiRNA, and ICP4-TmiRNA-attenuated HSV vector for the treatment of cancer or benign hyper-proliferative disorders. gB:NT: virus entry-enhancing double mutation in gB gene; BAC: loxP-flanked choramphenicol-resistance and lacZ sequences; Δjoint: deletion of the complete internal repeat region including one copy of the ICP4 gene; UL19: TmiRNA, ICP27:TmiRNA, & ICP4:TmiRNA: insertion of miRNA target sequences (e.g. let-7, miR-34a, miR-101, miR-125b, miR-145, etc.) into the 3' UTR of the UL19, ICP27, and ICP4 genes (also may be placed in 5' UTR).

The subsequent day, cells were individually counted and infected with ONCR-036, ONCR-063, ONCR-093, ONCR-094, ONCR-095, or ONCR-096 miR-attenuated HSV particles and ONCR-003 non-attenuated controls at a MOI of 0.01; each of the oHSV viruses were added in 50 μL for 1 hr, followed by addition of complete media. eGFP expressed by productive viral infection was assessed by fluorescence microscopy images taken 48 hrs post-infection. All images were exposed and processed identically. The results of this experiment are shown in FIG. 32C and are quantified by GFP detection using a SpectraMax® i3x Minimax multi-mode microplate reader (Molecular Devices) and analyzed using Softmax Pro in FIG. 32D. These data exemplify attenuated viral replication in the presence of miR-122 mimics for all viruses with the exception of the ONCR-003 (WT). Further, the level of attenuation was proportional to the copy number of miR target sequences present in the HSV constructs, with the greatest reduction in GFP in ONCR-063, ONCR-093, ONCR-096, each comprising 4 miR-122 target sequence repeats in the ICP27 gene. Further, these data exemplify attenuated viral replication in the presence of miR-125a mimics for ONCR-093, -094, -095, and -096, relative to ONCR-003 (WT) and ONCR-036/ONCR-063 (each comprising only only miR-122 target sequences).

Similar experiments were performed to assess the viral replication of additional constructs comprising multiple miR-TS cassettes in two or more viral genes (e.g., ONCR-129, ONCR-131, ONCR-125, ONCR-126, ONCR-128, ONCR-130). In each case, expression of one or more miRNAs was able to attenuate viral replication of a particular construct comprising a target sequence corresponding to the expressed miRNA (data not shown).

Example 7—Computational Method for Generating miR-TS Cassettes

Based on the data described in the previous examples, miR-target sequence (miR-TS) cassettes were generated for insertion into particular HSV genes. miR target sequences exhibiting differential expression between cancerous and non-cancerous cells of different tissue types were selected to generate cassettes that are capable of attenuating viral replication in a broad variety of healthy cells, while allowing viral replication in cancerous cells where expression of the cognate miRs is decreased.

This examples illustrates a method of generating candidate miR-TS cassettes and selected preferred candidates from the list. The method, implemented in the computer language Python, is depicted in FIG. 1. The inputs for the method include a list of seeds for exclusion—in this example, seed sequences for miRNAs that are expressed in cancers were excluded—and a list of miR-TSs to include in the cassette. The included miR-TSs used in this example are provided in Table 10, along with the parent miRNA sequence and length in nucleotides (nt) of each. miR-TSs tolerate imperfect matches between the microRNA and the miR-TS, so it will be understood that cassettes can be made with imperfect miR-TSs. miR-TS cassettes can be made with other miR-TSs, include miR-TSs based on any of the microRNAs known in the art or prospectively discovered.

For this example, we designed four miR-TS cassettes, one for each of four essential viral genes: ICP4, ICP27, ICP34.5, and UL8, as shown in Table 16. But in principle these cassettes could be used with other viral (or non-viral) genes. Because the viral genes are in the reverse complementary orientation in our favored vectors, in each case the reverse complementary sequence was used. The abbreviation "miR-126m" refers to a version of the miR-126 site mutagenized to improve the site by removing a seed match for the oncomiR miR-155. The abbreviation "miR-128m" refers to a version of the miR-128 site mutagenized to improve the site by removing a seed match for the oncomiR miR-27a-3p.

TABLE 16

Candidate miR-TS cassettes and target genes

| Cassette | miR-T | HSV gene | Protected Tissue | Indication Specificity |
|---|---|---|---|---|
| 1 | miR-124-3p<br>miR-1-3p<br>miR-143-3p | ICP4 | CNS/Brain/PNS, smooth muscle, striated muscle/heart | Lung, HnN |
| 2 | miR-128-3p<br>miR-219a-5p<br>miR-122-5p | ICP27 | CNS/Brain/PNS/oligodend rocytes, liver | Lung, HnN |
| 3 | miR-137-3p<br>miR-208b-3p<br>miR-126-3p | UL8 | CNS/Brain/PNS, heart, vasculature, hematopoietic stem cells | Lung, HnN, Bladder |
| 4 | miR-219a-5p<br>miR-204-5p<br>miR-128-3p | ICP34.5 | Spine, PNS, CNS (Oligodendrocytes, Glial cells, Neurons) | All |

The cassette designed for ICP4 can be used to down-regulate any gene, to which it is operatively linked, in smooth muscle (because of miR-143 target site) and striated muscale (because of miR-1 target site). The cassette designed for ICP27 can be used to down-regulate any gene, to which it is operatively linked, in healthy tissue because of miR-128m (expressed in cortical neurons), miR-122 (expressed in the liver), and miR-219 (expressed in the brain, spine and nerves) target sites. The cassette designed for ICP27 can be used to down-regulate any gene, to which it is operatively linked, in healthy tissue because of miR-128m, miR-204, and miR-219 target sites. The cassette designed for UL8 can be used to down-regulate any gene, to which it is operatively linked, in non-tumor tissue because of the mRNA target sites: miR-217, miR-137, and miR-126m.

The program was run, outputting 10,000-100,000 cassettes for each combination which match the criteria used for list example (each of which is optional): (1) four copies of each miR-TS sites (in reverse-complementary orientation) arranged in a random order; (2) except that the same miR-TS cannot repeat adjacent to itself; (3) separated by 4 nucleotide spacers having random sequence; (4) no seeds from the excluded seed list; and (4) no polyadenylation sequence (AATAAA). The program also can, optionally, add 5' arm (CATGGACGAGCTGTACAAGTAAAGC) and 3' arm (GCGACCGGCTAGCGTACTAGCTTAG) sequences for Gibson assembly cloning (*Nat Methods* 2009; 6(5):343-5).

The program next calculated a delta-G for folding of the candidate sequences using the "fold" subroutine of the ViennaRNA package (Lorenz et al. *Algorithms for Molecular Biology,* 6:1 26, 2011) with a 40 nt sliding window. The values for this sliding window calculation were stored as a list for each candidate sequence, and the candidate sequences are sorted by the maximum value of the absolute values of all delta-G values in the list (i.e., by the folding energy of the strongest secondary-structure element in the RNA). Sequences were further reviewed manually to eliminate candidate sequences with multiple, lower energy minima. Whenever possible, a candidate sequence with no local minima was chosen. In this manner, candidate sequences were identified in which there are no strong RNA secondary structure (low max of abs of delta-G) and also no local minima, or few local minima, in predicted secondary-structure folding energy.

Finally, a microRNA target scanning algorithm (miranda v3.3a) was run on each candidate sequence to ensure that the desired miR-TSs were present and that no undesirable miR-TS were inserted by the program.

Example sequences generated by this method are provided in Table 17. The length of the cassette is defined as the number of nucleotides from the first miR-TS to the last miR-TS, inclusive of the first and last miR-TS. Because the program adds a 5' first spacer of 4 nt and a 3' last space not including the definition of length used herein, the length of the cassette is the length of the sequence output by the program minus 8 nt (=2*4 nt first and last spacer).

TABLE 17

| Cassette | Sequence | SEQ ID | # of miR-TS | Length | Nucleo-tides/ miR-TS |
|---|---|---|---|---|---|
| miRT-1-143_1736 | ccatatacatacttctttacattccatcctg<br>agctacagtgcttcatctcattgcatacata<br>cttctttacattccaacgtgagctacagtgc<br>ttcatctcatccgatacatacttctttacat<br>tccacggcgagctacagtgcttcatctcacc<br>ttatacatacttctttacattccaaaaagag<br>ctacagtgcttcatctcaccat | 852 | 8 | 200 | 25 |
| miRT-128m-122-219_6793 | cacgagaattgcgtttggacaatcagacaca<br>aacaccattgtcacactccatcttaaagaga<br>ccggttcactgtggatgtcaaacaccattgt<br>cacactccaacttagaattgcgtttggacaa<br>tcaagggaaagagaccggttcactgtggcca<br>gcaaacaccattgtcacactccaaaacaaag<br>agaccggttcactgtggtacgagaattgcgt<br>ttggacaatcagaaaaaagagaccggttcac<br>tgtggaatacaaacaccattgtcacactcca<br>acaaagaattgcgtttggacaatcaggtt | 853 | 12 | 300 | 25 |
| miRT-128m-204-219_9304 | aagtaaagagaccggttcactgtggaataag<br>aattgcgtttggacaatcaaggtaggcatag<br>gatgacaaagggaacagcaaagagaccggtt<br>cactgtggggctagaattgcgtttggacaat<br>cacgtaaggcataggatgacaaagggaacga<br>gaaagagaccggttcactgtgggggaagaat<br>tgcgtttggacaatcatactaggcataggat<br>gacaaagggaattagaaagagaccggttcac<br>tgtggatttagaattgcgtttggacaatcat<br>agaaggcataggatgacaaagggaattgt | 854 | 12 | 300 | 25 |
| miRT-217-137-126m_3163 | tatgctacgcgtattcttaagcaataagact<br>tccaatcagttcctgatgcagtacgaccaca<br>ttattactcacggtacgaaagcctacgcgta<br>ttcttaagcaataaccgccacattattactc<br>acggtacgataaatccaatcagttcctgatg<br>cagtaattactacgcgtattcttaagcaata<br>actattccaatcagttcctgatgcagtaccc<br>ccacattattactcacggtacgagaattcca<br>atcagttcctgatgcagtacagtcacattat<br>tactcacggtacgatcaactacgcgtattct<br>taagcaataaccaa | 855 | 12 | 300 | 25 |

The ability of the miR-TS cassettes shown in Table 17 to attenuate viral replication is shown in FIG. 53A-FIG. 53B. Additional constructs comprising miR-TS cassettes designed with this method are shown in Table 18 were constructed.

TABLE 18

HSV constructs comprising candidate miR-TS cassettes

| Construct | ICP27 | UL8 | ICP34.5 | ICP4 | UL42 |
|---|---|---|---|---|---|
| ONCR-142 | 219a-5p (4x) | 137-3p (4x) | 128-3p$^{M}$ (4x) | 124-3p (4x) | X |
| ONCR-154 | 122-5p (4x)<br>128-3p (4x) | 208b-3p (4x)<br>126-3p (4x) | 204-5p (4x)$^{\Psi}$<br>219a-5p (4x)$^{\Psi}$ | 1-3p (4x)<br>143-3p (4x) | |

TABLE 18-continued

HSV constructs comprising candidate miR-TS cassettes

| Construct | ICP27 | UL8 | ICP34.5 | ICP4 | UL42 |
|---|---|---|---|---|---|
| ONCR-156 | 219a-5p (4x) | 137-3p (4x) | | 124-3p (4x) | X |
| | 122-5p (4x) | 208b-3p (4x) | | 1-3p (4x) | |
| | 128-3p (4x) | 126-3p (4x) | | 143-3p (4x) | |
| ONCR-158 | 219a-5p (4x) | 137-3p (4x) | 128-3p$^{M}$ (4x) | 124-3p (4x) | |
| | 122-5p (4x) | 208b-3p (4x) | 204-5p (4x) | 1-3p (4x) | |
| | 128-3p (4x) | 126-3p (4x) | 219a-5p (4x) | 143-3p (4x) | |
| ONCR-157 | 219a-5p (4x) | 137-3p (4x) | 128-3p$^{M}$ (4x) | 124-3p (4x) | X |
| | 122-5p (4x) | 217-5p (4x) | 204-5p (4x) | 1-3p (4x) | |
| | 128-3p (4x) | 126-3p (4x) | 219a-5p (4x) | 143-3p (4x) | |
| ONCR-159 | 219a-5p (4x) | 137-3p (4x) | 128-3p$^{M}$ (4x) | 124-3p (4x) | X |
| ONCR-165 | 122-5p (4x) | 217-5p (4x) | 204-5p (4x) | 1-3p (4x) | |
| ONCR-166 | 128-3p (4x) | 126-3p$^{M}$ (4x) | 219a-5p (4x) | 143-3p (4x) | |
| ONCR-167 | | | | | |
| ONCR-168 | | | | | |
| ONCR-169 | | | | | |
| ONCR-170 | | | | | |
| ONCR-171 | | | | | |
| ONCR-172 | | | | | |
| ONCR-173 | | | | | |
| ONCR-174 | | | | | |
| ONCR-175 | | | | | |
| ONCR-176 | | | | | |
| ONCR-177 | | | | | |
| ONCR-160 | 219a-5p (4x) | 137-3p (4x) | 128-3p$^{M}$ | 124-3p (4x) | X |
| | 122-5p (4x) | 208b-3p (4x) | 204-5p (4x)$^{\Psi}$ | 1-3p (4x) | |
| | 128-3p (4x) | 126-3p (4x) | 219a-5p (4x)$^{\Psi}$ | 143-3p (4x) | |
| ONCR-161 | 219a-5p (4x) | 137-3p (4x) | 128-3p$^{M}$ (4x) | 124-3p (4x) | X |
| | 122-5p (4x) | 208b-3p (4x) | 204-5p (4x)$^{\Psi}$ | 1-3p (4x) | |
| | 128-3p (4x) | 127 (4x) | 219-5p (4x)$^{\Psi}$ | 143-3p (4x) | |
| ONCR-162 | 219a-5p (4x) | 137-3p (4x) | 128-3p$^{M}$ (4x) | 124-3p (4x) | X |
| | 122-5p (4x) | 208b-3p (4x) | 204-5p (4x)$^{\Psi}$ | 1-3p (4x) | |
| | 128-3p (4x) | 128-3p (4x) | 219-5p (4x)$^{\Psi}$ | 143-3p (4x) | |
| ONCR-163 | 219a-5p (4x) | 137-3p (4x) | 128-3p$^{M}$ (4x) | 124-3p (4x) | X |
| | 122-5p (4x) | 208b-3p (4x) | 204-5p (4x)$^{\Psi}$ | 1-3p (4x) | |
| | 128-3p (4x) | 129 (4x) | 219-5p (4x)$^{\Psi}$ | 143-3p (4x) | |
| ONCR-164 | 219a-5p (4x) | 137-3p (4x) | 128-3p$^{M}$ (4x) | 124-3p (4x) | X |
| | 122-5p (4x) | 208b-3p (4x) | 204-5p (4x)$^{\Psi}$ | 1-3p (4x) | |
| | 128-3p (4x) | 130 (4x) | 219-5p (4x)$^{\Psi}$ | 143-3p (4x) | |

$^{\Psi}$one of the 4 target sequences was non-functional due to cloning error $^{M}$comprises a modified target sequence

Example 8—Cytotoxicity of miR-Attenuated HSV Constructs

Experiments were performed to assess the in vitro cytotoxicity of select miR-attenuated HSV constructs, ONCR-125, ONCR-131, ONCR-142, and ONCR-157. Various cancer cell lines were infected with the indicated constructs at MOIs of 30, 10, 3.33, 1.11, 0.37, 0.12, 0.04, 0.13, 0.0045, and 0.0015 and cell viability was assessed at 72 hours post infection. Cell lines used include the colorectal adenocarcinoma cell lines SW837 and COLO205, the melanoma cell lines SKMEL28 and A375, small cell lung cancer cell line H446, pancreatic adenocarcinoma cell line BXPC3, and the breast cancer cell line BT 549. The IC50 of each construct was calculated and is shown below in Table 19. Results of each of these experiments are shown in FIG. 54A-FIG. 54E.

TABLE 19

| | ONCR-125 | ONCR-131 | ONCR-142 | ONCR-157 |
|---|---|---|---|---|
| SW837 | 0.07 | 0.04 | 0.05 | 0.07 |
| COLO205 | 0.45 | 0.12 | 0.223 | 0.45 |
| SKMEL28 | 0.12 | 0.04 | 0.12 | 0.25 |
| A375 | 0.87 | 0.26 | 0.89 | 1.5 |
| H446 | 0.13 | 0.05 | 0.15 | 0.15 |

TABLE 19-continued

| | ONCR-125 | ONCR-131 | ONCR-142 | ONCR-157 |
|---|---|---|---|---|
| BXPC3 | 0.08 | 0.002 | 0.08 | 0.07 |
| BT549 | 0.45 | 0.17 | 0.6 | 1.0 |

Example 9—IL-12 Enhances Abscopal Efficacy of HSV

Experiments were performed to assess the effects of IL-12 on the absocpal effect of oncolytic HSV. Briefly, the ONCR-133 construct, comprising an ICP4 miR-TS cassette comprising 4 repeats of miR-124-3p and an expression cassette encoding murine IL-12 was administered to mice in an MC38 tumor model. As shown in FIG. 55, ONCR-133 significantly inhibited tumor growth of injected tumors compared to vehicle treated controls ($p<0.0001$). ONCR-133 treatment also significantly inhibited tumor growth of non-injected tumors ($p<0.005$), indicating an enhanced abscopal effect.

Surprisingly, expression of an additional immune-activating payload, UL8P3, did not further enhance the tumor growth inhibition effects of HSV expressing IL-12. As shown in FIG. 56, mice treated with ONCR-133+ONCR-007 (an HSV construct expressing UL8P3) or ONCR-133+ONCR-002 (an HSV construct that does not express any additional payload molecules) both demonstrated a significant inhibition of tumor growth compared to vehicle treated controls. However, there was no added benefit of UL8P3 expression in the inhibition of growth of injected or non-injected tumors. In fact, as shown in the table in FIG. 56, additional expression of UL8P3 slightly decreased the tumor growth inhibition observed with IL-12 expression alone.

Similarly, additional expression of CXCL10 did not further enhance and anti-tumor efficacy of HSV expressing IL-12. Mice treated with ONCR-113 (an HSV construct expressing IL-12 and MMP9)+ONCR-106 (an HSV construct expressing CXCL10 and MMP9) or ONCR-113+ONCR-031 (an HSV construct expressing MMP9). As shown in FIG. 57, the additional expression of CXCL10 in the ONCR-106+ONCR-113 treated group did not enhance the inhibition of tumor growth in either injected or non-injected tumors compared to mice treated with ONCR-031+ONCR-113. In fact, as shown in the table in FIG. 57, additional expression of CXCL10 slightly decreased the tumor growth inhibition in both injected and non-injected tumors.

Example 10—CCL4 Expression Further Enhances Abscopal Efficacy of HSV

Experiments were performed to assess the effects of CCL4 in tumor growth inhibition in the MC38 model described in Example F. Results of this experiment are shown in FIG. 58 and Table 20 below. Mice were treated with one of 4 constructs, ONCR-133 (expressing IL-12), ONCR-151 (expressing IL-12, CXCL10, and XCL1), ONCR-152 (expressing IL-12, CXCL10, and FLT3 ligand), or ONCR-153 (expressing IL-12, CXCL10, and CCL4). As shown in FIG. 58, treatment with all of ONCR-133, -151, -152, and -153 significantly inhibited tumor growth of injected and non-injected tumors compared to vehicle controls. However, mice treated with ONCR-153 demonstrated an increase in tumor growth inhibition in the injected tumors and in the non-injected tumors compared to treatment with ONCR-133, whereas ONCR-151 or -152 demonstrated a slight decrease in efficacy compared to treatment with ONCR-133. These results demonstrate that CCL4 expression can increase the tumor growth inhibition and abscopal effect of oncolytic HSV above the effects observed with IL-12 expression alone.

TABLE 20

| | | Injected | | | Non-injected | | |
|---|---|---|---|---|---|---|---|
| Combo | Payloads | CR | % TGI | p | CR | % TGI | p |
| ONCR-133 | IL-12 | 3/8 | 82 | <0.0001 | 0/8 | 44 | 0.19 |
| ONCR-151 | IL-12, CXCL10, XCL1 | 3/8 | 76 | <0.0001 | 0/8 | 33 | 0.35 |
| ONCR-152 | IL-12, CXCL10, FLT3L | 1/8 | 81 | <0.0001 | 0/8 | 34 | 0.3 |
| ONCR-153 | IL-12, CXCL10, CCL4 | 3/8 | 89 | <0.0001 | 0/8 | 58 | 0.001 |

Tumors from mice treated with ONCR-153 were harvested and assessed for the presence of HSV by RT-PCR analysis of the gD gene. As shown in FIG. 59A and FIG. 59B, HSV was detected in the injected tumors, but not in the non-injected tumors, indicating that the tumor growth inhibition observed in the non-injected tumors was not due to viral spread, but rather the abscopal effects of virus administration. Tumors were also assessed for the presence of the three payloads, IL-12, CXCL10, and CCL4. As shown in FIG. 60A-60C, payload expression peaked in the injected tumors at 24-hours post-treatment and decreased thereafter. Levels of the payloads were also assessed in the serum (FIG. 61A-61C) of mice treated with ONCR-153, where only CXCL10 expression was observed. However, as shown in FIG. 62, treatment of mice with ONCR-153 induced an intra-tumoral IFNγ response in both injected and non-injected tumors (left panel). Similarly, increased expression of IFNγ was observed in the serum of ONCR-153 treated mice. These data further indicate that the combination of IL-12 and CCL4 expression by HSV induce a localized immune response that may contribute to the abscopal effect observed with ONCR-153.

Example 11—FLT3 Expression Further Enhances Abscopal Efficacy of HSV

Experiments were performed to assess the effects of FLT3 in tumor growth inhibition in the MC38 model described in Example F. Results of this experiment are shown in FIG. 63 and Table 21 below. Mice were treated with one of 3 combinations of constructs expressing different payloads as outlined in Table 21. As shown in FIG. 63, treatment with a combination of ONCR-152 and ONCR-140 enhanced the tumor growth inhibition in non-injected tumors, indicating that FLT3L expression can enhance the abscopal effect over that observed with IL-12, CXL10, and CCL4.

TABLE 21

| | | Injected | | | Non-injected | | |
|---|---|---|---|---|---|---|---|
| Combo | Payloads | CR | % TGI | p | CR | % TGI | p |
| 152 + 140 | IL12, CXCL10, CCL4 | 8/8 | 97 | <0.0001 | 3/8 | 69 | 0.29 |
| 153 + 140 | IL12, CXCL10, FLT3 | 8/8 | 99 | <0.0001 | 3/8 | 58 | 0.22 |
| 152 + 153 | IL12, CXCL10, CCL4, FLT3 | 8/8 | 97 | <0.0001 | 3/8 | 75 | 0.005 |

Example 13—CD40L Expression Further Enhances Abscopal Efficacy of HSV

Experiments were performed to assess the effects of CD40L in tumor growth inhibition in the MC38 model described in Example F. Results of this experiment are shown in FIG. 64 and Table 22 below. Mice were treated with constructs expressing different payloads as outlined in Table 22. As shown in FIG. 64, treatment with a combination of ONCR-153 and ONCR-147 enhanced the tumor growth inhibition in non-injected tumors, indicating that CD40L expression can enhance the abscopal effect over that observed with IL-12, CXL10, and CCL4.

TABLE 22

| | | Injected | | | Non-injected | | |
|---|---|---|---|---|---|---|---|
| Combo | Payloads | CR | % TGI | p | CR | % TGI | p |
| 153 | IL12, CXCL10, CCL4 | 1/8 | 65 | 0.0005 | 0/8 | 41 | 0.02 |

TABLE 22-continued

| | | Injected | | | Non-injected | | |
|---|---|---|---|---|---|---|---|
| Combo | Payloads | CR | % TGI | p | CR | % TGI | p |
| 147 | CD40L, 41BBL | 0/8 | 14 | 0.35 | 0/8 | — | 0.83 |
| 153 + 147 | IL12, CXCL10, CCL4, CD40L, 41BBL | 2/8 | 73 | <0.0001 | 0/8 | 59 | 0.0005 |

Example 12—Anti-CTLA4 Expression Further Enhances Abscopal Efficacy of HSV

Experiments were performed to assess the effects of CTLA4 in tumor growth inhibition in the MC38 model described in Example F. Results of this experiment are shown in FIG. 66A-FIG. 66C and Table 23 below. Mice were treated with constructs expressing different payloads as outlined in Table 23. As shown in FIG. 66A-FIG. 66C, treatment with a combination of ONCR-149 and ONCR-139 enhanced the tumor growth inhibition in injected and non-injected tumors compared to treatment with ONCR-149 alone, indicating that anti-CTLA4 expression can enhance the anti-tumor effects and abscopal effect over that observed with IL-12.

TABLE 23

| | | Injected | | | Non-injected | | |
|---|---|---|---|---|---|---|---|
| Combo | Payloads | CR | % TGI | p | CR | % TGI | p |
| 149 | IL12 | 0/8 | 66 | <0.0001 | 0/8 | 41 | 0.0002 |
| 149 + 139 | IL12, anti-CTLA4 | 1/8 | 75 | <0.0001 | 1/8 | 57 | <0.0001 |

Similar experiments were performed to assess the effects of anti-CTLA4 over IL-12, CXCL10, FLT3L, and CCL4 expression in a 4T1-luc model. In brief, $1\times10^6$ 4 T1-luc cells in 100 μL of DPBS were injected subcutaneously into the right flank of Balb/c mice. When tumor volume reach an average of 100 $mm^3$, mice were intratumorally injected with HSV-1 at a dose of $3e^6$ PFU/injection. Dosing was repeated twice every third day for a total number of 3 doses (Q3D×3). Tumor growth and body weight was monitor twice weekly. The experiment concluded at Day 22 when the first clinical symptoms of metastatic disease were observed. Lung metastases were visualized ex vivo using IVIS Lumina LT system and analyzed with Living Image Software. Mice were treated with a combination of constructs as shown in Table 24. Results of this experiment are shown in FIG. 67. As shown, treatment with ONCR-152 and -139 demonstrated an enhanced effect in tumor growth inhibition compared to treatment with ONCR-139 alone.

TABLE 24

| Combo | Payloads |
|---|---|
| 152 | IL12, CXCL10, FLT3L |
| 139 | anti-CTLA4 |
| 152 + 139 | IL12, CXCL10, FLT3L, anti-CTLA4 |

Example 13—Treatment with Anti-PD1 Expression Further Enhances Efficacy of HSV

Experiments were performed to assess the effects of anti-PD1 treatment on HSV-mediated tumor growth inhibition in the MC38 model described in Example F. Results of this experiment are shown in FIG. 68 and Table 25 below. Mice were treated with constructs expressing different payloads as outlined in Table 25. As shown in FIG. 68, treatment with a combination of ONCR-153 and anti-PD1 enhanced the tumor growth inhibition in injected tumors compared to that observed with ONCR-152 or anti-PD1 alone.

TABLE 25

| | | Injected | | | Non-injected | | |
|---|---|---|---|---|---|---|---|
| Combo | Payloads | CR | % TGI | p | CR | % TGI | p |
| 153 | IL12, CXCL10, CCL4 | 2/8 | 79 | <0.0001 | 5/8 | 84 | <0.0001 |
| anti-PD1 | | 5/8 | 65 | 0.0005 | 0/8 | 41 | 0.02 |
| 153 + anti-PD1 | IL12, CXCL10, CCL4, anti-PD1 | 2/8 | 95 | <0.0001 | 0/8 | 83 | <0.0001 |

Example 14—Treatment of a Patient Suffering from Pancreatic Cancer, Lung Cancer, or Colon Cancer A patient suffering from pancreatic cancer, lung cancer, or colon cancer is treated using the compositions and methods disclosed herein. HSV-based viral stocks may be generated that are attenuated by incorporating one or more miRNA target sequences into UL19, ICP4, ICP27, or UL42 (or other viral genes) as shown in FIGS. 39-50. In some cases, genome-editing capabilities for tumor destruction and/or microenvironment remodeling are engineered into the virus in addition to miRNA target sequences, as shown in FIGS. 45-46. In a specific example, an HSV-based stock containing miR-124, miR-451a, miR-143-3p, and miR-559 attenuation cassettes incorporated into ICP4 and ICP27 is used. In another example, an HSV-based stock containing attenuation cassettes with one or more copies of miR-122 and miR-125a target sequences incorporated into ICP27 and/or UL42 genes. For any of these compositions, the HSV-based stock is generated according to the methods described in Example 3. The miRNA target sequence cassettes are introduced into the 3' UTR of the ICP4, ICP27UL19, and/or UL42 genes. BAC constructs are converted to virus particles with simultaneous removal of the BAC sequences located between loxP sites by transfection of Vero-Cre cells. Following plaque purification, virus stocks are further purified, buffer exchanged, and titered on Vero cells. For in vivo administration to a patient suffering from pancreatic cancer, lung cancer, or colon cancer, HSV particles are prepared in phosphate buffered solution (PBS) along with pharmaceutically acceptable stabilizing agents. On the day of treatment, $10^9$ vector genomes in a volume of 1.0 mL pharmaceutically acceptable carrier are administered via intratumoral infusion. The patient is monitored for tumor regression using standard of care procedures at an appropriate time interval based on that patient's particular prognosis.

Example 15—Treatment of Patients Suffering from Brain Cancer, Bladder Cancer, Breast Cancer, or Head and Neck Cancer A patient suffering from brain cancer, bladder cancer, breast cancer, or head and neck cancer is treated using the compositions and methods disclosed herein. An HSV-based viral stock is generated containing miR-124, miR-451a, miR-145-3p, and miR-559 attenuation cassettes according to the methods described in Example 3. The miRNA target sequence cassettes are introduced into the 3' UTR of the ICP4 (miR-124) and ICP27 (miR-451a, miR-145-3p, miR-559) genes as shown in FIG. 48. BAC constructs are converted to virus particles with simultaneous removal of the BAC sequences located between loxP sites by transfection of Vero-Cre cells. Following plaque purification, virus stocks are further purified, buffer exchanged, and titered on Vero cells. For in vivo administration to a patient suffering from brain cancer, bladder cancer, breast cancer, or head and neck cancer, HSV particles are prepared in phosphate buffered solution (PBS) along with pharmaceutically acceptable stabilizing agents. On the day of treatment, $10^9$ vector genomes in a volume of 1.0 mL pharmaceutically acceptable carrier are administered via intra-tumoral infusion. The patient is monitored using standard of care procedures at an appropriate time interval based on that patient's particular prognosis. Potential outcomes of these experiments include partial or complete inhibition of tumor growth, inhibition of tumor metastasis, prolonged time in remission, and/or reduced rate of relapse compared to standard of care therapies.

Example 16—Treatment of a Patient Suffering from Schwannoma

A patient suffering from schwannoma is treated using the compositions and methods disclosed herein. An HSV-based viral stock is generated containing miR-124-3p, miR-205-5p, miR-141-5p, and miR-31-5p attenuation cassettes according to the methods described in Example 3. The miRNA target sequence cassettes were recombined into the 3' UTR of the ICP4 (miR-124) and ICP27 (miR-205-5p, miR-141-5p, miR-31-5p) genes as shown in FIG. 49. BAC constructs are converted to virus particles with simultaneous removal of the BAC sequences located between loxP sites by transfection of Vero-Cre cells. Following plaque purification, virus stocks were further purified, buffer exchanged, and titered on Vero cells. For in vivo administration to a patient suffering from schwannoma, HSV particles are prepared in phosphate buffered solution (PBS) along with pharmaceutically acceptable stabilizing agents. On the day of treatment, $10^9$ vector genomes in a volume of 1.0 mL pharmaceutically acceptable carrier are administered via intra-tumoral infusion. The patient is monitored using standard of care procedures at an appropriate time interval based on that patient's particular prognosis. Potential outcomes of these experiments include partial or complete inhibition of tumor growth, inhibition of tumor metastasis, prolonged time in remission, and/or reduced rate of relapse compared to standard of care therapies While preferred embodiments of the present invention are shown and described herein, it will be obvious to those skilled in the art that such embodiments are provided by way of example only. Numerous variations, changes, and substitutions can be implemented by those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not, be taken as an acknowledgment or any form of suggestion that they constitute valid prior art or form part of the common general knowledge in any country in the world.

TABLE 1

Summary of relationships between 12 select oncomiRs (9 tumor suppressors and 3 oncogenic miRNAs) and various cancers

| | Down-regulated | | | | | | | | | Up-regulated | | |
|---|---|---|---|---|---|---|---|---|---|---|---|---|
| Malignancy | let-7 | miR-15a | miR-16 | miR-29a | miR-34a | miR-98 | miR-101 | miR-124 | miR-202 | miR-17 | miR-21 | miR-155 |
| acute lymphoblastic leukemia | X | | | | | | | X | | | | |
| acute myeloid leukemia | X | | | X | | | | | | X | | X |
| acute promyelocytic leukemia | X | | | | | | | | | | | |
| adrenal cortical carcinoma | | | | | | | | | | | X | |
| anaplastic astrocytoma | | | | | | | | X | | | | |
| anaplastic large-cell lymphoma | | | | | | | | | | | | X |
| astrocytoma | | | | | | | | X | | | | |
| B cell lymphoma | | | | | X | | | | | X | | |
| bladder cancer | | | X | | X | | X | X | | X | | X |
| breast cancer | X | X | X | X | X | X | | X | | X | | X |
| breast carcinoma | | | | | | | | | | X | | |
| bronchioloalveolar carcinoma | X | | | | | X | | | | | | |
| cervical cancer | | | | | | | | X | | X | | X |
| cervical carcinoma | | X | X | | X | | X | | | | | |
| cervical squamous cell carcinoma | | | | X | | | | X | | | | |
| cholangiocarcinoma | | | | | X | | X | | | X | | |
| chondrosarcoma | X | | | | | | | | | | | |
| chordoma | | | | | X | | | | | | | |
| choriocarcinoma | | | | | X | | | | | | | |
| chronic lymphocytic leukemia | | X | X | | | | | | | | | X |
| chronic myelogenous leukemia | | | X | | | | | | | | | X |
| clear cell renal cell cancer | | | | | X | | | | | | | X |
| colon cancer | X | | | | X | X | X | | | | | X |

TABLE 1-continued

Summary of relationships between 12 select oncomiRs (9 tumor suppressors and 3 oncogenic miRNAs) and various cancers

| | Down-regulated | | | | | | | | | Up-regulated | | |
|---|---|---|---|---|---|---|---|---|---|---|---|---|
| Malignancy | let-7 | miR-15a | miR-16 | miR-29a | miR-34a | miR-98 | miR-101 | miR-124 | miR-202 | miR-17 | miR-21 | miR-155 |
| colorectal cancer | X | X | X | X | X | | X | X | X | X | | X |
| colorectal carcinoma | | | | | | | | | | X | | X |
| cutaneous T cell lymphoma | | | | | | | | | | | | X |
| diffuse large B cell lymphoma | | | | | | | | | | | | X |
| endometrial cancer | | | | | X | | X | | | | | X |
| epithelial ovarian cancer | | | | | | | | X | | | | |
| esophageal cancer | | X | | | | | X | X | | | | |
| esophageal squamous cell carcinoma | X | | X | | X | X | X | | | X | | |
| extrahepatic cholangiocarcinoma | | | | | X | | | | | | | |
| follicular lymphoma | | | | | | | | | X | | | |
| gallbladder carcinoma | | | | | | | | | | | | X |
| gastric cancer | X | | | X | X | X | X | X | X | X | | X |
| glioblastoma | X | | | | X | | X | X | | | | |
| glioma | X | | X | | X | X | | X | | X | | X |
| head and neck cancer | | | | | | | | | | | | |
| head and neck squamous cell carcinoma | X | | X | X | X | | | | | | X | |
| hepatocellular carcinoma | X | | X | X | X | X | X | X | X | X | X | X |
| hypopharyngeal squamous cell carcinoma | | | | | | | | | | | X | |
| kidney cancer | | | | | | | | | | | X | |
| laryngeal carcinoma | | | X | | | | | | | | X | |
| laryngeal squamous cell carcinoma | | | | | | | X | | | | X | |
| liver cancer | | | | | | | X | | | | X | X |
| lung adenocarcinoma | | | X | | | | | | | | | X |
| lung cancer | X | X | X | | X | X | X | | | X | X | X |
| malignant melanoma | X | | | | X | X | X | | | X | X | X |
| malt lymphoma | | | | | | | | | | | | X |
| mantle cell lymphoma | | | | X | | | | X | | X | | X |
| medulloblastoma | | | | | | | | X | | X | | |
| mesenchymal cancer | | | | X | | | | | | | | |
| monocytic leukemia | | | | X | | | | | | | | |
| multiple myeloma | | | | | | | | | | | X | |
| nasopharyngeal cancer | | | | | | | | | | X | | |
| nasopharyngeal carcinoma | X | | | | | X | X | X | | | X | X |
| neuroblastoma | X | X | X | X | X | X | | X | | | | |
| non-small cell lung cancer | X | X | X | X | X | | X | X | | X | X | X |
| oral cancer | X | | | | X | | | | | | X | |
| oral squamous cell carcinoma | | | | X | | | | X | | | X | X |
| osteosarcoma | X | X | X | | X | | X | X | X | X | X | |
| ovarian cancer | X | | | | X | X | | X | | | X | X |
| ovarian carcinoma | | | | | | | X | | | | | |
| pancreatic adenocarcinoma | | | | | X | | | | | | X | |
| pancreatic cancer | | X | | | | | X | X | | X | X | |
| pancreatic ductal adenocarcinoma | X | X | X | | X | X | | | | | X | |
| papillary thyroid carcinoma | X | | X | | X | | X | | | | X | X |
| pituitary carcinoma | | | | | | | | | | X | | |
| prostate cancer | X | X | X | | X | | X | X | | | X | |
| rectal cancer | | | | | X | | | | | | X | X |
| renal cell carcinoma | X | | X | | X | | | | | | X | |
| renal clear cell carcinoma | X | | | | | | | | | | | X |
| retinoblastoma | | | | | X | | X | | | | X | |
| squamous carcinoma | | X | X | | X | | | | | | X | X |
| T cell lymphoblastic lymphoma | | | | | | | | | | X | | |
| uveal melanoma | | | | | X | | | | | | | |

TABLE 2

Summary of miRNA expression in cancer

| Malignancy | Down-regulated miRs | Up-regulated miRs |
|---|---|---|
| breast cancer | let-7a, let-7a-1, let-7a-2, let-7a-3, let-7b, let-7c, let-7d, let-7e, let-7f-1, let-7f-2, let-7g, let-7i, mir-100, mir-107, mir-10a, mir-10b, mir-122, mir-124, mir-1258, mir-125a-5p, mir-125b, mir-126, mir-127, mir-129, mir-130a, mir-132, mir-133a, mir-143, mir-145, mir-146a, mir-146b, mir-147, mir-148a, mir-149, mir-152, mir-153, mir-15a, mir-16, mir-17- | mir-10b, mir-125a, mir-135a, mir-140, mir-141, mir-142, mir-150, mir-155, mir-181a, mir-181b, mir-182, mir-18a, mir-18b, mir-191, mir-196a, mir-197, mir-19a, mir-19b, mir-200a, mir-200b, mir-200c, mir-203, mir-205, mir-20a, mir-20b, mir-21, mir-217, mir-221, mir-224, mir- |

TABLE 2-continued

| Summary of miRNA expression in cancer | | |
|---|---|---|
| Malignancy | Down-regulated miRs | Up-regulated miRs |
| | 5p, mir-181a, mir-1826, mir-183, mir-185, mir-191, mir-193a-3p, mir-193b, mir-195, mir-199b-5p, mir-19a-3p, mir-200a, mir-200b, mir-200c, mir-205, mir-206, mir-211, mir-216b, mir-218, mir-22, mir-26a, mir-26b, mir-300, mir-30a, mir-31, mir-335, mir-339-5p, mir-33b, mir-34a, mir-34b, mir-34c, mir-374a, mir-379, mir-381, mir-383, mir-425, mir-429, mir-450b-3p, mir-494, mir-495, mir-497, mir-502-5p, mir-517a, mir-574-3p, mir-638, mir-7, mir-720, mir-7515, mir-92a, mir-98, mir-99a, mmu-mir-290-3p, mmu-mir-290-5p | 23a, mir-24, mir-24-2-5p, mir-24-3p, mir-27a, mir-29a, mir-29b-1, mir-29b-2, mir-29c, mir-373, mir-378, mir-423, mir-429, mir-495, mir-503, mir-510, mir-520c, mir-526b, mir-96 |
| chondrosarcoma | let-7a, mir-100, mir-136, mir-145, mir-199a, mir-222, mir-30a, mir-335, mir-376a | |
| colorectal cancer | let-7a, mir-1, mir-100, mir-101, mir-124, mir-125a, mir-126, mir-129, mir-1295b-3p, mir-1307, mir-130b, mir-132, mir-133a, mir-133b, mir-137, mir-138, mir-139, mir-139-5p, mir-140-5p, mir-143, mir-145, mir-148a, mir-148b, mir-149, mir-150-5p, mir-154, mir-15a, mir-15b, mir-16, mir-18a, mir-191, mir-192, mir-193a-5p, mir-194, mir-195, mir-196a, mir-198, mir-199a-5p, mir-200c, mir-203, mir-204-5p, mir-206, mir-212, mir-215, mir-218, mir-22, mir-224, mir-24-3p, mir-26b, mir-27a, mir-28-3p, mir-28-5p, mir-29b, mir-30a-3p, mir-30b, mir-320a, mir-328, mir-338-3p, mir-342, mir-345, mir-34a, mir-34a-5p, mir-361-5p, mir-375, mir-378, mir-378a-3p, mir-378a-5p, mir-409-3p, mir-422a, mir-4487, mir-483, mir-497, mir-498, mir-518a-3p, mir-551a, mir-574-5p, mir-625, mir-638, mir-7, mir-96-5p | let-7a, mir-103, mir-106a, mir-10b, mir-1179, mir-1229, mir-1246, mir-125b-2*, mir-1269a, mir-130b, mir-133b, mir-135a, mir-135a-1, mir-135a-2, mir-135b, mir-139-3p, mir-145, mir-150, mir-150*, mir-155, mir-17, mir-181a, mir-182, mir-183, mir-18a, mir-191, mir-196a, mir-196b, mir-19a, mir-19b, mir-200b, mir-200c, mir-203, mir-204-5p, mir-20a, mir-20a-5p, mir-21, mir-210, mir-211, mir-221, mir-223, mir-224, mir-23a, mir-25, mir-27a, mir-29a, mir-301a, mir-31, mir-32, mir-320b, mir-326, mir-424, mir-429, mir-494, mir-497, mir-499-5p, mir-592, mir-630, mir-7-5p, mir-892a, mir-92, mir-92a, mir-93, mir-95, mir-96 |
| esophageal squamous cell carcinoma | let-7a, let-7a-1, let-7a-2, let-7a-3, let-7b, let-7c, let-7d, let-7e, let-7f-1, let-7f-2, let-7g, let-7i, mir-1, mir-100, mir-101, mir-126, mir-1294, mir-133a, mir-133b, mir-138, mir-143, mir-145, mir-150, mir-185, mir-195, mir-200b, mir-203, mir-21, mir-210, mir-214, mir-218, mir-22, mir-27a, mir-29b, mir-29c, mir-302b, mir-34a, mir-375, mir-494, mir-518b, mir-655, mir-98, mir-99a | mir-100, mir-1179, mir-1290, mir-130b, mir-145, mir-16, mir-17, mir-183, mir-18a, mir-19a, mir-19b, mir-208, mir-20a, mir-21, mir-218, mir-223, mir-25, mir-30a-5p, mir-31, mir-330-3p, mir-373, mir-9, mir-92a, mir-942 |
| gastric cancer | let-7a, let-7b, let-7g, mir-1, mir-101, mir-103a, mir-10a, mir-10b, mir-1207-5p, mir-122, mir-1228*, mir-124, mir-124-3p, mir-125a-3p, mir-126, mir-1266, mir-1271, mir-129-1-3p, mir-129-2-3p, mir-129-3p, mir-129-5p, mir-133a, mir-133b, mir-137, mir-141, mir-143, mir-144, mir-145, mir-146a, mir-146a-5p, mir-148a, mir-148b, mir-149, mir-152, mir-155, mir-155-5p, mir-181a, mir-181b, mir-182, mir-183, mir-185, mir-194, mir-195, mir-197, mir-199a-3p, mir-200b, mir-200c, mir-202-3p, mir-204, mir-204-5p, mir-205, mir-206, mir-210, mir-212, mir-217, mir-218, mir-22, mir-23b, mir-24, mir-26a, mir-29a, mir-29a-3p, mir-29b, mir-29b-1, mir-29b-2, mir-29c, mir-30a-5p, mir-30b, mir-31, mir-328, mir-329, mir-331-3p, mir-335-5p, mir-338, mir-338-3p, mir-34a, mir-34b, mir-34c, mir-361-5p, mir-367, mir-375, mir-378, mir-409-3p, mir-410, mir-429, mir-433, mir-449, mir-449a, mir-490-3p, mir-494, mir-497, mir-503, mir-506, mir-513b, mir-520d-3p, mir-542-3p, mir-622, mir-625, mir-638, mir-663, mir-7, mir-765, mir-9 | mir-100, mir-103, mir-106a, mir-106b, mir-107, mir-10a, mir-10b, mir-1259, mir-125b, mir-126, mir-1274a, mir-1303, mir-130b*, mir-135a-5p, mir-135b, mir-138, mir-143, mir-146a, mir-147, mir-148a, mir-150, mir-17, mir-17-5p, mir-181a, mir-181a-2*, mir-181a-5p, mir-181c, mir-183, mir-185, mir-18a, mir-191, mir-192, mir-196a, mir-196a*, mir-196a-5p, mir-196b, mir-199a, mir-199a-3p, mir-199a-5p, mir-19a, mir-19b, mir-200b, mir-20a, mir-21, mir-214, mir-215, mir-221, mir-221*, mir-222, mir-223, mir-224, mir-23a, mir-23b, mir-27a, mir-27b, mir-296-5p, mir-301a, mir-302f, mir-337-3p, mir-340*, mir-34a, mir-362-3p, mir-370, mir-374a, mir-377, mir-421, mir-425, mir-500, mir-520c-3p, mir-544, mir-575, mir-601, mir-616*, mir-650, mir-92, mir-98, mir-99a |
| glioma | let-7a, let-7f, mir-106a, mir-107, mir-122, mir-124, mir-124-5p, mir-124a, mir- | mir-106b, mir-106b-5p, mir-10b, mir-125b, mir-132, mir-155, mir- |

TABLE 2-continued

| Summary of miRNA expression in cancer | | |
|---|---|---|
| Malignancy | Down-regulated miRs | Up-regulated miRs |
| | 125b, mir-128, mir-136, mir-137, mir-139, mir-143, mir-145, mir-146a, mir-146b, mir-146b-5p, mir-152, mir-15b, mir-16, mir-181a, mir-181a-1, mir-181a-2, mir-181b, mir-181b-1, mir-181b-2, mir-181c, mir-181d, mir-184, mir-185, mir-195, mir-199a-3p, mir-200a, mir-200b, mir-203, mir-204, mir-205, mir-218, mir-219-5p, mir-23b, mir-26b, mir-27a, mir-29c, mir-320, mir-326, mir-328, mir-34a, mir-34c-3p, mir-34c-5p, mir-375, mir-383, mir-451, mir-452, mir-483-5p, mir-495, mir-584, mir-622, mir-656, mir-7, mir-98 | 17, mir-181a, mir-182, mir-183, mir-193b, mir-19a, mir-19b, mir-20a, mir-210, mir-214, mir-221, mir-222, mir-224, mir-23a, mir-24, mir-24-3p, mir-25, mir-26a, mir-27a-3p, mir-27b, mir-30a-5p, mir-30e, mir-30e*, mir-328, mir-335, mir-33a, mir-372, mir-486, mir-494, mir-497, mir-566, mir-603, mir-650, mir-675, mir-9, mir-92b, mir-93, mir-96 |
| nasopharyngeal carcinoma | let-7a, let-7a-1, let-7a-2, let-7a-3, let-7b, let-7c, let-7d, let-7e, let-7f-1, let-7f-2, let-7g, let-7i, mir-1, mir-101, mir-124, mir-138, mir-143, mir-145, mir-148a, mir-200b, mir-204, mir-216b, mir-29c, mir-320a, mir-324-3p, mir-34c, mir-375, mir-378, mir-451, mir-506, mir-9, mir-98 | mir-10b, mir-144, mir-149, mir-155, mir-18a, mir-21, mir-214, mir-24, mir-421, mir-663, mir-7-5p, mir-93 |
| non-small cell lung cancer | let-7a, let-7c, mir-1, mir-100, mir-101, mir-106a, mir-107, mir-124, mir-125a-3p, mir-125a-5p, mir-126*, mir-129, mir-133a, mir-137, mir-138, mir-140, mir-143, mir-145, mir-146a, mir-146b, mir-148a, mir-148b, mir-149, mir-152, mir-153, mir-154, mir-155, mir-15a, mir-16, mir-17-5p, mir-181a-1, mir-181a-2, mir-181b, mir-181b-1, mir-181b-2, mir-181c, mir-181d, mir-184, mir-186, mir-193b, mir-195, mir-199a, mir-204, mir-212, mir-221, mir-224, mir-26b, mir-27a, mir-27b, mir-29a, mir-29b, mir-29c, mir-30a, mir-30b, mir-30c, mir-30d, mir-30d-5p, mir-30e-5p, mir-32, mir-335, mir-338-3p, mir-340, mir-342-3p, mir-34a, mir-34b, mir-361-3p, mir-365, mir-373, mir-375, mir-429, mir-449a, mir-4500, mir-451, mir-4782-3p, mir-497, mir-503, mir-512-3p, mir-520a-3p, mir-526b, mir-625*, mir-96, mir-99a | mir-10b, mir-125a-5p, mir-1280, mir-136, mir-140, mir-141, mir-142-3p, mir-145, mir-146a, mir-150, mir-18a, mir-196a, mir-19a, mir-200a, mir-200c, mir-205, mir-205-5p, mir-21, mir-212, mir-22, mir-221, mir-222, mir-24, mir-25, mir-29c, mir-31, mir-328, mir-330-3p, mir-339, mir-34a, mir-375, mir-494, mir-675-5p, mir-9, mir-92b, mir-93, mir-95 |
| osteosarcoma | let-7a, mir-1, mir-100, mir-101, mir-122, mir-124, mir-125b, mir-126, mir-127-3p, mir-132, mir-133a, mir-141, mir-142-3p, mir-142-5p, mir-143, mir-144, mir-145, mir-153, mir-16, mir-183, mir-194, mir-195, mir-199a-3p, mir-204, mir-212, mir-217, mir-218, mir-22, mir-23a, mir-24, mir-26a, mir-26b, mir-29b, mir-32, mir-320, mir-335, mir-33b, mir-340, mir-34a, mir-34b, mir-34c, mir-375, mir-376c, mir-382, mir-3928, mir-424, mir-429, mir-449a, mir-451, mir-454, mir-503, mir-519d, mir-646 | mir-128, mir-151-3p, mir-17, mir-181a, mir-181b, mir-181c, mir-18a, mir-191, mir-195-5p, mir-199a-3p, mir-19a, mir-19b, mir-20a, mir-21, mir-210, mir-214, mir-221, mir-27a, mir-300, mir-320a, mir-374a-5p, mir-720, mir-9, mir-92a |
| pancreatic ductal adenocarcinoma | let-7a, let-7a-1, let-7a-2, let-7a-3, let-7b, let-7c, let-7d, let-7e, let-7f-1, let-7f-2, let-7g, let-7i, mir-126, mir-135a, mir-143, mir-144, mir-145, mir-148a, mir-150, mir-15a, mir-16, mir-200a, mir-200b, mir-200c, mir-217, mir-218, mir-337, mir-375, mir-494, mir-615-5p, mir-98 | mir-10b, mir-186, mir-18a, mir-192, mir-194, mir-196a, mir-198, mir-203, mir-21, mir-212, mir-30b-5p, mir-31, mir-34a, mir-369-5p, mir-376a, mir-541 |
| renal cell carcinoma | let-7a, let-7d, mir-1, mir-106a*, mir-126, mir-1285, mir-129-3p, mir-1291, mir-133a, mir-133b, mir-135a, mir-138, mir-141, mir-143, mir-145, mir-182-5p, mir-199a-3p, mir-200a, mir-205, mir-218, mir-28-5p, mir-30a, mir-30c, mir-30d, mir-34a, mir-378, mir-429, mir-509-3p, mir-509-5p, mir-646 | mir-100, mir-1233, mir-1260b, mir-146a, mir-146b, mir-16, mir-193a-3p, mir-203a, mir-21, mir-210, mir-27a, mir-362, mir-572, mir-7 |
| bronchioloalveolar carcinoma | let-7a-1, let-7a-2, let-7a-3, let-7b, let-7c, let-7d, let-7e, let-7f-1, let-7f-2, let-7g, let-7i, mir-98 | |
| colon cancer | let-7a-1, let-7a-2, let-7a-3, let-7b, let-7c, let-7d, let-7e, let-7f-1, let-7f-2, let-7g, | mir-1290, mir-145, mir-155, mir-181a, mir-18a, mir-200c, mir-31, |

TABLE 2-continued

| Summary of miRNA expression in cancer | | |
|---|---|---|
| Malignancy | Down-regulated miRs | Up-regulated miRs |
| | let-7i, mir-100, mir-101, mir-126, mir-142-3p, mir-143, mir-145, mir-192, mir-200c, mir-21, mir-214, mir-215, mir-25, mir-302a, mir-320, mir-320a, mir-34a, mir-34c, mir-365, mir-373, mir-424, mir-429, mir-455, mir-484, mir-502, mir-503, mir-93, mir-98 | mir-675 |
| hepatocellular carcinoma | let-7a-1, let-7a-2, let-7a-3, let-7b, let-7c, let-7d, let-7e, let-7f, let-7f-1, let-7f-2, let-7g, let-7i, mir-1, mir-100, mir-101, mir-105, mir-122, mir-122a, mir-1236, mir-124, mir-125b, mir-126, mir-127, mir-1271, mir-128-3p, mir-129-5p, mir-130a, mir-130b, mir-133a, mir-134, mir-137, mir-138, mir-139, mir-139-5p, mir-140-5p, mir-141, mir-142-3p, mir-143, mir-144, mir-145, mir-146a, mir-148a, mir-148b, mir-150-5p, mir-15b, mir-16, mir-181a-5p, mir-185, mir-188-5p, mir-193b, mir-195, mir-195-5p, mir-197, mir-198, mir-199a, mir-199a-5p, mir-199b, mir-199b-5p, mir-200a, mir-200b, mir-200c, mir-202, mir-203, mir-204-3p, mir-205, mir-206, mir-20a, mir-21, mir-21-3p, mir-211, mir-212, mir-214, mir-217, mir-218, mir-219-5p, mir-22, mir-26a, mir-26b, mir-29a, mir-29b-1, mir-29b-2, mir-29c, mir-302b, mir-302c, mir-30a, mir-30a-3p, mir-335, mir-338-3p, mir-33a, mir-34a, mir-34b, mir-365, mir-370, mir-372, mir-375, mir-376a, mir-377, mir-422a, mir-424, mir-424-5p, mir-433, mir-4458, mir-448, mir-450a, mir-451, mir-485-5p, mir-486-5p, mir-497, mir-503, mir-506, mir-519d, mir-520a, mir-520b, mir-520c-3p, mir-582-5p, mir-590-5p, mir-610, mir-612, mir-625, mir-637, mir-675, mir-7, mir-877, mir-940, mir-941, mir-98, mir-99a | mir-106b, mir-10b, mir-122, mir-1228, mir-1269, mir-128a, mir-130a, mir-130b, mir-146a, mir-153, mir-155, mir-17-5p, mir-181a, mir-181a-1, mir-181a-2, mir-181b, mir-181b-1, mir-181b-2, mir-181c, mir-181d, mir-182, mir-183, mir-184, mir-190b, mir-191, mir-20a, mir-20b, mir-21, mir-210, mir-214, mir-215, mir-216a, mir-217, mir-221, mir-222, mir-223, mir-224, mir-23a, mir-24, mir-25, mir-27a, mir-301a, mir-30d, mir-31, mir-3127, mir-32, mir-331-3p, mir-362-3p, mir-371-5p, mir-372, mir-373, mir-423, mir-429, mir-452, mir-483-3p, mir-483-5p, mir-485-3p, mir-490-3p, mir-494, mir-495, mir-500, mir-501-5p, mir-519d, mir-520g, mir-574-3p, mir-590-5p, mir-630, mir-650, mir-657, mir-664, mir-885-5p, mir-9, mir-92a, mir-96 |
| lung cancer | let-7a-1, let-7a-2, let-7a-3, let-7b, let-7c, let-7d, let-7e, let-7f-1, let-7f-2, let-7g, let-7i, mir-1, mir-101, mir-133b, mir-138, mir-142-5p, mir-144, mir-145, mir-1469, mir-146a, mir-153, mir-15a, mir-15b, mir-16-1, mir-16-2, mir-182, mir-192, mir-193a-3p, mir-194, mir-195, mir-198, mir-203, mir-217, mir-218, mir-22, mir-223, mir-26a, mir-26b, mir-29c, mir-33a, mir-34a, mir-34b, mir-34c, mir-365, mir-449a, mir-449b, mir-486-5p, mir-545, mir-610, mir-614, mir-630, mir-660, mir-7-5p, mir-9500, mir-98, mir-99b | mir-10b, mir-135b, mir-150, mir-155, mir-17, mir-182, mir-183-3p, mir-18a, mir-197, mir-19a, mir-19b, mir-205, mir-20a, mir-21, mir-210, mir-24, mir-30d, mir-4423, mir-5100, mir-570, mir-663, mir-7, mir-92a |
| neuroblastoma | let-7a-1, let-7a-2, let-7a-3, let-7b, let-7c, let-7d, let-7e, let-7f-1, let-7f-2, let-7g, let-7i, mir-124, mir-137, mir-145, mir-181c, mir-184, mir-200a, mir-29a, mir-335, mir-338-3p, mir-34a, mir-449a, mir-885-5p, mir-98 | mir-125b, mir-15a, mir-15b, mir-16-1, mir-16-2, mir-18a, mir-195, mir-19a, mir-23a, mir-421, mir-92 |
| prostate cancer | let-7a-3p, let-7c, mir-100, mir-101, mir-105, mir-124, mir-128, mir-1296, mir-130b, mir-133a-1, mir-133a-2, mir-133b, mir-135a, mir-143, mir-145, mir-146a, mir-154, mir-15a, mir-187, mir-188-5p, mir-199b, mir-200b, mir-203, mir-205, mir-212, mir-218, mir-221, mir-224, mir-23a, mir-23b, mir-25, mir-26a, mir-26b, mir-29b, mir-302a, mir-30a, mir-30b, mir-30c-1, mir-30c-2, mir-30d, mir-30e, mir-31, mir-330, mir-331-3p, mir-34a, mir-34b, mir-34c, mir-374b, mir-449a, mir-4723-5p, mir-497, mir-628-5p, mir-642a-5p, mir-720, mir-940 | mir-125b, mir-141, mir-153, mir-155, mir-181a-1, mir-181a-2, mir-181b, mir-181b-1, mir-181b-2, mir-181c, mir-181d, mir-182, mir-182-5p, mir-183, mir-18a, mir-204, mir-20a, mir-21, mir-221, mir-223-3p, mir-31, mir-429, mir-96 |
| acute lymphoblastic leukemia | let-7b, mir-124a, mir-142-3p | mir-128 |
| malignant melanoma | let-7b, mir-101, mir-125b, mir-1280, mir-143, mir-146a, mir-146b, mir-155, | mir-126, mir-141, mir-15b, mir-17, mir-17-5p, mir-182, mir-18a, |

TABLE 2-continued

| Summary of miRNA expression in cancer | | |
|---|---|---|
| Malignancy | Down-regulated miRs | Up-regulated miRs |
| | mir-17, mir-184, mir-185, mir-18b, mir-193b, mir-200c, mir-203, mir-204, mir-205, mir-206, mir-20a, mir-211, mir-218, mir-26a, mir-31, mir-33a, mir-34a, mir-34c, mir-376a, mir-376c, mir-573, mir-7, mir-9, mir-98 | mir-193b, mir-200a, mir-200b, mir-200c, mir-20a, mir-21, mir-210, mir-214, mir-221, mir-222, mir-429, mir-455-5p, mir-532-5p, mir-638, mir-92a |
| renal clear cell carcinoma | let-7b, let-7c, mir-138, mir-141, mir-200c, mir-204, mir-218, mir-335, mir-377, mir-506 | mir-122, mir-155, mir-630 |
| acute myeloid leukemia | let-7c, mir-17, mir-181a, mir-20a, mir-223, mir-26a, mir-29a, mir-30c, mir-7 | mir-125b, mir-126-5p, mir-128, mir-155, mir-29a, mir-32, mir-331, mir-370, mir-378 |
| acute promyelocytic leukemia | let-7c, mir-107, mir-342 | mir-181a, mir-181b, mir-92a |
| head and neck squamous cell carcinoma | let-7d, mir-1, mir-107, mir-128, mir-133a, mir-138, mir-149, mir-200c, mir-205, mir-218, mir-27a*, mir-29a, mir-29b-1, mir-29b-2, mir-29c, mir-300, mir-34a, mir-363, mir-375, mir-874 | mir-106b, mir-134, mir-16, mir-184, mir-196a, mir-21, mir-25, mir-30a-5p, mir-31, mir-372, mir-93 |
| oral cancer | let-7d, mir-218, mir-34a, mir-375, mir-494 | mir-10b, mir-196a-1, mir-196a-2, mir-196b, mir-21 |
| papillary thyroid carcinoma | mir-101, mir-130b, mir-138, mir-146a, mir-16, mir-195, mir-199a-3p, mir-204-5p, mir-219-5p, mir-26a, mir-34b, mir-613 | let-7e, mir-146b, mir-146b-5p, mir-151-5p, mir-155, mir-181a-1, mir-181a-2, mir-181b-1, mir-181b-2, mir-181c, mir-181d, mir-182, mir-183, mir-199b-5p, mir-21, mir-221, mir-222, mir-339-5p, mir-34a |
| glioblastoma | let-7g-5p, mir-100, mir-101, mir-106a, mir-124, mir-124a, mir-125a, mir-125a-5p, mir-125b, mir-127-3p, mir-128, mir-129, mir-136, mir-137, mir-139-5p, mir-142-3p, mir-143, mir-145, mir-146b-5p, mir-149, mir-152, mir-153, mir-195, mir-21, mir-212-3p, mir-219-5p, mir-222, mir-29b, mir-31, mir-3189-3p, mir-320, mir-320a, mir-326, mir-330, mir-331-3p, mir-340, mir-342, mir-34a, mir-376a, mir-449a, mir-483-5p, mir-503, mir-577, mir-663, mir-7, mir-744 | mir-10b, mir-125b, mir-127-3p, mir-148a, mir-18a, mir-196a, mir-196a-1, mir-196a-2, mir-196b, mir-21, mir-210, mir-210-3p, mir-223, mir-340, mir-576-5p, mir-626, mir-92b |
| ovarian cancer | let-7i, mir-100, mir-124, mir-125b, mir-129-5p, mir-130b, mir-133a, mir-137, mir-138, mir-141, mir-145, mir-148a, mir-152, mir-153, mir-155, mir-199a, mir-200a, mir-200b, mir-200c, mir-212, mir-335, mir-34a, mir-34b, mir-34c, mir-409-3p, mir-411, mir-429, mir-432, mir-449a, mir-494, mir-497, mir-498, mir-519d, mir-655, mir-9, mir-98 | mir-106a, mir-141, mir-148b, mir-181b, mir-182, mir-200a, mir-200c, mir-205, mir-20a, mir-21, mir-210, mir-214, mir-221, mir-224-5p, mir-23b, mir-25, mir-26a, mir-27a, mir-27b, mir-346, mir-378, mir-424, mir-503, mir-572, mir-9, mir-96 |
| bladder cancer | mir-1, mir-101, mir-1180, mir-1236, mir-124-3p, mir-125b, mir-126, mir-1280, mir-133a, mir-133b, mir-141, mir-143, mir-144, mir-145, mir-155, mir-16, mir-18a, mir-192, mir-195, mir-200a, mir-200b, mir-200c, mir-203, mir-205, mir-214, mir-218, mir-23b, mir-26a, mir-29c, mir-320c, mir-34a, mir-370, mir-409-3p, mir-429, mir-451, mir-490-5p, mir-493, mir-576-3p, mir-99a | mir-103a-3p, mir-10b, mir-135a, mir-137, mir-141, mir-155, mir-17-5p, mir-182, mir-182-5p, mir-183, mir-185, mir-19a, mir-203, mir-205, mir-210, mir-221, mir-222, mir-223, mir-23a, mir-23b, mir-26b, mir-639, mir-96 |
| chordoma | mir-1, mir-222, mir-31, mir-34a, mir-608 | mir-140-3p, mir-148a |
| kidney cancer | mir-1, mir-145, mir-1826, mir-199a, mir-199a-3p, mir-203, mir-205, mir-497, mir-508-3p, mir-509-3p | mir-183, mir-21, mir-210, mir-223 |
| cervical carcinoma | mir-100, mir-101, mir-15a, mir-16, mir-34a, mir-886-5p, mir-99a, mir-99b | mir-133b, mir-21, mir-25, mir-373 |
| mesenchymal cancer | mir-100, mir-141, mir-199b-5p, mir-200a, mir-200b, mir-200c, mir-29a, mir-29b-1, mir-29b-1-5p, mir-29b-2, mir-29c, mir-335, mir-429, mir-99a | mir-125b-1-3p, mir-182 |

TABLE 2-continued

Summary of miRNA expression in cancer

| Malignancy | Down-regulated miRs | Up-regulated miRs |
|---|---|---|
| oral squamous cell carcinoma | mir-100, mir-124, mir-1250, mir-125b, mir-126, mir-1271, mir-136, mir-138, mir-145, mir-147, mir-148a, mir-181a, mir-206, mir-220a, mir-26a, mir-26b, mir-29a, mir-32, mir-323-5p, mir-329, mir-338, mir-370, mir-410, mir-429, mir-433, mir-499a-5p, mir-503, mir-506, mir-632, mir-646, mir-668, mir-877, mir-9 | mir-125b, mir-126, mir-146a, mir-146b, mir-155, mir-181b, mir-196a-1, mir-196a-2, mir-196b, mir-21, mir-221, mir-222, mir-24, mir-27b, mir-31, mir-345 |
| ovarian carcinoma | mir-100, mir-101, mir-34b, mir-34c, mir-532-5p | mir-148b, mir-182 |
| cholangiocarcinoma | mir-101, mir-144, mir-200b, mir-200c | mir-17, mir-18a, mir-19a, mir-19b, mir-20a, mir-21, mir-26a, mir-92a |
| endometrial cancer | mir-101, mir-130a, mir-130b, mir-134, mir-143, mir-145, mir-152, mir-205, mir-223, mir-301a, mir-301b, mir-30c, mir-34a, mir-34c, mir-424, mir-449a, mir-543 | mir-106a, mir-145, mir-155, mir-182, mir-200b, mir-200c, mir-205, mir-21, mir-222-3p, mir-25, mir-93 |
| esophageal cancer | mir-124, mir-126, mir-140, mir-197, mir-203, mir-218, mir-223, mir-30b, mir-375, mir-454, mir-486, mir-574-3p | mir-101, mir-10b, mir-130a, mir-141, mir-143, mir-146b, mir-15a, mir-183, mir-196b, mir-200a, mir-203, mir-205, mir-21, mir-210, mir-221, mir-27a, mir-28-3p, mir-31, mir-452, mir-96, mir-99b |
| liver cancer | mir-101, mir-122, mir-132, mir-140-5p, mir-145, mir-148b, mir-31, mir-338-3p, mir-433 | mir-1301, mir-155, mir-21, mir-221, mir-27a, mir-525-3p |
| pancreatic cancer | mir-101, mir-1181, mir-124, mir-1247, mir-133a, mir-141, mir-145, mir-146a, mir-148a, mir-148b, mir-150*, mir-150-5p, mir-152, mir-15a, mir-198, mir-203, mir-214, mir-216a, mir-29c, mir-335, mir-34a, mir-34b, mir-34c, mir-373, mir-375, mir-410, mir-497, mir-615-5p, mir-630, mir-96 | mir-10a, mir-10b, mir-132, mir-15a, mir-17-5p, mir-181a, mir-18a, mir-191, mir-196a, mir-21, mir-212, mir-214, mir-222, mir-27a, mir-301a, mir-301a-3p, mir-367, mir-424-5p, mir-7, mir-92, mir-99a |
| retinoblastoma | mir-101, mir-183, mir-204, mir-34a, mir-365b-3p, mir-486-3p, mir-532-5p | mir-181b, mir-21 |
| cervical squamous cell carcinoma | mir-106a, mir-124, mir-148a, mir-214, mir-218, mir-29a, mir-375 | mir-205 |
| clear cell renal cell cancer | mir-106a-5p, mir-135a-5p, mir-206 | mir-142-5p, mir-155, mir-21-5p |
| laryngeal carcinoma | | mir-106b, mir-16, mir-21, mir-27a, mir-423-3p |
| medulloblastoma | mir-124, mir-128a, mir-199b-5p, mir-206, mir-22, mir-31, mir-383 | mir-106b, mir-17, mir-18a, mir-19a, mir-19b, mir-20a, mir-30b, mir-30d, mir-92 |
| pituitary carcinoma | | mir-106b, mir-122, mir-20a, mir-493 |
| prostate carcinoma | mir-107 | |
| cervical cancer | mir-143, mir-145, mir-17-5p, mir-203, mir-214, mir-218, mir-335, mir-342-3p, mir-372, mir-424, mir-491-5p, mir-497, mir-7, mir-99a, mir-99b | mir-10a, mir-155, mir-181a, mir-181b, mir-196a, mir-19a, mir-19b, mir-205, mir-20a, mir-21, mir-215, mir-224, mir-31, mir-494, mir-590-5p, mir-92a, mir-944 |
| chronic myelogenous leukemia | mir-10a, mir-146a, mir-150, mir-151, mir-155, mir-2278, mir-26a, mir-30e, mir-31, mir-326, mir-564 | mir-424, mir-96 |
| gastrointestinal cancer | mir-122a, mir-148a, mir-152 | |
| anaplastic astrocytoma | mir-124, mir-137 | |
| astrocytoma | mir-124-3p, mir-181b-5p, mir-200b, mir-3189-3p | mir-335 |
| epithelial ovarian cancer | mir-124a, mir-192, mir-193a, mir-7 | mir-372, mir-373 |
| mantle cell lymphoma | mir-142-3p, mir-142-5p, mir-150, mir-223, mir-29a, mir-29b, mir-29c | mir-124a, mir-155, mir-17, mir-18a, mir-19a, mir-19b, mir-20a, mir-92a |
| chronic lymphocytic leukemia | mir-125b, mir-138, mir-15a, mir-15b, mir-16, mir-16-1, mir-16-1-3p, mir-16-2, mir-181a, mir-181b, mir-195, mir-223, mir-29b, mir-34b, mir-34c, mir-424 | mir-150, mir-155 |
| follicular cancer | NA | mir-125b |
| malignant mesothelioma | mir-126 | |
| small cell lung cancer | mir-126, mir-138, mir-27a | mir-25 |

TABLE 2-continued

| Summary of miRNA expression in cancer | | |
|---|---|---|
| Malignancy | Down-regulated miRs | Up-regulated miRs |
| meningioma | mir-128, mir-200a | mir-224, mir-335 |
| laryngeal squamous cell carcinoma | mir-129-5p, mir-203, mir-205, mir-206, mir-24, mir-370, mir-375 | mir-21, mir-9, mir-93 |
| medullary thyroid carcinoma | mir-129-5p | mir-183 |
| lung adenocarcinoma | mir-1297, mir-141, mir-145, mir-16, mir-200a, mir-200b, mir-200c, mir-29b, mir-381, mir-409-3p, mir-429, mir-451, mir-511, mir-99a | mir-150, mir-155, mir-31 |
| pancreatic carcinoma | mir-132, mir-375 | mir-301b |
| lung squamous cell carcinoma | mir-133a, mir-218 | |
| multiple myeloma | mir-137, mir-197, mir-214 | mir-21 |
| squamous carcinoma | mir-15a, mir-16, mir-203, mir-205, mir-375 | mir-137, mir-155, mir-184, mir-196a, mir-203, mir-21, mir-221, mir-27a, mir-34a |
| uveal melanoma | mir-137, mir-144, mir-145, mir-182, mir-34a, mir-34b, mir-34c, mir-9 | NA |
| anaplastic thyroid carcinoma | mir-138 | mir-146b, mir-221, mir-222 |
| colorectal carcinoma | mir-139, mir-143, mir-145, mir-202-3p, mir-30a, mir-338-3p, mir-429, mir-451, mir-93 | mir-17, mir-182, mir-191, mir-21, mir-95 |
| malt lymphoma | | mir-142-5p, mir-155 |
| thyroid cancer | mir-144, mir-886-3p | |
| primary cns lymphomas | mir-145, mir-193b, mir-199a, mir-214 | |
| follicular thyroid carcinoma | mir-199b | mir-146b, mir-183, mir-197, mir-221, mir-346 |
| gallbladder carcinoma | mir-146b-5p | mir-155, mir-182 |
| adult t-cell leukemia | | mir-150 |
| anaplastic large-cell lymphoma | | mir-155 |
| cutaneous t-cell lymphoma | | mir-155 |
| diffuse large B-cell lymphoma | | mir-155, mir-21 |
| rectal cancer | | mir-155, mir-200c, mir-21-5p, mir-34a |
| tongue cancer | mir-15b, mir-200b | |
| b-cell lymphoma | mir-34a | mir-17, mir-18a, mir-19a, mir-19b, mir-20a, mir-92a |
| breast carcinoma | | mir-17, mir-18a, mir-19a, mir-19b, mir-20a, mir-24, mir-92a |
| nasopharyngeal cancer | mir-218, mir-223, mir-29c | mir-17, mir-20a |
| gastric adenocarcinoma | mir-181b, mir-182, mir-200a, mir-302b, mir-449a, mir-9 | mir-23a, mir-27a, mir-373 |
| colorectal adenocarcinoma | | mir-182 |
| colon carcinoma | mir-186, mir-30a-5p | mir-221, mir-23a |
| adrenal cortical carcinoma | mir-195, mir-1974, mir-335, mir-497 | mir-21, mir-210, mir-483-3p, mir-483-5p |
| esophageal adenocarcinoma | mir-203 | mir-196a, mir-199a-3p, mir-199a-5p, mir-199b-3p, mir-200a, mir-223 |
| gastrointestinal stromal tumor | mir-218, mir-221, mir-222 | mir-196a |
| uterine leiomyoma | mir-197 | |
| choriocarcinoma | mir-199b, mir-218, mir-34a | |
| follicular lymphoma | mir-202 | |
| basal cell carcinoma | mir-203 | |
| hypopharyngeal cancer | | mir-203 |
| pancreatic adenocarcinoma | | mir-203, mir-301a |
| rhabdomyosarcoma | mir-203 | |
| head and neck cancer | NA | mir-21 |
| hypopharyngeal squamous cell carcinoma | mir-451a, mir-504 | mir-21 |
| t-cell lymphoma | mir-22 | |
| thyroid carcinoma | | mir-221, mir-222 |
| splenic marginal zone lymphoma | mir-223 | |

TABLE 2-continued

| Summary of miRNA expression in cancer | | |
|---|---|---|
| Malignancy | Down-regulated miRs | Up-regulated miRs |
| laryngeal cancer | | mir-23a |
| primary thyroid lymphoma | mir-26a | |
| acute leukemia | mir-27a | |
| monocytic leukemia | mir-29a, mir-29b | |
| oral carcinoma | mir-375 | mir-31 |
| primary gallbladder carcinoma | mir-335 | |
| endometrial serous adenocarcinoma | mir-34b | |
| esophageal carcinoma | mir-451 | |
| hepatoblastoma | | mir-492 |
| colonic adenocarcinoma | mir-627 | |

TABLE 4

| Exemplary oncogenic miRs | |
|---|---|
| Cancer | miRNA |
| colorectal cancer | let-7a, mir-103, mir-106a, mir-10b, mir-1179, mir-1229, mir-1246, mir-125b-2*, mir-1269a, mir-130b, mir-133b, mir-135a, mir-135a-1, mir-135a-2, mir-135b, mir-139-3p, mir-145, mir-150, mir-150*, mir-155, mir-17, mir-181a, mir-182, mir-183, mir-18a, mir-191, mir-196a, mir-196b, mir-19a, mir-19b, mir-200b, mir-200c, mir-203, mir-204-5p, mir-20a, mir-20a-5p, mir-21, mir-210, mir-211, mir-221, mir-223, mir-224, mir-23a, mir-25, mir-27a, mir-29a, mir-301a, mir-31, mir-32, mir-320b, mir-326, mir-424, mir-429, mir-494, mir-497, mir-499-5p, mir-592, mir-630, mir-720, mir-892a, mir-92, mir-92a, mir-93, mir-95, mir-96 |
| papillary thyroid carcinoma | let-7e, mir-146b, mir-146b-5p, mir-151-5p, mir-155, mir-181a-1, mir-181a-2, mir-181b-1, mir-181b-2, mir-181c, mir-181d, mir-182, mir-183, mir-199b-5p, mir-21, mir-221, mir-222, mir-339-5p, mir-34a |
| esophageal squamous cell carcinoma | mir-100, mir-1179, mir-1290, mir-130b, mir-145, mir-16, mir-17, mir-183, mir-18a, mir-19a, mir-19b, mir-208, mir-20a, mir-21, mir-218, mir-223, mir-25, mir-30a-5p, mir-31, mir-330-3p, mir-373, mir-9, mir-92a, mir-942 |
| gastric cancer | mir-100, mir-103, mir-106a, mir-106b, mir-107, mir-10a, mir-10b, mir-1259, mir-125b, mir-126, mir-1274a, mir-1303, mir-130b*, mir-135a-5p, mir-135b, mir-138, mir-143, mir-146a, mir-147, mir-148a, mir-150, mir-17, mir-17-5p, mir-181a, mir-181a-2*, mir-181a-5p, mir-181c, mir-183, mir-185, mir-18a, mir-191, mir-192, mir-196a, mir-196a*, mir-196a-5p, mir-196b, mir-199a, mir-199a-3p, mir-199a-5p, mir-19a, mir-19b, mir-200b, mir-20a, mir-21, mir-214, mir-215, mir-221, mir-221*, mir-222, mir-223, mir-224, mir-23a, mir-23b, mir-25, mir-27a, mir-27b, mir-296-5p, mir-301a, mir-302f, mir-337-3p, mir-340*, mir-34a, mir-362-3p, mir-370, mir-374a, mir-377, mir-421, mir-425, mir-500, mir-520c-3p, mir-544, mir-575, mir-601, mir-616*, mir-650, mir-92, mir-98, mir-99a |
| renal cell carcinoma | mir-100, mir-1233, mir-1260b, mir-146a, mir-146b, mir-16, mir-193a-3p, mir-203a, mir-21, mir-210, mir-27a, mir-362, mir-572, mir-7 |
| esophageal cancer | mir-101, mir-10b, mir-130a, mir-141, mir-143, mir-146b, mir-15a, mir-183, mir-196b, mir-200a, mir-203, mir-205, mir-21, mir-210, mir-221, mir-27a, mir-28-3p, mir-31, mir-452, mir-96, mir-99b |
| bladder cancer | mir-103a-3p, mir-10b, mir-135a, mir-137, mir-141, mir-155, mir-17-5p, mir-182, mir-182-5p, mir-183, mir-185, mir-19a, mir-203, mir-205, mir-210, mir-221, mir-222, mir-223, mir-23a, mir-23b, mir-26b, mir-639, mir-96 |
| endometrial cancer | mir-106a, mir-145, mir-155, mir-182, mir-200b, mir-200c, mir-205, mir-21, mir-222-3p, mir-25, mir-93 |
| ovarian cancer | mir-106a, mir-141, mir-148b, mir-181b, mir-182, mir-200a, mir-200c, mir-205, mir-20a, mir-21, mir-210, mir-214, mir-221, mir-224-5p, mir-23b, mir-25, mir-26a, mir-27a, mir-27b, mir-346, mir-378, mir-424, mir-503, mir-572, mir-9, mir-96 |
| glioma | mir-106b, mir-106b-5p, mir-10b, mir-125b, mir-132, mir-155, mir-17, mir-181a, mir-182, mir-183, mir-193b, mir-19a, mir-19b, mir-20a, mir-210, mir-214, mir-221, mir-222, mir-224, mir-23a, mir-24, mir-24-3p, mir-25, mir-26a, mir-27a-3p, mir-27b, mir-30a-5p, mir-30e, mir-30e*, mir-328, mir-335, mir-33a, mir-372, mir-486, mir-494, mir-497, mir-566, mir-603, mir-650, mir-675, mir-9, mir-92b, mir-93, mir-96 |
| head and neck squamous cell carcinoma | mir-106b, mir-134, mir-16, mir-184, mir-196a, mir-21, mir-25, mir-30a-5p, mir-31, mir-372, mir-93 |
| hepatocellular carcinoma | mir-106b, mir-10b, mir-122, mir-1228, mir-1269, mir-128a, mir-130a, mir-130b, mir-146a, mir-153, mir-155, mir-17-5p, mir-181a, mir-181a-1, mir-181a-2, mir-181b, mir-181b-1, mir-181b-2, mir-181c, mir-181d, mir-182, mir-183, mir-184, mir-190b, mir-191, mir-20a, mir-20b, mir-21, mir-210, mir-214, mir-215, mir-216a, mir-217, mir-221, mir-222, mir-223, mir-224, mir-23a, mir-24, mir-25, mir-27a, mir-301a, mir-30d, mir-31, mir-3127, mir-32, mir-331-3p, mir-362-3p, mir-362-5p, mir-371-5p, mir-372, mir-373, mir-423, mir-429, mir-452, mir-483-3p, mir-483-5p, mir-485-3p, mir-490- |

TABLE 4-continued

| Exemplary oncogenic miRs | |
|---|---|
| Cancer | miRNA |
| | 3p, mir-494, mir-495, mir-500, mir-501, mir-501-5p, mir-519d, mir-520g, mir-574-3p, mir-590-5p, mir-630, mir-650, mir-657, mir-664, mir-885-5p, mir-9, mir-92a, mir-96 |
| laryngeal carcinoma | mir-106b, mir-16, mir-21, mir-27a, mir-423-3p |
| medulloblastoma | mir-106b, mir-17, mir-18a, mir-19a, mir-19b, mir-20a, mir-30b, mir-30d, mir-92 |
| pituitary carcinoma | mir-106b, mir-122, mir-17-5p, mir-20a, mir-493 |
| cervical cancer | mir-10a, mir-155, mir-181a, mir-181b, mir-196a, mir-19a, mir-19b, mir-205, mir-20a, mir-21, mir-215, mir-224, mir-31, mir-494, mir-590-5p, mir-92a, mir-944 |
| pancreatic cancer | mir-10a, mir-10b, mir-132, mir-15a, mir-17-5p, mir-181a, mir-18a, mir-191, mir-196a, mir-21, mir-212, mir-214, mir-221, mir-222, mir-27a, mir-301a, mir-301a-3p, mir-367, mir-424-5p, mir-7, mir-92, mir-99a |
| breast cancer | mir-10b, mir-125a, mir-135a, mir-140, mir-141, mir-142, mir-150, mir-155, mir-17, mir-17-5p, mir-181a, mir-181b, mir-182, mir-18a, mir-18b, mir-191, mir-196a, mir-197, mir-19a, mir-19b, mir-200a, mir-200b, mir-200c, mir-203, mir-205, mir-20a, mir-20b, mir-21, mir-217, mir-221, mir-222, mir-224, mir-23a, mir-24, mir-24-2-5p, mir-24-3p, mir-27a, mir-29a, mir-29b-1, mir-29b-2, mir-29c, mir-373, mir-378, mir-423, mir-429, mir-495, mir-503, mir-510, mir-520c, mir-526b, mir-96 |
| glioblastoma | mir-10b, mir-125b, mir-127-3p, mir-148a, mir-18a, mir-196a, mir-196a-1, mir-196a-2, mir-196b, mir-21, mir-210, mir-210-3p, mir-223, mir-340, mir-576-5p, mir-626, mir-92b |
| lung cancer | mir-10b, mir-135b, mir-150, mir-155, mir-17, mir-182, mir-183-3p, mir-18a, mir-197, mir-19a, mir-19b, mir-205, mir-20a, mir-21, mir-210, mir-24, mir-30d, mir-4423, mir-5100, mir-570, mir-663, mir-7, mir-92a |
| nasopharyngeal carcinoma | mir-10b, mir-144, mir-149, mir-155, mir-18a, mir-21, mir-214, mir-24, mir-421, mir-663, mir-744, mir-93 |
| non-small cell lung cancer | mir-10b, mir-125a-5p, mir-1280, mir-136, mir-140, mir-141, mir-142-3p, mir-145, mir-146a, mir-150, mir-18a, mir-196a, mir-19a, mir-200a, mir-200c, mir-205, mir-205-3p, mir-205-5p, mir-21, mir-212, mir-22, mir-221, mir-222, mir-24, mir-25, mir-29c, mir-31, mir-328, mir-330-3p, mir-339, mir-34a, mir-375, mir-494, mir-675-5p, mir-9, mir-92b, mir-93, mir-95 |
| oral cancer | mir-10b, mir-196a-1, mir-196a-2, mir-196b, mir-21 |
| pancreatic ductal adenocarcinoma | mir-10b, mir-186, mir-18a, mir-192, mir-194, mir-196a, mir-198, mir-203, mir-21, mir-212, mir-30b-5p, mir-31, mir-34a, mir-369-5p, mir-376a, mir-541 |
| renal clear cell carcinoma | mir-122, mir-155, mir-210, mir-630 |
| mantle cell lymphoma | mir-124a, mir-155, mir-17, mir-18a, mir-19a, mir-19b, mir-20a, mir-92a |
| acute myeloid leukemia | mir-125b, mir-126-5p, mir-128, mir-155, mir-29a, mir-32, mir-331, mir-370, mir-378 |
| follicular cancer | mir-125b |
| neuroblastoma | mir-125b, mir-15a, mir-15b, mir-16-1, mir-16-2, mir-18a, mir-195, mir-19a, mir-23a, mir-421, mir-92 |
| oral squamous cell carcinoma | mir-125b, mir-126, mir-146a, mir-146b, mir-155, mir-181b, mir-196a-1, mir-196a-2, mir-196b, mir-21, mir-221, mir-222, mir-24, mir-27b, mir-31, mir-345 |
| prostate cancer | mir-125b, mir-141, mir-153, mir-155, mir-181a-1, mir-181a-2, mir-181b, mir-181b-1, mir-181b-2, mir-181c, mir-181d, mir-182, mir-182-5p, mir-183, mir-18a, mir-204, mir-20a, mir-21, mir-221, mir-223-3p, mir-31, mir-429, mir-96 |
| mesenchymal cancer | mir-125b-1-3p, mir-182 |
| malignant melanoma | mir-126, mir-141, mir-15b, mir-17, mir-17-5p, mir-182, mir-18a, mir-193b, mir-200a, mir-200b, mir-200c, mir-20a, mir-21, mir-210, mir-214, mir-221, mir-222, mir-429, mir-455-5p, mir-532-5p, mir-638, mir-92a |
| acute lymphoblastic leukemia | mir-128 |
| osteosarcoma | mir-128, mir-151-3p, mir-17, mir-181a, mir-181b, mir-181c, mir-18a, mir-191, mir-195-5p, mir-199a-3p, mir-19a, mir-19b, mir-20a, mir-21, mir-210, mir-214, mir-221, mir-27a, mir-300, mir-320a, mir-374a-5p, mir-802, mir-9, mir-92a |
| colon cancer | mir-1290, mir-145, mir-155, mir-181a, mir-18a, mir-200c, mir-31, mir-675 |
| liver cancer | mir-1301, mir-155, mir-21, mir-221, mir-27a, mir-525-3p |
| cervical carcinoma | mir-133b, mir-21, mir-25, mir-373 |
| squamous carcinoma | mir-137, mir-155, mir-184, mir-196a, mir-203, mir-21, mir-221, mir-27a, mir-34a |
| chordoma | mir-140-3p, mir-148a |
| clear cell renal cell cancer | mir-142-5p, mir-155, mir-21-5p |
| malt lymphoma | mir-142-5p, mir-155 |
| anaplastic thyroid carcinoma | mir-146b, mir-221, mir-222 |
| follicular thyroid carcinoma | mir-146b, mir-183, mir-197, mir-221, mir-346 |
| primary thyroid lymphoma | mir-146b |
| ovarian carcinoma | mir-148b, mir-182 |
| adult t-cell leukemia | mir-150 |
| chronic lymphocytic leukemia | mir-150, mir-155 |

TABLE 4-continued

| Exemplary oncogenic miRs | |
|---|---|
| Cancer | miRNA |
| lung adenocarcinoma | mir-150, mir-155, mir-31 |
| anaplastic large-cell lymphoma | mir-155 |
| cutaneous t-cell lymphoma | mir-155 |
| diffuse large B-cell lymphoma | mir-155, mir-21 |
| gallbladder carcinoma | mir-155, mir-182 |
| rectal cancer | mir-155, mir-200c, mir-21-5p, mir-34a |
| b-cell lymphoma | mir-17, mir-18a, mir-19a, mir-19b, mir-20a, mir-92a |
| breast carcinoma | mir-17, mir-18a, mir-19a, mir-19b, mir-20a, mir-24, mir-92a |
| cholangiocarcinoma | mir-17, mir-18a, mir-19a, mir-19b, mir-20a, mir-21, mir-26a, mir-92a |
| colorectal carcinoma | mir-17, mir-182, mir-191, mir-21, mir-95 |
| nasopharyngeal cancer | mir-17, mir-20a |
| acute promyelocytic leukemia | mir-181a, mir-181b, mir-92a |
| retinoblastoma | mir-181b, mir-21 |
| colorectal adenocarcinoma | mir-182 |
| kidney cancer | mir-183, mir-21, mir-210, mir-223 |
| medullary thyroid carcinoma | mir-183 |
| esophageal adenocarcinoma | mir-196a, mir-199a-3p, mir-199a-5p, mir-199b-3p, mir-200a, mir-223 |
| gastrointestinal stromal tumor | mir-196a |
| hypopharyngeal cancer | mir-203 |
| pancreatic adenocarcinoma | mir-203, mir-301a |
| cervical squamous cell carcinoma | mir-205 |
| adrenal cortical carcinoma | mir-21, mir-210, mir-483-3p, mir-483-5p |
| head and neck cancer | mir-21 |
| hypopharyngeal squamous cell carcinoma | mir-21 |
| laryngeal squamous cell carcinoma | mir-21, mir-9, mir-93 |
| multiple myeloma | mir-21 |
| colon carcinoma | mir-221, mir-23a |
| thyroid carcinoma | mir-221, mir-222 |
| meningioma | mir-224, mir-335 |
| gastric adenocarcinoma | mir-23a, mir-27a, mir-373 |
| laryngeal cancer | mir-23a |
| small cell lung cancer | mir-25 |
| pancreatic carcinoma | mir-30 lb |
| oral carcinoma | mir-31 |
| astrocytoma | mir-335 |
| epithelial ovarian cancer | mir-372, mir-373 |
| chronic myelogenous leukemia | mir-424, mir-96 |
| hepatoblastoma | mir-492 |

TABLE 3

| Exemplary tumor suppressive miRs | |
|---|---|
| Cancer | Down regulated tumor suppressive miR |
| acute leukemia | mir-27a |
| acute lymphoblastic leukemia | let-7b, mir-124a, mir-142-3p |
| acute myeloid leukemia | let-7c, mir-17, mir-181a, mir-20a, mir-223, mir-26a, mir-29a, mir-30c, mir-720 |
| acute promyelocytic leukemia | let-7c, mir-107, mir-342 |
| adrenal cortical carcinoma | mir-195, mir-1974, mir-335, mir-497 |
| anaplastic astrocytoma | mir-124, mir-137 |
| anaplastic thyroid carcinoma | mir-138 |
| astrocytoma | mir-124-3p, mir-181b-5p, mir-200b, mir-3189-3p |
| basal cell carcinoma | mir-203 |
| b-cell lymphoma | mir-34a |

TABLE 3-continued

| Exemplary tumor suppressive miRs | |
|---|---|
| Cancer | Down regulated tumor suppressive miR |
| bladder cancer | mir-1, mir-101, mir-1180, mir-1236, mir-124-3p, mir-125b, mir-126, mir-1280, mir-133a, mir-133b, mir-141, mir-143, mir-144, mir-145, mir-155, mir-16, mir-18a, mir-192, mir-195, mir-200a, mir-200b, mir-200c, mir-203, mir-205, mir-214, mir-218, mir-23b, mir-26a, mir-29c, mir-320c, mir-34a, mir-370, mir-409-3p, mir-429, mir-451, mir-490-5p, mir-493, mir-576-3p, mir-99a |
| breast cancer | let-7a, let-7a-1, let-7a-2, let-7a-3, let-7b, let-7c, let-7d, let-7e, let-7f-1, let-7f-2, let-7g, let-7i, mir-100, mir-107, mir-10a, mir-10b, mir-122, mir-124, mir-1258, mir-125a-5p, mir-125b, mir-126, mir-127, mir-129, mir-130a, mir-132, mir-133a, mir-143, mir-145, mir-146a, mir-146b, mir-147, mir-148a, mir-149, mir-152, mir-153, mir-15a, mir-16, mir-17-5p, mir-181a, mir-1826, mir-183, mir-185, mir-191, mir-193a-3p, mir-193b, mir-195, mir-199b-5p, mir-19a-3p, mir-200a, mir-200b, mir-200c, mir-205, mir-206, mir-211, mir-216b, mir-218, mir-22, mir-26a, mir-26b, mir-300, mir-30a, mir-31, mir-335, mir-339-5p, mir-33b, mir-34a, mir-34b, mir-34c, mir-374a, mir-379, mir-381, mir-383, mir-425, mir-429, mir-450b-3p, mir-494, mir-495, mir-497, mir-502-5p, mir-517a, mir-574-3p, mir-638, mir-7, mir-720, mir-873, mir-874, mir-92a, mir-98, mir-99a, mmu-mir-290-3p, mmu-mir-290-5p |
| bronchioloalveolar carcinoma | let-7a-1, let-7a-2, let-7a-3, let-7b, let-7c, let-7d, let-7e, let-7f-1, let-7f-2, let-7g, let-7i, mir-98 |
| cervical cancer | mir-143, mir-145, mir-17-5p, mir-203, mir-214, mir-218, mir-335, mir-342-3p, mir-372, mir-424, mir-491-5p, mir-497, mir-7, mir-99a, mir-99b |
| cervical carcinoma | mir-100, mir-101, mir-15a, mir-16, mir-34a, mir-886-5p, mir-99a, mir-99b |
| cervical squamous cell carcinoma | mir-106a, mir-124, mir-148a, mir-214, mir-218, mir-29a, mir-375 |
| cholangiocarcinoma | mir-101, mir-144, mir-200b, mir-200c |
| chondrosarcoma | let-7a, mir-100, mir-136, mir-145, mir-199a, mir-222, mir-30a, mir-335, mir-376a |
| chordoma | mir-1, mir-222, mir-31, mir-34a, mir-608 |
| choriocarcinoma | mir-199b, mir-218, mir-34a |
| chronic lymphocytic leukemia | mir-125b, mir-138, mir-15a, mir-15b, mir-16, mir-16-1, mir-16-1-3p, mir-16-2, mir-181a, mir-181b, mir-195, mir-223, mir-29b, mir-34b, mir-34c, mir-424 |
| chronic myelogenous leukemia | mir-10a, mir-138, mir-146a, mir-150, mir-151, mir-155, mir-16, mir-2278, mir-26a, mir-30e, mir-31, mir-326, mir-564 |
| clear cell renal cell cancer | mir-106a-5p, mir-135a-5p, mir-206 |
| colon cancer | let-7a-1, let-7a-2, let-7a-3, let-7b, let-7c, let-7d, let-7e, let-7f-1, let-7f-2, let-7g, let-7i, mir-100, mir-101, mir-126, mir-142-3p, mir-143, mir-145, mir-192, mir-200c, mir-21, mir-214, mir-215, mir-22, mir-25, mir-302a, mir-320, mir-320a, mir-34a, mir-34c, mir-365, mir-373, mir-424, mir-429, mir-455, mir-484, mir-502, mir-503, mir-93, mir-98 |
| colon carcinoma | mir-186, mir-30a-5p |
| colonic adenocarcinoma | mir-627 |
| colorectal cancer | let-7a, mir-1, mir-100, mir-101, mir-124, mir-125a, mir-126, mir-129, mir-1295b-3p, mir-1307, mir-130b, mir-132, mir-133a, mir-133b, mir-137, mir-138, mir-139, mir-139-5p, mir-140-5p, mir-143, mir-145, mir-148a, mir-148b, mir-149, mir-150-5p, mir-154, mir-15a, mir-15b, mir-16, mir-18a, mir-191, mir-192, mir-193a-5p, mir-194, mir-195, mir-196a, mir-198, mir-199a-5p, mir-200c, mir-203, mir-204-5p, mir-206, mir-212, mir-215, mir-218, mir-22, mir-224, mir-24-3p, mir-26b, mir-27a, mir-28-3p, mir-28-5p, mir-29b, mir-30a-3p, mir-30b, mir-320a, mir-328, mir-338-3p, mir-342, mir-345, mir-34a, mir-34a-5p, mir-361-5p, mir-375, mir-378, mir-378a-3p, mir-378a-5p, mir-409-3p, mir-422a, mir-4487, mir-483, mir-497, mir-498, mir-518a-3p, mir-551a, mir-574-5p, mir-625, mir-638, mir-7, mir-96-5p |
| colorectal carcinoma | mir-139, mir-143, mir-145, mir-202-3p, mir-30a, mir-338-3p, mir-429, mir-451, mir-93 |
| endometrial cancer | mir-101, mir-130a, mir-130b, mir-134, mir-143, mir-145, mir-152, mir-205, mir-223, mir-301a, mir-301b, mir-30c, mir-34a, mir-34c, mir-424, mir-449a, mir-543 |
| endometrial serous adenocarcinoma | mir-34b |
| epithelial ovarian cancer | mir-124a, mir-192, mir-193a, mir-7 |
| esophageal adenocarcinoma | mir-203 |
| esophageal cancer | mir-124, mir-126, mir-140, mir-197, mir-203, mir-218, mir-223, mir-30b, mir-375, mir-454, mir-486, mir-574-3p |
| esophageal carcinoma | mir-451 |
| esophageal squamous cell carcinoma | let-7a, let-7a-1, let-7a-2, let-7a-3, let-7b, let-7c, let-7d, let-7e, let-7f-1, let-7f-2, let-7g, let-7i, mir-1, mir-100, mir-101, mir-126, mir-1294, mir-133a, mir-133b, mir-138, mir-143, mir-145, mir-150, mir-185, mir-195, mir-200b, mir-203, mir-21, mir-210, mir-214, mir-218, mir-22, mir-27a, mir-29b, mir-29c, mir-302b, mir-34a, mir-375, mir-494, mir-518b, mir-655, mir-98, mir-99a |
| follicular lymphoma | mir-202 |
| follicular thyroid carcinoma | mir-199b |
| gallbladder carcinoma | mir-146b-5p |

TABLE 3-continued

Exemplary tumor suppressive miRs

| Cancer | Down regulated tumor suppressive miR |
|---|---|
| gastric adenocarcinoma | mir-181b, mir-182, mir-200a, mir-302b, mir-449a, mir-9 |
| gastric cancer | let-7a, let-7b, let-7g, mir-1, mir-101, mir-103a, mir-10a, mir-10b, mir-1207-5p, mir-122, mir-1228*, mir-124, mir-124-3p, mir-125a-3p, mir-126, mir-1266, mir-127, mir-1271, mir-129-1-3p, mir-129-2-3p, mir-129-3p, mir-129-5p, mir-133a, mir-133b, mir-137, mir-141, mir-143, mir-144, mir-145, mir-146a, mir-146a-5p, mir-148a, mir-148b, mir-149, mir-152, mir-155, mir-155-5p, mir-181a, mir-181b, mir-182, mir-183, mir-185, mir-194, mir-195, mir-197, mir-199a-3p, mir-200b, mir-200c, mir-202-3p, mir-204, mir-204-5p, mir-205, mir-206, mir-210, mir-212, mir-217, mir-218, mir-22, mir-23b, mir-24, mir-26a, mir-29a, mir-29a-3p, mir-29b, mir-29b-1, mir-29b-2, mir-29c, mir-30a-5p, mir-30b, mir-31, mir-328, mir-329, mir-331-3p, mir-335-5p, mir-338, mir-338-3p, mir-34a, mir-34b, mir-34c, mir-361-5p, mir-367, mir-375, mir-378, mir-409-3p, mir-410, mir-429, mir-433, mir-449, mir-449a, mir-490-3p, mir-494, mir-497, mir-503, mir-506, mir-513b, mir-520d-3p, mir-542-3p, mir-622, mir-625, mir-638, mir-663, mir-7, mir-874, mir-9 |
| gastrointestinal cancer | mir-122a, mir-148a, mir-152 |
| gastrointestinal stromal tumor | mir-218, mir-221, mir-222 |
| glioblastoma | let-7g-5p, mir-100, mir-101, mir-106a, mir-124, mir-124a, mir-125a, mir-125a-5p, mir-125b, mir-127-3p, mir-128, mir-129, mir-136, mir-137, mir-139-5p, mir-142-3p, mir-143, mir-145, mir-146b-5p, mir-149, mir-152, mir-153, mir-195, mir-21, mir-212-3p, mir-219-5p, mir-222, mir-29b, mir-31, mir-3189-3p, mir-320, mir-320a, mir-326, mir-330, mir-331-3p, mir-340, mir-342, mir-34a, mir-376a, mir-449a, mir-483-5p, mir-503, mir-577, mir-663, mir-7, mir-7-5p, mir-873 |
| glioma | let-7a, let-7f, mir-106a, mir-107, mir-122, mir-124, mir-124-5p, mir-124a, mir-125b, mir-128, mir-136, mir-137, mir-139, mir-143, mir-145, mir-146a, mir-146b, mir-146b-5p, mir-152, mir-15b, mir-16, mir-181a, mir-181a-1, mir-181a-2, mir-181b, mir-181b-1, mir-181b-2, mir-181c, mir-181d, mir-184, mir-185, mir-195, mir-199a-3p, mir-200a, mir-200b, mir-203, mir-204, mir-205, mir-218, mir-219-5p, mir-23b, mir-26b, mir-27a, mir-29c, mir-320, mir-326, mir-328, mir-34a, mir-34c-3p, mir-34c-5p, mir-375, mir-383, mir-451, mir-452, mir-483-5p, mir-495, mir-584, mir-622, mir-656, mir-7, mir-98 |
| head and neck squamous cell carcinoma | let-7d, mir-1, mir-107, mir-128, mir-133a, mir-138, mir-149, mir-200c, mir-205, mir-218, mir-27a*, mir-29a, mir-29b-1, mir-29b-2, mir-29c, mir-300, mir-34a, mir-363, mir-375, mir-874 |
| hepatocellular carcinoma | let-7a-1, let-7a-2, let-7a-3, let-7b, let-7c, let-7d, let-7e, let-7f, let-7f-1, let-7f-2, let-7g, let-7i, mir-1, mir-100, mir-101, mir-105, mir-122, mir-122a, mir-1236, mir-124, mir-125b, mir-126, mir-127, mir-1271, mir-128-3p, mir-129-5p, mir-130a, mir-130b, mir-133a, mir-134, mir-137, mir-138, mir-139, mir-139-5p, mir-140-5p, mir-141, mir-142-3p, mir-143, mir-144, mir-145, mir-146a, mir-148a, mir-148b, mir-150-5p, mir-15b, mir-16, mir-181a-5p, mir-185, mir-188-5p, mir-193b, mir-195, mir-195-5p, mir-197, mir-198, mir-199a, mir-199a-5p, mir-199b, mir-199b-5p, mir-200a, mir-200b, mir-200c, mir-202, mir-203, mir-204-3p, mir-205, mir-206, mir-20a, mir-21, mir-21-3p, mir-211, mir-212, mir-214, mir-217, mir-218, mir-219-5p, mir-22, mir-223, mir-26a, mir-26b, mir-29a, mir-29b-1, mir-29b-2, mir-29c, mir-302b, mir-302c, mir-30a, mir-30a-3p, mir-335, mir-338-3p, mir-33a, mir-34a, mir-34b, mir-365, mir-370, mir-372, mir-375, mir-376a, mir-377, mir-422a, mir-424, mir-424-5p, mir-433, mir-4458, mir-448, mir-450a, mir-451, mir-485-5p, mir-486-5p, mir-497, mir-503, mir-506, mir-519d, mir-520a, mir-520b, mir-520c-3p, mir-582-5p, mir-590-5p, mir-610, mir-612, mir-625, mir-637, mir-675, mir-7, mir-877, mir-940, mir-941, mir-98, mir-99a |
| hypopharyngeal squamous cell carcinoma | mir-45 la, mir-504 |
| kidney cancer | mir-1, mir-145, mir-1826, mir-199a, mir-199a-3p, mir-203, mir-205, mir-497, mir-508-3p, mir-509-3p |
| laryngeal squamous cell carcinoma | mir-129-5p, mir-203, mir-205, mir-206, mir-24, mir-370, mir-375 |
| liver cancer | mir-101, mir-122, mir-132, mir-140-5p, mir-145, mir-148b, mir-31, mir-338-3p, mir-433 |
| lung adenocarcinoma | mir-1297, mir-141, mir-145, mir-16, mir-200a, mir-200b, mir-200c, mir-29b, mir-381, mir-409-3p, mir-429, mir-451, mir-511, mir-99a |
| lung cancer | let-7a-1, let-7a-2, let-7a-3, let-7b, let-7c, let-7d, let-7e, let-7f-1, let-7f-2, let-7g, let-7i, mir-1, mir-101, mir-133b, mir-138, mir-142-5p, mir-144, mir-145, mir-1469, mir-146a, mir-153, mir-15a, mir-15b, mir-16-1, mir-16-2, mir-182, mir-192, mir-193a-3p, mir-194, mir-195, mir-198, mir-203, mir-217, mir-218, mir-22, mir-223, mir-26a, mir-26b, mir-29c, mir-33a, mir-34a, mir-34b, mir-34c, mir-365, mir-449a, mir-449b, mir-486-5p, mir-545, mir-610, mir-614, mir-630, mir-660, mir-7515, mir-9500, mir-98, mir-99b |

TABLE 3-continued

| Exemplary tumor suppressive miRs | |
|---|---|
| Cancer | Down regulated tumor suppressive miR |
| lung squamous cell carcinoma | mir-133a, mir-218 |
| malignant melanoma | let-7b, mir-101, mir-125b, mir-1280, mir-143, mir-146a, mir-146b, mir-155, mir-17, mir-184, mir-185, mir-18b, mir-193b, mir-200c, mir-203, mir-204, mir-205, mir-206, mir-20a, mir-211, mir-218, mir-26a, mir-31, mir-33a, mir-34a, mir-34c, mir-376a, mir-376c, mir-573, mir-7-5p, mir-9, mir-98 |
| malignant mesothelioma | mir-126 |
| mantle cell lymphoma | mir-142-3p, mir-142-5p, mir-150, mir-223, mir-29a, mir-29b, mir-29c |
| medullary thyroid carcinoma | mir-129-5p |
| medulloblastoma | mir-124, mir-128a, mir-199b-5p, mir-206, mir-22, mir-31, mir-383 |
| meningioma | mir-128, mir-200a |
| mesenchymal cancer | mir-100, mir-141, mir-199b-5p, mir-200a, mir-200b, mir-200c, mir-29a, mir-29b-1, mir-29b-1-5p, mir-29b-2, mir-29c, mir-335, mir-429, mir-99a |
| monocytic leukemia | mir-29a, mir-29b |
| multiple myeloma | mir-137, mir-197, mir-214 |
| nasopharyngeal cancer | mir-218, mir-223, mir-29c |
| nasopharyngeal carcinoma | let-7a, let-7a-1, let-7a-2, let-7a-3, let-7b, let-7c, let-7d, let-7e, let-7f-1, let-7f-2, let-7g, let-7i, mir-1, mir-101, mir-124, mir-138, mir-143, mir-145, mir-148a, mir-200b, mir-204, mir-216b, mir-223, mir-29c, mir-320a, mir-324-3p, mir-34c, mir-375, mir-378, mir-451, mir-506, mir-9, mir-98 |
| neuroblastoma | let-7a-1, let-7a-2, let-7a-3, let-7b, let-7c, let-7d, let-7e, let-7f-1, let-7f-2, let-7g, let-7i, mir-124, mir-137, mir-145, mir-181c, mir-184, mir-200a, mir-29a, mir-335, mir-338-3p, mir-34a, mir-449a, mir-885-5p, mir-98 |
| non-small cell lung cancer | let-7a, let-7c, mir-1, mir-100, mir-101, mir-106a, mir-107, mir-124, mir-125a-3p, mir-125a-5p, mir-126, mir-126*, mir-129, mir-133a, mir-137, mir-138, mir-140, mir-143, mir-145, mir-146a, mir-146b, mir-148a, mir-148b, mir-149, mir-152, mir-153, mir-154, mir-155, mir-15a, mir-16, mir-17-5p, mir-181a-1, mir-181a-2, mir-181b, mir-181b-1, mir-181b-2, mir-181c, mir-181d, mir-184, mir-186, mir-193b, mir-195, mir-199a, mir-204, mir-212, mir-221, mir-224, mir-26b, mir-27a, mir-27b, mir-29a, mir-29b, mir-29c, mir-30a, mir-30b, mir-30c, mir-30d, mir-30d-5p, mir-30e-5p, mir-32, mir-335, mir-338-3p, mir-340, mir-342-3p, mir-34a, mir-34b, mir-361-3p, mir-365, mir-373, mir-375, mir-429, mir-449a, mir-4500, mir-451, mir-4782-3p, mir-497, mir-503, mir-512-3p, mir-520a-3p, mir-526b, mir-625*, mir-96, mir-99a |
| oral cancer | let-7d, mir-218, mir-34a, mir-375, mir-494 |
| oral carcinoma | mir-375 |
| oral squamous cell carcinoma | mir-100, mir-124, mir-1250, mir-125b, mir-126, mir-1271, mir-136, mir-138, mir-145, mir-147, mir-148a, mir-181a, mir-206, mir-220a, mir-26a, mir-26b, mir-29a, mir-32, mir-323-5p, mir-329, mir-338, mir-370, mir-410, mir-429, mir-433, mir-499a-5p, mir-503, mir-506, mir-632, mir-646, mir-668, mir-877, mir-9 |
| osteosarcoma | let-7a, mir-1, mir-100, mir-101, mir-122, mir-124, mir-125b, mir-126, mir-127-3p, mir-132, mir-133a, mir-141, mir-142-3p, mir-142-5p, mir-143, mir-144, mir-145, mir-153, mir-16, mir-183, mir-194, mir-195, mir-199a-3p, mir-204, mir-212, mir-217, mir-218, mir-22, mir-23a, mir-24, mir-26a, mir-26b, mir-29b, mir-32, mir-320, mir-335, mir-33b, mir-340, mir-34a, mir-34b, mir-34c, mir-375, mir-376c, mir-382, mir-3928, mir-424, mir-429, mir-449a, mir-451, mir-454, mir-503, mir-519d, mir-646 |
| ovarian cancer | let-7i, mir-100, mir-124, mir-125b, mir-129-5p, mir-130b, mir-133a, mir-137, mir-138, mir-141, mir-145, mir-148a, mir-152, mir-153, mir-155, mir-199a, mir-200a, mir-200b, mir-200c, mir-212, mir-335, mir-34a, mir-34b, mir-34c, mir-409-3p, mir-411, mir-429, mir-432, mir-449a, mir-494, mir-497, mir-498, mir-519d, mir-655, mir-9, mir-98 |
| ovarian carcinoma | mir-100, mir-101, mir-34b, mir-34c, mir-532-5p |
| pancreatic cancer | mir-101, mir-1181, mir-124, mir-1247, mir-133a, mir-141, mir-145, mir-146a, mir-148a, mir-148b, mir-150*, mir-150-5p, mir-152, mir-15a, mir-198, mir-203, mir-214, mir-216a, mir-29c, mir-335, mir-34a, mir-34b, mir-34c, mir-373, mir-375, mir-410, mir-497, mir-615-5p, mir-630, mir-96 |
| pancreatic carcinoma | mir-132, mir-375 |
| pancreatic ductal adenocarcinoma | let-7a, let-7a-1, let-7a-2, let-7a-3, let-7b, let-7c, let-7d, let-7e, let-7f-1, let-7f-2, let-7g, let-7i, mir-126, mir-135a, mir-143, mir-144, mir-145, mir-148a, mir-150, mir-15a, mir-16, mir-200a, mir-200b, mir-200c, mir-217, mir-218, mir-337, mir-375, mir-494, mir-615-5p, mir-98 |
| papillary thyroid carcinoma | mir-101, mir-130b, mir-138, mir-146a, mir-16, mir-195, mir-199a-3p, mir-204-5p, mir-219-5p, mir-26a, mir-34b, mir-613 |
| primary cns lymphomas | mir-145, mir-193b, mir-199a, mir-214 |
| primary gallbladder carcinoma | mir-335 |
| primary thyroid lymphoma | mir-26a |
| prostate cancer | let-7a-3p, let-7c, mir-100, mir-101, mir-105, mir-124, mir-128, mir-1296, mir-130b, mir-133a-1, mir-133a-2, mir-133b, mir-135a, mir-143, mir-145, mir-146a, mir-154, mir-15a, mir-187, mir-188-5p, mir-199b, mir-200b, mir-203, mir-205, mir-212, mir-218, mir-221, mir-224, mir-23a, mir-23b, mir-25, mir-26a, mir-26b, mir-29b, mir-302a, mir-30a, mir-30b, mir-30c-1, mir-30c-2, mir-30d, mir-30e, mir-31, mir-330, mir-331-3p, |

TABLE 3-continued

| Exemplary tumor suppressive miRs | |
|---|---|
| Cancer | Down regulated tumor suppressive miR |
| | mir-34a, mir-34b, mir-34c, mir-374b, mir-449a, mir-4723-5p, mir-497, mir-628-5p, mir-642a-5p, mir-765, mir-940 |
| prostate carcinoma | mir-107 |
| renal cell carcinoma | let-7a, let-7d, mir-1, mir-106a*, mir-126, mir-1285, mir-129-3p, mir-1291, mir-133a, mir-135a, mir-138, mir-141, mir-143, mir-145, mir-182-5p, mir-199a-3p, mir-200a, mir-205, mir-218, mir-28-5p, mir-30a, mir-30c, mir-30d, mir-34a, mir-378, mir-429, mir-509-3p, mir-509-5p, mir-646 |
| renal clear cell carcinoma | let-7b, let-7c, mir-138, mir-141, mir-200c, mir-204, mir-218, mir-335, mir-377, mir-506 |
| retinoblastoma | mir-101, mir-183, mir-204, mir-34a, mir-365b-3p, mir-486-3p, mir-532-5p |
| rhabdomyosarcoma | mir-203 |
| small cell lung cancer | mir-126, mir-138, mir-27a |
| splenic marginal zone lymphoma | mir-223 |
| squamous carcinoma | mir-15a, mir-16, mir-203, mir-205, mir-375 |
| t-cell lymphoma | mir-22 |
| thyroid cancer | mir-144, mir-886-3p |
| tongue cancer | mir-15b, mir-200b |
| uterine leiomyoma | mir-197 |
| uveal melanoma | mir-137, mir-144, mir-145, mir-182, mir-34a, mir-34b, mir-34c, mir-9 |

TABLE 5

| Summary of microRNA/MMP linked interactions in cancer. | | | | |
|---|---|---|---|---|
| microRNA | MMP Type and target molecule | Cancer type | Phenotype | Pathway |
| let-7 | MMP-9 | Melanoma | Cell proliferation and migration | — |
| | MMP-14, ERK1/2 activation | Pancreatic ductal adenocarcinoma | NA | ERK1/2 activation, TGF-β1 signaling |
| | Focal adhesion kinase (FAK), AKT, ERK, MMP-2 and MMP-9 | Glioblastoma | Migration and invasion | AKT and ERK |
| miR-9 | MMP-2, MMP-9 and VEGFA | Uveal melanoma | Migration and invasion | NF-κB1 signaling |
| | MMP-14 | Neuroblastoma | Invasion, metastasis, and angiogenesis | — |
| miR-10b | MMP-9, E-cadherin and vimentin | Nasopharyngeal carcinoma cells | Proliferation, migration, invasion | — |
| | MMP-14 and uPAR | Glioma | Cell invasiveness | — |
| | MMP-2, EGFR. | Glioblastoma multiforme | Apoptosis invasion and migration | EGFR pathways |
| miR-15b | MMP-3 | Glioma | Cell invasiveness | MEK-ERK pathway |
| miR-17 | MMP-3 | Hepatocellular carcinoma | Migration and invasion | p-AKT |
| miR-21 | RECK, MMP-9 | Prostate cancer | NA | — |
| | Phospho-c-Jun, MMP-2, MMP-9 | Hepatocellular carcinoma | Migration and invasion | — |
| | RECK, MMP-2 | Glioma | Apoptosis, migration, and invasiveness | — |
| | MMP-2, EGFR. | Glioblastoma multiforme | Apoptosis invasion and migration | EGFR pathways |
| miR-26a | MMP-2 | Lung cancer | Migration, invasion and metastasis | AKT phosphorylation |
| miR-29b | MMP-2 | Colon cancer | Migration | — |
| | MMP-2 | Hepatocellular carcinoma | Tumor angiogenesis, invasion, and metastasis | VEGFR-2-signaling |
| | MMP-2, Mcl-1, COL1A1, and COL4A1 | Prostate cancer | invasion and metastasis | — |
| miR-29c | MMP-2 | Nerve sheath tumours | Cell invasion and migration | — |
| miR-30d | SOCS1, phospho-STAT3, MMP-2 and MMP-9 | Prostate cancer | Proliferation and invasion | STAT3 signalling |
| miR-34a | Fra-1, p53 MMP-1 and MMP-9 | Colon cancer | Migration and invasion | — |
| miR-92a | MMP-2 and -9 | Lung cancer | Migration and invasion | STAT3 signaling |
| miR-101 | Enhancer of zeste homolog 2 (EZH2), CDH1 and MMP-2 | Lung cancer | Cell invasiveness | — |

TABLE 5-continued

Summary of microRNA/MMP linked interactions in cancer.

| microRNA | MMP Type and target molecule | Cancer type | Phenotype | Pathway |
|---|---|---|---|---|
| miR-106b | MMP-2 | Breast cancer | Migration and invasion | ERK signaling cascade |
| miR-125b | MMP-2 and MMP-9 | Glioblastoma | Invasion | — |
| miR-133 | MMP-14 | Lung cancer | Cell proliferation, migration and invasion | — |
| miR-138 | RhoC, MMP-2 and MMP-9 | Cholangiocarcinoma | Proliferation, migration and invasion | p-ERK signaling |
| miR-139 | IGF-IR and MMP-2 | Colorectal cancer | Migration, invasion and metastasis | IGF-IR/MEK/ERK signaling |
| miR-143 | MMP-13 | Prostate cancer | Migration and invasion | — |
| | MMP-2 and MMP-9 | Pancreatic cancer | Migration and invasion | — |
| | MMP-13 | Osteosarcoma | Cell invasiveness | — |
| miR-145 | Ets1, MMP-1 and -9 | Gastric cancer | Invasion, metastasis, and angiogenesis | — |
| miR-146a | MMP-1, uPA, and uPAR | Brain cancer | Migration, invasion and metastasis | — |
| | MMP-16 | Colon cancer | Invasion | — |
| miR-149 | M MP-2 and CyclinD1 | Glioma | Proliferation and invasion | AKT signaling |
| miR-152 | MMP-3 | Glioma | Cell invasiveness | MEK-ERK pathway |
| miR-18lb | MMP-2 and MMP-9 | Hepatocellular carcinomas | Migration and invasion | TGF- β, Smad signaling |
| miR-182 | MMP-9, RECK | Breast cancer | cell invasion and colony formation ability | — |
| miR-196b | Vimentin, MMP-2 and MMP-9 | Gastric cancer | Migration and invasion | — |
| miR-203 | MMP-9 and Robol | Glioblastoma | Proliferation, migration, and invasion | ERK phosphorylation |
| miR-206 | MMP-2 and MMP-9 | Breast cancer | Invasion and migration | — |
| miR-211 | MMP-9 | Glioblastoma multiforme | Cell invasion and migration | — |
| miR-218 | LEF1, MMP-2, -7 and -9 | Glioblastoma multiforme | Invasion | — |
| miR-218 | MMP-9 | Gliomas | Cell invasiveness | IKK-β/NF-κB pathway |
| miR-224 | MMP-9 via targeting HOXD10 | Human hepatocellular carcinoma | Migration and invasion | — |
| miR-338-3p | SMO and MMP-9 | Hepatocellular carcinoma | Invasion and metastasis | — |
| miR-340 | MMP-2 and MMP-9 | Breast cancer | Tumor cell growth, migration, and invasion | — |
| miR-430 | ERK, MMP-2 and MMP-9 | Bladder cancer | Proliferation, migration and colony formation ablility | — |
| miR-451 | Akt1, CyclinD1, MMP-2, MMP-9 and Bcl-2 | Glioblastoma | Proliferation, invasion and apoptosis | PI3K/AKT signaling |
| miR-491 | MMP-9 | Hepatocellular carcinoma | Migration | — |
| miR-491-5p | MMP-9 | Glioblastoma multiforme | Invasion | — |
| miRNA-590-3p | PI3K, Akt, MMP-2 and MMP-9 | Bladder cancer | Proliferation, migration and colony-formation | PI3K, Akt signaling |
| miR-874 | MMP-2 and -9, Aquaporin-3 | Human gastric cancer | Cell migration and invasion assays and in vivo tumorigenicity | — |
| miR-874 | MMP-2 and uPA | Non-small cell lung cancer | Tumor cell invasiveness and in vivo tumor growth | — |
| miR-885-5p | MMP-9 | Glioblastoma multiforme | Invasion | — |

TABLE 6

Target proteases and cancers associated with their overexpression.

| Family | Protease | Location | Cancer |
|---|---|---|---|
| Cysteine | General | Intracellular, lysosomes | Most |
| Cathepsins | Cathepsin K | Extracellular, bone | Breast |
| | Cathepsin B | Extracellular and pericellular under pathological conditions | Breast, cervix, colon, colorectal, gastric, head and neck, liver, lung, melanoma, ovarian, pancreatic, prostate, thyroid |
| | Cathepsin L | | Breast, colorectal |

TABLE 6-continued

| Target proteases and cancers associated with their overexpression. | | | |
|---|---|---|---|
| Family | Protease | Location | Cancer |
| Aspartic Cathepsins | Cathepsin E | Endosomal structures, ER, Golgi | Cervical, gastric, lung, pancreas adenocarcinomas |
| | Cathepsin D | Lysosome | Breast, colorectal, ovarian |
| Kallikreins (hK) | General | Intracellular, secreted | Most |
| | hK1 | | |
| | PSA (hK 3) | | Prostate, ovarian |
| | hK10 | | Colon, ovarian, pancreatic, head and neck |
| | hK15 | | Ovarian, prostate |
| Serine Proteases | uPA, uPAR | Membrane, Pericellular | Cervical, colorectal, gastric, prostate |
| Caspases | | Intracellular | |
| MMPs | General | Extracellular | Most |
| | MMP-1, -8, -13 | | Breast |
| | MMP-2, -9 | | Breast, colorectal, lung, malignant gliomas, ovarian |
| | MMP-14 | Membrane | Breast |
| ADAM | | Extracellular | |

TABLE 7

| List of selected oncogenes associated with human malignancy | | | |
|---|---|---|---|
| Gene Name | Gene Locus | Malignancies associated with | Comments |
| ABL1 (ABL) | 9q34.1 | Chronic myeloid leukemia | see tyrosine kinase Abelson murine leukemia protein |
| ABL2 (ABLL, ARG) | 1q24-q25 | acute myeloid leukemia | Member of the tyrosine kinase family. Important for synapse assembly and remodeling |
| AKAP13 (HT31, LBC. BRX) | 15q24-q25 | breast cancer | Blast crisis oncogene |
| ARAF1 | Xp11.4-p11.2 | angioimmunoblastic lymphadenopathy with dysproteinemia | Serine/threonine kinase |
| ARHGEF5 (TIM) | 7q33-q35 | Breast cancer | Codes for protein that controls cytoskeletal organization through regulation of small GTP-binding proteins |
| ATF1 | 12q13 | ATF1/EWS fusion gene associated with malignant melanoma of soft parts (MMSP) ATF1/FUS with histiocytoma. | Codes for cAMP-dependent transcription factor-1 |
| AXL | 19q13.1-q13.2 | Chronic myelogenous leukemia | transforming gene to acute leukemia |
| BCL2 | 18q21.3 | Burkitt lymphoma, follicular lymphoma | Mediator of apoptosis. Translocation is marker of poorer therapeutic response |
| BRAF (BRAF1, RAFB1) | 7q34 | Hairy cell leukemia, Malignant melanoma, thyroid papillary cancer, thyroid anaplastic carcinoma, bowel cancer, adenocarcinoma of lung, non-Hogkins lymphoma | see proto-oncogenes |
| BRCA1 | 17q21 | Hereditary breast-ovarian cancer syndrome. Familial Breast cancer, Papillary serous carcinoma of the peritoneum (PSCP), Prostate cancer | see BRCA1. |
| BRCA2(FANCD1) | 13q12.3 | Familial Breast cancer, prostate cancer, pancreatic cancer | see BRCA2 |
| BRIP1 | 17q22.2 | Ovarian cancer, breast cancer | BRCA1 interacting protein C-terminal helicase 1 which is important in normal double-strand break repair |
| CBL (CBL2) | 11q23.3 | | see proto-oncogenes |
| CSF1R (CSF-1, FMS, MCSF) | 5q33.2-q33.3 | Type M4 acute myeloblastic leukemia and chronic myelomonocytic leukemia | Codes for colony-stimulating factor-1 receptor, otherwise known as macrophage colony-stimulating factor |

TABLE 7-continued

| List of selected oncogenes associated with human malignancy | | | |
|---|---|---|---|
| Gene Name | Gene Locus | Malignancies associated with | Comments |
| DAPK1 (DAPK) | 9q34.1 | Bladder cancer | Codes for death-associated protein kinase a positive mediators of apoptosis induced by gamma-interferon. |
| DEK (D6S231E) | 6p23 | DEK/NUP214(DEK/CAN) fusion gene associated with acute myeloid leukemia | Codes for DNA binding protein involved in transcriptional regulation and signal transduction as a component of the splicing complex that remains associated with spliced exons. |
| DUSP6 (MKP3, PYST1) | 12q22-q23 | Non-small cell lung cancer, pancreatic cancer | Codes for member of mitogen-activated protein (MAP) kinase family and has key role in cellular signal transduction |
| EGF | | | see proto-oncogenes |
| EGFR (ERBB, ERBB1) | | | see proto-oncogenes |
| ERBB3 (HER3) | 12q13 | Non-small cell lung cancer | elevated ERBB3 mRNA levels in breast cancer |
| ERG | | | see proto-oncogenes |
| ETS1 | | | see proto-oncogenes |
| ETS2 | | Acute myeloid leukemia | Codes for a transcription factor |
| EWSR1 (EWS, ES, PNE,) | 22q12 | EWS/ERG in Ewing sarcoma, esthesioneuroblastoma EWS/FEV fusion gene in Ewing sarcoma, EWS/ZNF278 in small round cell sarcoma, EWS/FLI1 in Ewing sarcoma, EWS/ATF1 in malignant melanoma of soft parts (MMSP) EWS/WT1 in desmoplastic small round cell tumor | Ewing sarcoma breakpoint 1 gene |
| FES (FPS) | 15q26.1 | B cell lymphoma, acute promyelocytic leukemia, bladder carcinoma, lung cancer, breast cancer, colon cancer, neuroblastoma, pre-B lymphocyte neoplasm, plasmacytoma, multiple myeloma, T cell lymphoma, sarcoma | Codes for a tyrosine-specific protein kinase with a role in regulating immune response |
| FGF4 (HSTF1, KFGF) | 11q13 | Stomach cancer, kaposi sarcoma | A fibroblast growth factor Important in limb development. |
| FGFR1 | | | see proto-oncogenes |
| FGFR10P (FOP) | 6q27 | FGFR1/FGFR10P2 fusion gene in non-Hodgkin lymphoma | |
| FLCN | 17p11.2 | Renal cancer, bowel cancer | see FFCN |
| FOS (c-fos) | 14q24.3 | | see proto-oncogenes |
| FRAP1 | | | see tumor suppressors |
| FUS (TLS) | 16p11.2 | | see proto-oncogenes |
| HRAS | 11p15.5 | | see proto-oncogenes. |
| GLI1 | 12q13.2-q13.3 | Glioma, myxoid liposarcoma, salivary gland tumor | Codes for a Kruppel (Kr) zinc finger protein |
| GLI2 | 2q14 | Glioma | Codes for a Kruppel (Kr) zinc finger protein |
| GPC3 | Xq26 | Germ cell cancer, Hepatocellular cancer | see GPC3 |
| HER2 (ERBB2, TKR1, NEU) | 17q21.1 | Breast cancer, lung cancer | see HER2. Targeted by Trastuzumab. |
| HGF (SF) | 7q21.1 | Prostate cancer, renal cancer | Codes for hepatocyte growth factor (hepatopoietin A, scatter factor) which is upregulated in many malignancies |
| IRF4 (LSIRF, MUM1) | 6p25-p23 | B-cell lymphoma, B-cell leukemia, Multiple myeloma | Codes for an interferon regulatory factor essential for lymphocyte function |
| JUNB | 19p13.2 | | see proto-oncogenes |
| KIT(SCFR) | 4q12 | Gastrointestinal stromal tumor (GISTs), mast cell leukemia, mastocytosis, seminoma and dysgerminoma | Transmembrane tyrosine kinase receptor for stem cell factor (SCFR) is required for haematopoiesis, melanogenesis and gametogenesis. Mutations cause piebaldism. |

TABLE 7-continued

| List of selected oncogenes associated with human malignancy | | | |
|---|---|---|---|
| Gene Name | Gene Locus | Malignancies associated with | Comments |
| KRAS2 (RASK2) | 12p12.1 | | see proto-oncogenes. |
| LCK | 1p35-p34.3 | Non-small cell lung cancer, Neuroblastoma, non-Hodgkin lymphoma | codes for lymphocyte specific protein tyrosine kinase |
| LCO | 2q14-q21 | Hepatocellular carcinoma | |
| MAP3K8(TPL2, COT, EST) | 10p11.2 | Ewings sarcoma, adenocarcinoma of lung, thyroid carcinoma | Codes for a serine-threonine protein kinase. |
| MCF2 (DBL) | Xq27 | Breast cancer | Codes for a GDP-GTP exchange factor that modulates the activity of small GTPases of the Rho family |
| MDM2 | 12q14.3-q15 | Multiple | MDM2 acts as a major regulator of the tumor suppressor p53 by targeting its destruction. Direct association of p53 with the protein MDM2 results in ubiquitination and subsequent degradation of p53 |
| MET(HGFR, RCCP2) | 7q31 | | see proto-oncogenes |
| MLH type genes | | | see proto-oncogenes |
| MMD | 17q | Non small cell lung cancer, hepatocellular carcinoma, colon cancer | Codes for monocyte to macrophage differentiation associated protein. |
| MOS (MSV) | 8q11 | Burkitt lymphoma, acute myeloblastic leukemia | Function in man unknown. Above associations indirect but analogous gene to Moloney murine sarcoma virus. |
| MRAS (RRAS3) | 3q22.3 | Activated in many tumors | Codes for a RAS GTP-binding protein membrane-anchored, intracellular signal transducer |
| MSH type genes | | | see proto-oncogenes |
| MYB (AMV) | 6q22 | Alterations found in more than a third of human solid tumor lines | Encodes for proteins critical to hematopoietic cell proliferation and development |
| MYC | 8q24.12-q24.13 | Burkitt lymphoma Over expression in many malignancies, possibly associated with angiogenic, invasive promoting properties in excess. | A transcription factor that promotes cell proliferation |
| MYCL1 (LMYC) | 1p34.3 | Small cell lung cancer, adenocarcinoma of lung, neuroblastoma | |
| MYCN | 2p24.1 | Neuroblastomas | Overlaps with NMYC and is transcribed from opposite DNA strand |
| NCOA4 (ELE1, ARA70, PTC3) | 10q11.2 | Prostate cancer | Interacts with the androgen receptor in presence of dihydrotestosterone. |
| NF1 type genes | | | see tumor suppressors |
| NMYC | 2p24 | Neuroblastomas, retinoblastoma | Overlaps with MYCN and is transcribed from opposite DNA strand. Probably a DNA-binding protein. |
| NRAS | 1p13.2 | | see proto-oncogenes. |
| NTRK1 (TRK, TRKA) | 1q21-q22 | | see proto-oncogenes. |
| NUP214 (CAN, D9546E) | 9q34.1 | NUP214/DEK fusion gene associated with acute myeloid leukemia, NUP214/ABL1 associated with T-cell acute lymphoblastic leukemia (T-ALL). | Codes for nucleoporin component of the vertebrate nuclear pore complex. |
| OVC | 9p24 | Ovarian adenocarcinoma | Abnormal in about 40% ovarian adenocarcinoma |
| TP53 (P53) | 17p13.1 | | see tumor suppressors |
| PALB2 | 16p12 | Breast cancer | see PALB2 |
| PAX3 (HUP2) STAT1 | 2q35 | Alveolar rhabdomyosarcoma | Transcriptions factor, causes some forms of Waardenburg syndrome and regulates RET. |
| PDGFB (SIS) | | | see proto-oncogenes |
| PIM genes | | | see proto-oncogenes |
| PML (MYL) | 15q22 | | see tumour suppressors |
| PMS (PMSL) genes | | | see tumour suppressors |

TABLE 7-continued

List of selected oncogenes associated with human malignancy

| Gene Name | Gene Locus | Malignancies associated with | Comments |
|---|---|---|---|
| PPM1D (WIP1) | 17q22-q23 | Breast cancer, Osteosarcoma | Codes for a serine/threonine protein phosphatase that attenuates apoptosis and facilitates transformation of primary cells in cooperation with RAS |
| PTEN (MMAC1) | 10q23.31 | | see tumor suppressors |
| PVT1 | 8q24 | Burkitt lymphoma | |
| RAF1 (CRAF) | 3p25 | Stomach cancer, renal cancer, glioblastoma, laryngeal cancer | A regulator of endothelial cell survival during angiogenesis. Activated RAF counteracts apoptosis by suppressing the activation of mammalian sterile 20-like kinase (MST2). |
| RB1 (RB) | 13q14.1-q14.2 | Retinoblastoma, osteogenic sarcoma, small cell carcinoma of lung, bladder cancer | see RB1 |
| RET | 10q11.2 | Multiple endocrine neoplasia type 2a and 2b and Medullary thyroid carcinoma | see RET |
| RRAS2 (TC21) | 11pter-p15.5 | Teratocarcinoma, ovarian cancer | Single point mutation activates its oncogene potential |
| ROS1 (ROS, MCF3) | 6q22 | Glioblastoma and probably others | ROS1/FIG fusion protein is a tyrosine kinase found in astrocytoma |
| SMAD type genes | | | see tumor suppressors |
| SMARCB1 (SNF5, INI1 | 22q11 | | see tumor suppressors |
| SMURF1 | 7q21.1-q31.1 | Pancreatic cancer | Codes for a HECT domain E3 ubiquitin ligase that regulates tumor cell plasticity and motility through degradation of RhoA |
| SRC (AVS) | 20q12-q13 | hepatic metastatic bowel cancer, colon cancer, leukemia | Intracellular communication regulator protein. Mutations are activating, transforming, tumorigenic, and metastasis-promoting |
| STAT1 | 2q32.2-q32.3 | Non-small cell lung cancer | see STAT1 |
| STAT3 | 17q21 | Epithelial cancers | Codes signal protein that induces cell transformation through a combined inhibition of apoptosis and cell-cycle activation |
| STAT5 | 17q11.2 | Permissive for a wide range of malignancies | Codes signal protein that induces cell transformation through a combined inhibition of apoptosis and cell-cycle activation |
| TDGF1 (CRGF) | 3p23-p21 | teratocarcinoma | Probably codes for signaling protein for mesoderm development |
| TGFBR2 | 3p22 | | see proto-oncogenes |
| THRA (ERBA, EAR7 etc) | | | see proto-oncogenes |
| TFG (TRKT3) | 3q11-q12 | Papillary thyroid carcinoma | Chimeric oncogene with NTRK1 proto-oncogene |
| TIF1 (TRIM24, TIF1A) | 7q32-q34 | Fusion genes associated with papillary thyroid carcinoma and myleoproliferative disorder. | Codes for transcriptional intermediary factor 1 |
| TNC (TN, HXB) | 9q33 | Neurofibromatosis type 1, Pancreatic cancer | see TNC |
| TRK | 1q21-q22 | | see proto-oncogenes |
| TUSC3 | 8p22 | | see tumor suppressors |
| USP6 (TRE2) | 17p13 | Multiple cancers | Codes for a ubiquitin-specific protease found only in primates |
| WNT1 (INT1) | 12q12-q13 | | see proto-oncogenes |
| WT1 | 11p13 | Wilms tumour, over expressed in breast and lung cancer, myelodysplastic syndrome and acute myeloid leukemia | A zinc finger DNA-binding protein acting as a transcriptional activator or repressor depending on intracellular context |
| VHL | 3p26-p25 | | see tumor suppressors |

TABLE 8

| Tumor suppresor miRs that are downregulated in specific cancer types | |
|---|---|
| Cancer | miRNA |
| Bladder | mir-1; mir-101; mir-1180; mir-1236; mir-124-3p; mir-125b; mir-126; mir-1280; mir-133a; mir-133b; mir-141; mir-143; mir-144; mir-145; mir-155; mir-16; mir-18a; mir-192; mir-195; mir-200a; mir-200b; mir-200c; mir-203; mir-205; mir-214; mir-218; mir-23b; mir-26a; mir-29c; mir-320c; mir-34a; mir-370; mir-409-3p; mir-429; mir-451; mir-490-5p; mir-493; mir-576-3p; mir-99a |
| Brain (Astrocytoma, Glioblastoma, Glioma) | let-7g-5p; mir-100; mir-101; mir-106a; mir-124; mir-124a; mir-125a; mir-125a-5p; mir-125b; mir-127-3p; mir-128; mir-129; mir-136; mir-137; mir-139-5p; mir-142-3p; mir-143; mir-145; mir-146b-5p; mir-149; mir-152; mir-153; mir-195; mir-21; mir-212-3p; mir-219-5p; mir-222; mir-29b; mir-31; mir-3189-3p; mir-320; mir-320a; mir-326; mir-330; mir-331-3p; mir-340; mir-342; mir-34a; mir-376a; mir-449a; mir-483-5p; mir-503; mir-577; mir-663; mir-7; mir-7-5p; mir-873; let-7a; let-7f; mir-107; mir-122; mir-124-5p; mir-139; mir-146a; mir-146b; mir-15b; mir-16; mir-181a; mir-181a-1; mir-181a-2; mir-181b; mir-181b-1; mir-181b-2; mir-181c; mir-181d; mir-184; mir-185; mir-199a-3p; mir-200a; mir-200b; mir-203; mir-204; mir-205; mir-218; mir-23b; mir-26b; mir-27a; mir-29c; mir-328; mir-34c-3p; mir-34c-5p; mir-375; mir-383; mir-451; mir-452; mir-495; mir-584; mir-622; mir-656; mir-98; mir-124-3p; mir-181b-5p; mir-200b; mir-3189-3p |
| Breast | mir-193b; let-7a; let-7a-1; let-7a-2; let-7a-3; let-7b; let-7c; let-7d; let-7e; let-7f-1; let-7f-2; let-7g; let-7i; mir-100; mir-107; mir-10a; mir-10b; mir-122; mir-124; mir-1258; mir-125a-5p; mir-125b; mir-126; mir-127; mir-129; mir-130a; mir-132; mir-133a; mir-143; mir-145; mir-146a; mir-146b; mir-147; mir-148a; mir-149; mir-152; mir-153; mir-15a; mir-16; mir-17-5p; mir-181a; mir-1826; mir-183; mir-185; mir-191; mir-193a-3p; mir-195; mir-199b-5p; mir-19a-3p; mir-200a; mir-200b; mir-200c; mir-205; mir-206; mir-211; mir-216b; mir-218; mir-22; mir-26a; mir-26b; mir-300; mir-30a; mir-31; mir-335; mir-339-5p; mir-33b; mir-34a; mir-34b; mir-34c; mir-374a; mir-379; mir-381; mir-383; mir-425; mir-429; mir-450b-3p; mir-494; mir-495; mir-497; mir-502-5p; mir-517a; mir-574-3p; mir-638; mir-7; mir-720; mir-873; mir-874; mir-92a; mir-98; mir-99a; mmu-mir-290-3p; mmu-mir-290-5p |
| Cervical | mir-143; mir-145; mir-17-5p; mir-203; mir-214; mir-218; mir-335; mir-342-3p; mir-372; mir-424; mir-491-5p; mir-497; mir-7; mir-99a; mir-99b; mir-100; mir-101; mir-15a; mir-16; mir-34a; mir-886-5p; mir-106a; mir-124; mir-148a; mir-29a; mir-375 |
| Colon/Colorectal | let-7a-1; let-7a-2; let-7a-3; let-7b; let-7c; let-7d; let-7e; let-7f-1; let-7f-2; let-7g; let-7i; mir-100; mir-101; mir-126; mir-142-3p; mir-143; mir-145; mir-192; mir-200c; mir-21; mir-214; mir-215; mir-22; mir-25; mir-302a; mir-320; mir-320a; mir-34a; mir-34c; mir-365; mir-373; mir-424; mir-429; mir-455; mir-484; mir-502; mir-503; mir-93; mir-98; mir-186; mir-30a-5p; mir-627; let-7a; mir-1; mir-124; mir-125a; mir-129; mir-1295b-3p; mir-1307; mir-130b; mir-132; mir-133a; mir-133b; mir-137; mir-138; mir-139; mir-139-5p; mir-140-5p; mir-148a; mir-148b; mir-149; mir-150-5p; mir-154; mir-15a; mir-15b; mir-16; mir-18a; mir-191; mir-193a-5p; mir-194; mir-195; mir-196a; mir-198; mir-199a-5p; mir-203; mir-204-5p; mir-206; mir-212; mir-218; mir-224; mir-24-3p; mir-26b; mir-27a; mir-28-3p; mir-28-5p; mir-29b; mir-30a-3p; mir-30b; mir-328; mir-338-3p; mir-342; mir-345; mir-34a-5p; mir-361-5p; mir-375; mir-378; mir-378a-3p; mir-378a-5p; mir-409-3p; mir-422a; mir-4487; mir-483; mir-497; mir-498; mir-518a-3p; mir-551a; mir-574-5p; mir-625; mir-638; mir-7; mir-96-5p; mir-202-3p; mir-30a; mir-451 |
| Endometrial | mir-101; mir-130a; mir-130b; mir-134; mir-143; mir-145; mir-152; mir-205; mir-223; mir-301a; mir-301b; mir-30c; mir-34a; mir-34c; mir-424; mir-449a; mir-543; mir-34b |
| Hematologic (Leukemia, Lymphoma, Myeloma) | mir-125b; mir-138; mir-15a; mir-15b; mir-16; mir-16-1; mir-16-1-3p; mir-16-2; mir-181a; mir-181b; mir-195; mir-223; mir-29b; mir-34b; mir-34c; mir-424; mir-10a; mir-146a; mir-150; mir-151; mir-155; mir-2278; mir-26a; mir-30e; mir-31; mir-326; mir-564; mir-27a; let-7b; mir-124a; mir-142-3p; let-7c; mir-17; mir-20a; mir-29a; mir-30c; mir-720; mir-107; mir-342; mir-34a; mir-202; mir-142-5p; mir-29c; mir-145; mir-193b; mir-199a; mir-214; mir-22; mir-137; mir-197 |
| Kidney | mir-1; mir-145; mir-1826; mir-199a; mir-199a-3p; mir-203; mir-205; mir-497; mir-508-3p; mir-509-3p; let-7a; let-7d; mir-106a*; mir-126; mir-1285; mir-129-3p; mir-1291; mir-133a; mir-135a; mir-138; mir-141; mir-143; mir-182-5p; mir-200a; mir-218; mir-28-5p; mir-30a; mir-30c; mir-30d; mir-34a; mir-378; mir-429; mir-509-5p; mir-646; mir-133b; let-7b; let-7c; mir-200c; mir-204; mir-335; mir-377; mir-506 |
| Liver (Hepatocellular Carcinoma) | mir-137; mir-138; mir-139; mir-139-5p; mir-140-5p; mir-141; mir-142-3p; mir-143; mir-144; mir-145; mir-146a; mir-148a; mir-148b; mir-150-5p; mir-15b; mir-16; mir-181a-5p; mir-185; mir-188-5p; mir-193b; mir-195; mir-195-5p; mir-197; mir-198; mir-199a; mir-199a-5p; mir-199b; mir-199b-5p; mir-200a; mir-200b; mir-200c; mir-202; mir-203; mir-204-3p; mir-205; mir-206; mir-20a; mir-21; mir-21-3p; mir-211; mir-212; mir-214; mir-217; mir-218; mir-219-5p; mir-22; mir-223; mir-26a; mir-26b; mir-29a; mir-29b-1; mir-29b-2; mir-29c; mir-302b; mir-302c; mir-30a; mir-30a-3p; mir-335; mir-338-3p; mir-33a; mir-34a; mir-34b; mir-365; mir-370; mir-372; mir-375; mir-376a; mir-377; mir-422a; mir-424; mir-424-5p; mir-433; mir-4458; mir-448; mir-450a; mir-451; mir-485-5p; mir-486-5p; mir-497; mir-503; mir-506; mir-519d; mir-520a; mir- |

TABLE 8-continued

| Tumor suppresor miRs that are downregulated in specific cancer types | |
|---|---|
| Cancer | miRNA |
| | 520b; mir-520c-3p; mir-582-5p; mir-590-5p; mir-610; mir-612; mir-625; mir-637; mir-675; mir-7; mir-877; mir-940; mir-941; mir-98; mir-99a; mir-132; mir-31 |
| Lung | mir-1297; mir-141; mir-145; mir-16; mir-200a; mir-200b; mir-200c; mir-29b; mir-381; mir-409-3p; mir-429; mir-451; mir-511; mir-99a; let-7a-1; let-7a-2; let-7a-3; let-7b; let-7c; let-7d; let-7e; let-7f-1; let-7f-2; let-7g; let-7i; mir-1; mir-101; mir-133b; mir-138; mir-142-5p; mir-144; mir-1469; mir-146a; mir-153; mir-15a; mir-15b; mir-16-1; mir-16-2; mir-182; mir-192; mir-193a-3p; mir-194; mir-195; mir-198; mir-203; mir-217; mir-218; mir-22; mir-223; mir-26a; mir-26b; mir-29c; mir-33a; mir-34a; mir-34b; mir-34c; mir-365; mir-449a; mir-449b; mir-486-5p; mir-545; mir-610; mir-614; mir-630; mir-660; mir-7515; mir-9500; mir-98; mir-99b; mir-133a; let-7a; mir-100; mir-106a; mir-107; mir-124; mir-125a-3p; mir-125a-5p; mir-126; mir-126*; mir-129; mir-137; mir-140; mir-143; mir-146b; mir-148a; mir-148b; mir-149; mir-152; mir-154; mir-155; mir-17-5p; mir-181a-1; mir-181a-2; mir-181b; mir-181b-1; mir-181b-2; mir-181c; mir-181d; mir-184; mir-186; mir-193b; mir-199a; mir-204; mir-212; mir-221; mir-224; mir-27a; mir-27b; mir-29a; mir-30a; mir-30b; mir-30c; mir-30d; mir-30d-5p; mir-30e-5p; mir-32; mir-335; mir-338-3p; mir-340; mir-342-3p; mir-361-3p; mir-373; mir-375; mir-4500; mir-4782-3p; mir-497; mir-503; mir-512-3p; mir-520a-3p; mir-526b; mir-625*; mir-96 |
| Melanoma | let-7b; mir-101; mir-125b; mir-1280; mir-143; mir-146a; mir-146b; mir-155; mir-17; mir-184; mir-185; mir-18b; mir-193b; mir-200c; mir-203; mir-204; mir-205; mir-206; mir-20a; mir-211; mir-218; mir-26a; mir-31; mir-33a; mir-34a; mir-34c; mir-376a; mir-376c; mir-573; mir-7-5p; mir-9; mir-98 |
| Oral Cancer | let-7d; mir-218; mir-34a; mir-375; mir-494; mir-100; mir-124; mir-1250; mir-125b; mir-126; mir-1271; mir-136; mir-138; mir-145; mir-147; mir-148a; mir-181a; mir-206; mir-220a; mir-26a; mir-26b; mir-29a; mir-32; mir-323-5p; mir-329; mir-338; mir-370; mir-410; mir-429; mir-433; mir-499a-5p; mir-503; mir-506; mir-632; mir-646; mir-668; mir-877; mir-9 |
| Ovarian | let-7i; mir-100; mir-124; mir-125b; mir-129-5p; mir-130b; mir-133a; mir-137; mir-138; mir-141; mir-145; mir-148a; mir-152; mir-153; mir-155; mir-199a; mir-200a; mir-200b; mir-200c; mir-212; mir-335; mir-34a; mir-34b; mir-34c; mir-409-3p; mir-411; mir-429; mir-432; mir-449a; mir-494; mir-497; mir-498; mir-519d; mir-655; mir-9; mir-98; mir-101; mir-532-5p; mir-124a; mir-192; mir-193a; mir-7 |
| Pancreatic | mir-101; mir-1181; mir-124; mir-1247; mir-133a; mir-141; mir-145; mir-146a; mir-148a; mir-148b; mir-150*; mir-150-5p; mir-152; mir-15a; mir-198; mir-203; mir-214; mir-216a; mir-29c; mir-335; mir-34a; mir-34b; mir-34c; mir-373; mir-375; mir-410; mir-497; mir-615-5p; mir-630; mir-96; mir-132; let-7a; let-7a-1; let-7a-2; let-7a-3; let-7b; let-7c; let-7d; let-7e; let-7f-1; let-7f-2; let-7g; let-7i; mir-126; mir-135a; mir-143; mir-144; mir-150; mir-16; mir-200a; mir-200b; mir-200c; mir-217; mir-218; mir-337; mir-494; mir-98 |
| Prostate | let-7a-3p; let-7c; mir-100; mir-101; mir-105; mir-124; mir-128; mir-1296; mir-130b; mir-133a-1; mir-133a-2; mir-133b; mir-135a; mir-143; mir-145; mir-146a; mir-154; mir-15a; mir-187; mir-188-5p; mir-199b; mir-200b; mir-203; mir-205; mir-212; mir-218; mir-221; mir-224; mir-23a; mir-23b; mir-25; mir-26a; mir-26b; mir-29b; mir-302a; mir-30a; mir-30b; mir-30c-1; mir-30c-2; mir-30d; mir-30e; mir-31; mir-330; mir-331-3p; mir-34a; mir-34b; mir-34c; mir-374b; mir-449a; mir-4723-5p; mir-497; mir-628-5p; mir-642a-5p; mir-765; mir-940 |
| Retinoblastoma | mir-101; mir-183; mir-204; mir-34a; mir-365b-3p; mir-486-3p; mir-532-5p |

The invention claimed is:

1. A recombinant oncolytic herpes simplex virus (HSV) comprising:

(i) a first microRNA (miRNA) target sequence cassette (miR-TS cassette) inserted into a first viral gene and comprising at least 2 target sequences for each of miR-124, miR-1, and miR-143;

(ii) a second miR-TS cassette inserted into a second viral gene and comprising at least 2 target sequences for each of miR-128, miR-219a, and miR-122; and (iii) a third miR-TS cassette inserted into a third viral gene and comprising at least 2 target sequences for each of miR-219a, miR-204, and miR-128;

and wherein:

(a) the first miR-TS cassette comprises a nucleic acid sequence that is at least 95% identical to SEQ ID NO: 852;

(b) the second miR-TS cassette comprises a nucleic acid sequence that is at least 95% identical to SEQ ID NO: 853; or (c) the third miR-TS cassette comprises a nucleic acid sequence that is at least 95% identical to SEQ ID NO: 854.

2. The recombinant HSV of claim 1, further comprising a fourth miR-TS cassette inserted into a fourth viral gene and comprising at least 2 target sequences for each of miR-137, miR-217, and miR-126, and wherein the fourth miR-TS cassette comprises a nucleic acid sequence that is at least 95% identical to SEQ ID NO: 855.

3. The recombinant HSV of claim 1, wherein each of the miR-TS cassettes comprises 4 target sequences for each of the respectively miRNAs.

4. The recombinant HSV of claim 1, wherein the first viral gene comprises at least one ICP4.

5. The recombinant HSV of claim 1, wherein the second viral gene is ICP27.

6. The recombinant HSV of claim 1, wherein the third viral gene comprises at least one ICP34.5.

7. The recombinant HSV of claim 2, wherein the fourth viral gene is UL8.

8. The recombinant HSV of claim 2, wherein the first miR-TS cassette comprises a nucleic acid sequence that is at least 95% identical to SEQ ID NO: 852.

9. The recombinant HSV of claim 8, wherein the second miR-TS cassette comprises a nucleic acid sequence that is at least 95% identical to SEQ ID NO: 853.

10. The recombinant HSV of claim 9, wherein the third miR-TS cassette comprises a nucleic acid sequence that is at least 95% identical to SEQ ID NO: 854.

11. The recombinant HSV of claim 1, further comprising a heterologous polynucleotide sequence encoding one or more payload molecules.

12. The recombinant HSV of claim 11, wherein the heterologous polynucleotide sequence encodes a payload selected from the group consisting of IL-12, CCL4, and CXCL10.

13. The recombinant HSV of claim 11, wherein the heterologous polynucleotide sequence encodes two or more payloads selected from the group consisting of IL-12, CCL4, and CXCL10.

14. A viral stock comprising the oncolytic HSV of claim 1.

15. A composition comprising the oncolytic HSV of claim 1 and a pharmaceutically-acceptable carrier.

16. A method of killing a cancerous cell, comprising exposing the cancerous cell to the oncolytic HSV of claim 1 under conditions sufficient for the oncolytic HSV to infect and replicate within said cancerous cell, and wherein replication of the oncolytic HSV within the cancerous cell results in cell death.

17. The method of claim 16, wherein the cancerous cell has a reduced expression of a miR capable of binding to the one or more miR-target sequences compared to the expression of the miR in a non-cancerous cell.

18. The method of claim 16, wherein replication of the oncolytic virus is increased or maintained in cancerous cells with a reduced expression of the miR capable of binding to the one or more miR-target sequences.

19. The method of claim 16, wherein the cell is in vivo.

20. The method of claim 19, wherein the cell is within a tumor.

21. A method of treating cancer in a subject in need thereof, comprising administering the oncolytic virus of claim 1 to a subject in need thereof.

22. The method of claim 21, wherein the subject is a mouse, a rat, a rabbit, a cat, a dog, a horse, a non-human primate, or a human.

23. The method of claim 21, wherein the oncolytic virus or compositions thereof are administered intravenously, subcutaneously, intratumorally, intramuscularly, or intranasally.

24. The method of claim 21, wherein the cancer is selected from lung cancer, breast cancer, ovarian cancer, cervical cancer, prostate cancer, testicular cancer, colorectal cancer, colon cancer, pancreatic cancer, liver cancer, gastric cancer, head and neck cancer, thyroid cancer, malignant glioma, glioblastoma, melanoma, B-cell chronic lymphocytic leukemia, diffuse large B-cell lymphoma (DLBCL), and marginal zone lymphoma (MZL).

25. The method of claim 24, wherein the lung cancer is small cell lung cancer or non-small cell lung cancer.

26. The method of claim 24, wherein the liver cancer is hepatocellular carcinoma (HCC).

* * * * *

SEQUENCE LISTING

```
<160> NUMBER OF SEQ ID NOS: 855

<210> SEQ ID NO 1
<211> LENGTH: 22
<212> TYPE: RNA
<213> ORGANISM: Homo sapiens

<400> SEQUENCE: 1

uggaguguga caaugguguu ug                                              22


<210> SEQ ID NO 2
<211> LENGTH: 20
<212> TYPE: RNA
<213> ORGANISM: Homo sapiens
```

<400> SEQUENCE: 2
uaaggcacgc ggugaaugcc 20

<210> SEQ ID NO 3
<211> LENGTH: 24
<212> TYPE: RNA
<213> ORGANISM: Homo sapiens

<400> SEQUENCE: 3
ucccugagac ccuuuaaccu guga 24

<210> SEQ ID NO 4
<211> LENGTH: 22
<212> TYPE: RNA
<213> ORGANISM: Homo sapiens

<400> SEQUENCE: 4
ucguaccgug aguaauaaug cg 22

<210> SEQ ID NO 5
<211> LENGTH: 22
<212> TYPE: RNA
<213> ORGANISM: Homo sapiens

<400> SEQUENCE: 5
ucggauccgu cugagcuugg cu 22

<210> SEQ ID NO 6
<211> LENGTH: 21
<212> TYPE: RNA
<213> ORGANISM: Homo sapiens

<400> SEQUENCE: 6
ucacagugaa ccggucucuu u 21

<210> SEQ ID NO 7
<211> LENGTH: 22
<212> TYPE: RNA
<213> ORGANISM: Homo sapiens

<400> SEQUENCE: 7
aagcccuuac cccaaaaagu au 22

<210> SEQ ID NO 8
<211> LENGTH: 21
<212> TYPE: RNA
<213> ORGANISM: Homo sapiens

<400> SEQUENCE: 8
cuuuuugcgg ucugggcuug c 21

<210> SEQ ID NO 9
<211> LENGTH: 22
<212> TYPE: RNA
<213> ORGANISM: Homo sapiens

<400> SEQUENCE: 9
cagugcaaug augaaagggc au 22

<210> SEQ ID NO 10
<211> LENGTH: 21
<212> TYPE: RNA
<213> ORGANISM: Homo sapiens

<400> SEQUENCE: 10
acucuuuccc uguugcacua c 21

<210> SEQ ID NO 11
<211> LENGTH: 22
<212> TYPE: RNA
<213> ORGANISM: Homo sapiens

<400> SEQUENCE: 11
uuuggucccc uucaaccagc ug 22

<210> SEQ ID NO 12
<211> LENGTH: 22
<212> TYPE: RNA
<213> ORGANISM: Homo sapiens

<400> SEQUENCE: 12
uuuggucccc uucaaccagc ua 22

<210> SEQ ID NO 13
<211> LENGTH: 23
<212> TYPE: RNA
<213> ORGANISM: Homo sapiens

<400> SEQUENCE: 13
ccugugggcc accuagucac caa 23

<210> SEQ ID NO 14
<211> LENGTH: 23
<212> TYPE: RNA
<213> ORGANISM: Homo sapiens

<400> SEQUENCE: 14
uuauugcuua agaauacgcg uag 23

<210> SEQ ID NO 15
<211> LENGTH: 22
<212> TYPE: RNA
<213> ORGANISM: Homo sapiens

<400> SEQUENCE: 15
uggaauguaa agaaguaugu au 22

<210> SEQ ID NO 16
<211> LENGTH: 21
<212> TYPE: RNA
<213> ORGANISM: Homo sapiens

<400> SEQUENCE: 16
ugagaugaag cacuguagcu c 21

<210> SEQ ID NO 17
<211> LENGTH: 22
<212> TYPE: RNA
<213> ORGANISM: Homo sapiens

<400> SEQUENCE: 17
ggauuccugg aaauacuguu cu 22

<210> SEQ ID NO 18
<211> LENGTH: 23
<212> TYPE: RNA

<213> ORGANISM: Homo sapiens

<400> SEQUENCE: 18
guccaguuuu cccaggaauc ccu 23

<210> SEQ ID NO 19
<211> LENGTH: 22
<212> TYPE: RNA
<213> ORGANISM: Homo sapiens

<400> SEQUENCE: 19
uggacggaga acugauaagg gu 22

<210> SEQ ID NO 20
<211> LENGTH: 22
<212> TYPE: RNA
<213> ORGANISM: Homo sapiens

<400> SEQUENCE: 20
acaguagucu gcacauuggu ua 22

<210> SEQ ID NO 21
<211> LENGTH: 23
<212> TYPE: RNA
<213> ORGANISM: Homo sapiens

<400> SEQUENCE: 21
cccaguguuc agacuaccug uuc 23

<210> SEQ ID NO 22
<211> LENGTH: 22
<212> TYPE: RNA
<213> ORGANISM: Homo sapiens

<400> SEQUENCE: 22
uucccuuugu cauccuaugc cu 22

<210> SEQ ID NO 23
<211> LENGTH: 22
<212> TYPE: RNA
<213> ORGANISM: Homo sapiens

<400> SEQUENCE: 23
auaagacgaa caaaagguuu gu 22

<210> SEQ ID NO 24
<211> LENGTH: 22
<212> TYPE: RNA
<213> ORGANISM: Homo sapiens

<400> SEQUENCE: 24
acagcaggca cagacaggca gu 22

<210> SEQ ID NO 25
<211> LENGTH: 23
<212> TYPE: RNA
<213> ORGANISM: Homo sapiens

<400> SEQUENCE: 25
uacugcauca ggaacugauu gga 23

<210> SEQ ID NO 26
<211> LENGTH: 21

-continued

<212> TYPE: RNA
<213> ORGANISM: Homo sapiens

<400> SEQUENCE: 26
ugauugucca aacgcaauuc u 21

<210> SEQ ID NO 27
<211> LENGTH: 22
<212> TYPE: RNA
<213> ORGANISM: Homo sapiens

<400> SEQUENCE: 27
ugucaguuug ucaaauaccc ca 22

<210> SEQ ID NO 28
<211> LENGTH: 22
<212> TYPE: RNA
<213> ORGANISM: Homo sapiens

<400> SEQUENCE: 28
uggcaguguc uuagcugguu gu 22

<210> SEQ ID NO 29
<211> LENGTH: 22
<212> TYPE: RNA
<213> ORGANISM: Homo sapiens

<400> SEQUENCE: 29
aaaccguuac cauuacugag uu 22

<210> SEQ ID NO 30
<211> LENGTH: 21
<212> TYPE: RNA
<213> ORGANISM: Homo sapiens

<400> SEQUENCE: 30
uaaaguaaau augcaccaaa a 21

<210> SEQ ID NO 31
<211> LENGTH: 22
<212> TYPE: RNA
<213> ORGANISM: Homo sapiens

<400> SEQUENCE: 31
ugagguagua gguuguauag uu 22

<210> SEQ ID NO 32
<211> LENGTH: 23
<212> TYPE: RNA
<213> ORGANISM: Homo sapiens

<400> SEQUENCE: 32
ucuuugguua ucuagcugua uga 23

<210> SEQ ID NO 33
<211> LENGTH: 22
<212> TYPE: RNA
<213> ORGANISM: Homo sapiens

<400> SEQUENCE: 33
ugagguagua gguugugugg uu 22

<210> SEQ ID NO 34

<211> LENGTH: 22
<212> TYPE: RNA
<213> ORGANISM: Homo sapiens

<400> SEQUENCE: 34
ugagguagua gguuguaugg uu 22

<210> SEQ ID NO 35
<211> LENGTH: 22
<212> TYPE: RNA
<213> ORGANISM: Homo sapiens

<400> SEQUENCE: 35
agagguagua gguugcauag uu 22

<210> SEQ ID NO 36
<211> LENGTH: 22
<212> TYPE: RNA
<213> ORGANISM: Homo sapiens

<400> SEQUENCE: 36
ugagguagga gguuguauag uu 22

<210> SEQ ID NO 37
<211> LENGTH: 22
<212> TYPE: RNA
<213> ORGANISM: Homo sapiens

<400> SEQUENCE: 37
ugagguagua gauuguauag uu 22

<210> SEQ ID NO 38
<211> LENGTH: 22
<212> TYPE: RNA
<213> ORGANISM: Homo sapiens

<400> SEQUENCE: 38
ugagguagua guuuguacag uu 22

<210> SEQ ID NO 39
<211> LENGTH: 22
<212> TYPE: RNA
<213> ORGANISM: Homo sapiens

<400> SEQUENCE: 39
ugagguagua guuugugcug uu 22

<210> SEQ ID NO 40
<211> LENGTH: 22
<212> TYPE: RNA
<213> ORGANISM: Homo sapiens

<400> SEQUENCE: 40
aacccguaga uccgaacuug ug 22

<210> SEQ ID NO 41
<211> LENGTH: 21
<212> TYPE: RNA
<213> ORGANISM: Homo sapiens

<400> SEQUENCE: 41
uacaguacug ugauaacuga a 21

-continued

<210> SEQ ID NO 42
<211> LENGTH: 23
<212> TYPE: RNA
<213> ORGANISM: Homo sapiens

<400> SEQUENCE: 42
agcagcauug uacagggcua uga 23

<210> SEQ ID NO 43
<211> LENGTH: 23
<212> TYPE: RNA
<213> ORGANISM: Homo sapiens

<400> SEQUENCE: 43
ucaaaugcuc agacuccugu ggu 23

<210> SEQ ID NO 44
<211> LENGTH: 23
<212> TYPE: RNA
<213> ORGANISM: Homo sapiens

<400> SEQUENCE: 44
aaaagugcuu acagugcagg uag 23

<210> SEQ ID NO 45
<211> LENGTH: 21
<212> TYPE: RNA
<213> ORGANISM: Homo sapiens

<400> SEQUENCE: 45
uaaagugcug acagugcaga u 21

<210> SEQ ID NO 46
<211> LENGTH: 23
<212> TYPE: RNA
<213> ORGANISM: Homo sapiens

<400> SEQUENCE: 46
agcagcauug uacagggcua uca 23

<210> SEQ ID NO 47
<211> LENGTH: 23
<212> TYPE: RNA
<213> ORGANISM: Homo sapiens

<400> SEQUENCE: 47
uacccuguag auccgaauuu gug 23

<210> SEQ ID NO 48
<211> LENGTH: 23
<212> TYPE: RNA
<213> ORGANISM: Homo sapiens

<400> SEQUENCE: 48
uacccuguag aaccgaauuu gug 23

<210> SEQ ID NO 49
<211> LENGTH: 21
<212> TYPE: RNA
<213> ORGANISM: Homo sapiens

<400> SEQUENCE: 49
uugcucacug uucuucccua g 21

<210> SEQ ID NO 50
<211> LENGTH: 22
<212> TYPE: RNA
<213> ORGANISM: Homo sapiens

<400> SEQUENCE: 50
uuuccggcuc gcgugggugu gu 22

<210> SEQ ID NO 51
<211> LENGTH: 27
<212> TYPE: RNA
<213> ORGANISM: Homo sapiens

<400> SEQUENCE: 51
cacuguaggu gauggugaga gugggca 27

<210> SEQ ID NO 52
<211> LENGTH: 22
<212> TYPE: RNA
<213> ORGANISM: Homo sapiens

<400> SEQUENCE: 52
auauacaggg ggagacucuu au 22

<210> SEQ ID NO 53
<211> LENGTH: 22
<212> TYPE: RNA
<213> ORGANISM: Homo sapiens

<400> SEQUENCE: 53
auauacaggg ggagacucuc au 22

<210> SEQ ID NO 54
<211> LENGTH: 21
<212> TYPE: RNA
<213> ORGANISM: Homo sapiens

<400> SEQUENCE: 54
agaggauacc cuuuguaugu u 21

<210> SEQ ID NO 55
<211> LENGTH: 23
<212> TYPE: RNA
<213> ORGANISM: Homo sapiens

<400> SEQUENCE: 55
gggaugguag accggugacg ugc 23

<210> SEQ ID NO 56
<211> LENGTH: 21
<212> TYPE: RNA
<213> ORGANISM: Homo sapiens

<400> SEQUENCE: 56
uaggacacau ggucuacuuc u 21

<210> SEQ ID NO 57
<211> LENGTH: 22
<212> TYPE: RNA
<213> ORGANISM: Homo sapiens

<400> SEQUENCE: 57
cuccugagcc auucugagcc uc 22

```
<210> SEQ ID NO 58
<211> LENGTH: 21
<212> TYPE: RNA
<213> ORGANISM: Homo sapiens

<400> SEQUENCE: 58

gugccagcug caguggggga g                                              21

<210> SEQ ID NO 59
<211> LENGTH: 21
<212> TYPE: RNA
<213> ORGANISM: Homo sapiens

<400> SEQUENCE: 59

cccggagcca ggaugcagcu c                                              21

<210> SEQ ID NO 60
<211> LENGTH: 21
<212> TYPE: RNA
<213> ORGANISM: Homo sapiens

<400> SEQUENCE: 60

ucguggccug gucuccauua u                                              21

<210> SEQ ID NO 61
<211> LENGTH: 20
<212> TYPE: RNA
<213> ORGANISM: Homo sapiens

<400> SEQUENCE: 61

ucugcagggu uugcuuugag                                                20

<210> SEQ ID NO 62
<211> LENGTH: 21
<212> TYPE: RNA
<213> ORGANISM: Homo sapiens

<400> SEQUENCE: 62

uguucaugua gauguuuaag c                                              21

<210> SEQ ID NO 63
<211> LENGTH: 21
<212> TYPE: RNA
<213> ORGANISM: Homo sapiens

<400> SEQUENCE: 63

ccccaccucc ucucuccuca g                                              21

<210> SEQ ID NO 64
<211> LENGTH: 19
<212> TYPE: RNA
<213> ORGANISM: Homo sapiens

<400> SEQUENCE: 64

gugaggacuc gggaggugg                                                 19

<210> SEQ ID NO 65
<211> LENGTH: 22
<212> TYPE: RNA
<213> ORGANISM: Homo sapiens

<400> SEQUENCE: 65
```

ucaccagccc uguguucccu ag 22

<210> SEQ ID NO 66
<211> LENGTH: 20
<212> TYPE: RNA
<213> ORGANISM: Homo sapiens

<400> SEQUENCE: 66
ucacaccugc cucgcccccc 20

<210> SEQ ID NO 67
<211> LENGTH: 20
<212> TYPE: RNA
<213> ORGANISM: Homo sapiens

<400> SEQUENCE: 67
ugagcccugu ccuccegcag 20

<210> SEQ ID NO 68
<211> LENGTH: 22
<212> TYPE: RNA
<213> ORGANISM: Homo sapiens

<400> SEQUENCE: 68
ucggccugac cacccacccc ac 22

<210> SEQ ID NO 69
<211> LENGTH: 22
<212> TYPE: RNA
<213> ORGANISM: Homo sapiens

<400> SEQUENCE: 69
ccucuucccc uugucucucc ag 22

<210> SEQ ID NO 70
<211> LENGTH: 26
<212> TYPE: RNA
<213> ORGANISM: Homo sapiens

<400> SEQUENCE: 70
aaguaguugg uuuguaugag augguu 26

<210> SEQ ID NO 71
<211> LENGTH: 21
<212> TYPE: RNA
<213> ORGANISM: Homo sapiens

<400> SEQUENCE: 71
aagugaucua aaggccuaca u 21

<210> SEQ ID NO 72
<211> LENGTH: 22
<212> TYPE: RNA
<213> ORGANISM: Homo sapiens

<400> SEQUENCE: 72
ucagaugauc uaaaggccua ua 22

<210> SEQ ID NO 73
<211> LENGTH: 21
<212> TYPE: RNA
<213> ORGANISM: Homo sapiens

<400> SEQUENCE: 73
uaggccuuua gaucacuuaa a 21

<210> SEQ ID NO 74
<211> LENGTH: 19
<212> TYPE: RNA
<213> ORGANISM: Homo sapiens

<400> SEQUENCE: 74
aauggauuuu uggagcagg 19

<210> SEQ ID NO 75
<211> LENGTH: 22
<212> TYPE: RNA
<213> ORGANISM: Homo sapiens

<400> SEQUENCE: 75
acccgucccg uucgucccg ga 22

<210> SEQ ID NO 76
<211> LENGTH: 27
<212> TYPE: RNA
<213> ORGANISM: Homo sapiens

<400> SEQUENCE: 76
accuucuugu auaagcacug ugcuaaa 27

<210> SEQ ID NO 77
<211> LENGTH: 22
<212> TYPE: RNA
<213> ORGANISM: Homo sapiens

<400> SEQUENCE: 77
acgcccuucc cccccuucuu ca 22

<210> SEQ ID NO 78
<211> LENGTH: 24
<212> TYPE: RNA
<213> ORGANISM: Homo sapiens

<400> SEQUENCE: 78
aggagggagg agaugggcca aguu 24

<210> SEQ ID NO 79
<211> LENGTH: 21
<212> TYPE: RNA
<213> ORGANISM: Homo sapiens

<400> SEQUENCE: 79
acggugcugg auguggccuu u 21

<210> SEQ ID NO 80
<211> LENGTH: 22
<212> TYPE: RNA
<213> ORGANISM: Homo sapiens

<400> SEQUENCE: 80
agaaggaaau ugaauucauu ua 22

<210> SEQ ID NO 81
<211> LENGTH: 21
<212> TYPE: RNA
<213> ORGANISM: Homo sapiens

<400> SEQUENCE: 81
agagaagaag aucagccugc a 21

<210> SEQ ID NO 82
<211> LENGTH: 24
<212> TYPE: RNA
<213> ORGANISM: Homo sapiens

<400> SEQUENCE: 82
agccuggaag cuggagccug cagu 24

<210> SEQ ID NO 83
<211> LENGTH: 23
<212> TYPE: RNA
<213> ORGANISM: Homo sapiens

<400> SEQUENCE: 83
aggaugagca aagaaaguag auu 23

<210> SEQ ID NO 84
<211> LENGTH: 22
<212> TYPE: RNA
<213> ORGANISM: Homo sapiens

<400> SEQUENCE: 84
cggaugagca aagaaagugg uu 22

<210> SEQ ID NO 85
<211> LENGTH: 21
<212> TYPE: RNA
<213> ORGANISM: Homo sapiens

<400> SEQUENCE: 85
agugaaugau ggguucugac c 21

<210> SEQ ID NO 86
<211> LENGTH: 21
<212> TYPE: RNA
<213> ORGANISM: Homo sapiens

<400> SEQUENCE: 86
aguuaggauu aggucgugga a 21

<210> SEQ ID NO 87
<211> LENGTH: 22
<212> TYPE: RNA
<213> ORGANISM: Homo sapiens

<400> SEQUENCE: 87
acaggugagg uucuugggag cc 22

<210> SEQ ID NO 88
<211> LENGTH: 22
<212> TYPE: RNA
<213> ORGANISM: Homo sapiens

<400> SEQUENCE: 88
ucccugagac ccuaacuugu ga 22

<210> SEQ ID NO 89
<211> LENGTH: 18
<212> TYPE: RNA
<213> ORGANISM: Homo sapiens

<400> SEQUENCE: 89
aucccaccuc ugccacca 18

<210> SEQ ID NO 90
<211> LENGTH: 19
<212> TYPE: RNA
<213> ORGANISM: Homo sapiens

<400> SEQUENCE: 90
aucccaccac ugccaccau 19

<210> SEQ ID NO 91
<211> LENGTH: 19
<212> TYPE: RNA
<213> ORGANISM: Homo sapiens

<400> SEQUENCE: 91
auggauaagg cuuuggcuu 19

<210> SEQ ID NO 92
<211> LENGTH: 22
<212> TYPE: RNA
<213> ORGANISM: Homo sapiens

<400> SEQUENCE: 92
augggugaau uuguagaagg au 22

<210> SEQ ID NO 93
<211> LENGTH: 23
<212> TYPE: RNA
<213> ORGANISM: Homo sapiens

<400> SEQUENCE: 93
caagucuuau uugagcaccu guu 23

<210> SEQ ID NO 94
<211> LENGTH: 23
<212> TYPE: RNA
<213> ORGANISM: Homo sapiens

<400> SEQUENCE: 94
ccucagggcu guagaacagg gcu 23

<210> SEQ ID NO 95
<211> LENGTH: 18
<212> TYPE: RNA
<213> ORGANISM: Homo sapiens

<400> SEQUENCE: 95
cgggcguggu ggugggg 18

<210> SEQ ID NO 96
<211> LENGTH: 20
<212> TYPE: RNA
<213> ORGANISM: Homo sapiens

<400> SEQUENCE: 96
cgggcguggu gguggggug 20

<210> SEQ ID NO 97
<211> LENGTH: 22
<212> TYPE: RNA

-continued

<213> ORGANISM: Homo sapiens

<400> SEQUENCE: 97
cuggacugag ccgugcuacu gg 22

<210> SEQ ID NO 98
<211> LENGTH: 22
<212> TYPE: RNA
<213> ORGANISM: Homo sapiens

<400> SEQUENCE: 98
cuggacugag ccaugcuacu gg 22

<210> SEQ ID NO 99
<211> LENGTH: 23
<212> TYPE: RNA
<213> ORGANISM: Homo sapiens

<400> SEQUENCE: 99
cuggagauau ggaagagcug ugu 23

<210> SEQ ID NO 100
<211> LENGTH: 22
<212> TYPE: RNA
<213> ORGANISM: Homo sapiens

<400> SEQUENCE: 100
agugccugcu augugccagg ca 22

<210> SEQ ID NO 101
<211> LENGTH: 22
<212> TYPE: RNA
<213> ORGANISM: Homo sapiens

<400> SEQUENCE: 101
cuuggcaccu agcaagcacu ca 22

<210> SEQ ID NO 102
<211> LENGTH: 26
<212> TYPE: RNA
<213> ORGANISM: Homo sapiens

<400> SEQUENCE: 102
gaugaugaug gcagcaaauu cugaaa 26

<210> SEQ ID NO 103
<211> LENGTH: 22
<212> TYPE: RNA
<213> ORGANISM: Homo sapiens

<400> SEQUENCE: 103
ggcgacaaaa cgagacccug uc 22

<210> SEQ ID NO 104
<211> LENGTH: 17
<212> TYPE: RNA
<213> ORGANISM: Homo sapiens

<400> SEQUENCE: 104
gugggggaga ggcuguc 17

<210> SEQ ID NO 105
<211> LENGTH: 22

<212> TYPE: RNA
<213> ORGANISM: Homo sapiens

<400> SEQUENCE: 105
cugaagcuca gagggcucug au 22

<210> SEQ ID NO 106
<211> LENGTH: 20
<212> TYPE: RNA
<213> ORGANISM: Homo sapiens

<400> SEQUENCE: 106
uaaagagccc uguggagaca 20

<210> SEQ ID NO 107
<211> LENGTH: 22
<212> TYPE: RNA
<213> ORGANISM: Homo sapiens

<400> SEQUENCE: 107
uacguagaua uauauguauu uu 22

<210> SEQ ID NO 108
<211> LENGTH: 22
<212> TYPE: RNA
<213> ORGANISM: Homo sapiens

<400> SEQUENCE: 108
uaguacugug cauaucaucu au 22

<210> SEQ ID NO 109
<211> LENGTH: 17
<212> TYPE: RNA
<213> ORGANISM: Homo sapiens

<400> SEQUENCE: 109
ucauauugcu ucuuucu 17

<210> SEQ ID NO 110
<211> LENGTH: 17
<212> TYPE: RNA
<213> ORGANISM: Homo sapiens

<400> SEQUENCE: 110
ucgccuccuc cucuccc 17

<210> SEQ ID NO 111
<211> LENGTH: 23
<212> TYPE: RNA
<213> ORGANISM: Homo sapiens

<400> SEQUENCE: 111
cggggccgua gcacugucug aga 23

<210> SEQ ID NO 112
<211> LENGTH: 23
<212> TYPE: RNA
<213> ORGANISM: Homo sapiens

<400> SEQUENCE: 112
gggggccgau acacuguacg aga 23

<210> SEQ ID NO 113

<211> LENGTH: 22
<212> TYPE: RNA
<213> ORGANISM: Homo sapiens

<400> SEQUENCE: 113
ucuacaaagg aaagcgcuuu cu 22

<210> SEQ ID NO 114
<211> LENGTH: 22
<212> TYPE: RNA
<213> ORGANISM: Homo sapiens

<400> SEQUENCE: 114
ucugggcaac aaagugagac cu 22

<210> SEQ ID NO 115
<211> LENGTH: 21
<212> TYPE: RNA
<213> ORGANISM: Homo sapiens

<400> SEQUENCE: 115
gaucucacuu uguugcccag g 21

<210> SEQ ID NO 116
<211> LENGTH: 21
<212> TYPE: RNA
<213> ORGANISM: Homo sapiens

<400> SEQUENCE: 116
ugcaggacca agaugagccc u 21

<210> SEQ ID NO 117
<211> LENGTH: 22
<212> TYPE: RNA
<213> ORGANISM: Homo sapiens

<400> SEQUENCE: 117
cucuagccac agaugcagug au 22

<210> SEQ ID NO 118
<211> LENGTH: 22
<212> TYPE: RNA
<213> ORGANISM: Homo sapiens

<400> SEQUENCE: 118
ugcuggauca gugguucgag uc 22

<210> SEQ ID NO 119
<211> LENGTH: 21
<212> TYPE: RNA
<213> ORGANISM: Homo sapiens

<400> SEQUENCE: 119
uggacugccc ugaucuggag a 21

<210> SEQ ID NO 120
<211> LENGTH: 23
<212> TYPE: RNA
<213> ORGANISM: Homo sapiens

<400> SEQUENCE: 120
uggaguccag gaaucugcau uuu 23

<210> SEQ ID NO 121
<211> LENGTH: 19
<212> TYPE: RNA
<213> ORGANISM: Homo sapiens

<400> SEQUENCE: 121
uggauuuuug gaucaggga 19

<210> SEQ ID NO 122
<211> LENGTH: 24
<212> TYPE: RNA
<213> ORGANISM: Homo sapiens

<400> SEQUENCE: 122
uggcccugac ugaagaccag cagu 24

<210> SEQ ID NO 123
<211> LENGTH: 22
<212> TYPE: RNA
<213> ORGANISM: Homo sapiens

<400> SEQUENCE: 123
aagcccuuac cccaaaaagc au 22

<210> SEQ ID NO 124
<211> LENGTH: 22
<212> TYPE: RNA
<213> ORGANISM: Homo sapiens

<400> SEQUENCE: 124
ugggugggcu ggagauuugu gc 22

<210> SEQ ID NO 125
<211> LENGTH: 21
<212> TYPE: RNA
<213> ORGANISM: Homo sapiens

<400> SEQUENCE: 125
uuaggccgca gaucugggug a 21

<210> SEQ ID NO 126
<211> LENGTH: 22
<212> TYPE: RNA
<213> ORGANISM: Homo sapiens

<400> SEQUENCE: 126
gaguggggcu ucgacccuaa cc 22

<210> SEQ ID NO 127
<211> LENGTH: 22
<212> TYPE: RNA
<213> ORGANISM: Homo sapiens

<400> SEQUENCE: 127
uuagggcccu ggcuccaucu cc 22

<210> SEQ ID NO 128
<211> LENGTH: 17
<212> TYPE: RNA
<213> ORGANISM: Homo sapiens

<400> SEQUENCE: 128
uucaaguaau ucaggug 17

-continued

<210> SEQ ID NO 129
<211> LENGTH: 22
<212> TYPE: RNA
<213> ORGANISM: Homo sapiens

<400> SEQUENCE: 129
uucauucggc uguccagaug ua 22

<210> SEQ ID NO 130
<211> LENGTH: 22
<212> TYPE: RNA
<213> ORGANISM: Homo sapiens

<400> SEQUENCE: 130
uucuggaauu cugugugagg ga 22

<210> SEQ ID NO 131
<211> LENGTH: 24
<212> TYPE: RNA
<213> ORGANISM: Homo sapiens

<400> SEQUENCE: 131
uugcagcugc cugggaguga cuuc 24

<210> SEQ ID NO 132
<211> LENGTH: 21
<212> TYPE: RNA
<213> ORGANISM: Homo sapiens

<400> SEQUENCE: 132
uugggacaua cuuaugcuaa a 21

<210> SEQ ID NO 133
<211> LENGTH: 22
<212> TYPE: RNA
<213> ORGANISM: Homo sapiens

<400> SEQUENCE: 133
uuuagagacg gggucuugcu cu 22

<210> SEQ ID NO 134
<211> LENGTH: 22
<212> TYPE: RNA
<213> ORGANISM: Homo sapiens

<400> SEQUENCE: 134
ucucacugua gccucgaacc cc 22

<210> SEQ ID NO 135
<211> LENGTH: 22
<212> TYPE: RNA
<213> ORGANISM: Homo sapiens

<400> SEQUENCE: 135
uuugaggcua cagugagaug ug 22

<210> SEQ ID NO 136
<211> LENGTH: 22
<212> TYPE: RNA
<213> ORGANISM: Homo sapiens

<400> SEQUENCE: 136
uuuucaacuc uaaugggaga ga 22

<210> SEQ ID NO 137
<211> LENGTH: 18
<212> TYPE: RNA
<213> ORGANISM: Homo sapiens

<400> SEQUENCE: 137
acguuggcuc ugguggug 18

<210> SEQ ID NO 138
<211> LENGTH: 22
<212> TYPE: RNA
<213> ORGANISM: Homo sapiens

<400> SEQUENCE: 138
ccaccucccc ugcaaacguc ca 22

<210> SEQ ID NO 139
<211> LENGTH: 22
<212> TYPE: RNA
<213> ORGANISM: Homo sapiens

<400> SEQUENCE: 139
acucggcgug gcgucggucg ug 22

<210> SEQ ID NO 140
<211> LENGTH: 21
<212> TYPE: RNA
<213> ORGANISM: Homo sapiens

<400> SEQUENCE: 140
ucgaccggac cucgaccggc u 21

<210> SEQ ID NO 141
<211> LENGTH: 22
<212> TYPE: RNA
<213> ORGANISM: Homo sapiens

<400> SEQUENCE: 141
cagugcaaug uuaaaagggc au 22

<210> SEQ ID NO 142
<211> LENGTH: 22
<212> TYPE: RNA
<213> ORGANISM: Homo sapiens

<400> SEQUENCE: 142
cagugcaaug augaaagggc au 22

<210> SEQ ID NO 143
<211> LENGTH: 19
<212> TYPE: RNA
<213> ORGANISM: Homo sapiens

<400> SEQUENCE: 143
gaugaugcug cugaugcug 19

<210> SEQ ID NO 144
<211> LENGTH: 22
<212> TYPE: RNA
<213> ORGANISM: Homo sapiens

<400> SEQUENCE: 144
ucaaaacuga ggggcauuuu cu 22

<210> SEQ ID NO 145
<211> LENGTH: 22
<212> TYPE: RNA
<213> ORGANISM: Homo sapiens

<400> SEQUENCE: 145
uaacagucua cagccauggu cg 22

<210> SEQ ID NO 146
<211> LENGTH: 22
<212> TYPE: RNA
<213> ORGANISM: Homo sapiens

<400> SEQUENCE: 146
agcugguaaa auggaaccaa au 22

<210> SEQ ID NO 147
<211> LENGTH: 22
<212> TYPE: RNA
<213> ORGANISM: Homo sapiens

<400> SEQUENCE: 147
ugugacuggu ugaccagagg gg 22

<210> SEQ ID NO 148
<211> LENGTH: 23
<212> TYPE: RNA
<213> ORGANISM: Homo sapiens

<400> SEQUENCE: 148
uauggcuuuu uauuccuaug uga 23

<210> SEQ ID NO 149
<211> LENGTH: 23
<212> TYPE: RNA
<213> ORGANISM: Homo sapiens

<400> SEQUENCE: 149
uauggcuuuu cauuccuaug uga 23

<210> SEQ ID NO 150
<211> LENGTH: 23
<212> TYPE: RNA
<213> ORGANISM: Homo sapiens

<400> SEQUENCE: 150
acuccauuug uuuugaugau gga 23

<210> SEQ ID NO 151
<211> LENGTH: 23
<212> TYPE: RNA
<213> ORGANISM: Homo sapiens

<400> SEQUENCE: 151
agcugguguu gugaaucagg ccg 23

<210> SEQ ID NO 152
<211> LENGTH: 23
<212> TYPE: RNA
<213> ORGANISM: Homo sapiens

<400> SEQUENCE: 152
uggagacgcg gcccuguugg agu 23

<210> SEQ ID NO 153
<211> LENGTH: 23
<212> TYPE: RNA
<213> ORGANISM: Homo sapiens

<400> SEQUENCE: 153
ucuacagugc acgugucucc agu 23

<210> SEQ ID NO 154
<211> LENGTH: 21
<212> TYPE: RNA
<213> ORGANISM: Homo sapiens

<400> SEQUENCE: 154
uaccacaggg uagaaccacg g 21

<210> SEQ ID NO 155
<211> LENGTH: 22
<212> TYPE: RNA
<213> ORGANISM: Homo sapiens

<400> SEQUENCE: 155
cagugguuuu acccuauggu ag 22

<210> SEQ ID NO 156
<211> LENGTH: 22
<212> TYPE: RNA
<213> ORGANISM: Homo sapiens

<400> SEQUENCE: 156
uaacacuguc ugguaaagau gg 22

<210> SEQ ID NO 157
<211> LENGTH: 23
<212> TYPE: RNA
<213> ORGANISM: Homo sapiens

<400> SEQUENCE: 157
uguaguguuu ccuacuuuau gga 23

<210> SEQ ID NO 158
<211> LENGTH: 21
<212> TYPE: RNA
<213> ORGANISM: Homo sapiens

<400> SEQUENCE: 158
cauaaaguag aaagcacuac u 21

<210> SEQ ID NO 159
<211> LENGTH: 20
<212> TYPE: RNA
<213> ORGANISM: Homo sapiens

<400> SEQUENCE: 159
uacaguauag augauguacu 20

<210> SEQ ID NO 160
<211> LENGTH: 22
<212> TYPE: RNA
<213> ORGANISM: Homo sapiens

<400> SEQUENCE: 160
cucggcgcgg ggcgcgggcu cc 22

<210> SEQ ID NO 161
<211> LENGTH: 22
<212> TYPE: RNA
<213> ORGANISM: Homo sapiens

<400> SEQUENCE: 161
ugagaacuga auuccauggg uu 22

<210> SEQ ID NO 162
<211> LENGTH: 22
<212> TYPE: RNA
<213> ORGANISM: Homo sapiens

<400> SEQUENCE: 162
ugcccugugg acucaguucu gg 22

<210> SEQ ID NO 163
<211> LENGTH: 22
<212> TYPE: RNA
<213> ORGANISM: Homo sapiens

<400> SEQUENCE: 163
ugagaacuga auuccauagg cu 22

<210> SEQ ID NO 164
<211> LENGTH: 20
<212> TYPE: RNA
<213> ORGANISM: Homo sapiens

<400> SEQUENCE: 164
guguguggaa augcuucugc 20

<210> SEQ ID NO 165
<211> LENGTH: 22
<212> TYPE: RNA
<213> ORGANISM: Homo sapiens

<400> SEQUENCE: 165
gugugcggaa augcuucugc ua 22

<210> SEQ ID NO 166
<211> LENGTH: 22
<212> TYPE: RNA
<213> ORGANISM: Homo sapiens

<400> SEQUENCE: 166
ucagugcacu acagaacuuu gu 22

<210> SEQ ID NO 167
<211> LENGTH: 22
<212> TYPE: RNA
<213> ORGANISM: Homo sapiens

<400> SEQUENCE: 167
ucagugcauc acagaacuuu gu 22

<210> SEQ ID NO 168
<211> LENGTH: 23
<212> TYPE: RNA
<213> ORGANISM: Homo sapiens

<400> SEQUENCE: 168
ucuggcuccg ugucuucacu ccc 23

<210> SEQ ID NO 169
<211> LENGTH: 22
<212> TYPE: RNA
<213> ORGANISM: Homo sapiens

<400> SEQUENCE: 169
ucucccaacc cuuguaccag ug 22

<210> SEQ ID NO 170
<211> LENGTH: 21
<212> TYPE: RNA
<213> ORGANISM: Homo sapiens

<400> SEQUENCE: 170
cuagacugaa gcuccuugag g 21

<210> SEQ ID NO 171
<211> LENGTH: 21
<212> TYPE: RNA
<213> ORGANISM: Homo sapiens

<400> SEQUENCE: 171
ucgaggagcu cacagucuag u 21

<210> SEQ ID NO 172
<211> LENGTH: 18
<212> TYPE: RNA
<213> ORGANISM: Homo sapiens

<400> SEQUENCE: 172
ucgaggagcu cacagucu 18

<210> SEQ ID NO 173
<211> LENGTH: 21
<212> TYPE: RNA
<213> ORGANISM: Homo sapiens

<400> SEQUENCE: 173
ucagugcaug acagaacuug g 21

<210> SEQ ID NO 174
<211> LENGTH: 23
<212> TYPE: RNA
<213> ORGANISM: Homo sapiens

<400> SEQUENCE: 174
agguucugug auacacuccg acu 23

<210> SEQ ID NO 175
<211> LENGTH: 22
<212> TYPE: RNA
<213> ORGANISM: Homo sapiens

<400> SEQUENCE: 175
uugcauaguc acaaaaguga uc 22

<210> SEQ ID NO 176
<211> LENGTH: 22
<212> TYPE: RNA

<213> ORGANISM: Homo sapiens

<400> SEQUENCE: 176
aaaaccgucu aguuacaguu gu 22

<210> SEQ ID NO 177
<211> LENGTH: 22
<212> TYPE: RNA
<213> ORGANISM: Homo sapiens

<400> SEQUENCE: 177
uagguuaucc guguugccuu cg 22

<210> SEQ ID NO 178
<211> LENGTH: 23
<212> TYPE: RNA
<213> ORGANISM: Homo sapiens

<400> SEQUENCE: 178
uuaaugcuaa ucgugauagg ggu 23

<210> SEQ ID NO 179
<211> LENGTH: 22
<212> TYPE: RNA
<213> ORGANISM: Homo sapiens

<400> SEQUENCE: 179
uagcagcaca uaaugguuug ug 22

<210> SEQ ID NO 180
<211> LENGTH: 22
<212> TYPE: RNA
<213> ORGANISM: Homo sapiens

<400> SEQUENCE: 180
uagcagcaca ucaugguuua ca 22

<210> SEQ ID NO 181
<211> LENGTH: 22
<212> TYPE: RNA
<213> ORGANISM: Homo sapiens

<400> SEQUENCE: 181
acauacuucu uuauaugccc au 22

<210> SEQ ID NO 182
<211> LENGTH: 22
<212> TYPE: RNA
<213> ORGANISM: Homo sapiens

<400> SEQUENCE: 182
uagcagcacg uaaauauugg cg 22

<210> SEQ ID NO 183
<211> LENGTH: 22
<212> TYPE: RNA
<213> ORGANISM: Homo sapiens

<400> SEQUENCE: 183
accacugacc guugacugua cc 22

<210> SEQ ID NO 184
<211> LENGTH: 22

<212> TYPE: RNA
<213> ORGANISM: Homo sapiens

<400> SEQUENCE: 184
accaucgacc guugauugua cc 22

<210> SEQ ID NO 185
<211> LENGTH: 23
<212> TYPE: RNA
<213> ORGANISM: Homo sapiens

<400> SEQUENCE: 185
aacauucaac gcugucggug agu 23

<210> SEQ ID NO 186
<211> LENGTH: 20
<212> TYPE: RNA
<213> ORGANISM: Homo sapiens

<400> SEQUENCE: 186
cucacugauc aaugaaugca 20

<210> SEQ ID NO 187
<211> LENGTH: 23
<212> TYPE: RNA
<213> ORGANISM: Homo sapiens

<400> SEQUENCE: 187
aacauucauu gcugucggug ggu 23

<210> SEQ ID NO 188
<211> LENGTH: 22
<212> TYPE: RNA
<213> ORGANISM: Homo sapiens

<400> SEQUENCE: 188
aacauucaac cugucgguga gu 22

<210> SEQ ID NO 189
<211> LENGTH: 21
<212> TYPE: RNA
<213> ORGANISM: Homo sapiens

<400> SEQUENCE: 189
ccaccggggg augaauguca c 21

<210> SEQ ID NO 190
<211> LENGTH: 21
<212> TYPE: RNA
<213> ORGANISM: Homo sapiens

<400> SEQUENCE: 190
ugguucuaga cuugccaacu a 21

<210> SEQ ID NO 191
<211> LENGTH: 24
<212> TYPE: RNA
<213> ORGANISM: Homo sapiens

<400> SEQUENCE: 191
uuuggcaaug guagaacuca cacu 24

<210> SEQ ID NO 192

<211> LENGTH: 18
<212> TYPE: RNA
<213> ORGANISM: Homo sapiens

<400> SEQUENCE: 192
ugaggcagua gauugaau 18

<210> SEQ ID NO 193
<211> LENGTH: 22
<212> TYPE: RNA
<213> ORGANISM: Homo sapiens

<400> SEQUENCE: 193
uauggcacug guagaauuca cu 22

<210> SEQ ID NO 194
<211> LENGTH: 22
<212> TYPE: RNA
<213> ORGANISM: Homo sapiens

<400> SEQUENCE: 194
uggagagaaa ggcaguuccu ga 22

<210> SEQ ID NO 195
<211> LENGTH: 22
<212> TYPE: RNA
<213> ORGANISM: Homo sapiens

<400> SEQUENCE: 195
caaagaauuc uccuuuuggg cu 22

<210> SEQ ID NO 196
<211> LENGTH: 22
<212> TYPE: RNA
<213> ORGANISM: Homo sapiens

<400> SEQUENCE: 196
ucgugucuug uguugcagcc gg 22

<210> SEQ ID NO 197
<211> LENGTH: 21
<212> TYPE: RNA
<213> ORGANISM: Homo sapiens

<400> SEQUENCE: 197
cucccacaug cagggguuugc a 21

<210> SEQ ID NO 198
<211> LENGTH: 21
<212> TYPE: RNA
<213> ORGANISM: Homo sapiens

<400> SEQUENCE: 198
caucccuugc augguggagg g 21

<210> SEQ ID NO 199
<211> LENGTH: 23
<212> TYPE: RNA
<213> ORGANISM: Homo sapiens

<400> SEQUENCE: 199
uaaggugcau cuagugcaga uag 23

-continued

<210> SEQ ID NO 200
<211> LENGTH: 23
<212> TYPE: RNA
<213> ORGANISM: Homo sapiens

<400> SEQUENCE: 200
uaaggugcau cuagugcagu uag 23

<210> SEQ ID NO 201
<211> LENGTH: 21
<212> TYPE: RNA
<213> ORGANISM: Homo sapiens

<400> SEQUENCE: 201
ccggccgccg gcuccgcccc g 21

<210> SEQ ID NO 202
<211> LENGTH: 21
<212> TYPE: RNA
<213> ORGANISM: Homo sapiens

<400> SEQUENCE: 202
cggcggggac ggcgauuggu c 21

<210> SEQ ID NO 203
<211> LENGTH: 22
<212> TYPE: RNA
<213> ORGANISM: Homo sapiens

<400> SEQUENCE: 203
cgcaggggcc gggugcucac cg 22

<210> SEQ ID NO 204
<211> LENGTH: 21
<212> TYPE: RNA
<213> ORGANISM: Homo sapiens

<400> SEQUENCE: 204
cuauauauca aacauauucc u 21

<210> SEQ ID NO 205
<211> LENGTH: 22
<212> TYPE: RNA
<213> ORGANISM: Homo sapiens

<400> SEQUENCE: 205
ugauauguuu gauauauuag gu 22

<210> SEQ ID NO 206
<211> LENGTH: 21
<212> TYPE: RNA
<213> ORGANISM: Homo sapiens

<400> SEQUENCE: 206
ugauauguuu gauauugggu u 21

<210> SEQ ID NO 207
<211> LENGTH: 20
<212> TYPE: RNA
<213> ORGANISM: Homo sapiens

<400> SEQUENCE: 207
gaggcagaag caggaugaca 20

<210> SEQ ID NO 208
<211> LENGTH: 21
<212> TYPE: RNA
<213> ORGANISM: Homo sapiens

<400> SEQUENCE: 208
ccaguccugu gccugccgcc u 21

<210> SEQ ID NO 209
<211> LENGTH: 20
<212> TYPE: RNA
<213> ORGANISM: Homo sapiens

<400> SEQUENCE: 209
ccccagggcg acgcggcggg 20

<210> SEQ ID NO 210
<211> LENGTH: 23
<212> TYPE: RNA
<213> ORGANISM: Homo sapiens

<400> SEQUENCE: 210
caacggaauc ccaaaagcag cug 23

<210> SEQ ID NO 211
<211> LENGTH: 21
<212> TYPE: RNA
<213> ORGANISM: Homo sapiens

<400> SEQUENCE: 211
cugaccuaug aauugacagc c 21

<210> SEQ ID NO 212
<211> LENGTH: 22
<212> TYPE: RNA
<213> ORGANISM: Homo sapiens

<400> SEQUENCE: 212
aacuggccua caaaguccca gu 22

<210> SEQ ID NO 213
<211> LENGTH: 22
<212> TYPE: RNA
<213> ORGANISM: Homo sapiens

<400> SEQUENCE: 213
ugggucuuug cgggcgagau ga 22

<210> SEQ ID NO 214
<211> LENGTH: 22
<212> TYPE: RNA
<213> ORGANISM: Homo sapiens

<400> SEQUENCE: 214
aacuggcccu caaagucccg cu 22

<210> SEQ ID NO 215
<211> LENGTH: 22
<212> TYPE: RNA
<213> ORGANISM: Homo sapiens

<400> SEQUENCE: 215
uguaacagca acuccaugug ga 22

<210> SEQ ID NO 216
<211> LENGTH: 21
<212> TYPE: RNA
<213> ORGANISM: Homo sapiens

<400> SEQUENCE: 216
uagcagcaca gaaauauugg c 21

<210> SEQ ID NO 217
<211> LENGTH: 22
<212> TYPE: RNA
<213> ORGANISM: Homo sapiens

<400> SEQUENCE: 217
cggcaacaag aaacugccug ag 22

<210> SEQ ID NO 218
<211> LENGTH: 22
<212> TYPE: RNA
<213> ORGANISM: Homo sapiens

<400> SEQUENCE: 218
uagguaguuu cauguuguug gg 22

<210> SEQ ID NO 219
<211> LENGTH: 22
<212> TYPE: RNA
<213> ORGANISM: Homo sapiens

<400> SEQUENCE: 219
uagguaguuu ccuguuguug gg 22

<210> SEQ ID NO 220
<211> LENGTH: 22
<212> TYPE: RNA
<213> ORGANISM: Homo sapiens

<400> SEQUENCE: 220
ucaggccagg cacaguggcu ca 22

<210> SEQ ID NO 221
<211> LENGTH: 19
<212> TYPE: RNA
<213> ORGANISM: Homo sapiens

<400> SEQUENCE: 221
accgugcaaa gguagcaua 19

<210> SEQ ID NO 222
<211> LENGTH: 22
<212> TYPE: RNA
<213> ORGANISM: Homo sapiens

<400> SEQUENCE: 222
uucaccaccu ucuccaccca gc 22

<210> SEQ ID NO 223
<211> LENGTH: 23
<212> TYPE: RNA
<213> ORGANISM: Homo sapiens

<400> SEQUENCE: 223
cggguagaga gggcaguggg agg 23

<210> SEQ ID NO 224
<211> LENGTH: 20
<212> TYPE: RNA
<213> ORGANISM: Homo sapiens

<400> SEQUENCE: 224
ccuccugccc uccuugcugu 20

<210> SEQ ID NO 225
<211> LENGTH: 22
<212> TYPE: RNA
<213> ORGANISM: Homo sapiens

<400> SEQUENCE: 225
gguccagagg ggagauaggu uc 22

<210> SEQ ID NO 226
<211> LENGTH: 23
<212> TYPE: RNA
<213> ORGANISM: Homo sapiens

<400> SEQUENCE: 226
cccaguguuu agacuaucug uuc 23

<210> SEQ ID NO 227
<211> LENGTH: 23
<212> TYPE: RNA
<213> ORGANISM: Homo sapiens

<400> SEQUENCE: 227
ugugcaaauc uaugcaaaac uga 23

<210> SEQ ID NO 228
<211> LENGTH: 23
<212> TYPE: RNA
<213> ORGANISM: Homo sapiens

<400> SEQUENCE: 228
ugugcaaauc caugcaaaac uga 23

<210> SEQ ID NO 229
<211> LENGTH: 22
<212> TYPE: RNA
<213> ORGANISM: Homo sapiens

<400> SEQUENCE: 229
uaacacuguc ugguaacgau gu 22

<210> SEQ ID NO 230
<211> LENGTH: 22
<212> TYPE: RNA
<213> ORGANISM: Homo sapiens

<400> SEQUENCE: 230
uaauacugcc ugguaaugau ga 22

<210> SEQ ID NO 231
<211> LENGTH: 23
<212> TYPE: RNA
<213> ORGANISM: Homo sapiens

<400> SEQUENCE: 231
uaauacugcc ggguaaugau gga 23

<210> SEQ ID NO 232
<211> LENGTH: 20
<212> TYPE: RNA
<213> ORGANISM: Homo sapiens

<400> SEQUENCE: 232
agagguauag ggcaugggaa 20

<210> SEQ ID NO 233
<211> LENGTH: 22
<212> TYPE: RNA
<213> ORGANISM: Homo sapiens

<400> SEQUENCE: 233
gugaaauguu uaggaccacu ag 22

<210> SEQ ID NO 234
<211> LENGTH: 25
<212> TYPE: RNA
<213> ORGANISM: Homo sapiens

<400> SEQUENCE: 234
agugguucuu aacaguucaa caguu 25

<210> SEQ ID NO 235
<211> LENGTH: 23
<212> TYPE: RNA
<213> ORGANISM: Homo sapiens

<400> SEQUENCE: 235
guguuaauua aaccucuauu uac 23

<210> SEQ ID NO 236
<211> LENGTH: 22
<212> TYPE: RNA
<213> ORGANISM: Homo sapiens

<400> SEQUENCE: 236
uccuucauuc caccggaguc ug 22

<210> SEQ ID NO 237
<211> LENGTH: 22
<212> TYPE: RNA
<213> ORGANISM: Homo sapiens

<400> SEQUENCE: 237
uggaauguaa ggaagugugu gg 22

<210> SEQ ID NO 238
<211> LENGTH: 22
<212> TYPE: RNA
<213> ORGANISM: Homo sapiens

<400> SEQUENCE: 238
auaagacgag caaaaagcuu gu 22

<210> SEQ ID NO 239
<211> LENGTH: 22
<212> TYPE: RNA
<213> ORGANISM: Homo sapiens

<400> SEQUENCE: 239
aagcuuuuug cucgaauuau gu 22

<210> SEQ ID NO 240
<211> LENGTH: 23
<212> TYPE: RNA
<213> ORGANISM: Homo sapiens

<400> SEQUENCE: 240
uaaagugcuu auagugcagg uag 23

<210> SEQ ID NO 241
<211> LENGTH: 22
<212> TYPE: RNA
<213> ORGANISM: Homo sapiens

<400> SEQUENCE: 241
cugugcgugu gacagcggcu ga 22

<210> SEQ ID NO 242
<211> LENGTH: 22
<212> TYPE: RNA
<213> ORGANISM: Homo sapiens

<400> SEQUENCE: 242
agccccugcc caccgcacac ug 22

<210> SEQ ID NO 243
<211> LENGTH: 22
<212> TYPE: RNA
<213> ORGANISM: Homo sapiens

<400> SEQUENCE: 243
uuggggaaac ggccgcugag ug 22

<210> SEQ ID NO 244
<211> LENGTH: 21
<212> TYPE: RNA
<213> ORGANISM: Homo sapiens

<400> SEQUENCE: 244
auuugugcuu ggcucuguca c 21

<210> SEQ ID NO 245
<211> LENGTH: 21
<212> TYPE: RNA
<213> ORGANISM: Homo sapiens

<400> SEQUENCE: 245
gcagggacag caaaggggug c 21

<210> SEQ ID NO 246
<211> LENGTH: 22
<212> TYPE: RNA
<213> ORGANISM: Homo sapiens

<400> SEQUENCE: 246
uucccuuugu cauccuucgc cu 22

<210> SEQ ID NO 247
<211> LENGTH: 21
<212> TYPE: RNA
<213> ORGANISM: Homo sapiens

<400> SEQUENCE: 247
gguucuuagc auaggagguc u 21

<210> SEQ ID NO 248
<211> LENGTH: 21
<212> TYPE: RNA
<213> ORGANISM: Homo sapiens

<400> SEQUENCE: 248
uguucucuuu gccaaggaca g 21

<210> SEQ ID NO 249
<211> LENGTH: 21
<212> TYPE: RNA
<213> ORGANISM: Homo sapiens

<400> SEQUENCE: 249
uaacagucuc cagucacggc c 21

<210> SEQ ID NO 250
<211> LENGTH: 21
<212> TYPE: RNA
<213> ORGANISM: Homo sapiens

<400> SEQUENCE: 250
augaccuaug aauugacaga c 21

<210> SEQ ID NO 251
<211> LENGTH: 22
<212> TYPE: RNA
<213> ORGANISM: Homo sapiens

<400> SEQUENCE: 251
uagcuuauca gacugauguu ga 22

<210> SEQ ID NO 252
<211> LENGTH: 22
<212> TYPE: RNA
<213> ORGANISM: Homo sapiens

<400> SEQUENCE: 252
uaaucucagc uggcaacugu ga 22

<210> SEQ ID NO 253
<211> LENGTH: 22
<212> TYPE: RNA
<213> ORGANISM: Homo sapiens

<400> SEQUENCE: 253
aaaucucugc aggcaaaugu ga 22

<210> SEQ ID NO 254
<211> LENGTH: 21
<212> TYPE: RNA
<213> ORGANISM: Homo sapiens

<400> SEQUENCE: 254
uugugcuuga ucuaaccaug u 21

<210> SEQ ID NO 255
<211> LENGTH: 22
<212> TYPE: RNA

<213> ORGANISM: Homo sapiens

<400> SEQUENCE: 255
agaguugagu cuggacgucc cg 22

<210> SEQ ID NO 256
<211> LENGTH: 22
<212> TYPE: RNA
<213> ORGANISM: Homo sapiens

<400> SEQUENCE: 256
agaauugugg cuggacaucu gu 22

<210> SEQ ID NO 257
<211> LENGTH: 23
<212> TYPE: RNA
<213> ORGANISM: Homo sapiens

<400> SEQUENCE: 257
agaauugcgu uuggacaauc agu 23

<210> SEQ ID NO 258
<211> LENGTH: 23
<212> TYPE: RNA
<213> ORGANISM: Homo sapiens

<400> SEQUENCE: 258
agcuacauug ucugcugggu uuc 23

<210> SEQ ID NO 259
<211> LENGTH: 22
<212> TYPE: RNA
<213> ORGANISM: Homo sapiens

<400> SEQUENCE: 259
accuggcaua caauguagau uu 22

<210> SEQ ID NO 260
<211> LENGTH: 21
<212> TYPE: RNA
<213> ORGANISM: Homo sapiens

<400> SEQUENCE: 260
agcuacaucu ggcuacuggg u 21

<210> SEQ ID NO 261
<211> LENGTH: 22
<212> TYPE: RNA
<213> ORGANISM: Homo sapiens

<400> SEQUENCE: 261
aagcugccag uugaagaacu gu 22

<210> SEQ ID NO 262
<211> LENGTH: 21
<212> TYPE: RNA
<213> ORGANISM: Homo sapiens

<400> SEQUENCE: 262
caagucacua gugguuccgu u 21

<210> SEQ ID NO 263
<211> LENGTH: 22

<212> TYPE: RNA
<213> ORGANISM: Homo sapiens

<400> SEQUENCE: 263
gagagcagug uguguugccu gg 22

<210> SEQ ID NO 264
<211> LENGTH: 21
<212> TYPE: RNA
<213> ORGANISM: Homo sapiens

<400> SEQUENCE: 264
aucacauugc cagggauuuc c 21

<210> SEQ ID NO 265
<211> LENGTH: 21
<212> TYPE: RNA
<213> ORGANISM: Homo sapiens

<400> SEQUENCE: 265
aucacauugc cagggauuac c 21

<210> SEQ ID NO 266
<211> LENGTH: 22
<212> TYPE: RNA
<213> ORGANISM: Homo sapiens

<400> SEQUENCE: 266
aucacauugc cagugauuac cc 22

<210> SEQ ID NO 267
<211> LENGTH: 22
<212> TYPE: RNA
<213> ORGANISM: Homo sapiens

<400> SEQUENCE: 267
uggcucaguu cagcaggaac ag 22

<210> SEQ ID NO 268
<211> LENGTH: 22
<212> TYPE: RNA
<213> ORGANISM: Homo sapiens

<400> SEQUENCE: 268
cauugcacuu gucucggucu ga 22

<210> SEQ ID NO 269
<211> LENGTH: 21
<212> TYPE: RNA
<213> ORGANISM: Homo sapiens

<400> SEQUENCE: 269
aggcggagac uugggcaauu g 21

<210> SEQ ID NO 270
<211> LENGTH: 23
<212> TYPE: RNA
<213> ORGANISM: Homo sapiens

<400> SEQUENCE: 270
caggcaguga cuguucagac guc 23

<210> SEQ ID NO 271

```
<211> LENGTH: 22
<212> TYPE: RNA
<213> ORGANISM: Homo sapiens

<400> SEQUENCE: 271

uucaaguaau ccaggauagg cu                                           22

<210> SEQ ID NO 272
<211> LENGTH: 21
<212> TYPE: RNA
<213> ORGANISM: Homo sapiens

<400> SEQUENCE: 272

uucaaguaau ucaggauagg u                                            21

<210> SEQ ID NO 273
<211> LENGTH: 21
<212> TYPE: RNA
<213> ORGANISM: Homo sapiens

<400> SEQUENCE: 273

uucacagugg cuaaguuccg c                                            21

<210> SEQ ID NO 274
<211> LENGTH: 21
<212> TYPE: RNA
<213> ORGANISM: Homo sapiens

<400> SEQUENCE: 274

uucacagugg cuaaguucug c                                            21

<210> SEQ ID NO 275
<211> LENGTH: 22
<212> TYPE: RNA
<213> ORGANISM: Homo sapiens

<400> SEQUENCE: 275

cacuagauug ugagcuccug ga                                           22

<210> SEQ ID NO 276
<211> LENGTH: 22
<212> TYPE: RNA
<213> ORGANISM: Homo sapiens

<400> SEQUENCE: 276

aaggagcuca cagucuauug ag                                           22

<210> SEQ ID NO 277
<211> LENGTH: 22
<212> TYPE: RNA
<213> ORGANISM: Homo sapiens

<400> SEQUENCE: 277

gaggguuggg uggaggcucu cc                                           22

<210> SEQ ID NO 278
<211> LENGTH: 21
<212> TYPE: RNA
<213> ORGANISM: Homo sapiens

<400> SEQUENCE: 278

agggcccccc cucaauccug u                                            21
```

<210> SEQ ID NO 279
<211> LENGTH: 21
<212> TYPE: RNA
<213> ORGANISM: Homo sapiens

<400> SEQUENCE: 279
auguaugugu gcaugugcau g 21

<210> SEQ ID NO 280
<211> LENGTH: 24
<212> TYPE: RNA
<213> ORGANISM: Homo sapiens

<400> SEQUENCE: 280
agcagaagca gggagguucu ccca 24

<210> SEQ ID NO 281
<211> LENGTH: 22
<212> TYPE: RNA
<213> ORGANISM: Homo sapiens

<400> SEQUENCE: 281
uaugugggau gguaaaccgc uu 22

<210> SEQ ID NO 282
<211> LENGTH: 22
<212> TYPE: RNA
<213> ORGANISM: Homo sapiens

<400> SEQUENCE: 282
ugguuuaccg ucccacauac au 22

<210> SEQ ID NO 283
<211> LENGTH: 22
<212> TYPE: RNA
<213> ORGANISM: Homo sapiens

<400> SEQUENCE: 283
uagcaccauc ugaaaucggu ua 22

<210> SEQ ID NO 284
<211> LENGTH: 23
<212> TYPE: RNA
<213> ORGANISM: Homo sapiens

<400> SEQUENCE: 284
uagcaccauu ugaaaucagu guu 23

<210> SEQ ID NO 285
<211> LENGTH: 22
<212> TYPE: RNA
<213> ORGANISM: Homo sapiens

<400> SEQUENCE: 285
uagcaccauu ugaaaucggu ua 22

<210> SEQ ID NO 286
<211> LENGTH: 22
<212> TYPE: RNA
<213> ORGANISM: Homo sapiens

<400> SEQUENCE: 286
uauacaaggg cagacucucu cu 22

<210> SEQ ID NO 287
<211> LENGTH: 23
<212> TYPE: RNA
<213> ORGANISM: Homo sapiens

<400> SEQUENCE: 287
cagugcaaua guauugucaa agc 23

<210> SEQ ID NO 288
<211> LENGTH: 22
<212> TYPE: RNA
<213> ORGANISM: Homo sapiens

<400> SEQUENCE: 288
gcucugacuu uauugcacua cu 22

<210> SEQ ID NO 289
<211> LENGTH: 23
<212> TYPE: RNA
<213> ORGANISM: Homo sapiens

<400> SEQUENCE: 289
cagugcaaug auauugucaa agc 23

<210> SEQ ID NO 290
<211> LENGTH: 22
<212> TYPE: RNA
<213> ORGANISM: Homo sapiens

<400> SEQUENCE: 290
gcucugacga gguugcacua cu 22

<210> SEQ ID NO 291
<211> LENGTH: 23
<212> TYPE: RNA
<213> ORGANISM: Homo sapiens

<400> SEQUENCE: 291
uaagugcuuc cauguuuugg uga 23

<210> SEQ ID NO 292
<211> LENGTH: 23
<212> TYPE: RNA
<213> ORGANISM: Homo sapiens

<400> SEQUENCE: 292
acuuaaacgu ggauguacuu gcu 23

<210> SEQ ID NO 293
<211> LENGTH: 23
<212> TYPE: RNA
<213> ORGANISM: Homo sapiens

<400> SEQUENCE: 293
uaagugcuuc cauguuuuag uag 23

<210> SEQ ID NO 294
<211> LENGTH: 23
<212> TYPE: RNA
<213> ORGANISM: Homo sapiens

<400> SEQUENCE: 294
uaagugcuuc cauguuucag ugg 23

-continued

<210> SEQ ID NO 295
<211> LENGTH: 23
<212> TYPE: RNA
<213> ORGANISM: Homo sapiens

<400> SEQUENCE: 295
uaagugcuuc cauguuugag ugu 23

<210> SEQ ID NO 296
<211> LENGTH: 17
<212> TYPE: RNA
<213> ORGANISM: Homo sapiens

<400> SEQUENCE: 296
uaagugcuuc caugcuu 17

<210> SEQ ID NO 297
<211> LENGTH: 17
<212> TYPE: RNA
<213> ORGANISM: Homo sapiens

<400> SEQUENCE: 297
uaauugcuuc cauguuu 17

<210> SEQ ID NO 298
<211> LENGTH: 23
<212> TYPE: RNA
<213> ORGANISM: Homo sapiens

<400> SEQUENCE: 298
ucagcaccag gauauuguug gag 23

<210> SEQ ID NO 299
<211> LENGTH: 23
<212> TYPE: RNA
<213> ORGANISM: Homo sapiens

<400> SEQUENCE: 299
ucaacaaaau cacugaugcu gga 23

<210> SEQ ID NO 300
<211> LENGTH: 22
<212> TYPE: RNA
<213> ORGANISM: Homo sapiens

<400> SEQUENCE: 300
gauaucagcu caguaggcac cg 22

<210> SEQ ID NO 301
<211> LENGTH: 22
<212> TYPE: RNA
<213> ORGANISM: Homo sapiens

<400> SEQUENCE: 301
cuuucagucg gauguuugca gc 22

<210> SEQ ID NO 302
<211> LENGTH: 22
<212> TYPE: RNA
<213> ORGANISM: Homo sapiens

<400> SEQUENCE: 302

-continued uguaaacauc cucgacugga ag 22

<210> SEQ ID NO 303
<211> LENGTH: 22
<212> TYPE: RNA
<213> ORGANISM: Homo sapiens

<400> SEQUENCE: 303
uguaaacauc cuacacucag cu 22

<210> SEQ ID NO 304
<211> LENGTH: 23
<212> TYPE: RNA
<213> ORGANISM: Homo sapiens

<400> SEQUENCE: 304
uguaaacauc cuacacucuc agc 23

<210> SEQ ID NO 305
<211> LENGTH: 22
<212> TYPE: RNA
<213> ORGANISM: Homo sapiens

<400> SEQUENCE: 305
uguaaacauc cccgacugga ag 22

<210> SEQ ID NO 306
<211> LENGTH: 22
<212> TYPE: RNA
<213> ORGANISM: Homo sapiens

<400> SEQUENCE: 306
cuuucagucg gauguuuaca gc 22

<210> SEQ ID NO 307
<211> LENGTH: 22
<212> TYPE: RNA
<213> ORGANISM: Homo sapiens

<400> SEQUENCE: 307
uguaaacauc cuugacugga ag 22

<210> SEQ ID NO 308
<211> LENGTH: 23
<212> TYPE: RNA
<213> ORGANISM: Homo sapiens

<400> SEQUENCE: 308
aucagggcuu guggaauggg aag 23

<210> SEQ ID NO 309
<211> LENGTH: 21
<212> TYPE: RNA
<213> ORGANISM: Homo sapiens

<400> SEQUENCE: 309
gcugcaccgg agacugggua a 21

<210> SEQ ID NO 310
<211> LENGTH: 23
<212> TYPE: RNA
<213> ORGANISM: Homo sapiens

<400> SEQUENCE: 310
ucgaggacug guggaagggc cuu 23

<210> SEQ ID NO 311
<211> LENGTH: 23
<212> TYPE: RNA
<213> ORGANISM: Homo sapiens

<400> SEQUENCE: 311
cugacugaau agguaggguc auu 23

<210> SEQ ID NO 312
<211> LENGTH: 22
<212> TYPE: RNA
<213> ORGANISM: Homo sapiens

<400> SEQUENCE: 312
agcuuuuggg aauucaggua gu 22

<210> SEQ ID NO 313
<211> LENGTH: 21
<212> TYPE: RNA
<213> ORGANISM: Homo sapiens

<400> SEQUENCE: 313
accugaauua ccaaaagcuu u 21

<210> SEQ ID NO 314
<211> LENGTH: 22
<212> TYPE: RNA
<213> ORGANISM: Homo sapiens

<400> SEQUENCE: 314
auauaccugu ucggucucuu ua 22

<210> SEQ ID NO 315
<211> LENGTH: 22
<212> TYPE: RNA
<213> ORGANISM: Homo sapiens

<400> SEQUENCE: 315
aggggaccaa agagauauau ag 22

<210> SEQ ID NO 316
<211> LENGTH: 24
<212> TYPE: RNA
<213> ORGANISM: Homo sapiens

<400> SEQUENCE: 316
gguugggcag ugaggagggu guga 24

<210> SEQ ID NO 317
<211> LENGTH: 21
<212> TYPE: RNA
<213> ORGANISM: Homo sapiens

<400> SEQUENCE: 317
ugaggagauc gucgagguug g 21

<210> SEQ ID NO 318
<211> LENGTH: 21
<212> TYPE: RNA
<213> ORGANISM: Homo sapiens

<400> SEQUENCE: 318 ggugggcaa ugggaucagg u 21

<210> SEQ ID NO 319
<211> LENGTH: 22
<212> TYPE: RNA
<213> ORGANISM: Homo sapiens

<400> SEQUENCE: 319
aagggcuucc ucucugcagg ac 22

<210> SEQ ID NO 320
<211> LENGTH: 21
<212> TYPE: RNA
<213> ORGANISM: Homo sapiens

<400> SEQUENCE: 320
aggcaagaug cuggcauagc u 21

<210> SEQ ID NO 321
<211> LENGTH: 23
<212> TYPE: RNA
<213> ORGANISM: Homo sapiens

<400> SEQUENCE: 321
cugauaagaa cagaggccca gau 23

<210> SEQ ID NO 322
<211> LENGTH: 22
<212> TYPE: RNA
<213> ORGANISM: Homo sapiens

<400> SEQUENCE: 322
ugugacuuua agggaaaugg cg 22

<210> SEQ ID NO 323
<211> LENGTH: 17
<212> TYPE: RNA
<213> ORGANISM: Homo sapiens

<400> SEQUENCE: 323
gaguucuaca gucagac 17

<210> SEQ ID NO 324
<211> LENGTH: 22
<212> TYPE: RNA
<213> ORGANISM: Homo sapiens

<400> SEQUENCE: 324
agaaggggug aaauuuaaac gu 22

<210> SEQ ID NO 325
<211> LENGTH: 19
<212> TYPE: RNA
<213> ORGANISM: Homo sapiens

<400> SEQUENCE: 325
uggggcggag cuuccggag 19

<210> SEQ ID NO 326
<211> LENGTH: 22
<212> TYPE: RNA
<213> ORGANISM: Homo sapiens

<400> SEQUENCE: 326
uggggcggag cuuccggagg cc 22

<210> SEQ ID NO 327
<211> LENGTH: 25
<212> TYPE: RNA
<213> ORGANISM: Homo sapiens

<400> SEQUENCE: 327
cuuccagacg cuccgcccca cgucg 25

<210> SEQ ID NO 328
<211> LENGTH: 17
<212> TYPE: RNA
<213> ORGANISM: Homo sapiens

<400> SEQUENCE: 328
gcuucuguag uguaguc 17

<210> SEQ ID NO 329
<211> LENGTH: 23
<212> TYPE: RNA
<213> ORGANISM: Homo sapiens

<400> SEQUENCE: 329
agaagaaggc ggucggucug cgg 23

<210> SEQ ID NO 330
<211> LENGTH: 23
<212> TYPE: RNA
<213> ORGANISM: Homo sapiens

<400> SEQUENCE: 330
uguggaaggu agacggccag aga 23

<210> SEQ ID NO 331
<211> LENGTH: 23
<212> TYPE: RNA
<213> ORGANISM: Homo sapiens

<400> SEQUENCE: 331
ucugggaggu uguagcagug gaa 23

<210> SEQ ID NO 332
<211> LENGTH: 17
<212> TYPE: RNA
<213> ORGANISM: Homo sapiens

<400> SEQUENCE: 332
cgcgccgggc ccggguu 17

<210> SEQ ID NO 333
<211> LENGTH: 18
<212> TYPE: RNA
<213> ORGANISM: Homo sapiens

<400> SEQUENCE: 333
cggggcggca ggggccuc 18

<210> SEQ ID NO 334
<211> LENGTH: 22
<212> TYPE: RNA

```
<213> ORGANISM: Homo sapiens

<400> SEQUENCE: 334

uggaagggag aagagcuuua au                                          22

<210> SEQ ID NO 335
<211> LENGTH: 22
<212> TYPE: RNA
<213> ORGANISM: Homo sapiens

<400> SEQUENCE: 335

aaaagcuggg uugagagggc ga                                          22

<210> SEQ ID NO 336
<211> LENGTH: 22
<212> TYPE: RNA
<213> ORGANISM: Homo sapiens

<400> SEQUENCE: 336

aaaagcuggg uugagagggc aa                                          22

<210> SEQ ID NO 337
<211> LENGTH: 20
<212> TYPE: RNA
<213> ORGANISM: Homo sapiens

<400> SEQUENCE: 337

aaaagcuggg uugagagggu                                             20

<210> SEQ ID NO 338
<211> LENGTH: 19
<212> TYPE: RNA
<213> ORGANISM: Homo sapiens

<400> SEQUENCE: 338

aaaagcuggg uugagagga                                              19

<210> SEQ ID NO 339
<211> LENGTH: 18
<212> TYPE: RNA
<213> ORGANISM: Homo sapiens

<400> SEQUENCE: 339

aaagcugggu ugagaagg                                               18

<210> SEQ ID NO 340
<211> LENGTH: 21
<212> TYPE: RNA
<213> ORGANISM: Homo sapiens

<400> SEQUENCE: 340

cacauuacac ggucgaccuc u                                           21

<210> SEQ ID NO 341
<211> LENGTH: 22
<212> TYPE: RNA
<213> ORGANISM: Homo sapiens

<400> SEQUENCE: 341

aggugguccg uggcgcguuc gc                                          22

<210> SEQ ID NO 342
<211> LENGTH: 22
```

<212> TYPE: RNA
<213> ORGANISM: Homo sapiens

<400> SEQUENCE: 342
cccaauacac ggucgaccuc uu 22

<210> SEQ ID NO 343
<211> LENGTH: 23
<212> TYPE: RNA
<213> ORGANISM: Homo sapiens

<400> SEQUENCE: 343
agguuguccg uggugaguuc gca 23

<210> SEQ ID NO 344
<211> LENGTH: 20
<212> TYPE: RNA
<213> ORGANISM: Homo sapiens

<400> SEQUENCE: 344
acugccccag gugcugcugg 20

<210> SEQ ID NO 345
<211> LENGTH: 23
<212> TYPE: RNA
<213> ORGANISM: Homo sapiens

<400> SEQUENCE: 345
cgcauccccu agggcauugg ugu 23

<210> SEQ ID NO 346
<211> LENGTH: 23
<212> TYPE: RNA
<213> ORGANISM: Homo sapiens

<400> SEQUENCE: 346
ccuaguaggu guccaguaag ugu 23

<210> SEQ ID NO 347
<211> LENGTH: 22
<212> TYPE: RNA
<213> ORGANISM: Homo sapiens

<400> SEQUENCE: 347
uauugcacau uacuaaguug ca 22

<210> SEQ ID NO 348
<211> LENGTH: 20
<212> TYPE: RNA
<213> ORGANISM: Homo sapiens

<400> SEQUENCE: 348
ccucugggcc cuuccuccag 20

<210> SEQ ID NO 349
<211> LENGTH: 22
<212> TYPE: RNA
<213> ORGANISM: Homo sapiens

<400> SEQUENCE: 349
cuggcccucu cugcccuucc gu 22

<210> SEQ ID NO 350

-continued

<211> LENGTH: 23
<212> TYPE: RNA
<213> ORGANISM: Homo sapiens

<400> SEQUENCE: 350 ggggggcag gaggggcuca ggg 23

<210> SEQ ID NO 351
<211> LENGTH: 22
<212> TYPE: RNA
<213> ORGANISM: Homo sapiens

<400> SEQUENCE: 351
aacacaccug guuaaccucu uu 22

<210> SEQ ID NO 352
<211> LENGTH: 23
<212> TYPE: RNA
<213> ORGANISM: Homo sapiens

<400> SEQUENCE: 352
gagguuuucu ggguuucugu uuc 23

<210> SEQ ID NO 353
<211> LENGTH: 23
<212> TYPE: RNA
<213> ORGANISM: Homo sapiens

<400> SEQUENCE: 353
gcaaagcaca cggccugcag aga 23

<210> SEQ ID NO 354
<211> LENGTH: 22
<212> TYPE: RNA
<213> ORGANISM: Homo sapiens

<400> SEQUENCE: 354
ucucugggcc ugugucuuag gc 22

<210> SEQ ID NO 355
<211> LENGTH: 21
<212> TYPE: RNA
<213> ORGANISM: Homo sapiens

<400> SEQUENCE: 355
gccccugggc cuauccuaga a 21

<210> SEQ ID NO 356
<211> LENGTH: 22
<212> TYPE: RNA
<213> ORGANISM: Homo sapiens

<400> SEQUENCE: 356
cuagguaugg ucccagggau cc 22

<210> SEQ ID NO 357
<211> LENGTH: 23
<212> TYPE: RNA
<213> ORGANISM: Homo sapiens

<400> SEQUENCE: 357
ucaagagcaa uaacgaaaaa ugu 23

<210> SEQ ID NO 358
<211> LENGTH: 22
<212> TYPE: RNA
<213> ORGANISM: Homo sapiens

<400> SEQUENCE: 358
cuccuauaug augccuuucu uc 22

<210> SEQ ID NO 359
<211> LENGTH: 21
<212> TYPE: RNA
<213> ORGANISM: Homo sapiens

<400> SEQUENCE: 359
gaacggcuuc auacaggagu u 21

<210> SEQ ID NO 360
<211> LENGTH: 22
<212> TYPE: RNA
<213> ORGANISM: Homo sapiens

<400> SEQUENCE: 360
aacaauaucc uggugcugag ug 22

<210> SEQ ID NO 361
<211> LENGTH: 23
<212> TYPE: RNA
<213> ORGANISM: Homo sapiens

<400> SEQUENCE: 361
ugagcgccuc gacgacagag ccg 23

<210> SEQ ID NO 362
<211> LENGTH: 23
<212> TYPE: RNA
<213> ORGANISM: Homo sapiens

<400> SEQUENCE: 362
ucccuguccu ccaggagcuc acg 23

<210> SEQ ID NO 363
<211> LENGTH: 21
<212> TYPE: RNA
<213> ORGANISM: Homo sapiens

<400> SEQUENCE: 363
gugcauugua guugcauugc a 21

<210> SEQ ID NO 364
<211> LENGTH: 20
<212> TYPE: RNA
<213> ORGANISM: Homo sapiens

<400> SEQUENCE: 364
gugcauugcu guugcauugc 20

<210> SEQ ID NO 365
<211> LENGTH: 22
<212> TYPE: RNA
<213> ORGANISM: Homo sapiens

<400> SEQUENCE: 365
uuauaaagca augagacuga uu 22

<210> SEQ ID NO 366
<211> LENGTH: 23
<212> TYPE: RNA
<213> ORGANISM: Homo sapiens

<400> SEQUENCE: 366
ucucacacag aaaucgcacc cgu 23

<210> SEQ ID NO 367
<211> LENGTH: 21
<212> TYPE: RNA
<213> ORGANISM: Homo sapiens

<400> SEQUENCE: 367
aggggugcua ucugugauug a 21

<210> SEQ ID NO 368
<211> LENGTH: 22
<212> TYPE: RNA
<213> ORGANISM: Homo sapiens

<400> SEQUENCE: 368
gcccugaacg aggggucugg ag 22

<210> SEQ ID NO 369
<211> LENGTH: 22
<212> TYPE: RNA
<213> ORGANISM: Homo sapiens

<400> SEQUENCE: 369
gcugacuccu aguccagggc uc 22

<210> SEQ ID NO 370
<211> LENGTH: 23
<212> TYPE: RNA
<213> ORGANISM: Homo sapiens

<400> SEQUENCE: 370
ugucugcccg caugccugcc ucu 23

<210> SEQ ID NO 371
<211> LENGTH: 22
<212> TYPE: RNA
<213> ORGANISM: Homo sapiens

<400> SEQUENCE: 371
caaucacuaa cuccacugcc au 22

<210> SEQ ID NO 372
<211> LENGTH: 22
<212> TYPE: RNA
<213> ORGANISM: Homo sapiens

<400> SEQUENCE: 372
aaucacuaac cacacggcca gg 22

<210> SEQ ID NO 373
<211> LENGTH: 23
<212> TYPE: RNA
<213> ORGANISM: Homo sapiens

<400> SEQUENCE: 373
aggcagugua guuagcugau ugc 23

<210> SEQ ID NO 374
<211> LENGTH: 23
<212> TYPE: RNA
<213> ORGANISM: Homo sapiens

<400> SEQUENCE: 374
ccuccguguu accuguccuc uag 23

<210> SEQ ID NO 375
<211> LENGTH: 23
<212> TYPE: RNA
<213> ORGANISM: Homo sapiens

<400> SEQUENCE: 375
ugaggaugga uagcaaggaa gcc 23

<210> SEQ ID NO 376
<211> LENGTH: 24
<212> TYPE: RNA
<213> ORGANISM: Homo sapiens

<400> SEQUENCE: 376
acaaaaaaaa aagcccaacc cuuc 24

<210> SEQ ID NO 377
<211> LENGTH: 22
<212> TYPE: RNA
<213> ORGANISM: Homo sapiens

<400> SEQUENCE: 377
uguuguacuu uuuuuuuugu uc 22

<210> SEQ ID NO 378
<211> LENGTH: 23
<212> TYPE: RNA
<213> ORGANISM: Homo sapiens

<400> SEQUENCE: 378
ucccccaggu gugauucuga uuu 23

<210> SEQ ID NO 379
<211> LENGTH: 23
<212> TYPE: RNA
<213> ORGANISM: Homo sapiens

<400> SEQUENCE: 379
uagccuucag aucuuggugu uuu 23

<210> SEQ ID NO 380
<211> LENGTH: 23
<212> TYPE: RNA
<213> ORGANISM: Homo sapiens

<400> SEQUENCE: 380
ccacuuggau cugaaggcug ccc 23

<210> SEQ ID NO 381
<211> LENGTH: 21
<212> TYPE: RNA
<213> ORGANISM: Homo sapiens

<400> SEQUENCE: 381
ucucucggcu ccucgcggcu c 21

<210> SEQ ID NO 382
<211> LENGTH: 22
<212> TYPE: RNA
<213> ORGANISM: Homo sapiens

<400> SEQUENCE: 382
uuaucagaau cuccaggggu ac 22

<210> SEQ ID NO 383
<211> LENGTH: 22
<212> TYPE: RNA
<213> ORGANISM: Homo sapiens

<400> SEQUENCE: 383
aacacaccua uucaaggauu ca 22

<210> SEQ ID NO 384
<211> LENGTH: 24
<212> TYPE: RNA
<213> ORGANISM: Homo sapiens

<400> SEQUENCE: 384
aauccuugga accuaggugu gagu 24

<210> SEQ ID NO 385
<211> LENGTH: 22
<212> TYPE: RNA
<213> ORGANISM: Homo sapiens

<400> SEQUENCE: 385
aauugcacgg uauccaucug ua 22

<210> SEQ ID NO 386
<211> LENGTH: 22
<212> TYPE: RNA
<213> ORGANISM: Homo sapiens

<400> SEQUENCE: 386
cggguggauc acgaugcaau uu 22

<210> SEQ ID NO 387
<211> LENGTH: 22
<212> TYPE: RNA
<213> ORGANISM: Homo sapiens

<400> SEQUENCE: 387
uaaugccccu aaaaauccuu au 22

<210> SEQ ID NO 388
<211> LENGTH: 22
<212> TYPE: RNA
<213> ORGANISM: Homo sapiens

<400> SEQUENCE: 388
agggacuuuc aggggcagcu gu 22

<210> SEQ ID NO 389
<211> LENGTH: 22
<212> TYPE: RNA
<213> ORGANISM: Homo sapiens

<400> SEQUENCE: 389
aauugcacuu uagcaauggu ga 22

<210> SEQ ID NO 390
<211> LENGTH: 23
<212> TYPE: RNA
<213> ORGANISM: Homo sapiens

<400> SEQUENCE: 390
accuggaccc agcguagaca aag 23

<210> SEQ ID NO 391
<211> LENGTH: 21
<212> TYPE: RNA
<213> ORGANISM: Homo sapiens

<400> SEQUENCE: 391
aauaauacau gguugaucuu u 21

<210> SEQ ID NO 392
<211> LENGTH: 22
<212> TYPE: RNA
<213> ORGANISM: Homo sapiens

<400> SEQUENCE: 392
agaucgaccg uguuauauuc gc 22

<210> SEQ ID NO 393
<211> LENGTH: 22
<212> TYPE: RNA
<213> ORGANISM: Homo sapiens

<400> SEQUENCE: 393
gccugcuggg guggaaccug gu 22

<210> SEQ ID NO 394
<211> LENGTH: 22
<212> TYPE: RNA
<213> ORGANISM: Homo sapiens

<400> SEQUENCE: 394
caggucacgu cucugcaguu ac 22

<210> SEQ ID NO 395
<211> LENGTH: 20
<212> TYPE: RNA
<213> ORGANISM: Homo sapiens

<400> SEQUENCE: 395
acucaaacug ugggggcacu 20

<210> SEQ ID NO 396
<211> LENGTH: 22
<212> TYPE: RNA
<213> ORGANISM: Homo sapiens

<400> SEQUENCE: 396
acucaaaaga uggcggcacu uu 22

<210> SEQ ID NO 397
<211> LENGTH: 23
<212> TYPE: RNA
<213> ORGANISM: Homo sapiens

<400> SEQUENCE: 397
aaagugcugc gacauuugag cgu 23

<210> SEQ ID NO 398
<211> LENGTH: 23
<212> TYPE: RNA
<213> ORGANISM: Homo sapiens

<400> SEQUENCE: 398
gaagugcuuc gauuuugggg ugu 23

<210> SEQ ID NO 399
<211> LENGTH: 22
<212> TYPE: RNA
<213> ORGANISM: Homo sapiens

<400> SEQUENCE: 399
cuuaucagau uguauuguaa uu 22

<210> SEQ ID NO 400
<211> LENGTH: 22
<212> TYPE: RNA
<213> ORGANISM: Homo sapiens

<400> SEQUENCE: 400
uuauaauaca accugauaag ug 22

<210> SEQ ID NO 401
<211> LENGTH: 22
<212> TYPE: RNA
<213> ORGANISM: Homo sapiens

<400> SEQUENCE: 401
auauaauaca accugcuaag ug 22

<210> SEQ ID NO 402
<211> LENGTH: 22
<212> TYPE: RNA
<213> ORGANISM: Homo sapiens

<400> SEQUENCE: 402
auaauacaac cugcuaagug cu 22

<210> SEQ ID NO 403
<211> LENGTH: 22
<212> TYPE: RNA
<213> ORGANISM: Homo sapiens

<400> SEQUENCE: 403
uuuguucguu cggcucgcgu ga 22

<210> SEQ ID NO 404
<211> LENGTH: 21
<212> TYPE: RNA
<213> ORGANISM: Homo sapiens

<400> SEQUENCE: 404
gguagauuuu ccuucuaugg u 21

<210> SEQ ID NO 405
<211> LENGTH: 21
<212> TYPE: RNA
<213> ORGANISM: Homo sapiens

<400> SEQUENCE: 405
aucauagagg aaaauccacg u 21

<210> SEQ ID NO 406
<211> LENGTH: 22
<212> TYPE: RNA
<213> ORGANISM: Homo sapiens

<400> SEQUENCE: 406
aucauagagg aaaauccaug uu 22

<210> SEQ ID NO 407
<211> LENGTH: 21
<212> TYPE: RNA
<213> ORGANISM: Homo sapiens

<400> SEQUENCE: 407
aacauagagg aaauuccacg u 21

<210> SEQ ID NO 408
<211> LENGTH: 21
<212> TYPE: RNA
<213> ORGANISM: Homo sapiens

<400> SEQUENCE: 408
gguggauauu ccuucuaugu u 21

<210> SEQ ID NO 409
<211> LENGTH: 22
<212> TYPE: RNA
<213> ORGANISM: Homo sapiens

<400> SEQUENCE: 409
aucacacaaa ggcaacuuuu gu 22

<210> SEQ ID NO 410
<211> LENGTH: 19
<212> TYPE: RNA
<213> ORGANISM: Homo sapiens

<400> SEQUENCE: 410
acuggacuug gaggcagaa 19

<210> SEQ ID NO 411
<211> LENGTH: 25
<212> TYPE: RNA
<213> ORGANISM: Homo sapiens

<400> SEQUENCE: 411
acuggacuug gagucagaag agugg 25

<210> SEQ ID NO 412
<211> LENGTH: 20
<212> TYPE: RNA
<213> ORGANISM: Homo sapiens

<400> SEQUENCE: 412
acuggacuug gagucagaaa 20

<210> SEQ ID NO 413
<211> LENGTH: 19
<212> TYPE: RNA

<213> ORGANISM: Homo sapiens

<400> SEQUENCE: 413
acuggacuug gagucagga 19

<210> SEQ ID NO 414
<211> LENGTH: 20
<212> TYPE: RNA
<213> ORGANISM: Homo sapiens

<400> SEQUENCE: 414
acuggacuug gagccagaag 20

<210> SEQ ID NO 415
<211> LENGTH: 20
<212> TYPE: RNA
<213> ORGANISM: Homo sapiens

<400> SEQUENCE: 415
acugggcuug gagucagaag 20

<210> SEQ ID NO 416
<211> LENGTH: 21
<212> TYPE: RNA
<213> ORGANISM: Homo sapiens

<400> SEQUENCE: 416
acuggacuug gugucagaug g 21

<210> SEQ ID NO 417
<211> LENGTH: 21
<212> TYPE: RNA
<213> ORGANISM: Homo sapiens

<400> SEQUENCE: 417
acuggacuag gagucagaag g 21

<210> SEQ ID NO 418
<211> LENGTH: 21
<212> TYPE: RNA
<213> ORGANISM: Homo sapiens

<400> SEQUENCE: 418
ugguagacua uggaacguag g 21

<210> SEQ ID NO 419
<211> LENGTH: 22
<212> TYPE: RNA
<213> ORGANISM: Homo sapiens

<400> SEQUENCE: 419
uauguaauau gguccacauc uu 22

<210> SEQ ID NO 420
<211> LENGTH: 22
<212> TYPE: RNA
<213> ORGANISM: Homo sapiens

<400> SEQUENCE: 420
uauacaaggg caagcucucu gu 22

<210> SEQ ID NO 421
<211> LENGTH: 22

<212> TYPE: RNA
<213> ORGANISM: Homo sapiens

<400> SEQUENCE: 421
agcgagguug cccuuuguau au 22

<210> SEQ ID NO 422
<211> LENGTH: 21
<212> TYPE: RNA
<213> ORGANISM: Homo sapiens

<400> SEQUENCE: 422
aaucauucac ggacaacacu u 21

<210> SEQ ID NO 423
<211> LENGTH: 22
<212> TYPE: RNA
<213> ORGANISM: Homo sapiens

<400> SEQUENCE: 423
gaaguuguuc gugguggauu cg 22

<210> SEQ ID NO 424
<211> LENGTH: 22
<212> TYPE: RNA
<213> ORGANISM: Homo sapiens

<400> SEQUENCE: 424
agaucagaag gugauugugg cu 22

<210> SEQ ID NO 425
<211> LENGTH: 20
<212> TYPE: RNA
<213> ORGANISM: Homo sapiens

<400> SEQUENCE: 425
auuccuagaa auuguucaua 20

<210> SEQ ID NO 426
<211> LENGTH: 26
<212> TYPE: RNA
<213> ORGANISM: Homo sapiens

<400> SEQUENCE: 426
aagaggaaga aauggcuggu ucucag 26

<210> SEQ ID NO 427
<211> LENGTH: 21
<212> TYPE: RNA
<213> ORGANISM: Homo sapiens

<400> SEQUENCE: 427
acagggccgc agauggagac u 21

<210> SEQ ID NO 428
<211> LENGTH: 22
<212> TYPE: RNA
<213> ORGANISM: Homo sapiens

<400> SEQUENCE: 428
ggaggaaccu uggagcuucg gc 22

<210> SEQ ID NO 429

-continued

<211> LENGTH: 22
<212> TYPE: RNA
<213> ORGANISM: Homo sapiens

<400> SEQUENCE: 429
ucaggugugg aaacugaggc ag 22

<210> SEQ ID NO 430
<211> LENGTH: 22
<212> TYPE: RNA
<213> ORGANISM: Homo sapiens

<400> SEQUENCE: 430
gaauguugcu cggugaaccc cu 22

<210> SEQ ID NO 431
<211> LENGTH: 23
<212> TYPE: RNA
<213> ORGANISM: Homo sapiens

<400> SEQUENCE: 431
agguuacccg agcaacuuug cau 23

<210> SEQ ID NO 432
<211> LENGTH: 21
<212> TYPE: RNA
<213> ORGANISM: Homo sapiens

<400> SEQUENCE: 432
aauauaacac agauggccug u 21

<210> SEQ ID NO 433
<211> LENGTH: 21
<212> TYPE: RNA
<213> ORGANISM: Homo sapiens

<400> SEQUENCE: 433
uaguagaccg uauagcguac g 21

<210> SEQ ID NO 434
<211> LENGTH: 23
<212> TYPE: RNA
<213> ORGANISM: Homo sapiens

<400> SEQUENCE: 434
acuucaccug guccacuagc cgu 23

<210> SEQ ID NO 435
<211> LENGTH: 23
<212> TYPE: RNA
<213> ORGANISM: Homo sapiens

<400> SEQUENCE: 435
aucaacagac auuaauuggg cgc 23

<210> SEQ ID NO 436
<211> LENGTH: 22
<212> TYPE: RNA
<213> ORGANISM: Homo sapiens

<400> SEQUENCE: 436
acuggacuua gggucagaag gc 22

<210> SEQ ID NO 437
<211> LENGTH: 23
<212> TYPE: RNA
<213> ORGANISM: Homo sapiens

<400> SEQUENCE: 437
agcucggucu gaggccccuc agu 23

<210> SEQ ID NO 438
<211> LENGTH: 23
<212> TYPE: RNA
<213> ORGANISM: Homo sapiens

<400> SEQUENCE: 438
ugaggggcag agagcgagac uuu 23

<210> SEQ ID NO 439
<211> LENGTH: 22
<212> TYPE: RNA
<213> ORGANISM: Homo sapiens

<400> SEQUENCE: 439
cagcagcaau ucauguuuug aa 22

<210> SEQ ID NO 440
<211> LENGTH: 23
<212> TYPE: RNA
<213> ORGANISM: Homo sapiens

<400> SEQUENCE: 440
aaugacacga ucacucccgu uga 23

<210> SEQ ID NO 441
<211> LENGTH: 18
<212> TYPE: RNA
<213> ORGANISM: Homo sapiens

<400> SEQUENCE: 441
gggcucacau caccccau 18

<210> SEQ ID NO 442
<211> LENGTH: 17
<212> TYPE: RNA
<213> ORGANISM: Homo sapiens

<400> SEQUENCE: 442
accccacucc ugguacc 17

<210> SEQ ID NO 443
<211> LENGTH: 22
<212> TYPE: RNA
<213> ORGANISM: Homo sapiens

<400> SEQUENCE: 443
uaauacuguc ugguaaaacc gu 22

<210> SEQ ID NO 444
<211> LENGTH: 21
<212> TYPE: RNA
<213> ORGANISM: Homo sapiens

<400> SEQUENCE: 444
ugucuugcag gccgucaugc a 21

<210> SEQ ID NO 445
<211> LENGTH: 23
<212> TYPE: RNA
<213> ORGANISM: Homo sapiens

<400> SEQUENCE: 445
ucuuggagua ggucauuggg ugg 23

<210> SEQ ID NO 446
<211> LENGTH: 22
<212> TYPE: RNA
<213> ORGANISM: Homo sapiens

<400> SEQUENCE: 446
aucaugaugg gcuccucggu gu 22

<210> SEQ ID NO 447
<211> LENGTH: 22
<212> TYPE: RNA
<213> ORGANISM: Homo sapiens

<400> SEQUENCE: 447
uacggugagc cugucauuau uc 22

<210> SEQ ID NO 448
<211> LENGTH: 22
<212> TYPE: RNA
<213> ORGANISM: Homo sapiens

<400> SEQUENCE: 448
accugucugu ggaaaggagc ua 22

<210> SEQ ID NO 449
<211> LENGTH: 22
<212> TYPE: RNA
<213> ORGANISM: Homo sapiens

<400> SEQUENCE: 449
uguugggauu cagcaggacc au 22

<210> SEQ ID NO 450
<211> LENGTH: 22
<212> TYPE: RNA
<213> ORGANISM: Homo sapiens

<400> SEQUENCE: 450
gcgacucuga aaacuagaag gu 22

<210> SEQ ID NO 451
<211> LENGTH: 22
<212> TYPE: RNA
<213> ORGANISM: Homo sapiens

<400> SEQUENCE: 451
auggccagag cucacacaga gg 22

<210> SEQ ID NO 452
<211> LENGTH: 17
<212> TYPE: RNA
<213> ORGANISM: Homo sapiens

<400> SEQUENCE: 452
uuggaggcgu ggguuuu 17

```
<210> SEQ ID NO 453
<211> LENGTH: 20
<212> TYPE: RNA
<213> ORGANISM: Homo sapiens

<400> SEQUENCE: 453

ggcuccuugg ucuaggggua                                              20

<210> SEQ ID NO 454
<211> LENGTH: 17
<212> TYPE: RNA
<213> ORGANISM: Homo sapiens

<400> SEQUENCE: 454

ugguagagcu gaggaca                                                 17

<210> SEQ ID NO 455
<211> LENGTH: 20
<212> TYPE: RNA
<213> ORGANISM: Homo sapiens

<400> SEQUENCE: 455

ggauccgagu cacggcacca                                              20

<210> SEQ ID NO 456
<211> LENGTH: 17
<212> TYPE: RNA
<213> ORGANISM: Homo sapiens

<400> SEQUENCE: 456

agggugugug uguuuuu                                                 17

<210> SEQ ID NO 457
<211> LENGTH: 19
<212> TYPE: RNA
<213> ORGANISM: Homo sapiens

<400> SEQUENCE: 457

agagguaggu guggaagaa                                               19

<210> SEQ ID NO 458
<211> LENGTH: 23
<212> TYPE: RNA
<213> ORGANISM: Homo sapiens

<400> SEQUENCE: 458

gauugagacu aguagggcua ggc                                          23

<210> SEQ ID NO 459
<211> LENGTH: 22
<212> TYPE: RNA
<213> ORGANISM: Homo sapiens

<400> SEQUENCE: 459

uugcauaugu aggauguccc au                                           22

<210> SEQ ID NO 460
<211> LENGTH: 20
<212> TYPE: RNA
<213> ORGANISM: Homo sapiens

<400> SEQUENCE: 460
```

uaacggccgc gguacccuaa 20

<210> SEQ ID NO 461
<211> LENGTH: 18
<212> TYPE: RNA
<213> ORGANISM: Homo sapiens

<400> SEQUENCE: 461
agggggcggg cuccggcg 18

<210> SEQ ID NO 462
<211> LENGTH: 22
<212> TYPE: RNA
<213> ORGANISM: Homo sapiens

<400> SEQUENCE: 462
uggcagugua uuguuagcug gu 22

<210> SEQ ID NO 463
<211> LENGTH: 22
<212> TYPE: RNA
<213> ORGANISM: Homo sapiens

<400> SEQUENCE: 463
aggcagugua uuguuagcug gc 22

<210> SEQ ID NO 464
<211> LENGTH: 25
<212> TYPE: RNA
<213> ORGANISM: Homo sapiens

<400> SEQUENCE: 464
uaggcagugu auugcuagcg gcugu 25

<210> SEQ ID NO 465
<211> LENGTH: 22
<212> TYPE: RNA
<213> ORGANISM: Homo sapiens

<400> SEQUENCE: 465
auugggaaca uuuugcaugu au 22

<210> SEQ ID NO 466
<211> LENGTH: 22
<212> TYPE: RNA
<213> ORGANISM: Homo sapiens

<400> SEQUENCE: 466
auuggggaca uuuugcauuc au 22

<210> SEQ ID NO 467
<211> LENGTH: 22
<212> TYPE: RNA
<213> ORGANISM: Homo sapiens

<400> SEQUENCE: 467
uuuugcgaug uguuccuaau au 22

<210> SEQ ID NO 468
<211> LENGTH: 22
<212> TYPE: RNA
<213> ORGANISM: Homo sapiens

<400> SEQUENCE: 468

-continued uugggaucau uuugcaucca ua 22

<210> SEQ ID NO 469
<211> LENGTH: 22
<212> TYPE: RNA
<213> ORGANISM: Homo sapiens

<400> SEQUENCE: 469
uuuugcaaua uguuccugaa ua 22

<210> SEQ ID NO 470
<211> LENGTH: 17
<212> TYPE: RNA
<213> ORGANISM: Homo sapiens

<400> SEQUENCE: 470
gggagaaggg ucggggc 17

<210> SEQ ID NO 471
<211> LENGTH: 22
<212> TYPE: RNA
<213> ORGANISM: Homo sapiens

<400> SEQUENCE: 471
gcuaaggaag uccugugcuc ag 22

<210> SEQ ID NO 472
<211> LENGTH: 22
<212> TYPE: RNA
<213> ORGANISM: Homo sapiens

<400> SEQUENCE: 472
auagcagcau gaaccugucu ca 22

<210> SEQ ID NO 473
<211> LENGTH: 22
<212> TYPE: RNA
<213> ORGANISM: Homo sapiens

<400> SEQUENCE: 473
aacuguuugc agaggaaacu ga 22

<210> SEQ ID NO 474
<211> LENGTH: 17
<212> TYPE: RNA
<213> ORGANISM: Homo sapiens

<400> SEQUENCE: 474
auggagaagg cuucuga 17

<210> SEQ ID NO 475
<211> LENGTH: 17
<212> TYPE: RNA
<213> ORGANISM: Homo sapiens

<400> SEQUENCE: 475
ccccggggag cccggcg 17

<210> SEQ ID NO 476
<211> LENGTH: 21
<212> TYPE: RNA
<213> ORGANISM: Homo sapiens

<400> SEQUENCE: 476
ucgugcauau aucuaccaca u 21

<210> SEQ ID NO 477
<211> LENGTH: 21
<212> TYPE: RNA
<213> ORGANISM: Homo sapiens

<400> SEQUENCE: 477
ugugguagau auaugcacga u 21

<210> SEQ ID NO 478
<211> LENGTH: 23
<212> TYPE: RNA
<213> ORGANISM: Homo sapiens

<400> SEQUENCE: 478
uagugcaaua uugcuuauag ggu 23

<210> SEQ ID NO 479
<211> LENGTH: 21
<212> TYPE: RNA
<213> ORGANISM: Homo sapiens

<400> SEQUENCE: 479
gcaguccaug ggcauauaca c 21

<210> SEQ ID NO 480
<211> LENGTH: 22
<212> TYPE: RNA
<213> ORGANISM: Homo sapiens

<400> SEQUENCE: 480
uaugugccuu uggacuacau cg 22

<210> SEQ ID NO 481
<211> LENGTH: 23
<212> TYPE: RNA
<213> ORGANISM: Homo sapiens

<400> SEQUENCE: 481
gaagauggug cugugcugag gaa 23

<210> SEQ ID NO 482
<211> LENGTH: 22
<212> TYPE: RNA
<213> ORGANISM: Homo sapiens

<400> SEQUENCE: 482
agcccgcccc agccgagguu cu 22

<210> SEQ ID NO 483
<211> LENGTH: 23
<212> TYPE: RNA
<213> ORGANISM: Homo sapiens

<400> SEQUENCE: 483
gccccggcgc gggcggguuc ugg 23

<210> SEQ ID NO 484
<211> LENGTH: 23
<212> TYPE: RNA
<213> ORGANISM: Homo sapiens

<400> SEQUENCE: 484
cgggcugucc ggaggggucg gcu 23

<210> SEQ ID NO 485
<211> LENGTH: 22
<212> TYPE: RNA
<213> ORGANISM: Homo sapiens

<400> SEQUENCE: 485
uuucccuuca gagccuggcu uu 22

<210> SEQ ID NO 486
<211> LENGTH: 24
<212> TYPE: RNA
<213> ORGANISM: Homo sapiens

<400> SEQUENCE: 486
gaugcgccgc ccacugcccc gcgc 24

<210> SEQ ID NO 487
<211> LENGTH: 22
<212> TYPE: RNA
<213> ORGANISM: Homo sapiens

<400> SEQUENCE: 487
gcgggggugg cggcggcauc cc 22

<210> SEQ ID NO 488
<211> LENGTH: 18
<212> TYPE: RNA
<213> ORGANISM: Homo sapiens

<400> SEQUENCE: 488
cggugagcgc ucgcuggc 18

<210> SEQ ID NO 489
<211> LENGTH: 21
<212> TYPE: RNA
<213> ORGANISM: Homo sapiens

<400> SEQUENCE: 489
ucacuccucu ccucccgucu u 21

<210> SEQ ID NO 490
<211> LENGTH: 22
<212> TYPE: RNA
<213> ORGANISM: Homo sapiens

<400> SEQUENCE: 490
aagacgggag gaaagaaggg ag 22

<210> SEQ ID NO 491
<211> LENGTH: 22
<212> TYPE: RNA
<213> ORGANISM: Homo sapiens

<400> SEQUENCE: 491
ucaggcucag uccccucccg au 22

<210> SEQ ID NO 492
<211> LENGTH: 22
<212> TYPE: RNA

<213> ORGANISM: Homo sapiens

<400> SEQUENCE: 492
gucauacacg gcucuccucu cu 22

<210> SEQ ID NO 493
<211> LENGTH: 22
<212> TYPE: RNA
<213> ORGANISM: Homo sapiens

<400> SEQUENCE: 493
agaggcuggc cgugaugaau uc 22

<210> SEQ ID NO 494
<211> LENGTH: 21
<212> TYPE: RNA
<213> ORGANISM: Homo sapiens

<400> SEQUENCE: 494
cggggcagcu caguacagga u 21

<210> SEQ ID NO 495
<211> LENGTH: 22
<212> TYPE: RNA
<213> ORGANISM: Homo sapiens

<400> SEQUENCE: 495
aaucauacag ggacauccag uu 22

<210> SEQ ID NO 496
<211> LENGTH: 22
<212> TYPE: RNA
<213> ORGANISM: Homo sapiens

<400> SEQUENCE: 496
aaucguacag ggucauccac uu 22

<210> SEQ ID NO 497
<211> LENGTH: 22
<212> TYPE: RNA
<213> ORGANISM: Homo sapiens

<400> SEQUENCE: 497
gugguuaucc cuguccuguu cg 22

<210> SEQ ID NO 498
<211> LENGTH: 21
<212> TYPE: RNA
<213> ORGANISM: Homo sapiens

<400> SEQUENCE: 498
uugaaaggcu auuucuuggu c 21

<210> SEQ ID NO 499
<211> LENGTH: 22
<212> TYPE: RNA
<213> ORGANISM: Homo sapiens

<400> SEQUENCE: 499
gugacaucac auauacggca gc 22

<210> SEQ ID NO 500
<211> LENGTH: 22

<212> TYPE: RNA
<213> ORGANISM: Homo sapiens

<400> SEQUENCE: 500
caaccuggag gacuccaugc ug 22

<210> SEQ ID NO 501
<211> LENGTH: 20
<212> TYPE: RNA
<213> ORGANISM: Homo sapiens

<400> SEQUENCE: 501
ccauggaucu ccaggugggu 20

<210> SEQ ID NO 502
<211> LENGTH: 22
<212> TYPE: RNA
<213> ORGANISM: Homo sapiens

<400> SEQUENCE: 502
cuuaugcaag auucccuucu ac 22

<210> SEQ ID NO 503
<211> LENGTH: 22
<212> TYPE: RNA
<213> ORGANISM: Homo sapiens

<400> SEQUENCE: 503
aguggggaac ccuuccauga gg 22

<210> SEQ ID NO 504
<211> LENGTH: 23
<212> TYPE: RNA
<213> ORGANISM: Homo sapiens

<400> SEQUENCE: 504
aggaccugcg ggacaagauu cuu 23

<210> SEQ ID NO 505
<211> LENGTH: 22
<212> TYPE: RNA
<213> ORGANISM: Homo sapiens

<400> SEQUENCE: 505
ugaaggucua cugugugcca gg 22

<210> SEQ ID NO 506
<211> LENGTH: 22
<212> TYPE: RNA
<213> ORGANISM: Homo sapiens

<400> SEQUENCE: 506
ugaaacauac acgggaaacc uc 22

<210> SEQ ID NO 507
<211> LENGTH: 23
<212> TYPE: RNA
<213> ORGANISM: Homo sapiens

<400> SEQUENCE: 507
agguuguccg uguugucuuc ucu 23

<210> SEQ ID NO 508

<211> LENGTH: 22
<212> TYPE: RNA
<213> ORGANISM: Homo sapiens

<400> SEQUENCE: 508
aaacaaacau ggugcacuuc uu 22

<210> SEQ ID NO 509
<211> LENGTH: 22
<212> TYPE: RNA
<213> ORGANISM: Homo sapiens

<400> SEQUENCE: 509
gaaguugccc auguuauuuu cg 22

<210> SEQ ID NO 510
<211> LENGTH: 22
<212> TYPE: RNA
<213> ORGANISM: Homo sapiens

<400> SEQUENCE: 510
ugaguauuac auggccaauc uc 22

<210> SEQ ID NO 511
<211> LENGTH: 21
<212> TYPE: RNA
<213> ORGANISM: Homo sapiens

<400> SEQUENCE: 511
cagcagcaca cugugguuug u 21

<210> SEQ ID NO 512
<211> LENGTH: 23
<212> TYPE: RNA
<213> ORGANISM: Homo sapiens

<400> SEQUENCE: 512
uuucaagcca gggggcguuu uuc 23

<210> SEQ ID NO 513
<211> LENGTH: 22
<212> TYPE: RNA
<213> ORGANISM: Homo sapiens

<400> SEQUENCE: 513
aacaucacag caagucugug cu 22

<210> SEQ ID NO 514
<211> LENGTH: 21
<212> TYPE: RNA
<213> ORGANISM: Homo sapiens

<400> SEQUENCE: 514
uuaagacuug cagugauguu u 21

<210> SEQ ID NO 515
<211> LENGTH: 22
<212> TYPE: RNA
<213> ORGANISM: Homo sapiens

<400> SEQUENCE: 515
aacaucacug caagucuuaa ca 22

<210> SEQ ID NO 516
<211> LENGTH: 21
<212> TYPE: RNA
<213> ORGANISM: Homo sapiens

<400> SEQUENCE: 516
acagacuugc ugugauguuc a 21

<210> SEQ ID NO 517
<211> LENGTH: 22
<212> TYPE: RNA
<213> ORGANISM: Homo sapiens

<400> SEQUENCE: 517
uucugccucu guccaggucc uu 22

<210> SEQ ID NO 518
<211> LENGTH: 24
<212> TYPE: RNA
<213> ORGANISM: Homo sapiens

<400> SEQUENCE: 518
agggcuggac ucagcggcgg agcu 24

<210> SEQ ID NO 519
<211> LENGTH: 23
<212> TYPE: RNA
<213> ORGANISM: Homo sapiens

<400> SEQUENCE: 519
uaauccuugc uaccugggug aga 23

<210> SEQ ID NO 520
<211> LENGTH: 22
<212> TYPE: RNA
<213> ORGANISM: Homo sapiens

<400> SEQUENCE: 520
uuuugugucu cccauucccc ag 22

<210> SEQ ID NO 521
<211> LENGTH: 22
<212> TYPE: RNA
<213> ORGANISM: Homo sapiens

<400> SEQUENCE: 521
agggggaugg cagagcaaaa uu 22

<210> SEQ ID NO 522
<211> LENGTH: 22
<212> TYPE: RNA
<213> ORGANISM: Homo sapiens

<400> SEQUENCE: 522
aaugcacccg ggcaaggauu cu 22

<210> SEQ ID NO 523
<211> LENGTH: 22
<212> TYPE: RNA
<213> ORGANISM: Homo sapiens

<400> SEQUENCE: 523
aaugcaccug ggcaaggauu ca 22

<210> SEQ ID NO 524
<211> LENGTH: 21
<212> TYPE: RNA
<213> ORGANISM: Homo sapiens

<400> SEQUENCE: 524
auccuugcua ucugggugcu a 21

<210> SEQ ID NO 525
<211> LENGTH: 23
<212> TYPE: RNA
<213> ORGANISM: Homo sapiens

<400> SEQUENCE: 525
gggguauugu uuccgcugcc agg 23

<210> SEQ ID NO 526
<211> LENGTH: 23
<212> TYPE: RNA
<213> ORGANISM: Homo sapiens

<400> SEQUENCE: 526
uagcagcggg aacaguucug cag 23

<210> SEQ ID NO 527
<211> LENGTH: 21
<212> TYPE: RNA
<213> ORGANISM: Homo sapiens

<400> SEQUENCE: 527
gggagugcag ggcagguuu c 21

<210> SEQ ID NO 528
<211> LENGTH: 22
<212> TYPE: RNA
<213> ORGANISM: Homo sapiens

<400> SEQUENCE: 528
agacccuggu cugcacucua uc 22

<210> SEQ ID NO 529
<211> LENGTH: 22
<212> TYPE: RNA
<213> ORGANISM: Homo sapiens

<400> SEQUENCE: 529
cgucaacacu ugcugguuuc cu 22

<210> SEQ ID NO 530
<211> LENGTH: 21
<212> TYPE: RNA
<213> ORGANISM: Homo sapiens

<400> SEQUENCE: 530
uaaggcaccc uucugaguag a 21

<210> SEQ ID NO 531
<211> LENGTH: 22
<212> TYPE: RNA
<213> ORGANISM: Homo sapiens

<400> SEQUENCE: 531
uauucaggaa gguguuacuu aa 22

<210> SEQ ID NO 532
<211> LENGTH: 21
<212> TYPE: RNA
<213> ORGANISM: Homo sapiens

<400> SEQUENCE: 532
uuuugcaccu uuuggaguga a 21

<210> SEQ ID NO 533
<211> LENGTH: 23
<212> TYPE: RNA
<213> ORGANISM: Homo sapiens

<400> SEQUENCE: 533
ugauuguagc cuuuuggagu aga 23

<210> SEQ ID NO 534
<211> LENGTH: 23
<212> TYPE: RNA
<213> ORGANISM: Homo sapiens

<400> SEQUENCE: 534
uacuccagag ggcgucacuc aug 23

<210> SEQ ID NO 535
<211> LENGTH: 22
<212> TYPE: RNA
<213> ORGANISM: Homo sapiens

<400> SEQUENCE: 535
uacugcagac guggcaauca ug 22

<210> SEQ ID NO 536
<211> LENGTH: 22
<212> TYPE: RNA
<213> ORGANISM: Homo sapiens

<400> SEQUENCE: 536
ugauugguac gucugugggu ag 22

<210> SEQ ID NO 537
<211> LENGTH: 21
<212> TYPE: RNA
<213> ORGANISM: Homo sapiens

<400> SEQUENCE: 537
uacugcagac aguggcaauc a 21

<210> SEQ ID NO 538
<211> LENGTH: 21
<212> TYPE: RNA
<213> ORGANISM: Homo sapiens

<400> SEQUENCE: 538
auugaaaccu cuaagagugg a 21

<210> SEQ ID NO 539
<211> LENGTH: 22
<212> TYPE: RNA
<213> ORGANISM: Homo sapiens

<400> SEQUENCE: 539
uacucaggag aguggcaauc ac 22

<210> SEQ ID NO 540
<211> LENGTH: 21
<212> TYPE: RNA
<213> ORGANISM: Homo sapiens

<400> SEQUENCE: 540
gugucuuuug cucugcaguc a 21

<210> SEQ ID NO 541
<211> LENGTH: 22
<212> TYPE: RNA
<213> ORGANISM: Homo sapiens

<400> SEQUENCE: 541
aagugcuguc auagcugagg uc 22

<210> SEQ ID NO 542
<211> LENGTH: 23
<212> TYPE: RNA
<213> ORGANISM: Homo sapiens

<400> SEQUENCE: 542
cacucagccu ugagggcacu uuc 23

<210> SEQ ID NO 543
<211> LENGTH: 23
<212> TYPE: RNA
<213> ORGANISM: Homo sapiens

<400> SEQUENCE: 543
uaaauuucac cuuucugaga agg 23

<210> SEQ ID NO 544
<211> LENGTH: 18
<212> TYPE: RNA
<213> ORGANISM: Homo sapiens

<400> SEQUENCE: 544
uucacaggga ggugucau 18

<210> SEQ ID NO 545
<211> LENGTH: 22
<212> TYPE: RNA
<213> ORGANISM: Homo sapiens

<400> SEQUENCE: 545
uucacaagga ggugucauuu au 22

<210> SEQ ID NO 546
<211> LENGTH: 23
<212> TYPE: RNA
<213> ORGANISM: Homo sapiens

<400> SEQUENCE: 546
uaaauuucac cuuucugaga aga 23

<210> SEQ ID NO 547
<211> LENGTH: 22
<212> TYPE: RNA
<213> ORGANISM: Homo sapiens

<400> SEQUENCE: 547
uucucaagga ggugucguuu au 22

<210> SEQ ID NO 548
<211> LENGTH: 21
<212> TYPE: RNA
<213> ORGANISM: Homo sapiens

<400> SEQUENCE: 548
auugacacuu cugugaguag a 21

<210> SEQ ID NO 549
<211> LENGTH: 23
<212> TYPE: RNA
<213> ORGANISM: Homo sapiens

<400> SEQUENCE: 549
uacucuggag agugacaauc aug 23

<210> SEQ ID NO 550
<211> LENGTH: 21
<212> TYPE: RNA
<213> ORGANISM: Homo sapiens

<400> SEQUENCE: 550
auugacaccu cugugagugg a 21

<210> SEQ ID NO 551
<211> LENGTH: 22
<212> TYPE: RNA
<213> ORGANISM: Homo sapiens

<400> SEQUENCE: 551
uucucaagag ggaggcaauc au 22

<210> SEQ ID NO 552
<211> LENGTH: 22
<212> TYPE: RNA
<213> ORGANISM: Homo sapiens

<400> SEQUENCE: 552
gagugccuuc uuuuggagcg uu 22

<210> SEQ ID NO 553
<211> LENGTH: 24
<212> TYPE: RNA
<213> ORGANISM: Homo sapiens

<400> SEQUENCE: 553
uucuccaaaa gaaagcacuu ucug 24

<210> SEQ ID NO 554
<211> LENGTH: 18
<212> TYPE: RNA
<213> ORGANISM: Homo sapiens

<400> SEQUENCE: 554
ugcuuccuuu cagagggu 18

<210> SEQ ID NO 555
<211> LENGTH: 23
<212> TYPE: RNA
<213> ORGANISM: Homo sapiens

<400> SEQUENCE: 555
uucucgagga aagaagcacu uuc 23

<210> SEQ ID NO 556
<211> LENGTH: 22
<212> TYPE: RNA
<213> ORGANISM: Homo sapiens

<400> SEQUENCE: 556
aucuggaggu aagaagcacu uu 22

<210> SEQ ID NO 557
<211> LENGTH: 22
<212> TYPE: RNA
<213> ORGANISM: Homo sapiens

<400> SEQUENCE: 557
aucgugcauc ccuuuagagu gu 22

<210> SEQ ID NO 558
<211> LENGTH: 22
<212> TYPE: RNA
<213> ORGANISM: Homo sapiens

<400> SEQUENCE: 558
aucgugcauc ccuuuagagu gu 22

<210> SEQ ID NO 559
<211> LENGTH: 22
<212> TYPE: RNA
<213> ORGANISM: Homo sapiens

<400> SEQUENCE: 559
aucgugcauc cuuuuagagu gu 22

<210> SEQ ID NO 560
<211> LENGTH: 22
<212> TYPE: RNA
<213> ORGANISM: Homo sapiens

<400> SEQUENCE: 560
caaagcgcuc cccuuuagag gu 22

<210> SEQ ID NO 561
<211> LENGTH: 23
<212> TYPE: RNA
<213> ORGANISM: Homo sapiens

<400> SEQUENCE: 561
caaagcgcuu cucuuuagag ugu 23

<210> SEQ ID NO 562
<211> LENGTH: 21
<212> TYPE: RNA
<213> ORGANISM: Homo sapiens

<400> SEQUENCE: 562
caaagcgcuu cccuuuggag c 21

<210> SEQ ID NO 563
<211> LENGTH: 21
<212> TYPE: RNA
<213> ORGANISM: Homo sapiens

<400> SEQUENCE: 563
aaagcgcuuc ccuucagagu g 21

<210> SEQ ID NO 564
<211> LENGTH: 21
<212> TYPE: RNA
<213> ORGANISM: Homo sapiens

<400> SEQUENCE: 564
gaaagcgcuu cucuuuagag g 21

<210> SEQ ID NO 565
<211> LENGTH: 21
<212> TYPE: RNA
<213> ORGANISM: Homo sapiens

<400> SEQUENCE: 565
ucauccucgu cucccuccca g 21

<210> SEQ ID NO 566
<211> LENGTH: 22
<212> TYPE: RNA
<213> ORGANISM: Homo sapiens

<400> SEQUENCE: 566
agggaagggg acgaggguug gg 22

<210> SEQ ID NO 567
<211> LENGTH: 22
<212> TYPE: RNA
<213> ORGANISM: Homo sapiens

<400> SEQUENCE: 567
aaagugcauc cuuuuagagg uu 22

<210> SEQ ID NO 568
<211> LENGTH: 22
<212> TYPE: RNA
<213> ORGANISM: Homo sapiens

<400> SEQUENCE: 568
cucuagaggg aagcgcuuuc ug 22

<210> SEQ ID NO 569
<211> LENGTH: 22
<212> TYPE: RNA
<213> ORGANISM: Homo sapiens

<400> SEQUENCE: 569
aaagugcauc uuuuuagagg au 22

<210> SEQ ID NO 570
<211> LENGTH: 22
<212> TYPE: RNA
<213> ORGANISM: Homo sapiens

<400> SEQUENCE: 570
caaagugccu cccuuuagag ug 22

<210> SEQ ID NO 571
<211> LENGTH: 22
<212> TYPE: RNA

<213> ORGANISM: Homo sapiens

<400> SEQUENCE: 571
aagugccucc uuuuagagug uu 22

<210> SEQ ID NO 572
<211> LENGTH: 22
<212> TYPE: RNA
<213> ORGANISM: Homo sapiens

<400> SEQUENCE: 572
aaagugcuuc ccuuuggacu gu 22

<210> SEQ ID NO 573
<211> LENGTH: 21
<212> TYPE: RNA
<213> ORGANISM: Homo sapiens

<400> SEQUENCE: 573
cuccagaggg aaguacuuuc u 21

<210> SEQ ID NO 574
<211> LENGTH: 21
<212> TYPE: RNA
<213> ORGANISM: Homo sapiens

<400> SEQUENCE: 574
aaagugcuuc cuuuuagagg g 21

<210> SEQ ID NO 575
<211> LENGTH: 22
<212> TYPE: RNA
<213> ORGANISM: Homo sapiens

<400> SEQUENCE: 575
aaagugcuuc cuuuuagagg gu 22

<210> SEQ ID NO 576
<211> LENGTH: 22
<212> TYPE: RNA
<213> ORGANISM: Homo sapiens

<400> SEQUENCE: 576
aaagugcuuc ucuuuggugg gu 22

<210> SEQ ID NO 577
<211> LENGTH: 20
<212> TYPE: RNA
<213> ORGANISM: Homo sapiens

<400> SEQUENCE: 577
cuacaaaggg aagcccuuuc 20

<210> SEQ ID NO 578
<211> LENGTH: 21
<212> TYPE: RNA
<213> ORGANISM: Homo sapiens

<400> SEQUENCE: 578
aaagugcuuc cuuuuugagg g 21

<210> SEQ ID NO 579
<211> LENGTH: 22

<212> TYPE: RNA
<213> ORGANISM: Homo sapiens

<400> SEQUENCE: 579
aagugcuucc uuuuagaggg uu 22

<210> SEQ ID NO 580
<211> LENGTH: 24
<212> TYPE: RNA
<213> ORGANISM: Homo sapiens

<400> SEQUENCE: 580
acaaagugcu ucccuuuaga gugu 24

<210> SEQ ID NO 581
<211> LENGTH: 22
<212> TYPE: RNA
<213> ORGANISM: Homo sapiens

<400> SEQUENCE: 581
acaaagugcu ucccuuuaga gu 22

<210> SEQ ID NO 582
<211> LENGTH: 22
<212> TYPE: RNA
<213> ORGANISM: Homo sapiens

<400> SEQUENCE: 582
aacgcacuuc ccuuuagagu gu 22

<210> SEQ ID NO 583
<211> LENGTH: 22
<212> TYPE: RNA
<213> ORGANISM: Homo sapiens

<400> SEQUENCE: 583
aaaaugguuc ccuuuagagu gu 22

<210> SEQ ID NO 584
<211> LENGTH: 23
<212> TYPE: RNA
<213> ORGANISM: Homo sapiens

<400> SEQUENCE: 584
gaacgcgcuu cccuauagag ggu 23

<210> SEQ ID NO 585
<211> LENGTH: 21
<212> TYPE: RNA
<213> ORGANISM: Homo sapiens

<400> SEQUENCE: 585
gaaggcgcuu cccuuuggag u 21

<210> SEQ ID NO 586
<211> LENGTH: 22
<212> TYPE: RNA
<213> ORGANISM: Homo sapiens

<400> SEQUENCE: 586
gaaggcgcuu cccuuuagag cg 22

<210> SEQ ID NO 587

<211> LENGTH: 21
<212> TYPE: RNA
<213> ORGANISM: Homo sapiens

<400> SEQUENCE: 587
cuccagaggg augcacuuuc u 21

<210> SEQ ID NO 588
<211> LENGTH: 22
<212> TYPE: RNA
<213> ORGANISM: Homo sapiens

<400> SEQUENCE: 588
cucuagaggg aagcacuuuc ug 22

<210> SEQ ID NO 589
<211> LENGTH: 23
<212> TYPE: RNA
<213> ORGANISM: Homo sapiens

<400> SEQUENCE: 589
cucuugaggg aagcacuuuc ugu 23

<210> SEQ ID NO 590
<211> LENGTH: 22
<212> TYPE: RNA
<213> ORGANISM: Homo sapiens

<400> SEQUENCE: 590
ccucccacac ccaaggcuug ca 22

<210> SEQ ID NO 591
<211> LENGTH: 22
<212> TYPE: RNA
<213> ORGANISM: Homo sapiens

<400> SEQUENCE: 591
caugccuuga guguaggacc gu 22

<210> SEQ ID NO 592
<211> LENGTH: 22
<212> TYPE: RNA
<213> ORGANISM: Homo sapiens

<400> SEQUENCE: 592
aucauacaag gacaauuucu uu 22

<210> SEQ ID NO 593
<211> LENGTH: 22
<212> TYPE: RNA
<213> ORGANISM: Homo sapiens

<400> SEQUENCE: 593
ggagaaauua uccuuggugu gu 22

<210> SEQ ID NO 594
<211> LENGTH: 22
<212> TYPE: RNA
<213> ORGANISM: Homo sapiens

<400> SEQUENCE: 594
uggugggcac agaaucugga cu 22

<210> SEQ ID NO 595
<211> LENGTH: 22
<212> TYPE: RNA
<213> ORGANISM: Homo sapiens

<400> SEQUENCE: 595
ugugacagau ugauaacuga aa 22

<210> SEQ ID NO 596
<211> LENGTH: 23
<212> TYPE: RNA
<213> ORGANISM: Homo sapiens

<400> SEQUENCE: 596
ucggggauca ucaugucacg aga 23

<210> SEQ ID NO 597
<211> LENGTH: 22
<212> TYPE: RNA
<213> ORGANISM: Homo sapiens

<400> SEQUENCE: 597
aaacauucgc ggugcacuuc uu 22

<210> SEQ ID NO 598
<211> LENGTH: 22
<212> TYPE: RNA
<213> ORGANISM: Homo sapiens

<400> SEQUENCE: 598
auucugcauu uuuagcaagu uc 22

<210> SEQ ID NO 599
<211> LENGTH: 22
<212> TYPE: RNA
<213> ORGANISM: Homo sapiens

<400> SEQUENCE: 599
ucagcaaaca uuuauugugu gc 22

<210> SEQ ID NO 600
<211> LENGTH: 22
<212> TYPE: RNA
<213> ORGANISM: Homo sapiens

<400> SEQUENCE: 600
caaaacuggc aauuacuuuu gc 22

<210> SEQ ID NO 601
<211> LENGTH: 22
<212> TYPE: RNA
<213> ORGANISM: Homo sapiens

<400> SEQUENCE: 601
aaaaguaauu gcgaguuuua cc 22

<210> SEQ ID NO 602
<211> LENGTH: 25
<212> TYPE: RNA
<213> ORGANISM: Homo sapiens

<400> SEQUENCE: 602
aaaaaccaca auuacuuuug cacca 25

<210> SEQ ID NO 603
<211> LENGTH: 22
<212> TYPE: RNA
<213> ORGANISM: Homo sapiens

<400> SEQUENCE: 603
gaaaacgaca augacuuuug ca 22

<210> SEQ ID NO 604
<211> LENGTH: 20
<212> TYPE: RNA
<213> ORGANISM: Homo sapiens

<400> SEQUENCE: 604
aaaagugauu gcaguguuug 20

<210> SEQ ID NO 605
<211> LENGTH: 22
<212> TYPE: RNA
<213> ORGANISM: Homo sapiens

<400> SEQUENCE: 605
aaagguaauu gcaguuuuuc cc 22

<210> SEQ ID NO 606
<211> LENGTH: 21
<212> TYPE: RNA
<213> ORGANISM: Homo sapiens

<400> SEQUENCE: 606
aaaaguaacu gcgguuuuug a 21

<210> SEQ ID NO 607
<211> LENGTH: 22
<212> TYPE: RNA
<213> ORGANISM: Homo sapiens

<400> SEQUENCE: 607
aacggcaaug acuuuuguac ca 22

<210> SEQ ID NO 608
<211> LENGTH: 21
<212> TYPE: RNA
<213> ORGANISM: Homo sapiens

<400> SEQUENCE: 608
uaaaacugca guuauuuuug c 21

<210> SEQ ID NO 609
<211> LENGTH: 21
<212> TYPE: RNA
<213> ORGANISM: Homo sapiens

<400> SEQUENCE: 609
aaaaguaauu gcaguuuuug c 21

<210> SEQ ID NO 610
<211> LENGTH: 22
<212> TYPE: RNA
<213> ORGANISM: Homo sapiens

<400> SEQUENCE: 610
caagaaccuc aguugcuuuu gu 22

<210> SEQ ID NO 611
<211> LENGTH: 22
<212> TYPE: RNA
<213> ORGANISM: Homo sapiens

<400> SEQUENCE: 611
aaaaguaauu gcgguuuuug cc 22

<210> SEQ ID NO 612
<211> LENGTH: 22
<212> TYPE: RNA
<213> ORGANISM: Homo sapiens

<400> SEQUENCE: 612
caaaaaccac aguuucuuuu gc 22

<210> SEQ ID NO 613
<211> LENGTH: 22
<212> TYPE: RNA
<213> ORGANISM: Homo sapiens

<400> SEQUENCE: 613
aaaaguaauu gugguuuuug cc 22

<210> SEQ ID NO 614
<211> LENGTH: 22
<212> TYPE: RNA
<213> ORGANISM: Homo sapiens

<400> SEQUENCE: 614
aaaaacugag acuacuuuug ca 22

<210> SEQ ID NO 615
<211> LENGTH: 22
<212> TYPE: RNA
<213> ORGANISM: Homo sapiens

<400> SEQUENCE: 615
caaaagcaau cgcgguuuuu gc 22

<210> SEQ ID NO 616
<211> LENGTH: 22
<212> TYPE: RNA
<213> ORGANISM: Homo sapiens

<400> SEQUENCE: 616
aaaacuguaa uuacuuuugu ac 22

<210> SEQ ID NO 617
<211> LENGTH: 22
<212> TYPE: RNA
<213> ORGANISM: Homo sapiens

<400> SEQUENCE: 617
aaaaguaauc gcgguuuuug uc 22

<210> SEQ ID NO 618
<211> LENGTH: 22
<212> TYPE: RNA
<213> ORGANISM: Homo sapiens

<400> SEQUENCE: 618

```
aaaaguaauu gcggauuuug cc                                              22

<210> SEQ ID NO 619
<211> LENGTH: 21
<212> TYPE: RNA
<213> ORGANISM: Homo sapiens

<400> SEQUENCE: 619

caaaaacugc auuacuuuug c                                               21

<210> SEQ ID NO 620
<211> LENGTH: 22
<212> TYPE: RNA
<213> ORGANISM: Homo sapiens

<400> SEQUENCE: 620

aaaaguaauu gcggucuuug gu                                              22

<210> SEQ ID NO 621
<211> LENGTH: 22
<212> TYPE: RNA
<213> ORGANISM: Homo sapiens

<400> SEQUENCE: 621

aaaaguacuu gcggauuuug cu                                              22

<210> SEQ ID NO 622
<211> LENGTH: 22
<212> TYPE: RNA
<213> ORGANISM: Homo sapiens

<400> SEQUENCE: 622

aaaaguauuu gcggguuuug uc                                              22

<210> SEQ ID NO 623
<211> LENGTH: 21
<212> TYPE: RNA
<213> ORGANISM: Homo sapiens

<400> SEQUENCE: 623

caaagguauu ugugguuuuu g                                               21

<210> SEQ ID NO 624
<211> LENGTH: 22
<212> TYPE: RNA
<213> ORGANISM: Homo sapiens

<400> SEQUENCE: 624

caaaaguaau ugugga uuuu gu                                             22

<210> SEQ ID NO 625
<211> LENGTH: 22
<212> TYPE: RNA
<213> ORGANISM: Homo sapiens

<400> SEQUENCE: 625

ccaaaacugc aguuacuuuu gc                                              22

<210> SEQ ID NO 626
<211> LENGTH: 22
<212> TYPE: RNA
<213> ORGANISM: Homo sapiens

<400> SEQUENCE: 626
```

gcuggugcaa aaguaauggc gg 22

<210> SEQ ID NO 627
<211> LENGTH: 22
<212> TYPE: RNA
<213> ORGANISM: Homo sapiens

<400> SEQUENCE: 627
agcuacaguu acuuuugcac ca 22

<210> SEQ ID NO 628
<211> LENGTH: 22
<212> TYPE: RNA
<213> ORGANISM: Homo sapiens

<400> SEQUENCE: 628
aaaaguaauc acuguuuuug cc 22

<210> SEQ ID NO 629
<211> LENGTH: 23
<212> TYPE: RNA
<213> ORGANISM: Homo sapiens

<400> SEQUENCE: 629
caaaaaccgc aauuacuuuu gca 23

<210> SEQ ID NO 630
<211> LENGTH: 21
<212> TYPE: RNA
<213> ORGANISM: Homo sapiens

<400> SEQUENCE: 630
ugacaacuau ggaugagcuc u 21

<210> SEQ ID NO 631
<211> LENGTH: 23
<212> TYPE: RNA
<213> ORGANISM: Homo sapiens

<400> SEQUENCE: 631
agugccugag ggaguaagag ccc 23

<210> SEQ ID NO 632
<211> LENGTH: 21
<212> TYPE: RNA
<213> ORGANISM: Homo sapiens

<400> SEQUENCE: 632
gcgacccacu cuugguuucc a 21

<210> SEQ ID NO 633
<211> LENGTH: 21
<212> TYPE: RNA
<213> ORGANISM: Homo sapiens

<400> SEQUENCE: 633
gcgacccaua cuugguuuca g 21

<210> SEQ ID NO 634
<211> LENGTH: 21
<212> TYPE: RNA
<213> ORGANISM: Homo sapiens

<400> SEQUENCE: 634
aacaggugac ugguuagaca a 21

<210> SEQ ID NO 635
<211> LENGTH: 21
<212> TYPE: RNA
<213> ORGANISM: Homo sapiens

<400> SEQUENCE: 635
aaaacgguga gauuuuguuu u 21

<210> SEQ ID NO 636
<211> LENGTH: 21
<212> TYPE: RNA
<213> ORGANISM: Homo sapiens

<400> SEQUENCE: 636
gcuaguccug acucagccag u 21

<210> SEQ ID NO 637
<211> LENGTH: 21
<212> TYPE: RNA
<213> ORGANISM: Homo sapiens

<400> SEQUENCE: 637
aggguaagcu gaaccucuga u 21

<210> SEQ ID NO 638
<211> LENGTH: 22
<212> TYPE: RNA
<213> ORGANISM: Homo sapiens

<400> SEQUENCE: 638
auauuaccau uagcucaucu uu 22

<210> SEQ ID NO 639
<211> LENGTH: 22
<212> TYPE: RNA
<213> ORGANISM: Homo sapiens

<400> SEQUENCE: 639
gaugagcuca uuguaauaug ag 22

<210> SEQ ID NO 640
<211> LENGTH: 22
<212> TYPE: RNA
<213> ORGANISM: Homo sapiens

<400> SEQUENCE: 640
caaaguuuaa gauccuugaa gu 22

<210> SEQ ID NO 641
<211> LENGTH: 22
<212> TYPE: RNA
<213> ORGANISM: Homo sapiens

<400> SEQUENCE: 641
aucaaggauc uuaaacuuug cc 22

<210> SEQ ID NO 642
<211> LENGTH: 20
<212> TYPE: RNA
<213> ORGANISM: Homo sapiens

<400> SEQUENCE: 642
aaaguagcug uaccauuugc 20

<210> SEQ ID NO 643
<211> LENGTH: 19
<212> TYPE: RNA
<213> ORGANISM: Homo sapiens

<400> SEQUENCE: 643
agguugacau acguuuccc 19

<210> SEQ ID NO 644
<211> LENGTH: 19
<212> TYPE: RNA
<213> ORGANISM: Homo sapiens

<400> SEQUENCE: 644
aggcacggug ucagcaggc 19

<210> SEQ ID NO 645
<211> LENGTH: 19
<212> TYPE: RNA
<213> ORGANISM: Homo sapiens

<400> SEQUENCE: 645
gggcgccugu gaucccaac 19

<210> SEQ ID NO 646
<211> LENGTH: 23
<212> TYPE: RNA
<213> ORGANISM: Homo sapiens

<400> SEQUENCE: 646
aguauguucu uccaggacag aac 23

<210> SEQ ID NO 647
<211> LENGTH: 20
<212> TYPE: RNA
<213> ORGANISM: Homo sapiens

<400> SEQUENCE: 647
auguauaaau guauacacac 20

<210> SEQ ID NO 648
<211> LENGTH: 22
<212> TYPE: RNA
<213> ORGANISM: Homo sapiens

<400> SEQUENCE: 648
cgaaaacagc aauuaccuuu gc 22

<210> SEQ ID NO 649
<211> LENGTH: 21
<212> TYPE: RNA
<213> ORGANISM: Homo sapiens

<400> SEQUENCE: 649
ugaguuggcc aucugaguga g 21

<210> SEQ ID NO 650
<211> LENGTH: 20
<212> TYPE: RNA

<213> ORGANISM: Homo sapiens

<400> SEQUENCE: 650
guccgcucgg cgguggccca 20

<210> SEQ ID NO 651
<211> LENGTH: 24
<212> TYPE: RNA
<213> ORGANISM: Homo sapiens

<400> SEQUENCE: 651
cugaagugau guguaacuga ucag 24

<210> SEQ ID NO 652
<211> LENGTH: 22
<212> TYPE: RNA
<213> ORGANISM: Homo sapiens

<400> SEQUENCE: 652
cacgcucaug cacacaccca ca 22

<210> SEQ ID NO 653
<211> LENGTH: 23
<212> TYPE: RNA
<213> ORGANISM: Homo sapiens

<400> SEQUENCE: 653
ugagugugug ugugugagug ugu 23

<210> SEQ ID NO 654
<211> LENGTH: 19
<212> TYPE: RNA
<213> ORGANISM: Homo sapiens

<400> SEQUENCE: 654
gagccaguug gacaggagc 19

<210> SEQ ID NO 655
<211> LENGTH: 22
<212> TYPE: RNA
<213> ORGANISM: Homo sapiens

<400> SEQUENCE: 655
aagaugugga aaaauuggaa uc 22

<210> SEQ ID NO 656
<211> LENGTH: 22
<212> TYPE: RNA
<213> ORGANISM: Homo sapiens

<400> SEQUENCE: 656
auucuaauuu cuccacgucu uu 22

<210> SEQ ID NO 657
<211> LENGTH: 21
<212> TYPE: RNA
<213> ORGANISM: Homo sapiens

<400> SEQUENCE: 657
uagauaaaau auugguaccu g 21

<210> SEQ ID NO 658
<211> LENGTH: 21

<212> TYPE: RNA
<213> ORGANISM: Homo sapiens

<400> SEQUENCE: 658
cuucuugugc ucuaggauug u 21

<210> SEQ ID NO 659
<211> LENGTH: 23
<212> TYPE: RNA
<213> ORGANISM: Homo sapiens

<400> SEQUENCE: 659
uucauuuggu auaaaccgcg auu 23

<210> SEQ ID NO 660
<211> LENGTH: 22
<212> TYPE: RNA
<213> ORGANISM: Homo sapiens

<400> SEQUENCE: 660
ucgcgguuug ugccagauga cg 22

<210> SEQ ID NO 661
<211> LENGTH: 22
<212> TYPE: RNA
<213> ORGANISM: Homo sapiens

<400> SEQUENCE: 661
uugagaauga ugaaucauua gg 22

<210> SEQ ID NO 662
<211> LENGTH: 22
<212> TYPE: RNA
<213> ORGANISM: Homo sapiens

<400> SEQUENCE: 662
uaacugguug aacaacugaa cc 22

<210> SEQ ID NO 663
<211> LENGTH: 23
<212> TYPE: RNA
<213> ORGANISM: Homo sapiens

<400> SEQUENCE: 663
uuacaguugu ucaaccaguu acu 23

<210> SEQ ID NO 664
<211> LENGTH: 22
<212> TYPE: RNA
<213> ORGANISM: Homo sapiens

<400> SEQUENCE: 664
ucaguuccag gccaaccagg cu 22

<210> SEQ ID NO 665
<211> LENGTH: 22
<212> TYPE: RNA
<213> ORGANISM: Homo sapiens

<400> SEQUENCE: 665
uuaugguuug ccugggacug ag 22

<210> SEQ ID NO 666

<211> LENGTH: 19
<212> TYPE: RNA
<213> ORGANISM: Homo sapiens

<400> SEQUENCE: 666
ugggcguauc uguaugcua 19

<210> SEQ ID NO 667
<211> LENGTH: 21
<212> TYPE: RNA
<213> ORGANISM: Homo sapiens

<400> SEQUENCE: 667
uuuccauagg ugaugaguca c 21

<210> SEQ ID NO 668
<211> LENGTH: 22
<212> TYPE: RNA
<213> ORGANISM: Homo sapiens

<400> SEQUENCE: 668
ugagaaccac gucugcucug ag 22

<210> SEQ ID NO 669
<211> LENGTH: 21
<212> TYPE: RNA
<213> ORGANISM: Homo sapiens

<400> SEQUENCE: 669
uaauuuuaug uauaagcuag u 21

<210> SEQ ID NO 670
<211> LENGTH: 22
<212> TYPE: RNA
<213> ORGANISM: Homo sapiens

<400> SEQUENCE: 670
gagcuuauuc auaaaagugc ag 22

<210> SEQ ID NO 671
<211> LENGTH: 20
<212> TYPE: RNA
<213> ORGANISM: Homo sapiens

<400> SEQUENCE: 671
agaccauggg uucucauugu 20

<210> SEQ ID NO 672
<211> LENGTH: 22
<212> TYPE: RNA
<213> ORGANISM: Homo sapiens

<400> SEQUENCE: 672
uugugucaau augcgaugau gu 22

<210> SEQ ID NO 673
<211> LENGTH: 19
<212> TYPE: RNA
<213> ORGANISM: Homo sapiens

<400> SEQUENCE: 673
ugucucugcu gggguuucu 19

<210> SEQ ID NO 674
<211> LENGTH: 21
<212> TYPE: RNA
<213> ORGANISM: Homo sapiens

<400> SEQUENCE: 674
gaagugugcc guggugugc u 21

<210> SEQ ID NO 675
<211> LENGTH: 21
<212> TYPE: RNA
<213> ORGANISM: Homo sapiens

<400> SEQUENCE: 675
aagccugccc ggcuccucgg g 21

<210> SEQ ID NO 676
<211> LENGTH: 22
<212> TYPE: RNA
<213> ORGANISM: Homo sapiens

<400> SEQUENCE: 676
ugugucacuc gaugaccacu gu 22

<210> SEQ ID NO 677
<211> LENGTH: 22
<212> TYPE: RNA
<213> ORGANISM: Homo sapiens

<400> SEQUENCE: 677
uacgucaucg uugucaucgu ca 22

<210> SEQ ID NO 678
<211> LENGTH: 20
<212> TYPE: RNA
<213> ORGANISM: Homo sapiens

<400> SEQUENCE: 678
guugugucag uuuaucaaac 20

<210> SEQ ID NO 679
<211> LENGTH: 23
<212> TYPE: RNA
<213> ORGANISM: Homo sapiens

<400> SEQUENCE: 679
acuuacagac aagagccuug cuc 23

<210> SEQ ID NO 680
<211> LENGTH: 22
<212> TYPE: RNA
<213> ORGANISM: Homo sapiens

<400> SEQUENCE: 680
uggucuagga uuguuggagg ag 22

<210> SEQ ID NO 681
<211> LENGTH: 22
<212> TYPE: RNA
<213> ORGANISM: Homo sapiens

<400> SEQUENCE: 681
cacacacugc aauuacuuuu gc 22

<210> SEQ ID NO 682
<211> LENGTH: 19
<212> TYPE: RNA
<213> ORGANISM: Homo sapiens

<400> SEQUENCE: 682
aggcugcgga auucaggac 19

<210> SEQ ID NO 683
<211> LENGTH: 23
<212> TYPE: RNA
<213> ORGANISM: Homo sapiens

<400> SEQUENCE: 683
uaaaucccau ggugccuucu ccu 23

<210> SEQ ID NO 684
<211> LENGTH: 21
<212> TYPE: RNA
<213> ORGANISM: Homo sapiens

<400> SEQUENCE: 684
aaacuacuga aaaucaaaga u 21

<210> SEQ ID NO 685
<211> LENGTH: 21
<212> TYPE: RNA
<213> ORGANISM: Homo sapiens

<400> SEQUENCE: 685
guucaaaucc agaucuauaa c 21

<210> SEQ ID NO 686
<211> LENGTH: 25
<212> TYPE: RNA
<213> ORGANISM: Homo sapiens

<400> SEQUENCE: 686 aggggguggug uugggacagc uccgu 25

<210> SEQ ID NO 687
<211> LENGTH: 21
<212> TYPE: RNA
<213> ORGANISM: Homo sapiens

<400> SEQUENCE: 687
ugagcuaaau gugugcuggg a 21

<210> SEQ ID NO 688
<211> LENGTH: 25
<212> TYPE: RNA
<213> ORGANISM: Homo sapiens

<400> SEQUENCE: 688
gcugggcagg gcuucugagc uccuu 25

<210> SEQ ID NO 689
<211> LENGTH: 20
<212> TYPE: RNA
<213> ORGANISM: Homo sapiens

<400> SEQUENCE: 689
aggaauguuc cuucuuugcc 20

<210> SEQ ID NO 690
<211> LENGTH: 23
<212> TYPE: RNA
<213> ORGANISM: Homo sapiens

<400> SEQUENCE: 690
gaacgccugu ucuugccagg ugg 23

<210> SEQ ID NO 691
<211> LENGTH: 22
<212> TYPE: RNA
<213> ORGANISM: Homo sapiens

<400> SEQUENCE: 691
uccgagccug ggucucccuc uu 22

<210> SEQ ID NO 692
<211> LENGTH: 22
<212> TYPE: RNA
<213> ORGANISM: Homo sapiens

<400> SEQUENCE: 692
gggggucccc ggugcucgga uc 22

<210> SEQ ID NO 693
<211> LENGTH: 22
<212> TYPE: RNA
<213> ORGANISM: Homo sapiens

<400> SEQUENCE: 693
agucauugga ggguuugagc ag 22

<210> SEQ ID NO 694
<211> LENGTH: 22
<212> TYPE: RNA
<213> ORGANISM: Homo sapiens

<400> SEQUENCE: 694
agacuuccca uuugaaggug gc 22

<210> SEQ ID NO 695
<211> LENGTH: 24
<212> TYPE: RNA
<213> ORGANISM: Homo sapiens

<400> SEQUENCE: 695
gaccuggaca uguuugugcc cagu 24

<210> SEQ ID NO 696
<211> LENGTH: 20
<212> TYPE: RNA
<213> ORGANISM: Homo sapiens

<400> SEQUENCE: 696
auggagauag auauagaaau 20

<210> SEQ ID NO 697
<211> LENGTH: 21
<212> TYPE: RNA
<213> ORGANISM: Homo sapiens

<400> SEQUENCE: 697
cacaagguau ugguauuacc u 21

<210> SEQ ID NO 698
<211> LENGTH: 21
<212> TYPE: RNA
<213> ORGANISM: Homo sapiens

<400> SEQUENCE: 698 aggggaaag uucuauaguc c 21

<210> SEQ ID NO 699
<211> LENGTH: 19
<212> TYPE: RNA
<213> ORGANISM: Homo sapiens

<400> SEQUENCE: 699
agcugucuga aaaugucuu 19

<210> SEQ ID NO 700
<211> LENGTH: 20
<212> TYPE: RNA
<213> ORGANISM: Homo sapiens

<400> SEQUENCE: 700
ucuuuucuuu gagacucacu 20

<210> SEQ ID NO 701
<211> LENGTH: 22
<212> TYPE: RNA
<213> ORGANISM: Homo sapiens

<400> SEQUENCE: 701
gugagucucu aagaaaagag ga 22

<210> SEQ ID NO 702
<211> LENGTH: 21
<212> TYPE: RNA
<213> ORGANISM: Homo sapiens

<400> SEQUENCE: 702
ucuaguaaga guggcagucg a 21

<210> SEQ ID NO 703
<211> LENGTH: 22
<212> TYPE: RNA
<213> ORGANISM: Homo sapiens

<400> SEQUENCE: 703
augcugacau auuuacuaga gg 22

<210> SEQ ID NO 704
<211> LENGTH: 21
<212> TYPE: RNA
<213> ORGANISM: Homo sapiens

<400> SEQUENCE: 704
uggguuuacg uugggagaac u 21

<210> SEQ ID NO 705
<211> LENGTH: 22
<212> TYPE: RNA
<213> ORGANISM: Homo sapiens

<400> SEQUENCE: 705
aguauucugu accagggaag gu 22

<210> SEQ ID NO 706
<211> LENGTH: 21
<212> TYPE: RNA
<213> ORGANISM: Homo sapiens

<400> SEQUENCE: 706
agaccuggcc cagaccucag c 21

<210> SEQ ID NO 707
<211> LENGTH: 24
<212> TYPE: RNA
<213> ORGANISM: Homo sapiens

<400> SEQUENCE: 707
acugggggcu uucgggcucu gcgu 24

<210> SEQ ID NO 708
<211> LENGTH: 25
<212> TYPE: RNA
<213> ORGANISM: Homo sapiens

<400> SEQUENCE: 708
agggaucgcg ggcggguggc ggccu 25

<210> SEQ ID NO 709
<211> LENGTH: 23
<212> TYPE: RNA
<213> ORGANISM: Homo sapiens

<400> SEQUENCE: 709
aucgcugcgg uugcgagcgc ugu 23

<210> SEQ ID NO 710
<211> LENGTH: 21
<212> TYPE: RNA
<213> ORGANISM: Homo sapiens

<400> SEQUENCE: 710
augauccagg aaccugccuc u 21

<210> SEQ ID NO 711
<211> LENGTH: 24
<212> TYPE: RNA
<213> ORGANISM: Homo sapiens

<400> SEQUENCE: 711
aaagacauag gauagaguca ccuc 24

<210> SEQ ID NO 712
<211> LENGTH: 22
<212> TYPE: RNA
<213> ORGANISM: Homo sapiens

<400> SEQUENCE: 712
agacacauuu ggagagggaa cc 22

<210> SEQ ID NO 713
<211> LENGTH: 22
<212> TYPE: RNA
<213> ORGANISM: Homo sapiens

<400> SEQUENCE: 713
gucccucucc aaaugugucu ug 22

<210> SEQ ID NO 714
<211> LENGTH: 22
<212> TYPE: RNA
<213> ORGANISM: Homo sapiens

<400> SEQUENCE: 714
acuuguaugc uagcucaggu ag 22

<210> SEQ ID NO 715
<211> LENGTH: 19
<212> TYPE: RNA
<213> ORGANISM: Homo sapiens

<400> SEQUENCE: 715
aguguggcuu ucuuagagc 19

<210> SEQ ID NO 716
<211> LENGTH: 19
<212> TYPE: RNA
<213> ORGANISM: Homo sapiens

<400> SEQUENCE: 716
aagugugcag ggcacuggu 19

<210> SEQ ID NO 717
<211> LENGTH: 22
<212> TYPE: RNA
<213> ORGANISM: Homo sapiens

<400> SEQUENCE: 717
aaaccugugu uguucaagag uc 22

<210> SEQ ID NO 718
<211> LENGTH: 21
<212> TYPE: RNA
<213> ORGANISM: Homo sapiens

<400> SEQUENCE: 718
aggaggcagc gcucucagga c 21

<210> SEQ ID NO 719
<211> LENGTH: 21
<212> TYPE: RNA
<213> ORGANISM: Homo sapiens

<400> SEQUENCE: 719
gggacuagga ugcagaccuc c 21

<210> SEQ ID NO 720
<211> LENGTH: 23
<212> TYPE: RNA
<213> ORGANISM: Homo sapiens

<400> SEQUENCE: 720
aggucugcau ucaaaucccc aga 23

<210> SEQ ID NO 721
<211> LENGTH: 22
<212> TYPE: RNA
<213> ORGANISM: Homo sapiens

<400> SEQUENCE: 721
ccucaccauc ccuucugccu gc 22

<210> SEQ ID NO 722
<211> LENGTH: 23
<212> TYPE: RNA
<213> ORGANISM: Homo sapiens

<400> SEQUENCE: 722
caggcagaag uggggcugac agg 23

<210> SEQ ID NO 723
<211> LENGTH: 22
<212> TYPE: RNA
<213> ORGANISM: Homo sapiens

<400> SEQUENCE: 723
aaaggaaagu guauccuaaa ag 22

<210> SEQ ID NO 724
<211> LENGTH: 22
<212> TYPE: RNA
<213> ORGANISM: Homo sapiens

<400> SEQUENCE: 724
uuuaggauaa gcuugacuuu ug 22

<210> SEQ ID NO 725
<211> LENGTH: 21
<212> TYPE: RNA
<213> ORGANISM: Homo sapiens

<400> SEQUENCE: 725
aauggcgcca cuaggguugu g 21

<210> SEQ ID NO 726
<211> LENGTH: 25
<212> TYPE: RNA
<213> ORGANISM: Homo sapiens

<400> SEQUENCE: 726
caacccuagg agagggugcc auuca 25

<210> SEQ ID NO 727
<211> LENGTH: 22
<212> TYPE: RNA
<213> ORGANISM: Homo sapiens

<400> SEQUENCE: 727
uaugucugcu gaccaucacc uu 22

<210> SEQ ID NO 728
<211> LENGTH: 22
<212> TYPE: RNA
<213> ORGANISM: Homo sapiens

<400> SEQUENCE: 728
uggugggccg cagaacaugu gc 22

<210> SEQ ID NO 729
<211> LENGTH: 22
<212> TYPE: RNA

```
<213> ORGANISM: Homo sapiens

<400> SEQUENCE: 729

auaauacaug guuaaccucu uu                                          22

<210> SEQ ID NO 730
<211> LENGTH: 21
<212> TYPE: RNA
<213> ORGANISM: Homo sapiens

<400> SEQUENCE: 730

aauauuauac agucaaccuc u                                           21

<210> SEQ ID NO 731
<211> LENGTH: 21
<212> TYPE: RNA
<213> ORGANISM: Homo sapiens

<400> SEQUENCE: 731

accuccugug ugcauggauu a                                           21

<210> SEQ ID NO 732
<211> LENGTH: 22
<212> TYPE: RNA
<213> ORGANISM: Homo sapiens

<400> SEQUENCE: 732

uacccauugc auaucggagu ug                                          22

<210> SEQ ID NO 733
<211> LENGTH: 24
<212> TYPE: RNA
<213> ORGANISM: Homo sapiens

<400> SEQUENCE: 733

ugccuggguc ucuggccugc gcgu                                        24

<210> SEQ ID NO 734
<211> LENGTH: 22
<212> TYPE: RNA
<213> ORGANISM: Homo sapiens

<400> SEQUENCE: 734

aggcggggcg ccgcgggacc gc                                          22

<210> SEQ ID NO 735
<211> LENGTH: 23
<212> TYPE: RNA
<213> ORGANISM: Homo sapiens

<400> SEQUENCE: 735

uauucauuua uccccagccu aca                                         23

<210> SEQ ID NO 736
<211> LENGTH: 22
<212> TYPE: RNA
<213> ORGANISM: Homo sapiens

<400> SEQUENCE: 736

uucauuugcc ucccagccua ca                                          22

<210> SEQ ID NO 737
<211> LENGTH: 24
```

<212> TYPE: RNA
<213> ORGANISM: Homo sapiens

<400> SEQUENCE: 737
ugggcuaagg gagaugauug ggua 24

<210> SEQ ID NO 738
<211> LENGTH: 20
<212> TYPE: RNA
<213> ORGANISM: Homo sapiens

<400> SEQUENCE: 738
accaggaggc ugaggccccu 20

<210> SEQ ID NO 739
<211> LENGTH: 21
<212> TYPE: RNA
<213> ORGANISM: Homo sapiens

<400> SEQUENCE: 739
uccgguucuc agggcuccac c 21

<210> SEQ ID NO 740
<211> LENGTH: 23
<212> TYPE: RNA
<213> ORGANISM: Homo sapiens

<400> SEQUENCE: 740
aggaagcccu ggaggggcug gag 23

<210> SEQ ID NO 741
<211> LENGTH: 22
<212> TYPE: RNA
<213> ORGANISM: Homo sapiens

<400> SEQUENCE: 741
cgcgccugca ggaacuggua ga 22

<210> SEQ ID NO 742
<211> LENGTH: 23
<212> TYPE: RNA
<213> ORGANISM: Homo sapiens

<400> SEQUENCE: 742
ugggcagggg cuuauuguag gag 23

<210> SEQ ID NO 743
<211> LENGTH: 23
<212> TYPE: RNA
<213> ORGANISM: Homo sapiens

<400> SEQUENCE: 743
cugggcccgc ggcgggcgug ggg 23

<210> SEQ ID NO 744
<211> LENGTH: 23
<212> TYPE: RNA
<213> ORGANISM: Homo sapiens

<400> SEQUENCE: 744
uggugcggag agggcccaca gug 23

<210> SEQ ID NO 745

<211> LENGTH: 23
<212> TYPE: RNA
<213> ORGANISM: Homo sapiens

<400> SEQUENCE: 745
aaggagcuua caaucuagcu ggg 23

<210> SEQ ID NO 746
<211> LENGTH: 22
<212> TYPE: RNA
<213> ORGANISM: Homo sapiens

<400> SEQUENCE: 746
ugcggggcua gggcuaacag ca 22

<210> SEQ ID NO 747
<211> LENGTH: 22
<212> TYPE: RNA
<213> ORGANISM: Homo sapiens

<400> SEQUENCE: 747
uuugugaccu gguccacuaa cc 22

<210> SEQ ID NO 748
<211> LENGTH: 22
<212> TYPE: RNA
<213> ORGANISM: Homo sapiens

<400> SEQUENCE: 748
gaugguugac cagagagcac ac 22

<210> SEQ ID NO 749
<211> LENGTH: 23
<212> TYPE: RNA
<213> ORGANISM: Homo sapiens

<400> SEQUENCE: 749
uggaagacua gugauuuugu ugu 23

<210> SEQ ID NO 750
<211> LENGTH: 20
<212> TYPE: RNA
<213> ORGANISM: Homo sapiens

<400> SEQUENCE: 750
cggcucuggg ucugugggga 20

<210> SEQ ID NO 751
<211> LENGTH: 22
<212> TYPE: RNA
<213> ORGANISM: Homo sapiens

<400> SEQUENCE: 751
gcagcagggu gaaacugaca ca 22

<210> SEQ ID NO 752
<211> LENGTH: 22
<212> TYPE: RNA
<213> ORGANISM: Homo sapiens

<400> SEQUENCE: 752
gcaggugcuc acuuguccuc cu 22

<210> SEQ ID NO 753
<211> LENGTH: 21
<212> TYPE: RNA
<213> ORGANISM: Homo sapiens

<400> SEQUENCE: 753
uggaggagaa ggaaggugau g 21

<210> SEQ ID NO 754
<211> LENGTH: 22
<212> TYPE: RNA
<213> ORGANISM: Homo sapiens

<400> SEQUENCE: 754
acuccagccc cacagccuca gc 22

<210> SEQ ID NO 755
<211> LENGTH: 22
<212> TYPE: RNA
<213> ORGANISM: Homo sapiens

<400> SEQUENCE: 755
aggaggaauu ggugcugguc uu 22

<210> SEQ ID NO 756
<211> LENGTH: 23
<212> TYPE: RNA
<213> ORGANISM: Homo sapiens

<400> SEQUENCE: 756
ucugcucaua ccccaugguu ucu 23

<210> SEQ ID NO 757
<211> LENGTH: 23
<212> TYPE: RNA
<213> ORGANISM: Homo sapiens

<400> SEQUENCE: 757
ugcaccaugg uugucugagc aug 23

<210> SEQ ID NO 758
<211> LENGTH: 23
<212> TYPE: RNA
<213> ORGANISM: Homo sapiens

<400> SEQUENCE: 758
cugggaucuc cggggucuug guu 23

<210> SEQ ID NO 759
<211> LENGTH: 22
<212> TYPE: RNA
<213> ORGANISM: Homo sapiens

<400> SEQUENCE: 759
ugagaccucu ggguucugag cu 22

<210> SEQ ID NO 760
<211> LENGTH: 23
<212> TYPE: RNA
<213> ORGANISM: Homo sapiens

<400> SEQUENCE: 760
uccaguacca cgugucaggg cca 23

<210> SEQ ID NO 761
<211> LENGTH: 23
<212> TYPE: RNA
<213> ORGANISM: Homo sapiens

<400> SEQUENCE: 761
caguaacaaa gauucauccu ugu 23

<210> SEQ ID NO 762
<211> LENGTH: 22
<212> TYPE: RNA
<213> ORGANISM: Homo sapiens

<400> SEQUENCE: 762
ggagacugau gaguucccgg ga 22

<210> SEQ ID NO 763
<211> LENGTH: 21
<212> TYPE: RNA
<213> ORGANISM: Homo sapiens

<400> SEQUENCE: 763
gcaggaacuu gugagucucc u 21

<210> SEQ ID NO 764
<211> LENGTH: 22
<212> TYPE: RNA
<213> ORGANISM: Homo sapiens

<400> SEQUENCE: 764
cugcccuggc ccgagggacc ga 22

<210> SEQ ID NO 765
<211> LENGTH: 23
<212> TYPE: RNA
<213> ORGANISM: Homo sapiens

<400> SEQUENCE: 765
cggccccacg caccagggua aga 23

<210> SEQ ID NO 766
<211> LENGTH: 21
<212> TYPE: RNA
<213> ORGANISM: Homo sapiens

<400> SEQUENCE: 766
ccuggaaaca cugagguugu g 21

<210> SEQ ID NO 767
<211> LENGTH: 22
<212> TYPE: RNA
<213> ORGANISM: Homo sapiens

<400> SEQUENCE: 767
uggugguuua caaaguaauu ca 22

<210> SEQ ID NO 768
<211> LENGTH: 22
<212> TYPE: RNA
<213> ORGANISM: Homo sapiens

<400> SEQUENCE: 768
uggauuucuu ugugaaucac ca 22

<210> SEQ ID NO 769
<211> LENGTH: 20
<212> TYPE: RNA
<213> ORGANISM: Homo sapiens

<400> SEQUENCE: 769
guagaggaga uggcgcaggg 20

<210> SEQ ID NO 770
<211> LENGTH: 22
<212> TYPE: RNA
<213> ORGANISM: Homo sapiens

<400> SEQUENCE: 770
aggcagcggg guguagugga ua 22

<210> SEQ ID NO 771
<211> LENGTH: 22
<212> TYPE: RNA
<213> ORGANISM: Homo sapiens

<400> SEQUENCE: 771
uccauuacac uacccugccu cu 22

<210> SEQ ID NO 772
<211> LENGTH: 22
<212> TYPE: RNA
<213> ORGANISM: Homo sapiens

<400> SEQUENCE: 772
gugaacgggc gccaucccga gg 22

<210> SEQ ID NO 773
<211> LENGTH: 21
<212> TYPE: RNA
<213> ORGANISM: Homo sapiens

<400> SEQUENCE: 773
cuugggagcc cuguuagacu c 21

<210> SEQ ID NO 774
<211> LENGTH: 21
<212> TYPE: RNA
<213> ORGANISM: Homo sapiens

<400> SEQUENCE: 774
uacucaaaaa gcugucaguc a 21

<210> SEQ ID NO 775
<211> LENGTH: 21
<212> TYPE: RNA
<213> ORGANISM: Homo sapiens

<400> SEQUENCE: 775
uuaauaucgg acaaccauug u 21

<210> SEQ ID NO 776
<211> LENGTH: 21
<212> TYPE: RNA
<213> ORGANISM: Homo sapiens

<400> SEQUENCE: 776

```
uacuuggaaa ggcaucaguu g                                             21

<210> SEQ ID NO 777
<211> LENGTH: 22
<212> TYPE: RNA
<213> ORGANISM: Homo sapiens

<400> SEQUENCE: 777

ugcaacgaac cugagccacu ga                                            22

<210> SEQ ID NO 778
<211> LENGTH: 22
<212> TYPE: RNA
<213> ORGANISM: Homo sapiens

<400> SEQUENCE: 778

ugcaacuuac cugagucauu ga                                            22

<210> SEQ ID NO 779
<211> LENGTH: 21
<212> TYPE: RNA
<213> ORGANISM: Homo sapiens

<400> SEQUENCE: 779

cacugugucc uuucugcgua g                                             21

<210> SEQ ID NO 780
<211> LENGTH: 22
<212> TYPE: RNA
<213> ORGANISM: Homo sapiens

<400> SEQUENCE: 780

cacuggcucc uuucugggua ga                                            22

<210> SEQ ID NO 781
<211> LENGTH: 23
<212> TYPE: RNA
<213> ORGANISM: Homo sapiens

<400> SEQUENCE: 781

gcagcagaga auaggacuac guc                                           23

<210> SEQ ID NO 782
<211> LENGTH: 20
<212> TYPE: RNA
<213> ORGANISM: Homo sapiens

<400> SEQUENCE: 782

agagucuugu gaugucuugc                                               20

<210> SEQ ID NO 783
<211> LENGTH: 23
<212> TYPE: RNA
<213> ORGANISM: Homo sapiens

<400> SEQUENCE: 783

agguugggau cgguugcaau gcu                                           23

<210> SEQ ID NO 784
<211> LENGTH: 22
<212> TYPE: RNA
<213> ORGANISM: Homo sapiens

<400> SEQUENCE: 784
```

uauugcacuu gucccggccu gu 22

<210> SEQ ID NO 785
<211> LENGTH: 22
<212> TYPE: RNA
<213> ORGANISM: Homo sapiens

<400> SEQUENCE: 785
uauugcacuc gucccggccu cc 22

<210> SEQ ID NO 786
<211> LENGTH: 22
<212> TYPE: RNA
<213> ORGANISM: Homo sapiens

<400> SEQUENCE: 786
ugugcgcagg gagaccucuc cc 22

<210> SEQ ID NO 787
<211> LENGTH: 22
<212> TYPE: RNA
<213> ORGANISM: Homo sapiens

<400> SEQUENCE: 787
ugucuacuac uggagacacu gg 22

<210> SEQ ID NO 788
<211> LENGTH: 23
<212> TYPE: RNA
<213> ORGANISM: Homo sapiens

<400> SEQUENCE: 788
ccaguuaccg cuuccgcuac cgc 23

<210> SEQ ID NO 789
<211> LENGTH: 23
<212> TYPE: RNA
<213> ORGANISM: Homo sapiens

<400> SEQUENCE: 789
caaagugcug uucgugcagg uag 23

<210> SEQ ID NO 790
<211> LENGTH: 22
<212> TYPE: RNA
<213> ORGANISM: Homo sapiens

<400> SEQUENCE: 790
acaguagagg gaggaaucgc ag 22

<210> SEQ ID NO 791
<211> LENGTH: 22
<212> TYPE: RNA
<213> ORGANISM: Homo sapiens

<400> SEQUENCE: 791
auccgcgcuc ugacucucug cc 22

<210> SEQ ID NO 792
<211> LENGTH: 24
<212> TYPE: RNA
<213> ORGANISM: Homo sapiens

<400> SEQUENCE: 792
uggggagcug aggcucuggg ggug 24

<210> SEQ ID NO 793
<211> LENGTH: 21
<212> TYPE: RNA
<213> ORGANISM: Homo sapiens

<400> SEQUENCE: 793
aaggcagggc ccccgcuccc c 21

<210> SEQ ID NO 794
<211> LENGTH: 23
<212> TYPE: RNA
<213> ORGANISM: Homo sapiens

<400> SEQUENCE: 794
cacccggcug ugugcacaug ugc 23

<210> SEQ ID NO 795
<211> LENGTH: 22
<212> TYPE: RNA
<213> ORGANISM: Homo sapiens

<400> SEQUENCE: 795
cacauggccg aaacagagaa gu 22

<210> SEQ ID NO 796
<211> LENGTH: 22
<212> TYPE: RNA
<213> ORGANISM: Homo sapiens

<400> SEQUENCE: 796
ucuucucugu uuuggccaug ug 22

<210> SEQ ID NO 797
<211> LENGTH: 22
<212> TYPE: RNA
<213> ORGANISM: Homo sapiens

<400> SEQUENCE: 797
aaauuauugu acaucggaug ag 22

<210> SEQ ID NO 798
<211> LENGTH: 22
<212> TYPE: RNA
<213> ORGANISM: Homo sapiens

<400> SEQUENCE: 798
uucaacgggu auuuauugag ca 22

<210> SEQ ID NO 799
<211> LENGTH: 23
<212> TYPE: RNA
<213> ORGANISM: Homo sapiens

<400> SEQUENCE: 799
uuuggcacua gcacauuuuu gcu 23

<210> SEQ ID NO 800
<211> LENGTH: 22
<212> TYPE: RNA
<213> ORGANISM: Homo sapiens

<400> SEQUENCE: 800
cuauacaacu uacuacuuuc cc 22

<210> SEQ ID NO 801
<211> LENGTH: 22
<212> TYPE: RNA
<213> ORGANISM: Homo sapiens

<400> SEQUENCE: 801
ugagguagua aguuguauug uu 22

<210> SEQ ID NO 802
<211> LENGTH: 22
<212> TYPE: RNA
<213> ORGANISM: Homo sapiens

<400> SEQUENCE: 802
aacccguaga uccgaucuug ug 22

<210> SEQ ID NO 803
<211> LENGTH: 22
<212> TYPE: RNA
<213> ORGANISM: Homo sapiens

<400> SEQUENCE: 803
cacccguaga accgaccuug cg 22

<210> SEQ ID NO 804
<211> LENGTH: 22
<212> TYPE: DNA
<213> ORGANISM: Homo sapiens

<400> SEQUENCE: 804
caaacaccat tgtcacactc ca 22

<210> SEQ ID NO 805
<211> LENGTH: 20
<212> TYPE: DNA
<213> ORGANISM: Homo sapiens

<400> SEQUENCE: 805
ggcattcacc gcgtgcctta 20

<210> SEQ ID NO 806
<211> LENGTH: 24
<212> TYPE: DNA
<213> ORGANISM: Homo sapiens

<400> SEQUENCE: 806
tcacaggtta aagggtctca ggga 24

<210> SEQ ID NO 807
<211> LENGTH: 22
<212> TYPE: DNA
<213> ORGANISM: Homo sapiens

<400> SEQUENCE: 807
cgcattatta ctcacggtac ga 22

<210> SEQ ID NO 808
<211> LENGTH: 22
<212> TYPE: DNA

<213> ORGANISM: Homo sapiens

<400> SEQUENCE: 808
cacattatta ctcacggtac ga 22

<210> SEQ ID NO 809
<211> LENGTH: 22
<212> TYPE: DNA
<213> ORGANISM: Homo sapiens

<400> SEQUENCE: 809
agccaagctc agacggatcc ga 22

<210> SEQ ID NO 810
<211> LENGTH: 21
<212> TYPE: DNA
<213> ORGANISM: Homo sapiens

<400> SEQUENCE: 810
aaagagaccg gttcactgtg a 21

<210> SEQ ID NO 811
<211> LENGTH: 21
<212> TYPE: DNA
<213> ORGANISM: Homo sapiens

<400> SEQUENCE: 811
aaagagaccg gttcactgtg g 21

<210> SEQ ID NO 812
<211> LENGTH: 22
<212> TYPE: DNA
<213> ORGANISM: Homo sapiens

<400> SEQUENCE: 812
atactttttg gggtaagggc tt 22

<210> SEQ ID NO 813
<211> LENGTH: 21
<212> TYPE: DNA
<213> ORGANISM: Homo sapiens

<400> SEQUENCE: 813
gcaagcccag accgcaaaaa g 21

<210> SEQ ID NO 814
<211> LENGTH: 22
<212> TYPE: DNA
<213> ORGANISM: Homo sapiens

<400> SEQUENCE: 814
atgccctttc atcattgcac tg 22

<210> SEQ ID NO 815
<211> LENGTH: 21
<212> TYPE: DNA
<213> ORGANISM: Homo sapiens

<400> SEQUENCE: 815
gtagtgcaac agggaaagag t 21

<210> SEQ ID NO 816
<211> LENGTH: 22

<212> TYPE: DNA
<213> ORGANISM: Homo sapiens

<400> SEQUENCE: 816
cagctggttg aaggggacca aa 22

<210> SEQ ID NO 817
<211> LENGTH: 22
<212> TYPE: DNA
<213> ORGANISM: Homo sapiens

<400> SEQUENCE: 817
tagctggttg aaggggacca aa 22

<210> SEQ ID NO 818
<211> LENGTH: 23
<212> TYPE: DNA
<213> ORGANISM: Homo sapiens

<400> SEQUENCE: 818
ttggtgacta ggtggcccac agg 23

<210> SEQ ID NO 819
<211> LENGTH: 23
<212> TYPE: DNA
<213> ORGANISM: Homo sapiens

<400> SEQUENCE: 819
ctacgcgtat tcttaagcaa taa 23

<210> SEQ ID NO 820
<211> LENGTH: 22
<212> TYPE: DNA
<213> ORGANISM: Homo sapiens

<400> SEQUENCE: 820
atacatactt ctttacattc ca 22

<210> SEQ ID NO 821
<211> LENGTH: 21
<212> TYPE: DNA
<213> ORGANISM: Homo sapiens

<400> SEQUENCE: 821
gagctacagt gcttcatctc a 21

<210> SEQ ID NO 822
<211> LENGTH: 22
<212> TYPE: DNA
<213> ORGANISM: Homo sapiens

<400> SEQUENCE: 822
agaacagtat ttccaggaat cc 22

<210> SEQ ID NO 823
<211> LENGTH: 23
<212> TYPE: DNA
<213> ORGANISM: Homo sapiens

<400> SEQUENCE: 823
agggattcct gggaaaactg gac 23

<210> SEQ ID NO 824

<211> LENGTH: 22
<212> TYPE: DNA
<213> ORGANISM: Homo sapiens

<400> SEQUENCE: 824
acccttatca gttctccgtc ca 22

<210> SEQ ID NO 825
<211> LENGTH: 22
<212> TYPE: DNA
<213> ORGANISM: Homo sapiens

<400> SEQUENCE: 825
taaccaatgt gcagactact gt 22

<210> SEQ ID NO 826
<211> LENGTH: 23
<212> TYPE: DNA
<213> ORGANISM: Homo sapiens

<400> SEQUENCE: 826
gaacaggtag tctgaacact ggg 23

<210> SEQ ID NO 827
<211> LENGTH: 22
<212> TYPE: DNA
<213> ORGANISM: Homo sapiens

<400> SEQUENCE: 827
aggcatagga tgacaaaggg aa 22

<210> SEQ ID NO 828
<211> LENGTH: 22
<212> TYPE: DNA
<213> ORGANISM: Homo sapiens

<400> SEQUENCE: 828
acaaaccttt tgttcgtctt at 22

<210> SEQ ID NO 829
<211> LENGTH: 22
<212> TYPE: DNA
<213> ORGANISM: Homo sapiens

<400> SEQUENCE: 829
actgcctgtc tgtgcctgct gt 22

<210> SEQ ID NO 830
<211> LENGTH: 23
<212> TYPE: DNA
<213> ORGANISM: Homo sapiens

<400> SEQUENCE: 830
tccaatcagt tcctgatgca gta 23

<210> SEQ ID NO 831
<211> LENGTH: 21
<212> TYPE: DNA
<213> ORGANISM: Homo sapiens

<400> SEQUENCE: 831
agaattgcgt ttggacaatc a 21

<210> SEQ ID NO 832
<211> LENGTH: 22
<212> TYPE: DNA
<213> ORGANISM: Homo sapiens

<400> SEQUENCE: 832
tggggtattt gacaaactga ca 22

<210> SEQ ID NO 833
<211> LENGTH: 22
<212> TYPE: DNA
<213> ORGANISM: Homo sapiens

<400> SEQUENCE: 833
acaaccagct aagacactgc ca 22

<210> SEQ ID NO 834
<211> LENGTH: 22
<212> TYPE: DNA
<213> ORGANISM: Homo sapiens

<400> SEQUENCE: 834
aactcagtaa tggtaacggt tt 22

<210> SEQ ID NO 835
<211> LENGTH: 21
<212> TYPE: DNA
<213> ORGANISM: Homo sapiens

<400> SEQUENCE: 835
ttttggtgca tatttacttt a 21

<210> SEQ ID NO 836
<211> LENGTH: 22
<212> TYPE: DNA
<213> ORGANISM: Homo sapiens

<400> SEQUENCE: 836
aactatacaa cctactacct ca 22

<210> SEQ ID NO 837
<211> LENGTH: 23
<212> TYPE: DNA
<213> ORGANISM: Homo sapiens

<400> SEQUENCE: 837
tcatacagct agataaccaa aga 23

<210> SEQ ID NO 838
<211> LENGTH: 9
<212> TYPE: PRT
<213> ORGANISM: Artificial Sequence
<220> FEATURE:
<223> OTHER INFORMATION: mutated viral glycoprotein gB:D285
<220> FEATURE:
<221> NAME/KEY: misc_feature
<222> LOCATION: (5)..(5)
<223> OTHER INFORMATION: Xaa can be any naturally occurring amino acid

<400> SEQUENCE: 838

Val Tyr Pro Tyr Xaa Glu Phe Val Leu
1 5

<210> SEQ ID NO 839
<211> LENGTH: 9

<212> TYPE: PRT
<213> ORGANISM: Artificial Sequence
<220> FEATURE:
<223> OTHER INFORMATION: mutated viral glycoprotein gB:A549
<220> FEATURE:
<221> NAME/KEY: misc_feature
<222> LOCATION: (6)..(6)
<223> OTHER INFORMATION: Xaa can be any naturally occurring amino acid

<400> SEQUENCE: 839

Lys Leu Asn Pro Asn Xaa Ile Ala Ser
1               5

<210> SEQ ID NO 840
<211> LENGTH: 9
<212> TYPE: PRT
<213> ORGANISM: Artificial Sequence
<220> FEATURE:
<223> OTHER INFORMATION: mutated viral glycoprotein gB:S668
<220> FEATURE:
<221> NAME/KEY: misc_feature
<222> LOCATION: (5)..(5)
<223> OTHER INFORMATION: Xaa can be any naturally occurring amino acid

<400> SEQUENCE: 840

Ile Thr Thr Val Xaa Thr Phe Ile Asp
1               5

<210> SEQ ID NO 841
<211> LENGTH: 9
<212> TYPE: PRT
<213> ORGANISM: Artificial Sequence
<220> FEATURE:
<223> OTHER INFORMATION: mutated viral glycoprotein gH:N753
<220> FEATURE:
<221> NAME/KEY: misc_feature
<222> LOCATION: (5)..(5)
<223> OTHER INFORMATION: Xaa can be any naturally occurring amino acid

<400> SEQUENCE: 841

Val Asp Thr Asp Xaa Thr Gln Gln Gln
1               5

<210> SEQ ID NO 842
<211> LENGTH: 9
<212> TYPE: PRT
<213> ORGANISM: Artificial Sequence
<220> FEATURE:
<223> OTHER INFORMATION: mutated viral glycoprotein gH:A778
<220> FEATURE:
<221> NAME/KEY: misc_feature
<222> LOCATION: (5)..(5)
<223> OTHER INFORMATION: Xaa can be any naturally occurring amino acid

<400> SEQUENCE: 842

Val Pro Ser Thr Xaa Leu Leu Leu Phe
1               5

<210> SEQ ID NO 843
<211> LENGTH: 32767
<212> TYPE: DNA
<213> ORGANISM: Artificial Sequence
<220> FEATURE:
<223> OTHER INFORMATION: recombinant viral vector ONCR-131

<400> SEQUENCE: 843
aaaaaagctg aacgagaaac gtaaaatgat ataaatatca atatattaaa ttagattttg     60
cataaaaaac agactacata atactgtaaa acacaacata tccagtcact atgaatcaac    120

-continued tacttagatg gtattagtga cctgtagtcg accgacagcc ttccaaatgt tcttcgggtg 180
atgctgccaa cttagtcgac cgacagcctt ccaaatgttc ttctcaaacg gaatcgtcgt 240
atccagccta ctcgctattg tcctcaatgc cgtattaaat cataaaaaga aataagaaaa 300
agaggtgcga gcctcttttt tgtgtgacaa aataaaaaca tctacctatt catatacgct 360
agtgtcatag tcctgaaaat catctgcatc aagaacaatt tcacaactct tatacttttc 420
tcttacaagt cgttcggctt catctggatt ttcagcctct atacttacta aacgtgataa 480
agtttctgta atttctactg tatcgacctg cagactggct gtgtataagg gagcctgaca 540
tttatattcc ccagaacatc aggttaatgg cgtttttgat gtcattttcg cggtggctga 600
gatcagccac ttcttccccg ataacggaga ccggcacact ggccatatcg gtggtcatca 660
tgcgccagct ttcatccccg atatgcacca ccgggtaaag ttcacgggag actttatctg 720
acagcagacg tgcactggcc agggggatca ccatccgtcg cccgggcgtg tcaataatat 780
cactctgtac atccacaaac agacgataac ggctctctct tttataggtg taaaccttaa 840
actgcatttc accagcccct gttctcgtca gcaaaagagc cgttcatttc aataaaccgg 900
gcgacctcag ccatcccttc ctgattttcc gctttccagc gttcggcacg cagacgacgg 960
gcttcattct gcatggttgt gcttaccaga ccggagatat tgacatcata tatgccttga 1020
gcaactgata gctgtcgctg tcaactgtca ctgtaatacg ctgcttcata gcatacctct 1080
ttttgacata cttcgggtat acatatcagt atatattctt ataccgcaaa aatcagcgcg 1140
caaatacgca tactgttatc tggcttttag taagccggat ccacgcggcg tttacgcccc 1200
ccctgccact catcgcagta ctgttgtaat tcattaagca ttctgccgac atggaagcca 1260
tcacaaacgg catgatgaac ctgaatcgcc agcggcatca gcaccttgtc gccttgcgta 1320
taatatttgc ccatggtgaa aacgggggcg aagaagttgt ccatattggc cacgtttaaa 1380
aaggccgtaa tatccagctg aacggtctgg ttataggtac attgagcaac tgactgaaat 1440
gcctcaaaat gttctttacg atgccattgg gatatatcaa cggtggtata tccagtgatt 1500
tttttctcca ttttagcttc cttagctcct gaaaatctcg ataactcaaa aaatacgccc 1560
ggtagtgatc ttatttcatt atggtgaaag ttggaacctc ttacgtgccg atcaacgtct 1620
cattttcgcc aaaagttggc ccagggcttc ccggtatcaa cagggacacc aggatttatt 1680
tattctgcga agtgatcttc cgtcacaggt atttattcgg cgcaaagtgc gtcgggtgat 1740
gctgccaact tagtcgacta caggtcacta ataccatcta agtagttgat tcatagtgac 1800
tggatatgtt gtgttttaca gtattatgta gtctgttttt tatgcaaaat ctaatttaat 1860
atattgatat ttatatcatt ttacgtttct cgttcagctt tcttgtacaa agtggtttta 1920
atggaccgcc cgcaaggggg ggggggcatt tcagtgtcgg gtgacgagcg cgatccggcc 1980
gggatcctag gaccccaaaa gtttgtctgc gtattccagg gcggggctca gttgaatctc 2040
ccgcagcacc tctaccagca ggtccgcggt gggctggaga aactcggccg tcccggggca 2100
ggcggttgtc gggggtggag gcgcggcgcc caccccgtgt gccgcgcctg gcgtctcctc 2160
tgggggcgac ccgtaaatgg ttgcagtgat gtaaatggtg tccgcggtcc agaccacggt 2220
caaaatgccg gccgtggcgc tccgggcgct ttcgccgcgc gaggagctga cccaggagtc 2280
gaacggatac gcgtacatat gggcgtccca cccgcgttcg agcttctggt tgctgtcccg 2340
gcctataaag cggtaggcac aaaattcggc gcgacagtcg ataatcacca acagcccaat 2400
gggggtgtgc tggataacaa cgcctccgcg cggcaggcgg tcctggcgct cccggccccg 2460
taccatgatc gcgcgggtgc cgtactcaaa aacatgcacc acctgcgcgg cgtcgggcag 2520

-continued

```
tgcgctggtc agcgaggccc tggcgtggca taggctatac gcgatggtcg tctgtggatt   2580
ggacatctcg cggtgggtag tgagtccccc gggccgggtt cggtggaact gtaaggggac   2640
ggcgggttaa tagacaatga ccacgttcgg atcgcgcaga gccgatagta tgtgctcact   2700
aatgacgtca tcgcgctcgt ggcgctcccg gagcggattt aagttcatgc gaaggaattc   2760
ggaggaggtg gtgcgggaca tggccacgta cgcgctgttg aggcgcaggt tgccgggcgt   2820
aaagcagatg gcgaccttgt ccaggctaag gccctgggag cgcgtgatgg tcatggcaag   2880
cttggagctg atgccgtagt cggcgtttat ggccatggcc agctccgtag agtcaatgga   2940
ctcgacaaac tcgctgatgt tggtgttgac gacggacatg aagccgtgtt ggtcccgcaa   3000
gaccacgtaa ggcagggggg cctcttccag taactcggcc acgttggccg tcgcgtgccg   3060
cctccgcagc tcgtccgcaa aggcaaacac ccgtgcgtac gtgtatccca tgagcgtata   3120
attgtccgtc tgcagggcga cggacatcag ccccccgcgc ggcgagccgg tcagcatctc   3180
gcagccccgg aagataacgt tgtccacgta cgtgctaaag gggcgactt caaatgcctc   3240
cccgaagagc tcttggagga ttcggaatct cccgaggaag gcccgcttca gcagcgcaaa   3300
ctgggtgtga acggcggcgg tggtctccgg ttccccgggg gtgtagtggc agtaaaacac   3360
gtcgagctgt tgttcgtcca gccccgcgaa aataacgtcg aggtcgtcgt cgggaaaatc   3420
gtccgggccc ccgtcccgcg gccccagttg cttaaaatca aacgcacgct cgccgggggc   3480
gcctgcgtcg gccattaccg acgcctgcgt cggcaccccc gaagatttgg ggcgcagaga   3540
cagaatctcc gccgttagtt ctcccatgcg ggcgtaggcg agggtcctct gggtcgcatc   3600
caggcccggg cgctgcagaa agttgtaaaa ggagataagc ccgctaaata tgagccgcga   3660
caggaacctg taggcaaact ccaccgaagt ctccccctga gtctttacaa agctgtcgtc   3720
acgcaacact gcctcgaagg cccggaacgt cccactaaac ccaaaaacca gttttcgcag   3780
gcgcgcggtc accgcgatct ggctgttgag gacgtaagtg acgtcgttgc gggccacgac   3840
cagctgctgt ttgctgtgca cctcgcagcg catgtgcccc gcgtcctggt cctggctctg   3900
cgagtagttg gtgatgcggc tggcgttggc cgtgagccac ttttcaatcg tcaggccggg   3960
ctggtgtgtc agccgtcggt attcgtcaaa ctccttgacc gacacgaacg taagcacggg   4020
gagggtgaac acgacgaact ccccctcacg ggtcaccttc aggtaggcgt ggagcttggc   4080
catgtacgcg ctcacctctt tgtgggagga gaacagccgc gtccagccgg ggaggttggc   4140
ggggttggtg atgtagtttt ccgggacgac gaagcgatcc acgaactgca tgtgctcctc   4200
ggtgatgggc aggccgtact ccagcacctt catgaggtta ccgaactcgt gctcgacgca   4260
ccgtttgttg ttaataaaaa tggcccagct atacgagagg cgggcgtact cgcgcagcgt   4320
gcggttgcag atgaggtacg tgagcacgtt ctcgctctgg cggacggaac accgcagttt   4380
ctggtgctcg aaggtcgact ccagggacgc cgtctgcgtc ggcgagccca cacacaccaa   4440
cacgggccgc aggcgggccg cgtactgggg ggtgtggtac agggcgttaa tcatccacca   4500
gcaatacacc acggccgtga ggaggtgacg cccaaggagc ccggcctcgt cgatgacgat   4560
cacgttgctg cgggtaaagg ccggcagcgc cccgtgggtg gccggggcca accgcgtcag   4620
ggcgccctcg gccaacccca gggtccgttc cagggcggcc agggcgcgaa actcgttccg   4680
caactcctcg cccccggagg cggccagggc gcgcttcgtg aggtccaaaa tcacctccca   4740
gtagtacgtc agatctcgtc gctgcaggtc ctccagcgag gcggggttgc tggtcagggt   4800
gtacgggtac tgtcccagtt gggcctggac gtgattcccg cgaaacccaa attcatgaaa   4860
```

-continued

```
gatggtgttg atgggtcggc tgagaaaggc gcccgagagt ttggcgtaca tgttttgggc   4920
cgcaatgcgc gtggcgcccg tcaccacaca gtccaagacc tcgttgattg tctgcacgca   4980
cgtgctcttt ccggagccag cgttgccggt gataagatac accgcgaacg gaaactccct   5040
gaggggcagg cctgcggggg actctaaggc cgccacgtcc cggaaccact gcagatgggg   5100
cacttgcgct ccgtcgagct gttgttgcga gagctctcgg atgcgcttaa ggattggctg   5160
caccccgtgc atagacgtaa aatttaaaaa ggcctcggcc ctccctggaa cggctggtcg   5220
gtccccgggt tgctgaaggt gcggcgggcc gggtttctgt ccgtctagct ggcgctcccc   5280
gccggccgcc gccatgaccg caccacgctc gcgggccccc actacgcgtg cgcgggggga   5340
cacggaagcg ctgtgctccc ccgaggacgg ctgggtaaag gttcacccca gccccggtac   5400
gatgctgttc cgcgagattc tccacgggca gctggggtat accgagggcc agggggtgta   5460
caacgtcgtc cggtccagcg aggcgaccac ccggcagctg caggcggcga tctttcacgc   5520
gctcctcaac gccaccactt accgggacct cgaggcggac tggctcggcc acgtggcggc   5580
ccgcggtctg cagccccaac ggctggttcg ccggtacagg aacgcccggg aggcggatat   5640
cgccggggtg gccgagcggg tgttcgacac gtggcggaac acgcttagga cgacgctgct   5700
ggactttgcc cacgggttgg tcgcctgctt tgcgccgggc ggcccgagcg gcccgtcaag   5760
cttccccaaa tatatcgact ggctgacgtg cctggggctg gtccccatat tacgcaagcg   5820
acaagaaggg ggtgtgacgc agggtctgag ggcgtttctc aagcagcacc cgctgacccg   5880
ccagctggcc acggtcgcgg aggccgcgga gcgcgccggc cccgggtttt ttgagctggc   5940
gctggccttc gactccacgc gcgtggcgga ctacgaccgc gtgtatatct actacaacca   6000
ccgccggggc gactggctcg tgcgagaccc catcagcggg cagcgcggag aatgtctggt   6060
gctgtggccc cccttgtgga ccggggaccg tctggtcttc gattcgcccg tccagcggct   6120
gtttcccgag atcgtcgcgt gtcactccct ccgggaacac gcgcacgtct gccggctgcg   6180
caataccgcg tccgtcaagg tgctgctggg gcgcaagagc gacagcgagc gcggggtggc   6240
cggtgccgcg cgggtcgtta acaaggtgtt gggggaggac gacgagacca aggccgggtc   6300
ggccgcctcg cgcctcgtgc ggcttatcat caacatgaag ggcatgcgcc acgtaggcga   6360
cattaacgac accgtgcgtt cctacctcga cgaggccggg gggcacctga tagacgcccc   6420
ggccgtcgac ggtaccctcc ctggattcgg caagggcgga aacagccgcg ggtctgcggg   6480
ccaggaccag ggggggcggg cgccgcagct tcgccaggcc ttccgcacgg ccgtggttaa   6540
caacatcaac ggcgtgttgg agggctatat aaataacctg tttggaacca tcgagcgcct   6600
gcgcgagacc aacgcgggcc tggcgaccca attgcaggag cgcgaccgcg agctccggcg   6660
cgcaacagcg ggggccctgg agcgccagca gcgcgcggcc gacctggcgg ccgagtccgt   6720
gaccggtgga tgcggcagcc gccctgcggg ggcggacctg ctccgggccg actatgacat   6780
tatcgacgtc agcaagtcca tggacgacga cacgtacgtc gccaacagct ttcagcaccc   6840
gtacatccct tcgtacgccc aggacctgga gcgcctgtcg cgcctctggg agcacgagct   6900
ggtgcgctgt tttaaaattc tgtgtcaccg caacaaccag ggccaagaga cgtcgatctc   6960
gtactccagc ggggcgatcg ccgcattcgt cgccccctac tttgagtcag tgcttcgggc   7020
cccccgggta ggcgcgccca tcacgggctc cgatgtcatc ctgggggagg aggagttatg   7080
ggatgcggtg tttaagaaaa cccgcctgca aacgtacctg acagacatcg cggccctgtt   7140
cgtcgcggac gtccagcacg cagcgctgcc cccgcccccc tccccggtcg gcgccgattt   7200
ccggcccggc gcgtccccgc ggggccggtc cagatcgcgg tcgcccggaa gaactgcgcg   7260
```

aggcgcgccg gaccagggcg ggggcatcgg gcaccgggat ggccgccgcg acggccgacg 7320
atgaggggtc ggccgccacc atcctcaagc aggccatcgc cggggaccgc agcctggtcg 7380
aggcggccga ggcgattagc cagcagacgc tgctccgcct ggcctgcgag gtgcgccagg 7440
tcggcgaccg ccagccgcgg tttaccgcca ccagcatcgc gcgcgtcgac gtcgcgcctg 7500
ggtgccggtt gcggttcgtt ctggacggga gtcccgagga cgcctatgtg acgtcggagg 7560
attactttaa gcgctgctgc ggccagtcca gttatcgcgg cttcgcggtg gcggtcctga 7620
cggccaacga ggaccacgtg cacagcctgg ccgtgccccc cctcgttctg ctgcaccggt 7680
tctccctgtt caaccccagg gacctcctgg actttgagct tgcctgtctg ctgatgtacc 7740
tggagaactg cccccgaagc cacgccaccc cgtcgacctt tgccaaggtt ctggcgtggc 7800
tcggggtcgc gggtcgccgc acgtccccat tcgaacgcgt tcgctgcctt ttcctccgca 7860
gttgccactg ggtcctaaac acactcatgt tcatggtgta cgtaaaaccg ttcgacgacg 7920
agttcgtcct gccccactgg tacatggccc ggtacctgct ggccaacaac ccgccccccg 7980
ttctctcggc cctgttctgt gccaccccga cgagctcctc attccggctg ccggggccgc 8040
ccccccgctc cgactgcgtg gcctataacc ccgccgggat catggggagc tgctgggcgt 8100
cggaggaggt gcgcgcgcct ctggtctatt ggtggctttc ggagacccca aaacgacaga 8160
cgtcgtcgct gttttatcag ttttgttgaa ttttaggaaa taaacccggt tttgtttctg 8220
tggcctcccg acggatgcgc gtgtccttac tccgtcttgg tgggtgggtg gctgtgtatg 8280
gcgtcccatc tgtgcgggga ggggggcaag tcggcacgta ttcggacaga ctcaagcaca 8340
taagacgaac aaaaggtttg taacttcgta ccgtgagtaa taatgtggac tttattgctt 8400
aagaatacgc gtagagaaat aagacgaaca aaaggtttgt gattttattg cttaagaata 8460
cgcgtagatg gtcgtaccgt gagtaataat gtggttcata agacgaacaa aaggtttgtg 8520
acattattgc ttaagaatac gcgtaggtgg tcgtaccgtg agtaataatg tgtactttat 8580
tgcttaagaa tacgcgtagg ctatcgtacc gtgagtaata atgtgcctta taagacgaac 8640
aaaaggtttg tacacggggg agcgctcttg tctcagggca atgtttttat tggtcaaact 8700
caggcaaaca gaaacgacat cttgtcgtca aagggataca caaacttccc cccctcgccc 8760
catactcccg ccagcacccc ggtaaacacc aactcaatct cgcgcaggat ttcgcgcagg 8820
tgatgagcgc agtccacggg ggggagcaca aggggccgcg ggtatagatc gacggggacg 8880
ccgaccgact ccccgcctcc gggacagaca cgcacgacgc gccgccagta gtgctctgcg 8940
tccagcaagg cgccgccgcg gaaggcagtg gggggcaagg ggtcgctggc ctcaaagggg 9000
gacacccgaa cgctccagta ctccgcgtcc aaccgtttat taaacgcgtc caagataagg 9060
cggtcgcagg cgtcctccat aaggccccgg gccgtgagtg cgtcctcctc cggcacgcat 9120
gccgttgtca ggcccaggac ccgtcgcagc gtgtcgcgta cgacccctgc cgccgtggtg 9180
tacgcgggcc cgcggagagg aaatccccca agatggtcag tgttgtcgcg ggagttccag 9240
aaccacactc ccgcctggct ccaggcgact gcgtgggtgt agacgccctc gagggccagg 9300
cacagtgggt gccgcagccg gacggcgttg gccctaagca cggctcccac ggccgtctcg 9360
atggcccgcc gggcgtcctc gatcaccccg gaagccgcat ccgcgtcttg ggggtccacg 9420
ttaaagacac cccagaacgc acccccatcg cccccgcaga ccgcgaactt caccgagctg 9480
gccgtctcct cgatctgcag gcagacggcg gccattaccc cacccaggag ctgccgcagc 9540
gcagggcagg cgttgcacgt gtccgggacc aggcgctcca agacggcccc ggcccagggc 9600

-continued

```
tctgagggag cggccaccac cagcgcgtcc agtcttgcta ggcccgtccg gccgtggggg   9660
tccgccagcc cgctcccccc gaggtcggcc agggccgcca ggagctgggc gcgaagtccg   9720
gggaagcaaa accgcgccgt ccagacgggc ccgacggccg cgggcgggtc taacagttgg   9780
atgattttag tggcgggatg ccaccgcgcc accgcctccc gcaccgcggg caggaggcat   9840
ccggctgccg ccgaggccac gccgggccag gctcgcgggg ggaggacgac cctggccccc   9900
accgcgggcc aggcccccag gagcgcggcg taagcggccg cggcccgcg caccaggtcc   9960
cgtgccgact cggccgtggc cggcacggtg aacgtgggcc aacccggaaa ccccaggacg  10020
gcaaagtacg ggacgggtcc cccccggacc tcaaactcgg gccccagaaa ggcaaagacg  10080
ggggccaggg ccccgggggc ggcgtggacc gtggtatgcc actgccggaa aagggcgacg  10140
agcgccggcg cggagaactt ctcgccggcg cttacaaagt agtcgtaatc gcggggcagc  10200
agcacccgtg ccgtgactcg ttgcgggtgc ccgcgtggcc gcaggcccac ctcgcacacc  10260
tcgaccaggt ccccgaacgc gccctccttc ttgatcggcg gaaacgcaag agtctggtat  10320
tcgcgcgcaa atagcgcggt tccggtggtg atgttaacgg tcagcgaagc ggcggacgcg  10380
cactgggggg tgtcgcgaat ggccgccagg cgcgcccacg ccagccgcgc gtcgggatgc  10440
tcggcaacgc gcgccgccag ggccataggg tcgatgtcaa tgttggcctc cgcgaccagg  10500
agagcggcgc gaggggcggc gggcgggccc cacgacgctc tctcaacttt caccaccagt  10560
cccgtgcgtg ggtccgagcc gatacgcagc ggggcgaaca gggccaccgg cccggtctgg  10620
cgctccaggg ccgccaggac gcacgcgtac agcgcccgcc acagagtcgg gttctccagg  10680
ggctccagcg gggaggcggc cggcgtcgtc gcggcgcggg cggccgccac gacggcctgg  10740
acggagacgt ccgcggagcc gtagaaatcc cgcagctccg tcgcggtgac ggagacctcc  10800
gcaaagcgcg cgcgaccctc ccctgcggcg ttgcgacata caaaatacac cagggcgtgg  10860
aagtactcgc gagcgcgggg gggcagccat accgcgtaaa gggtaatggc gctgacgctc  10920
tcctccaccc acacgatatc tgcggtgtcc atcgcacggc ccctaaggat cacgggcggt  10980
ctgtgggtcc catgctgccg tgcctggccg ggcccggtgg gtcgcggaaa ccggtgacgg  11040
gggggggcg gtttttgggg ttggggtggg ggtgggaaac ggcccgggtc cgggggccaa  11100
cttggcccct cggtgcgttc cggcaacagc gccgccggtc cgcggacgac cacgtaccga  11160
acgagtgcgg tcccgagact tatagggtgc taaagttcac cgccccctgc atcatgggcc  11220
aggcctcggt ggggagctcc gacagcgccg cctccaggat gatgtcagcg ttggggttgg  11280
cgctggatga gtgcgtgcgc aaacagcgcc cccacgcggg cacgcgtagc ttgaagcgcg  11340
cgcccgcaaa ctcccgcttg tgggccataa gcagggcgta cagctgcctg tgggtccggc  11400
aggcgctgtg gtcgatgtgg tgggcgtcca acaaccccac gattgtctgt ttggtgaggt  11460
ttttaacgcg ccccgccccg ggaaacgtct gcgtgctttt ggccatctgc acgccaaaca  11520
gttcgcccca gattatcttg aacagcgcca ccgcgtggtc cgtctcgcta acggacccgc  11580
gcgggggaca gccgcttagg gcgtcggcga cgcgcttgac ggcttcctcc gagagcagaa  11640
gtccgtcggt tacgttacag tggcccagtt cgaacaccag ctgcatgtag cggtcgtagt  11700
ggggggtcag taggtccagc acgtcatcgg ggccgaaggt cctcccagat cccccggccg  11760
ccgagtccca atgcaggcgc gcggccatgg tgctgcacag gcacaacagc tcccagacgg  11820
gggttacgtt cagggtgggg ggcagggcca cgagctccag ctctccggtg acgttgatcg  11880
tggggatgac gcccgtggcg tagtggtcat agatccgccg aaatatggcg ctgctgcggg  11940
tggccatggg aacgcggaga caggcctcca gcaacgccag gtaaataaac cgcgtgcgtc  12000
```

```
ccatcaggct gttgaggttg cgcatgagcg cgacaatttc cgccggcgcg acatcggacc  12060
ggaggtattt ttcgacgaaa agacccacct cctccgtctc ggcggcctgg gccggcagcg  12120
acgcctcggg atcccggcac cgcagctccc gtagatcgcg ctgggccctg agggcgtcga  12180
aatgtacgcc ccgcaaaaac agacagaagt cctttggggt cagggtatcg tcgtgtcccc  12240
agaagcgcac gcgtatgcag tttagggtca gcagcatgtg aaggatgtta aggctgtccg  12300
agagacacgc cagcgtgcat ctctcaaagt agtgtttgta acggaatttg ttgtagatgc  12360
gcgacccccg ccccagcgac gtgtcgcatg ccgacgcgtc acagcgcccc ttgaaccggc  12420
gacacagcag gtttgtgacc tgggagaact gcgcgggcca ctggccgcag gaactgacca  12480
cgtgattaag gagcatgggc gtaaagacgg gctccgagcg cgccccggag ccgtccatgt  12540
aaatcagtag ctccccccttg cggagggtgc gcacccgtcc cagggactgg tacacggaca  12600
ccatgtccgg tccgtagttc atgggtttca cgtaggcgaa catgccatca aagtgcaggg  12660
gatcgaagct gaggcccacg gttacgaccg tcgtgtatat aaccacgcgg tattggcccc  12720
acgtggtcac gtccccgagg ggggtgagcg agtgaagcaa cagcacgcgg tccgtaaact  12780
gacggcagaa ccgggccacg atctccgcga aggagaccgt cgacgaaaaa atgcagatgt  12840
tatcgccccc gccaaggcgc gcttccagct ccccaaagaa cgtggccccc cgggcctccg  12900
gagaggcgtc cggagacggg ccgctcggcg gcccgggcgg gcgcagggca gcctgcagga  12960
gctcggtccc cagacgcggg agaaacaggc accggcgcgc cgaaaacccg ggcatggcgt  13020
actcgccgac caccacatgc acgttttttt cgccccggag accgcacagg aagtccacca  13080
actgcgcgtt ggcggttgcg tccatggcga tgatccgagg acagatgcgc agcaggcgta  13140
gcattaacgc atccacgcgg cccagttgct gcatcgttgg cgaatagagc tggcccagcg  13200
tcgacataac ctcgtccaga acgaggacgt cgtagttgtt cagaaggttg gggcccacgc  13260
gatgaaggct ttccacctgg acgataagtc ggtggaaggg gcggtcgttc ataatgtaat  13320
tggtggatga gaagtaggtg acaaagtcga ccaggcctga ctcagcgaac cgcgtcgcta  13380
gggtctgggt aaaactccga cgacaggaga cgacgagcac actcgtgtcc ggagagtgga  13440
tcgcttcccg cagccagcgg atcagcgcgg tagtttttcc cgaccccatt ggcgcgcgga  13500
ccacagtcac gcacctggcc gtcggggcgc tcgcgttggg gaaggtgacg ggtccgtgct  13560
gctgccgctc gatcgttgtt ttcgggtgaa cccggggcac ccattcggcc aaatcccccc  13620
cgtacaacat ccgcgctagc gatacgctcg acgtgtactg ttcgcactcg tcgtccccaa  13680
tgggacgccc ggcccccaga ggatctcccg actccgcgcc ccccacgaaa ggcatgaccg  13740
gggcgcggac ggcgtggtgg gtctggtgtg tgcaggtggc gacgtttgtg gtctctgcgg  13800
tctgcgtcac ggggctcctc gtcctggcct ctgtgttccg ggcacggttt ccctgctttt  13860
acgccacggc gagctcttat gccggggtga actccacggc cgaggtgcgc gggggtgtag  13920
ccgtgcccct caggttggac acgcagagcc ttgtgggcac ttatgtaatc acggccgtgt  13980
tgttgttggc cgtggccgtg tatgccgtgg tcggcgccgt gacctcccgc tacgaccgcg  14040
ccctggacgc gggccgccgt ctggctgcgg cccgcatggc catgccgcac gccacgctga  14100
tcgccggaaa cgtctgctct tggttgctgc agatcaccgt cctgttgctg gcccatcgca  14160
tcagccagct ggcccacctg gtttacgtcc tgcactttgc gtgtctggtg tattttgcgg  14220
cccatttttg caccaggggg gtcctgagcg ggacgtatct gcgtcaggtg cacggcctga  14280
tggagctggc cccgacccat catcgcgtcg tcggcccggc tcgcgccgtg ctgacaaacg  14340
```

```
ccttgctgtt gggcgtcttc ctgtgcacgg ccgacgccgc ggtatccctg aataccatcg  14400
ccgcgttcaa ctttaatttt tcggccccgg gcatgctcat ctgcctgacc gtgctgttcg  14460
ccattctcgt cgtatcgctg ttgttggtgg tcgagggggt gttgtgtcac tacgtgcgcg  14520
tgttggtggg cccccacctg ggggccgtgg ccgccacggg catcgtcggc ctggcctgcg  14580
agcactatta caccaacggc tactacgttg tggagacgca gtggccgggg gctcagacgg  14640
gagtccgcgt cgccctcgcc ctggtcgccg cctttgccct cggcatggcc gtgctccgct  14700
gcacccgcgc ctatctgtat cacaggcggc accacaccaa atttttatg cgcatgcgcg  14760
acacgcgaca ccgcgcacat tccgccctca agcgcgtacg cagttccatg cgcggatcgc  14820
gagacggccg ccacaggccc gcacccggca gcccgcccgg gattcccgaa tatgcggaag  14880
acccctacgc gatctcatac ggcggccagc tcgaccggta cggagattcc gacggggagc  14940
cgatttacga cgaggtggcg gacgaccaaa ccgacgtatt gtacgccaag atacaacacc  15000
cgcggcacct gcccgacgac gatcccatct atgacaccgt tggggggtac gaccccgagc  15060
ccgccgagga ccccgtgtac agcaccgtcc gccgttggta gctgtttggt tccgttttaa  15120
taaaccgttt gtgtttaacc cgaccgtggt gtatgtctgg tgtgtggcgt ccgatcccgt  15180
tactatcacc gtcccccccc cccccctcaac cccggcgatt gtgggttttt taaaaacgac  15240
acgcgtgcga ccgtatacag aacattgttt tggtttttat tcgctatcgg acatgggggg  15300
tggaaactgg gtggcggggc aggcgcctcc gggggtccgc cggtgagtgt ggcgcgaggg  15360
ggggtccgat gaacgcaggc gctgtctccc cggggcccgc gtaaccccgc gcatatccgg  15420
gggcacgtag aaattacctt cctcttcgga ctcgatatcc acgacgtcaa agtcgtgggc  15480
ggtcagcgag acgacctccc cgtcgtcggt gatgaggacg ttgtttcggc agcagcaggg  15540
ccgggccccg gagaacgaga ggcccatagc tcggcgagcg tgtcgtcgaa tgccaggcgg  15600
ctgcttcgct ggatggcctt atagatctcc ggatcgatgc ggacgggggt aatgatcagg  15660
gcgatcggaa cggcctggtt cgggagaatg gacgccttgc tgggtcctgc ggccccgaga  15720
gccccggcgc cgtcctccag gcggaacgtt acgccctcct ccgcgctggt gcggtgcctg  15780
ccgataaacg tcaccagatg cgggtggggg gggcagtcgg ggaagtggct gtcgagcacg  15840
tagccctgca ccaagatctg cttaaagttc gggtgacggg ggttcgcgaa gacgggctcg  15900
cggcggacca gatccccgga gctccaggac acgggggaga tggtgtggcg tccgaggtcg  15960
ggggcgccaa acagaagcac ctccgagaca acgccgctat ttaactccac caaggcccga  16020
tccgcggcgg agcaccgcct tttttcgccc gaggcgtggg cctctgacca ggcctggtct  16080
tgcgtgacga gagcctcctc cgggccgggg acgcgcccgg gcgcgaagta tcgcacgctg  16140
ggcttcggga tcgaccggat aaatgcccgg aacgcctccg gggaccggtg tgccatcaag  16200
tcctcgtacg cggaggccgt ggggtcgctg gggtccatgg ggtcgaaagc gtacttggcc  16260
cggcatttga cctcgtaaaa ggccaggggg gtcttgggga ctggggccag gtagccgtga  16320
atgtcccgag gacagacgag aatatccagg gacgccccga ccatccccgt gtgaccgtcc  16380
atgaggaccc cacacgtatg cacgttctct tcggcgaggt cgctgggttc gtggaagata  16440
aagcgccgcg tgtcggcgcc ggcctcgccg ccgtcgtccg cgcggcccac gcagtagcga  16500
aacagcaggc ttcgggccgt cggctcgttc acccgcccga acatcaccgc cgaagactgt  16560
acatccggcc gcaggctggc gttgtgcttc agccactggg gcgagaaaca cggaccctgg  16620
gggccccagc ggagggtgga tgcggtcgtg aggccccgcc ggagcagggc ccatagctgg  16680
cagtcggcct ggttttgcgt ggccgcctcg taaaacccca tgaggggccg gggcgccacg  16740
```

-continued gcgtccgcgg cggccggggg cccgcggcgc gtcaggcgcc ataggtgccg accgagtccg 16800
cggtccacca tacccgcctc ctcgaggacc acggccaggg aacacagata atccaggcgg 16860
gcccagaggg gaccgatggc cagaggggcg cggacgccgc gcagcaaccc gcgcaggtgg 16920
cgctcgaacg tctcggctag tatatgggag ggcagcgcgt tggggatcac cgacgccgac 16980
cacatagagt caaggtccgg ggagtcggga tcggcgtccg ggtcgcgggc gtgggtgccc 17040
ccaggagata gcggaatgtc tggggtcgga ggccctgagg cgtcagaaag tgccggcgac 17100
gcggcccggg gcttttcgtc tgcggtgtcg gtggcgtgct gatcacgtgg ggggttaacg 17160
ggcgaatggg agctcgggtc cacagctgat gtcgtctggg gtgggggggg caggggacgg 17220
aaggtggttg tcagcggaag actgttaggg cgggggcgct tgggggggct gtcggggcca 17280
cgaggggtgt cctcggccag ggcccaggga cgcttagtca cggtgcgtcc cggcggacat 17340
gctgggccta ccgtggactc catttccgag acgacgtggg gggagcggtg gttgagcgcg 17400
ccgccgggtg aacgctgatt ctcacgacag cgcgtgccgc gcgcacgggt tggtgtgaca 17460
caggcgggac accagcacca ggagaggctt aagctcggga ggcagcgcca ccgacgacag 17520
tatcgccttg tgtgtgtgct ggtaatttat acaccgatcc gtaaacgcgc gccgaatctt 17580
gggattgcgg aggtggcgcc ggatgccctc tgggacgtca tacgccaggc cgtgggtgtt 17640
ggtctcggcc gagttgacaa acagggctgg gtgcagcacg cagcgatagg cgagcagggc 17700
cagggcgaag tccggcgaca gctggttgtt aaaatactgg taaccgggaa accgggtcac 17760
gggtacgccc aggctcgggg cgacgtacac gctaaccacc aactccagca gcgtctggcc 17820
cagggcgtac aggtcaaccg ctaacccgac gtcgtgcttc aggcggtggt tggtaaattc 17880
ggcccgttcg ttgttaaggt atttcaccaa cagctccggg ggctggttat acccgtgacc 17940
caccagggtg tgaaagttgg ctgtggttag ggcggtgggc atgccaaaca tccgggggga 18000
cttgaggtcc ggctcctgga ggcaaaactg cccccgggcg atcgtggagt tggagttgag 18060
ggtgacgagg ctaaagtcgg cgaggacggc ccgccggagc gagacggcgt ccgaccgcag 18120
catgacgagg atgttggcgc acttgatatc caggtggctg atcccgcagg tggtgtttaa 18180
aaacacaacg gcgcgggcca gctccgtgaa gcactggtgg agggccgtcg agaccgaggg 18240
gtttgttgtg cgcagggacg ccagttggcc gatatactta ccgaggtcca tgtcgtacgc 18300
ggggaacact atctgtcgtt gttgcagcga gaacccgagg ggcgcgatga agccgcggat 18360
gttgtgggtg cggccggcgc gtagaacgca ctccccgacc aacagggtcg cgatgagctc 18420
aacggcaaac cactcctttt cctttatggt cttaacggca agcttatgtt cgcgaatcag 18480
ttggacgtca ccgtatcccc cagacccccc gaagcttcgg gccccgggga tctcgagggt 18540
cgtgtagtgt agggcggggt tgatggcgaa cacggggctg catagcttgc ggatgcgcgt 18600
gagggtgagg atgtgcgagg gggacgaggg gggtgcggtt aacgccgcct gggatctgcg 18660
caggggcggg cggttcagtt tggccgccgt accgggcgtc tcgggggacg cgcggcgatg 18720
agacgagcgg ctcattcgcc atcgggatag tcccgcgcga agccgctcgc ggaggccgga 18780
tcggtggcgg gacccgtggg aggagcggga gacggcggcg tcctggagag aggggccgct 18840
ggggcgcccg gaggccccgt gggggttgga gtgtacgtag gatgcgagcc aatccttgaa 18900
ggaccgttgg cgtgcacctt gggggctgag gttagctgcc acatgaccag caggtcgctg 18960
tctgcgggac tcatccatcc ttcggccagg tcgccgtctc cccacagaga agcgttggtc 19020
gctgcttcct cgagttgctc ctcctggtcc gcaagacgat cgtccacggc gtccaggcgc 19080
tcaccaagcg ccggatcgag gtaccgtcgg tgtgcggtta gaaagtcacg acgcgccgct 19140
tgctcctcca cgcgaatttt aacacaggtc gcgcgctgtc gcatcatctc taagcgcgcg 19200
cgggacttta gccgcgcctc caattccaag tgggccgcct ttgcagccat aaaggcgcca 19260
acaaaccgag gatcttgggt gctgacgccc tcccggtgca gctgcagggt ctggtccttg 19320
taaatctcgg ctcggaggtg cgtctcggcc aggcgtcggc gcagggccgc gtgggcggca 19380
tctcggtcca ttccgccacc ctgcgggcga cccgggggt gctctgatag tctcgcgtgc 19440
ccaaggcccg tgatcggggt acttcgccgc cgcgacccgc cacccggtgt gcgcgatgtt 19500
tggtcagcag ctggcgtccg acgtccagca gtacctggag cgcctcgaga aacagaggca 19560
acttaaggtg ggcgcggacg aggcgtcggc gggcctcacc atgggcggcg atgccctacg 19620
agtgcccttt ttagatttcg cgaccgcgac cccaagcgc caccagaccg tggtccctgg 19680
cgtcgggacg ctccacgact gctgcgagca ctcgccgctc ttctcggccg tggcgcggcg 19740
gctgctgttt aatagcctgg tgccggcgca actaaagggg cgtgatttcg ggggcgacca 19800
cacggccaag ctggaattcc tggcccccga gttggtacgg gcggtggcgc gactgcggtt 19860
taaggagtgc gcgccggcgg acgtggtgcc tcagcgtaac gcctactata gcgttctgaa 19920
tacgtttcag gccctccacc gctccgaagc ctttcgccag ctggtgcact ttgtgcggga 19980
ctttgcccag ctgctcaaaa cctccttccg ggcctccagc ctcacggaga ccacgggccc 20040
ccccaaaaaa cgggccaagg tggacgtggc cacccacggc cggacgtacg gcacgctgga 20100
gctgttccaa aaaatgatcc ttatgcacgc cacctacttt ctggccgccg tgctcctcgg 20160
ggaccacgcg gagcaggtca acacgttcct gcgtctcgtg tttgagatcc ccctgtttag 20220
cgacgcggcc gtgcgccact tccgccagcg cgccaccgtg tttctcgtcc cccggcgcca 20280
cggcaagacc tggtttctgg tgcccctcat cgcgctgtcg ctggcctcct ttcgggggat 20340
caagatcggc tacacggcgc acatccgcaa ggcgaccgag ccggtgtttg aggagatcga 20400
cgcctgcctg cggggctggt tcggttcggc ccgagtggac cacgttaaag gggaaaccat 20460
ctccttctcg tttccggacg ggtcgcgcag taccatcgtg tttgcctcca gccacaacac 20520
aaacgtaagt cctcttttct ttcgcatggc tctcccaagg ggcccgggt cgacccgacc 20580
cacacccacc cacccacata cacacacaac cagacgcggg aggaaagtct gccccgtggg 20640
cactgatttt tattcgggat cgcttgagga ggcccgggca acggcccggg caacggtggg 20700
gcaactcgta gcaaataggc gactgatgta cgaagagaag acacacaggc gccacccggc 20760
gctggtcggg gggatgttgt ccgcgccgca ccgtcccccg acgacctctt gcagacggtc 20820
cgtgatgcaa ggacggcggg gggcctgcag cagggtgacc gtatccacgg gatggccaaa 20880
gagaagcgga cacaggctag catcccccctg gaccgccagg gtacactggg ccatcttggc 20940
ccacagacac ggggcgacgc agggacagga ctccgttacg acggaggaga gccacagtgc 21000
gttggcggaa tcgatgtggg gcggcggggc gcaggactcg cagccccccg ggtggttggt 21060
gatcctggcc aggagccatc ccagatggcg ggccctgctt cccggtggac agagcgaccc 21120
caggtcgctg tccatggccc agcagtagat ctggccgctg gggaggtgcc accaggcccc 21180
cgggcccaag gcgcagcacg cgcccggctc cggggggtc ttcgcgggga ccagatacgc 21240
gccatccagc tcgccgacca ctggctcctc cgcgagctgt tcggtggttg ggtcgggggt 21300
ttcctccggg ggggtggccg cccgtatgcg tgcgaacgtg agggtgcaca ggagcggggt 21360
cagggggtgc gtcacgctcc ggaggtggac gatcgcgcag tagcggcgct cgcggttaaa 21420
gaaaaagagg gcaaagaagg tgttcggggg caaccgcagc gccttggggc gcgtcagata 21480
cagaaaaatc tcgcagaaga gggcgcgccc ggggtctggg ttaggaaggg ccacctgaca 21540
cagaggctcg gtgaggaccg ttagacaccg aaagatcttg agccgctcgt ccgcccgaac 21600
gacgcgccac acaaagacgg agttgacaat gcgcgcgata gagtcgacgt ccgtccccag 21660
gtcgtcgact ctatcgcgcg tgccgcgagc tccggcccgg gaatccggcc ggggcaaggt 21720
ccccggggga ccaggcggcg ccaggggccg ccggggtccc agctgcgcca tgccgggggc 21780
ggggggaggg caaaccccag aggcgggggc caacggcgcg gggaggagtg ggtgggcgag 21840
gtggccgggg gaaggcgccc gctagcgaga ccggccgttc ccggacgaca ccttgcgaca 21900
aaacctaagg acagcggccc gcgcgacggg gtccgagagg ctaaggtagg ccgcgatgtt 21960
aatggtgaac gcaaagccgc cgggaaagac aactatgcca cagaggcggc gattaaaccc 22020
caggcagagg taggcgtagc tttccccggg caggtattgc tcgcagaccc tgcgtggggc 22080
tgtggagggg acggcctcca tgaagcgaca tttactctgc tcgcgtttac tgacgtcacc 22140
atccatcgcc acggcgattg gacgattgtt aagccgcagc gtgtctccgc ttgtgctgta 22200
gtagtcaaaa acgtaatggc cgtcggagtc ggcaaagcgg gccgggaggt cgtcgccgag 22260
cgggacgacc cgccgccccc gaccgccccg tccccccagg tgtgccagga cggccagggc 22320
atacgcggtg tgaaaaaagg cgtcgggggc ggtcccctcg acggcgcgca tcaggttctc 22380
gaggagaatg gggaagcgcc tggtcacctc ccccaaccac gcgcgttggt cggggccaaa 22440
gtcatagcgc aggcgctgtg agattcgcgg gccgccctga agcgcggccc ggatggcctg 22500
gcccagggcc cggaggcacg ccagatgtat gcgcgcggta aaggcgacct cggcggcgat 22560
gtcaaagggc ggcaggacgg ggcgcgggtg gcgcaggggc acctcgagcg cgggaaagcg 22620
tagcagcagc tccgcctgcc cagcgggaga cagctggtgg gggcgcacga cgcgttctgc 22680
ggcgcaggcc tcggtcaggg ccgtggccag cgccgaggac agcagcggag ggcgggcgcg 22740
tcgcccgccc cacgccacgg agttctcgta ggagacgacg acgaagcgct gcttggttcc 22800
gtagtggtgg cgcaggacca cggagataga acgacggctc cacagccagt ccggccggtc 22860
gccgccggcc agggcttccc atccgcgatc caaccactcg accagcgacc gcggctttgc 22920
ggtaccaggg gtaagggtta gaacgtcgtt caggatgtcc tcgcccccgg gcccgtgggg 22980
cgctggggcc acaaagcggc ccccgccggg gggctccaga cccgccagca ccgcatctgc 23040
gtcagccgcc cccatggcgc ccccgctgac ggcctggtga accagggcgc cctggcgtag 23100
ccccgatgca acgccacagg ccgcacgccc ggtccgcgct cggaccgggt ggcggcgggt 23160
gacgtcctgc actgcccgct gaaccaacgc gaggatctcc tcgttctcct gtgcgatgga 23220
cacgtcctgg gccgcggtcg tgtcgccgcc gggggccgtc agctgctcct ccggggagat 23280
gggggggtcg gacgccccga cgatgggcgg gtctgcgggc gcccccgcgt ggggccgggc 23340
caagggctgc ggacgcgggg acgcgctttc ccccagaccc atggacaggt gggccgcagc 23400
ctccttcgcg gccggcgggg cggcggcgcc aagcagagcg acgtagcggc acaaatgccg 23460
acagacgcgc atgatgcgcg tgctgtcggc cgcgtagcgc gtgttggggg ggacgagctc 23520
gtcgtaacta aacagaatca cgcgggcaca gctcgccccc gagccccacg caaggcgcag 23580
cgccgccacg gcgtacgggt catagacgcc ctgcgcgtca cacaccacgg gcagggagac 23640
gaacaacccc ccggcgctgg acgcacgcgg aaggaggcca gggtgtgccg gcacgacggg 23700
ggccagaagc tcccccaccg catccgcggg cacgtaggcg gcaaacgccg tgcaccacgg 23760
ggtacagtcg ccggtggcat gagcccgagt ctggatttcg acctggaagt ttgcggccgt 23820

```
cccgagtccg gggcggccgc gcatcagggc ggccagaggg attcccgcgg ccgccaggca  23880
ctcgctggat atgatgacgt gaaccaaaga ccgagggccg acccgggccg tggccgagat  23940
cgtctggacc tcgttggcca agtgcgcgtt catggttcgg gggtgggtgt gggtgtgtag  24000
gcgatgcggg tcccccgagt ccgcgggaag ggcgtgggtt tggcgcgcgt atgcgtattc  24060
gccaacggag gcgtgcgtgc ttatgcgcgg cgcgtttctt ctgtctctag ggaatccgag  24120
gccaggactt taacctgctc tttgtcgacg aggccaactt tattcgcccg gatgcggtcc  24180
agacgattat gggctttctc aaccaggcca actgcaagat tatcttcgtg tcgtccacca  24240
acaccgggaa ggccagtacg agctttttgt acaacctccg cggggccgca gacgagcttc  24300
tcaacgtggt gacctatata tgcgatgatc acatgccgag ggtggtgacg cacacaaacg  24360
ccacggcctg ttcttgttat atcctcaaca agcccgtttt catcacgatg gacggggcgg  24420
ttcgccggac cgccgatttg tttctggccg attccttcat gcaggagatc atcgggggcc  24480
aggccaggga gaccggcgac gaccggcccg ttctgaccaa gtctgcgggg gagcggtttc  24540
tgttgtaccg cccctcgacc accaccaaca gcggcctcat ggccccccgat ttgtacgtgt  24600
acgtggatcc cgcgttcacg gccaacaccc gagcctccgg gaccggcgtc gctgtcgtcg  24660
ggcggtaccg cgacgattat atcatcttcg ccctggagca ctttttctc cgcgcgctca  24720
cgggctcggc cccgccgac atcgcccgct gcgtcgtcca cagtctgacg caggtcctgg  24780
ccctgcatcc cggggcgttt cgcggcgtcc gggtggcggt cgagggaaat agcagccagg  24840
actcggccgt cgccatcgcc acgcacgtgc acacagagat gcaccgccta ctggcctcgg  24900
agggggccga cgcgggctcg ggccccgagc ttctcttcta ccactgcgag cctcccggga  24960
gcgcggtgct gtaccccttt ttcctgctca acaaacagaa gacgcccgcc tttgaacact  25020
ttattaaaaa gtttaactcc gggggcgtca tggcctccca ggagatcgtt tccgcgacgg  25080
tgcgcctgca gaccgacccg gtcgagtatc tgctcgagca gctaaataac ctcaccgaaa  25140
ccgtctcccc caacactgac gtccgtacgt attccggaaa acggaacggc gcctcggatg  25200
accttatggt cgccgtcatt atggccatct acctcgcggc ccaggccgga cctccgcaca  25260
cattcgctcc tatcacacgc gtctcgtgag cgcccaataa acacacccag gtatgctacg  25320
cacgaccacg gtgtcgtctg ttaagggggg ggggggaagg gggtgttggc gggaagcgtg  25380
ggaacacggg ggattctctc acgaccggca ccagtaccac ccccctgtga acacagaaac  25440
cccaacccaa atcccataaa catacgacac acaggcatat tttggaattt cttaggtttt  25500
tatttattta ggtatgctgg ggtttctccc tggatgccca cccccacccc cccgtgggtc  25560
tagccgggcc ttagggatag cgtataacgg gggccatgtc tccggaccgc acaacggccg  25620
cgccgtcaaa ggtgcacacc cgaaccacgg gagccagggc caaggtgtct cctagttggc  25680
ccgcgtgggt cagccaggcg acgagcgcct cgtaaagcgg cagccttcgc tctccatcct  25740
gcatcagggc cggggcttcg gggtgaatga gctgggcggc ctcccgcgtg acactctgca  25800
tctgcagtag agcgttcacg tacccgtcct gggcacttag cgcaaagagc cgggggatta  25860
gcgtaaggat gatggtggtt ccctccgtga tcgagtaaac catgttaagg accagcgatc  25920
gcagctcggc gtttacggga ccgagttgtt ggacgtccgc cagcagcgag aggcgactcc  25980
cgttgtagta cagcacgttg aggtctggca gccctccggg gtttctgggg ctggggttca  26040
ggtcccggat gcccctggcc acgagccgcg ccacgatttc gcgcgccagg ggcgatggaa  26100
gcggaacggg aaaccgcaac gtgaggtcca gcgaatccag gcgcacgtcc gtcgcttggc  26160
cctcgaacac gggcgggacg aggctgatgg ggtccccgtt acagagatct acgggggagg  26220
```

```
tgttgcgaag gttaacggtg ccggcgtggg tgaggcccac gtccaggggg caggcgacga  26280
ttcgcgtggg aagcacccgg gtgatgaccg cggggaagcg ccttcggtac gccagcaaca  26340
accccaacgt gtcgggactg acgcctccgg agacgaagga ttcgtgcgcc acgtcggcca  26400
gcgtcagttg ccggcggatg gtcggcagga ataccacccg cccttcgcag cgctgcagcg  26460
ccgccgcatc ggggcgcgag atgcccgagg gtatcgcgat gtcagtttca aagccgtccg  26520
ccagcatggc gccgatccac gcggcaggga gtgcagtggt ggttcgggtg gcgggaggag  26580
cgcggtgggg gtcagcggcg tagcagagac gggcgaccaa cctcgcatag gacgggggt  26640
gggtcttagg gggttgggag gcgacaggga ccccagagca tgcgcgggga ggtctgtcgg  26700
gcccagacgc accgagagcg aatccgtccg cggagtcccg gcttgggttt tatggggccc  26760
ggccctcgga atcgcggctt gtcggcgggg acaaaggggg cggggctagg ggcttgcgga  26820
aacagaagac gcgtgggata aaagaatcgc actaccccaa ggaagggcgg ggcggtttat  26880
tacagagcca gtcccttgag cggggatgcg tcatagacga gatactgcgc gaagtgggtc  26940
tcccgcgcgt gggcttcccc gttgcgggca ctgcggagga gggcggggtc gctggcgcag  27000
gtgagcgggt aggcctcctg aaacaggcca cacgggtcct ccacgagttc gcggcacccc  27060
ggggggcgct taaactgtac gtcgctggcg gcggtggccg tggacaccgc cgaacccgtc  27120
tccacgatca ggcgctccag gcagcgatgt ttggcggcga tgtcggccga cgtaaagaac  27180
ttaaagcagg ggctgagcac cggcgaggcc ccgttgaggt ggtaggcccc gttatagagc  27240
aggtccccgt acgaaaatcg ctgcgacgcc cacgggttgg ccgtggccgc gaaggcccgg  27300
gacgggtcgc tctggccgtg gtcgtacatg agggcggtga catccccctc cttgtccccc  27360
gcgtaaacgc ccccggcggc gcgtccccgg gggttgcagg gccggcggaa gtagttgacg  27420
tcggtcgaca cgggggtggc gataaactca cacacggcgt cctggccgtg gtccatccct  27480
gcgcgccgcg gcacctgggc gcacccgaac acggggacgg gctgggccgg ccccaggcgg  27540
tttcccgcca cgaccgcgtt ccgcaggtac acggctgccg cgttgtccag gagaggggga  27600
gccccgcggc ccaggtaaaa gttttgggga aggttgccca tgtcggtgac ggggttgcgg  27660
acggttgccg tggccacgac ggcggtgtag cccacgccca ggtccacgtt cgcgcgcggc  27720
tgggtgagcg tgaagtttac ccccccgcca gtttcgtgcc gggccacctg gagctggccc  27780
aggaagtacg cctccgacgc gcgctccgag aacagcacgt tctcagtcac aaagcggtcc  27840
tgtcggacga cggtgaaccc aaacccggga tggaggcccg tcttgagctg atgatgcaag  27900
gccacgggac tgatcttgaa gtaccccgcc atgagcgcgt aggtcagcgc gttctccccg  27960
gccgcgctct cgcggacgtg ctgcacgacg ggctgtcgga tcgacgaaaa gtagttggcc  28020
cccagagccg gggggaccag gggacctgc cgcgacaggt cgcgcagggc cggggggaaa  28080
ttgggcgcgt tcgccacgtg gtcggccccg gcgaacagcg cgtggacggg gagggggtaa  28140
aaatagtcgc cattttggat ggtatggtcc agatgctggg gggccatcag caggattccg  28200
gcgtgcaacg ccccgtcgaa tatgcgcatg ttggtggtgg acgcggtgtt ggcgcccgcg  28260
tcgggcgccg ccgagcagag cagcgccgtt gtgcgttcgg ccatgttgtg ggccagcacc  28320
tgcagcgtga gcatggcggg cccgtccact accacgcgcc cgttgtgaaa catggcgttg  28380
accgtgttgg ccaccagatt ggccgggtgc agggggtgcg cggggtccgt cacggggtcg  28440
ctggggcact cctcgccggg ggcgatctcc gggaccacca tgttctgcag ggtggcgtat  28500
acgcggtcga agcgaacccc cgcggtgcag cagcggcccc gcgagaaggc gggcaccatc  28560
```

acgtagtagt aaatcttgtg gtgcacggtc cagtccgccc cccggtgcgg ccggtcatcc 28620
gcggcgtccg cggctcgggc ctgggtgttg tgcagcagct ggccgtcgtt gcggttgaag 28680
tccgcggtcg ccacgttaca tgccgccgcg tacacggggt cgtggccccc cgcgctaacc 28740
cggcagtcgc gatggcggtc cagggccgcg cgccgcatca gggcgtcaca gtcccacacg 28800
aggggtggca gcagcgccgg gtctcgcatt aggtgattca gctcggcttg cgcctgcccg 28860
cccagctccg ggccggtcag ggtaaagtca tcaaccagct gggccagggc ctcgacgtgc 28920
gccaccaggt cccggtacac ggccatgcac tcctcgggaa ggtctccccc gaggtaggtc 28980
acgacgtacg agaccagcga gtagtcgttc acgaacgccg cgcaccgcgt gttgttccag 29040
tagctggtga tgcactggac cacgagccgg gccagggcgc agaagacgtg ctcgctgccg 29100
tgtatggcgg cctgcagcag gtaaaacacc gccgggtagt tgcggtcgtc gaacgccccg 29160
cgaacggcgg cgatggtggc gggggccatg gcgtggcgtc ccaccccccag ctccaggccc 29220 cgggcgtccc ggaacgccgc cggacatagc gccaggggca agttgccgtt caccacgcgc 29280
caggtggcct ggatctcccc cgggccggcc gggggaacgt cccccccccgg cagctccacg 29340 tcggccaccc ccacaaagaa gtcgaacgcg gggtgcagct caagagccag gttggcgttg 29400
tcgggctgca taaactgctc cggggtcatc tggccttccg cgacccatcg gacccgcccg 29460
tgggccaggc gctgccccca ggcgttcaaa aacagctgct gcatgtctgc ggcggggccg 29520
gccggggccg ccacgtacgc cccgtacgga ttggcggctt cgacggggtc gcggttaagg 29580
cccccgaccg ccgcgtcaac gttcatcagc gaagggtggc acacggtccc gatcgcgtgt 29640
tccagagaca ggcgcagcac ctggcggtcc ttcccccaaa aaaacagctg gcggggcggg 29700
aaggcgcggg gatccgggtg gccgggggcg gggactaggt ccccggcgtg cgcggcaaac 29760
cgttccatga ccggattgaa caggcccagg ggcaggacga acgtcaggtc catggcgccc 29820
accagggggt agggaacgtt ggtggcggcg tagatgcgct tctccagggc ctccagaaag 29880
accagcttct cgccgatgga caccagatcc gcgcgcacgc gcgtcgtctg gggggcgctc 29940
tcgagctcgt ccagcgtctg ccggttcagg tcgagctgct cctcctgcat ctccagcagg 30000
tggcggccca cgtcgtccag acttcgcacg gccttgccca tcacgagcgc cgtgaccagg 30060
ttggccccgt tcaggaccat ctcgccgtac gtcaccggca cgtcggcttc ggtgtcctcc 30120
actttcagga aggactgcag gaggcgctgt ttgatcgggg cggtggtgac gagcaccccg 30180
tcgaccggcc gcccgcgcgt gtcggcatgc gtcagacggg gcacggccac ggagggctgc 30240
gtggccgtgg tgaggtccac gagccaggcc tcgacggcct cccggcggtg gcccgccttg 30300
cccaggaaaa agctcgtctc gcagaagctt cgctttagct cggcgaccag ggtcgcccgg 30360
gccaccctgg tggccaggcg gccgttgtcc aggtatcgtt gcatcggcaa caacaaagcc 30420
aggggcggcg ccttttccag cagcacgtgc agcatctggt cggccgtgcc gcgctcaaac 30480
gccccgagga cggcctggac gttgcgagcg agctgttgga tggcgcgcaa ctggcgatgc 30540
gcgccgatac ccgtcccgtc cagggcctcc cccgtgagca gggcgatggc ctcggtggcc 30600
aggctgaagg cggcgttcag ggcccggcgg tcgataatct tggtcatgta attgtgtgtg 30660
ggttgctcga tggggtgcgg gccgtcgcgg gcaatcagcg gctggtggac ctcgaactgt 30720
acgcgcccct cgttcatgta ggccagctcc ggaaacttgg tacacacgca cgccaccgac 30780
aacccgagct ccagaaagcg cacgagcgac agggtgttgc aatacgaccc cagcagggcg 30840
tcgaactcga cgtcgtacag gctgtttgca tcggagcgca cgcgggaaaa aaaatcaaac 30900
aggcgtcgat gcgacgccac ctcgatcgtg ctaaggaggg acccggtcgg caccatggcc 30960
gcggcatacc ggtatcccgg agggtcgcgg ttgggagcgg ccatggggtc gcgtggagat 31020
cggctgtctc tagcgatatt ggcccgggga ggctaagatc caccccaacg cccggccacc 31080
cgtgtacgtg cccgacggcc caaggtccac cgaaagacac gacgggcccg gacccaaaaa 31140
ggcgggggat gctgtgtgag aggccgggtg ccggtcgggg gggaaaggca ccgggagaag 31200
gctgcggcct cgttccagga gaacccagtg tccccaacag acccggggac gtgggatccc 31260
aggccttata taccccccc cccgccccac ccccgttaga acgcgacggg tgcattcaag 31320
atggccctgg tccaaaagcg tgccaggaag aaattggcag aggcggcaaa gctgtccgcc 31380
gccgccaccc acatcgaggc ccggccgcg caggctatcc ccagggcccg tgtgcgcagg 31440
ggatcggtgg gcggcagcat ttggttggtg gcgataaagt ggaaaagccc gtccggactg 31500
aaggtctcgt gggcggcggc gaacaaggca cacagggccg tgcctcccaa aaacacggac 31560
atcccccaaa acacgggcgc cgacaacggc agacgatccc tcttgatgtt aacgtacagg 31620
aggagcgccc gcaccgccca cgtaacgtag tagccgacga tggcggccag gatacaggcc 31680
ggcgccacca cccttccggt cagcccgtaa tacatgcccg ctgccaccat ctccaacggc 31740
ttcaggacca aaaacgacca aaggaacaga atcacgcgct ttgaaaagac cggctgggta 31800
tggggcggaa gacgcgagta tgccgaactg acaaaaaaat cagaggtgcc gtacgaggac 31860
aatgaaaact gttcctccag cggcagttct ccctcctccc ccccgaaggc ggcctcgtcg 31920
accagatctc gatccaccag aggaaggtca tcccgcatgg tcatggggtg tgcggtggag 31980
gtggggagac cgaaaccgca aagggtcgct tacgtcagca ggatcccgag atcaaagaca 32040
cccgggttct tgcacaaaca ccacccgggt tgcatccgcg gaggcgagtg ttttgataag 32100
gccgttccgc gccttgatat aacctttgat gttgaccaca aaacccggaa tttacgccta 32160
cgccccaatg cccacgcaag atgaggtagg taaccccccc gtgggtgtga cgttgcgttt 32220
agttcattgg aggccaaggg gaaaaatggg gtggggagga aacggaaaac ccagtaggcc 32280
gtgtcgggaa cacgcccggg gttgtcctca aaaggcaggg tccatactac ggaagccgtc 32340
gttgtattcg agacctgcct gtgcaacgca cgtcggggtt gcctgtgtcc ggttcggccc 32400
ccaccgcgtg cggcacgcac gaggacgagt ccgcgtgctt tattggcgtt ccaagcgttg 32460
ccctccagtt tctgttgtcg gtgttccccc atacccacgc ccacatccac cgtagggggc 32520
ctctgggccg tgttacgtcg ccgcccgcga tggagcttag ctacgccacc accatgcact 32580
accgggacgt tgtgttttac gtcacaacgg accgaaaccg ggcctacttt gtgtgcgggg 32640
ggtgtgttta ttccgtgggg cggccgtgtg cctcgcagcc cggggagatt gccaagtttg 32700
gtctggtcgt tcgagggaca ggcccagacg accgcgtggt cgccaactat gtacgaagcg 32760
agctccg 32767

<210> SEQ ID NO 844
<211> LENGTH: 32767
<212> TYPE: DNA
<213> ORGANISM: Artificial Sequence
<220> FEATURE:
<223> OTHER INFORMATION: recombinant viral vector ONCR-136

<400> SEQUENCE: 844
aaaaaagctg aacgagaaac gtaaaatgat ataaatatca atatattaaa ttagattttg 60
cataaaaaac agactacata atactgtaaa acacaacata tccagtcact atgaatcaac 120
tacttagatg gtattagtga cctgtagtcg accgacagcc ttccaaatgt tcttcgggtg 180

```
atgctgccaa cttagtcgac cgacagcctt ccaaatgttc ttctcaaacg gaatcgtcgt    240
atccagccta ctcgctattg tcctcaatgc cgtattaaat cataaaaaga aataagaaaa    300
agaggtgcga gcctcttttt tgtgtgacaa aataaaaaca tctacctatt catatacgct    360
agtgtcatag tcctgaaaat catctgcatc aagaacaatt tcacaactct tatacttttc    420
tcttacaagt cgttcggctt catctggatt ttcagcctct atacttacta aacgtgataa    480
agtttctgta atttctactg tatcgacctg cagactggct gtgtataagg gagcctgaca    540
tttatattcc ccagaacatc aggttaatgg cgtttttgat gtcattttcg cggtggctga    600
gatcagccac ttcttccccg ataacggaga ccggcacact ggccatatcg gtggtcatca    660
tgcgccagct ttcatccccg atatgcacca ccgggtaaag ttcacgggag actttatctg    720
acagcagacg tgcactggcc agggggatca ccatccgtcg cccgggcgtg tcaataatat    780
cactctgtac atccacaaac agacgataac ggctctctct tttataggtg taaaccttaa    840
actgcatttc accagcccct gttctcgtca gcaaaagagc cgttcatttc aataaaccgg    900
gcgacctcag ccatcccttc ctgattttcc gctttccagc gttcggcacg cagacgacgg    960
gcttcattct gcatggttgt gcttaccaga ccggagatat tgacatcata tatgccttga   1020
gcaactgata gctgtcgctg tcaactgtca ctgtaatacg ctgcttcata gcatacctct   1080
ttttgacata cttcgggtat acatatcagt atatattctt ataccgcaaa aatcagcgcg   1140
caaatacgca tactgttatc tggcttttag taagccggat ccacgcggcg tttacgcccc   1200
ccctgccact catcgcagta ctgttgtaat tcattaagca ttctgccgac atggaagcca   1260
tcacaaacgg catgatgaac ctgaatcgcc agcggcatca gcaccttgtc gccttgcgta   1320
taatatttgc ccatggtgaa aacgggggcg aagaagttgt ccatattggc cacgtttaaa   1380
aaggccgtaa tatccagctg aacggtctgg ttataggtac attgagcaac tgactgaaat   1440
gcctcaaaat gttctttacg atgccattgg gatatatcaa cggtggtata tccagtgatt   1500
tttttctcca ttttagcttc cttagctcct gaaaatctcg ataactcaaa aaatacgccc   1560
ggtagtgatc ttatttcatt atggtgaaag ttggaacctc ttacgtgccg atcaacgtct   1620
cattttcgcc aaaagttggc ccagggcttc ccggtatcaa cagggacacc aggatttatt   1680
tattctgcga agtgatcttc cgtcacaggt atttattcgg cgcaaagtgc gtcgggtgat   1740
gctgccaact tagtcgacta caggtcacta ataccatcta agtagttgat tcatagtgac   1800
tggatatgtt gtgttttaca gtattatgta gtctgttttt tatgcaaaat ctaatttaat   1860
atattgatat ttatatcatt ttacgtttct cgttcagctt tcttgtacaa agtggtttta   1920
atggaccgcc cgcaaggggg ggggggcatt tcagtgtcgg gtgacgagcg cgatccggcc   1980
gggatcctag gaccccaaaa gtttgtctgc gtattccagg gcggggctca gttgaatctc   2040
ccgcagcacc tctaccagca ggtccgcggt gggctggaga aactcggccg tcccggggca   2100
ggcggttgtc gggggtggag gcgcggcgcc caccccgtgt gccgcgcctg gcgtctcctc   2160
tgggggcgac ccgtaaatgg ttgcagtgat gtaaatggtg tccgcggtcc agaccacggt   2220
caaaatgccg gccgtggcgc tccgggcgct ttcgccgcgc gaggagctga cccaggagtc   2280
gaacggatac gcgtacatat gggcgtccca cccgcgttcg agcttctggt tgctgtcccg   2340
gcctataaag cggtaggcac aaaattcggc gcgacagtcg ataatcacca acagcccaat   2400
gggggtgtgc tggataacaa cgcctccgcg cggcaggcgg tcctggcgct cccggccccg   2460
taccatgatc gcgcgggtgc cgtactcaaa aacatgcacc acctgcgcgg cgtcgggcag   2520
tgcgctggtc agcgaggccc tggcgtggca taggctatac gcgatggtcg tctgtggatt   2580
```

-continued ggacatctcg cggtgggtag tgagtccccc gggccgggtt cggtggaact gtaaggggac 2640
ggcgggttaa tagacaatga ccacgttcgg atcgcgcaga gccgatagta tgtgctcact 2700
aatgacgtca tcgcgctcgt ggcgctcccg gagcggattt aagttcatgc gaaggaattc 2760
ggaggaggtg gtgcgggaca tggccacgta cgcgctgttg aggcgcaggt tgccgggcgt 2820
aaagcagatg gcgaccttgt ccaggctaag gccctgggag cgcgtgatgg tcatggcaag 2880
cttggagctg atgccgtagt cggcgtttat ggccatggcc agctccgtag agtcaatgga 2940
ctcgacaaac tcgctgatgt tggtgttgac gacggacatg aagccgtgtt ggtcccgcaa 3000
gaccacgtaa ggcagggggg cctcttccag taactcggcc acgttggccg tcgcgtgccg 3060
cctccgcagc tcgtccgcaa aggcaaacac ccgtgcgtac gtgtatccca tgagcgtata 3120
attgtccgtc tgcagggcga cggacatcag ccccccgcgc ggcgagccgg tcagcatctc 3180
gcagccccgg aagataacgt tgtccacgta cgtgctaaag ggggcgactt caaatgcctc 3240
cccgaagagc tcttggagga ttcggaatct cccgaggaag gcccgcttca gcagcgcaaa 3300
ctgggtgtga acggcggcgg tggtctccgg ttccccgggg gtgtagtggc agtaaaacac 3360
gtcgagctgt tgttcgtcca gccccgcgaa aataacgtcg aggtcgtcgt cgggaaaatc 3420
gtccgggccc ccgtcccgcg gccccagttg cttaaaatca aacgcacgct cgccgggggc 3480
gcctgcgtcg gccattaccg acgcctgcgt cggcaccccc gaagatttgg ggcgcagaga 3540
cagaatctcc gccgttagtt ctcccatgcg ggcgtaggcg agggtcctct gggtcgcatc 3600
caggcccggg cgctgcagaa agttgtaaaa ggagataagc ccgctaaata tgagccgcga 3660
caggaacctg taggcaaact ccaccgaagt ctccccctga gtctttacaa agctgtcgtc 3720
acgcaacact gcctcgaagg cccggaacgt cccactaaac ccaaaaacca gttttcgcag 3780
gcgcgcggtc accgcgatct ggctgttgag gacgtaagtg acgtcgttgc gggccacgac 3840
cagctgctgt ttgctgtgca cctcgcagcg catgtgcccc gcgtcctggt cctggctctg 3900
cgagtagttg gtgatgcggc tggcgttggc cgtgagccac ttttcaatcg tcaggccggg 3960
ctggtgtgtc agccgtcggt attcgtcaaa ctccttgacc gacacgaacg taagcacggg 4020
gagggtgaac acgacgaact ccccctcacg ggtcaccttc aggtaggcgt ggagcttggc 4080
catgtacgcg ctcacctctt tgtgggagga gaacagccgc gtccagccgg ggaggttggc 4140
ggggttggtg atgtagtttt ccgggacgac gaagcgatcc acgaactgca tgtgctcctc 4200
ggtgatgggc aggccgtact ccagcacctt catgaggtta ccgaactcgt gctcgacgca 4260
ccgtttgttg ttaataaaaa tggcccagct atacgagagg cgggcgtact cgcgcagcgt 4320
gcggttgcag atgaggtacg tgagcacgtt ctcgctctgg cggacggaac accgcagttt 4380
ctggtgctcg aaggtcgact ccagggacgc cgtctgcgtc ggcgagccca cacacaccaa 4440
cacgggccgc aggcgggccg cgtactgggg ggtgtggtac agggcgttaa tcatccacca 4500
gcaatacacc acggccgtga ggaggtgacg cccaaggagc ccggcctcgt cgatgacgat 4560
cacgttgctg cgggtaaagg ccggcagcgc cccgtgggtg gccggggcca accgcgtcag 4620
ggcgccctcg gccaacccca gggtccgttc cagggcggcc agggcgcgaa actcgttccg 4680
caactcctcg cccccggagg cggccagggc gcgcttcgtg aggtccaaaa tcacctccca 4740
gtagtacgtc agatctcgtc gctgcaggtc ctccagcgag gcggggttgc tggtcagggt 4800
gtacgggtac tgtcccagtt gggcctggac gtgattcccg cgaaacccaa attcatgaaa 4860
gatggtgttg atgggtcggc tgagaaaggc gcccgagagt ttggcgtaca tgttttgggc 4920

-continued

```
cgcaatgcgc gtggcgcccg tcaccacaca gtccaagacc tcgttgattg tctgcacgca   4980
cgtgctcttt ccggagccag cgttgccggt gataagatac accgcgaacg gaaactccct   5040
gaggggcagg cctgcggggg actctaaggc cgccacgtcc cggaaccact gcagatgggg   5100
cacttgcgct ccgtcgagct gttgttgcga gagctctcgg atgcgcttaa ggattggctg   5160
caccccgtgc atagacgtaa aatttaaaaa ggcctcggcc ctccctggaa cggctggtcg   5220
gtccccgggt tgctgaaggt gcggcgggcc gggtttctgt ccgtctagct ggcgctcccc   5280
gccggccgcc gccatgaccg caccacgctc gcgggccccc actacgcgtg cgcgggggga   5340
cacggaagcg ctgtgctccc ccgaggacgg ctgggtaaag gttcacccca gccccggtac   5400
gatgctgttc cgcgagattc tccacgggca gctggggtat accgagggcc agggggtgta   5460
caacgtcgtc cggtccagcg aggcgaccac ccggcagctg caggcggcga tctttcacgc   5520
gctcctcaac gccaccactt accgggacct cgaggcggac tggctcggcc acgtggcggc   5580
ccgcggtctg cagccccaac ggctggttcg ccggtacagg aacgcccggg aggcggatat   5640
cgccggggtg gccgagcggg tgttcgacac gtggcggaac acgcttagga cgacgctgct   5700
ggactttgcc cacgggttgg tcgcctgctt tgcgccgggc ggcccgagcg gcccgtcaag   5760
cttccccaaa tatatcgact ggctgacgtg cctggggctg gtccccatat tacgcaagcg   5820
acaagaaggg ggtgtgacgc agggtctgag ggcgtttctc aagcagcacc cgctgacccg   5880
ccagctggcc acggtcgcgg aggccgcgga gcgcgccggc cccgggtttt ttgagctggc   5940
gctggccttc gactccacgc gcgtggcgga ctacgaccgc gtgtatatct actacaacca   6000
ccgccggggc gactggctcg tgcgagaccc catcagcggg cagcgcggag aatgtctggt   6060
gctgtggccc cccttgtgga ccggggaccg tctggtcttc gattcgcccg tccagcggct   6120
gtttcccgag atcgtcgcgt gtcactccct ccgggaacac gcgcacgtct gccggctgcg   6180
caataccgcg tccgtcaagg tgctgctggg gcgcaagagc gacagcgagc gcggggtggc   6240
cggtgccgcg cgggtcgtta acaaggtgtt gggggaggac gacgagacca aggccgggtc   6300
ggccgcctcg cgcctcgtgc ggcttatcat caacatgaag ggcatgcgcc acgtaggcga   6360
cattaacgac accgtgcgtt cctacctcga cgaggccggg gggcacctga tagacgcccc   6420
ggccgtcgac ggtaccctcc ctggattcgg caagggcgga aacagccgcg ggtctgcggg   6480
ccaggaccag ggggggcggg cgccgcagct tcgccaggcc ttccgcacgg ccgtggttaa   6540
caacatcaac ggcgtgttgg agggctatat aaataacctg tttggaacca tcgagcgcct   6600
gcgcgagacc aacgcgggcc tggcgaccca attgcaggag cgcgaccgcg agctccggcg   6660
cgcaacagcg ggggccctgg agcgccagca gcgcgcggcc gacctggcgg ccgagtccgt   6720
gaccggtgga tgcggcagcc gccctgcggg ggcggacctg ctccgggccg actatgacat   6780
tatcgacgtc agcaagtcca tggacgacga cacgtacgtc gccaacagct ttcagcaccc   6840
gtacatccct tcgtacgccc aggacctgga gcgcctgtcg cgcctctggg agcacgagct   6900
ggtgcgctgt tttaaaattc tgtgtcaccg caacaaccag ggccaagaga cgtcgatctc   6960
gtactccagc ggggcgatcg ccgcattcgt cgccccctac tttgagtcag tgcttcgggc   7020
cccccgggta ggcgcgccca tcacgggctc cgatgtcatc ctgggggagg aggagttatg   7080
ggatgcggtg tttaagaaaa cccgcctgca aacgtacctg acagacatcg cggccctgtt   7140
cgtcgcggac gtccagcacg cagcgctgcc cccgcccccc tccccggtcg gcgccgattt   7200
ccggcccggc gcgtccccgc ggggccggtc cagatcgcgg tcgcccggaa gaactgcgcg   7260
aggcgcgccg gaccagggcg ggggcatcgg gcaccgggat ggccgccgcg acggccgacg   7320
```

-continued

```
atgaggggtc ggccgccacc atcctcaagc aggccatcgc cggggaccgc agcctggtcg   7380
aggcggccga ggcgattagc cagcagacgc tgctccgcct ggcctgcgag gtgcgccagg   7440
tcggcgaccg ccagccgcgg tttaccgcca ccagcatcgc gcgcgtcgac gtcgcgcctg   7500
ggtgccggtt gcggttcgtt ctggacggga gtcccgagga cgcctatgtg acgtcggagg   7560
attactttaa gcgctgctgc ggccagtcca gttatcgcgg cttcgcggtg gcggtcctga   7620
cggccaacga ggaccacgtg cacagcctgg ccgtgccccc cctcgttctg ctgcaccggt   7680
tctccctgtt caaccccagg gacctcctgg actttgagct tgcctgtctg ctgatgtacc   7740
tggagaactg cccccgaagc cacgccaccc cgtcgacctt tgccaaggtt ctggcgtggc   7800
tcggggtcgc gggtcgccgc acgtccccat tcgaacgcgt tcgctgcctt ttcctccgca   7860
gttgccactg ggtcctaaac acactcatgt tcatggtgta cgtaaaaccg ttcgacgacg   7920
agttcgtcct gccccactgg tacatggccc ggtacctgct ggccaacaac ccgccccccg   7980
ttctctcggc cctgttctgt gccaccccga cgagctcctc attccggctg ccggggccgc   8040
ccccccgctc cgactgcgtg gcctataacc ccgccgggat catggggagc tgctgggcgt   8100
cggaggaggt gcgcgcgcct ctggtctatt ggtggctttc ggagacccca aaacgacaga   8160
cgtcgtcgct gttttatcag ttttgttgaa ttttaggaaa taaacccggt tttgtttctg   8220
tggcctcccg acggatgcgc gtgtccttac tccgtcttgg tgggtgggtg gctgtgtatg   8280
gcgtcccatc tgtgcgggga ggggggcaag tcggcacgta ttcggacaga ctcaagcaca   8340
taagacgaac aaaaggtttg taacttcgta ccgtgagtaa taatgtggac tttattgctt   8400
aagaatacgc gtagagaaat aagacgaaca aaaggtttgt gattttattg cttaagaata   8460
cgcgtagatg gtcgtaccgt gagtaataat gtggttcata agacgaacaa aaggtttgtg   8520
acattattgc ttaagaatac gcgtaggtgg tcgtaccgtg agtaataatg tgtactttat   8580
tgcttaagaa tacgcgtagg ctatcgtacc gtgagtaata atgtgcctta taagacgaac   8640
aaaaggtttg tacacggggg agcgctcttg tctcagggca atgtttttat tggtcaaact   8700
caggcaaaca gaaacgacat cttgtcgtca aagggataca caaacttccc cccctcgccc   8760
catactcccg ccagcacccc ggtaaacacc aactcaatct cgcgcaggat ttcgcgcagg   8820
tgatgagcgc agtccacggg ggggagcaca aggggccgcg ggtatagatc gacggggacg   8880
ccgaccgact ccccgcctcc gggacagaca cgcacgacgc gccgccagta gtgctctgcg   8940
tccagcaagg cgccgccgcg gaaggcagtg gggggcaagg ggtcgctggc ctcaaagggg   9000
gacacccgaa cgctccagta ctccgcgtcc aaccgtttat taaacgcgtc caagataagg   9060
cggtcgcagg cgtcctccat aaggccccgg gccgtgagtg cgtcctcctc cggcacgcat   9120
gccgttgtca ggcccaggac ccgtcgcagc gtgtcgcgta cgacccctgc cgccgtggtg   9180
tacgcgggcc cgcggagagg aaatccccca agatggtcag tgttgtcgcg ggagttccag   9240
aaccacactc ccgcctggct ccaggcgact gcgtgggtgt agacgccctc gagggccagg   9300
cacagtgggt gccgcagccg gacggcgttg gccctaagca cggctcccac ggcccgtctcg   9360
atggcccgcc gggcgtcctc gatcaccccg gaagccgcat ccgcgtcttg gggggtccacg   9420
ttaaagacac cccagaacgc acccccatcg cccccgcaga ccgcgaactt caccgagctg   9480
gccgtctcct cgatctgcag gcagacggcg gccattaccc cacccaggag ctgccgcagc   9540
gcagggcagg cgttgcacgt gtccgggacc aggcgctcca agacggcccc ggcccagggc   9600
tctgagggag cggccaccac cagcgcgtcc agtcttgcta ggcccgtccg gccgtggggg   9660
```

```
tccgccagcc cgctcccccc gaggtcggcc agggccgcca ggagctgggc gcgaagtccg   9720
gggaagcaaa accgcgccgt ccagacgggc ccgacggccg cgggcgggtc taacagttgg   9780
atgattttag tggcgggatg ccaccgcgcc accgcctccc gcaccgcggg caggaggcat   9840
ccggctgccg ccgaggccac gccgggccag gctcgcgggg ggaggacgac cctggccccc   9900
accgcgggcc aggcccccag gagcgcggcg taagcggccg cggccccgcg caccaggtcc   9960
cgtgccgact cggccgtggc cggcacggtg aacgtgggcc aacccggaaa ccccaggacg  10020
gcaaagtacg ggacgggtcc cccccggacc tcaaactcgg gccccagaaa ggcaaagacg  10080
ggggccaggg ccccgggggc ggcgtggacc gtggtatgcc actgccggaa aagggcgacg  10140
agcgccggcg cggagaactt ctcgccggcg cttacaaagt agtcgtaatc gcggggcagc  10200
agcacccgtg ccgtgactcg ttgcgggtgc ccgcgtggcc gcaggcccac ctcgcacacc  10260
tcgaccaggt ccccgaacgc gccctccttc ttgatcggcg gaaacgcaag agtctggtat  10320
tcgcgcgcaa atagcgcggt tccggtggtg atgttaacgg tcagcgaagc ggcggacgcg  10380
cactgggggg tgtcgcgaat ggccgccagg cgcgcccacg ccagccgcgc gtcgggatgc  10440
tcggcaacgc gcgccgccag ggccataggg tcgatgtcaa tgttggcctc cgcgaccagg  10500
agagcggcgc gaggggcggc gggcgggccc cacgacgctc tctcaacttt caccaccagt  10560
cccgtgcgtg ggtccgagcc gatacgcagc ggggcgaaca gggccaccgg cccggtctgg  10620
cgctccaggg ccgccaggac gcacgcgtac agcgcccgcc acagagtcgg gttctccagg  10680
ggctccagcg gggaggcggc cggcgtcgtc gcggcgcggg cggccgccac gacggcctgg  10740
acggagacgt ccgcggagcc gtagaaatcc cgcagctccg tcgcggtgac ggagacctcc  10800
gcaaagcgcg cgcgaccctc ccctgcggcg ttgcgacata caaaatacac cagggcgtgg  10860
aagtactcgc gagcgcgggg gggcagccat accgcgtaaa gggtaatggc gctgacgctc  10920
tcctccaccc acacgatatc tgcggtgtcc atcgcacggc ccctaaggat cacgggcggt  10980
ctgtgggtcc catgctgccg tgcctggccg ggcccggtgg gtcgcggaaa ccggtgacgg  11040
ggggggggcg gtttttgggg ttggggtggg ggtgggaaac ggcccgggtc cgggggccaa  11100
cttggcccct cggtgcgttc cggcaacagc gccgccggtc cgcggacgac cacgtaccga  11160
acgagtgcgg tcccgagact tatagggtgc taaagttcac cgccccctgc atcatgggcc  11220
aggcctcggt ggggagctcc gacagcgccg cctccaggat gatgtcagcg ttggggttgg  11280
cgctggatga gtgcgtgcgc aaacagcgcc cccacgcggg cacgcgtagc ttgaagcgcg  11340
cgcccgcaaa ctcccgcttg tgggccataa gcagggcgta cagctgcctg tgggtccggc  11400
aggcgctgtg gtcgatgtgg tgggcgtcca acaaccccac gattgtctgt ttggtgaggt  11460
ttttaacgcg ccccgccccg ggaaacgtct gcgtgctttt ggccatctgc acgccaaaca  11520
gttcgcccca gattatcttg aacagcgcca ccgcgtggtc cgtctcgcta acggacccgc  11580
gcgggggaca gccgcttagg gcgtcggcga cgcgcttgac ggcttcctcc gagagcagaa  11640
gtccgtcggt tacgttacag tggcccagtt cgaacaccag ctgcatgtag cggtcgtagt  11700
ggggggtcag taggtccagc acgtcatcgg ggccgaaggt cctcccagat cccccggccg  11760
ccgagtccca atgcaggcgc gcggccatgg tgctgcacag gcacaacagc tcccagacgg  11820
gggttacgtt cagggtgggg ggcagggcca cgagctccag ctctccggtg acgttgatcg  11880
tggggatgac gcccgtggcg tagtggtcat agatccgccg aaatatggcg ctgctgcggg  11940
tggccatggg aacgcggaga caggcctcca gcaacgccag gtaaataaac cgcgtgcgtc  12000
ccatcaggct gttgaggttg cgcatgagcg cgacaatttc cgccggcgcg acatcggacc  12060
```

ggaggtattt ttcgacgaaa agacccacct cctccgtctc ggcggcctgg gccggcagcg 12120
acgcctcggg atcccggcac cgcagctccc gtagatcgcg ctgggccctg agggcgtcga 12180
aatgtacgcc ccgcaaaaac agacagaagt cctttggggt cagggtatcg tcgtgtcccc 12240
agaagcgcac gcgtatgcag tttagggtca gcagcatgtg aaggatgtta aggctgtccg 12300
agagacacgc cagcgtgcat ctctcaaagt agtgtttgta acggaatttg ttgtagatgc 12360
gcgacccccg ccccagcgac gtgtcgcatg ccgacgcgtc acagcgcccc ttgaaccggc 12420
gacacagcag gtttgtgacc tgggagaact gcgcgggcca ctggccgcag gaactgacca 12480
cgtgattaag gagcatgggc gtaaagacgg gctccgagcg cgccccggag ccgtccatgt 12540
aaatcagtag ctcccccttg cggagggtgc gcacccgtcc cagggactgg tacacggaca 12600
ccatgtccgg tccgtagttc atgggtttca cgtaggcgaa catgccatca aagtgcaggg 12660
gatcgaagct gaggcccacg gttacgaccg tcgtgtatat aaccacgcgg tattggcccc 12720
acgtggtcac gtccccgagg ggggtgagcg agtgaagcaa cagcacgcgg tccgtaaact 12780
gacggcagaa ccgggccacg atctccgcga aggagaccgt cgacgaaaaa atgcagatgt 12840
tatcgccccc gccaaggcgc gcttccagct ccccaaagaa cgtggccccc cgggcctccg 12900
gagaggcgtc cggagacggg ccgctcggcg gcccgggcgg gcgcagggca gcctgcagga 12960
gctcggtccc cagacgcggg agaaacaggc accggcgcgc cgaaaacccg ggcatggcgt 13020
actcgccgac caccacatgc acgttttttt cgccccggag accgcacagg aagtccacca 13080
actgcgcgtt ggcggttgcg tccatggcga tgatccgagg acagatgcgc agcaggcgta 13140
gcattaacgc atccacgcgg cccagttgct gcatcgttgg cgaatagagc tggcccagcg 13200
tcgacataac ctcgtccaga acgaggacgt cgtagttgtt cagaaggttg gggcccacgc 13260
gatgaaggct ttccacctgg acgataagtc ggtggaaggg gcggtcgttc ataatgtaat 13320
tggtggatga gaagtaggtg acaaagtcga ccaggcctga ctcagcgaac cgcgtcgcta 13380
gggtctgggt aaaactccga cgacaggaga cgacgagcac actcgtgtcc ggagagtgga 13440
tcgcttcccg cagccagcgg atcagcgcgg tagtttttcc cgaccccatt ggcgcgcgga 13500
ccacagtcac gcacctggcc gtcggggcgc tcgcgttggg gaaggtgacg ggtccgtgct 13560
gctgccgctc gatcgttgtt ttcgggtgaa cccggggcac ccattcggcc aaatcccccc 13620
cgtacaacat ccgcgctagc gatacgctcg acgtgtactg ttcgcactcg tcgtccccaa 13680
tgggacgccc ggcccccaga ggatctcccg actccgcgcc ccccacgaaa ggcatgaccg 13740
gggcgcggac ggcgtggtgg gtctggtgtg tgcaggtggc gacgtttgtg gtctctgcgg 13800
tctgcgtcac ggggctcctc gtcctggcct ctgtgttccg ggcacggttt ccctgctttt 13860
acgccacggc gagctcttat gccggggtga actccacggc cgaggtgcgc gggggtgtag 13920
ccgtgcccct caggttggac acgcagagcc ttgtgggcac ttatgtaatc acggccgtgt 13980
tgttgttggc cgtggccgtg tatgccgtgg tcggcgccgt gacctcccgc tacgaccgcg 14040
ccctggacgc gggccgccgt ctggctgcgg cccgcatggc catgccgcac gccacgctga 14100
tcgccggaaa cgtctgctct tggttgctgc agatcaccgt cctgttgctg gcccatcgca 14160
tcagccagct ggcccacctg gtttacgtcc tgcactttgc gtgtctggtg tattttgcgg 14220
cccatttttg caccaggggg gtcctgagcg ggacgtatct gcgtcaggtg cacggcctga 14280
tggagctggc cccgacccat catcgcgtcg tcggcccggc tcgcgccgtg ctgacaaacg 14340
ccttgctgtt gggcgtcttc ctgtgcacgg ccgacgccgc ggtatccctg aataccatcg 14400

-continued

```
ccgcgttcaa ctttaatttt tcggccccgg gcatgctcat ctgcctgacc gtgctgttcg  14460
ccattctcgt cgtatcgctg ttgttggtgg tcgagggggt gttgtgtcac tacgtgcgcg  14520
tgttggtggg cccccacctg ggggccgtgg ccgccacggg catcgtcggc ctggcctgcg  14580
agcactatta caccaacggc tactacgttg tggagacgca gtggccgggg gctcagacgg  14640
gagtccgcgt cgccctcgcc ctggtcgccg cctttgccct cggcatggcc gtgctccgct  14700
gcacccgcgc ctatctgtat cacaggcggc accacaccaa attttttatg cgcatgcgcg  14760
acacgcgaca ccgcgcacat tccgccctca agcgcgtacg cagttccatg cgcggatcgc  14820
gagacggccg ccacaggccc gcacccggca gcccgcccgg gattcccgaa tatgcggaag  14880
accccctacgc gatctcatac ggcggccagc tcgaccggta cggagattcc gacggggagc  14940
cgatttacga cgaggtggcg gacgaccaaa ccgacgtatt gtacgccaag atacaacacc  15000
cgcggcacct gcccgacgac gatcccatct atgacaccgt tggggggtac gaccccgagc  15060
ccgccgagga ccccgtgtac agcaccgtcc gccgttggta gctgtttggt tccgttttaa  15120
taaaccgttt gtgtttaacc cgaccgtggt gtatgtctgg tgtgtggcgt ccgatcccgt  15180
tactatcacc gtcccccccc ccccctcaac cccggcgatt gtgggttttt taaaaacgac  15240
acgcgtgcga ccgtatacag aacattgttt tggtttttat tcgctatcgg acatgggggg  15300
tggaaactgg gtggcggggc aggcgcctcc gggggtccgc cggtgagtgt ggcgcgaggg  15360
ggggtccgat gaacgcaggc gctgtctccc cggggcccgc gtaaccccgc gcatatccgg  15420
gggcacgtag aaattacctt cctcttcgga ctcgatatcc acgacgtcaa agtcgtgggc  15480
ggtcagcgag acgacctccc cgtcgtcggt gatgaggacg ttgtttcggc agcagcaggg  15540
ccgggccccg gagaacgaga ggcccatagc tcggcgagcg tgtcgtcgaa tgccaggcgg  15600
ctgcttcgct ggatggcctt atagatctcc ggatcgatgc ggacgggggt aatgatcagg  15660
gcgatcggaa cggcctggtt cgggagaatg gacgccttgc tgggtcctgc ggccccgaga  15720
gccccggcgc cgtcctccag gcggaacgtt acgccctcct ccgcgctggt gcggtgcctg  15780
ccgataaacg tcaccagatg cgggtggggg gggcagtcgg ggaagtggct gtcgagcacg  15840
tagccctgca ccaagatctg cttaaagttc gggtgacggg ggttcgcgaa gacgggctcg  15900
cggcggacca gatccccgga gctccaggac acgggggaga tggtgtggcg tccgaggtcg  15960
ggggcgccaa acagaagcac ctccgagaca acgccgctat ttaactccac caaggcccga  16020
tccgcggcgg agcaccgcct tttttcgccc gaggcgtggg cctctgacca ggcctggtct  16080
tgcgtgacga gagcctcctc cgggccgggg acgcgcccgg gcgcgaagta tcgcacgctg  16140
ggcttcggga tcgaccggat aaatgcccgg aacgcctccg gggaccggtg tgccatcaag  16200
tcctcgtacg cggaggccgt ggggtcgctg gggtccatgg ggtcgaaagc gtacttggcc  16260
cggcatttga cctcgtaaaa ggccaggggg gtcttgggga ctggggccag gtagccgtga  16320
atgtcccgag gacagacgag aatatccagg gacgccccga ccatccccgt gtgaccgtcc  16380
atgaggaccc cacacgtatg cacgttctct tcggcgaggt cgctgggttc gtggaagata  16440
aagcgccgcg tgtcggcgcc ggcctcgccg ccgtcgtccg cgcggcccac gcagtagcga  16500
aacagcaggc ttcgggccgt cggctcgttc acccgcccga acatcaccgc cgaagactgt  16560
acatccggcc gcaggctggc gttgtgcttc agccactggg gcgagaaaca cggaccctgg  16620
gggccccagc ggagggtgga tgcggtcgtg aggccccgcc ggagcagggc ccatagctgg  16680
cagtcggcct ggttttgcgt ggccgcctcg taaaacccca tgaggggccg gggcgccacg  16740
gcgtccgcgg cggccggggg cccgcggcgc gtcaggcgcc ataggtgccg accgagtccg  16800
```

cggtccacca tacccgcctc ctcgaggacc acggccaggg aacacagata atccaggcgg 16860
gcccagaggg gaccgatggc cagaggggcg cggacgccgc gcagcaaccc gcgcaggtgg 16920
cgctcgaacg tctcggctag tatatgggag ggcagcgcgt tggggatcac cgacgccgac 16980
cacatagagt caaggtccgg ggagtcggga tcggcgtccg ggtcgcgggc gtgggtgccc 17040
ccaggagata gcggaatgtc tggggtcgga ggccctgagg cgtcagaaag tgccggcgac 17100
gcggcccggg gcttttcgtc tgcggtgtcg gtggcgtgct gatcacgtgg ggggttaacg 17160
ggcgaatggg agctcgggtc cacagctgat gtcgtctggg gtgggggggg caggggacgg 17220
aaggtggttg tcagcggaag actgttaggg cgggggcgct tgggggggct gtcggggcca 17280
cgaggggtgt cctcggccag ggcccaggga cgcttagtca cggtgcgtcc cggcggacat 17340
gctgggccta ccgtggactc catttccgag acgacgtggg gggagcggtg gttgagcgcg 17400
ccgccgggtg aacgctgatt ctcacgacag cgcgtgccgc gcgcacgggt tggtgtgaca 17460
caggcgggac accagcacca ggagaggctt aagctcggga ggcagcgcca ccgacgacag 17520
tatcgccttg tgtgtgtgct ggtaatttat acaccgatcc gtaaacgcgc gccgaatctt 17580
gggattgcgg aggtggcgcc ggatgccctc tgggacgtca tacgccaggc cgtgggtgtt 17640
ggtctcggcc gagttgacaa acagggctgg gtgcagcacg cagcgatagg cgagcagggc 17700
cagggcgaag tccggcgaca gctggttgtt aaaatactgg taaccgggaa accgggtcac 17760
gggtacgccc aggctcgggg cgacgtacac gctaaccacc aactccagca gcgtctggcc 17820
cagggcgtac aggtcaaccg ctaacccgac gtcgtgcttc aggcggtggt tggtaaattc 17880
ggcccgttcg ttgttaaggt atttcaccaa cagctccggg ggctggttat acccgtgacc 17940
caccagggtg tgaaagttgg ctgtggttag ggcggtgggc atgccaaaca tccgggggga 18000
cttgaggtcc ggctcctgga ggcaaaactg cccccgggcg atcgtggagt tggagttgag 18060
ggtgacgagg ctaaagtcgg cgaggacggc ccgccggagc gagacggcgt ccgaccgcag 18120
catgacgagg atgttggcgc acttgatatc caggtggctg atcccgcagg tggtgtttaa 18180
aaacacaacg gcgcgggcca gctccgtgaa gcactggtgg agggccgtcg agaccgaggg 18240
gtttgttgtg cgcagggacg ccagttggcc gatatactta ccgaggtcca tgtcgtacgc 18300
ggggaacact atctgtcgtt gttgcagcga gaacccgagg ggcgcgatga agccgcggat 18360
gttgtgggtg cggccggcgc gtagaacgca ctccccgacc aacagggtcg cgatgagctc 18420
aacggcaaac cactcctttt cctttatggt cttaacggca agcttatgtt cgcgaatcag 18480
ttggacgtca ccgtatcccc cagaccccc gaagcttcgg gccccgggga tctcgagggt 18540
cgtgtagtgt agggcggggt tgatggcgaa cacggggctg catagcttgc ggatgcgcgt 18600
gagggtgagg atgtgcgagg gggacgaggg gggtgcggtt aacgccgcct gggatctgcg 18660
caggggcggg cggttcagtt tggccgccgt accgggcgtc tcgggggacg cgcggcgatg 18720
agacgagcgg ctcattcgcc atcgggatag tcccgcgcga agccgctcgc ggaggccgga 18780
tcggtggcgg gacccgtggg aggagcggga gacggcggcg tcctggagag aggggccgct 18840
ggggcgcccg gaggccccgt gggggttgga gtgtacgtag gatgcgagcc aatccttgaa 18900
ggaccgttgg cgtgcacctt gggggctgag gttagctgcc acatgaccag caggtcgctg 18960
tctgcgggac tcatccatcc ttcggccagg tcgccgtctc cccacagaga agcgttggtc 19020
gctgcttcct cgagttgctc ctcctggtcc gcaagacgat cgtccacggc gtccaggcgc 19080
tcaccaagcg ccggatcgag gtaccgtcgg tgtgcggtta gaaagtcacg acgcgccgct 19140

```
tgctcctcca cgcgaatttt aacacaggtc gcgcgctgtc gcatcatctc taagcgcgcg  19200
cgggacttta gccgcgcctc caattccaag tgggccgcct ttgcagccat aaaggcgcca  19260
acaaaccgag gatcttgggt gctgacgccc tcccggtgca gctgcagggt ctggtccttg  19320
taaatctcgg ctcggaggtg cgtctcggcc aggcgtcggc gcagggccgc gtgggcggca  19380
tctcggtcca ttccgccacc ctgcgggcga cccggggggt gctctgatag tctcgcgtgc  19440
ccaaggcccg tgatcggggt acttcgccgc cgcgacccgc cacccggtgt gcgcgatgtt  19500
tggtcagcag ctggcgtccg acgtccagca gtacctggag cgcctcgaga aacagaggca  19560
acttaaggtg ggcgcggacg aggcgtcggc gggcctcacc atgggcggcg atgccctacg  19620
agtgcccttt ttagatttcg cgaccgcgac ccccaagcgc caccagaccg tggtccctgg  19680
cgtcgggacg ctccacgact gctgcgagca ctcgccgctc ttctcggccg tggcgcggcg  19740
gctgctgttt aatagcctgg tgccggcgca actaaagggg cgtgatttcg gggcgacca  19800
cacggccaag ctggaattcc tggcccccga gttggtacgg gcggtggcgc gactgcggtt  19860
taaggagtgc gcgccggcgg acgtggtgcc tcagcgtaac gcctactata gcgttctgaa  19920
tacgtttcag gccctccacc gctccgaagc ctttcgccag ctggtgcact ttgtgcggga  19980
ctttgcccag ctgctcaaaa cctccttccg ggcctccagc ctcacggaga ccacgggccc  20040
ccccaaaaaa cgggccaagg tggacgtggc cacccacggc cggacgtacg gcacgctgga  20100
gctgttccaa aaaatgatcc ttatgcacgc cacctacttt ctggccgccg tgctcctcgg  20160
ggaccacgcg gagcaggtca acacgttcct gcgtctcgtg tttgagatcc ccctgtttag  20220
cgacgcggcc gtgcgccact tccgccagcg cgccaccgtg tttctcgtcc cccggcgcca  20280
cggcaagacc tggtttctgg tgcccctcat cgcgctgtcg ctggcctcct ttcgggggat  20340
caagatcggc tacacggcgc acatccgcaa ggcgaccgag ccggtgtttg aggagatcga  20400
cgcctgcctg cggggctggt tcggttcggc ccgagtggac cacgttaaag gggaaaccat  20460
ctccttctcg tttccggacg ggtcgcgcag taccatcgtg tttgcctcca gccacaacac  20520
aaacgtaagt cctcttttct ttcgcatggc tctcccaagg ggccccgggt cgacccgacc  20580
cacacccacc cacccacata cacacacaac cagacgcggg aggaaagtct gccccgtggg  20640
cactgatttt tattcgggat cgcttgagga ggcccgggca acggcccggg caacggtggg  20700
gcaactcgta gcaaataggc gactgatgta cgaagagaag acacacaggc gccacccggc  20760
gctggtcggg gggatgttgt ccgcgccgca ccgtcccccg acgacctctt gcagacggtc  20820
cgtgatgcaa ggacggcggg gggcctgcag cagggtgacc gtatccacgg gatggccaaa  20880
gagaagcgga cacaggctag catccccctg gaccgccagg gtacactggg ccatcttggc  20940
ccacagacac ggggcgacgc agggacagga ctccgttacg acggaggaga gccacagtgc  21000
gttggcggaa tcgatgtggg gcggcggggc gcaggactcg cagcccccgg ggtggttggt  21060
gatcctggcc aggagccatc ccagatggcg ggccctgctt cccggtggac agagcgaccc  21120
caggtcgctg tccatggccc agcagtagat ctggccgctg gggaggtgcc accaggcccc  21180
cgggcccaag gcgcagcacg cgcccggctc cggggggtc ttcgcgggga ccagatacgc  21240
gccatccagc tcgccgacca ctggctcctc cgcgagctgt tcggtggttg ggtcgggggt  21300
ttcctccggg ggggtggccg cccgtatgcg tgcgaacgtg agggtgcaca ggagcggggt  21360
cagggggtgc gtcacgctcc ggaggtggac gatcgcgcag tagcggcgct cgcggttaaa  21420
gaaaaagagg gcaaagaagg tgttcggggg caaccgcagc gccttggggc gcgtcagata  21480
cagaaaaatc tcgcagaaga gggcgcgccc ggggtctggg ttaggaaggg ccacctgaca  21540
```

```
cagaggctcg gtgaggaccg ttagacaccg aaagatcttg agccgctcgt ccgcccgaac  21600
gacgcgccac acaaagacgg agttgacaat gcgcgcgata gagtcgacgt ccgtccccag  21660
gtcgtcgact ctatcgcgcg tgccgcgagc tccggcccgg gaatccggcc ggggcaaggt  21720
ccccgggggga ccaggcggcg ccagggggccg ccggggtccc agctgcgcca tgccgggggc  21780
gggggggaggg caaaccccag aggcgggggc caacggcgcg gggaggagtg ggtgggcgag  21840
gtggccgggg gaaggcgccc gctagcgaga ccggccgttc ccggacgaca ccttgcgaca  21900
aaacctaagg acagcggccc gcgcgacggg gtccgagagg ctaaggtagg ccgcgatgtt  21960
aatggtgaac gcaaagccgc cgggaaagac aactatgcca cagaggcggc gattaaaccc  22020
caggcagagg taggcgtagc tttccccggg caggtattgc tcgcagaccc tgcgtggggc  22080
tgtggagggg acggcctcca tgaagcgaca tttactctgc tcgcgtttac tgacgtcacc  22140
atccatcgcc acggcgattg gacgattgtt aagccgcagc gtgtctccgc ttgtgctgta  22200
gtagtcaaaa acgtaatggc cgtcggagtc ggcaaagcgg gccgggaggt cgtcgccgag  22260
cgggacgacc cgccgccccc gaccgccccg tccccccagg tgtgccagga cggccagggc  22320
atacgcggtg tgaaaaaagg cgtcgggggc ggtcccctcg acggcgcgca tcaggttctc  22380
gaggagaatg gggaagcgcc tggtcacctc ccccaaccac gcgcgttggt cggggccaaa  22440
gtcatagcgc aggcgctgtg agattcgcgg gccgccctga agcgcggccc ggatggcctg  22500
gcccagggcc cggaggcacg ccagatgtat gcgcgcggta aaggcgacct cggcggcgat  22560
gtcaaagggc ggcaggacgg ggcgcgggtg gcgcaggggc acctcgagcg cgggaaagcg  22620
tagcagcagc tccgcctgcc cagcgggaga cagctggtgg gggcgcacga cgcgttctgc  22680
ggcgcaggcc tcggtcaggg ccgtggccag cgccgaggac agcagcggag ggcgggcgcg  22740
tcgcccgccc cacgccacgg agttctcgta ggagacgacg acgaagcgct gcttggttcc  22800
gtagtggtgg cgcaggacca cggagataga acgacggctc cacagccagt ccggccggtc  22860
gccgccggcc agggcttccc atccgcgatc caaccactcg accagcgacc gcggctttgc  22920
ggtaccaggg gtaagggtta gaacgtcgtt caggatgtcc tcgcccccgg gcccgtgggg  22980
cgctggggcc acaaagcggc ccccgccggg gggctccaga cccgccagca ccgcatctgc  23040
gtcagccgcc cccatggcgc ccccgctgac ggcctggtga accagggcgc cctggcgtag  23100
ccccgatgca acgccacagg ccgcacgccc ggtccgcgct cggaccgggt ggcggcgggt  23160
gacgtcctgc actgcccgct gaaccaacgc gaggatctcc tcgttctcct gtgcgatgga  23220
cacgtcctgg gccgcggtcg tgtcgccgcc gggggccgtc agctgctcct ccggggagat  23280
ggggggggtcg gacgccccga cgatgggcgg gtctgcgggc gcccccgcgt ggggccgggc  23340
caagggctgc ggacgcgggg acgcgctttc ccccagaccc atggacaggt gggccgcagc  23400
ctccttcgcg gccggcgggg cggcggcgcc aagcagagcg acgtagcggc acaaatgccg  23460
acagacgcgc atgatgcgcg tgctgtcggc cgcgtagcgc gtgttggggg ggacgagctc  23520
gtcgtaacta aacagaatca cgcgggcaca gctcgccccc gagccccacg caaggcgcag  23580
cgccgccacg gcgtacgggt catagacgcc ctgcgcgtca cacaccacgg gcagggagac  23640
gaacaacccc ccggcgctgg acgcacgcgg aaggaggcca gggtgtgccg gcacgacggg  23700
ggccagaagc tcccccaccg catccgcggg cacgtaggcg gcaaacgccg tgcaccacgg  23760
ggtacagtcg ccggtggcat gagcccgagt ctggatttcg acctggaagt ttgcggccgt  23820
cccgagtccg gggcggccgc gcatcagggc ggccagaggg attcccgcgg ccgccaggca  23880
```

```
ctcgctggat atgatgacgt gaaccaaaga ccgagggccg acccgggccg tggccgagat  23940
cgtctggacc tcgttggcca agtgcgcgtt catggttcgg gggtgggtgt gggtgtgtag  24000
gcgatgcggg tcccccgagt ccgcgggaag ggcgtgggtt tggcgcgcgt atgcgtattc  24060
gccaacggag gcgtgcgtgc ttatgcgcgg cgcgtttctt ctgtctctag ggaatccgag  24120
gccaggactt taacctgctc tttgtcgacg aggccaactt tattcgcccg gatgcggtcc  24180
agacgattat gggctttctc aaccaggcca actgcaagat tatcttcgtg tcgtccacca  24240
acaccgggaa ggccagtacg agctttttgt acaacctccg cggggccgca gacgagcttc  24300
tcaacgtggt gacctatata tgcgatgatc acatgccgag ggtggtgacg cacacaaacg  24360
ccacggcctg ttcttgttat atcctcaaca agcccgtttt catcacgatg gacggggcgg  24420
ttcgccggac cgccgatttg tttctggccg attccttcat gcaggagatc atcgggggcc  24480
aggccaggga gaccggcgac gaccggcccg ttctgaccaa gtctgcgggg gagcggtttc  24540
tgttgtaccg cccctcgacc accaccaaca gcggcctcat ggcccccgat ttgtacgtgt  24600
acgtggatcc cgcgttcacg gccaacaccc gagcctccgg gaccggcgtc gctgtcgtcg  24660
ggcggtaccg cgacgattat atcatcttcg ccctggagca ctttttctc cgcgcgctca  24720
cgggctcggc ccccgccgac atcgcccgct gcgtcgtcca cagtctgacg caggtcctgg  24780
ccctgcatcc cggggcgttt cgcggcgtcc gggtggcggt cgagggaaat agcagccagg  24840
actcggccgt cgccatcgcc acgcacgtgc acacagagat gcaccgccta ctggcctcgg  24900
agggggccga cgcgggctcg ggccccgagc ttctcttcta ccactgcgag cctcccggga  24960
gcgcggtgct gtaccccttt ttcctgctca acaaacagaa gacgcccgcc tttgaacact  25020
ttattaaaaa gtttaactcc gggggcgtca tggcctccca ggagatcgtt tccgcgacgg  25080
tgcgcctgca gaccgacccg gtcgagtatc tgctcgagca gctaaataac ctcaccgaaa  25140
ccgtctcccc caacactgac gtccgtacgt attccggaaa acggaacggc gcctcggatg  25200
accttatggt cgccgtcatt atggccatct acctcgcggc ccaggccgga cctccgcaca  25260
cattcgctcc tatcacacgc gtctcgtgag cgcccaataa acacacccag gtatgctacg  25320
cacgaccacg gtgtcgtctg ttaagggggg ggggggaagg gggtgttggc gggaagcgtg  25380
ggaacacggg ggattctctc acgaccggca ccagtaccac ccccctgtga acacagaaac  25440
cccaacccaa atcccataaa catacgacac acaggcatat tttggaattt cttaggtttt  25500
tatttattta ggtatgctgg ggtttctccc tggatgccca cccccacccc cccgtgggtc  25560
tagccgggcc ttagggatag cgtataacgg gggccatgtc tccggaccgc acaacggccg  25620
cgccgtcaaa ggtgcacacc cgaaccacgg gagccagggc caaggtgtct cctagttggc  25680
ccgcgtgggt cagccaggcg acgagcgcct cgtaaagcgg cagccttcgc tctccatcct  25740
gcatcagggc cggggcttcg gggtgaatga gctgggcggc ctcccgcgtg acactctgca  25800
tctgcagtag agcgttcacg tacccgtcct gggcacttag cgcaaagagc cgggggatta  25860
gcgtaaggat gatggtggtt ccctccgtga tcgagtaaac catgttaagg accagcgatc  25920
gcagctcggc gtttacggga ccgagttgtt ggacgtccgc cagcagcgag aggcgactcc  25980
cgttgtagta cagcacgttg aggtctggca gccctccggg gtttctgggg ctggggttca  26040
ggtcccggat gcccctggcc acgagccgcg ccacgatttc gcgcgccagg ggcgatggaa  26100
gcggaacggg aaaccgcaac gtgaggtcca gcgaatccag gcgcacgtcc gtcgcttggc  26160
cctcgaacac gggcgggacg aggctgatgg ggtccccgtt acagagatct acgggggagg  26220
tgttgcgaag gttaacggtg ccggcgtggg tgaggcccac gtccaggggg caggcgacga  26280
```

```
ttcgcgtggg aagcacccgg gtgatgaccg cggggaagcg ccttcggtac gccagcaaca  26340
accccaacgt gtcgggactg acgcctccgg agacgaagga ttcgtgcgcc acgtcggcca  26400
gcgtcagttg ccggcggatg gtcggcagga ataccacccg cccttcgcag cgctgcagcg  26460
ccgccgcatc ggggcgcgag atgcccgagg gtatcgcgat gtcagtttca aagccgtccg  26520
ccagcatggc gccgatccac gcggcaggga gtgcagtggt ggttcgggtg gcgggaggag  26580
cgcggtgggg gtcagcggcg tagcagagac gggcgaccaa cctcgcatag gacggggggt  26640
gggtcttagg gggttgggag gcgacaggga ccccagagca tgcgcgggga ggtctgtcgg  26700
gcccagacgc accgagagcg aatccgtccg cggagtcccg gcttgggttt tatggggccc  26760
ggccctcgga atcgcggctt gtcggcgggg acaaaggggg cggggctagg ggcttgcgga  26820
aacagaagac gcgtgggata aaagaatcgc actaccccaa ggaagggcgg ggcggtttat  26880
tacagagcca gtcccttgag cggggatgcg tcatagacga gatactgcgc gaagtgggtc  26940
tcccgcgcgt gggcttcccc gttgcgggca ctgcggagga gggcggggtc gctggcgcag  27000
gtgagcgggt aggcctcctg aaacaggcca cacgggtcct ccacgagttc gcggcacccc  27060
ggggggcgct taaactgtac gtcgctggcg gcggtggccg tggacaccgc cgaacccgtc  27120
tccacgatca ggcgctccag gcagcgatgt ttggcggcga tgtcggccga cgtaaagaac  27180
ttaaagcagg ggctgagcac cggcgaggcc ccgttgaggt ggtaggcccc gttatagagc  27240
aggtccccgt acgaaaatcg ctgcgacgcc cacgggttgg ccgtggccgc gaaggcccgg  27300
gacgggtcgc tctggccgtg gtcgtacatg agggcggtga catccccctc cttgtccccc  27360
gcgtaaacgc ccccggcggc gcgtccccgg gggttgcagg gccggcggaa gtagttgacg  27420
tcggtcgaca cgggggtggc gataaactca cacacggcgt cctggccgtg gtccatccct  27480
gcgcgccgcg gcacctgggc gcacccgaac acggggacgg gctgggccgg ccccaggcgg  27540
tttcccgcca cgaccgcgtt ccgcaggtac acggctgccg cgttgtccag gagaggggga  27600
gccccgcggc ccaggtaaaa gttttgggga aggttgccca tgtcggtgac ggggttgcgg  27660
acggttgccg tggccacgac ggcggtgtag cccacgccca ggtccacgtt cgcgcgcggc  27720
tgggtgagcg tgaagtttac ccccccgcca gtttcgtgcc gggccacctg gagctggccc  27780
aggaagtacg cctccgacgc gcgctccgag aacagcacgt tctcagtcac aaagcggtcc  27840
tgtcggacga cggtgaaccc aaacccggga tggaggcccg tcttgagctg atgatgcaag  27900
gccacgggac tgatcttgaa gtaccccgcc atgagcgcgt aggtcagcgc gttctccccg  27960
gccgcgctct cgcggacgtg ctgcacgacg ggctgtcgga tcgacgaaaa gtagttggcc  28020
cccagagccg gggggaccag ggggacctgc cgcgacaggt cgcgcagggc cgggggggaaa  28080
ttgggcgcgt tcgccacgtg gtcggccccg gcgaacagcg cgtggacggg gagggggtaa  28140
aaatagtcgc cattttggat ggtatggtcc agatgctggg gggccatcag caggattccg  28200
gcgtgcaacg ccccgtcgaa tatgcgcatg ttggtggtgg acgcggtgtt ggcgcccgcg  28260
tcgggcgccg ccgagcagag cagcgccgtt gtgcgttcgg ccatgttgtg ggccagcacc  28320
tgcagcgtga gcatggcggg cccgtccact accacgcgcc cgttgtgaaa catggcgttg  28380
accgtgttgg ccaccagatt ggccgggtgc agggggtgcg cggggtccgt cacggggtcg  28440
ctggggcact cctcgccggg ggcgatctcc gggaccacca tgttctgcag ggtggcgtat  28500
acgcggtcga agcgaacccc cgcggtgcag cagcggcccc gcgagaaggc gggcaccatc  28560
acgtagtagt aaatcttgtg gtgcacggtc cagtccgccc cccggtgcgg ccggtcatcc  28620
```

gcggcgtccg cggctcgggc ctgggtgttg tgcagcagct ggccgtcgtt gcggttgaag 28680
tccgcggtcg ccacgttaca tgccgccgcg tacacggggt cgtggccccc cgcgctaacc 28740
cggcagtcgc gatggcggtc cagggccgcg cgccgcatca gggcgtcaca gtcccacacg 28800
aggggtggca gcagcgccgg gtctcgcatt aggtgattca gctcggcttg cgcctgcccg 28860
cccagctccg ggccggtcag ggtaaagtca tcaaccagct gggccagggc ctcgacgtgc 28920
gccaccaggt cccggtacac ggccatgcac tcctcgggaa ggtctccccc gaggtaggtc 28980
acgacgtacg agaccagcga gtagtcgttc acgaacgccg cgcaccgcgt gttgttccag 29040
tagctggtga tgcactggac cacgagccgg gccagggcgc agaagacgtg ctcgctgccg 29100
tgtatggcgg cctgcagcag gtaaaacacc gccgggtagt tgcggtcgtc gaacgccccg 29160
cgaacggcgg cgatggtggc gggggccatg gcgtggcgtc ccaccccccag ctccaggccc 29220
cgggcgtccc ggaacgccgc cggacatagc gccaggggca agttgccgtt caccacgcgc 29280
caggtggcct ggatctcccc cgggccggcc gggggaacgt cccccccgg cagctccacg 29340
tcggccaccc ccacaaagaa gtcgaacgcg gggtgcagct caagagccag gttggcgttg 29400
tcgggctgca taaactgctc cggggtcatc tggccttccg cgacccatcg gacccgcccg 29460
tgggccaggc gctgccccca ggcgttcaaa aacagctgct gcatgtctgc ggcggggccg 29520
gccggggccg ccacgtacgc cccgtacgga ttggcggctt cgacggggtc gcggttaagg 29580
cccccgaccg ccgcgtcaac gttcatcagc gaagggtggc acacggtccc gatcgcgtgt 29640
tccagagaca ggcgcagcac ctggcggtcc ttcccccaaa aaaacagctg gcggggcggg 29700
aaggcgcggg gatccgggtg gccgggggcg gggactaggt ccccggcgtg cgcggcaaac 29760
cgttccatga ccggattgaa caggcccagg ggcaggacga acgtcaggtc catggcgccc 29820
accagggggt agggaacgtt ggtggcggcg tagatgcgct tctccagggc ctccagaaag 29880
accagcttct cgccgatgga caccagatcc gcgcgcacgc gcgtcgtctg gggggcgctc 29940
tcgagctcgt ccagcgtctg ccggttcagg tcgagctgct cctcctgcat ctccagcagg 30000
tggcggccca cgtcgtccag acttcgcacg gccttgccca tcacgagcgc cgtgaccagg 30060
ttggccccgt tcaggaccat ctcgccgtac gtcaccggca cgtcggcttc ggtgtcctcc 30120
actttcagga aggactgcag gaggcgctgt ttgatcgggg cggtggtgac gagcaccccg 30180
tcgaccggcc gcccgcgcgt gtcggcatgc gtcagacggg gcacggccac ggagggctgc 30240
gtggccgtgg tgaggtccac gagccaggcc tcgacggcct cccggcggtg gcccgccttg 30300
cccaggaaaa agctcgtctc gcagaagctt cgctttagct cggcgaccag ggtcgcccgg 30360
gccaccctgg tggccaggcg gccgttgtcc aggtatcgtt gcatcggcaa caacaaagcc 30420
aggggcggcg ccttttccag cagcacgtgc agcatctggt cggccgtgcc gcgctcaaac 30480
gccccgagga cggcctggac gttgcgagcg agctgttgga tggcgcgcaa ctggcgatgc 30540
gcgccgatac ccgtcccgtc cagggcctcc cccgtgagca gggcgatggc ctcggtggcc 30600
aggctgaagg cggcgttcag ggcccggcgg tcgataatct tggtcatgta attgtgtgtg 30660
ggttgctcga tggggtgcgg gccgtcgcgg gcaatcagcg gctggtggac ctcgaactgt 30720
acgcgcccct cgttcatgta ggccagctcc ggaaacttgg tacacacgca cgccaccgac 30780
aacccgagct ccagaaagcg cacgagcgac agggtgttgc aatacgaccc cagcagggcg 30840
tcgaactcga cgtcgtacag gctgtttgca tcggagcgca cgcgggaaaa aaaatcaaac 30900
aggcgtcgat gcgacgccac ctcgatcgtg ctaaggaggg acccggtcgg caccatggcc 30960
gcggcatacc ggtatcccgg agggtcgcgg ttgggagcgg ccatggggtc gcgtggagat 31020
cggctgtctc tagcgatatt ggcccgggga ggctaagatc caccccaacg cccggccacc 31080
cgtgtacgtg cccgacggcc caaggtccac cgaaagacac gacgggcccg gacccaaaaa 31140
ggcgggggat gctgtgtgag aggccgggtg ccggtcgggg gggaaaggca ccgggagaag 31200
gctgcggcct cgttccagga gaacccagtg tccccaacag acccggggac gtgggatccc 31260
aggccttata tacccccccc cccgccccac ccccgttaga acgcgacggg tgcattcaag 31320
atggccctgg tccaaaagcg tgccaggaag aaattggcag aggcggcaaa gctgtccgcc 31380
gccgccaccc acatcgaggc cccggccgcg caggctatcc ccagggcccg tgtgcgcagg 31440
ggatcggtgg gcggcagcat ttggttggtg gcgataaagt ggaaaagccc gtccggactg 31500
aaggtctcgt gggcggcggc gaacaaggca cacagggccg tgcctcccaa aaacacggac 31560
atcccccaaa acacgggcgc cgacaacggc agacgatccc tcttgatgtt aacgtacagg 31620
aggagcgccc gcaccgccca cgtaacgtag tagccgacga tggcggccag gatacaggcc 31680
ggcgccacca cccttccggt cagcccgtaa tacatgcccg ctgccaccat ctccaacggc 31740
ttcaggacca aaaacgacca aaggaacaga atcacgcgct ttgaaaagac cggctgggta 31800
tggggcggaa gacgcgagta tgccgaactg acaaaaaaat cagaggtgcc gtacgaggac 31860
aatgaaaact gttcctccag cggcagttct ccctcctccc ccccgaaggc ggcctcgtcg 31920
accagatctc gatccaccag aggaaggtca tcccgcatgg tcatggggtg tgcggtggag 31980
gtggggagac cgaaaccgca aagggtcgct tacgtcagca ggatcccgag atcaaagaca 32040
cccgggttct tgcacaaaca ccacccgggt tgcatccgcg gaggcgagtg ttttgataag 32100
gccgttccgc gccttgatat aacctttgat gttgaccaca aaacccggaa tttacgccta 32160
cgccccaatg cccacgcaag atgaggtagg taaccccccc gtgggtgtga cgttgcgttt 32220
agttcattgg aggccaaggg gaaaaatggg gtggggagga aacggaaaac ccagtaggcc 32280
gtgtcgggaa cacgcccggg gttgtcctca aaaggcaggg tccatactac ggaagccgtc 32340
gttgtattcg agacctgcct gtgcaacgca cgtcggggtt gcctgtgtcc ggttcggccc 32400
ccaccgcgtg cggcacgcac gaggacgagt ccgcgtgctt tattggcgtt ccaagcgttg 32460
ccctccagtt tctgttgtcg gtgttccccc atacccacgc ccacatccac cgtagggggc 32520
ctctgggccg tgttacgtcg ccgcccgcga tggagcttag ctacgccacc accatgcact 32580
accgggacgt tgtgttttac gtcacaacgg accgaaaccg ggcctacttt gtgtgcgggg 32640
ggtgtgttta ttccgtgggg cggccgtgtg cctcgcagcc cggggagatt gccaagtttg 32700
gtctggtcgt tcgagggaca ggcccagacg accgcgtggt cgccaactat gtacgaagcg 32760
agctccg 32767

<210> SEQ ID NO 845
<211> LENGTH: 32767
<212> TYPE: DNA
<213> ORGANISM: Artificial Sequence
<220> FEATURE:
<223> OTHER INFORMATION: recombinant viral vector ONCR-142

<400> SEQUENCE: 845
aaaaaagctg aacgagaaac gtaaaatgat ataaatatca atatattaaa ttagattttg 60
cataaaaaac agactacata atactgtaaa acacaacata tccagtcact atgaatcaac 120
tacttagatg gtattagtga cctgtagtcg accgacagcc ttccaaatgt tcttcgggtg 180
atgctgccaa cttagtcgac cgacagcctt ccaaatgttc ttctcaaacg gaatcgtcgt 240

```
atccagccta ctcgctattg tcctcaatgc cgtattaaat cataaaaaga aataagaaaa    300
agaggtgcga gcctcttttt tgtgtgacaa aataaaaaca tctacctatt catatacgct    360
agtgtcatag tcctgaaaat catctgcatc aagaacaatt tcacaactct tatacttttc    420
tcttacaagt cgttcggctt catctggatt ttcagcctct atacttacta aacgtgataa    480
agtttctgta atttctactg tatcgacctg cagactggct gtgtataagg gagcctgaca    540
tttatattcc ccagaacatc aggttaatgg cgtttttgat gtcattttcg cggtggctga    600
gatcagccac ttcttccccg ataacggaga ccggcacact ggccatatcg gtggtcatca    660
tgcgccagct ttcatccccg atatgcacca ccgggtaaag ttcacgggag actttatctg    720
acagcagacg tgcactggcc aggggggatca ccatccgtcg cccgggcgtg tcaataatat    780
cactctgtac atccacaaac agacgataac ggctctctct tttataggtg taaaccttaa    840
actgcatttc accagcccct gttctcgtca gcaaaagagc cgttcatttc aataaaccgg    900
gcgacctcag ccatcccttc ctgattttcc gctttccagc gttcggcacg cagacgacgg    960
gcttcattct gcatggttgt gcttaccaga ccggagatat tgacatcata tatgccttga   1020
gcaactgata gctgtcgctg tcaactgtca ctgtaatacg ctgcttcata gcatacctct   1080
ttttgacata cttcgggtat acatatcagt atatattctt ataccgcaaa aatcagcgcg   1140
caaatacgca tactgttatc tggcttttag taagccggat ccacgcggcg tttacgcccc   1200
ccctgccact catcgcagta ctgttgtaat tcattaagca ttctgccgac atggaagcca   1260
tcacaaacgg catgatgaac ctgaatcgcc agcggcatca gcaccttgtc gccttgcgta   1320
taatatttgc ccatggtgaa aacgggggcg aagaagttgt ccatattggc cacgtttaaa   1380
aaggccgtaa tatccagctg aacggtctgg ttataggtac attgagcaac tgactgaaat   1440
gcctcaaaat gttctttacg atgccattgg gatatatcaa cggtggtata tccagtgatt   1500
tttttctcca ttttagcttc cttagctcct gaaaatctcg ataactcaaa aaatacgccc   1560
ggtagtgatc ttatttcatt atggtgaaag ttggaacctc ttacgtgccg atcaacgtct   1620
cattttcgcc aaaagttggc ccagggcttc ccggtatcaa cagggacacc aggatttatt   1680
tattctgcga agtgatcttc cgtcacaggt atttattcgg cgcaaagtgc gtcgggtgat   1740
gctgccaact tagtcgacta caggtcacta ataccatcta agtagttgat tcatagtgac   1800
tggatatgtt gtgttttaca gtattatgta gtctgttttt tatgcaaaat ctaatttaat   1860
atattgatat ttatatcatt ttacgtttct cgttcagctt tcttgtacaa agtggtttta   1920
atggaccgcc cgcaaggggg ggggggcatt tcagtgtcgg gtgacgagcg cgatccggcc   1980
gggatcctag gaccccaaaa gtttgtctgc gtattccagg gcggggctca gttgaatctc   2040
ccgcagcacc tctaccagca ggtccgcggt gggctggaga aactcggccg tcccggggca   2100
ggcggttgtc gggggtggag gcgcggcgcc caccccgtgt gccgcgcctg gcgtctcctc   2160
tgggggcgac ccgtaaatgg ttgcagtgat gtaaatggtg tccgcggtcc agaccacggt   2220
caaaatgccg gccgtggcgc tccgggcgct ttcgccgcgc gaggagctga cccaggagtc   2280
gaacggatac gcgtacatat gggcgtccca cccgcgttcg agcttctggt tgctgtcccg   2340
gcctataaag cggtaggcac aaaattcggc gcgacagtcg ataatcacca acagcccaat   2400
gggggtgtgc tggataacaa cgcctccgcg cggcaggcgg tcctggcgct cccggccccg   2460
taccatgatc gcgcgggtgc cgtactcaaa aacatgcacc acctgcgcgg cgtcgggcag   2520
tgcgctggtc agcgaggccc tggcgtggca taggctatac gcgatggtcg tctgtggatt   2580
ggacatctcg cggtgggtag tgagtccccc gggccgggtt cggtggaact gtaaggggac   2640
```

ggcgggttaa tagacaatga ccacgttcgg atcgcgcaga gccgatagta tgtgctcact 2700
aatgacgtca tcgcgctcgt ggcgctcccg gagcggattt aagttcatgc gaaggaattc 2760
ggaggaggtg gtgcgggaca tggccacgta cgcgctgttg aggcgcaggt tgccgggcgt 2820
aaagcagatg gcgaccttgt ccaggctaag gccctgggag cgcgtgatgg tcatggcaag 2880
cttggagctg atgccgtagt cggcgtttat ggccatggcc agctccgtag agtcaatgga 2940
ctcgacaaac tcgctgatgt tggtgttgac gacggacatg aagccgtgtt ggtcccgcaa 3000
gaccacgtaa ggcagggggg cctcttccag taactcggcc acgttggccg tcgcgtgccg 3060
cctccgcagc tcgtccgcaa aggcaaacac ccgtgcgtac gtgtatccca tgagcgtata 3120
attgtccgtc tgcagggcga cggacatcag ccccccgcgc ggcgagccgg tcagcatctc 3180
gcagccccgg aagataacgt tgtccacgta cgtgctaaag gggcgactt caaatgcctc 3240
cccgaagagc tcttggagga ttcggaatct cccgaggaag gcccgcttca gcagcgcaaa 3300
ctgggtgtga acggcggcgg tggtctccgg ttccccgggg gtgtagtggc agtaaaacac 3360
gtcgagctgt tgttcgtcca gccccgcgaa aataacgtcg aggtcgtcgt cgggaaaatc 3420
gtccgggccc ccgtcccgcg gccccagttg cttaaaatca aacgcacgct cgccgggggc 3480
gcctgcgtcg gccattaccg acgcctgcgt cggcaccccc gaagatttgg ggcgcagaga 3540
cagaatctcc gccgttagtt ctcccatgcg ggcgtaggcg agggtcctct gggtcgcatc 3600
caggcccggg cgctgcagaa agttgtaaaa ggagataagc ccgctaaata tgagccgcga 3660
caggaacctg taggcaaact ccaccgaagt ctccccctga gtctttacaa agctgtcgtc 3720
acgcaacact gcctcgaagg cccggaacgt cccactaaac ccaaaaacca gttttcgcag 3780
gcgcgcggtc accgcgatct ggctgttgag gacgtaagtg acgtcgttgc gggccacgac 3840
cagctgctgt ttgctgtgca cctcgcagcg catgtgcccc gcgtcctggt cctggctctg 3900
cgagtagttg gtgatgcggc tggcgttggc cgtgagccac ttttcaatcg tcaggccggg 3960
ctggtgtgtc agccgtcggt attcgtcaaa ctccttgacc gacacgaacg taagcacggg 4020
gagggtgaac acgacgaact ccccctcacg ggtcaccttc aggtaggcgt ggagcttggc 4080
catgtacgcg ctcacctctt tgtgggagga gaacagccgc gtccagccgg ggaggttggc 4140
ggggttggtg atgtagtttt ccgggacgac gaagcgatcc acgaactgca tgtgctcctc 4200
ggtgatgggc aggccgtact ccagcacctt catgaggtta ccgaactcgt gctcgacgca 4260
ccgtttgttg ttaataaaaa tggcccagct atacgagagg cgggcgtact cgcgcagcgt 4320
gcggttgcag atgaggtacg tgagcacgtt ctcgctctgg cggacggaac accgcagttt 4380
ctggtgctcg aaggtcgact ccagggacgc cgtctgcgtc ggcgagccca cacacaccaa 4440
cacgggccgc aggcgggccg cgtactgggg ggtgtggtac agggcgttaa tcatccacca 4500
gcaatacacc acggccgtga ggaggtgacg cccaaggagc ccggcctcgt cgatgacgat 4560
cacgttgctg cgggtaaagg ccggcagcgc cccgtgggtg gccggggcca accgcgtcag 4620
ggcgccctcg gccaacccca gggtccgttc cagggcggcc agggcgcgaa actcgttccg 4680
caactcctcg cccccggagg cggccagggc gcgcttcgtg aggtccaaaa tcacctccca 4740
gtagtacgtc agatctcgtc gctgcaggtc ctccagcgag gcggggttgc tggtcagggt 4800
gtacgggtac tgtcccagtt gggcctggac gtgattcccg cgaaacccaa attcatgaaa 4860
gatggtgttg atgggtcggc tgagaaaggc gcccgagagt ttggcgtaca tgttttgggc 4920
cgcaatgcgc gtggcgcccg tcaccacaca gtccaagacc tcgttgattg tctgcacgca 4980

-continued

```
cgtgctcttt ccggagccag cgttgccggt gataagatac accgcgaacg gaaactccct   5040
gaggggcagg cctgcggggg actctaaggc cgccacgtcc cggaaccact gcagatgggg   5100
cacttgcgct ccgtcgagct gttgttgcga gagctctcgg atgcgcttaa ggattggctg   5160
caccccgtgc atagacgtaa aatttaaaaa ggcctcggcc ctccctggaa cggctggtcg   5220
gtccccgggt tgctgaaggt gcggcgggcc gggtttctgt ccgtctagct ggcgctcccc   5280
gccggccgcc gccatgaccg caccacgctc gcgggccccc actacgcgtg cgcgggggga   5340
cacggaagcg ctgtgctccc ccgaggacgg ctgggtaaag gttcacccca gccccggtac   5400
gatgctgttc cgcgagattc tccacgggca gctggggtat accgagggcc agggggtgta   5460
caacgtcgtc cggtccagcg aggcgaccac ccggcagctg caggcggcga tctttcacgc   5520
gctcctcaac gccaccactt accgggacct cgaggcggac tggctcggcc acgtggcggc   5580
ccgcggtctg cagccccaac ggctggttcg ccggtacagg aacgcccggg aggcggatat   5640
cgccggggtg gccgagcggg tgttcgacac gtggcggaac acgcttagga cgacgctgct   5700
ggactttgcc cacgggttgg tcgcctgctt tgcgccgggc ggcccgagcg gcccgtcaag   5760
cttccccaaa tatatcgact ggctgacgtg cctggggctg gtccccatat tacgcaagcg   5820
acaagaaggg ggtgtgacgc agggtctgag ggcgtttctc aagcagcacc cgctgacccg   5880
ccagctggcc acggtcgcgg aggccgcgga gcgcgccggc cccgggtttt ttgagctggc   5940
gctggccttc gactccacgc gcgtggcgga ctacgaccgc gtgtatatct actacaacca   6000
ccgccggggc gactggctcg tgcgagaccc catcagcggg cagcgcggag aatgtctggt   6060
gctgtggccc cccttgtgga ccggggaccg tctggtcttc gattcgcccg tccagcggct   6120
gtttcccgag atcgtcgcgt gtcactccct ccgggaacac gcgcacgtct gccggctgcg   6180
caataccgcg tccgtcaagg tgctgctggg gcgcaagagc gacagcgagc gcggggtggc   6240
cggtgccgcg cgggtcgtta acaaggtgtt gggggaggac gacgagacca aggccgggtc   6300
ggccgcctcg cgcctcgtgc ggcttatcat caacatgaag ggcatgcgcc acgtaggcga   6360
cattaacgac accgtgcgtt cctacctcga cgaggccggg gggcacctga tagacgcccc   6420
ggccgtcgac ggtaccctcc ctggattcgg caagggcgga aacagccgcg ggtctgcggg   6480
ccaggaccag ggggggcggg cgccgcagct tcgccaggcc ttccgcacgg ccgtggttaa   6540
caacatcaac ggcgtgttgg agggctatat aaataacctg tttggaacca tcgagcgcct   6600
gcgcgagacc aacgcgggcc tggcgaccca attgcaggag cgcgaccgcg agctccggcg   6660
cgcaacagcg gggggccctgg agcgccagca gcgcgcggcc gacctggcgg ccgagtccgt   6720
gaccggtgga tgcggcagcc gccctgcggg ggcggacctg ctccgggccg actatgacat   6780
tatcgacgtc agcaagtcca tggacgacga cacgtacgtc gccaacagct ttcagcaccc   6840
gtacatccct tcgtacgccc aggacctgga gcgcctgtcg cgcctctggg agcacgagct   6900
ggtgcgctgt tttaaaattc tgtgtcaccg caacaaccag ggccaagaga cgtcgatctc   6960
gtactccagc ggggcgatcg ccgcattcgt cgccccctac tttgagtcag tgcttcgggc   7020
cccccgggta ggcgcgccca tcacgggctc cgatgtcatc ctgggggagg aggagttatg   7080
ggatgcggtg tttaagaaaa cccgcctgca aacgtacctg acagacatcg cggccctgtt   7140
cgtcgcggac gtccagcacg cagcgctgcc cccgcccccc tccccggtcg gcgccgattt   7200
ccggcccggc gcgtccccgc ggggccggtc cagatcgcgg tcgcccggaa gaactgcgcg   7260
aggcgcgccg gaccagggcg ggggcatcgg gcaccgggat ggccgccgcg acggccgacg   7320
atgaggggtc ggccgccacc atcctcaagc aggccatcgc cggggaccgc agcctggtcg   7380
```

-continued

```
aggcggccga ggcgattagc cagcagacgc tgctccgcct ggcctgcgag gtgcgccagg   7440
tcggcgaccg ccagccgcgg tttaccgcca ccagcatcgc gcgcgtcgac gtcgcgcctg   7500
ggtgccggtt gcggttcgtt ctggacggga gtcccgagga cgcctatgtg acgtcggagg   7560
attactttaa gcgctgctgc ggccagtcca gttatcgcgg cttcgcggtg gcggtcctga   7620
cggccaacga ggaccacgtg cacagcctgg ccgtgccccc cctcgttctg ctgcaccggt   7680
tctccctgtt caaccccagg gacctcctgg actttgagct tgcctgtctg ctgatgtacc   7740
tggagaactg cccccgaagc cacgccaccc cgtcgacctt tgccaaggtt ctggcgtggc   7800
tcggggtcgc gggtcgccgc acgtccccat tcgaacgcgt tcgctgcctt ttcctccgca   7860
gttgccactg ggtcctaaac acactcatgt tcatggtgta cgtaaaaccg ttcgacgacg   7920
agttcgtcct gccccactgg tacatggccc ggtacctgct ggccaacaac ccgccccccg   7980
ttctctcggc cctgttctgt gccaccccga cgagctcctc attccggctg ccggggccgc   8040
ccccccgctc cgactgcgtg gcctataacc ccgccgggat catggggagc tgctgggcgt   8100
cggaggaggt gcgcgcgcct ctggtctatt ggtggctttc ggagacccca aaacgacaga   8160
cgtcgtcgct gttttatcag ttttgttgaa ttttaggaaa taaacccggt tttgtttctg   8220
tggcctcccg acggatgcgc gtgtccttac tccgtcttgg tgggtgggtg gctgtgtatg   8280
gcgtcccatc tgtgcgggga ggggggcaag tcggcacgta ttcggacaga ctcaagcaca   8340
taagacgaac aaaaggtttg taacttcgta ccgtgagtaa taatgtggac tttattgctt   8400
aagaatacgc gtagagaaat aagacgaaca aaaggtttgt gattttattg cttaagaata   8460
cgcgtagatg gtcgtaccgt gagtaataat gtggttcata agacgaacaa aaggtttgtg   8520
acattattgc ttaagaatac gcgtaggtgg tcgtaccgtg agtaataatg tgtactttat   8580
tgcttaagaa tacgcgtagg ctatcgtacc gtgagtaata atgtgcctta taagacgaac   8640
aaaaggtttg tacacggggg agcgctcttg tctcagggca atgtttttat tggtcaaact   8700
caggcaaaca gaaacgacat cttgtcgtca aagggataca caaacttccc cccctcgccc   8760
catactcccg ccagcacccc ggtaaacacc aactcaatct cgcgcaggat ttcgcgcagg   8820
tgatgagcgc agtccacggg ggggagcaca aggggccgcg ggtatagatc gacggggacg   8880
ccgaccgact ccccgcctcc gggacagaca cgcacgacgc gccgccagta gtgctctgcg   8940
tccagcaagg cgccgccgcg gaaggcagtg gggggcaagg ggtcgctggc ctcaaagggg   9000
gacacccgaa cgctccagta ctccgcgtcc aaccgtttat taaacgcgtc caagataagg   9060
cggtcgcagg cgtcctccat aaggccccgg gccgtgagtg cgtcctcctc cggcacgcat   9120
gccgttgtca ggcccaggac ccgtcgcagc gtgtcgcgta cgacccctgc cgccgtggtg   9180
tacgcgggcc cgcggagagg aaatccccca agatggtcag tgttgtcgcg ggagttccag   9240
aaccacactc ccgcctggct ccaggcgact gcgtgggtgt agacgccctc gagggccagg   9300
cacagtgggt gccgcagccg gacggcgttg gccctaagca cggctcccac ggccgtctcg   9360
atggcccgcc gggcgtcctc gatcaccccg gaagccgcat ccgcgtcttg ggggtccacg   9420
ttaaagacac cccagaacgc acccccatcg cccccgcaga ccgcgaactt caccgagctg   9480
gccgtctcct cgatctgcag gcagacggcg gccattaccc cacccaggag ctgccgcagc   9540
gcagggcagg cgttgcacgt gtccgggacc aggcgctcca agacggcccc ggcccagggc   9600
tctgagggag cggccaccac cagcgcgtcc agtcttgcta ggcccgtccg gccgtggggg   9660
tccgccagcc cgctccccc gaggtcggcc agggccgcca ggagctgggc gcgaagtccg   9720
```

-continued

```
gggaagcaaa accgcgccgt ccagacgggc ccgacggccg cgggcgggtc taacagttgg   9780
atgattttag tggcgggatg ccaccgcgcc accgcctccc gcaccgcggg caggaggcat   9840
ccggctgccg ccgaggccac gccgggccag gctcgcgggg ggaggacgac cctggccccc   9900
accgcgggcc aggcccccag gagcgcggcg taagcggccg cggccccgcg caccaggtcc   9960
cgtgccgact cggccgtggc cggcacggtg aacgtgggcc aacccggaaa ccccaggacg  10020
gcaaagtacg ggacgggtcc cccccggacc tcaaactcgg gccccagaaa ggcaaagacg  10080
ggggccaggg ccccgggggc ggcgtggacc gtggtatgcc actgccggaa aagggcgacg  10140
agcgccggcg cggagaactt ctcgccggcg cttacaaagt agtcgtaatc gcggggcagc  10200
agcacccgtg ccgtgactcg ttgcgggtgc ccgcgtggcc gcaggcccac ctcgcacacc  10260
tcgaccaggt ccccgaacgc gccctccttc ttgatcggcg gaaacgcaag agtctggtat  10320
tcgcgcgcaa atagcgcggt tccggtggtg atgttaacgg tcagcgaagc ggcggacgcg  10380
cactgggggg tgtcgcgaat ggccgccagg cgcgcccacg ccagccgcgc gtcgggatgc  10440
tcggcaacgc gcgccgccag ggccataggg tcgatgtcaa tgttggcctc cgcgaccagg  10500
agagcggcgc gaggggcggc gggcgggccc cacgacgctc tctcaacttt caccaccagt  10560
cccgtgcgtg ggtccgagcc gatacgcagc ggggcgaaca gggccaccgg cccggtctgg  10620
cgctccaggg ccgccaggac gcacgcgtac agcgcccgcc acagagtcgg gttctccagg  10680
ggctccagcg gggaggcggc cggcgtcgtc gcggcgcggg cggccgccac gacggcctgg  10740
acggagacgt ccgcggagcc gtagaaatcc cgcagctccg tcgcggtgac ggagacctcc  10800
gcaaagcgcg cgcgaccctc ccctgcggcg ttgcgacata caaaatacac cagggcgtgg  10860
aagtactcgc gagcgcgggg gggcagccat accgcgtaaa gggtaatggc gctgacgctc  10920
tcctccaccc acacgatatc tgcggtgtcc atcgcacggc ccctaaggat cacgggcggt  10980
ctgtgggtcc catgctgccg tgcctggccg ggcccggtgg gtcgcggaaa ccggtgacgg  11040
ggggggggcg gtttttgggg ttggggtggg ggtgggaaac ggcccgggtc cgggggccaa  11100
cttggcccct cggtgcgttc cggcaacagc gccgccggtc cgcggacgac cacgtaccga  11160
acgagtgcgg tcccgagact tatagggtgc taaagttcac cgccccctgc atcatgggcc  11220
aggcctcggt ggggagctcc gacagcgccg cctccaggat gatgtcagcg ttggggttgg  11280
cgctggatga gtgcgtgcgc aaacagcgcc cccacgcggg cacgcgtagc ttgaagcgcg  11340
cgcccgcaaa ctcccgcttg tgggccataa gcagggcgta cagctgcctg tgggtccggc  11400
aggcgctgtg gtcgatgtgg tgggcgtcca acaaccccac gattgtctgt ttggtgaggt  11460
ttttaacgcg ccccgccccg ggaaacgtct gcgtgctttt ggccatctgc acgccaaaca  11520
gttcgcccca gattatcttg aacagcgcca ccgcgtggtc cgtctcgcta acggacccgc  11580
gcgggggaca gccgcttagg gcgtcggcga cgcgcttgac ggcttcctcc gagagcagaa  11640
gtccgtcggt tacgttacag tggcccagtt cgaacaccag ctgcatgtag cggtcgtagt  11700
ggggggtcag taggtccagc acgtcatcgg ggccgaaggt cctcccagat cccccggccg  11760
ccgagtccca atgcaggcgc gcggccatgg tgctgcacag gcacaacagc tcccagacgg  11820
gggttacgtt cagggtgggg ggcagggcca cgagctccag ctctccggtg acgttgatcg  11880
tggggatgac gcccgtggcg tagtggtcat agatccgccg aaatatggcg ctgctgcggg  11940
tggccatggg aacgcggaga caggcctcca gcaacgccag gtaaataaac cgcgtgcgtc  12000
ccatcaggct gttgaggttg cgcatgagcg cgacaatttc cgccggcgcg acatcggacc  12060
ggaggtattt ttcgacgaaa agacccacct cctccgtctc ggcggcctgg gccggcagcg  12120
```

```
acgcctcggg atcccggcac cgcagctccc gtagatcgcg ctgggccctg agggcgtcga  12180
aatgtacgcc ccgcaaaaac agacagaagt cctttggggt cagggtatcg tcgtgtcccc  12240
agaagcgcac gcgtatgcag tttagggtca gcagcatgtg aaggatgtta aggctgtccg  12300
agagacacgc cagcgtgcat ctctcaaagt agtgtttgta acggaatttg ttgtagatgc  12360
gcgacccccg ccccagcgac gtgtcgcatg ccgacgcgtc acagcgcccc ttgaaccggc  12420
gacacagcag gtttgtgacc tgggagaact gcgcgggcca ctggccgcag gaactgacca  12480
cgtgattaag gagcatgggc gtaaagacgg gctccgagcg cgccccggag ccgtccatgt  12540
aaatcagtag ctccccccttg cggagggtgc gcacccgtcc cagggactgg tacacggaca  12600
ccatgtccgg tccgtagttc atgggtttca cgtaggcgaa catgccatca aagtgcaggg  12660
gatcgaagct gaggcccacg gttacgaccg tcgtgtatat aaccacgcgg tattggcccc  12720
acgtggtcac gtccccgagg ggggtgagcg agtgaagcaa cagcacgcgg tccgtaaact  12780
gacggcagaa ccgggccacg atctccgcga aggagaccgt cgacgaaaaa atgcagatgt  12840
tatcgccccc gccaaggcgc gcttccagct ccccaaagaa cgtggccccc cgggcctccg  12900
gagaggcgtc cggagacggg ccgctcggcg gcccgggcgg gcgcagggca gcctgcagga  12960
gctcggtccc cagacgcggg agaaacaggc accggcgcgc cgaaaacccg ggcatggcgt  13020
actcgccgac caccacatgc acgttttttt cgccccggag accgcacagg aagtccacca  13080
actgcgcgtt ggcggttgcg tccatggcga tgatccgagg acagatgcgc agcaggcgta  13140
gcattaacgc atccacgcgg cccagttgct gcatcgttgg cgaatagagc tggcccagcg  13200
tcgacataac ctcgtccaga acgaggacgt cgtagttgtt cagaaggttg ggcccacgc   13260
gatgaaggct ttccacctgg acgataagtc ggtggaaggg gcggtcgttc ataatgtaat  13320
tggtggatga gaagtaggtg acaaagtcga ccaggcctga ctcagcgaac cgcgtcgcta  13380
gggtctgggt aaaactccga cgacaggaga cgacgagcac actcgtgtcc ggagagtgga  13440
tcgcttcccg cagccagcgg atcagcgcgg tagtttttcc cgaccccatt ggcgcgcgga  13500
ccacagtcac gcacctggcc gtcggggcgc tcgcgttggg gaaggtgacg ggtccgtgct  13560
gctgccgctc gatcgttgtt ttcgggtgaa cccggggcac ccattcggcc aaatcccccc  13620
cgtacaacat ccgcgctagc gatacgctcg acgtgtactg ttcgcactcg tcgtccccaa  13680
tgggacgccc ggcccccaga ggatctcccg actccgcgcc ccccacgaaa ggcatgaccg  13740
gggcgcggac ggcgtggtgg gtctggtgtg tgcaggtggc gacgtttgtg gtctctgcgg  13800
tctgcgtcac ggggctcctc gtcctggcct ctgtgttccg ggcacggttt ccctgctttt  13860
acgccacggc gagctcttat gccggggtga actccacggc cgaggtgcgc gggggtgtag  13920
ccgtgcccct caggttggac acgcagagcc ttgtgggcac ttatgtaatc acggccgtgt  13980
tgttgttggc cgtggccgtg tatgccgtgg tcggcgccgt gacctcccgc tacgaccgcg  14040
ccctggacgc gggccgccgt ctggctgcgg cccgcatggc catgccgcac gccacgctga  14100
tcgccggaaa cgtctgctct tggttgctgc agatcaccgt cctgttgctg gcccatcgca  14160
tcagccagct ggcccacctg gtttacgtcc tgcactttgc gtgtctggtg tattttgcgg  14220
cccatttttg caccaggggg gtcctgagcg ggacgtatct gcgtcaggtg cacggcctga  14280
tggagctggc cccgacccat catcgcgtcg tcggcccggc tcgcgccgtg ctgacaaacg  14340
ccttgctgtt gggcgtcttc ctgtgcacgg ccgacgccgc ggtatccctg aataccatcg  14400
ccgcgttcaa ctttaatttt tcggccccgg gcatgctcat ctgcctgacc gtgctgttcg  14460
```

ccattctcgt cgtatcgctg ttgttggtgg tcgagggggt gttgtgtcac tacgtgcgcg 14520
tgttggtggg cccccacctg ggggccgtgg ccgccacggg catcgtcggc ctggcctgcg 14580
agcactatta caccaacggc tactacgttg tggagacgca gtggccgggg gctcagacgg 14640
gagtccgcgt cgccctcgcc ctggtcgccg cctttgccct cggcatggcc gtgctccgct 14700
gcacccgcgc ctatctgtat cacaggcggc accacaccaa attttttatg cgcatgcgcg 14760
acacgcgaca ccgcgcacat tccgccctca agcgcgtacg cagttccatg cgcggatcgc 14820
gagacggccg ccacaggccc gcacccggca gcccgcccgg gattcccgaa tatgcggaag 14880
acccctacgc gatctcatac ggcggccagc tcgaccggta cggagattcc gacggggagc 14940
cgatttacga cgaggtggcg gacgaccaaa ccgacgtatt gtacgccaag atacaacacc 15000
cgcggcacct gcccgacgac gatcccatct atgacaccgt tggggggtac gaccccgagc 15060
ccgccgagga ccccgtgtac agcaccgtcc gccgttggta gctgtttggt tccgttttaa 15120
taaaccgttt gtgtttaacc cgaccgtggt gtatgtctgg tgtgtggcgt ccgatcccgt 15180
tactatcacc gtcccccccc ccccctcaac cccggcgatt gtgggttttt taaaaacgac 15240
acgcgtgcga ccgtatacag aacattgttt tggtttttat tcgctatcgg acatgggggg 15300
tggaaactgg gtggcggggc aggcgcctcc gggggtccgc cggtgagtgt ggcgcgaggg 15360
ggggtccgat gaacgcaggc gctgtctccc cggggcccgc gtaaccccgc gcatatccgg 15420
gggcacgtag aaattacctt cctcttcgga ctcgatatcc acgacgtcaa agtcgtgggc 15480
ggtcagcgag acgacctccc cgtcgtcggt gatgaggacg ttgtttcggc agcagcaggg 15540
ccgggccccg gagaacgaga ggcccatagc tcggcgagcg tgtcgtcgaa tgccaggcgg 15600
ctgcttcgct ggatggcctt atagatctcc ggatcgatgc ggacgggggt aatgatcagg 15660
gcgatcggaa cggcctggtt cgggagaatg gacgccttgc tgggtcctgc ggccccgaga 15720
gccccggcgc cgtcctccag gcggaacgtt acgccctcct ccgcgctggt gcggtgcctg 15780
ccgataaacg tcaccagatg cgggtggggg gggcagtcgg ggaagtggct gtcgagcacg 15840
tagccctgca ccaagatctg cttaaagttc gggtgacggg ggttcgcgaa gacgggctcg 15900
cggcggacca gatccccgga gctccaggac acgggggaga tggtgtggcg tccgaggtcg 15960
ggggcgccaa acagaagcac ctccgagaca acgccgctat ttaactccac caaggcccga 16020
tccgcggcgg agcaccgcct tttttcgccc gaggcgtggg cctctgacca ggcctggtct 16080
tgcgtgacga gagcctcctc cgggccgggg acgcgcccgg gcgcgaagta tcgcacgctg 16140
ggcttcggga tcgaccggat aaatgcccgg aacgcctccg gggaccggtg tgccatcaag 16200
tcctcgtacg cggaggccgt ggggtcgctg gggtccatgg ggtcgaaagc gtacttggcc 16260
cggcatttga cctcgtaaaa ggccaggggg gtcttgggga ctggggccag gtagccgtga 16320
atgtcccgag gacagacgag aatatccagg gacgccccga ccatccccgt gtgaccgtcc 16380
atgaggaccc cacacgtatg cacgttctct tcggcgaggt cgctgggttc gtggaagata 16440
aagcgccgcg tgtcggcgcc ggcctcgccg ccgtcgtccg cgcggcccac gcagtagcga 16500
aacagcaggc ttcgggccgt cggctcgttc acccgcccga acatcaccgc cgaagactgt 16560
acatccggcc gcaggctggc gttgtgcttc agccactggg gcgagaaaca cggaccctgg 16620
gggccccagc ggagggtgga tgcggtcgtg aggccccgcc ggagcagggc ccatagctgg 16680
cagtcggcct ggttttgcgt ggccgcctcg taaaacccca tgaggggccg gggcgccacg 16740
gcgtccgcgg cggccggggg cccgcggcgc gtcaggcgcc ataggtgccg accgagtccg 16800
cggtccacca tacccgcctc ctcgaggacc acggccaggg aacacagata atccaggcgg 16860

```
gcccagaggg gaccgatggc cagaggggcg cggacgccgc gcagcaaccc gcgcaggtgg  16920
cgctcgaacg tctcggctag tatatgggag ggcagcgcgt tggggatcac cgacgccgac  16980
cacatagagt caaggtccgg ggagtcggga tcggcgtccg ggtcgcgggc gtgggtgccc  17040
ccaggagata gcggaatgtc tggggtcgga ggccctgagg cgtcagaaag tgccggcgac  17100
gcggcccggg gcttttcgtc tgcggtgtcg gtggcgtgct gatcacgtgg ggggttaacg  17160
ggcgaatggg agctcgggtc cacagctgat gtcgtctggg gtgggggggg caggggacgg  17220
aaggtggttg tcagcggaag actgttaggg cgggggcgct tggggggggct gtcggggcca  17280
cgaggggtgt cctcggccag ggcccaggga cgcttagtca cggtgcgtcc cggcggacat  17340
gctgggccta ccgtggactc catttccgag acgacgtggg gggagcggtg gttgagcgcg  17400
ccgccgggtg aacgctgatt ctcacgacag cgcgtgccgc gcgcacgggt tggtgtgaca  17460
caggcgggac accagcacca ggagaggctt aagctcggga ggcagcgcca ccgacgacag  17520
tatcgccttg tgtgtgtgct ggtaatttat acaccgatcc gtaaacgcgc gccgaatctt  17580
gggattgcgg aggtggcgcc ggatgccctc tgggacgtca tacgccaggc cgtgggtgtt  17640
ggtctcggcc gagttgacaa acagggctgg gtgcagcacg cagcgatagg cgagcagggc  17700
cagggcgaag tccggcgaca gctggttgtt aaaatactgg taaccgggaa accgggtcac  17760
gggtacgccc aggctcgggg cgacgtacac gctaaccacc aactccagca gcgtctggcc  17820
cagggcgtac aggtcaaccg ctaacccgac gtcgtgcttc aggcggtggt tggtaaattc  17880
ggcccgttcg ttgttaaggt atttcaccaa cagctccggg ggctggttat acccgtgacc  17940
caccagggtg tgaaagttgg ctgtggttag ggcggtgggc atgccaaaca tccgggggga  18000
cttgaggtcc ggctcctgga ggcaaaactg cccccgggcg atcgtggagt tggagttgag  18060
ggtgacgagg ctaaagtcgg cgaggacggc ccgccggagc gagacggcgt ccgaccgcag  18120
catgacgagg atgttggcgc acttgatatc caggtggctg atcccgcagg tggtgtttaa  18180
aaacacaacg gcgcgggcca gctccgtgaa gcactggtgg agggccgtcg agaccgaggg  18240
gtttgttgtg cgcagggacg ccagttggcc gatatactta ccgaggtcca tgtcgtacgc  18300
ggggaacact atctgtcgtt gttgcagcga gaacccgagg ggcgcgatga agccgcggat  18360
gttgtgggtg cggccggcgc gtagaacgca ctccccgacc aacagggtcg cgatgagctc  18420
aacggcaaac cactcctttt cctttatggt cttaacggca agcttatgtt cgcgaatcag  18480
ttggacgtca ccgtatcccc cagaccccccc gaagcttcgg gccccgggga tctcgagggt  18540
cgtgtagtgt agggcggggt tgatggcgaa cacggggctg catagcttgc ggatgcgcgt  18600
gagggtgagg atgtgcgagg gggacgaggg gggtgcggtt aacgccgcct gggatctgcg  18660
caggggcggg cggttcagtt tggccgccgt accgggcgtc tcgggggacg cgcggcgatg  18720
agacgagcgg ctcattcgcc atcgggatag tcccgcgcga agccgctcgc ggaggccgga  18780
tcggtggcgg gacccgtggg aggagcggga gacggcggcg tcctggagag aggggccgct  18840
ggggcgcccg gaggccccgt gggggttgga gtgtacgtag gatgcgagcc aatccttgaa  18900
ggaccgttgg cgtgcacctt gggggctgag gttagctgcc acatgaccag caggtcgctg  18960
tctgcgggac tcatccatcc ttcggccagg tcgccgtctc cccacagaga agcgttggtc  19020
gctgcttcct cgagttgctc ctcctggtcc gcaagacgat cgtccacggc gtccaggcgc  19080
tcaccaagcg ccggatcgag gtaccgtcgg tgtgcggtta gaaagtcacg acgcgccgct  19140
tgctcctcca cgcgaatttt aacacaggtc gcgcgctgtc gcatcatctc taagcgcgcg  19200
```

cgggacttta gccgcgcctc caattccaag tgggccgcct ttgcagccat aaaggcgcca 19260
acaaaccgag gatcttgggt gctgacgccc tcccggtgca gctgcagggt ctggtccttg 19320
taaatctcgg ctcggaggtg cgtctcggcc aggcgtcggc gcagggccgc gtgggcggca 19380
tctcggtcca ttccgccacc ctgcgggcga cccggggggt gctctgatag tctcgcgtgc 19440
ccaaggcccg tgatcggggt acttcgccgc cgcgacccgc cacccggtgt gcgcgatgtt 19500
tggtcagcag ctggcgtccg acgtccagca gtacctggag cgcctcgaga aacagaggca 19560
acttaaggtg ggcgcggacg aggcgtcggc gggcctcacc atgggcggcg atgccctacg 19620
agtgcccttt ttagatttcg cgaccgcgac ccccaagcgc caccagaccg tggtccctgg 19680
cgtcgggacg ctccacgact gctgcgagca ctcgccgctc ttctcggccg tggcgcggcg 19740
gctgctgttt aatagcctgg tgccggcgca actaaagggg cgtgatttcg gggcgacca 19800 cacggccaag ctggaattcc tggcccccga gttggtacgg gcggtggcgc gactgcggtt 19860
taaggagtgc gcgccggcgg acgtggtgcc tcagcgtaac gcctactata gcgttctgaa 19920
tacgtttcag gccctccacc gctccgaagc ctttcgccag ctggtgcact ttgtgcggga 19980
ctttgcccag ctgctcaaaa cctccttccg ggcctccagc ctcacggaga ccacgggccc 20040
ccccaaaaaa cgggccaagg tggacgtggc cacccacggc cggacgtacg gcacgctgga 20100
gctgttccaa aaaatgatcc ttatgcacgc cacctacttt ctggccgccg tgctcctcgg 20160
ggaccacgcg gagcaggtca acacgttcct gcgtctcgtg tttgagatcc ccctgtttag 20220
cgacgcggcc gtgcgccact tccgccagcg cgccaccgtg tttctcgtcc cccggcgcca 20280
cggcaagacc tggtttctgg tgcccctcat cgcgctgtcg ctggcctcct ttcgggggat 20340
caagatcggc tacacggcgc acatccgcaa ggcgaccgag ccggtgtttg aggagatcga 20400
cgcctgcctg cggggctggt tcggttcggc ccgagtggac cacgttaaag gggaaaccat 20460
ctccttctcg tttccggacg ggtcgcgcag taccatcgtg tttgcctcca gccacaacac 20520
aaacgtaagt cctcttttct ttcgcatggc tctcccaagg ggccccgggt cgacccgacc 20580
cacacccacc cacccacata cacacacaac cagacgcggg aggaaagtct gccccgtggg 20640
cactgatttt tattcgggat cgcttgagga ggcccgggca acggcccggg caacggtggg 20700
gcaactcgta gcaaataggc gactgatgta cgaagagaag acacacaggc gccacccggc 20760
gctggtcggg gggatgttgt ccgcgccgca ccgtcccccg acgacctctt gcagacggtc 20820
cgtgatgcaa ggacggcggg gggcctgcag cagggtgacc gtatccacgg gatggccaaa 20880
gagaagcgga cacaggctag catccccctg gaccgccagg gtacactggg ccatcttggc 20940
ccacagacac ggggcgacgc agggacagga ctccgttacg acggaggaga gccacagtgc 21000
gttggcggaa tcgatgtggg gcggcggggc gcaggactcg cagccccccg ggtggttggt 21060
gatcctggcc aggagccatc ccagatggcg ggccctgctt cccggtggac agagcgaccc 21120
caggtcgctg tccatggccc agcagtagat ctggccgctg gggaggtgcc accaggcccc 21180
cgggcccaag gcgcagcacg cgcccggctc cggggggg tc ttcgcgggga ccagatacgc 21240
gccatccagc tcgccgacca ctggctcctc cgcgagctgt tcggtggttg ggtcgggggt 21300
ttcctccggg ggggtggccg cccgtatgcg tgcgaacgtg agggtgcaca ggagcggggt 21360
cagggggtgc gtcacgctcc ggaggtggac gatcgcgcag tagcggcgct cgcggttaaa 21420
gaaaaagagg gcaaagaagg tgttcggggg caaccgcagc gccttggggc gcgtcagata 21480
cagaaaaatc tcgcagaaga gggcgcgccc ggggtctggg ttaggaaggg ccacctgaca 21540
cagaggctcg gtgaggaccg ttagacaccg aaagatcttg agccgctcgt ccgcccgaac 21600

```
gacgcgccac acaaagacgg agttgacaat gcgcgcgata gagtcgacgt ccgtccccag  21660
gtcgtcgact ctatcgcgcg tgccgcgagc tccggcccgg gaatccggcc ggggcaaggt  21720
ccccggggga ccaggcggcg ccaggggccg ccggggtccc agctgcgcca tgccgggggc  21780
ggggggaggg caaaccccag aggcgggggc caacggcgcg gggaggagtg ggtgggcgag  21840
gtggccgggg gaaggcgccc gctagcgaga ccggccgttc ccggacgaca ccttgcgaca  21900
aaacctaagg acagcggccc gcgcgacggg gtccgagagg ctaaggtagg ccgcgatgtt  21960
aatggtgaac gcaaagccgc cgggaaagac aactatgcca cagaggcggc gattaaaccc  22020
caggcagagg taggcgtagc tttccccggg caggtattgc tcgcagaccc tgcgtggggc  22080
tgtggagggg acggcctcca tgaagcgaca tttactctgc tcgcgtttac tgacgtcacc  22140
atccatcgcc acggcgattg gacgattgtt aagccgcagc gtgtctccgc ttgtgctgta  22200
gtagtcaaaa acgtaatggc cgtcggagtc ggcaaagcgg gccgggaggt cgtcgccgag  22260
cgggacgacc cgccgccccc gaccgccccg tccccccagg tgtgccagga cggccagggc  22320
atacgcggtg tgaaaaaagg cgtcgggggc ggtcccctcg acggcgcgca tcaggttctc  22380
gaggagaatg gggaagcgcc tggtcacctc ccccaaccac gcgcgttggt cggggccaaa  22440
gtcatagcgc aggcgctgtg agattcgcgg gccgccctga agcgcggccc ggatggcctg  22500
gcccagggcc cggaggcacg ccagatgtat gcgcgcggta aaggcgacct cggcggcgat  22560
gtcaaagggc ggcaggacgg ggcgcgggtg gcgcaggggc acctcgagcg cgggaaagcg  22620
tagcagcagc tccgcctgcc cagcgggaga cagctggtgg gggcgcacga cgcgttctgc  22680
ggcgcaggcc tcggtcaggg ccgtggccag cgccgaggac agcagcggag ggcgggcgcg  22740
tcgcccgccc cacgccacgg agttctcgta ggagacgacg acgaagcgct gcttggttcc  22800
gtagtggtgg cgcaggacca cggagataga acgacggctc cacagccagt ccggccggtc  22860
gccgccggcc agggcttccc atccgcgatc caaccactcg accagcgacc gcggctttgc  22920
ggtaccaggg gtaagggtta gaacgtcgtt caggatgtcc tcgcccccgg gcccgtgggg  22980
cgctggggcc acaaagcggc ccccgccggg gggctccaga cccgccagca ccgcatctgc  23040
gtcagccgcc cccatggcgc ccccgctgac ggcctggtga accagggcgc cctggcgtag  23100
ccccgatgca acgccacagg ccgcacgccc ggtccgcgct cggaccgggt ggcggcgggt  23160
gacgtcctgc actgcccgct gaaccaacgc gaggatctcc tcgttctcct gtgcgatgga  23220
cacgtcctgg gccgcggtcg tgtcgccgcc gggggccgtc agctgctcct ccggggagat  23280
gggggggtcg gacgccccga cgatgggcgg gtctgcgggc gcccccgcgt ggggccgggc  23340
caagggctgc ggacgcgggg acgcgctttc ccccagaccc atggacaggt gggccgcagc  23400
ctccttcgcg gccggcgggg cggcggcgcc aagcagagcg acgtagcggc acaaatgccg  23460
acagacgcgc atgatgcgcg tgctgtcggc cgcgtagcgc gtgttggggg ggacgagctc  23520
gtcgtaacta aacagaatca cgcgggcaca gctcgccccc gagccccacg caaggcgcag  23580
cgccgccacg gcgtacgggt catagacgcc ctgcgcgtca cacaccacgg gcagggagac  23640
gaacaacccc ccggcgctgg acgcacgcgg aaggaggcca gggtgtgccg gcacgacggg  23700
ggccagaagc tcccccaccg catccgcggg cacgtaggcg gcaaacgccg tgcaccacgg  23760
ggtacagtcg ccggtggcat gagcccgagt ctggatttcg acctggaagt ttgcggccgt  23820
cccgagtccg gggcggccgc gcatcagggc ggccagaggg attcccgcgg ccgccaggca  23880
ctcgctggat atgatgacgt gaaccaaaga ccgagggccg acccgggccg tggccgagat  23940
```

-continued

```
cgtctggacc tcgttggcca agtgcgcgtt catggttcgg gggtgggtgt gggtgtgtag  24000
gcgatgcggg tcccccgagt ccgcgggaag ggcgtgggtt tggcgcgcgt atgcgtattc  24060
gccaacggag gcgtgcgtgc ttatgcgcgg cgcgtttctt ctgtctctag ggaatccgag  24120
gccaggactt taacctgctc tttgtcgacg aggccaactt tattcgcccg gatgcggtcc  24180
agacgattat gggctttctc aaccaggcca actgcaagat tatcttcgtg tcgtccacca  24240
acaccgggaa ggccagtacg agctttttgt acaacctccg cggggccgca gacgagcttc  24300
tcaacgtggt gacctatata tgcgatgatc acatgccgag ggtggtgacg cacacaaacg  24360
ccacggcctg ttcttgttat atcctcaaca agcccgtttt catcacgatg gacggggcgg  24420
ttcgccggac cgccgatttg tttctggccg attccttcat gcaggagatc atcgggggcc  24480
aggccaggga gaccggcgac gaccggcccg ttctgaccaa gtctgcgggg gagcggtttc  24540
tgttgtaccg cccctcgacc accaccaaca gcggcctcat ggcccccgat ttgtacgtgt  24600
acgtggatcc cgcgttcacg gccaacaccc gagcctccgg gaccggcgtc gctgtcgtcg  24660
ggcggtaccg cgacgattat atcatcttcg ccctggagca ctttttctc cgcgcgctca  24720
cgggctcggc cccgccgac atcgcccgct gcgtcgtcca cagtctgacg caggtcctgg  24780
ccctgcatcc cggggcgttt cgcggcgtcc gggtggcggt cgagggaaat agcagccagg  24840
actcggccgt cgccatcgcc acgcacgtgc acacagagat gcaccgccta ctggcctcgg  24900
agggggccga cgcgggctcg ggccccgagc ttctcttcta ccactgcgag cctcccggga  24960
gcgcggtgct gtaccccttt ttcctgctca acaaacagaa gacgcccgcc tttgaacact  25020
ttattaaaaa gtttaactcc gggggcgtca tggcctccca ggagatcgtt tccgcgacgg  25080
tgcgcctgca gaccgacccg gtcgagtatc tgctcgagca gctaaataac ctcaccgaaa  25140
ccgtctcccc caacactgac gtccgtacgt attccggaaa acggaacggc gcctcggatg  25200
accttatggt cgccgtcatt atggccatct acctcgcggc ccaggccgga cctccgcaca  25260
cattcgctcc tatcacacgc gtctcgtgag cgcccaataa acacacccag gtatgctacg  25320
cacgaccacg gtgtcgtctg ttaagggggg ggggggaagg gggtgttggc gggaagcgtg  25380
ggaacacggg ggattctctc acgaccggca ccagtaccac ccccctgtga acacagaaac  25440
cccaacccaa atcccataaa catacgacac acaggcatat tttggaattt cttaggtttt  25500
tatttattta ggtatgctgg ggtttctccc tggatgccca cccccacccc cccgtgggtc  25560
tagccgggcc ttagggatag cgtataacgg gggccatgtc tccggaccgc acaacggccg  25620
cgccgtcaaa ggtgcacacc cgaaccacgg gagccagggc caaggtgtct cctagttggc  25680
ccgcgtgggt cagccaggcg acgagcgcct cgtaaagcgg cagccttcgc tctccatcct  25740
gcatcagggc cggggcttcg gggtgaatga gctgggcggc ctcccgcgtg acactctgca  25800
tctgcagtag agcgttcacg tacccgtcct gggcacttag cgcaaagagc cgggggatta  25860
gcgtaaggat gatggtggtt ccctccgtga tcgagtaaac catgttaagg accagcgatc  25920
gcagctcggc gtttacggga ccgagttgtt ggacgtccgc cagcagcgag aggcgactcc  25980
cgttgtagta cagcacgttg aggtctggca gccctccggg gtttctgggg ctggggttca  26040
ggtcccggat gcccctggcc acgagccgcg ccacgatttc gcgcgccagg ggcgatggaa  26100
gcggaacggg aaaccgcaac gtgaggtcca gcgaatccag gcgcacgtcc gtcgcttggc  26160
cctcgaacac gggcgggacg aggctgatgg ggtccccgtt acagagatct acgggggagg  26220
tgttgcgaag gttaacggtg ccggcgtggg tgaggcccac gtccaggggg caggcgacga  26280
ttcgcgtggg aagcacccgg gtgatgaccg cggggaagcg ccttcggtac gccagcaaca  26340
```

accccaacgt gtcgggactg acgcctccgg agacgaagga ttcgtgcgcc acgtcggcca 26400
gcgtcagttg ccggcggatg gtcggcagga ataccacccg cccttcgcag cgctgcagcg 26460
ccgccgcatc ggggcgcgag atgcccgagg gtatcgcgat gtcagtttca aagccgtccg 26520
ccagcatggc gccgatccac gcggcaggga gtgcagtggt ggttcgggtg gcgggaggag 26580
cgcggtgggg gtcagcggcg tagcagagac gggcgaccaa cctcgcatag gacggggggt 26640
gggtcttagg gggttgggag gcgacaggga ccccagagca tgcgcgggga ggtctgtcgg 26700
gcccagacgc accgagagcg aatccgtccg cggagtcccg gcttgggttt tatggggccc 26760
ggccctcgga atcgcggctt gtcggcgggg acaaaggggg cggggctagg ggcttgcgga 26820
aacagaagac gcgtgggata aaagaatcgc actaccccaa ggaagggcgg ggcggtttat 26880
tacagagcca gtcccttgag cggggatgcg tcatagacga gatactgcgc gaagtgggtc 26940
tcccgcgcgt gggcttcccc gttgcgggca ctgcggagga gggcggggtc gctggcgcag 27000
gtgagcgggt aggcctcctg aaacaggcca cacgggtcct ccacgagttc gcggcacccc 27060
ggggggcgct taaactgtac gtcgctggcg gcggtggccg tggacaccgc cgaacccgtc 27120
tccacgatca ggcgctccag gcagcgatgt ttggcggcga tgtcggccga cgtaaagaac 27180
ttaaagcagg ggctgagcac cggcgaggcc ccgttgaggt ggtaggcccc gttatagagc 27240
aggtccccgt acgaaaatcg ctgcgacgcc cacgggttgg ccgtggccgc gaaggcccgg 27300
gacgggtcgc tctggccgtg gtcgtacatg agggcggtga catccccctc cttgtccccc 27360
gcgtaaacgc ccccggcggc gcgtccccgg gggttgcagg gccggcggaa gtagttgacg 27420
tcggtcgaca cgggggtggc gataaactca cacacggcgt cctggccgtg gtccatccct 27480
gcgcgccgcg gcacctgggc gcacccgaac acggggacgg gctgggccgg ccccaggcgg 27540
tttcccgcca cgaccgcgtt ccgcaggtac acggctgccg cgttgtccag gagaggggga 27600
gccccgcggc ccaggtaaaa gttttgggga aggttgccca tgtcggtgac ggggttgcgg 27660
acggttgccg tggccacgac ggcggtgtag cccacgccca ggtccacgtt cgcgcgcggc 27720
tgggtgagcg tgaagtttac ccccccgcca gtttcgtgcc gggccacctg gagctggccc 27780
aggaagtacg cctccgacgc gcgctccgag aacagcacgt tctcagtcac aaagcggtcc 27840
tgtcggacga cggtgaaccc aaacccggga tggaggcccg tcttgagctg atgatgcaag 27900
gccacgggac tgatcttgaa gtaccccgcc atgagcgcgt aggtcagcgc gttctccccg 27960
gccgcgctct cgcggacgtg ctgcacgacg ggctgtcgga tcgacgaaaa gtagttggcc 28020
cccagagccg gggggaccag ggggacctgc cgcgacaggt cgcgcagggc cggggggaaa 28080
ttgggcgcgt tcgccacgtg gtcggccccg gcgaacagcg cgtggacggg gagggggtaa 28140
aaatagtcgc cattttggat ggtatggtcc agatgctggg gggccatcag caggattccg 28200
gcgtgcaacg ccccgtcgaa tatgcgcatg ttggtggtgg acgcggtgtt ggcgcccgcg 28260
tcgggcgccg ccgagcagag cagcgccgtt gtgcgttcgg ccatgttgtg ggccagcacc 28320
tgcagcgtga gcatggcggg cccgtccact accacgcgcc cgttgtgaaa catggcgttg 28380
accgtgttgg ccaccagatt ggccgggtgc agggggtgcg cggggtccgt cacggggtcg 28440
ctggggcact cctcgccggg ggcgatctcc gggaccacca tgttctgcag ggtggcgtat 28500
acgcggtcga agcgaacccc cgcggtgcag cagcggcccc gcgagaaggc gggcaccatc 28560
acgtagtagt aaatcttgtg gtgcacggtc cagtccgccc cccggtgcgg ccggtcatcc 28620
gcggcgtccg cggctcgggc ctgggtgttg tgcagcagct ggccgtcgtt gcggttgaag 28680

-continued

```
tccgcggtcg ccacgttaca tgccgccgcg tacacggggt cgtggccccc cgcgctaacc  28740
cggcagtcgc gatggcggtc cagggccgcg cgccgcatca gggcgtcaca gtcccacacg  28800
aggggtggca gcagcgccgg gtctcgcatt aggtgattca gctcggcttg cgcctgcccg  28860
cccagctccg ggccggtcag ggtaaagtca tcaaccagct gggccagggc ctcgacgtgc  28920
gccaccaggt cccggtacac ggccatgcac tcctcgggaa ggtctccccc gaggtaggtc  28980
acgacgtacg agaccagcga gtagtcgttc acgaacgccg cgcaccgcgt gttgttccag  29040
tagctggtga tgcactggac cacgagccgg gccagggcgc agaagacgtg ctcgctgccg  29100
tgtatggcgg cctgcagcag gtaaaacacc gccgggtagt tgcggtcgtc gaacgccccg  29160
cgaacggcgg cgatggtggc gggggccatg gcgtggcgtc ccacccccag ctccaggccc  29220
cgggcgtccc ggaacgccgc cggacatagc gccaggggca agttgccgtt caccacgcgc  29280
caggtggcct ggatctcccc cgggccggcc gggggaacgt ccccccccgg cagctccacg  29340
tcggccaccc ccacaaagaa gtcgaacgcg gggtgcagct caagagccag gttggcgttg  29400
tcgggctgca taaactgctc cggggtcatc tggccttccg cgacccatcg gacccgcccg  29460
tgggccaggc gctgccccca ggcgttcaaa aacagctgct gcatgtctgc ggcggggccg  29520
gccggggccg ccacgtacgc cccgtacgga ttggcggctt cgacggggtc gcggttaagg  29580
cccccgaccg ccgcgtcaac gttcatcagc gaagggtggc acacggtccc gatcgcgtgt  29640
tccagagaca ggcgcagcac ctggcggtcc ttcccccaaa aaaacagctg gcggggcggg  29700
aaggcgcggg gatccgggtg gccgggggcg gggactaggt ccccggcgtg cgcggcaaac  29760
cgttccatga ccggattgaa caggcccagg ggcaggacga acgtcaggtc catggcgccc  29820
accaggggggt agggaacgtt ggtggcggcg tagatgcgct tctccagggc ctccagaaag  29880
accagcttct cgccgatgga caccagatcc gcgcgcacgc gcgtcgtctg gggggcgctc  29940
tcgagctcgt ccagcgtctg ccggttcagg tcgagctgct cctcctgcat ctccagcagg  30000
tggcggccca cgtcgtccag acttcgcacg gccttgccca tcacgagcgc cgtgaccagg  30060
ttggccccgt tcaggaccat ctcgccgtac gtcaccggca cgtcggcttc ggtgtcctcc  30120
actttcagga aggactgcag gaggcgctgt ttgatcgggg cggtggtgac gagcaccccg  30180
tcgaccggcc gcccgcgcgt gtcggcatgc gtcagacggg gcacggccac ggagggctgc  30240
gtggccgtgg tgaggtccac gagccaggcc tcgacggcct cccggcggtg gcccgccttg  30300
cccaggaaaa agctcgtctc gcagaagctt cgctttagct cggcgaccag ggtcgcccgg  30360
gccaccctgg tggccaggcg gccgttgtcc aggtatcgtt gcatcggcaa caacaaagcc  30420
aggggcggcg ccttttccag cagcacgtgc agcatctggt cggccgtgcc gcgctcaaac  30480
gccccgagga cggcctggac gttgcgagcg agctgttgga tggcgcgcaa ctggcgatgc  30540
gcgccgatac ccgtcccgtc cagggcctcc cccgtgagca gggcgatggc ctcggtggcc  30600
aggctgaagg cggcgttcag ggcccggcgg tcgataatct tggtcatgta attgtgtgtg  30660
ggttgctcga tggggtgcgg gccgtcgcgg gcaatcagcg gctggtggac ctcgaactgt  30720
acgcgcccct cgttcatgta ggccagctcc ggaaacttgg tacacacgca cgccaccgac  30780
aacccgagct ccagaaagcg cacgagcgac agggtgttgc aatacgaccc cagcagggcg  30840
tcgaactcga cgtcgtacag gctgtttgca tcggagcgca cgcgggaaaa aaaatcaaac  30900
aggcgtcgat gcgacgccac ctcgatcgtg ctaaggaggg acccggtcgg caccatggcc  30960
gcggcatacc ggtatcccgg agggtcgcgg ttgggagcgg ccatggggtc gcgtggagat  31020
cggctgtctc tagcgatatt ggcccgggga ggctaagatc caccccaacg cccggccacc  31080
```

cgtgtacgtg cccgacggcc caaggtccac cgaaagacac gacgggcccg gacccaaaaa 31140
ggcgggggat gctgtgtgag aggccgggtg ccggtcgggg gggaaaggca ccgggagaag 31200
gctgcggcct cgttccagga gaacccagtg tccccaacag acccggggac gtgggatccc 31260
aggccttata taccccccc cccgccccac ccccgttaga acgcgacggg tgcattcaag 31320
atggccctgg tccaaaagcg tgccaggaag aaattggcag aggcggcaaa gctgtccgcc 31380
gccgccaccc acatcgaggc cccggccgcg caggctatcc ccagggcccg tgtgcgcagg 31440
ggatcggtgg gcggcagcat ttggttggtg gcgataaagt ggaaaagccc gtccggactg 31500
aaggtctcgt gggcggcggc gaacaaggca cacagggccg tgcctcccaa aaacacggac 31560
atcccccaaa acacgggcgc cgacaacggc agacgatccc tcttgatgtt aacgtacagg 31620
aggagcgccc gcaccgccca cgtaacgtag tagccgacga tggcggccag gatacaggcc 31680
ggcgccacca cccttccggt cagcccgtaa tacatgcccg ctgccaccat ctccaacggc 31740
ttcaggacca aaaacgacca aaggaacaga atcacgcgct ttgaaaagac cggctgggta 31800
tggggcggaa gacgcgagta tgccgaactg acaaaaaaat cagaggtgcc gtacgaggac 31860
aatgaaaact gttcctccag cggcagttct ccctcctccc ccccgaaggc ggcctcgtcg 31920
accagatctc gatccaccag aggaaggtca tcccgcatgg tcatggggtg tgcggtggag 31980
gtggggagac cgaaaccgca aagggtcgct tacgtcagca ggatcccgag atcaaagaca 32040
cccgggttct tgcacaaaca ccacccgggt tgcatccgcg gaggcgagtg ttttgataag 32100
gccgttccgc gccttgatat aacctttgat gttgaccaca aaacccggaa tttacgccta 32160
cgccccaatg cccacgcaag atgaggtagg taaccccccc gtgggtgtga cgttgcgttt 32220
agttcattgg aggccaaggg gaaaaatggg gtggggagga aacggaaaac ccagtaggcc 32280
gtgtcgggaa cacgcccggg gttgtcctca aaaggcaggg tccatactac ggaagccgtc 32340
gttgtattcg agacctgcct gtgcaacgca cgtcggggtt gcctgtgtcc ggttcggccc 32400
ccaccgcgtg cggcacgcac gaggacgagt ccgcgtgctt tattggcgtt ccaagcgttg 32460
ccctccagtt tctgttgtcg gtgttccccc atacccacgc ccacatccac cgtagggggc 32520
ctctgggccg tgttacgtcg ccgcccgcga tggagcttag ctacgccacc accatgcact 32580
accgggacgt tgtgttttac gtcacaacgg accgaaaccg ggcctacttt gtgtgcgggg 32640
ggtgtgttta ttccgtgggg cggccgtgtg cctcgcagcc cggggagatt gccaagtttg 32700
gtctggtcgt tcgagggaca ggcccagacg accgcgtggt cgccaactat gtacgaagcg 32760
agctccg 32767

<210> SEQ ID NO 846
<211> LENGTH: 32767
<212> TYPE: DNA
<213> ORGANISM: Artificial Sequence
<220> FEATURE:
<223> OTHER INFORMATION: recombinant viral vector ONCR-154

<400> SEQUENCE: 846
aaaaaagctg aacgagaaac gtaaaatgat ataaatatca atatattaaa ttagattttg 60
cataaaaaac agactacata atactgtaaa acacaacata tccagtcact atgaatcaac 120
tacttagatg gtattagtga cctgtagtcg accgacagcc ttccaaatgt tcttcgggtg 180
atgctgccaa cttagtcgac cgacagcctt ccaaatgttc ttctcaaacg gaatcgtcgt 240
atccagccta ctcgctattg tcctcaatgc cgtattaaat cataaaaaga aataagaaaa 300

-continued

```
agaggtgcga gcctcttttt tgtgtgacaa aataaaaaca tctacctatt catatacgct    360
agtgtcatag tcctgaaaat catctgcatc aagaacaatt tcacaactct tatacttttc    420
tcttacaagt cgttcggctt catctggatt ttcagcctct atacttacta aacgtgataa    480
agtttctgta atttctactg tatcgacctg cagactggct gtgtataagg gagcctgaca    540
tttatattcc ccagaacatc aggttaatgg cgtttttgat gtcattttcg cggtggctga    600
gatcagccac ttcttccccg ataacggaga ccggcacact ggccatatcg gtggtcatca    660
tgcgccagct ttcatccccg atatgcacca ccgggtaaag ttcacgggag actttatctg    720
acagcagacg tgcactggcc aggggggatca ccatccgtcg cccgggcgtg tcaataatat    780
cactctgtac atccacaaac agacgataac ggctctctct tttataggtg taaaccttaa    840
actgcatttc accagcccct gttctcgtca gcaaaagagc cgttcatttc aataaaccgg    900
gcgacctcag ccatcccttc ctgattttcc gctttccagc gttcggcacg cagacgacgg    960
gcttcattct gcatggttgt gcttaccaga ccggagatat tgacatcata tatgccttga   1020
gcaactgata gctgtcgctg tcaactgtca ctgtaatacg ctgcttcata gcatacctct   1080
ttttgacata cttcgggtat acatatcagt atatattctt ataccgcaaa aatcagcgcg   1140
caaatacgca tactgttatc tggcttttag taagccggat ccacgcggcg tttacgcccc   1200
ccctgccact catcgcagta ctgttgtaat tcattaagca ttctgccgac atggaagcca   1260
tcacaaacgg catgatgaac ctgaatcgcc agcggcatca gcaccttgtc gccttgcgta   1320
taatatttgc ccatggtgaa aacgggggcg aagaagttgt ccatattggc cacgtttaaa   1380
aaggccgtaa tatccagctg aacggtctgg ttataggtac attgagcaac tgactgaaat   1440
gcctcaaaat gttctttacg atgccattgg gatatatcaa cggtggtata tccagtgatt   1500
tttttctcca ttttagcttc cttagctcct gaaaatctcg ataactcaaa aaatacgccc   1560
ggtagtgatc ttatttcatt atggtgaaag ttggaacctc ttacgtgccg atcaacgtct   1620
cattttcgcc aaaagttggc ccagggcttc ccggtatcaa cagggacacc aggatttatt   1680
tattctgcga agtgatcttc cgtcacaggt atttattcgg cgcaaagtgc gtcgggtgat   1740
gctgccaact tagtcgacta caggtcacta ataccatcta agtagttgat tcatagtgac   1800
tggatatgtt gtgttttaca gtattatgta gtctgttttt tatgcaaaat ctaatttaat   1860
atattgatat ttatatcatt ttacgtttct cgttcagctt tcttgtacaa agtggtttta   1920
atggaccgcc cgcaaggggg ggggggcatt tcagtgtcgg gtgacgagcg cgatccggcc   1980
gggatcctag gaccccaaaa gtttgtctgc gtattccagg gcggggctca gttgaatctc   2040
ccgcagcacc tctaccagca ggtccgcggt gggctggaga aactcggccg tcccggggca   2100
ggcggttgtc gggggtggag gcgcggcgcc caccccgtgt gccgcgcctg gcgtctcctc   2160
tgggggcgac ccgtaaatgg ttgcagtgat gtaaatggtg tccgcggtcc agaccacggt   2220
caaaatgccg gccgtggcgc tccgggcgct ttcgccgcgc gaggagctga cccaggagtc   2280
gaacggatac gcgtacatat gggcgtccca cccgcgttcg agcttctggt tgctgtcccg   2340
gcctataaag cggtaggcac aaaattcggc gcgacagtcg ataatcacca acagcccaat   2400
gggggtgtgc tggataacaa cgcctccgcg cggcaggcgg tcctggcgct cccggccccg   2460
taccatgatc gcgcgggtgc cgtactcaaa aacatgcacc acctgcgcgg cgtcgggcag   2520
tgcgctggtc agcgaggccc tggcgtggca taggctatac gcgatggtcg tctgtggatt   2580
ggacatctcg cggtgggtag tgagtccccc gggccgggtt cggtggaact gtaaggggac   2640
ggcgggttaa tagacaatga ccacgttcgg atcgcgcaga gccgatagta tgtgctcact   2700
```

```
aatgacgtca tcgcgctcgt ggcgctcccg gagcggattt aagttcatgc gaaggaattc   2760
ggaggaggtg gtgcgggaca tggccacgta cgcgctgttg aggcgcaggt tgccgggcgt   2820
aaagcagatg gcgaccttgt ccaggctaag gccctgggag cgcgtgatgg tcatggcaag   2880
cttggagctg atgccgtagt cggcgtttat ggccatggcc agctccgtag agtcaatgga   2940
ctcgacaaac tcgctgatgt tggtgttgac gacggacatg aagccgtgtt ggtcccgcaa   3000
gaccacgtaa ggcagggggg cctcttccag taactcggcc acgttggccg tcgcgtgccg   3060
cctccgcagc tcgtccgcaa aggcaaacac ccgtgcgtac gtgtatccca tgagcgtata   3120
attgtccgtc tgcagggcga cggacatcag ccccccgcgc ggcgagccgg tcagcatctc   3180
gcagccccgg aagataacgt tgtccacgta cgtgctaaag gggcgactt caaatgcctc   3240
cccgaagagc tcttggagga ttcggaatct cccgaggaag gcccgcttca gcagcgcaaa   3300
ctgggtgtga acggcggcgg tggtctccgg ttccccgggg gtgtagtggc agtaaaacac   3360
gtcgagctgt tgttcgtcca gccccgcgaa aataacgtcg aggtcgtcgt cgggaaaatc   3420
gtccgggccc ccgtcccgcg gccccagttg cttaaaatca aacgcacgct cgccgggggc   3480
gcctgcgtcg gccattaccg acgcctgcgt cggcaccccc gaagatttgg ggcgcagaga   3540
cagaatctcc gccgttagtt ctcccatgcg ggcgtaggcg agggtcctct gggtcgcatc   3600
caggcccggg cgctgcagaa agttgtaaaa ggagataagc ccgctaaata tgagccgcga   3660
caggaacctg taggcaaact ccaccgaagt ctccccctga gtctttacaa agctgtcgtc   3720
acgcaacact gcctcgaagg cccggaacgt cccactaaac ccaaaaacca gttttcgcag   3780
gcgcgcggtc accgcgatct ggctgttgag gacgtaagtg acgtcgttgc gggccacgac   3840
cagctgctgt ttgctgtgca cctcgcagcg catgtgcccc gcgtcctggt cctggctctg   3900
cgagtagttg gtgatgcggc tggcgttggc cgtgagccac ttttcaatcg tcaggccggg   3960
ctggtgtgtc agccgtcggt attcgtcaaa ctccttgacc gacacgaacg taagcacggg   4020
gagggtgaac acgacgaact ccccctcacg ggtcaccttc aggtaggcgt ggagcttggc   4080
catgtacgcg ctcacctctt tgtgggagga gaacagccgc gtccagccgg ggaggttggc   4140
ggggttggtg atgtagtttt ccgggacgac gaagcgatcc acgaactgca tgtgctcctc   4200
ggtgatgggc aggccgtact ccagcacctt catgaggtta ccgaactcgt gctcgacgca   4260
ccgtttgttg ttaataaaaa tggcccagct atacgagagg cgggcgtact cgcgcagcgt   4320
gcggttgcag atgaggtacg tgagcacgtt ctcgctctgg cggacggaac accgcagttt   4380
ctggtgctcg aaggtcgact ccagggacgc cgtctgcgtc ggcgagccca cacacaccaa   4440
cacgggccgc aggcgggccg cgtactgggg ggtgtggtac agggcgttaa tcatccacca   4500
gcaatacacc acggccgtga ggaggtgacg cccaaggagc ccggcctcgt cgatgacgat   4560
cacgttgctg cgggtaaagg ccggcagcgc cccgtgggtg gccggggcca accgcgtcag   4620
ggcgccctcg gccaacccca gggtccgttc cagggcggcc agggcgcgaa actcgttccg   4680
caactcctcg cccccggagg cggccagggc gcgcttcgtg aggtccaaaa tcacctccca   4740
gtagtacgtc agatctcgtc gctgcaggtc ctccagcgag gcggggttgc tggtcagggt   4800
gtacgggtac tgtcccagtt gggcctggac gtgattcccg cgaaacccaa attcatgaaa   4860
gatggtgttg atgggtcggc tgagaaaggc gcccgagagt ttggcgtaca tgttttgggc   4920
cgcaatgcgc gtggcgcccg tcaccacaca gtccaagacc tcgttgattg tctgcacgca   4980
cgtgctcttt ccggagccag cgttgccggt gataagatac accgcgaacg gaaactccct   5040
```

```
gaggggcagg cctgcggggg actctaaggc cgccacgtcc cggaaccact gcagatgggg   5100
cacttgcgct ccgtcgagct gttgttgcga gagctctcgg atgcgcttaa ggattggctg   5160
caccccgtgc atagacgtaa aatttaaaaa ggcctcggcc ctccctggaa cggctggtcg   5220
gtccccgggt tgctgaaggt gcggcgggcc gggtttctgt ccgtctagct ggcgctcccc   5280
gccggccgcc gccatgaccg caccacgctc gcgggccccc actacgcgtg cgcgggggga   5340
cacggaagcg ctgtgctccc ccgaggacgg ctgggtaaag gttcacccca gccccggtac   5400
gatgctgttc cgcgagattc tccacgggca gctggggtat accgagggcc agggggtgta   5460
caacgtcgtc cggtccagcg aggcgaccac ccggcagctg caggcggcga tctttcacgc   5520
gctcctcaac gccaccactt accgggacct cgaggcggac tggctcggcc acgtggcggc   5580
ccgcggtctg cagccccaac ggctggttcg ccggtacagg aacgcccggg aggcggatat   5640
cgccggggtg gccgagcggg tgttcgacac gtggcggaac acgcttagga cgacgctgct   5700
ggactttgcc cacgggttgg tcgcctgctt tgcgccgggc ggcccgagcg gcccgtcaag   5760
cttccccaaa tatatcgact ggctgacgtg cctggggctg gtccccatat tacgcaagcg   5820
acaagaaggg ggtgtgacgc agggtctgag ggcgtttctc aagcagcacc cgctgacccg   5880
ccagctggcc acggtcgcgg aggccgcgga gcgcgccggc cccgggtttt ttgagctggc   5940
gctggccttc gactccacgc gcgtggcgga ctacgaccgc gtgtatatct actacaacca   6000
ccgccggggc gactggctcg tgcgagaccc catcagcggg cagcgcggag aatgtctggt   6060
gctgtggccc cccttgtgga ccggggaccg tctggtcttc gattcgcccg tccagcggct   6120
gtttcccgag atcgtcgcgt gtcactccct ccgggaacac gcgcacgtct gccggctgcg   6180
caataccgcg tccgtcaagg tgctgctggg gcgcaagagc gacagcgagc gcggggtggc   6240
cggtgccgcg cgggtcgtta acaaggtgtt gggggaggac gacgagacca aggccgggtc   6300
ggccgcctcg cgcctcgtgc ggcttatcat caacatgaag ggcatgcgcc acgtaggcga   6360
cattaacgac accgtgcgtt cctacctcga cgaggccggg gggcacctga tagacgcccc   6420
ggccgtcgac ggtaccctcc ctggattcgg caagggcgga aacagccgcg ggtctgcggg   6480
ccaggaccag ggggggcggg cgccgcagct tcgccaggcc ttccgcacgg ccgtggttaa   6540
caacatcaac ggcgtgttgg agggctatat aaataacctg tttggaacca tcgagcgcct   6600
gcgcgagacc aacgcgggcc tggcgaccca attgcaggag cgcgaccgcg agctccggcg   6660
cgcaacagcg gggggccctgg agcgccagca gcgcgcggcc gacctggcgg ccgagtccgt   6720
gaccggtgga tgcggcagcc gccctgcggg ggcggacctg ctccgggccg actatgacat   6780
tatcgacgtc agcaagtcca tggacgacga cacgtacgtc gccaacagct ttcagcaccc   6840
gtacatccct tcgtacgccc aggacctgga gcgcctgtcg cgcctctggg agcacgagct   6900
ggtgcgctgt tttaaaattc tgtgtcaccg caacaaccag ggccaagaga cgtcgatctc   6960
gtactccagc ggggcgatcg ccgcattcgt cgccccctac tttgagtcag tgcttcgggc   7020
cccccgggta ggcgcgccca tcacgggctc cgatgtcatc ctgggggagg aggagttatg   7080
ggatgcggtg tttaagaaaa cccgcctgca aacgtacctg acagacatcg cggccctgtt   7140
cgtcgcggac gtccagcacg cagcgctgcc cccgcccccc tccccggtcg gcgccgattt   7200
ccggcccggc gcgtccccgc ggggccggtc cagatcgcgg tcgcccggaa gaactgcgcg   7260
aggcgcgccg gaccagggcg ggggcatcgg gcaccgggat ggccgccgcg acggccgacg   7320
atgaggggtc ggccgccacc atcctcaagc aggccatcgc cggggaccgc agcctggtcg   7380
aggcggccga ggcgattagc cagcagacgc tgctccgcct ggcctgcgag gtgcgccagg   7440
```

```
tcggcgaccg ccagccgcgg tttaccgcca ccagcatcgc gcgcgtcgac gtcgcgcctg   7500
ggtgccggtt gcggttcgtt ctggacggga gtcccgagga cgcctatgtg acgtcggagg   7560
attactttaa gcgctgctgc ggccagtcca gttatcgcgg cttcgcggtg gcggtcctga   7620
cggccaacga ggaccacgtg cacagcctgg ccgtgccccc cctcgttctg ctgcaccggt   7680
tctccctgtt caaccccagg gacctcctgg actttgagct tgcctgtctg ctgatgtacc   7740
tggagaactg cccccgaagc cacgccaccc cgtcgacctt tgccaaggtt ctggcgtggc   7800
tcggggtcgc gggtcgccgc acgtccccat tcgaacgcgt tcgctgcctt ttcctccgca   7860
gttgccactg ggtcctaaac acactcatgt tcatggtgta cgtaaaaccg ttcgacgacg   7920
agttcgtcct gccccactgg tacatggccc ggtacctgct ggccaacaac ccgccccccg   7980
ttctctcggc cctgttctgt gccaccccga cgagctcctc attccggctg ccggggccgc   8040
ccccccgctc cgactgcgtg gcctataacc ccgccgggat catggggagc tgctgggcgt   8100
cggaggaggt gcgcgcgcct ctggtctatt ggtggctttc ggagacccca aaacgacaga   8160
cgtcgtcgct gttttatcag ttttgttgaa ttttaggaaa taaacccggt tttgtttctg   8220
tggcctcccg acggatgcgc gtgtccttac tccgtcttgg tgggtgggtg gctgtgtatg   8280
gcgtcccatc tgtgcgggga ggggggcaag tcggcacgta ttcggacaga ctcaagcaca   8340
taagacgaac aaaaggtttg taacttcgta ccgtgagtaa taatgtggac tttattgctt   8400
aagaatacgc gtagagaaat aagacgaaca aaaggtttgt gattttattg cttaagaata   8460
cgcgtagatg gtcgtaccgt gagtaataat gtggttcata agacgaacaa aaggtttgtg   8520
acattattgc ttaagaatac gcgtaggtgg tcgtaccgtg agtaataatg tgtactttat   8580
tgcttaagaa tacgcgtagg ctatcgtacc gtgagtaata atgtgcctta taagacgaac   8640
aaaaggtttg tacacggggg agcgctcttg tctcagggca atgtttttat tggtcaaact   8700
caggcaaaca gaaacgacat cttgtcgtca aagggataca caaacttccc cccctcgccc   8760
catactcccg ccagcacccc ggtaaacacc aactcaatct cgcgcaggat ttcgcgcagg   8820
tgatgagcgc agtccacggg ggggagcaca aggggccgcg ggtatagatc gacggggacg   8880
ccgaccgact ccccgcctcc gggacagaca cgcacgacgc gccgccagta gtgctctgcg   8940
tccagcaagg cgccgccgcg gaaggcagtg gggggcaagg ggtcgctggc ctcaaagggg   9000
gacacccgaa cgctccagta ctccgcgtcc aaccgtttat taaacgcgtc caagataagg   9060
cggtcgcagg cgtcctccat aaggccccgg gccgtgagtg cgtcctcctc cggcacgcat   9120
gccgttgtca ggcccaggac ccgtcgcagc gtgtcgcgta cgacccctgc cgccgtggtg   9180
tacgcgggcc cgcggagagg aaatccccca agatggtcag tgttgtcgcg ggagttccag   9240
aaccacactc ccgcctggct ccaggcgact gcgtgggtgt agacgccctc gagggccagg   9300
cacagtgggt gccgcagccg gacggcgttg gccctaagca cggctcccac ggccgtctcg   9360
atggcccgcc gggcgtcctc gatcaccccg gaagccgcat ccgcgtcttg gggtccacg   9420
ttaaagacac cccagaacgc acccccatcg cccccgcaga ccgcgaactt caccgagctg   9480
gccgtctcct cgatctgcag gcagacggcg gccattaccc cacccaggag ctgccgcagc   9540
gcagggcagg cgttgcacgt gtccgggacc aggcgctcca agacggcccc ggcccagggc   9600
tctgagggag cggccaccac cagcgcgtcc agtcttgcta ggcccgtccg gccgtggggg   9660
tccgccagcc cgctcccccc gaggtcggcc agggccgcca ggagctgggc gcgaagtccg   9720
gggaagcaaa accgcgccgt ccagacgggc ccgacggccg cgggcgggtc taacagttgg   9780
```

-continued

```
atgattttag tggcgggatg ccaccgcgcc accgcctccc gcaccgcggg caggaggcat   9840
ccggctgccg ccgaggccac gccgggccag gctcgcgggg ggaggacgac cctggccccc   9900
accgcgggcc aggcccccag gagcgcggcg taagcggccg cggccccgcg caccaggtcc   9960
cgtgccgact cggccgtggc cggcacggtg aacgtgggcc aacccggaaa ccccaggacg  10020
gcaaagtacg ggacgggtcc cccccggacc tcaaactcgg gccccagaaa ggcaaagacg  10080
ggggccaggg ccccgggggc ggcgtggacc gtggtatgcc actgccggaa aagggcgacg  10140
agcgccggcg cggagaactt ctcgccggcg cttacaaagt agtcgtaatc gcggggcagc  10200
agcacccgtg ccgtgactcg ttgcgggtgc ccgcgtggcc gcaggcccac ctcgcacacc  10260
tcgaccaggt ccccgaacgc gccctccttc ttgatcggcg gaaacgcaag agtctggtat  10320
tcgcgcgcaa atagcgcggt tccggtggtg atgttaacgg tcagcgaagc ggcggacgcg  10380
cactgggggg tgtcgcgaat ggccgccagg cgcgcccacg ccagccgcgc gtcgggatgc  10440
tcggcaacgc gcgccgccag ggccataggg tcgatgtcaa tgttggcctc cgcgaccagg  10500
agagcggcgc gaggggcggc gggcgggccc cacgacgctc tctcaacttt caccaccagt  10560
cccgtgcgtg ggtccgagcc gatacgcagc ggggcgaaca gggccaccgg cccggtctgg  10620
cgctccaggg ccgccaggac gcacgcgtac agcgcccgcc acagagtcgg gttctccagg  10680
ggctccagcg gggaggcggc cggcgtcgtc gcggcgcggg cggccgccac gacggcctgg  10740
acggagacgt ccgcggagcc gtagaaatcc cgcagctccg tcgcggtgac ggagacctcc  10800
gcaaagcgcg cgcgaccctc ccctgcggcg ttgcgacata caaaatacac cagggcgtgg  10860
aagtactcgc gagcgcgggg gggcagccat accgcgtaaa gggtaatggc gctgacgctc  10920
tcctccaccc acacgatatc tgcggtgtcc atcgcacggc ccctaaggat cacgggcggt  10980
ctgtgggtcc catgctgccg tgcctggccg ggcccggtgg gtcgcggaaa ccggtgacgg  11040
gggggggcg gtttttgggg ttggggtggg ggtgggaaac ggcccgggtc cgggggccaa  11100
cttggcccct cggtgcgttc cggcaacagc gccgccggtc cgcggacgac cacgtaccga  11160
acgagtgcgg tcccgagact tatagggtgc taaagttcac cgccccctgc atcatgggcc  11220
aggcctcggt ggggagctcc gacagcgccg cctccaggat gatgtcagcg ttggggttgg  11280
cgctggatga gtgcgtgcgc aaacagcgcc cccacgcggg cacgcgtagc ttgaagcgcg  11340
cgcccgcaaa ctcccgcttg tgggccataa gcagggcgta cagctgcctg tgggtccggc  11400
aggcgctgtg gtcgatgtgg tgggcgtcca acaaccccac gattgtctgt ttggtgaggt  11460
ttttaacgcg ccccgccccg ggaaacgtct gcgtgctttt ggccatctgc acgccaaaca  11520
gttcgcccca gattatcttg aacagcgcca ccgcgtggtc cgtctcgcta acggacccgc  11580
gcgggggaca gccgcttagg gcgtcggcga cgcgcttgac ggcttcctcc gagagcagaa  11640
gtccgtcggt tacgttacag tggcccagtt cgaacaccag ctgcatgtag cggtcgtagt  11700
ggggggtcag taggtccagc acgtcatcgg ggccgaaggt cctcccagat cccccggccg  11760
ccgagtccca atgcaggcgc gcggccatgg tgctgcacag gcacaacagc tcccagacgg  11820
gggttacgtt cagggtgggg ggcagggcca cgagctccag ctctccggtg acgttgatcg  11880
tggggatgac gcccgtggcg tagtggtcat agatccgccg aaatatggcg ctgctgcggg  11940
tggccatggg aacgcggaga caggcctcca gcaacgccag gtaaataaac cgcgtgcgtc  12000
ccatcaggct gttgaggttg cgcatgagcg cgacaatttc cgccggcgcg acatcggacc  12060
ggaggtattt ttcgacgaaa agacccacct cctccgtctc ggcggcctgg gccggcagcg  12120
acgcctcggg atcccggcac cgcagctccc gtagatcgcg ctgggccctg agggcgtcga  12180
```

-continued aatgtacgcc ccgcaaaaac agacagaagt cctttggggt cagggtatcg tcgtgtcccc 12240
agaagcgcac gcgtatgcag tttagggtca gcagcatgtg aaggatgtta aggctgtccg 12300
agagacacgc cagcgtgcat ctctcaaagt agtgtttgta acggaatttg ttgtagatgc 12360
gcgacccccg ccccagcgac gtgtcgcatg ccgacgcgtc acagcgcccc ttgaaccggc 12420
gacacagcag gtttgtgacc tgggagaact gcgcgggcca ctggccgcag gaactgacca 12480
cgtgattaag gagcatgggc gtaaagacgg gctccgagcg cgccccggag ccgtccatgt 12540
aaatcagtag ctccccttg cggagggtgc gcacccgtcc cagggactgg tacacggaca 12600
ccatgtccgg tccgtagttc atgggtttca cgtaggcgaa catgccatca aagtgcaggg 12660
gatcgaagct gaggcccacg gttacgaccg tcgtgtatat aaccacgcgg tattggcccc 12720
acgtggtcac gtccccgagg ggggtgagcg agtgaagcaa cagcacgcgg tccgtaaact 12780
gacggcagaa ccgggccacg atctccgcga aggagaccgt cgacgaaaaa atgcagatgt 12840
tatcgccccc gccaaggcgc gcttccagct ccccaaagaa cgtggccccc cgggcctccg 12900
gagaggcgtc cggagacggg ccgctcggcg gcccgggcgg gcgcagggca gcctgcagga 12960
gctcggtccc cagacgcggg agaaacaggc accggcgcgc cgaaaacccg ggcatggcgt 13020
actcgccgac caccacatgc acgttttttt cgccccggag accgcacagg aagtccacca 13080
actgcgcgtt ggcggttgcg tccatggcga tgatccgagg acagatgcgc agcaggcgta 13140
gcattaacgc atccacgcgg cccagttgct gcatcgttgg cgaatagagc tggcccagcg 13200
tcgacataac ctcgtccaga acgaggacgt cgtagttgtt cagaaggttg gggcccacgc 13260
gatgaaggct ttccacctgg acgataagtc ggtggaaggg gcggtcgttc ataatgtaat 13320
tggtggatga gaagtaggtg acaaagtcga ccaggcctga ctcagcgaac cgcgtcgcta 13380
gggtctgggt aaaactccga cgacaggaga cgacgagcac actcgtgtcc ggagagtgga 13440
tcgcttcccg cagccagcgg atcagcgcgg tagtttttcc cgaccccatt ggcgcgcgga 13500
ccacagtcac gcacctggcc gtcggggcgc tcgcgttggg gaaggtgacg ggtccgtgct 13560
gctgccgctc gatcgttgtt ttcgggtgaa cccggggcac ccattcggcc aaatcccccc 13620
cgtacaacat ccgcgctagc gatacgctcg acgtgtactg ttcgcactcg tcgtccccaa 13680
tgggacgccc ggcccccaga ggatctcccg actccgcgcc ccccacgaaa ggcatgaccg 13740
gggcgcggac ggcgtggtgg gtctggtgtg tgcaggtggc gacgtttgtg gtctctgcgg 13800
tctgcgtcac ggggctcctc gtcctggcct ctgtgttccg ggcacggttt ccctgctttt 13860
acgccacggc gagctcttat gccggggtga actccacggc cgaggtgcgc gggggtgtag 13920
ccgtgcccct caggttggac acgcagagcc ttgtgggcac ttatgtaatc acggccgtgt 13980
tgttgttggc cgtggccgtg tatgccgtgg tcggcgccgt gacctcccgc tacgaccgcg 14040
ccctggacgc gggccgccgt ctggctgcgg cccgcatggc catgccgcac gccacgctga 14100
tcgccggaaa cgtctgctct tggttgctgc agatcaccgt cctgttgctg gcccatcgca 14160
tcagccagct ggcccacctg gtttacgtcc tgcactttgc gtgtctggtg tattttgcgg 14220
cccatttttg caccaggggg gtcctgagcg ggacgtatct gcgtcaggtg cacggcctga 14280
tggagctggc cccgacccat catcgcgtcg tcggcccggc tcgcgccgtg ctgacaaacg 14340
ccttgctgtt gggcgtcttc ctgtgcacgg ccgacgccgc ggtatccctg aataccatcg 14400
ccgcgttcaa ctttaatttt tcggccccgg gcatgctcat ctgcctgacc gtgctgttcg 14460
ccattctcgt cgtatcgctg ttgttggtgg tcgagggggt gttgtgtcac tacgtgcgcg 14520

-continued

```
tgttggtggg cccccacctg gggccgtgg ccgccacggg catcgtcggc ctggcctgcg  14580
agcactatta caccaacggc tactacgttg tggagacgca gtggccgggg gctcagacgg  14640
gagtccgcgt cgccctcgcc ctggtcgccg cctttgccct cggcatggcc gtgctccgct  14700
gcacccgcgc ctatctgtat cacaggcggc accacaccaa attttttatg cgcatgcgcg  14760
acacgcgaca ccgcgcacat tccgccctca agcgcgtacg cagttccatg cgcggatcgc  14820
gagacggccg ccacaggccc gcacccggca gcccgcccgg gattcccgaa tatgcggaag  14880
acccctacgc gatctcatac ggcggccagc tcgaccggta cggagattcc gacggggagc  14940
cgatttacga cgaggtggcg gacgaccaaa ccgacgtatt gtacgccaag atacaacacc  15000
cgcggcacct gcccgacgac gatcccatct atgacaccgt tggggggtac gaccccgagc  15060
ccgccgagga ccccgtgtac agcaccgtcc gccgttggta gctgtttggt tccgttttaa  15120
taaaccgttt gtgtttaacc cgaccgtggt gtatgtctgg tgtgtggcgt ccgatcccgt  15180
tactatcacc gtcccccccc cccccctcaac cccggcgatt gtgggttttt taaaaacgac  15240
acgcgtgcga ccgtatacag aacattgttt tggtttttat tcgctatcgg acatgggggg  15300
tggaaactgg gtggcggggc aggcgcctcc gggggtccgc cggtgagtgt ggcgcgaggg  15360
ggggtccgat gaacgcaggc gctgtctccc cggggcccgc gtaaccccgc gcatatccgg  15420
gggcacgtag aaattacctt cctcttcgga ctcgatatcc acgacgtcaa agtcgtgggc  15480
ggtcagcgag acgacctccc cgtcgtcggt gatgaggacg ttgtttcggc agcagcaggg  15540
ccgggccccg gagaacgaga ggcccatagc tcggcgagcg tgtcgtcgaa tgccaggcgg  15600
ctgcttcgct ggatggcctt atagatctcc ggatcgatgc ggacgggggt aatgatcagg  15660
gcgatcggaa cggcctggtt cgggagaatg gacgccttgc tgggtcctgc ggccccgaga  15720
gccccggcgc cgtcctccag gcggaacgtt acgccctcct ccgcgctggt gcggtgcctg  15780
ccgataaacg tcaccagatg cgggtggggg gggcagtcgg ggaagtggct gtcgagcacg  15840
tagccctgca ccaagatctg cttaaagttc gggtgacggg ggttcgcgaa gacgggctcg  15900
cggcggacca gatccccgga gctccaggac acgggggaga tggtgtggcg tccgaggtcg  15960
ggggcgccaa acagaagcac ctccgagaca acgccgctat ttaactccac caaggcccga  16020
tccgcggcgg agcaccgcct tttttcgccc gaggcgtggg cctctgacca ggcctggtct  16080
tgcgtgacga gagcctcctc cgggccgggg acgcgcccgg gcgcgaagta tcgcacgctg  16140
ggcttcggga tcgaccggat aaatgcccgg aacgcctccg gggaccggtg tgccatcaag  16200
tcctcgtacg cggaggccgt ggggtcgctg gggtccatgg ggtcgaaagc gtacttggcc  16260
cggcatttga cctcgtaaaa ggccaggggg gtcttgggga ctggggccag gtagccgtga  16320
atgtcccgag gacagacgag aatatccagg gacgccccga ccatccccgt gtgaccgtcc  16380
atgaggaccc cacacgtatg cacgttctct tcggcgaggt cgctgggttc gtggaagata  16440
aagcgccgcg tgtcggcgcc ggcctcgccg ccgtcgtccg cgcggcccac gcagtagcga  16500
aacagcaggc ttcgggccgt cggctcgttc acccgcccga acatcaccgc cgaagactgt  16560
acatccggcc gcaggctggc gttgtgcttc agccactggg gcgagaaaca cggaccctgg  16620
gggccccagc ggagggtgga tgcggtcgtg aggccccgcc ggagcagggc ccatagctgg  16680
cagtcggcct ggttttgcgt ggccgcctcg taaaacccca tgaggggccg gggcgccacg  16740
gcgtccgcgg cggccggggg cccgcggcgc gtcaggcgcc ataggtgccg accgagtccg  16800
cggtccacca tacccgcctc ctcgaggacc acggccaggg aacacagata atccaggcgg  16860
gcccagaggg gaccgatggc cagaggggcg cggacgccgc gcagcaaccc gcgcaggtgg  16920
```

cgctcgaacg tctcggctag tatatgggag ggcagcgcgt tggggatcac cgacgccgac 16980
cacatagagt caaggtccgg ggagtcggga tcggcgtccg ggtcgcgggc gtgggtgccc 17040
ccaggagata gcggaatgtc tggggtcgga ggccctgagg cgtcagaaag tgccggcgac 17100
gcggcccggg gcttttcgtc tgcggtgtcg gtggcgtgct gatcacgtgg ggggttaacg 17160
ggcgaatggg agctcgggtc cacagctgat gtcgtctggg gtgggggggg caggggacgg 17220
aaggtggttg tcagcggaag actgttaggg cgggggcgct tggggggggct gtcggggcca 17280
cgaggggtgt cctcggccag ggcccaggga cgcttagtca cggtgcgtcc cggcggacat 17340
gctgggccta ccgtggactc catttccgag acgacgtggg gggagcggtg gttgagcgcg 17400
ccgccgggtg aacgctgatt ctcacgacag cgcgtgccgc gcgcacgggt tggtgtgaca 17460
caggcgggac accagcacca ggagaggctt aagctcggga ggcagcgcca ccgacgacag 17520
tatcgccttg tgtgtgtgct ggtaatttat acaccgatcc gtaaacgcgc gccgaatctt 17580
gggattgcgg aggtggcgcc ggatgccctc tgggacgtca tacgccaggc cgtgggtgtt 17640
ggtctcggcc gagttgacaa acagggctgg gtgcagcacg cagcgatagg cgagcagggc 17700
cagggcgaag tccggcgaca gctggttgtt aaaatactgg taaccgggaa accgggtcac 17760
gggtacgccc aggctcgggg cgacgtacac gctaaccacc aactccagca gcgtctggcc 17820
cagggcgtac aggtcaaccg ctaacccgac gtcgtgcttc aggcggtggt tggtaaattc 17880
ggcccgttcg ttgttaaggt atttcaccaa cagctccggg ggctggttat acccgtgacc 17940
caccagggtg tgaaagttgg ctgtggttag ggcggtgggc atgccaaaca tccgggggga 18000
cttgaggtcc ggctcctgga ggcaaaactg cccccgggcg atcgtggagt tggagttgag 18060
ggtgacgagg ctaaagtcgg cgaggacggc ccgccggagc gagacggcgt ccgaccgcag 18120
catgacgagg atgttggcgc acttgatatc caggtggctg atcccgcagg tggtgtttaa 18180
aaacacaacg gcgcgggcca gctccgtgaa gcactggtgg agggccgtcg agaccgaggg 18240
gtttgttgtg cgcagggacg ccagttggcc gatatactta ccgaggtcca tgtcgtacgc 18300
ggggaacact atctgtcgtt gttgcagcga gaacccgagg ggcgcgatga agccgcggat 18360
gttgtgggtg cggccggcgc gtagaacgca ctccccgacc aacagggtcg cgatgagctc 18420
aacggcaaac cactcctttt cctttatggt cttaacggca agcttatgtt cgcgaatcag 18480
ttggacgtca ccgtatcccc cagacccccc gaagcttcgg gccccgggga tctcgagggt 18540
cgtgtagtgt agggcggggt tgatggcgaa cacggggctg catagcttgc ggatgcgcgt 18600
gagggtgagg atgtgcgagg gggacgaggg gggtgcggtt aacgccgcct gggatctgcg 18660
caggggcggg cggttcagtt tggccgccgt accgggcgtc tcgggggacg cgcggcgatg 18720
agacgagcgg ctcattcgcc atcgggatag tcccgcgcga agccgctcgc ggaggccgga 18780
tcggtggcgg gacccgtggg aggagcggga gacggcggcg tcctggagag aggggccgct 18840
ggggcgcccg gaggccccgt gggggttgga gtgtacgtag gatgcgagcc aatccttgaa 18900
ggaccgttgg cgtgcacctt gggggctgag gttagctgcc acatgaccag caggtcgctg 18960
tctgcgggac tcatccatcc ttcggccagg tcgccgtctc cccacagaga agcgttggtc 19020
gctgcttcct cgagttgctc ctcctggtcc gcaagacgat cgtccacggc gtccaggcgc 19080
tcaccaagcg ccggatcgag gtaccgtcgg tgtgcggtta gaaagtcacg acgcgccgct 19140
tgctcctcca cgcgaatttt aacacaggtc gcgcgctgtc gcatcatctc taagcgcgcg 19200
cgggacttta gccgcgcctc caattccaag tgggccgcct ttgcagccat aaaggcgcca 19260
acaaaccgag gatcttgggt gctgacgccc tcccggtgca gctgcagggt ctggtccttg 19320
taaatctcgg ctcggaggtg cgtctcggcc aggcgtcggc gcagggccgc gtgggcggca 19380
tctcggtcca ttccgccacc ctgcgggcga cccggggggt gctctgatag tctcgcgtgc 19440
ccaaggcccg tgatcggggt acttcgccgc cgcgacccgc cacccggtgt gcgcgatgtt 19500
tggtcagcag ctggcgtccg acgtccagca gtacctggag cgcctcgaga aacagaggca 19560
acttaaggtg ggcgcggacg aggcgtcggc gggcctcacc atgggcggcg atgccctacg 19620
agtgcccttt ttagatttcg cgaccgcgac ccccaagcgc caccagaccg tggtccctgg 19680
cgtcgggacg ctccacgact gctgcgagca ctcgccgctc ttctcggccg tggcgcggcg 19740
gctgctgttt aatagcctgg tgccggcgca actaaagggg cgtgatttcg gggcgacca 19800
cacggccaag ctggaattcc tggcccccga gttggtacgg gcggtggcgc gactgcggtt 19860
taaggagtgc gcgccggcgg acgtggtgcc tcagcgtaac gcctactata gcgttctgaa 19920
tacgtttcag gccctccacc gctccgaagc ctttcgccag ctggtgcact ttgtgcggga 19980
ctttgcccag ctgctcaaaa cctccttccg ggcctccagc ctcacggaga ccacgggccc 20040
ccccaaaaaa cgggccaagg tggacgtggc cacccacggc cggacgtacg gcacgctgga 20100
gctgttccaa aaaatgatcc ttatgcacgc cacctacttt ctggccgccg tgctcctcgg 20160
ggaccacgcg gagcaggtca acacgttcct gcgtctcgtg tttgagatcc ccctgtttag 20220
cgacgcggcc gtgcgccact tccgccagcg cgccaccgtg tttctcgtcc cccggcgcca 20280
cggcaagacc tggtttctgg tgcccctcat cgcgctgtcg ctggcctcct ttcgggggat 20340
caagatcggc tacacggcgc acatccgcaa ggcgaccgag ccggtgtttg aggagatcga 20400
cgcctgcctg cggggctggt tcggttcggc ccgagtggac cacgttaaag ggaaaccat 20460
ctccttctcg tttccggacg ggtcgcgcag taccatcgtg tttgcctcca gccacaacac 20520
aaacgtaagt cctcttttct ttcgcatggc tctcccaagg ggccccgggt cgacccgacc 20580
cacacccacc cacccacata cacacacaac cagacgcggg aggaaagtct gccccgtggg 20640
cactgatttt tattcgggat cgcttgagga ggcccgggca acggcccggg caacggtggg 20700
gcaactcgta gcaaataggc gactgatgta cgaagagaag acacacaggc gccacccggc 20760
gctggtcggg gggatgttgt ccgcgccgca ccgtccccg acgacctctt gcagacggtc 20820
cgtgatgcaa ggacggcggg gggcctgcag cagggtgacc gtatccacgg gatggccaaa 20880
gagaagcgga cacaggctag catccccctg gaccgccagg gtacactggg ccatcttggc 20940
ccacagacac ggggcgacgc agggacagga ctccgttacg acggaggaga gccacagtgc 21000
gttggcggaa tcgatgtggg gcggcggggc gcaggactcg cagccccccg ggtggttggt 21060
gatcctggcc aggagccatc ccagatggcg ggccctgctt cccggtggac agagcgaccc 21120
caggtcgctg tccatggccc agcagtagat ctggccgctg gggaggtgcc accaggcccc 21180
cgggcccaag gcgcagcacg cgcccggctc cggggggggtc ttcgcgggga ccagatacgc 21240
gccatccagc tcgccgacca ctggctcctc cgcgagctgt tcggtggttg ggtcgggggt 21300
ttcctccggg ggggtggccg cccgtatgcg tgcgaacgtg agggtgcaca ggagcggggt 21360
cagggggtgc gtcacgctcc ggaggtggac gatcgcgcag tagcggcgct cgcggttaaa 21420
gaaaaagagg gcaaagaagg tgttcggggg caaccgcagc gccttggggc gcgtcagata 21480
cagaaaaatc tcgcagaaga gggcgcgccc ggggtctggg ttaggaaggg ccacctgaca 21540
cagaggctcg gtgaggaccg ttagacaccg aaagatcttg agccgctcgt ccgcccgaac 21600
gacgcgccac acaaagacgg agttgacaat gcgcgcgata gagtcgacgt ccgtccccag 21660
gtcgtcgact ctatcgcgcg tgccgcgagc tccggcccgg gaatccggcc ggggcaaggt 21720
ccccgggggga ccaggcggcg ccaggggccg ccggggtccc agctgcgcca tgccgggggc 21780
gggggggaggg caaaccccag aggcgggggc caacggcgcg gggaggagtg ggtgggcgag 21840
gtggccgggg gaaggcgccc gctagcgaga ccggccgttc ccggacgaca ccttgcgaca 21900
aaacctaagg acagcggccc gcgcgacggg gtccgagagg ctaaggtagg ccgcgatgtt 21960
aatggtgaac gcaaagccgc cgggaaagac aactatgcca cagaggcggc gattaaaccc 22020
caggcagagg taggcgtagc tttccccggg caggtattgc tcgcagaccc tgcgtggggc 22080
tgtggagggg acggcctcca tgaagcgaca tttactctgc tcgcgtttac tgacgtcacc 22140
atccatcgcc acggcgattg gacgattgtt aagccgcagc gtgtctccgc ttgtgctgta 22200
gtagtcaaaa acgtaatggc cgtcggagtc ggcaaagcgg gccgggaggt cgtcgccgag 22260
cgggacgacc cgccgccccc gaccgccccg tccccccagg tgtgccagga cggccagggc 22320
atacgcggtg tgaaaaaagg cgtcgggggc ggtcccctcg acggcgcgca tcaggttctc 22380
gaggagaatg gggaagcgcc tggtcacctc ccccaaccac gcgcgttggt cggggccaaa 22440
gtcatagcgc aggcgctgtg agattcgcgg gccgccctga agcgcggccc ggatggcctg 22500
gcccagggcc cggaggcacg ccagatgtat gcgcgcggta aaggcgacct cggcggcgat 22560
gtcaaagggc ggcaggacgg ggcgcgggtg gcgcaggggc acctcgagcg cgggaaagcg 22620
tagcagcagc tccgcctgcc cagcgggaga cagctggtgg gggcgcacga cgcgttctgc 22680
ggcgcaggcc tcggtcaggg ccgtggccag cgccgaggac agcagcggag ggcgggcgcg 22740
tcgcccgccc cacgccacgg agttctcgta ggagacgacg acgaagcgct gcttggttcc 22800
gtagtggtgg cgcaggacca cggagataga acgacggctc cacagccagt ccggccggtc 22860
gccgccggcc agggcttccc atccgcgatc caaccactcg accagcgacc gcggctttgc 22920
ggtaccaggg gtaagggtta gaacgtcgtt caggatgtcc tcgcccccgg gcccgtgggg 22980
cgctggggcc acaaagcggc ccccgccggg gggctccaga cccgccagca ccgcatctgc 23040
gtcagccgcc cccatggcgc ccccgctgac ggcctggtga accagggcgc cctggcgtag 23100
ccccgatgca acgccacagg ccgcacgccc ggtccgcgct cggaccgggt ggcggcgggt 23160
gacgtcctgc actgcccgct gaaccaacgc gaggatctcc tcgttctcct gtgcgatgga 23220
cacgtcctgg gccgcggtcg tgtcgccgcc gggggccgtc agctgctcct ccggggagat 23280
gggggggtcg gacgccccga cgatgggcgg gtctgcgggc gcccccgcgt ggggccgggc 23340
caagggctgc ggacgcgggg acgcgctttc ccccagaccc atggacaggt gggccgcagc 23400
ctccttcgcg gccggcgggg cggcggcgcc aagcagagcg acgtagcggc acaaatgccg 23460
acagacgcgc atgatgcgcg tgctgtcggc cgcgtagcgc gtgttggggg ggacgagctc 23520
gtcgtaacta aacagaatca cgcgggcaca gctcgccccc gagccccacg caaggcgcag 23580
cgccgccacg gcgtacgggt catagacgcc ctgcgcgtca cacaccacgg gcagggagac 23640
gaacaacccc ccggcgctgg acgcacgcgg aaggaggcca gggtgtgccg gcacgacggg 23700
ggccagaagc tcccccaccg catccgcggg cacgtaggcg gcaaacgccg tgcaccacgg 23760
ggtacagtcg ccggtggcat gagcccgagt ctggatttcg acctggaagt ttgcggccgt 23820
cccgagtccg gggcggccgc gcatcagggc ggccagaggg attcccgcgg ccgccaggca 23880
ctcgctggat atgatgacgt gaaccaaaga ccgagggccg acccgggccg tggccgagat 23940
cgtctggacc tcgttggcca agtgcgcgtt catggttcgg gggtgggtgt gggtgtgtag 24000

-continued

```
gcgatgcggg tcccccgagt ccgcgggaag ggcgtgggtt tggcgcgcgt atgcgtattc  24060
gccaacggag gcgtgcgtgc ttatgcgcgg cgcgtttctt ctgtctctag ggaatccgag  24120
gccaggactt taacctgctc tttgtcgacg aggccaactt tattcgcccg gatgcggtcc  24180
agacgattat gggctttctc aaccaggcca actgcaagat tatcttcgtg tcgtccacca  24240
acaccgggaa ggccagtacg agctttttgt acaacctccg cggggccgca gacgagcttc  24300
tcaacgtggt gacctatata tgcgatgatc acatgccgag ggtggtgacg cacacaaacg  24360
ccacggcctg ttcttgttat atcctcaaca agcccgtttt catcacgatg gacggggcgg  24420
ttcgccggac cgccgatttg tttctggccg attccttcat gcaggagatc atcgggggcc  24480
aggccaggga gaccggcgac gaccggcccg ttctgaccaa gtctgcgggg gagcggtttc  24540
tgttgtaccg cccctcgacc accaccaaca gcggcctcat ggcccccgat ttgtacgtgt  24600
acgtggatcc cgcgttcacg gccaacaccc gagcctccgg gaccggcgtc gctgtcgtcg  24660
ggcggtaccg cgacgattat atcatcttcg ccctggagca ctttttctc cgcgcgctca  24720
cgggctcggc cccgccgac atcgcccgct gcgtcgtcca cagtctgacg caggtcctgg  24780
ccctgcatcc cggggcgttt cgcggcgtcc gggtggcggt cgagggaaat agcagccagg  24840
actcggccgt cgccatcgcc acgcacgtgc acacagagat gcaccgccta ctggcctcgg  24900
agggggccga cgcgggctcg ggccccgagc ttctcttcta ccactgcgag cctcccggga  24960
gcgcggtgct gtaccccttt ttcctgctca acaaacagaa gacgcccgcc tttgaacact  25020
ttattaaaaa gtttaactcc gggggcgtca tggcctccca ggagatcgtt tccgcgacgg  25080
tgcgcctgca gaccgacccg gtcgagtatc tgctcgagca gctaaataac ctcaccgaaa  25140
ccgtctcccc caacactgac gtccgtacgt attccggaaa acggaacggc gcctcggatg  25200
accttatggt cgccgtcatt atggccatct acctcgcggc ccaggccgga cctccgcaca  25260
cattcgctcc tatcacacgc gtctcgtgag cgcccaataa acacacccag gtatgctacg  25320
cacgaccacg gtgtcgtctg ttaagggggg ggggggaagg gggtgttggc gggaagcgtg  25380
ggaacacggg ggattctctc acgaccggca ccagtaccac ccccctgtga acacagaaac  25440
cccaacccaa atcccataaa catacgacac acaggcatat tttggaattt cttaggtttt  25500
tatttattta ggtatgctgg ggtttctccc tggatgccca cccccacccc cccgtgggtc  25560
tagccgggcc ttagggatag cgtataacgg gggccatgtc tccggaccgc acaacggccg  25620
cgccgtcaaa ggtgcacacc cgaaccacgg gagccagggc caaggtgtct cctagttggc  25680
ccgcgtgggt cagccaggcg acgagcgcct cgtaaagcgg cagccttcgc tctccatcct  25740
gcatcagggc cggggcttcg gggtgaatga gctgggcggc ctcccgcgtg acactctgca  25800
tctgcagtag agcgttcacg tacccgtcct gggcacttag cgcaaagagc cgggggatta  25860
gcgtaaggat gatggtggtt ccctccgtga tcgagtaaac catgttaagg accagcgatc  25920
gcagctcggc gtttacggga ccgagttgtt ggacgtccgc cagcagcgag aggcgactcc  25980
cgttgtagta cagcacgttg aggtctggca gccctccggg gtttctgggg ctggggttca  26040
ggtcccggat gcccctggcc acgagccgcg ccacgatttc gcgcgccagg ggcgatggaa  26100
gcggaacggg aaaccgcaac gtgaggtcca gcgaatccag gcgcacgtcc gtcgcttggc  26160
cctcgaacac gggcgggacg aggctgatgg ggtccccgtt acagagatct acgggggagg  26220
tgttgcgaag gttaacggtg ccggcgtggg tgaggcccac gtccaggggg caggcgacga  26280
ttcgcgtggg aagcacccgg gtgatgaccg cggggaagcg ccttcggtac gccagcaaca  26340
accccaacgt gtcgggactg acgcctccgg agacgaagga ttcgtgcgcc acgtcggcca  26400
```

gcgtcagttg ccggcggatg gtcggcagga ataccacccg cccttcgcag cgctgcagcg 26460
ccgccgcatc ggggcgcgag atgcccgagg gtatcgcgat gtcagtttca aagccgtccg 26520
ccagcatggc gccgatccac gcggcaggga gtgcagtggt ggttcgggtg gcgggaggag 26580
cgcggtgggg gtcagcggcg tagcagagac gggcgaccaa cctcgcatag gacggggggt 26640
gggtcttagg gggttgggag gcgacaggga ccccagagca tgcgcgggga ggtctgtcgg 26700
gcccagacgc accgagagcg aatccgtccg cggagtcccg gcttgggttt tatggggccc 26760
ggccctcgga atcgcggctt gtcggcgggg acaaaggggg cggggctagg ggcttgcgga 26820
aacagaagac gcgtgggata aaagaatcgc actaccccaa ggaagggcgg ggcggtttat 26880
tacagagcca gtcccttgag cggggatgcg tcatagacga gatactgcgc gaagtgggtc 26940
tcccgcgcgt gggcttcccc gttgcgggca ctgcggagga gggcggggtc gctggcgcag 27000
gtgagcgggt aggcctcctg aaacaggcca cacgggtcct ccacgagttc gcggcacccc 27060
ggggggcgct taaactgtac gtcgctggcg gcggtggccg tggacaccgc cgaacccgtc 27120
tccacgatca ggcgctccag gcagcgatgt ttggcggcga tgtcggccga cgtaaagaac 27180
ttaaagcagg ggctgagcac cggcgaggcc ccgttgaggt ggtaggcccc gttatagagc 27240
aggtccccgt acgaaaatcg ctgcgacgcc cacgggttgg ccgtggccgc gaaggcccgg 27300
gacgggtcgc tctggccgtg gtcgtacatg agggcggtga catccccctc cttgtccccc 27360
gcgtaaacgc ccccggcggc gcgtccccgg gggttgcagg gccggcggaa gtagttgacg 27420
tcggtcgaca cgggggtggc gataaactca cacacggcgt cctggccgtg gtccatccct 27480
gcgcgccgcg gcacctgggc gcacccgaac acggggacgg gctgggccgg ccccaggcgg 27540
tttcccgcca cgaccgcgtt ccgcaggtac acggctgccg cgttgtccag gagaggggga 27600
gccccgcggc ccaggtaaaa gttttgggga aggttgccca tgtcggtgac ggggttgcgg 27660
acggttgccg tggccacgac ggcggtgtag cccacgccca ggtccacgtt cgcgcgcggc 27720
tgggtgagcg tgaagtttac ccccccgcca gtttcgtgcc gggccacctg gagctggccc 27780
aggaagtacg cctccgacgc gcgctccgag aacagcacgt tctcagtcac aaagcggtcc 27840
tgtcggacga cggtgaaccc aaacccggga tggaggcccg tcttgagctg atgatgcaag 27900
gccacgggac tgatcttgaa gtaccccgcc atgagcgcgt aggtcagcgc gttctccccg 27960
gccgcgctct cgcggacgtg ctgcacgacg ggctgtcgga tcgacgaaaa gtagttggcc 28020
cccagagccg gggggaccag ggggacctgc cgcgacaggt cgcgcagggc cggggggaaa 28080
ttgggcgcgt tcgccacgtg gtcggccccg gcgaacagcg cgtggacggg gagggggtaa 28140
aaatagtcgc cattttggat ggtatggtcc agatgctggg gggccatcag caggattccg 28200
gcgtgcaacg ccccgtcgaa tatgcgcatg ttggtggtgg acgcggtgtt ggcgcccgcg 28260
tcgggcgccg ccgagcagag cagcgccgtt gtgcgttcgg ccatgttgtg ggccagcacc 28320
tgcagcgtga gcatggcggg cccgtccact accacgcgcc cgttgtgaaa catggcgttg 28380
accgtgttgg ccaccagatt ggccgggtgc agggggtgcg cggggtccgt cacggggtcg 28440
ctggggcact cctcgccggg ggcgatctcc gggaccacca tgttctgcag ggtggcgtat 28500
acgcggtcga agcgaacccc cgcggtgcag cagcggcccc gcgagaaggc gggcaccatc 28560
acgtagtagt aaatcttgtg gtgcacggtc cagtccgccc cccggtgcgg ccggtcatcc 28620
gcggcgtccg cggctcgggc ctgggtgttg tgcagcagct ggccgtcgtt gcggttgaag 28680
tccgcggtcg ccacgttaca tgccgccgcg tacacggggt cgtggccccc cgcgctaacc 28740

-continued cggcagtcgc gatggcggtc cagggccgcg cgccgcatca gggcgtcaca gtcccacacg 28800
aggggtggca gcagcgccgg gtctcgcatt aggtgattca gctcggcttg cgcctgcccg 28860
cccagctccg ggccggtcag ggtaaagtca tcaaccagct gggccagggc ctcgacgtgc 28920
gccaccaggt cccggtacac ggccatgcac tcctcgggaa ggtctccccc gaggtaggtc 28980
acgacgtacg agaccagcga gtagtcgttc acgaacgccg cgcaccgcgt gttgttccag 29040
tagctggtga tgcactggac cacgagccgg gccagggcgc agaagacgtg ctcgctgccg 29100
tgtatggcgg cctgcagcag gtaaaacacc gccgggtagt tgcggtcgtc gaacgccccg 29160
cgaacggcgg cgatggtggc gggggccatg gcgtggcgtc ccaccccag ctccaggccc 29220
cgggcgtccc ggaacgccgc cggacatagc gccaggggca agttgccgtt caccacgcgc 29280
caggtggcct ggatctcccc cgggccggcc gggggaacgt cccccccgg cagctccacg 29340
tcggccaccc ccacaaagaa gtcgaacgcg gggtgcagct caagagccag gttggcgttg 29400
tcgggctgca taaactgctc cggggtcatc tggccttccg cgacccatcg gacccgcccg 29460
tgggccaggc gctgcccca ggcgttcaaa aacagctgct gcatgtctgc ggcggggccg 29520
gccggggccg ccacgtacgc cccgtacgga ttggcggctt cgacggggtc gcggttaagg 29580
cccccgaccg ccgcgtcaac gttcatcagc gaagggtggc acacggtccc gatcgcgtgt 29640
tccagagaca ggcgcagcac ctggcggtcc ttcccccaaa aaaacagctg gcggggcggg 29700
aaggcgcggg gatccgggtg gccgggggcg gggactaggt ccccggcgtg cgcggcaaac 29760
cgttccatga ccggattgaa caggcccagg ggcaggacga acgtcaggtc catggcgccc 29820
accaggggt agggaacgtt ggtggcggcg tagatgcgct tctccagggc ctccagaaag 29880
accagcttct cgccgatgga caccagatcc gcgcgcacgc gcgtcgtctg gggggcgctc 29940
tcgagctcgt ccagcgtctg ccggttcagg tcgagctgct cctcctgcat ctccagcagg 30000
tggcggccca cgtcgtccag acttcgcacg gccttgccca tcacgagcgc cgtgaccagg 30060
ttggccccgt tcaggaccat ctcgccgtac gtcaccggca cgtcggcttc ggtgtcctcc 30120
actttcagga aggactgcag gaggcgctgt ttgatcgggg cggtggtgac gagcaccccg 30180
tcgaccggcc gcccgcgcgt gtcggcatgc gtcagacggg gcacggccac ggagggctgc 30240
gtggccgtgg tgaggtccac gagccaggcc tcgacggcct cccggcggtg gcccgccttg 30300
cccaggaaaa agctcgtctc gcagaagctt cgctttagct cggcgaccag ggtcgcccgg 30360
gccaccctgg tggccaggcg gccgttgtcc aggtatcgtt gcatcggcaa caacaaagcc 30420
aggggcggcg ccttttccag cagcacgtgc agcatctggt cggccgtgcc gcgctcaaac 30480
gccccgagga cggcctggac gttgcgagcg agctgttgga tggcgcgcaa ctggcgatgc 30540
gcgccgatac ccgtcccgtc cagggcctcc cccgtgagca gggcgatggc ctcggtggcc 30600
aggctgaagg cggcgttcag ggcccggcgg tcgataatct tggtcatgta attgtgtgtg 30660
ggttgctcga tggggtgcgg gccgtcgcgg gcaatcagcg gctggtggac ctcgaactgt 30720
acgcgcccct cgttcatgta ggccagctcc ggaaacttgg tacacacgca cgccaccgac 30780
aacccgagct ccagaaagcg cacgagcgac agggtgttgc aatacgaccc cagcagggcg 30840
tcgaactcga cgtcgtacag gctgtttgca tcggagcgca cgcgggaaaa aaaatcaaac 30900
aggcgtcgat gcgacgccac ctcgatcgtg ctaaggaggg acccggtcgg caccatggcc 30960
gcggcatacc ggtatcccgg agggtcgcgg ttgggagcgg ccatggggtc gcgtggagat 31020
cggctgtctc tagcgatatt ggcccgggga ggctaagatc caccccaacg cccggccacc 31080
cgtgtacgtg cccgacggcc caaggtccac cgaaagacac gacgggcccg gacccaaaaa 31140

```
ggcgggggat gctgtgtgag aggccgggtg ccggtcgggg gggaaaggca ccgggagaag  31200
gctgcggcct cgttccagga gaacccagtg tccccaacag acccggggac gtgggatccc  31260
aggccttata tacccccccc cccgccccac ccccgttaga acgcgacggg tgcattcaag  31320
atggccctgg tccaaaagcg tgccaggaag aaattggcag aggcggcaaa gctgtccgcc  31380
gccgccaccc acatcgaggc cccggccgcg caggctatcc ccagggcccg tgtgcgcagg  31440
ggatcggtgg gcggcagcat ttggttggtg gcgataaagt ggaaaagccc gtccggactg  31500
aaggtctcgt gggcggcggc gaacaaggca cacagggccg tgcctcccaa aaacacggac  31560
atcccccaaa acacgggcgc cgacaacggc agacgatccc tcttgatgtt aacgtacagg  31620
aggagcgccc gcaccgccca cgtaacgtag tagccgacga tggcggccag gatacaggcc  31680
ggcgccacca cccttccggt cagcccgtaa tacatgcccg ctgccaccat ctccaacggc  31740
ttcaggacca aaaacgacca aaggaacaga atcacgcgct ttgaaaagac cggctgggta  31800
tggggcggaa gacgcgagta tgccgaactg acaaaaaaat cagaggtgcc gtacgaggac  31860
aatgaaaact gttcctccag cggcagttct ccctcctccc ccccgaaggc ggcctcgtcg  31920
accagatctc gatccaccag aggaaggtca tcccgcatgg tcatggggtg tgcggtggag  31980
gtggggagac cgaaaccgca aagggtcgct tacgtcagca ggatcccgag atcaaagaca  32040
cccgggttct tgcacaaaca ccacccgggt tgcatccgcg gaggcgagtg ttttgataag  32100
gccgttccgc gccttgatat aacctttgat gttgaccaca aaacccggaa tttacgccta  32160
cgccccaatg cccacgcaag atgaggtagg taaccccccc gtgggtgtga cgttgcgttt  32220
agttcattgg aggccaaggg gaaaaatggg gtggggagga aacggaaaac ccagtaggcc  32280
gtgtcgggaa cacgcccggg gttgtcctca aaaggcaggg tccatactac ggaagccgtc  32340
gttgtattcg agacctgcct gtgcaacgca cgtcggggtt gcctgtgtcc ggttcggccc  32400
ccaccgcgtg cggcacgcac gaggacgagt ccgcgtgctt tattggcgtt ccaagcgttg  32460
ccctccagtt tctgttgtcg gtgttccccc atacccacgc ccacatccac cgtagggggc  32520
ctctgggccg tgttacgtcg ccgcccgcga tggagcttag ctacgccacc accatgcact  32580
accgggacgt tgtgttttac gtcacaacgg accgaaaccg ggcctacttt gtgtgcgggg  32640
ggtgtgttta ttccgtgggg cggccgtgtg cctcgcagcc cggggagatt gccaagtttg  32700
gtctggtcgt tcgagggaca ggcccagacg accgcgtggt cgccaactat gtacgaagcg  32760
agctccg                                                             32767
```

<210> SEQ ID NO 847
<211> LENGTH: 32767
<212> TYPE: DNA
<213> ORGANISM: Artificial Sequence
<220> FEATURE:
<223> OTHER INFORMATION: recombinant viral vector ONCR-155

<400> SEQUENCE: 847

```
aaaaaagctg aacgagaaac gtaaaatgat ataaatatca atatattaaa ttagattttg     60
cataaaaaac agactacata atactgtaaa acacaacata tccagtcact atgaatcaac    120
tacttagatg gtattagtga cctgtagtcg accgacagcc ttccaaatgt tcttcgggtg    180
atgctgccaa cttagtcgac cgacagcctt ccaaatgttc ttctcaaacg gaatcgtcgt    240
atccagccta ctcgctattg tcctcaatgc cgtattaaat cataaaaaga aataagaaaa    300
agaggtgcga gcctcttttt tgtgtgacaa aataaaaaca tctacctatt catatacgct    360
```

```
agtgtcatag tcctgaaaat catctgcatc aagaacaatt tcacaactct tatacttttc    420
tcttacaagt cgttcggctt catctggatt ttcagcctct atacttacta aacgtgataa    480
agtttctgta atttctactg tatcgacctg cagactggct gtgtataagg gagcctgaca    540
tttatattcc ccagaacatc aggttaatgg cgtttttgat gtcattttcg cggtggctga    600
gatcagccac ttcttccccg ataacggaga ccggcacact ggccatatcg gtggtcatca    660
tgcgccagct ttcatccccg atatgcacca ccgggtaaag ttcacgggag actttatctg    720
acagcagacg tgcactggcc aggggggatca ccatccgtcg cccgggcgtg tcaataatat    780
cactctgtac atccacaaac agacgataac ggctctctct tttataggtg taaaccttaa    840
actgcatttc accagcccct gttctcgtca gcaaaagagc cgttcatttc aataaaccgg    900
gcgacctcag ccatcccttc ctgattttcc gctttccagc gttcggcacg cagacgacgg    960
gcttcattct gcatggttgt gcttaccaga ccggagatat tgacatcata tatgccttga   1020
gcaactgata gctgtcgctg tcaactgtca ctgtaatacg ctgcttcata gcatacctct   1080
ttttgacata cttcgggtat acatatcagt atatattctt ataccgcaaa aatcagcgcg   1140
caaatacgca tactgttatc tggcttttag taagccggat ccacgcggcg tttacgcccc   1200
ccctgccact catcgcagta ctgttgtaat tcattaagca ttctgccgac atggaagcca   1260
tcacaaacgg catgatgaac ctgaatcgcc agcggcatca gcaccttgtc gccttgcgta   1320
taatatttgc ccatggtgaa aacgggggcg aagaagttgt ccatattggc cacgtttaaa   1380
aaggccgtaa tatccagctg aacggtctgg ttataggtac attgagcaac tgactgaaat   1440
gcctcaaaat gttctttacg atgccattgg gatatatcaa cggtggtata tccagtgatt   1500
tttttctcca ttttagcttc cttagctcct gaaaatctcg ataactcaaa aaatacgccc   1560
ggtagtgatc ttatttcatt atggtgaaag ttggaacctc ttacgtgccg atcaacgtct   1620
cattttcgcc aaaagttggc ccagggcttc ccggtatcaa cagggacacc aggatttatt   1680
tattctgcga agtgatcttc cgtcacaggt atttattcgg cgcaaagtgc gtcgggtgat   1740
gctgccaact tagtcgacta caggtcacta ataccatcta agtagttgat tcatagtgac   1800
tggatatgtt gtgttttaca gtattatgta gtctgttttt tatgcaaaat ctaatttaat   1860
atattgatat ttatatcatt ttacgtttct cgttcagctt tcttgtacaa agtggtttta   1920
atggaccgcc cgcaaggggg ggggggcatt tcagtgtcgg gtgacgagcg cgatccggcc   1980
gggatcctag gaccccaaaa gtttgtctgc gtattccagg gcggggctca gttgaatctc   2040
ccgcagcacc tctaccagca ggtccgcggt gggctggaga aactcggccg tcccggggca   2100
ggcggttgtc gggggtggag gcgcggcgcc caccccgtgt gccgcgcctg gcgtctcctc   2160
tgggggcgac ccgtaaatgg ttgcagtgat gtaaatggtg tccgcggtcc agaccacggt   2220
caaaatgccg gccgtggcgc tccgggcgct ttcgccgcgc gaggagctga cccaggagtc   2280
gaacggatac gcgtacatat gggcgtccca cccgcgttcg agcttctggt tgctgtcccg   2340
gcctataaag cggtaggcac aaaattcggc gcgacagtcg ataatcacca acagcccaat   2400
gggggtgtgc tggataacaa cgcctccgcg cggcaggcgg tcctggcgct cccggccccg   2460
taccatgatc gcgcgggtgc cgtactcaaa aacatgcacc acctgcgcgg cgtcgggcag   2520
tgcgctggtc agcgaggccc tggcgtggca taggctatac gcgatggtcg tctgtggatt   2580
ggacatctcg cggtgggtag tgagtccccc gggccgggtt cggtggaact gtaaggggac   2640
ggcgggttaa tagacaatga ccacgttcgg atcgcgcaga gccgatagta tgtgctcact   2700
aatgacgtca tcgcgctcgt ggcgctcccg gagcggattt aagttcatgc gaaggaattc   2760
```

```
ggaggaggtg gtgcgggaca tggccacgta cgcgctgttg aggcgcaggt tgccgggcgt   2820
aaagcagatg gcgaccttgt ccaggctaag gccctgggag cgcgtgatgg tcatggcaag   2880
cttggagctg atgccgtagt cggcgtttat ggccatggcc agctccgtag agtcaatgga   2940
ctcgacaaac tcgctgatgt tggtgttgac gacggacatg aagccgtgtt ggtcccgcaa   3000
gaccacgtaa ggcagggggg cctcttccag taactcggcc acgttggccg tcgcgtgccg   3060
cctccgcagc tcgtccgcaa aggcaaacac ccgtgcgtac gtgtatccca tgagcgtata   3120
attgtccgtc tgcagggcga cggacatcag ccccccgcgc ggcgagccgg tcagcatctc   3180
gcagccccgg aagataacgt tgtccacgta cgtgctaaag gggcgactt caaatgcctc    3240
cccgaagagc tcttggagga ttcggaatct cccgaggaag gcccgcttca gcagcgcaaa   3300
ctgggtgtga acggcggcgg tggtctccgg ttccccgggg gtgtagtggc agtaaaacac   3360
gtcgagctgt tgttcgtcca gccccgcgaa aataacgtcg aggtcgtcgt cgggaaaatc   3420
gtccgggccc ccgtcccgcg gccccagttg cttaaaatca aacgcacgct cgccgggggc   3480
gcctgcgtcg gccattaccg acgcctgcgt cggcaccccc gaagatttgg ggcgcagaga   3540
cagaatctcc gccgttagtt ctcccatgcg ggcgtaggcg agggtcctct gggtcgcatc   3600
caggcccggg cgctgcagaa agttgtaaaa ggagataagc ccgctaaata tgagccgcga   3660
caggaacctg taggcaaact ccaccgaagt ctccccctga gtctttacaa agctgtcgtc   3720
acgcaacact gcctcgaagg cccggaacgt cccactaaac ccaaaaacca gttttcgcag   3780
gcgcgcggtc accgcgatct ggctgttgag gacgtaagtg acgtcgttgc gggccacgac   3840
cagctgctgt ttgctgtgca cctcgcagcg catgtgcccc gcgtcctggt cctggctctg   3900
cgagtagttg gtgatgcggc tggcgttggc cgtgagccac ttttcaatcg tcaggccggg   3960
ctggtgtgtc agccgtcggt attcgtcaaa ctccttgacc gacacgaacg taagcacggg   4020
gagggtgaac acgacgaact ccccctcacg ggtcaccttc aggtaggcgt ggagcttggc   4080
catgtacgcg ctcacctctt tgtgggagga gaacagccgc gtccagccgg ggaggttggc   4140
ggggttggtg atgtagtttt ccgggacgac gaagcgatcc acgaactgca tgtgctcctc   4200
ggtgatgggc aggccgtact ccagcacctt catgaggtta ccgaactcgt gctcgacgca   4260
ccgtttgttg ttaataaaaa tggcccagct atacgagagg cgggcgtact cgcgcagcgt   4320
gcggttgcag atgaggtacg tgagcacgtt ctcgctctgg cggacggaac accgcagttt   4380
ctggtgctcg aaggtcgact ccagggacgc cgtctgcgtc ggcgagccca cacacaccaa   4440
cacgggccgc aggcgggccg cgtactgggg ggtgtggtac agggcgttaa tcatccacca   4500
gcaatacacc acggccgtga ggaggtgacg cccaaggagc ccggcctcgt cgatgacgat   4560
cacgttgctg cgggtaaagg ccggcagcgc cccgtgggtg gccggggcca accgcgtcag   4620
ggcgccctcg gccaacccca gggtccgttc cagggcggcc agggcgcgaa actcgttccg   4680
caactcctcg cccccggagg cggccagggc gcgcttcgtg aggtccaaaa tcacctccca   4740
gtagtacgtc agatctcgtc gctgcaggtc ctccagcgag gcggggttgc tggtcagggt   4800
gtacgggtac tgtcccagtt gggcctggac gtgattcccg cgaaacccaa attcatgaaa   4860
gatggtgttg atgggtcggc tgagaaaggc gcccgagagt ttggcgtaca tgttttgggc   4920
cgcaatgcgc gtggcgcccg tcaccacaca gtccaagacc tcgttgattg tctgcacgca   4980
cgtgctcttt ccggagccag cgttgccggt gataagatac accgcgaacg gaaactccct   5040
gaggggcagg cctgcggggg actctaaggc cgccacgtcc cggaaccact gcagatgggg   5100
```

-continued

```
cacttgcgct ccgtcgagct gttgttgcga gagctctcgg atgcgcttaa ggattggctg   5160
caccccgtgc atagacgtaa aatttaaaaa ggcctcggcc ctccctggaa cggctggtcg   5220
gtccccgggt tgctgaaggt gcggcgggcc gggtttctgt ccgtctagct ggcgctcccc   5280
gccggccgcc gccatgaccg caccacgctc gcgggccccc actacgcgtg cgcgggggga   5340
cacggaagcg ctgtgctccc ccgaggacgg ctgggtaaag gttcacccca gccccggtac   5400
gatgctgttc cgcgagattc tccacgggca gctggggtat accgagggcc agggggtgta   5460
caacgtcgtc cggtccagcg aggcgaccac ccggcagctg caggcggcga tctttcacgc   5520
gctcctcaac gccaccactt accgggacct cgaggcggac tggctcggcc acgtggcggc   5580
ccgcggtctg cagccccaac ggctggttcg ccggtacagg aacgcccggg aggcggatat   5640
cgccggggtg gccgagcggg tgttcgacac gtggcggaac acgcttagga cgacgctgct   5700
ggactttgcc cacgggttgg tcgcctgctt tgcgccgggc ggcccgagcg gcccgtcaag   5760
cttccccaaa tatatcgact ggctgacgtg cctggggctg gtccccatat tacgcaagcg   5820
acaagaaggg ggtgtgacgc agggtctgag ggcgtttctc aagcagcacc cgctgacccg   5880
ccagctggcc acggtcgcgg aggccgcgga gcgcgccggc cccgggtttt ttgagctggc   5940
gctggccttc gactccacgc gcgtggcgga ctacgaccgc gtgtatatct actacaacca   6000
ccgccggggc gactggctcg tgcgagaccc catcagcggg cagcgcggag aatgtctggt   6060
gctgtggccc cccttgtgga ccggggaccg tctggtcttc gattcgcccg tccagcggct   6120
gtttcccgag atcgtcgcgt gtcactccct ccgggaacac gcgcacgtct gccggctgcg   6180
caataccgcg tccgtcaagg tgctgctggg gcgcaagagc gacagcgagc gcggggtggc   6240
cggtgccgcg cgggtcgtta acaaggtgtt gggggaggac gacgagacca aggccgggtc   6300
ggccgcctcg cgcctcgtgc ggcttatcat caacatgaag ggcatgcgcc acgtaggcga   6360
cattaacgac accgtgcgtt cctacctcga cgaggccggg gggcacctga tagacgcccc   6420
ggccgtcgac ggtaccctcc ctggattcgg caagggcgga aacagccgcg ggtctgcggg   6480
ccaggaccag ggggggcggg cgccgcagct tcgccaggcc ttccgcacgg ccgtggttaa   6540
caacatcaac ggcgtgttgg agggctatat aaataacctg tttggaacca tcgagcgcct   6600
gcgcgagacc aacgcgggcc tggcgaccca attgcaggag cgcgaccgcg agctccggcg   6660
cgcaacagcg ggggccctgg agcgccagca gcgcgcggcc gacctggcgg ccgagtccgt   6720
gaccggtgga tgcggcagcc gccctgcggg ggcggacctg ctccgggccg actatgacat   6780
tatcgacgtc agcaagtcca tggacgacga cacgtacgtc gccaacagct ttcagcaccc   6840
gtacatccct tcgtacgccc aggacctgga gcgcctgtcg cgcctctggg agcacgagct   6900
ggtgcgctgt tttaaaattc tgtgtcaccg caacaaccag ggccaagaga cgtcgatctc   6960
gtactccagc ggggcgatcg ccgcattcgt cgccccctac tttgagtcag tgcttcgggc   7020
cccccgggta ggcgcgccca tcacgggctc cgatgtcatc ctgggggagg aggagttatg   7080
ggatgcggtg tttaagaaaa cccgcctgca aacgtacctg acagacatcg cggccctgtt   7140
cgtcgcggac gtccagcacg cagcgctgcc cccgcccccc tccccggtcg gcgccgattt   7200
ccggcccggc gcgtccccgc ggggccggtc cagatcgcgg tcgcccggaa gaactgcgcg   7260
aggcgcgccg gaccagggcg ggggcatcgg gcaccgggat ggccgccgcg acggccgacg   7320
atgaggggtc ggccgccacc atcctcaagc aggccatcgc cggggaccgc agcctggtcg   7380
aggcggccga ggcgattagc cagcagacgc tgctccgcct ggcctgcgag gtgcgccagg   7440
tcggcgaccg ccagccgcgg tttaccgcca ccagcatcgc gcgcgtcgac gtcgcgcctg   7500
```

-continued

```
ggtgccggtt gcggttcgtt ctggacggga gtcccgagga cgcctatgtg acgtcggagg   7560
attactttaa gcgctgctgc ggccagtcca gttatcgcgg cttcgcggtg gcggtcctga   7620
cggccaacga ggaccacgtg cacagcctgg ccgtgccccc cctcgttctg ctgcaccggt   7680
tctccctgtt caaccccagg gacctcctgg actttgagct tgcctgtctg ctgatgtacc   7740
tggagaactg cccccgaagc cacgccaccc cgtcgacctt tgccaaggtt ctggcgtggc   7800
tcggggtcgc gggtcgccgc acgtccccat tcgaacgcgt tcgctgcctt ttcctccgca   7860
gttgccactg ggtcctaaac acactcatgt tcatggtgta cgtaaaaccg ttcgacgacg   7920
agttcgtcct gccccactgg tacatggccc ggtacctgct ggccaacaac ccgccccccg   7980
ttctctcggc cctgttctgt gccaccccga cgagctcctc attccggctg ccggggccgc   8040
ccccccgctc cgactgcgtg gcctataacc ccgccgggat catggggagc tgctgggcgt   8100
cggaggaggt gcgcgcgcct ctggtctatt ggtggctttc ggagacccca aaacgacaga   8160
cgtcgtcgct gttttatcag ttttgttgaa ttttaggaaa taaacccggt tttgtttctg   8220
tggcctcccg acggatgcgc gtgtccttac tccgtcttgg tgggtgggtg gctgtgtatg   8280
gcgtcccatc tgtgcgggga gggggcaag tcggcacgta ttcggacaga ctcaagcaca   8340
taagacgaac aaaaggtttg taacttcgta ccgtgagtaa taatgtggac tttattgctt   8400
aagaatacgc gtagagaaat aagacgaaca aaaggtttgt gattttattg cttaagaata   8460
cgcgtagatg gtcgtaccgt gagtaataat gtggttcata agacgaacaa aaggtttgtg   8520
acattattgc ttaagaatac gcgtaggtgg tcgtaccgtg agtaataatg tgtactttat   8580
tgcttaagaa tacgcgtagg ctatcgtacc gtgagtaata atgtgcctta taagacgaac   8640
aaaaggtttg tacacggggg agcgctcttg tctcagggca atgtttttat tggtcaaact   8700
caggcaaaca gaaacgacat cttgtcgtca aagggataca caaacttccc cccctcgccc   8760
catactcccg ccagcacccc ggtaaacacc aactcaatct cgcgcaggat ttcgcgcagg   8820
tgatgagcgc agtccacggg ggggagcaca aggggccgcg ggtatagatc gacggggacg   8880
ccgaccgact ccccgcctcc gggacagaca cgcacgacgc gccgccagta gtgctctgcg   8940
tccagcaagg cgccgccgcg gaaggcagtg gggggcaagg ggtcgctggc ctcaaagggg   9000
gacacccgaa cgctccagta ctccgcgtcc aaccgtttat taaacgcgtc caagataagg   9060
cggtcgcagg cgtcctccat aaggccccgg gccgtgagtg cgtcctcctc cggcacgcat   9120
gccgttgtca ggcccaggac ccgtcgcagc gtgtcgcgta cgacccctgc cgccgtggtg   9180
tacgcgggcc cgcggagagg aaatccccca agatggtcag tgttgtcgcg ggagttccag   9240
aaccacactc ccgcctggct ccaggcgact gcgtgggtgt agacgccctc gagggccagg   9300
cacagtgggt gccgcagccg gacggcgttg gccctaagca cggctcccac ggccgtctcg   9360
atggcccgcc gggcgtcctc gatcaccccg gaagccgcat ccgcgtcttg ggggtccacg   9420
ttaaagacac cccagaacgc acccccatcg cccccgcaga ccgcgaactt caccgagctg   9480
gccgtctcct cgatctgcag gcagacggcg gccattaccc cacccaggag ctgccgcagc   9540
gcagggcagg cgttgcacgt gtccgggacc aggcgctcca agacggcccc ggcccagggc   9600
tctgagggag cggccaccac cagcgcgtcc agtcttgcta ggcccgtccg gccgtggggg   9660
tccgccagcc cgctcccccc gaggtcggcc agggccgcca ggagctgggc gcgaagtccg   9720
gggaagcaaa accgcgccgt ccagacgggc ccgacggccg cgggcgggtc taacagttgg   9780
atgattttag tggcgggatg ccaccgcgcc accgcctccc gcaccgcggg caggaggcat   9840
```

-continued

```
ccggctgccg ccgaggccac gccgggccag gctcgcgggg ggaggacgac cctggccccc   9900
accgcgggcc aggcccccag gagcgcggcg taagcggccg cggccccgcg caccaggtcc   9960
cgtgccgact cggccgtggc cggcacggtg aacgtgggcc aacccggaaa ccccaggacg  10020
gcaaagtacg ggacgggtcc cccccggacc tcaaactcgg gccccagaaa ggcaaagacg  10080
ggggccaggg ccccgggggc ggcgtggacc gtggtatgcc actgccggaa aagggcgacg  10140
agcgccggcg cggagaactt ctcgccggcg cttacaaagt agtcgtaatc gcggggcagc  10200
agcacccgtg ccgtgactcg ttgcgggtgc ccgcgtggcc gcaggcccac ctcgcacacc  10260
tcgaccaggt ccccgaacgc gccctccttc ttgatcggcg gaaacgcaag agtctggtat  10320
tcgcgcgcaa atagcgcggt tccggtggtg atgttaacgg tcagcgaagc ggcggacgcg  10380
cactgggggg tgtcgcgaat ggccgccagg cgcgcccacg ccagccgcgc gtcgggatgc  10440
tcggcaacgc gcgccgccag ggccataggg tcgatgtcaa tgttggcctc cgcgaccagg  10500
agagcggcgc gaggggcggc gggcgggccc cacgacgctc tctcaacttt caccaccagt  10560
cccgtgcgtg ggtccgagcc gatacgcagc ggggcgaaca gggccaccgg cccggtctgg  10620
cgctccaggg ccgccaggac gcacgcgtac agcgcccgcc acagagtcgg gttctccagg  10680
ggctccagcg gggaggcggc cggcgtcgtc gcggcgcggg cggccgccac gacggcctgg  10740
acggagacgt ccgcggagcc gtagaaatcc cgcagctccg tcgcggtgac ggagacctcc  10800
gcaaagcgcg cgcgaccctc ccctgcggcg ttgcgacata caaaatacac cagggcgtgg  10860
aagtactcgc gagcgcgggg gggcagccat accgcgtaaa gggtaatggc gctgacgctc  10920
tcctccaccc acacgatatc tgcggtgtcc atcgcacggc ccctaaggat cacgggcggt  10980
ctgtgggtcc catgctgccg tgcctggccg ggcccggtgg gtcgcggaaa ccggtgacgg  11040
ggggggggcg gtttttgggg ttggggtggg ggtgggaaac ggcccgggtc cgggggccaa  11100
cttggcccct cggtgcgttc cggcaacagc gccgccggtc cgcggacgac cacgtaccga  11160
acgagtgcgg tcccgagact tatagggtgc taaagttcac cgccccctgc atcatgggcc  11220
aggcctcggt ggggagctcc gacagcgccg cctccaggat gatgtcagcg ttggggttgg  11280
cgctggatga gtgcgtgcgc aaacagcgcc cccacgcggg cacgcgtagc ttgaagcgcg  11340
cgcccgcaaa ctcccgcttg tgggccataa gcagggcgta cagctgcctg tgggtccggc  11400
aggcgctgtg gtcgatgtgg tgggcgtcca acaaccccac gattgtctgt ttggtgaggt  11460
ttttaacgcg ccccgccccg ggaaacgtct gcgtgctttt ggccatctgc acgccaaaca  11520
gttcgcccca gattatcttg aacagcgcca ccgcgtggtc cgtctcgcta acggacccgc  11580
gcgggggaca gccgcttagg gcgtcggcga cgcgcttgac ggcttcctcc gagagcagaa  11640
gtccgtcggt tacgttacag tggcccagtt cgaacaccag ctgcatgtag cggtcgtagt  11700
ggggggtcag taggtccagc acgtcatcgg ggccgaaggt cctcccagat cccccggccg  11760
ccgagtccca atgcaggcgc gcggccatgg tgctgcacag gcacaacagc tcccagacgg  11820
gggttacgtt cagggtgggg ggcagggcca cgagctccag ctctccggtg acgttgatcg  11880
tggggatgac gcccgtggcg tagtggtcat agatccgccg aaatatggcg ctgctgcggg  11940
tggccatggg aacgcggaga caggcctcca gcaacgccag gtaaataaac cgcgtgcgtc  12000
ccatcaggct gttgaggttg cgcatgagcg cgacaatttc cgccggcgcg acatcggacc  12060
ggaggtattt ttcgacgaaa agacccacct cctccgtctc ggcggcctgg gccggcagcg  12120
acgcctcggg atcccggcac cgcagctccc gtagatcgcg ctgggccctg agggcgtcga  12180
aatgtacgcc ccgcaaaaac agacagaagt cctttggggt cagggtatcg tcgtgtcccc  12240
```

agaagcgcac gcgtatgcag tttagggtca gcagcatgtg aaggatgtta aggctgtccg 12300
agagacacgc cagcgtgcat ctctcaaagt agtgtttgta acggaatttg ttgtagatgc 12360
gcgacccccg ccccagcgac gtgtcgcatg ccgacgcgtc acagcgcccc ttgaaccggc 12420
gacacagcag gtttgtgacc tgggagaact gcgcgggcca ctggccgcag gaactgacca 12480
cgtgattaag gagcatgggc gtaaagacgg gctccgagcg cgccccggag ccgtccatgt 12540
aaatcagtag ctcccccttg cggagggtgc gcacccgtcc cagggactgg tacacggaca 12600
ccatgtccgg tccgtagttc atgggtttca cgtaggcgaa catgccatca aagtgcaggg 12660
gatcgaagct gaggcccacg gttacgaccg tcgtgtatat aaccacgcgg tattggcccc 12720
acgtggtcac gtccccgagg ggggtgagcg agtgaagcaa cagcacgcgg tccgtaaact 12780
gacggcagaa ccgggccacg atctccgcga aggagaccgt cgacgaaaaa atgcagatgt 12840
tatcgccccc gccaaggcgc gcttccagct ccccaaagaa cgtggccccc cgggcctccg 12900
gagaggcgtc cggagacggg ccgctcggcg gcccgggcgg gcgcagggca gcctgcagga 12960
gctcggtccc cagacgcggg agaaacaggc accggcgcgc cgaaaacccg ggcatggcgt 13020
actcgccgac caccacatgc acgttttttt cgccccggag accgcacagg aagtccacca 13080
actgcgcgtt ggcggttgcg tccatggcga tgatccgagg acagatgcgc agcaggcgta 13140
gcattaacgc atccacgcgg cccagttgct gcatcgttgg cgaatagagc tggcccagcg 13200
tcgacataac ctcgtccaga acgaggacgt cgtagttgtt cagaaggttg gggcccacgc 13260
gatgaaggct ttccacctgg acgataagtc ggtggaaggg gcggtcgttc ataatgtaat 13320
tggtggatga gaagtaggtg acaaagtcga ccaggcctga ctcagcgaac cgcgtcgcta 13380
gggtctgggt aaaactccga cgacaggaga cgacgagcac actcgtgtcc ggagagtgga 13440
tcgcttcccg cagccagcgg atcagcgcgg tagtttttcc cgaccccatt ggcgcgcgga 13500
ccacagtcac gcacctggcc gtcggggcgc tcgcgttggg gaaggtgacg ggtccgtgct 13560
gctgccgctc gatcgttgtt ttcgggtgaa cccggggcac ccattcggcc aaatcccccc 13620
cgtacaacat ccgcgctagc gatacgctcg acgtgtactg ttcgcactcg tcgtccccaa 13680
tgggacgccc ggcccccaga ggatctcccg actccgcgcc ccccacgaaa ggcatgaccg 13740
gggcgcggac ggcgtggtgg gtctggtgtg tgcaggtggc gacgtttgtg gtctctgcgg 13800
tctgcgtcac ggggctcctc gtcctggcct ctgtgttccg ggcacggttt ccctgctttt 13860
acgccacggc gagctcttat gccggggtga actccacggc cgaggtgcgc gggggtgtag 13920
ccgtgcccct caggttggac acgcagagcc ttgtgggcac ttatgtaatc acggccgtgt 13980
tgttgttggc cgtggccgtg tatgccgtgg tcggcgccgt gacctcccgc tacgaccgcg 14040
ccctggacgc gggccgccgt ctggctgcgg cccgcatggc catgccgcac gccacgctga 14100
tcgccggaaa cgtctgctct tggttgctgc agatcaccgt cctgttgctg gcccatcgca 14160
tcagccagct ggcccacctg gtttacgtcc tgcactttgc gtgtctggtg tattttgcgg 14220
cccatttttg caccaggggg gtcctgagcg ggacgtatct gcgtcaggtg cacggcctga 14280
tggagctggc cccgacccat catcgcgtcg tcggcccggc tcgcgccgtg ctgacaaacg 14340
ccttgctgtt gggcgtcttc ctgtgcacgg ccgacgccgc ggtatccctg aataccatcg 14400
ccgcgttcaa ctttaatttt tcggccccgg gcatgctcat ctgcctgacc gtgctgttcg 14460
ccattctcgt cgtatcgctg ttgttggtgg tcgagggggt gttgtgtcac tacgtgcgcg 14520
tgttggtggg cccccacctg gggggccgtgg ccgccacggg catcgtcggc ctggcctgcg 14580

```
agcactatta caccaacggc tactacgttg tggagacgca gtggccgggg gctcagacgg  14640
gagtccgcgt cgccctcgcc ctggtcgccg cctttgccct cggcatggcc gtgctccgct  14700
gcacccgcgc ctatctgtat cacaggcggc accacaccaa attttttatg cgcatgcgcg  14760
acacgcgaca ccgcgcacat tccgccctca agcgcgtacg cagttccatg cgcggatcgc  14820
gagacggccg ccacaggccc gcacccggca gcccgcccgg gattcccgaa tatgcggaag  14880
acccctacgc gatctcatac ggcggccagc tcgaccggta cggagattcc gacggggagc  14940
cgatttacga cgaggtggcg gacgaccaaa ccgacgtatt gtacgccaag atacaacacc  15000
cgcggcacct gcccgacgac gatcccatct atgacaccgt tggggggtac gaccccgagc  15060
ccgccgagga ccccgtgtac agcaccgtcc gccgttggta gctgtttggt tccgttttaa  15120
taaaccgttt gtgtttaacc cgaccgtggt gtatgtctgg tgtgtggcgt ccgatcccgt  15180
tactatcacc gtcccccccc cccccctcaac cccggcgatt gtgggttttt taaaaacgac  15240
acgcgtgcga ccgtatacag aacattgttt tggtttttat tcgctatcgg acatgggggg  15300
tggaaactgg gtggcggggc aggcgcctcc gggggtccgc cggtgagtgt ggcgcgaggg  15360
ggggtccgat gaacgcaggc gctgtctccc cggggcccgc gtaaccccgc gcatatccgg  15420
gggcacgtag aaattacctt cctcttcgga ctcgatatcc acgacgtcaa agtcgtgggc  15480
ggtcagcgag acgacctccc cgtcgtcggt gatgaggacg ttgtttcggc agcagcaggg  15540
ccgggccccg gagaacgaga ggcccatagc tcggcgagcg tgtcgtcgaa tgccaggcgg  15600
ctgcttcgct ggatggcctt atagatctcc ggatcgatgc ggacgggggt aatgatcagg  15660
gcgatcggaa cggcctggtt cgggagaatg gacgccttgc tgggtcctgc ggccccgaga  15720
gccccggcgc cgtcctccag gcggaacgtt acgccctcct ccgcgctggt gcggtgcctg  15780
ccgataaacg tcaccagatg cgggtggggg gggcagtcgg ggaagtggct gtcgagcacg  15840
tagccctgca ccaagatctg cttaaagttc gggtgacggg ggttcgcgaa gacgggctcg  15900
cggcggacca gatccccgga gctccaggac acgggggaga tggtgtggcg tccgaggtcg  15960
ggggcgccaa acagaagcac ctccgagaca acgccgctat ttaactccac caaggcccga  16020
tccgcggcgg agcaccgcct tttttcgccc gaggcgtggg cctctgacca ggcctggtct  16080
tgcgtgacga gagcctcctc cgggccgggg acgcgcccgg gcgcgaagta tcgcacgctg  16140
ggcttcggga tcgaccggat aaatgcccgg aacgcctccg gggaccggtg tgccatcaag  16200
tcctcgtacg cggaggccgt ggggtcgctg gggtccatgg ggtcgaaagc gtacttggcc  16260
cggcatttga cctcgtaaaa ggccaggggg gtcttgggga ctggggccag gtagccgtga  16320
atgtcccgag gacagacgag aatatccagg gacgccccga ccatccccgt gtgaccgtcc  16380
atgaggaccc cacacgtatg cacgttctct tcggcgaggt cgctgggttc gtggaagata  16440
aagcgccgcg tgtcggcgcc ggcctcgccg ccgtcgtccg cgcggcccac gcagtagcga  16500
aacagcaggc ttcgggccgt cggctcgttc acccgcccga acatcaccgc cgaagactgt  16560
acatccggcc gcaggctggc gttgtgcttc agccactggg gcgagaaaca cggaccctgg  16620
gggccccagc ggagggtgga tgcggtcgtg aggccccgcc ggagcagggc ccatagctgg  16680
cagtcggcct ggttttgcgt ggccgcctcg taaaacccca tgaggggccg gggcgccacg  16740
gcgtccgcgg cggccggggg cccgcggcgc gtcaggcgcc ataggtgccg accgagtccg  16800
cggtccacca tacccgcctc ctcgaggacc acggccaggg aacacagata atccaggcgg  16860
gcccagaggg gaccgatggc cagaggggcg cggacgccgc gcagcaaccc gcgcaggtgg  16920
cgctcgaacg tctcggctag tatatgggag ggcagcgcgt tggggatcac cgacgccgac  16980
```

-continued

```
cacatagagt caaggtccgg ggagtcggga tcggcgtccg ggtcgcgggc gtgggtgccc  17040
ccaggagata gcggaatgtc tggggtcgga ggccctgagg cgtcagaaag tgccggcgac  17100
gcggcccggg gcttttcgtc tgcggtgtcg gtggcgtgct gatcacgtgg ggggttaacg  17160
ggcgaatggg agctcgggtc cacagctgat gtcgtctggg gtgggggggg caggggacgg  17220
aaggtggttg tcagcggaag actgttaggg cgggggcgct tggggggget gtcggggcca  17280
cgaggggtgt cctcggccag ggcccaggga cgcttagtca cggtgcgtcc cggcggacat  17340
gctgggccta ccgtggactc catttccgag acgacgtggg gggagcggtg gttgagcgcg  17400
ccgccgggtg aacgctgatt ctcacgacag cgcgtgccgc gcgcacgggt tggtgtgaca  17460
caggcgggac accagcacca ggagaggctt aagctcggga ggcagcgcca ccgacgacag  17520
tatcgccttg tgtgtgtgct ggtaatttat acaccgatcc gtaaacgcgc gccgaatctt  17580
gggattgcgg aggtggcgcc ggatgccctc tgggacgtca tacgccaggc cgtgggtgtt  17640
ggtctcggcc gagttgacaa acagggctgg gtgcagcacg cagcgatagg cgagcagggc  17700
cagggcgaag tccggcgaca gctggttgtt aaaatactgg taaccgggaa accgggtcac  17760
gggtacgccc aggctcgggg cgacgtacac gctaaccacc aactccagca gcgtctggcc  17820
cagggcgtac aggtcaaccg ctaacccgac gtcgtgcttc aggcggtggt tggtaaattc  17880
ggcccgttcg ttgttaaggt atttcaccaa cagctccggg ggctggttat acccgtgacc  17940
caccagggtg tgaaagttgg ctgtggttag ggcggtgggc atgccaaaca tccgggggga  18000
cttgaggtcc ggctcctgga ggcaaaactg cccccgggcg atcgtggagt tggagttgag  18060
ggtgacgagg ctaaagtcgg cgaggacggc ccgccggagc gagacggcgt ccgaccgcag  18120
catgacgagg atgttggcgc acttgatatc caggtggctg atcccgcagg tggtgtttaa  18180
aaacacaacg gcgcgggcca gctccgtgaa gcactggtgg agggccgtcg agaccgaggg  18240
gtttgttgtg cgcagggacg ccagttggcc gatatactta ccgaggtcca tgtcgtacgc  18300
ggggaacact atctgtcgtt gttgcagcga gaacccgagg ggcgcgatga agccgcggat  18360
gttgtgggtg cggccggcgc gtagaacgca ctccccgacc aacagggtcg cgatgagctc  18420
aacggcaaac cactcctttt cctttatggt cttaacggca agcttatgtt cgcgaatcag  18480
ttggacgtca ccgtatcccc cagacccccc gaagcttcgg gccccgggga tctcgagggt  18540
cgtgtagtgt agggcggggt tgatggcgaa cacggggctg catagcttgc ggatgcgcgt  18600
gagggtgagg atgtgcgagg gggacgaggg gggtgcggtt aacgccgcct gggatctgcg  18660
caggggcggg cggttcagtt tggccgccgt accgggcgtc tcgggggacg cgcggcgatg  18720
agacgagcgg ctcattcgcc atcgggatag tcccgcgcga agccgctcgc ggaggccgga  18780
tcggtggcgg gacccgtggg aggagcggga gacggcggcg tcctggagag aggggccgct  18840
ggggcgcccg gaggccccgt gggggttgga gtgtacgtag gatgcgagcc aatccttgaa  18900
ggaccgttgg cgtgcacctt gggggctgag gttagctgcc acatgaccag caggtcgctg  18960
tctgcgggac tcatccatcc ttcggccagg tcgccgtctc cccacagaga agcgttggtc  19020
gctgcttcct cgagttgctc ctcctggtcc gcaagacgat cgtccacggc gtccaggcgc  19080
tcaccaagcg ccggatcgag gtaccgtcgg tgtgcggtta gaaagtcacg acgcgccgct  19140
tgctcctcca cgcgaatttt aacacaggtc gcgcgctgtc gcatcatctc taagcgcgcg  19200
cgggacttta gccgcgcctc caattccaag tgggccgcct ttgcagccat aaaggcgcca  19260
acaaaccgag gatcttgggt gctgacgccc tcccggtgca gctgcagggt ctggtccttg  19320
```

```
taaatctcgg ctcggaggtg cgtctcggcc aggcgtcggc gcagggccgc gtgggcggca  19380
tctcggtcca ttccgccacc ctgcgggcga cccggggggt gctctgatag tctcgcgtgc  19440
ccaaggcccg tgatcggggt acttcgccgc cgcgacccgc cacccggtgt gcgcgatgtt  19500
tggtcagcag ctggcgtccg acgtccagca gtacctggag cgcctcgaga aacagaggca  19560
acttaaggtg ggcgcggacg aggcgtcggc gggcctcacc atgggcggcg atgccctacg  19620
agtgcccttt ttagatttcg cgaccgcgac ccccaagcgc caccagaccg tggtccctgg  19680
cgtcgggacg ctccacgact gctgcgagca ctcgccgctc ttctcggccg tggcgcggcg  19740
gctgctgttt aatagcctgg tgccggcgca actaaagggg cgtgatttcg gggcgacca  19800
cacggccaag ctggaattcc tggcccccga gttggtacgg gcggtggcgc gactgcggtt  19860
taaggagtgc gcgccggcgg acgtggtgcc tcagcgtaac gcctactata gcgttctgaa  19920
tacgtttcag gccctccacc gctccgaagc ctttcgccag ctggtgcact ttgtgcggga  19980
ctttgcccag ctgctcaaaa cctccttccg ggcctccagc ctcacggaga ccacgggccc  20040
ccccaaaaaa cgggccaagg tggacgtggc cacccacggc cggacgtacg gcacgctgga  20100
gctgttccaa aaaatgatcc ttatgcacgc cacctacttt ctggccgccg tgctcctcgg  20160
ggaccacgcg gagcaggtca acacgttcct gcgtctcgtg tttgagatcc ccctgtttag  20220
cgacgcggcc gtgcgccact tccgccagcg cgccaccgtg tttctcgtcc cccggcgcca  20280
cggcaagacc tggtttctgg tgcccctcat cgcgctgtcg ctggcctcct ttcgggggat  20340
caagatcggc tacacggcgc acatccgcaa ggcgaccgag ccggtgtttg aggagatcga  20400
cgcctgcctg cggggctggt tcggttcggc ccgagtggac cacgttaaag gggaaaccat  20460
ctccttctcg tttccggacg ggtcgcgcag taccatcgtg tttgcctcca gccacaacac  20520
aaacgtaagt cctcttttct ttcgcatggc tctcccaagg ggccccgggt cgacccgacc  20580
cacacccacc cacccacata cacacacaac cagacgcggg aggaaagtct gccccgtggg  20640
cactgatttt tattcgggat cgcttgagga ggcccgggca acggcccggg caacggtggg  20700
gcaactcgta gcaaataggc gactgatgta cgaagagaag acacacaggc gccacccggc  20760
gctggtcggg gggatgttgt ccgcgccgca ccgtcccccg acgacctctt gcagacggtc  20820
cgtgatgcaa ggacggcggg gggcctgcag cagggtgacc gtatccacgg gatggccaaa  20880
gagaagcgga cacaggctag catccccctg gaccgccagg gtacactggg ccatcttggc  20940
ccacagacac ggggcgacgc agggacagga ctccgttacg acggaggaga gccacagtgc  21000
gttggcggaa tcgatgtggg gcggcggggc gcaggactcg cagcccccccg ggtggttggt  21060
gatcctggcc aggagccatc ccagatggcg ggccctgctt cccggtggac agagcgaccc  21120
caggtcgctg tccatggccc agcagtagat ctggccgctg gggaggtgcc accaggcccc  21180
cgggcccaag gcgcagcacg cgcccggctc cggggggggtc ttcgcgggga ccagatacgc  21240
gccatccagc tcgccgacca ctggctcctc cgcgagctgt tcggtggttg ggtcgggggt  21300
ttcctccggg ggggtggccg cccgtatgcg tgcgaacgtg agggtgcaca ggagcggggt  21360
caggggggtgc gtcacgctcc ggaggtggac gatcgcgcag tagcggcgct cgcggttaaa  21420
gaaaaagagg gcaaagaagg tgttcggggg caaccgcagc gccttggggc gcgtcagata  21480
cagaaaaatc tcgcagaaga gggcgcgccc ggggtctggg ttaggaaggg ccacctgaca  21540
cagaggctcg gtgaggaccg ttagacaccg aaagatcttg agccgctcgt ccgcccgaac  21600
gacgcgccac acaaagacgg agttgacaat gcgcgcgata gagtcgacgt ccgtccccag  21660
gtcgtcgact ctatcgcgcg tgccgcgagc tccggcccgg gaatccggcc ggggcaaggt  21720
```

-continued

```
cccccgggga ccaggcggcg ccaggggccg ccggggtccc agctgcgcca tgccgggggc  21780
gggggaggg caaaccccag aggcgggggc caacggcgcg gggaggagtg ggtgggcgag  21840
gtggccgggg gaaggcgccc gctagcgaga ccggccgttc ccggacgaca ccttgcgaca  21900
aaacctaagg acagcggccc gcgcgacggg gtccgagagg ctaaggtagg ccgcgatgtt  21960
aatggtgaac gcaaagccgc cgggaaagac aactatgcca cagaggcggc gattaaaccc  22020
caggcagagg taggcgtagc tttccccggg caggtattgc tcgcagaccc tgcgtggggc  22080
tgtggagggg acggcctcca tgaagcgaca tttactctgc tcgcgtttac tgacgtcacc  22140
atccatcgcc acggcgattg gacgattgtt aagccgcagc gtgtctccgc ttgtgctgta  22200
gtagtcaaaa acgtaatggc cgtcggagtc ggcaaagcgg gccgggaggt cgtcgccgag  22260
cgggacgacc cgccgccccc gaccgccccg tccccccagg tgtgccagga cggccagggc  22320
atacgcggtg tgaaaaaagg cgtcgggggc ggtcccctcg acggcgcgca tcaggttctc  22380
gaggagaatg gggaagcgcc tggtcacctc ccccaaccac gcgcgttggt cggggccaaa  22440
gtcatagcgc aggcgctgtg agattcgcgg gccgccctga agcgcggccc ggatggcctg  22500
gcccagggcc cggaggcacg ccagatgtat gcgcgcggta aaggcgacct cggcggcgat  22560
gtcaaagggc ggcaggacgg ggcgcgggtg gcgcaggggc acctcgagcg cgggaaagcg  22620
tagcagcagc tccgcctgcc cagcgggaga cagctggtgg gggcgcacga cgcgttctgc  22680
ggcgcaggcc tcggtcaggg ccgtggccag cgccgaggac agcagcggag ggcgggcgcg  22740
tcgcccgccc cacgccacgg agttctcgta ggagacgacg acgaagcgct gcttggttcc  22800
gtagtggtgg cgcaggacca cggagataga acgacggctc cacagccagt ccggccggtc  22860
gccgccggcc agggcttccc atccgcgatc caaccactcg accagcgacc gcggctttgc  22920
ggtaccaggg gtaagggtta gaacgtcgtt caggatgtcc tcgcccccgg gcccgtgggg  22980
cgctggggcc acaaagcggc ccccgccggg gggctccaga cccgccagca ccgcatctgc  23040
gtcagccgcc cccatggcgc ccccgctgac ggcctggtga accagggcgc cctggcgtag  23100
ccccgatgca acgccacagg ccgcacgccc ggtccgcgct cggaccgggt ggcggcgggt  23160
gacgtcctgc actgcccgct gaaccaacgc gaggatctcc tcgttctcct gtgcgatgga  23220
cacgtcctgg gccgcggtcg tgtcgccgcc gggggccgtc agctgctcct ccggggagat  23280
gggggggtcg gacgccccga cgatgggcgg gtctgcgggc gcccccgcgt ggggccgggc  23340
caagggctgc ggacgcgggg acgcgctttc ccccagaccc atggacaggt gggccgcagc  23400
ctccttcgcg gccggcgggg cggcggcgcc aagcagagcg acgtagcggc acaaatgccg  23460
acagacgcgc atgatgcgcg tgctgtcggc cgcgtagcgc gtgttggggg ggacgagctc  23520
gtcgtaacta aacagaatca cgcgggcaca gctcgccccc gagccccacg caaggcgcag  23580
cgccgccacg gcgtacgggt catagacgcc ctgcgcgtca cacaccacgg gcagggagac  23640
gaacaacccc ccggcgctgg acgcacgcgg aaggaggcca gggtgtgccg gcacgacggg  23700
ggccagaagc tcccccaccg catccgcggg cacgtaggcg gcaaacgccg tgcaccacgg  23760
ggtacagtcg ccggtggcat gagcccgagt ctggatttcg acctggaagt ttgcggccgt  23820
cccgagtccg gggcggccgc gcatcagggc ggccagaggg attcccgcgg ccgccaggca  23880
ctcgctggat atgatgacgt gaaccaaaga ccgagggccg acccgggccg tggccgagat  23940
cgtctggacc tcgttggcca agtgcgcgtt catggttcgg gggtgggtgt gggtgtgtag  24000
gcgatgcggg tcccccgagt ccgcgggaag ggcgtgggtt tggcgcgcgt atgcgtattc  24060
```

gccaacggag gcgtgcgtgc ttatgcgcgg cgcgtttctt ctgtctctag ggaatccgag 24120
gccaggactt taacctgctc tttgtcgacg aggccaactt tattcgcccg gatgcggtcc 24180
agacgattat gggctttctc aaccaggcca actgcaagat tatcttcgtg tcgtccacca 24240
acaccgggaa ggccagtacg agctttttgt acaacctccg cggggccgca gacgagcttc 24300
tcaacgtggt gacctatata tgcgatgatc acatgccgag ggtggtgacg cacacaaacg 24360
ccacggcctg ttcttgttat atcctcaaca agcccgtttt catcacgatg gacggggcgg 24420
ttcgccggac cgccgatttg tttctggccg attccttcat gcaggagatc atcgggggcc 24480
aggccaggga gaccggcgac gaccggcccg ttctgaccaa gtctgcgggg gagcggtttc 24540
tgttgtaccg cccctcgacc accaccaaca gcggcctcat ggcccccgat ttgtacgtgt 24600
acgtggatcc cgcgttcacg gccaacaccc gagcctccgg gaccggcgtc gctgtcgtcg 24660
ggcggtaccg cgacgattat atcatcttcg ccctggagca ctttttctc cgcgcgctca 24720
cgggctcggc cccgccgac atcgcccgct gcgtcgtcca cagtctgacg caggtcctgg 24780
ccctgcatcc cggggcgttt cgcggcgtcc gggtggcggt cgagggaaat agcagccagg 24840
actcggccgt cgccatcgcc acgcacgtgc acacagagat gcaccgccta ctggcctcgg 24900
agggggccga cgcgggctcg ggccccgagc ttctcttcta ccactgcgag cctcccggga 24960
gcgcggtgct gtaccccttt ttcctgctca acaaacagaa gacgcccgcc tttgaacact 25020
ttattaaaaa gtttaactcc gggggcgtca tggcctccca ggagatcgtt tccgcgacgg 25080
tgcgcctgca gaccgacccg gtcgagtatc tgctcgagca gctaaataac ctcaccgaaa 25140
ccgtctcccc caacactgac gtccgtacgt attccggaaa acggaacggc gcctcggatg 25200
accttatggt cgccgtcatt atggccatct acctcgcggc ccaggccgga cctccgcaca 25260
cattcgctcc tatcacacgc gtctcgtgag cgcccaataa acacacccag gtatgctacg 25320
cacgaccacg gtgtcgtctg ttaagggggg ggggggaagg gggtgttggc gggaagcgtg 25380
ggaacacggg ggattctctc acgaccggca ccagtaccac ccccctgtga acacagaaac 25440
cccaacccaa atcccataaa catacgacac acaggcatat tttggaattt cttaggtttt 25500
tatttattta ggtatgctgg ggtttctccc tggatgccca cccccacccc cccgtgggtc 25560
tagccgggcc ttagggatag cgtataacgg gggccatgtc tccggaccgc acaacggccg 25620
cgccgtcaaa ggtgcacacc cgaaccacgg gagccagggc caaggtgtct cctagttggc 25680
ccgcgtgggt cagccaggcg acgagcgcct cgtaaagcgg cagccttcgc tctccatcct 25740
gcatcagggc cggggcttcg gggtgaatga gctgggcggc ctcccgcgtg acactctgca 25800
tctgcagtag agcgttcacg tacccgtcct gggcacttag cgcaaagagc cgggggatta 25860
gcgtaaggat gatggtggtt ccctccgtga tcgagtaaac catgttaagg accagcgatc 25920
gcagctcggc gtttacggga ccgagttgtt ggacgtccgc cagcagcgag aggcgactcc 25980
cgttgtagta cagcacgttg aggtctggca gccctccggg gtttctgggg ctggggttca 26040
ggtcccggat gcccctggcc acgagccgcg ccacgatttc gcgcgccagg ggcgatggaa 26100
gcggaacggg aaaccgcaac gtgaggtcca gcgaatccag gcgcacgtcc gtcgcttggc 26160
cctcgaacac gggcgggacg aggctgatgg ggtccccgtt acagagatct acgggggagg 26220
tgttgcgaag gttaacggtg ccggcgtggg tgaggcccac gtccaggggg caggcgacga 26280
ttcgcgtggg aagcacccgg gtgatgaccg cggggaagcg ccttcggtac gccagcaaca 26340
accccaacgt gtcgggactg acgcctccgg agacgaagga ttcgtgcgcc acgtcggcca 26400
gcgtcagttg ccggcggatg gtcggcagga ataccacccg cccttcgcag cgctgcagcg 26460
ccgccgcatc ggggcgcgag atgcccgagg gtatcgcgat gtcagtttca aagccgtccg 26520
ccagcatggc gccgatccac gcggcaggga gtgcagtggt ggttcgggtg gcgggaggag 26580
cgcggtgggg gtcagcggcg tagcagagac gggcgaccaa cctcgcatag gacggggggt 26640
gggtcttagg gggttgggag gcgacaggga ccccagagca tgcgcgggga ggtctgtcgg 26700
gcccagacgc accgagagcg aatccgtccg cggagtcccg gcttgggttt tatggggccc 26760
ggccctcgga atcgcggctt gtcggcgggg acaaaggggg cggggctagg ggcttgcgga 26820
aacagaagac gcgtgggata aaagaatcgc actaccccaa ggaagggcgg ggcggtttat 26880
tacagagcca gtcccttgag cggggatgcg tcatagacga gatactgcgc gaagtgggtc 26940
tcccgcgcgt gggcttcccc gttgcgggca ctgcggagga gggcggggtc gctggcgcag 27000
gtgagcgggt aggcctcctg aaacaggcca cacgggtcct ccacgagttc gcggcacccc 27060
ggggggcgct taaactgtac gtcgctggcg gcggtggccg tggacaccgc cgaacccgtc 27120
tccacgatca ggcgctccag gcagcgatgt ttggcggcga tgtcggccga cgtaaagaac 27180
ttaaagcagg ggctgagcac cggcgaggcc ccgttgaggt ggtaggcccc gttatagagc 27240
aggtccccgt acgaaaatcg ctgcgacgcc cacgggttgg ccgtggccgc gaaggcccgg 27300
gacgggtcgc tctggccgtg gtcgtacatg agggcggtga catccccctc cttgtccccc 27360
gcgtaaacgc ccccggcggc gcgtccccgg gggttgcagg gccggcggaa gtagttgacg 27420
tcggtcgaca cgggggtggc gataaactca cacacggcgt cctggccgtg gtccatccct 27480
gcgcgccgcg gcacctgggc gcacccgaac acggggacgg gctgggccgg ccccaggcgg 27540
tttcccgcca cgaccgcgtt ccgcaggtac acggctgccg cgttgtccag gagaggggga 27600
gccccgcggc ccaggtaaaa gttttgggga aggttgccca tgtcggtgac ggggttgcgg 27660
acggttgccg tggccacgac ggcggtgtag cccacgccca ggtccacgtt cgcgcgcggc 27720
tgggtgagcg tgaagtttac ccccccgcca gtttcgtgcc gggccacctg gagctggccc 27780
aggaagtacg cctccgacgc gcgctccgag aacagcacgt tctcagtcac aaagcggtcc 27840
tgtcggacga cggtgaaccc aaacccggga tggaggcccg tcttgagctg atgatgcaag 27900
gccacgggac tgatcttgaa gtaccccgcc atgagcgcgt aggtcagcgc gttctccccg 27960
gccgcgctct cgcggacgtg ctgcacgacg ggctgtcgga tcgacgaaaa gtagttggcc 28020
cccagagccg gggggaccag ggggacctgc cgcgacaggt cgcgcagggc cggggggaaa 28080
ttgggcgcgt tcgccacgtg gtcggccccg gcgaacagcg cgtggacggg gagggggtaa 28140
aaatagtcgc cattttggat ggtatggtcc agatgctggg gggccatcag caggattccg 28200
gcgtgcaacg ccccgtcgaa tatgcgcatg ttggtggtgg acgcggtgtt ggcgcccgcg 28260
tcgggcgccg ccgagcagag cagcgccgtt gtgcgttcgg ccatgttgtg ggccagcacc 28320
tgcagcgtga gcatggcggg cccgtccact accacgcgcc cgttgtgaaa catggcgttg 28380
accgtgttgg ccaccagatt ggccgggtgc agggggtgcg cggggtccgt cacggggtcg 28440
ctggggcact cctcgccggg ggcgatctcc gggaccacca tgttctgcag ggtggcgtat 28500
acgcggtcga agcgaacccc cgcggtgcag cagcggcccc gcgagaaggc gggcaccatc 28560
acgtagtagt aaatcttgtg gtgcacggtc cagtccgccc cccggtgcgg ccggtcatcc 28620
gcggcgtccg cggctcgggc ctgggtgttg tgcagcagct ggccgtcgtt gcggttgaag 28680
tccgcggtcg ccacgttaca tgccgccgcg tacacggggt cgtggccccc cgcgctaacc 28740
cggcagtcgc gatggcggtc cagggccgcg cgccgcatca gggcgtcaca gtcccacacg 28800

-continued

```
aggggtggca gcagcgccgg gtctcgcatt aggtgattca gctcggcttg cgcctgcccg  28860
cccagctccg ggccggtcag ggtaaagtca tcaaccagct gggccagggc ctcgacgtgc  28920
gccaccaggt cccggtacac ggccatgcac tcctcgggaa ggtctccccc gaggtaggtc  28980
acgacgtacg agaccagcga gtagtcgttc acgaacgccg cgcaccgcgt gttgttccag  29040
tagctggtga tgcactggac cacgagccgg gccagggcgc agaagacgtg ctcgctgccg  29100
tgtatggcgg cctgcagcag gtaaaacacc gccgggtagt tgcggtcgtc gaacgccccg  29160
cgaacggcgg cgatggtggc gggggccatg gcgtggcgtc ccacccccag ctccaggccc  29220
cgggcgtccc ggaacgccgc cggacatagc gccaggggca agttgccgtt caccacgcgc  29280
caggtggcct ggatctcccc cgggccggcc gggggaacgt cccccccgg cagctccacg  29340
tcggccaccc ccacaaagaa gtcgaacgcg gggtgcagct caagagccag gttggcgttg  29400
tcgggctgca taaactgctc cggggtcatc tggccttccg cgacccatcg gacccgcccg  29460
tgggccaggc gctgccccca ggcgttcaaa aacagctgct gcatgtctgc ggcggggccg  29520
gccggggccg ccacgtacgc cccgtacgga ttggcggctt cgacggggtc gcggttaagg  29580
cccccgaccg ccgcgtcaac gttcatcagc gaagggtggc acacggtccc gatcgcgtgt  29640
tccagagaca ggcgcagcac ctggcggtcc ttcccccaaa aaaacagctg gcggggcggg  29700
aaggcgcggg gatccgggtg gccgggggcg gggactaggt ccccggcgtg cgcggcaaac  29760
cgttccatga ccggattgaa caggcccagg ggcaggacga acgtcaggtc catggcgccc  29820
accagggggt agggaacgtt ggtggcggcg tagatgcgct tctccagggc ctccagaaag  29880
accagcttct cgccgatgga caccagatcc gcgcgcacgc gcgtcgtctg gggggcgctc  29940
tcgagctcgt ccagcgtctg ccggttcagg tcgagctgct cctcctgcat ctccagcagg  30000
tggcggccca cgtcgtccag acttcgcacg gccttgccca tcacgagcgc cgtgaccagg  30060
ttggccccgt tcaggaccat ctcgccgtac gtcaccggca cgtcggcttc ggtgtcctcc  30120
actttcagga aggactgcag gaggcgctgt ttgatcgggg cggtggtgac gagcaccccg  30180
tcgaccggcc gcccgcgcgt gtcggcatgc gtcagacggg gcacggccac ggagggctgc  30240
gtggccgtgg tgaggtccac gagccaggcc tcgacggcct cccggcggtg gcccgccttg  30300
cccaggaaaa agctcgtctc gcagaagctt cgctttagct cggcgaccag ggtcgcccgg  30360
gccaccctgg tggccaggcg gccgttgtcc aggtatcgtt gcatcggcaa caacaaagcc  30420
aggggcggcg ccttttccag cagcacgtgc agcatctggt cggccgtgcc gcgctcaaac  30480
gccccgagga cggcctggac gttgcgagcg agctgttgga tggcgcgcaa ctggcgatgc  30540
gcgccgatac ccgtcccgtc cagggcctcc cccgtgagca gggcgatggc ctcggtggcc  30600
aggctgaagg cggcgttcag ggcccggcgg tcgataatct tggtcatgta attgtgtgtg  30660
ggttgctcga tggggtgcgg gccgtcgcgg gcaatcagcg gctggtggac ctcgaactgt  30720
acgcgcccct cgttcatgta ggccagctcc ggaaacttgg tacacacgca cgccaccgac  30780
aacccgagct ccagaaagcg cacgagcgac agggtgttgc aatacgaccc cagcagggcg  30840
tcgaactcga cgtcgtacag gctgtttgca tcggagcgca cgcgggaaaa aaaatcaaac  30900
aggcgtcgat gcgacgccac ctcgatcgtg ctaaggaggg acccggtcgg caccatggcc  30960
gcggcatacc ggtatcccgg agggtcgcgg ttgggagcgg ccatggggtc gcgtggagat  31020
cggctgtctc tagcgatatt ggcccgggga ggctaagatc caccccaacg cccggccacc  31080
cgtgtacgtg cccgacggcc caaggtccac cgaaagacac gacgggcccg gacccaaaaa  31140
ggcgggggat gctgtgtgag aggccgggtg ccggtcgggg gggaaaggca ccgggagaag  31200
```

gctgcggcct cgttccagga gaacccagtg tccccaacag acccggggac gtgggatccc 31260
aggccttata taccccccccc cccgccccac ccccgttaga acgcgacggg tgcattcaag 31320
atggccctgg tccaaaagcg tgccaggaag aaattggcag aggcggcaaa gctgtccgcc 31380
gccgccaccc acatcgaggc ccccggccgcg caggctatcc ccagggcccg tgtgcgcagg 31440
ggatcggtgg gcggcagcat ttggttggtg gcgataaagt ggaaaagccc gtccggactg 31500
aaggtctcgt gggcggcggc gaacaaggca cacagggccg tgcctcccaa aaacacggac 31560
atcccccaaa acacgggcgc cgacaacggc agacgatccc tcttgatgtt aacgtacagg 31620
aggagcgccc gcaccgccca cgtaacgtag tagccgacga tggcggccag gatacaggcc 31680
ggcgccacca cccttccggt cagcccgtaa tacatgcccg ctgccaccat ctccaacggc 31740
ttcaggacca aaaacgacca aaggaacaga atcacgcgct ttgaaaagac cggctgggta 31800
tggggcggaa gacgcgagta tgccgaactg acaaaaaaat cagaggtgcc gtacgaggac 31860
aatgaaaact gttcctccag cggcagttct ccctcctccc ccccgaaggc ggcctcgtcg 31920
accagatctc gatccaccag aggaaggtca tcccgcatgg tcatggggtg tgcggtggag 31980
gtggggagac cgaaaccgca aagggtcgct tacgtcagca ggatcccgag atcaaagaca 32040
cccgggttct tgcacaaaca ccacccgggt tgcatccgcg gaggcgagtg ttttgataag 32100
gccgttccgc gccttgatat aacctttgat gttgaccaca aaacccggaa tttacgccta 32160
cgccccaatg cccacgcaag atgaggtagg taacccccccc gtgggtgtga cgttgcgttt 32220
agttcattgg aggccaaggg gaaaaatggg gtggggagga aacggaaaac ccagtaggcc 32280
gtgtcgggaa cacgcccggg gttgtcctca aaaggcaggg tccatactac ggaagccgtc 32340
gttgtattcg agacctgcct gtgcaacgca cgtcggggtt gcctgtgtcc ggttcggccc 32400
ccaccgcgtg cggcacgcac gaggacgagt ccgcgtgctt tattggcgtt ccaagcgttg 32460
ccctccagtt tctgttgtcg gtgttccccc atacccacgc ccacatccac cgtagggggc 32520
ctctgggccg tgttacgtcg ccgcccgcga tggagcttag ctacgccacc accatgcact 32580
accgggacgt tgtgttttac gtcacaacgg accgaaaccg ggcctacttt gtgtgcgggg 32640
ggtgtgttta ttccgtgggg cggccgtgtg cctcgcagcc cggggagatt gccaagtttg 32700
gtctggtcgt tcgagggaca ggcccagacg accgcgtggt cgccaactat gtacgaagcg 32760
agctccg 32767

<210> SEQ ID NO 848
<211> LENGTH: 32767
<212> TYPE: DNA
<213> ORGANISM: Artificial Sequence
<220> FEATURE:
<223> OTHER INFORMATION: recombinant viral vector ONCR-156

<400> SEQUENCE: 848
aaaaaagctg aacgagaaac gtaaaatgat ataaatatca atatattaaa ttagattttg 60
cataaaaaac agactacata atactgtaaa acacaacata tccagtcact atgaatcaac 120
tacttagatg gtattagtga cctgtagtcg accgacagcc ttccaaatgt tcttcgggtg 180
atgctgccaa cttagtcgac cgacagcctt ccaaatgttc ttctcaaacg gaatcgtcgt 240
atccagccta ctcgctattg tcctcaatgc cgtattaaat cataaaaaga aataagaaaa 300
agaggtgcga gcctcttttt tgtgtgacaa aataaaaaca tctacctatt catatacgct 360
agtgtcatag tcctgaaaat catctgcatc aagaacaatt tcacaactct tatacttttc 420

-continued

```
tcttacaagt cgttcggctt catctggatt ttcagcctct atacttacta aacgtgataa    480
agtttctgta atttctactg tatcgacctg cagactggct gtgtataagg gagcctgaca    540
tttatattcc ccagaacatc aggttaatgg cgtttttgat gtcattttcg cggtggctga    600
gatcagccac ttcttccccg ataacggaga ccggcacact ggccatatcg gtggtcatca    660
tgcgccagct ttcatccccg atatgcacca ccgggtaaag ttcacgggag actttatctg    720
acagcagacg tgcactggcc aggggggatca ccatccgtcg cccgggcgtg tcaataatat    780
cactctgtac atccacaaac agacgataac ggctctctct tttataggtg taaaccttaa    840
actgcatttc accagcccct gttctcgtca gcaaaagagc cgttcatttc aataaaccgg    900
gcgacctcag ccatcccttc ctgattttcc gctttccagc gttcggcacg cagacgacgg    960
gcttcattct gcatggttgt gcttaccaga ccggagatat tgacatcata tatgccttga   1020
gcaactgata gctgtcgctg tcaactgtca ctgtaatacg ctgcttcata gcatacctct   1080
ttttgacata cttcgggtat acatatcagt atatattctt ataccgcaaa aatcagcgcg   1140
caaatacgca tactgttatc tggcttttag taagccggat ccacgcggcg tttacgcccc   1200
ccctgccact catcgcagta ctgttgtaat tcattaagca ttctgccgac atggaagcca   1260
tcacaaacgg catgatgaac ctgaatcgcc agcggcatca gcaccttgtc gccttgcgta   1320
taatatttgc ccatggtgaa aacgggggcg aagaagttgt ccatattggc cacgtttaaa   1380
aaggccgtaa tatccagctg aacggtctgg ttataggtac attgagcaac tgactgaaat   1440
gcctcaaaat gttctttacg atgccattgg gatatatcaa cggtggtata tccagtgatt   1500
tttttctcca ttttagcttc cttagctcct gaaaatctcg ataactcaaa aaatacgccc   1560
ggtagtgatc ttatttcatt atggtgaaag ttggaacctc ttacgtgccg atcaacgtct   1620
cattttcgcc aaaagttggc ccagggcttc ccggtatcaa cagggacacc aggatttatt   1680
tattctgcga agtgatcttc cgtcacaggt atttattcgg cgcaaagtgc gtcgggtgat   1740
gctgccaact tagtcgacta caggtcacta ataccatcta agtagttgat tcatagtgac   1800
tggatatgtt gtgttttaca gtattatgta gtctgttttt tatgcaaaat ctaatttaat   1860
atattgatat ttatatcatt ttacgtttct cgttcagctt tcttgtacaa agtggtttta   1920
atggaccgcc cgcaaggggg ggggggcatt tcagtgtcgg gtgacgagcg cgatccggcc   1980
gggatcctag gaccccaaaa gtttgtctgc gtattccagg gcggggctca gttgaatctc   2040
ccgcagcacc tctaccagca ggtccgcggt gggctggaga aactcggccg tcccggggca   2100
ggcggttgtc gggggtggag gcgcggcgcc caccccgtgt gccgcgcctg gcgtctcctc   2160
tgggggcgac ccgtaaatgg ttgcagtgat gtaaatggtg tccgcggtcc agaccacggt   2220
caaaatgccg gccgtggcgc tccgggcgct ttcgccgcgc gaggagctga cccaggagtc   2280
gaacggatac gcgtacatat gggcgtccca cccgcgttcg agcttctggt tgctgtcccg   2340
gcctataaag cggtaggcac aaaattcggc gcgacagtcg ataatcacca acagcccaat   2400
gggggtgtgc tggataacaa cgcctccgcg cggcaggcgg tcctggcgct cccggccccg   2460
taccatgatc gcgcgggtgc cgtactcaaa aacatgcacc acctgcgcgg cgtcgggcag   2520
tgcgctggtc agcgaggccc tggcgtggca taggctatac gcgatggtcg tctgtggatt   2580
ggacatctcg cggtgggtag tgagtccccc gggccgggtt cggtggaact gtaaggggac   2640
ggcgggttaa tagacaatga ccacgttcgg atcgcgcaga gccgatagta tgtgctcact   2700
aatgacgtca tcgcgctcgt ggcgctcccg gagcggattt aagttcatgc gaaggaattc   2760
ggaggaggtg gtgcgggaca tggccacgta cgcgctgttg aggcgcaggt tgccgggcgt   2820
```

```
aaagcagatg gcgaccttgt ccaggctaag gccctgggag cgcgtgatgg tcatggcaag   2880
cttggagctg atgccgtagt cggcgtttat ggccatggcc agctccgtag agtcaatgga   2940
ctcgacaaac tcgctgatgt tggtgttgac gacggacatg aagccgtgtt ggtcccgcaa   3000
gaccacgtaa ggcagggggg cctcttccag taactcggcc acgttggccg tcgcgtgccg   3060
cctccgcagc tcgtccgcaa aggcaaacac ccgtgcgtac gtgtatccca tgagcgtata   3120
attgtccgtc tgcagggcga cggacatcag ccccccgcgc ggcgagccgg tcagcatctc   3180
gcagccccgg aagataacgt tgtccacgta cgtgctaaag gggcgactt caaatgcctc    3240
cccgaagagc tcttggagga ttcggaatct cccgaggaag gcccgcttca gcagcgcaaa   3300
ctgggtgtga acggcggcgg tggtctccgg ttccccgggg gtgtagtggc agtaaaacac   3360
gtcgagctgt tgttcgtcca gccccgcgaa aataacgtcg aggtcgtcgt cgggaaaatc   3420
gtccgggccc ccgtcccgcg gccccagttg cttaaaatca aacgcacgct cgccgggggc   3480
gcctgcgtcg gccattaccg acgcctgcgt cggcaccccc gaagatttgg ggcgcagaga   3540
cagaatctcc gccgttagtt ctcccatgcg ggcgtaggcg agggtcctct gggtcgcatc   3600
caggcccggg cgctgcagaa agttgtaaaa ggagataagc ccgctaaata tgagccgcga   3660
caggaacctg taggcaaact ccaccgaagt ctccccctga gtctttacaa agctgtcgtc   3720
acgcaacact gcctcgaagg cccggaacgt cccactaaac ccaaaaacca gttttcgcag   3780
gcgcgcggtc accgcgatct ggctgttgag gacgtaagtg acgtcgttgc gggccacgac   3840
cagctgctgt ttgctgtgca cctcgcagcg catgtgcccc gcgtcctggt cctggctctg   3900
cgagtagttg gtgatgcggc tggcgttggc cgtgagccac ttttcaatcg tcaggccggg   3960
ctggtgtgtc agccgtcggt attcgtcaaa ctccttgacc gacacgaacg taagcacggg   4020
gagggtgaac acgacgaact ccccctcacg ggtcaccttc aggtaggcgt ggagcttggc   4080
catgtacgcg ctcacctctt tgtgggagga gaacagccgc gtccagccgg ggaggttggc   4140
ggggttggtg atgtagtttt ccgggacgac gaagcgatcc acgaactgca tgtgctcctc   4200
ggtgatgggc aggccgtact ccagcacctt catgaggtta ccgaactcgt gctcgacgca   4260
ccgtttgttg ttaataaaaa tggcccagct atacgagagg cgggcgtact cgcgcagcgt   4320
gcggttgcag atgaggtacg tgagcacgtt ctcgctctgg cggacggaac accgcagttt   4380
ctggtgctcg aaggtcgact ccagggacgc cgtctgcgtc ggcgagccca cacacaccaa   4440
cacgggccgc aggcgggccg cgtactgggg ggtgtggtac agggcgttaa tcatccacca   4500
gcaatacacc acggccgtga ggaggtgacg cccaaggagc ccggcctcgt cgatgacgat   4560
cacgttgctg cgggtaaagg ccggcagcgc cccgtgggtg gccggggcca accgcgtcag   4620
ggcgccctcg gccaacccca gggtccgttc cagggcggcc agggcgcgaa actcgttccg   4680
caactcctcg cccccggagg cggccagggc gcgcttcgtg aggtccaaaa tcacctccca   4740
gtagtacgtc agatctcgtc gctgcaggtc ctccagcgag gcggggttgc tggtcagggt   4800
gtacgggtac tgtcccagtt gggcctggac gtgattcccg cgaaacccaa attcatgaaa   4860
gatggtgttg atgggtcggc tgagaaaggc gcccgagagt ttggcgtaca tgttttgggc   4920
cgcaatgcgc gtggcgcccg tcaccacaca gtccaagacc tcgttgattg tctgcacgca   4980
cgtgctcttt ccggagccag cgttgccggt gataagatac accgcgaacg gaaactccct   5040
gaggggcagg cctgcggggg actctaaggc cgccacgtcc cggaaccact gcagatgggg   5100
cacttgcgct ccgtcgagct gttgttgcga gagctctcgg atgcgcttaa ggattggctg   5160
```

-continued

```
caccccgtgc atagacgtaa aatttaaaaa ggcctcggcc ctccctggaa cggctggtcg   5220
gtccccgggt tgctgaaggt gcggcgggcc gggtttctgt ccgtctagct ggcgctcccc   5280
gccggccgcc gccatgaccg caccacgctc gcgggccccc actacgcgtg cgcgggggga   5340
cacggaagcg ctgtgctccc ccgaggacgg ctgggtaaag gttcacccca gccccggtac   5400
gatgctgttc cgcgagattc tccacgggca gctggggtat accgagggcc agggggtgta   5460
caacgtcgtc cggtccagcg aggcgaccac ccggcagctg caggcggcga tctttcacgc   5520
gctcctcaac gccaccactt accgggacct cgaggcggac tggctcggcc acgtggcggc   5580
ccgcggtctg cagccccaac ggctggttcg ccggtacagg aacgcccggg aggcggatat   5640
cgccggggtg gccgagcggg tgttcgacac gtggcggaac acgcttagga cgacgctgct   5700
ggactttgcc cacgggttgg tcgcctgctt tgcgccgggc ggcccgagcg gcccgtcaag   5760
cttccccaaa tatatcgact ggctgacgtg cctggggctg gtccccatat tacgcaagcg   5820
acaagaaggg ggtgtgacgc agggtctgag ggcgtttctc aagcagcacc cgctgacccg   5880
ccagctggcc acggtcgcgg aggccgcgga gcgcgccggc cccgggtttt ttgagctggc   5940
gctggccttc gactccacgc gcgtggcgga ctacgaccgc gtgtatatct actacaacca   6000
ccgccggggc gactggctcg tgcgagaccc catcagcggg cagcgcggag aatgtctggt   6060
gctgtggccc cccttgtgga ccggggaccg tctggtcttc gattcgcccg tccagcggct   6120
gtttcccgag atcgtcgcgt gtcactccct ccgggaacac gcgcacgtct gccggctgcg   6180
caataccgcg tccgtcaagg tgctgctggg gcgcaagagc gacagcgagc gcggggtggc   6240
cggtgccgcg cgggtcgtta acaaggtgtt gggggaggac gacgagacca aggccgggtc   6300
ggccgcctcg cgcctcgtgc ggcttatcat caacatgaag ggcatgcgcc acgtaggcga   6360
cattaacgac accgtgcgtt cctacctcga cgaggccggg gggcacctga tagacgcccc   6420
ggccgtcgac ggtaccctcc ctggattcgg caagggcgga aacagccgcg ggtctgcggg   6480
ccaggaccag ggggggcggg cgccgcagct tcgccaggcc ttccgcacgg ccgtggttaa   6540
caacatcaac ggcgtgttgg agggctatat aaataacctg tttggaacca tcgagcgcct   6600
gcgcgagacc aacgcgggcc tggcgaccca attgcaggag cgcgaccgcg agctccggcg   6660
cgcaacagcg ggggccctgg agcgccagca gcgcgcggcc gacctggcgg ccgagtccgt   6720
gaccggtgga tgcggcagcc gccctgcggg ggcggacctg ctccgggccg actatgacat   6780
tatcgacgtc agcaagtcca tggacgacga cacgtacgtc gccaacagct ttcagcaccc   6840
gtacatccct tcgtacgccc aggacctgga gcgcctgtcg cgcctctggg agcacgagct   6900
ggtgcgctgt tttaaaattc tgtgtcaccg caacaaccag ggccaagaga cgtcgatctc   6960
gtactccagc ggggcgatcg ccgcattcgt cgccccctac tttgagtcag tgcttcgggc   7020
cccccgggta ggcgcgccca tcacgggctc cgatgtcatc ctgggggagg aggagttatg   7080
ggatgcggtg tttaagaaaa cccgcctgca aacgtacctg acagacatcg cggccctgtt   7140
cgtcgcggac gtccagcacg cagcgctgcc cccgcccccc tccccggtcg gcgccgattt   7200
ccggcccggc gcgtccccgc ggggccggtc cagatcgcgg tcgcccggaa gaactgcgcg   7260
aggcgcgccg gaccagggcg ggggcatcgg gcaccgggat ggccgccgcg acggccgacg   7320
atgaggggtc ggccgccacc atcctcaagc aggccatcgc cggggaccgc agcctggtcg   7380
aggcggccga ggcgattagc cagcagacgc tgctccgcct ggcctgcgag gtgcgccagg   7440
tcggcgaccg ccagccgcgg tttaccgcca ccagcatcgc gcgcgtcgac gtcgcgcctg   7500
ggtgccggtt gcggttcgtt ctggacggga gtcccgagga cgcctatgtg acgtcggagg   7560
```

attactttaa gcgctgctgc ggccagtcca gttatcgcgg cttcgcggtg gcggtcctga 7620
cggccaacga ggaccacgtg cacagcctgg ccgtgccccc cctcgttctg ctgcaccggt 7680
tctccctgtt caaccccagg gacctcctgg actttgagct tgcctgtctg ctgatgtacc 7740
tggagaactg cccccgaagc cacgccaccc cgtcgacctt tgccaaggtt ctggcgtggc 7800
tcggggtcgc gggtcgccgc acgtccccat tcgaacgcgt tcgctgcctt ttcctccgca 7860
gttgccactg ggtcctaaac acactcatgt tcatggtgta cgtaaaaccg ttcgacgacg 7920
agttcgtcct gccccactgg tacatggccc ggtacctgct ggccaacaac ccgccccccg 7980
ttctctcggc cctgttctgt gccaccccga cgagctcctc attccggctg ccggggccgc 8040
ccccccgctc cgactgcgtg gcctataacc ccgccgggat catggggagc tgctgggcgt 8100
cggaggaggt gcgcgcgcct ctggtctatt ggtggctttc ggagacccca aaacgacaga 8160
cgtcgtcgct gttttatcag ttttgttgaa ttttaggaaa taaacccggt tttgtttctg 8220
tggcctcccg acggatgcgc gtgtccttac tccgtcttgg tgggtgggtg gctgtgtatg 8280
gcgtcccatc tgtgcgggga ggggggcaag tcggcacgta ttcggacaga ctcaagcaca 8340
taagacgaac aaaaggtttg taacttcgta ccgtgagtaa taatgtggac tttattgctt 8400
aagaatacgc gtagagaaat aagacgaaca aaaggtttgt gattttattg cttaagaata 8460
cgcgtagatg gtcgtaccgt gagtaataat gtggttcata agacgaacaa aaggtttgtg 8520
acattattgc ttaagaatac gcgtaggtgg tcgtaccgtg agtaataatg tgtactttat 8580
tgcttaagaa tacgcgtagg ctatcgtacc gtgagtaata atgtgcctta taagacgaac 8640
aaaaggtttg tacacggggg agcgctcttg tctcagggca atgtttttat tggtcaaact 8700
caggcaaaca gaaacgacat cttgtcgtca aagggataca caaacttccc cccctcgccc 8760
catactcccg ccagcacccc ggtaaacacc aactcaatct cgcgcaggat ttcgcgcagg 8820
tgatgagcgc agtccacggg ggggagcaca aggggccgcg ggtatagatc gacggggacg 8880
ccgaccgact ccccgcctcc gggacagaca cgcacgacgc gccgccagta gtgctctgcg 8940
tccagcaagg cgccgccgcg gaaggcagtg gggggcaagg ggtcgctggc ctcaaagggg 9000
gacacccgaa cgctccagta ctccgcgtcc aaccgtttat taaacgcgtc caagataagg 9060
cggtcgcagg cgtcctccat aaggccccgg gccgtgagtg cgtcctcctc cggcacgcat 9120
gccgttgtca ggcccaggac ccgtcgcagc gtgtcgcgta cgacccctgc cgccgtggtg 9180
tacgcgggcc cgcggagagg aaatccccca agatggtcag tgttgtcgcg ggagttccag 9240
aaccacactc ccgcctggct ccaggcgact gcgtgggtgt agacgccctc gagggccagg 9300
cacagtgggt gccgcagccg gacggcgttg gccctaagca cggctcccac ggccgtctcg 9360
atggcccgcc gggcgtcctc gatcaccccg gaagccgcat ccgcgtcttg gggtccacg 9420
ttaaagacac cccagaacgc acccccatcg cccccgcaga ccgcgaactt caccgagctg 9480
gccgtctcct cgatctgcag gcagacggcg gccattaccc cacccaggag ctgccgcagc 9540
gcagggcagg cgttgcacgt gtccgggacc aggcgctcca agacggcccc ggcccagggc 9600
tctgagggag cggccaccac cagcgcgtcc agtcttgcta ggcccgtccg gccgtggggg 9660
tccgccagcc cgctcccccc gaggtcggcc agggccgcca ggagctgggc gcgaagtccg 9720
gggaagcaaa accgcgccgt ccagacgggc ccgacggccg cgggcgggtc taacagttgg 9780
atgattttag tggcgggatg ccaccgcgcc accgcctccc gcaccgcggg caggaggcat 9840
ccggctgccg ccgaggccac gccgggccag gctcgcgggg ggaggacgac cctggccccc 9900

-continued

```
accgcgggcc aggcccccag gagcgcggcg taagcggccg cggccccgcg caccaggtcc   9960
cgtgccgact cggccgtggc cggcacggtg aacgtgggcc aacccggaaa ccccaggacg  10020
gcaaagtacg ggacgggtcc cccccggacc tcaaactcgg gccccagaaa ggcaaagacg  10080
ggggccaggg ccccgggggc ggcgtggacc gtggtatgcc actgccggaa aagggcgacg  10140
agcgccggcg cggagaactt ctcgccggcg cttacaaagt agtcgtaatc gcggggcagc  10200
agcacccgtg ccgtgactcg ttgcgggtgc ccgcgtggcc gcaggcccac ctcgcacacc  10260
tcgaccaggt ccccgaacgc gccctccttc ttgatcggcg gaaacgcaag agtctggtat  10320
tcgcgcgcaa atagcgcggt tccggtggtg atgttaacgg tcagcgaagc ggcggacgcg  10380
cactgggggg tgtcgcgaat ggccgccagg cgcgcccacg ccagccgcgc gtcgggatgc  10440
tcggcaacgc gcgccgccag ggccataggg tcgatgtcaa tgttggcctc cgcgaccagg  10500
agagcggcgc gaggggcggc gggcgggccc cacgacgctc tctcaacttt caccaccagt  10560
cccgtgcgtg ggtccgagcc gatacgcagc ggggcgaaca gggccaccgg cccggtctgg  10620
cgctccaggg ccgccaggac gcacgcgtac agcgcccgcc acagagtcgg gttctccagg  10680
ggctccagcg gggaggcggc cggcgtcgtc gcggcgcggg cggccgccac gacggcctgg  10740
acggagacgt ccgcggagcc gtagaaatcc cgcagctccg tcgcggtgac ggagacctcc  10800
gcaaagcgcg cgcgaccctc ccctgcggcg ttgcgacata caaaatacac cagggcgtgg  10860
aagtactcgc gagcgcgggg gggcagccat accgcgtaaa gggtaatggc gctgacgctc  10920
tcctccaccc acacgatatc tgcggtgtcc atcgcacggc ccctaaggat cacgggcggt  10980
ctgtgggtcc catgctgccg tgcctggccg ggcccggtgg gtcgcggaaa ccggtgacgg  11040
gggggggcg gtttttgggg ttggggtggg ggtgggaaac ggcccgggtc cgggggccaa  11100
cttggcccct cggtgcgttc cggcaacagc gccgccggtc cgcggacgac cacgtaccga  11160
acgagtgcgg tcccgagact tatagggtgc taaagttcac cgccccctgc atcatgggcc  11220
aggcctcggt ggggagctcc gacagcgccg cctccaggat gatgtcagcg ttggggttgg  11280
cgctggatga gtgcgtgcgc aaacagcgcc cccacgcggg cacgcgtagc ttgaagcgcg  11340
cgcccgcaaa ctcccgcttg tgggccataa gcagggcgta cagctgcctg tgggtccggc  11400
aggcgctgtg gtcgatgtgg tgggcgtcca acaaccccac gattgtctgt ttggtgaggt  11460
ttttaacgcg ccccgccccg ggaaacgtct gcgtgctttt ggccatctgc acgccaaaca  11520
gttcgcccca gattatcttg aacagcgcca ccgcgtggtc cgtctcgcta acggacccgc  11580
gcgggggaca gccgcttagg gcgtcggcga cgcgcttgac ggcttcctcc gagagcagaa  11640
gtccgtcggt tacgttacag tggcccagtt cgaacaccag ctgcatgtag cggtcgtagt  11700
ggggggtcag taggtccagc acgtcatcgg ggccgaaggt cctcccagat cccccggccg  11760
ccgagtccca atgcaggcgc gcggccatgg tgctgcacag gcacaacagc tcccagacgg  11820
gggttacgtt cagggtgggg ggcagggcca cgagctccag ctctccggtg acgttgatcg  11880
tggggatgac gcccgtggcg tagtggtcat agatccgccg aaatatggcg ctgctgcggg  11940
tggccatggg aacgcggaga caggcctcca gcaacgccag gtaaataaac cgcgtgcgtc  12000
ccatcaggct gttgaggttg cgcatgagcg cgacaatttc cgccggcgcg acatcggacc  12060
ggaggtattt ttcgacgaaa agacccacct cctccgtctc ggcggcctgg gccggcagcg  12120
acgcctcggg atcccggcac cgcagctccc gtagatcgcg ctgggccctg agggcgtcga  12180
aatgtacgcc ccgcaaaaac agacagaagt cctttggggt cagggtatcg tcgtgtcccc  12240
agaagcgcac gcgtatgcag tttagggtca gcagcatgtg aaggatgtta aggctgtccg  12300
```

```
agagacacgc cagcgtgcat ctctcaaagt agtgtttgta acggaatttg ttgtagatgc  12360
gcgacccccg ccccagcgac gtgtcgcatg ccgacgcgtc acagcgcccc ttgaaccggc  12420
gacacagcag gtttgtgacc tgggagaact gcgcgggcca ctggccgcag gaactgacca  12480
cgtgattaag gagcatgggc gtaaagacgg gctccgagcg cgccccggag ccgtccatgt  12540
aaatcagtag ctccccccttg cggagggtgc gcacccgtcc cagggactgg tacacggaca  12600
ccatgtccgg tccgtagttc atgggtttca cgtaggcgaa catgccatca aagtgcaggg  12660
gatcgaagct gaggcccacg gttacgaccg tcgtgtatat aaccacgcgg tattggcccc  12720
acgtggtcac gtccccgagg ggggtgagcg agtgaagcaa cagcacgcgg tccgtaaact  12780
gacggcagaa ccgggccacg atctccgcga aggagaccgt cgacgaaaaa atgcagatgt  12840
tatcgccccc gccaaggcgc gcttccagct ccccaaagaa cgtggccccc cgggcctccg  12900
gagaggcgtc cggagacggg ccgctcggcg gcccgggcgg gcgcagggca gcctgcagga  12960
gctcggtccc cagacgcggg agaaacaggc accggcgcgc cgaaaacccg ggcatggcgt  13020
actcgccgac caccacatgc acgttttttt cgccccggag accgcacagg aagtccacca  13080
actgcgcgtt ggcggttgcg tccatggcga tgatccgagg acagatgcgc agcaggcgta  13140
gcattaacgc atccacgcgg cccagttgct gcatcgttgg cgaatagagc tggcccagcg  13200
tcgacataac ctcgtccaga acgaggacgt cgtagttgtt cagaaggttg gggcccacgc  13260
gatgaaggct ttccacctgg acgataagtc ggtggaaggg gcggtcgttc ataatgtaat  13320
tggtggatga gaagtaggtg acaaagtcga ccaggcctga ctcagcgaac cgcgtcgcta  13380
gggtctgggt aaaactccga cgacaggaga cgacgagcac actcgtgtcc ggagagtgga  13440
tcgcttcccg cagccagcgg atcagcgcgg tagtttttcc cgaccccatt ggcgcgcgga  13500
ccacagtcac gcacctggcc gtcggggcgc tcgcgttggg gaaggtgacg ggtccgtgct  13560
gctgccgctc gatcgttgtt ttcgggtgaa cccggggcac ccattcggcc aaatcccccc  13620
cgtacaacat ccgcgctagc gatacgctcg acgtgtactg ttcgcactcg tcgtccccaa  13680
tgggacgccc ggcccccaga ggatctcccg actccgcgcc ccccacgaaa ggcatgaccg  13740
gggcgcggac ggcgtggtgg gtctggtgtg tgcaggtggc gacgtttgtg gtctctgcgg  13800
tctgcgtcac ggggctcctc gtcctggcct ctgtgttccg ggcacggttt ccctgctttt  13860
acgccacggc gagctcttat gccggggtga actccacggc cgaggtgcgc gggggtgtag  13920
ccgtgcccct caggttggac acgcagagcc ttgtgggcac ttatgtaatc acggccgtgt  13980
tgttgttggc cgtggccgtg tatgccgtgg tcggcgccgt gacctcccgc tacgaccgcg  14040
ccctggacgc gggccgccgt ctggctgcgg cccgcatggc catgccgcac gccacgctga  14100
tcgccggaaa cgtctgctct tggttgctgc agatcaccgt cctgttgctg gcccatcgca  14160
tcagccagct ggcccacctg gtttacgtcc tgcactttgc gtgtctggtg tattttgcgg  14220
cccatttttg caccaggggg gtcctgagcg ggacgtatct gcgtcaggtg cacggcctga  14280
tggagctggc cccgacccat catcgcgtcg tcggcccggc tcgcgccgtg ctgacaaacg  14340
ccttgctgtt gggcgtcttc ctgtgcacgg ccgacgccgc ggtatccctg aataccatcg  14400
ccgcgttcaa ctttaatttt tcggccccgg gcatgctcat ctgcctgacc gtgctgttcg  14460
ccattctcgt cgtatcgctg ttgttggtgg tcgagggggt gttgtgtcac tacgtgcgcg  14520
tgttggtggg cccccacctg gggggccgtgg ccgccacggg catcgtcggc ctggcctgcg  14580
agcactatta caccaacggc tactacgttg tggagacgca gtggccgggg gctcagacgg  14640
```

gagtccgcgt cgccctcgcc ctggtcgccg cctttgccct cggcatggcc gtgctccgct 14700
gcacccgcgc ctatctgtat cacaggcggc accacaccaa attttttatg cgcatgcgcg 14760
acacgcgaca ccgcgcacat tccgccctca agcgcgtacg cagttccatg cgcggatcgc 14820
gagacggccg ccacaggccc gcacccggca gcccgcccgg gattcccgaa tatgcggaag 14880
acccctacgc gatctcatac ggcggccagc tcgaccggta cggagattcc gacggggagc 14940
cgatttacga cgaggtggcg gacgaccaaa ccgacgtatt gtacgccaag atacaacacc 15000
cgcggcacct gcccgacgac gatcccatct atgacaccgt tggggggtac gaccccgagc 15060
ccgccgagga ccccgtgtac agcaccgtcc gccgttggta gctgtttggt tccgttttaa 15120
taaaccgttt gtgtttaacc cgaccgtggt gtatgtctgg tgtgtggcgt ccgatcccgt 15180
tactatcacc gtcccccccc ccccctcaac cccggcgatt gtgggttttt taaaaacgac 15240
acgcgtgcga ccgtatacag aacattgttt tggtttttat tcgctatcgg acatgggggg 15300
tggaaactgg gtggcggggc aggcgcctcc gggggtccgc cggtgagtgt ggcgcgaggg 15360
ggggtccgat gaacgcaggc gctgtctccc cggggcccgc gtaaccccgc gcatatccgg 15420
gggcacgtag aaattacctt cctcttcgga ctcgatatcc acgacgtcaa agtcgtgggc 15480
ggtcagcgag acgacctccc cgtcgtcggt gatgaggacg ttgtttcggc agcagcaggg 15540
ccgggccccg gagaacgaga ggcccatagc tcggcgagcg tgtcgtcgaa tgccaggcgg 15600
ctgcttcgct ggatggcctt atagatctcc ggatcgatgc ggacgggggt aatgatcagg 15660
gcgatcggaa cggcctggtt cgggagaatg gacgccttgc tgggtcctgc ggccccgaga 15720
gccccggcgc cgtcctccag gcggaacgtt acgccctcct ccgcgctggt gcggtgcctg 15780
ccgataaacg tcaccagatg cgggtggggg gggcagtcgg ggaagtggct gtcgagcacg 15840
tagccctgca ccaagatctg cttaaagttc gggtgacggg ggttcgcgaa gacgggctcg 15900
cggcggacca gatccccgga gctccaggac acgggggaga tggtgtggcg tccgaggtcg 15960
ggggcgccaa acagaagcac ctccgagaca acgccgctat ttaactccac caaggcccga 16020
tccgcggcgg agcaccgcct tttttcgccc gaggcgtggg cctctgacca ggcctggtct 16080
tgcgtgacga gagcctcctc cgggccgggg acgcgcccgg gcgcgaagta tcgcacgctg 16140
ggcttcggga tcgaccggat aaatgcccgg aacgcctccg gggaccggtg tgccatcaag 16200
tcctcgtacg cggaggccgt ggggtcgctg gggtccatgg ggtcgaaagc gtacttggcc 16260
cggcatttga cctcgtaaaa ggccaggggg gtcttgggga ctggggccag gtagccgtga 16320
atgtcccgag gacagacgag aatatccagg gacgccccga ccatccccgt gtgaccgtcc 16380
atgaggaccc cacacgtatg cacgttctct tcggcgaggt cgctgggttc gtggaagata 16440
aagcgccgcg tgtcggcgcc ggcctcgccg ccgtcgtccg cgcggcccac gcagtagcga 16500
aacagcaggc ttcgggccgt cggctcgttc acccgcccga acatcaccgc cgaagactgt 16560
acatccggcc gcaggctggc gttgtgcttc agccactggg gcgagaaaca cggaccctgg 16620
gggccccagc ggagggtgga tgcggtcgtg aggccccgcc ggagcagggc ccatagctgg 16680
cagtcggcct ggttttgcgt ggccgcctcg taaaacccca tgaggggccg gggcgccacg 16740
gcgtccgcgg cggccggggg cccgcggcgc gtcaggcgcc ataggtgccg accgagtccg 16800
cggtccacca tacccgcctc ctcgaggacc acggccaggg aacacagata atccaggcgg 16860
gcccagaggg gaccgatggc cagaggggcg cggacgccgc gcagcaaccc gcgcaggtgg 16920
cgctcgaacg tctcggctag tatatgggag ggcagcgcgt tggggatcac cgacgccgac 16980
cacatagagt caaggtccgg ggagtcggga tcggcgtccg ggtcgcgggc gtgggtgccc 17040

-continued ccaggagata gcggaatgtc tggggtcgga ggccctgagg cgtcagaaag tgccggcgac 17100
gcggcccggg gcttttcgtc tgcggtgtcg gtggcgtgct gatcacgtgg ggggttaacg 17160
ggcgaatggg agctcgggtc cacagctgat gtcgtctggg gtgggggggg caggggacgg 17220
aaggtggttg tcagcggaag actgttaggg cgggggcgct tggggggggct gtcggggcca 17280 cgaggggtgt cctcggccag ggcccaggga cgcttagtca cggtgcgtcc cggcggacat 17340
gctgggccta ccgtggactc catttccgag acgacgtggg gggagcggtg gttgagcgcg 17400
ccgccgggtg aacgctgatt ctcacgacag cgcgtgccgc gcgcacgggt tggtgtgaca 17460
caggcgggac accagcacca ggagaggctt aagctcggga ggcagcgcca ccgacgacag 17520
tatcgccttg tgtgtgtgct ggtaatttat acaccgatcc gtaaacgcgc gccgaatctt 17580
gggattgcgg aggtggcgcc ggatgccctc tgggacgtca tacgccaggc cgtgggtgtt 17640
ggtctcggcc gagttgacaa acagggctgg gtgcagcacg cagcgatagg cgagcagggc 17700
cagggcgaag tccggcgaca gctggttgtt aaaatactgg taaccgggaa accgggtcac 17760
gggtacgccc aggctcgggg cgacgtacac gctaaccacc aactccagca gcgtctggcc 17820
cagggcgtac aggtcaaccg ctaacccgac gtcgtgcttc aggcggtggt tggtaaattc 17880
ggcccgttcg ttgttaaggt atttcaccaa cagctccggg ggctggttat acccgtgacc 17940
caccagggtg tgaaagttgg ctgtggttag ggcggtgggc atgccaaaca tccgggggga 18000
cttgaggtcc ggctcctgga ggcaaaactg cccccgggcg atcgtggagt tggagttgag 18060
ggtgacgagg ctaaagtcgg cgaggacggc ccgccggagc gagacggcgt ccgaccgcag 18120
catgacgagg atgttggcgc acttgatatc caggtggctg atcccgcagg tggtgtttaa 18180
aaacacaacg gcgcgggcca gctccgtgaa gcactggtgg agggccgtcg agaccgaggg 18240
gtttgttgtg cgcagggacg ccagttggcc gatatactta ccgaggtcca tgtcgtacgc 18300
ggggaacact atctgtcgtt gttgcagcga gaacccgagg ggcgcgatga agccgcggat 18360
gttgtgggtg cggccggcgc gtagaacgca ctccccgacc aacagggtcg cgatgagctc 18420
aacggcaaac cactcctttt cctttatggt cttaacggca agcttatgtt cgcgaatcag 18480
ttggacgtca ccgtatcccc cagacccccc gaagcttcgg gccccgggga tctcgagggt 18540
cgtgtagtgt agggcggggt tgatggcgaa cacggggctg catagcttgc ggatgcgcgt 18600
gagggtgagg atgtgcgagg gggacgaggg gggtgcggtt aacgccgcct gggatctgcg 18660
caggggcggg cggttcagtt tggccgccgt accgggcgtc tcgggggacg cgcggcgatg 18720
agacgagcgg ctcattcgcc atcgggatag tcccgcgcga agccgctcgc ggaggccgga 18780
tcggtggcgg gacccgtggg aggagcggga gacggcggcg tcctggagag aggggccgct 18840
ggggcgcccg gaggccccgt gggggttgga gtgtacgtag gatgcgagcc aatccttgaa 18900
ggaccgttgg cgtgcacctt gggggctgag gttagctgcc acatgaccag caggtcgctg 18960
tctgcgggac tcatccatcc ttcggccagg tcgccgtctc cccacagaga agcgttggtc 19020
gctgcttcct cgagttgctc ctcctggtcc gcaagacgat cgtccacggc gtccaggcgc 19080
tcaccaagcg ccggatcgag gtaccgtcgg tgtgcggtta gaaagtcacg acgcgccgct 19140
tgctcctcca cgcgaatttt aacacaggtc gcgcgctgtc gcatcatctc taagcgcgcg 19200
cgggacttta gccgcgcctc caattccaag tgggccgcct ttgcagccat aaaggcgcca 19260
acaaaccgag gatcttgggt gctgacgccc tcccggtgca gctgcagggt ctggtccttg 19320
taaatctcgg ctcggaggtg cgtctcggcc aggcgtcggc gcagggccgc gtgggcggca 19380

-continued

```
tctcggtcca ttccgccacc ctgcgggcga cccggggggt gctctgatag tctcgcgtgc  19440
ccaaggcccg tgatcggggt acttcgccgc cgcgacccgc cacccggtgt gcgcgatgtt  19500
tggtcagcag ctggcgtccg acgtccagca gtacctggag cgcctcgaga aacagaggca  19560
acttaaggtg ggcgcggacg aggcgtcggc gggcctcacc atgggcggcg atgccctacg  19620
agtgcccttt ttagatttcg cgaccgcgac ccccaagcgc caccagaccg tggtccctgg  19680
cgtcgggacg ctccacgact gctgcgagca ctcgccgctc ttctcggccg tggcgcggcg  19740
gctgctgttt aatagcctgg tgccggcgca actaaagggg cgtgatttcg gggcgacca  19800
cacggccaag ctggaattcc tggcccccga gttggtacgg gcggtggcgc gactgcggtt  19860
taaggagtgc gcgccggcgg acgtggtgcc tcagcgtaac gcctactata gcgttctgaa  19920
tacgtttcag gccctccacc gctccgaagc ctttcgccag ctggtgcact ttgtgcggga  19980
ctttgcccag ctgctcaaaa cctccttccg ggcctccagc ctcacggaga ccacgggccc  20040
ccccaaaaaa cgggccaagg tggacgtggc cacccacggc cggacgtacg gcacgctgga  20100
gctgttccaa aaaatgatcc ttatgcacgc cacctacttt ctggccgccg tgctcctcgg  20160
ggaccacgcg gagcaggtca acacgttcct gcgtctcgtg tttgagatcc ccctgtttag  20220
cgacgcggcc gtgcgccact tccgccagcg cgccaccgtg tttctcgtcc cccggcgcca  20280
cggcaagacc tggtttctgg tgcccctcat cgcgctgtcg ctggcctcct ttcgggggat  20340
caagatcggc tacacggcgc acatccgcaa ggcgaccgag ccggtgtttg aggagatcga  20400
cgcctgcctg cggggctggt tcggttcggc ccgagtggac cacgttaaag gggaaaccat  20460
ctccttctcg tttccggacg ggtcgcgcag taccatcgtg tttgcctcca gccacaacac  20520
aaacgtaagt cctcttttct ttcgcatggc tctcccaagg ggccccgggt cgacccgacc  20580
cacacccacc cacccacata cacacacaac cagacgcggg aggaaagtct gccccgtggg  20640
cactgatttt tattcgggat cgcttgagga ggcccgggca acggcccggg caacggtggg  20700
gcaactcgta gcaaataggc gactgatgta cgaagagaag acacacaggc gccacccggc  20760
gctggtcggg ggatgttgt ccgcgccgca ccgtcccccg acgacctctt gcagacggtc  20820
cgtgatgcaa ggacggcggg gggcctgcag cagggtgacc gtatccacgg gatggccaaa  20880
gagaagcgga cacaggctag catcccccctg gaccgccagg gtacactggg ccatcttggc  20940
ccacagacac ggggcgacgc agggacagga ctccgttacg acggaggaga gccacagtgc  21000
gttggcggaa tcgatgtggg gcggcggggc gcaggactcg cagccccccg ggtggttggt  21060
gatcctggcc aggagccatc ccagatggcg ggccctgctt cccggtggac agagcgaccc  21120
caggtcgctg tccatggccc agcagtagat ctggccgctg gggaggtgcc accaggcccc  21180
cgggcccaag gcgcagcacg cgcccggctc cgggggggtc ttcgcgggga ccagatacgc  21240
gccatccagc tcgccgacca ctggctcctc cgcgagctgt tcggtggttg ggtcgggggt  21300
ttcctccggg ggggtggccg cccgtatgcg tgcgaacgtg agggtgcaca ggagcggggt  21360
cagggggtgc gtcacgctcc ggaggtggac gatcgcgcag tagcggcgct cgcggttaaa  21420
gaaaaagagg gcaaagaagg tgttcggggg caaccgcagc gccttggggc gcgtcagata  21480
cagaaaaatc tcgcagaaga gggcgcgccc ggggtctggg ttaggaaggg ccacctgaca  21540
cagaggctcg gtgaggaccg ttagacaccg aaagatcttg agccgctcgt ccgcccgaac  21600
gacgcgccac acaaagacgg agttgacaat gcgcgcgata gagtcgacgt ccgtccccag  21660
gtcgtcgact ctatcgcgcg tgccgcgagc tccggcccgg gaatccggcc ggggcaaggt  21720
ccccggggga ccaggcggcg ccaggggccg ccggggtccc agctgcgcca tgccgggggc  21780
```

gggggggaggg caaaccccag aggcgggggc caacggcgcg gggaggagtg ggtgggcgag 21840
gtggccgggg gaaggcgccc gctagcgaga ccggccgttc ccggacgaca ccttgcgaca 21900
aaacctaagg acagcggccc gcgcgacggg gtccgagagg ctaaggtagg ccgcgatgtt 21960
aatggtgaac gcaaagccgc cgggaaagac aactatgcca cagaggcggc gattaaaccc 22020
caggcagagg taggcgtagc tttccccggg caggtattgc tcgcagaccc tgcgtggggc 22080
tgtggagggg acggcctcca tgaagcgaca tttactctgc tcgcgtttac tgacgtcacc 22140
atccatcgcc acggcgattg gacgattgtt aagccgcagc gtgtctccgc ttgtgctgta 22200
gtagtcaaaa acgtaatggc cgtcggagtc ggcaaagcgg gccgggaggt cgtcgccgag 22260
cgggacgacc cgccgccccc gaccgccccg tccccccagg tgtgccagga cggccagggc 22320
atacgcggtg tgaaaaaagg cgtcgggggc ggtcccctcg acggcgcgca tcaggttctc 22380
gaggagaatg gggaagcgcc tggtcacctc ccccaaccac gcgcgttggt cggggccaaa 22440
gtcatagcgc aggcgctgtg agattcgcgg gccgccctga agcgcggccc ggatggcctg 22500
gcccagggcc cggaggcacg ccagatgtat gcgcgcggta aaggcgacct cggcggcgat 22560
gtcaaagggc ggcaggacgg ggcgcgggtg gcgcaggggc acctcgagcg cgggaaagcg 22620
tagcagcagc tccgcctgcc cagcgggaga cagctggtgg gggcgcacga cgcgttctgc 22680
ggcgcaggcc tcggtcaggg ccgtggccag cgccgaggac agcagcggag ggcgggcgcg 22740
tcgcccgccc cacgccacgg agttctcgta ggagacgacg acgaagcgct gcttggttcc 22800
gtagtggtgg cgcaggacca cggagataga acgacggctc cacagccagt ccggccggtc 22860
gccgccggcc agggcttccc atccgcgatc caaccactcg accagcgacc gcggctttgc 22920
ggtaccaggg gtaagggtta gaacgtcgtt caggatgtcc tcgcccccgg gcccgtgggg 22980
cgctggggcc acaaagcggc ccccgccggg gggctccaga cccgccagca ccgcatctgc 23040
gtcagccgcc cccatggcgc ccccgctgac ggcctggtga accagggcgc cctggcgtag 23100
ccccgatgca acgccacagg ccgcacgccc ggtccgcgct cggaccgggt ggcggcgggt 23160
gacgtcctgc actgcccgct gaaccaacgc gaggatctcc tcgttctcct gtgcgatgga 23220
cacgtcctgg gccgcggtcg tgtcgccgcc gggggccgtc agctgctcct ccggggagat 23280
gggggggtcg gacgccccga cgatgggcgg gtctgcgggc gcccccgcgt ggggccgggc 23340
caagggctgc ggacgcgggg acgcgctttc ccccagaccc atggacaggt gggccgcagc 23400
ctccttcgcg gccggcgggg cggcggcgcc aagcagagcg acgtagcggc acaaatgccg 23460
acagacgcgc atgatgcgcg tgctgtcggc cgcgtagcgc gtgttggggg ggacgagctc 23520
gtcgtaacta aacagaatca cgcgggcaca gctcgccccc gagccccacg caaggcgcag 23580
cgccgccacg gcgtacgggt catagacgcc ctgcgcgtca cacaccacgg gcagggagac 23640
gaacaacccc ccggcgctgg acgcacgcgg aaggaggcca gggtgtgccg gcacgacggg 23700
ggccagaagc tcccccaccg catccgcggg cacgtaggcg gcaaacgccg tgcaccacgg 23760
ggtacagtcg ccggtggcat gagcccgagt ctggatttcg acctggaagt ttgcggccgt 23820
cccgagtccg gggcggccgc gcatcagggc ggccagaggg attcccgcgg ccgccaggca 23880
ctcgctggat atgatgacgt gaaccaaaga ccgagggccg acccgggccg tggccgagat 23940
cgtctggacc tcgttggcca agtgcgcgtt catggttcgg gggtgggtgt gggtgtgtag 24000
gcgatgcggg tcccccgagt ccgcgggaag ggcgtgggtt tggcgcgcgt atgcgtattc 24060
gccaacggag gcgtgcgtgc ttatgcgcgg cgcgtttctt ctgtctctag ggaatccgag 24120

-continued

```
gccaggactt taacctgctc tttgtcgacg aggccaactt tattcgcccg gatgcggtcc  24180
agacgattat gggctttctc aaccaggcca actgcaagat tatcttcgtg tcgtccacca  24240
acaccgggaa ggccagtacg agctttttgt acaacctccg cggggccgca gacgagcttc  24300
tcaacgtggt gacctatata tgcgatgatc acatgccgag ggtggtgacg cacacaaacg  24360
ccacggcctg ttcttgttat atcctcaaca agcccgtttt catcacgatg gacggggcgg  24420
ttcgccggac cgccgatttg tttctggccg attccttcat gcaggagatc atcgggggcc  24480
aggccaggga gaccggcgac gaccggcccg ttctgaccaa gtctgcgggg gagcggtttc  24540
tgttgtaccg cccctcgacc accaccaaca gcggcctcat ggcccccgat ttgtacgtgt  24600
acgtggatcc cgcgttcacg gccaacaccc gagcctccgg gaccggcgtc gctgtcgtcg  24660
ggcggtaccg cgacgattat atcatcttcg ccctggagca ctttttctc cgcgcgctca  24720
cgggctcggc cccgccgac atcgcccgct gcgtcgtcca cagtctgacg caggtcctgg  24780
ccctgcatcc cggggcgttt cgcggcgtcc gggtggcggt cgagggaaat agcagccagg  24840
actcggccgt cgccatcgcc acgcacgtgc acacagagat gcaccgccta ctggcctcgg  24900
agggggccga cgcgggctcg ggccccgagc ttctcttcta ccactgcgag cctcccggga  24960
gcgcggtgct gtacccccttt ttcctgctca acaaacagaa gacgcccgcc tttgaacact  25020
ttattaaaaa gtttaactcc gggggcgtca tggcctccca ggagatcgtt tccgcgacgg  25080
tgcgcctgca gaccgacccg gtcgagtatc tgctcgagca gctaaataac ctcaccgaaa  25140
ccgtctcccc caacactgac gtccgtacgt attccggaaa acggaacggc gcctcggatg  25200
accttatggt cgccgtcatt atggccatct acctcgcggc ccaggccgga cctccgcaca  25260
cattcgctcc tatcacacgc gtctcgtgag cgcccaataa acacacccag gtatgctacg  25320
cacgaccacg gtgtcgtctg ttaagggggg ggggggaagg gggtgttggc gggaagcgtg  25380
ggaacacggg ggattctctc acgaccggca ccagtaccac ccccctgtga acacagaaac  25440
cccaacccaa atcccataaa catacgacac acaggcatat tttggaattt cttaggtttt  25500
tatttattta ggtatgctgg ggtttctccc tggatgccca cccccacccc cccgtgggtc  25560
tagccgggcc ttagggatag cgtataacgg gggccatgtc tccggaccgc acaacggccg  25620
cgccgtcaaa ggtgcacacc cgaaccacgg gagccagggc caaggtgtct cctagttggc  25680
ccgcgtgggt cagccaggcg acgagcgcct cgtaaagcgg cagccttcgc tctccatcct  25740
gcatcagggc cggggcttcg gggtgaatga gctgggcggc ctcccgcgtg acactctgca  25800
tctgcagtag agcgttcacg tacccgtcct gggcacttag cgcaaagagc cgggggatta  25860
gcgtaaggat gatggtggtt ccctccgtga tcgagtaaac catgttaagg accagcgatc  25920
gcagctcggc gtttacggga ccgagttgtt ggacgtccgc cagcagcgag aggcgactcc  25980
cgttgtagta cagcacgttg aggtctggca gccctccggg gtttctgggg ctggggttca  26040
ggtcccggat gcccctggcc acgagccgcg ccacgatttc gcgcgccagg ggcgatggaa  26100
gcggaacggg aaaccgcaac gtgaggtcca gcgaatccag gcgcacgtcc gtcgcttggc  26160
cctcgaacac gggcgggacg aggctgatgg ggtccccgtt acagagatct acgggggagg  26220
tgttgcgaag gttaacggtg ccggcgtggg tgaggcccac gtccaggggg caggcgacga  26280
ttcgcgtggg aagcacccgg gtgatgaccg cggggaagcg ccttcggtac gccagcaaca  26340
accccaacgt gtcgggactg acgcctccgg agacgaagga ttcgtgcgcc acgtcggcca  26400
gcgtcagttg ccggcggatg gtcggcagga ataccacccg cccttcgcag cgctgcagcg  26460
ccgccgcatc ggggcgcgag atgcccgagg gtatcgcgat gtcagtttca aagccgtccg  26520
```

-continued

```
ccagcatggc gccgatccac gcggcaggga gtgcagtggt ggttcgggtg gcgggaggag  26580
cgcggtgggg gtcagcggcg tagcagagac gggcgaccaa cctcgcatag gacggggggt  26640
gggtcttagg gggttgggag gcgacaggga ccccagagca tgcgcgggga ggtctgtcgg  26700
gcccagacgc accgagagcg aatccgtccg cggagtcccg gcttgggttt tatggggccc  26760
ggccctcgga atcgcggctt gtcggcgggg acaaaggggg cggggctagg ggcttgcgga  26820
aacagaagac gcgtgggata aaagaatcgc actaccccaa ggaagggcgg ggcggtttat  26880
tacagagcca gtcccttgag cggggatgcg tcatagacga gatactgcgc gaagtgggtc  26940
tcccgcgcgt gggcttcccc gttgcgggca ctgcggagga gggcggggtc gctggcgcag  27000
gtgagcgggt aggcctcctg aaacaggcca cacgggtcct ccacgagttc gcggcacccc  27060
ggggggcgct taaactgtac gtcgctggcg gcggtggccg tggacaccgc cgaacccgtc  27120
tccacgatca ggcgctccag gcagcgatgt ttggcggcga tgtcggccga cgtaaagaac  27180
ttaaagcagg ggctgagcac cggcgaggcc ccgttgaggt ggtaggcccc gttatagagc  27240
aggtccccgt acgaaaatcg ctgcgacgcc cacgggttgg ccgtggccgc gaaggcccgg  27300
gacgggtcgc tctggccgtg gtcgtacatg agggcggtga catccccctc cttgtccccc  27360
gcgtaaacgc ccccggcggc gcgtccccgg gggttgcagg gccggcggaa gtagttgacg  27420
tcggtcgaca cgggggtggc gataaactca cacacggcgt cctggccgtg gtccatccct  27480
gcgcgccgcg gcacctgggc gcacccgaac acggggacgg gctgggccgg ccccaggcgg  27540
tttcccgcca cgaccgcgtt ccgcaggtac acggctgccg cgttgtccag gagaggggga  27600
gccccgcggc ccaggtaaaa gttttgggga aggttgccca tgtcggtgac ggggttgcgg  27660
acggttgccg tggccacgac ggcggtgtag cccacgccca ggtccacgtt cgcgcgcggc  27720
tgggtgagcg tgaagtttac ccccccgcca gtttcgtgcc gggccacctg gagctggccc  27780
aggaagtacg cctccgacgc gcgctccgag aacagcacgt tctcagtcac aaagcggtcc  27840
tgtcggacga cggtgaaccc aaacccggga tggaggcccg tcttgagctg atgatgcaag  27900
gccacgggac tgatcttgaa gtaccccgcc atgagcgcgt aggtcagcgc gttctccccg  27960
gccgcgctct cgcggacgtg ctgcacgacg ggctgtcgga tcgacgaaaa gtagttggcc  28020
cccagagccg gggggaccag ggggacctgc cgcgacaggt cgcgcagggc cggggggaaa  28080
ttgggcgcgt tcgccacgtg gtcggccccg gcgaacagcg cgtggacggg gagggggtaa  28140
aaatagtcgc cattttggat ggtatggtcc agatgctggg gggccatcag caggattccg  28200
gcgtgcaacg ccccgtcgaa tatgcgcatg ttggtggtgg acgcggtgtt ggcgcccgcg  28260
tcgggcgccg ccgagcagag cagcgccgtt gtgcgttcgg ccatgttgtg ggccagcacc  28320
tgcagcgtga gcatggcggg cccgtccact accacgcgcc cgttgtgaaa catggcgttg  28380
accgtgttgg ccaccagatt ggccgggtgc agggggtgcg cggggtccgt cacggggtcg  28440
ctggggcact cctcgccggg ggcgatctcc gggaccacca tgttctgcag ggtggcgtat  28500
acgcggtcga agcgaacccc cgcggtgcag cagcggcccc gcgagaaggc gggcaccatc  28560
acgtagtagt aaatcttgtg gtgcacggtc cagtccgccc cccggtgcgg ccggtcatcc  28620
gcggcgtccg cggctcgggc ctgggtgttg tgcagcagct ggccgtcgtt gcggttgaag  28680
tccgcggtcg ccacgttaca tgccgccgcg tacacggggt cgtggccccc cgcgctaacc  28740
cggcagtcgc gatggcggtc cagggccgcg cgccgcatca gggcgtcaca gtcccacacg  28800
aggggtggca gcagcgccgg gtctcgcatt aggtgattca gctcggcttg cgcctgcccg  28860
```

-continued

```
cccagctccg ggccggtcag ggtaaagtca tcaaccagct gggccagggc ctcgacgtgc  28920
gccaccaggt cccggtacac ggccatgcac tcctcgggaa ggtctccccc gaggtaggtc  28980
acgacgtacg agaccagcga gtagtcgttc acgaacgccg cgcaccgcgt gttgttccag  29040
tagctggtga tgcactggac cacgagccgg gccagggcgc agaagacgtg ctcgctgccg  29100
tgtatggcgg cctgcagcag gtaaaacacc gccgggtagt tgcggtcgtc gaacgccccg  29160
cgaacggcgg cgatggtggc gggggccatg gcgtggcgtc ccaccccag ctccaggccc  29220
cgggcgtccc ggaacgccgc cggacatagc gccaggggca agttgccgtt caccacgcgc  29280
caggtggcct ggatctcccc cgggccggcc gggggaacgt cccccccgg cagctccacg  29340
tcggccaccc ccacaaagaa gtcgaacgcg gggtgcagct caagagccag gttggcgttg  29400
tcgggctgca taaactgctc cggggtcatc tggccttccg cgacccatcg gacccgcccg  29460
tgggccaggc gctgccccca ggcgttcaaa aacagctgct gcatgtctgc ggcggggccg  29520
gccggggccg ccacgtacgc cccgtacgga ttggcggctt cgacggggtc gcggttaagg  29580
cccccgaccg ccgcgtcaac gttcatcagc gaagggtggc acacggtccc gatcgcgtgt  29640
tccagagaca ggcgcagcac ctggcggtcc ttcccccaaa aaaacagctg gcggggcggg  29700
aaggcgcggg gatccgggtg gccgggggcg gggactaggt ccccggcgtg cgcggcaaac  29760
cgttccatga ccggattgaa caggcccagg ggcaggacga acgtcaggtc catggcgccc  29820
accaggggt agggaacgtt ggtggcggcg tagatgcgct tctccagggc ctccagaaag  29880
accagcttct cgccgatgga caccagatcc gcgcgcacgc gcgtcgtctg gggggcgctc  29940
tcgagctcgt ccagcgtctg ccggttcagg tcgagctgct cctcctgcat ctccagcagg  30000
tggcggccca cgtcgtccag acttcgcacg gccttgccca tcacgagcgc cgtgaccagg  30060
ttggccccgt tcaggaccat ctcgccgtac gtcaccggca cgtcggcttc ggtgtcctcc  30120
actttcagga aggactgcag gaggcgctgt ttgatcgggg cggtggtgac gagcaccccg  30180
tcgaccggcc gcccgcgcgt gtcggcatgc gtcagacggg gcacggccac ggagggctgc  30240
gtggccgtgg tgaggtccac gagccaggcc tcgacggcct cccggcggtg gcccgccttg  30300
cccaggaaaa agctcgtctc gcagaagctt cgctttagct cggcgaccag ggtcgcccgg  30360
gccaccctgg tggccaggcg gccgttgtcc aggtatcgtt gcatcggcaa caacaaagcc  30420
aggggcggcg ccttttccag cagcacgtgc agcatctggt cggccgtgcc gcgctcaaac  30480
gccccgagga cggcctggac gttgcgagcg agctgttgga tggcgcgcaa ctggcgatgc  30540
gcgccgatac ccgtcccgtc cagggcctcc cccgtgagca gggcgatggc ctcggtggcc  30600
aggctgaagg cggcgttcag ggcccggcgg tcgataatct tggtcatgta attgtgtgtg  30660
ggttgctcga tggggtgcgg gccgtcgcgg gcaatcagcg gctggtggac ctcgaactgt  30720
acgcgcccct cgttcatgta ggccagctcc ggaaacttgg tacacacgca cgccaccgac  30780
aacccgagct ccagaaagcg cacgagcgac agggtgttgc aatacgaccc cagcagggcg  30840
tcgaactcga cgtcgtacag gctgtttgca tcggagcgca cgcgggaaaa aaaatcaaac  30900
aggcgtcgat gcgacgccac ctcgatcgtg ctaaggaggg acccggtcgg caccatggcc  30960
gcggcatacc ggtatcccgg agggtcgcgg ttgggagcgg ccatggggtc gcgtggagat  31020
cggctgtctc tagcgatatt ggcccgggga ggctaagatc caccccaacg cccggccacc  31080
cgtgtacgtg cccgacggcc caaggtccac cgaaagacac gacgggcccg gacccaaaaa  31140
ggcgggggat gctgtgtgag aggccgggtg ccggtcgggg gggaaaggca ccgggagaag  31200
gctgcggcct cgttccagga gaacccagtg tccccaacag acccggggac gtgggatccc  31260
```

```
aggccttata taccccccccc cccgccccac ccccgttaga acgcgacggg tgcattcaag  31320
atggccctgg tccaaaagcg tgccaggaag aaattggcag aggcggcaaa gctgtccgcc  31380
gccgccaccc acatcgaggc cccggccgcg caggctatcc ccagggcccg tgtgcgcagg  31440
ggatcggtgg gcggcagcat ttggttggtg gcgataaagt ggaaaagccc gtccggactg  31500
aaggtctcgt gggcggcggc gaacaaggca cacagggccg tgcctcccaa aaacacggac  31560
atcccccaaa acacgggcgc cgacaacggc agacgatccc tcttgatgtt aacgtacagg  31620
aggagcgccc gcaccgccca cgtaacgtag tagccgacga tggcggccag gatacaggcc  31680
ggcgccacca cccttccggt cagcccgtaa tacatgcccg ctgccaccat ctccaacggc  31740
ttcaggacca aaaacgacca aaggaacaga atcacgcgct ttgaaaagac cggctgggta  31800
tggggcggaa gacgcgagta tgccgaactg acaaaaaaat cagaggtgcc gtacgaggac  31860
aatgaaaact gttcctccag cggcagttct ccctcctccc ccccgaaggc ggcctcgtcg  31920
accagatctc gatccaccag aggaaggtca tcccgcatgg tcatggggtg tgcggtggag  31980
gtggggagac cgaaaccgca aagggtcgct tacgtcagca ggatcccgag atcaaagaca  32040
cccgggttct tgcacaaaca ccacccgggt tgcatccgcg gaggcgagtg ttttgataag  32100
gccgttccgc gccttgatat aacctttgat gttgaccaca aaacccggaa tttacgccta  32160
cgccccaatg cccacgcaag atgaggtagg taaccccccc gtgggtgtga cgttgcgttt  32220
agttcattgg aggccaaggg gaaaaatggg gtggggagga aacggaaaac ccagtaggcc  32280
gtgtcgggaa cacgcccggg gttgtcctca aaaggcaggg tccatactac ggaagccgtc  32340
gttgtattcg agacctgcct gtgcaacgca cgtcggggtt gcctgtgtcc ggttcggccc  32400
ccaccgcgtg cggcacgcac gaggacgagt ccgcgtgctt tattggcgtt ccaagcgttg  32460
ccctccagtt tctgttgtcg gtgttccccc atacccacgc ccacatccac cgtagggggc  32520
ctctgggccg tgttacgtcg ccgcccgcga tggagcttag ctacgccacc accatgcact  32580
accgggacgt tgtgttttac gtcacaacgg accgaaaccg ggcctacttt gtgtgcgggg  32640
ggtgtgttta ttccgtgggg cggccgtgtg cctcgcagcc cggggagatt gccaagtttg  32700
gtctggtcgt tcgagggaca ggcccagacg accgcgtggt cgccaactat gtacgaagcg  32760
agctccg                                                             32767
```

<210> SEQ ID NO 849
<211> LENGTH: 32767
<212> TYPE: DNA
<213> ORGANISM: Artificial Sequence
<220> FEATURE:
<223> OTHER INFORMATION: recombinant viral vector ONCR-157

<400> SEQUENCE: 849

```
aaaaaagctg aacgagaaac gtaaaatgat ataaatatca atatattaaa ttagattttg     60
cataaaaaac agactacata atactgtaaa acacaacata tccagtcact atgaatcaac    120
tacttagatg gtattagtga cctgtagtcg accgacagcc ttccaaatgt tcttcgggtg    180
atgctgccaa cttagtcgac cgacagcctt ccaaatgttc ttctcaaacg gaatcgtcgt    240
atccagccta ctcgctattg tcctcaatgc cgtattaaat cataaaaaga aataagaaaa    300
agaggtgcga gcctcttttt tgtgtgacaa aataaaaaca tctacctatt catatacgct    360
agtgtcatag tcctgaaaat catctgcatc aagaacaatt tcacaactct tatacttttc    420
tcttacaagt cgttcggctt catctggatt ttcagcctct atacttacta aacgtgataa    480
```

-continued

```
agtttctgta atttctactg tatcgacctg cagactggct gtgtataagg gagcctgaca    540
tttatattcc ccagaacatc aggttaatgg cgtttttgat gtcattttcg cggtggctga    600
gatcagccac ttcttccccg ataacggaga ccggcacact ggccatatcg gtggtcatca    660
tgcgccagct ttcatccccg atatgcacca ccgggtaaag ttcacgggag actttatctg    720
acagcagacg tgcactggcc agggggatca ccatccgtcg cccgggcgtg tcaataatat    780
cactctgtac atccacaaac agacgataac ggctctctct tttataggtg taaaccttaa    840
actgcatttc accagcccct gttctcgtca gcaaaagagc cgttcatttc aataaaccgg    900
gcgacctcag ccatcccttc ctgattttcc gctttccagc gttcggcacg cagacgacgg    960
gcttcattct gcatggttgt gcttaccaga ccggagatat tgacatcata tatgccttga   1020
gcaactgata gctgtcgctg tcaactgtca ctgtaatacg ctgcttcata gcatacctct   1080
ttttgacata cttcgggtat acatatcagt atatattctt ataccgcaaa aatcagcgcg   1140
caaatacgca tactgttatc tggcttttag taagccggat ccacgcggcg tttacgcccc   1200
ccctgccact catcgcagta ctgttgtaat tcattaagca ttctgccgac atggaagcca   1260
tcacaaacgg catgatgaac ctgaatcgcc agcggcatca gcaccttgtc gccttgcgta   1320
taatatttgc ccatggtgaa aacgggggcg aagaagttgt ccatattggc cacgtttaaa   1380
aaggccgtaa tatccagctg aacggtctgg ttataggtac attgagcaac tgactgaaat   1440
gcctcaaaat gttctttacg atgccattgg gatatatcaa cggtggtata tccagtgatt   1500
tttttctcca ttttagcttc cttagctcct gaaaatctcg ataactcaaa aaatacgccc   1560
ggtagtgatc ttatttcatt atggtgaaag ttggaacctc ttacgtgccg atcaacgtct   1620
cattttcgcc aaaagttggc ccagggcttc ccggtatcaa cagggacacc aggatttatt   1680
tattctgcga agtgatcttc cgtcacaggt atttattcgg cgcaaagtgc gtcgggtgat   1740
gctgccaact tagtcgacta caggtcacta ataccatcta agtagttgat tcatagtgac   1800
tggatatgtt gtgttttaca gtattatgta gtctgttttt tatgcaaaat ctaatttaat   1860
atattgatat ttatatcatt ttacgtttct cgttcagctt tcttgtacaa agtggtttta   1920
atggaccgcc cgcaaggggg gggggggcatt tcagtgtcgg gtgacgagcg cgatccggcc   1980
gggatcctag gaccccaaaa gtttgtctgc gtattccagg gcggggctca gttgaatctc   2040
ccgcagcacc tctaccagca ggtccgcggt gggctggaga aactcggccg tcccggggca   2100
ggcggttgtc gggggtggag gcgcggcgcc caccccgtgt gccgcgcctg gcgtctcctc   2160
tgggggcgac ccgtaaatgg ttgcagtgat gtaaatggtg tccgcggtcc agaccacggt   2220
caaaatgccg gccgtggcgc tccgggcgct ttcgccgcgc gaggagctga cccaggagtc   2280
gaacggatac gcgtacatat gggcgtccca cccgcgttcg agcttctggt tgctgtcccg   2340
gcctataaag cggtaggcac aaaattcggc gcgacagtcg ataatcacca acagcccaat   2400
gggggtgtgc tggataacaa cgcctccgcg cggcaggcgg tcctggcgct cccggccccg   2460
taccatgatc gcgcgggtgc cgtactcaaa aacatgcacc acctgcgcgg cgtcgggcag   2520
tgcgctggtc agcgaggccc tggcgtggca taggctatac gcgatggtcg tctgtggatt   2580
ggacatctcg cggtgggtag tgagtccccc gggccgggtt cggtggaact gtaaggggac   2640
ggcgggttaa tagacaatga ccacgttcgg atcgcgcaga gccgatagta tgtgctcact   2700
aatgacgtca tcgcgctcgt ggcgctcccg gagcggattt aagttcatgc gaaggaattc   2760
ggaggaggtg gtgcgggaca tggccacgta cgcgctgttg aggcgcaggt tgccgggcgt   2820
aaagcagatg gcgaccttgt ccaggctaag gccctgggag cgcgtgatgg tcatggcaag   2880
```

-continued

```
cttggagctg atgccgtagt cggcgtttat ggccatggcc agctccgtag agtcaatgga   2940
ctcgacaaac tcgctgatgt tggtgttgac gacggacatg aagccgtgtt ggtcccgcaa   3000
gaccacgtaa ggcagggggg cctcttccag taactcggcc acgttggccg tcgcgtgccg   3060
cctccgcagc tcgtccgcaa aggcaaacac ccgtgcgtac gtgtatccca tgagcgtata   3120
attgtccgtc tgcagggcga cggacatcag ccccccgcgc ggcgagccgg tcagcatctc   3180
gcagccccgg aagataacgt tgtccacgta cgtgctaaag gggcgactt caaatgcctc    3240
cccgaagagc tcttggagga ttcggaatct cccgaggaag gcccgcttca gcagcgcaaa   3300
ctgggtgtga acggcggcgg tggtctccgg ttccccgggg gtgtagtggc agtaaaacac   3360
gtcgagctgt tgttcgtcca gccccgcgaa aataacgtcg aggtcgtcgt cgggaaaatc   3420
gtccgggccc ccgtcccgcg gccccagttg cttaaaatca aacgcacgct cgccgggggc   3480
gcctgcgtcg gccattaccg acgcctgcgt cggcaccccc gaagatttgg ggcgcagaga   3540
cagaatctcc gccgttagtt ctcccatgcg ggcgtaggcg agggtcctct gggtcgcatc   3600
caggcccggg cgctgcagaa agttgtaaaa ggagataagc ccgctaaata tgagccgcga   3660
caggaacctg taggcaaact ccaccgaagt ctccccctga gtctttacaa agctgtcgtc   3720
acgcaacact gcctcgaagg cccggaacgt cccactaaac ccaaaaacca gttttcgcag   3780
gcgcgcggtc accgcgatct ggctgttgag gacgtaagtg acgtcgttgc gggccacgac   3840
cagctgctgt ttgctgtgca cctcgcagcg catgtgcccc gcgtcctggt cctggctctg   3900
cgagtagttg gtgatgcggc tggcgttggc cgtgagccac ttttcaatcg tcaggccggg   3960
ctggtgtgtc agccgtcggt attcgtcaaa ctccttgacc gacacgaacg taagcacggg   4020
gagggtgaac acgacgaact ccccctcacg ggtcaccttc aggtaggcgt ggagcttggc   4080
catgtacgcg ctcacctctt tgtgggagga gaacagccgc gtccagccgg ggaggttggc   4140
ggggttggtg atgtagtttt ccgggacgac gaagcgatcc acgaactgca tgtgctcctc   4200
ggtgatgggc aggccgtact ccagcacctt catgaggtta ccgaactcgt gctcgacgca   4260
ccgtttgttg ttaataaaaa tggcccagct atacgagagg cgggcgtact cgcgcagcgt   4320
gcggttgcag atgaggtacg tgagcacgtt ctcgctctgg cggacggaac accgcagttt   4380
ctggtgctcg aaggtcgact ccagggacgc cgtctgcgtc ggcgagccca cacacaccaa   4440
cacgggccgc aggcgggccg cgtactgggg ggtgtggtac agggcgttaa tcatccacca   4500
gcaatacacc acggccgtga ggaggtgacg cccaaggagc ccggcctcgt cgatgacgat   4560
cacgttgctg cgggtaaagg ccggcagcgc cccgtgggtg gccggggcca accgcgtcag   4620
ggcgccctcg gccaacccca gggtccgttc cagggcggcc agggcgcgaa actcgttccg   4680
caactcctcg cccccggagg cggccagggc gcgcttcgtg aggtccaaaa tcacctccca   4740
gtagtacgtc agatctcgtc gctgcaggtc ctccagcgag gcggggttgc tggtcagggt   4800
gtacgggtac tgtcccagtt gggcctggac gtgattcccg cgaaacccaa attcatgaaa   4860
gatggtgttg atgggtcggc tgagaaaggc gcccgagagt ttggcgtaca tgttttgggc   4920
cgcaatgcgc gtggcgcccg tcaccacaca gtccaagacc tcgttgattg tctgcacgca   4980
cgtgctcttt ccggagccag cgttgccggt gataagatac accgcgaacg gaaactccct   5040
gaggggcagg cctgcggggg actctaaggc cgccacgtcc cggaaccact gcagatgggg   5100
cacttgcgct ccgtcgagct gttgttgcga gagctctcgg atgcgcttaa ggattggctg   5160
caccccgtgc atagacgtaa aatttaaaaa ggcctcggcc ctccctggaa cggctggtcg   5220
```

-continued gtccccgggt tgctgaaggt gcggcgggcc gggtttctgt ccgtctagct ggcgctcccc 5280
gccggccgcc gccatgaccg caccacgctc gcgggccccc actacgcgtg cgcgggggga 5340
cacggaagcg ctgtgctccc ccgaggacgg ctgggtaaag gttcacccca gccccggtac 5400
gatgctgttc cgcgagattc tccacgggca gctggggtat accgagggcc agggggtgta 5460
caacgtcgtc cggtccagcg aggcgaccac ccggcagctg caggcggcga tctttcacgc 5520
gctcctcaac gccaccactt accgggacct cgaggcggac tggctcggcc acgtggcggc 5580
ccgcggtctg cagccccaac ggctggttcg ccggtacagg aacgcccggg aggcggatat 5640
cgccggggtg gccgagcggg tgttcgacac gtggcggaac acgcttagga cgacgctgct 5700
ggactttgcc cacgggttgg tcgcctgctt tgcgccgggc ggcccgagcg gcccgtcaag 5760
cttccccaaa tatatcgact ggctgacgtg cctggggctg gtccccatat tacgcaagcg 5820
acaagaaggg ggtgtgacgc agggtctgag ggcgtttctc aagcagcacc cgctgacccg 5880
ccagctggcc acggtcgcgg aggccgcgga gcgcgccggc cccgggtttt ttgagctggc 5940
gctggccttc gactccacgc gcgtggcgga ctacgaccgc gtgtatatct actacaacca 6000
ccgccggggc gactggctcg tgcgagaccc catcagcggg cagcgcggag aatgtctggt 6060
gctgtggccc cccttgtgga ccggggaccg tctggtcttc gattcgcccg tccagcggct 6120
gtttcccgag atcgtcgcgt gtcactccct ccgggaacac gcgcacgtct gccggctgcg 6180
caataccgcg tccgtcaagg tgctgctggg gcgcaagagc gacagcgagc gcggggtggc 6240
cggtgccgcg cgggtcgtta acaaggtgtt gggggaggac gacgagacca aggccgggtc 6300
ggccgcctcg cgcctcgtgc ggcttatcat caacatgaag ggcatgcgcc acgtaggcga 6360
cattaacgac accgtgcgtt cctacctcga cgaggccggg gggcacctga tagacgcccc 6420
ggccgtcgac ggtaccctcc ctggattcgg caagggcgga aacagccgcg ggtctgcggg 6480
ccaggaccag ggggggcggg cgccgcagct tcgccaggcc ttccgcacgg ccgtggttaa 6540
caacatcaac ggcgtgttgg agggctatat aaataacctg tttggaacca tcgagcgcct 6600
gcgcgagacc aacgcgggcc tggcgaccca attgcaggag cgcgaccgcg agctccggcg 6660
cgcaacagcg ggggccctgg agcgccagca gcgcgcggcc gacctggcgg ccgagtccgt 6720
gaccggtgga tgcggcagcc gccctgcggg ggcggacctg ctccgggccg actatgacat 6780
tatcgacgtc agcaagtcca tggacgacga cacgtacgtc gccaacagct ttcagcaccc 6840
gtacatccct tcgtacgccc aggacctgga gcgcctgtcg cgcctctggg agcacgagct 6900
ggtgcgctgt tttaaaattc tgtgtcaccg caacaaccag ggccaagaga cgtcgatctc 6960
gtactccagc ggggcgatcg ccgcattcgt cgccccctac tttgagtcag tgcttcgggc 7020
cccccgggta ggcgcgccca tcacgggctc cgatgtcatc ctgggggagg aggagttatg 7080
ggatgcggtg tttaagaaaa cccgcctgca aacgtacctg acagacatcg cggccctgtt 7140
cgtcgcggac gtccagcacg cagcgctgcc cccgcccccc tccccggtcg gcgccgattt 7200
ccggcccggc gcgtccccgc ggggccggtc cagatcgcgg tcgcccggaa gaactgcgcg 7260
aggcgcgccg gaccagggcg ggggcatcgg gcaccgggat ggccgccgcg acggccgacg 7320
atgaggggtc ggccgccacc atcctcaagc aggccatcgc cggggaccgc agcctggtcg 7380
aggcggccga ggcgattagc cagcagacgc tgctccgcct ggcctgcgag gtgcgccagg 7440
tcggcgaccg ccagccgcgg tttaccgcca ccagcatcgc gcgcgtcgac gtcgcgcctg 7500
ggtgccggtt gcggttcgtt ctggacggga gtcccgagga cgcctatgtg acgtcggagg 7560
attactttaa gcgctgctgc ggccagtcca gttatcgcgg cttcgcggtg gcggtcctga 7620

-continued

```
cggccaacga ggaccacgtg cacagcctgg ccgtgccccc cctcgttctg ctgcaccggt   7680
tctccctgtt caaccccagg gacctcctgg actttgagct tgcctgtctg ctgatgtacc   7740
tggagaactg cccccgaagc cacgccaccc cgtcgacctt tgccaaggtt ctggcgtggc   7800
tcggggtcgc gggtcgccgc acgtccccat tcgaacgcgt tcgctgcctt ttcctccgca   7860
gttgccactg ggtcctaaac acactcatgt tcatggtgta cgtaaaaccg ttcgacgacg   7920
agttcgtcct gccccactgg tacatggccc ggtacctgct ggccaacaac ccgccccccg   7980
ttctctcggc cctgttctgt gccaccccga cgagctcctc attccggctg ccggggccgc   8040
ccccccgctc cgactgcgtg gcctataacc ccgccgggat catggggagc tgctgggcgt   8100
cggaggaggt gcgcgcgcct ctggtctatt ggtggctttc ggagacccca aaacgacaga   8160
cgtcgtcgct gttttatcag ttttgttgaa ttttaggaaa taaacccggt tttgtttctg   8220
tggcctcccg acggatgcgc gtgtccttcc tccgtcttgg tgggtgggtg tctgtgtatc   8280
gcgtcccatc tgtgcggaga ggggggggcat gtcggcacgt attcggacag actcaagcac   8340
acacggggga gcgctcttgt ctcagggcaa tgtttttatt ggtcaaactt ggttattgct   8400
taagaatacg cgtagttgat cgtaccgtga gtaataatgt gactgtactg catcaggaac   8460
tgattggaat tctcgtaccg tgagtaataa tgtgggggta ctgcatcagg aactgattgg   8520
aatagttatt gcttaagaat acgcgtagta attactgcat caggaactga ttggatttat   8580
cgtaccgtga gtaataatgt ggcggttatt gcttaagaat acgcgtaggc tttcgtaccg   8640
tgagtaataa tgtggtcgta ctgcatcagg aactgattgg aagtcttatt gcttaagaat   8700
acgcgtagca tatcaggcaa acagaaacga catcttgtcg tcaaagggat acacaaactt   8760
ccccccctct ccccatactc ccgccagcac cccggtaaac accaactcaa tctcgcgcag   8820
gatttcgcgc aggtgatgag cgcagtccac ggggggggagc acaaggggcc gcgggtatag   8880
atcgacgggg acgccgaccg actccccgcc tccgggacag acacgcacga cgcgccgcca   8940
gtagtgctct gcgtccagca aggcgccgcc gcggaaggca gtgggggggca aggggtcgct   9000
ggcctcaaag gggacaccc gaacgctcca gtactccgcg tccaaccgtt tattaaacgc   9060
gtccaagata aggcggtcgc aggcgtcctc cataaggccc cgggccgtga gtgcgtcctc   9120
ctccggcacg catgccgttg tcaggcccag gacccgtcgc agcgtgtcgc gtacgacccc   9180
tgccgccgtg gtgtacgcgg gcccgcggag aggaaatccc ccaagatggt cagtgttgtc   9240
gcgggagttc cagaaccaca ctcccgcctg gctccaggcg actgcgtggg tgtagacgcc   9300
ctcgagggcc aggcacagtg ggtgccgcag ccggacggcg ttggccctaa gcacggctcc   9360
cacggccgtc tcgatggccc gccgggcgtc ctcgatcacc ccggaagccg catccgcgtc   9420
ttgggggtcc acgttaaaga caccccagaa cgcaccccca tcgcccccgc agaccgcgaa   9480
cttcaccgag ctggccgtct cctcgatctg caggcagacg gcggccatta ccccacccag   9540
gagctgccgc agcgcagggc aggcgttgca cgtgtccggg accaggcgct ccaagacggc   9600
cccggcccag ggctctgagg gagcggccac caccagcgcg tccagtcttg ctaggcccgt   9660
ccggccgtgg gggtccgcca gcccgctccc cccgaggtcg gccagggccg ccaggagctg   9720
ggcgcgaagt ccggggaagc aaaaccgcgc cgtccagacg ggcccgacgg ccgcgggcgg   9780
gtctaacagt tggatgattt tagtggcggg atgccaccgc gccaccgcct cccgcaccgc   9840
gggcaggagg catccggctg ccgccgaggc cacgccgggc caggctcgcg gggggaggac   9900
gaccctggcc cccaccgcgg gccaggcccc caggagcgcg gcgtaagcgg ccgcggcccc   9960
```

-continued gcgcaccagg tcccgtgccg actcggccgt ggccggcacg gtgaacgtgg gccaacccgg 10020
aaaccccagg acggcaaagt acgggacggg tccccccgg acctcaaact cgggccccag 10080
aaaggcaaag acgggggcca gggccccggg ggcggcgtgg accgtggtat gccactgccg 10140
gaaaagggcg acgagcgccg gcgcggagaa cttctcgccg gcgcttacaa agtagtcgta 10200
atcgcggggc agcagcaccc gtgccgtgac tcgttgcggg tgcccgcgtg gccgcaggcc 10260
cacctcgcac acctcgacca ggtccccgaa cgcgccctcc ttcttgatcg gcggaaacgc 10320
aagagtctgg tattcgcgcg caaatagcgc ggttccggtg gtgatgttaa cggtcagcga 10380
agcggcggac gcgcactggg gggtgtcgcg aatggccgcc aggcgcgccc acgccagccg 10440
cgcgtcggga tgctcggcaa cgcgcgccgc cagggccata gggtcgatgt caatgttggc 10500
ctccgcgacc aggagagcgg cgcgaggggc ggcgggcggg ccccacgacg ctctctcaac 10560
tttcaccacc agtcccgtgc gtgggtccga gccgatacgc agcggggcga acagggccac 10620
cggcccggtc tggcgctcca gggccgccag gacgcacgcg tacagcgccc gccacagagt 10680
cgggttctcc aggggctcca gcggggaggc ggccggcgtc gtcgcggcgc gggcggccgc 10740
cacgacggcc tggacggaga cgtccgcgga gccgtagaaa tcccgcagct ccgtcgcggt 10800
gacggagacc tccgcaaagc gcgcgcgacc ctcccctgcg gcgttgcgac atacaaaata 10860
caccagggcg tggaagtact cgcgagcgcg ggggggcagc cataccgcgt aaagggtaat 10920
ggcgctgacg ctctcctcca cccacacgat atctgcggtg tccatcgcac ggcccctaag 10980
gatcacgggc ggtctgtggg tcccatgctg ccgtgcctgg ccgggcccgg tgggtcgcgg 11040
aaaccggtga cggggggggg gcggtttttg gggttggggt gggggtggga aacggcccgg 11100
gtccgggggc caacttggcc cctcggtgcg ttccggcaac agcgccgccg gtccgcggac 11160
gaccacgtac cgaacgagtg cggtcccgag acttataggg tgctaaagtt caccgccccc 11220
tgcatcatgg gccaggcctc ggtggggagc tccgacagcg ccgcctccag gatgatgtca 11280
gcgttggggt tggcgctgga tgagtgcgtg cgcaaacagc gcccccacgc gggcacgcgt 11340
agcttgaagc gcgcgcccgc aaactcccgc ttgtgggcca taagcagggc gtacagctgc 11400
ctgtgggtcc ggcaggcgct gtggtcgatg tggtgggcgt ccaacaaccc cacgattgtc 11460
tgtttggtga ggtttttaac gcgccccgcc ccgggaaacg tctgcgtgct tttggccatc 11520
tgcacgccaa acagttcgcc ccagattatc ttgaacagcg ccaccgcgtg gtccgtctcg 11580
ctaacggacc cgcgcggggg acagccgctt agggcgtcgg cgacgcgctt gacggcttcc 11640
tccgagagca gaagtccgtc ggttacgtta cagtggccca gttcgaacac cagctgcatg 11700
tagcggtcgt agtgggggt cagtaggtcc agcacgtcat cggggccgaa ggtcctccca 11760
gatcccccgg ccgccgagtc ccaatgcagg cgcgcggcca tggtgctgca caggcacaac 11820
agctcccaga cgggggttac gttcagggtg gggggcaggg ccacgagctc cagctctccg 11880
gtgacgttga tcgtggggat gacgcccgtg gcgtagtggt catagatccg ccgaaatatg 11940
gcgctgctgc gggtggccat gggaacgcgg agacaggcct ccagcaacgc caggtaaata 12000
aaccgcgtgc gtcccatcag gctgttgagg ttgcgcatga gcgcgacaat ttccgccggc 12060
gcgacatcgg accggaggta tttttcgacg aaaagaccca cctcctccgt ctcggcggcc 12120
tgggccggca gcgacgcctc gggatcccgg caccgcagct cccgtagatc gcgctgggcc 12180
ctgagggcgt cgaaatgtac gccccgcaaa aacagacaga agtcctttgg ggtcagggta 12240
tcgtcgtgtc cccagaagcg cacgcgtatg cagtttaggg tcagcagcat gtgaaggatg 12300
ttaaggctgt ccgagagaca cgccagcgtg catctctcaa agtagtgttt gtaacggaat 12360

```
ttgttgtaga tgcgcgaccc ccgccccagc gacgtgtcgc atgccgacgc gtcacagcgc  12420
cccttgaacc ggcgacacag caggtttgtg acctgggaga actgcgcggg ccactggccg  12480
caggaactga ccacgtgatt aaggagcatg ggcgtaaaga cgggctccga gcgcgccccg  12540
gagccgtcca tgtaaatcag tagctccccc ttgcggaggg tgcgcacccg tcccagggac  12600
tggtacacgg acaccatgtc cggtccgtag ttcatgggtt tcacgtaggc gaacatgcca  12660
tcaaagtgca ggggatcgaa gctgaggccc acggttacga ccgtcgtgta tataaccacg  12720
cggtattggc cccacgtggt cacgtccccg aggggggtga gcgagtgaag caacagcacg  12780
cggtccgtaa actgacggca gaaccgggcc acgatctccg cgaaggagac cgtcgacgaa  12840
aaaatgcaga tgttatcgcc cccgccaagg cgcgcttcca gctccccaaa gaacgtggcc  12900
ccccgggcct ccggagaggc gtccggagac gggccgctcg gcggcccggg cgggcgcagg  12960
gcagcctgca ggagctcggt ccccagacgc gggagaaaca ggcaccggcg cgccgaaaac  13020
ccgggcatgg cgtactcgcc gaccaccaca tgcacgtttt tttcgccccg gagaccgcac  13080
aggaagtcca ccaactgcgc gttggcggtt gcgtccatgg cgatgatccg aggacagatg  13140
cgcagcaggc gtagcattaa cgcatccacg cggcccagtt gctgcatcgt tggcgaatag  13200
agctggccca gcgtcgacat aacctcgtcc agaacgagga cgtcgtagtt gttcagaagg  13260
ttggggccca cgcgatgaag gctttccacc tggacgataa gtcggtggaa ggggcggtcg  13320
ttcataatgt aattggtgga tgagaagtag gtgacaaagt cgaccaggcc tgactcagcg  13380
aaccgcgtcg ctagggtctg ggtaaaactc cgacgacagg agacgacgag cacactcgtg  13440
tccggagagt ggatcgcttc ccgcagccag cggatcagcg cggtagtttt tcccgacccc  13500
attggcgcgc ggaccacagt cacgcacctg gccgtcgggg cgctcgcgtt ggggaaggtg  13560
acgggtccgt gctgctgccg ctcgatcgtt gttttcgggt gaacccgggg cacccattcg  13620
gccaaatccc ccccgtacaa catccgcgct agcgatacgc tcgacgtgta ctgttcgcac  13680
tcgtcgtccc caatgggacg cccggccccc agaggatctc ccgactccgc gccccccacg  13740
aaaggcatga ccggggcgcg gacggcgtgg tgggtctggt gtgtgcaggt ggcgacgttt  13800
gtggtctctg cggtctgcgt cacggggctc ctcgtcctgg cctctgtgtt ccgggcacgg  13860
tttccctgct tttacgccac ggcgagctct tatgccgggg tgaactccac ggccgaggtg  13920
cgcgggggtg tagccgtgcc cctcaggttg gacacgcaga gccttgtggg cacttatgta  13980
atcacggccg tgttgttgtt ggccgtggcc gtgtatgccg tggtcggcgc cgtgacctcc  14040
cgctacgacc gcgccctgga cgcgggccgc cgtctggctg cggcccgcat ggccatgccg  14100
cacgccacgc tgatcgccgg aaacgtctgc tcttggttgc tgcagatcac cgtcctgttg  14160
ctggcccatc gcatcagcca gctggcccac ctggtttacg tcctgcactt tgcgtgtctg  14220
gtgtattttg cggcccattt ttgcaccagg ggggtcctga gcgggacgta tctgcgtcag  14280
gtgcacggcc tgatggagct ggccccgacc catcatcgcg tcgtcggccc ggctcgcgcc  14340
gtgctgacaa acgccttgct gttgggcgtc ttcctgtgca cggccgacgc cgcggtatcc  14400
ctgaatacca tcgccgcgtt caactttaat ttttcggccc cgggcatgct catctgcctg  14460
accgtgctgt tcgccattct cgtcgtatcg ctgttgttgg tggtcgaggg ggtgttgtgt  14520
cactacgtgc gcgtgttggt gggcccccac ctgggggccg tggccgccac gggcatcgtc  14580
ggcctggcct gcgagcacta ttacaccaac ggctactacg ttgtggagac gcagtggccg  14640
ggggctcaga cgggagtccg cgtcgccctc gccctggtcg ccgcctttgc cctcggcatg  14700
```

gccgtgctcc gctgcacccg cgcctatctg tatcacaggc ggcaccacac caaatttttt 14760
atgcgcatgc gcgacacgcg acaccgcgca cattccgccc tcaagcgcgt acgcagttcc 14820
atgcgcggat cgcgagacgg ccgccacagg cccgcacccg gcagcccgcc cgggattccc 14880
gaatatgcgg aagaccccta cgcgatctca tacggcggcc agctcgaccg gtacggagat 14940
tccgacgggg agccgattta cgacgaggtg gcggacgacc aaaccgacgt attgtacgcc 15000
aagatacaac acccgcggca cctgcccgac gacgatccca tctatgacac cgttgggggg 15060
tacgaccccg agcccgccga ggaccccgtg tacagcaccg tccgccgttg gtagctgttt 15120
ggttccgttt taataaaccg tttgtgttta acccgaccgt ggtgtatgtc tggtgtgtgg 15180
cgtccgatcc cgttactatc accgtccccc cccccccctc aaccccggcg attgtgggtt 15240
ttttaaaaac gacacgcgtg cgaccgtata cagaacattg ttttggtttt tattcgctat 15300
cggacatggg gggtggaaac tgggtggcgg ggcaggcgcc tccgggggtc cgccggtgag 15360
tgtggcgcga ggggggggtcc gatgaacgca ggcgctgtct ccccggggcc cgcgtaaccc 15420
cgcgcatatc cgggggcacg tagaaattac cttcctcttc ggactcgata tccacgacgt 15480
caaagtcgtg ggcggtcagc gagacgacct ccccgtcgtc ggtgatgagg acgttgtttc 15540
ggcagcagca gggccgggcc ccggagaacg agaggcccat agctcggcga gcgtgtcgtc 15600
gaatgccagg cggctgcttc gctggatggc cttatagatc tccggatcga tgcggacggg 15660
ggtaatgatc agggcgatcg gaacggcctg gttcgggaga atggacgcct tgctgggtcc 15720
tgcggccccg agagccccgg cgccgtcctc caggcggaac gttacgccct cctccgcgct 15780
ggtgcggtgc ctgccgataa acgtcaccag atgcgggtgg ggggggcagt cggggaagtg 15840
gctgtcgagc acgtagccct gcaccaagat ctgcttaaag ttcgggtgac gggggttcgc 15900
gaagacgggc tcgcggcgga ccagatcccc ggagctccag gacacggggg agatggtgtg 15960
gcgtccgagg tcgggggcgc caaacagaag cacctccgag acaacgccgc tatttaactc 16020
caccaaggcc cgatccgcgg cggagcaccg cctttttttcg cccgaggcgt gggcctctga 16080
ccaggcctgg tcttgcgtga cgagagcctc ctccgggccg gggacgcgcc cgggcgcgaa 16140
gtatcgcacg ctgggcttcg ggatcgaccg gataaatgcc cggaacgcct ccggggaccg 16200
gtgtgccatc aagtcctcgt acgcggaggc cgtggggtcg ctggggtcca tggggtcgaa 16260
agcgtacttg gcccggcatt tgacctcgta aaaggccagg ggggtcttgg ggactggggc 16320
caggtagccg tgaatgtccc gaggacagac gagaatatcc agggacgccc cgaccatccc 16380
cgtgtgaccg tccatgagga ccccacacgt atgcacgttc tcttcggcga ggtcgctggg 16440
ttcgtggaag ataaagcgcc gcgtgtcggc gccggcctcg ccgccgtcgt ccgcgcggcc 16500
cacgcagtag cgaaacagca ggcttcgggc cgtcggctcg ttcacccgcc cgaacatcac 16560
cgccgaagac tgtacatccg gccgcaggct ggcgttgtgc ttcagccact ggggcgagaa 16620
acacggaccc tgggggcccc agcggagggt ggatgcggtc gtgaggcccc gccggagcag 16680
ggcccatagc tggcagtcgg cctggttttg cgtggccgcc tcgtaaaacc ccatgagggg 16740
ccggggcgcc acggcgtccg cggcggccgg gggcccgcgg cgcgtcaggc gccataggtg 16800
ccgaccgagt ccgcggtcca ccatacccgc ctcctcgagg accacggcca gggaacacag 16860
ataatccagg cgggcccaga ggggaccgat ggccagaggg gcgcggacgc cgcgcagcaa 16920
cccgcgcagg tggcgctcga acgtctcggc tagtatatgg gagggcagcg cgttggggat 16980
caccgacgcc gaccacatag agtcaaggtc cggggagtcg ggatcggcgt ccgggtcgcg 17040
ggcgtgggtg cccccaggag atagcggaat gtctggggtc ggaggccctg aggcgtcaga 17100

-continued

```
aagtgccggc gacgcggccc ggggcttttc gtctgcggtg tcggtggcgt gctgatcacg  17160
tggggggtta acgggcgaat gggagctcgg gtccacagct gatgtcgtct ggggtggggg  17220
gggcagggga cggaaggtgg ttgtcagcgg aagactgtta gggcgggggc gcttgggggg  17280
gctgtcgggg ccacgagggg tgtcctcggc cagggcccag ggacgcttag tcacggtgcg  17340
tcccggcgga catgctgggc ctaccgtgga ctccatttcc gagacgacgt ggggggagcg  17400
gtggttgagc gcgccgccgg gtgaacgctg attctcacga cagcgcgtgc cgcgcgcacg  17460
ggttggtgtg acacaggcgg gacaccagca ccaggagagg cttaagctcg ggaggcagcg  17520
ccaccgacga cagtatcgcc ttgtgtgtgt gctggtaatt tatacaccga tccgtaaacg  17580
cgcgccgaat cttgggattg cggaggtggc gccggatgcc ctctgggacg tcatacgcca  17640
ggccgtgggt gttggtctcg gccgagttga caaacaggc tgggtgcagc acgcagcgat  17700
aggcgagcag ggccagggcg aagtccggcg acagctggtt gttaaaatac tggtaaccgg  17760
gaaaccgggt cacgggtacg cccaggctcg gggcgacgta cacgctaacc accaactcca  17820
gcagcgtctg gcccagggcg tacaggtcaa ccgctaaccc gacgtcgtgc ttcaggcggt  17880
ggttggtaaa ttcggcccgt tcgttgttaa ggtatttcac caacagctcc ggggctggt  17940
tatacccgtg acccaccagg gtgtgaaagt tggctgtggt tagggcggtg ggcatgccaa  18000
acatccgggg ggacttgagg tccggctcct ggaggcaaaa ctgcccccgg gcgatcgtgg  18060
agttggagtt gagggtgacg aggctaaagt cggcgaggac ggcccgccgg agcgagacgg  18120
cgtccgaccg cagcatgacg aggatgttgg cgcacttgat atccaggtgg ctgatcccgc  18180
aggtggtgtt taaaaacaca acggcgcggg ccagctccgt gaagcactgg tggagggccg  18240
tcgagaccga ggggtttgtt gtgcgcaggg acgccagttg gccgatatac ttaccgaggt  18300
ccatgtcgta cgcggggaac actatctgtc gttgttgcag cgagaacccg aggggcgcga  18360
tgaagccgcg gatgttgtgg gtgcggccgg cgcgtagaac gcactccccg accaacaggg  18420
tcgcgatgag ctcaacggca aaccactcct tttcctttat ggtcttaacg gcaagcttat  18480
gttcgcgaat cagttggacg tcaccgtatc ccccagaccc cccgaagctt cgggcccgg  18540
ggatctcgag ggtcgtgtag tgtagggcgg ggttgatggc gaacacgggg ctgcatagct  18600
tgcggatgcg cgtgagggtg aggatgtgcg agggggacga ggggggtgcg gttaacgccg  18660
cctgggatct gcgcaggggc gggcggttca gtttggccgc cgtaccgggc gtctcggggg  18720
acgcgcggcg atgagacgag cggctcattc gccatcggga tagtcccgcg cgaagccgct  18780
cgcggaggcc ggatcggtgg cgggacccgt gggaggagcg ggagacggcg gcgtcctgga  18840
gagaggggcc gctggggcgc ccggaggccc cgtgggggtt ggagtgtacg taggatgcga  18900
gccaatcctt gaaggaccgt tggcgtgcac cttgggggct gaggttagct gccacatgac  18960
cagcaggtcg ctgtctgcgg gactcatcca tccttcggcc aggtcgccgt ctccccacag  19020
agaagcgttg gtcgctgctt cctcgagttg ctcctcctgg tccgcaagac gatcgtccac  19080
ggcgtccagg cgctcaccaa gcgccggatc gaggtaccgt cggtgtgcgg ttagaaagtc  19140
acgacgcgcc gcttgctcct ccacgcgaat tttaacacag gtcgcgcgct gtcgcatcat  19200
ctctaagcgc gcgcgggact ttagccgcgc ctccaattcc aagtgggccg cctttgcagc  19260
cataaaggcg ccaacaaacc gaggatcttg ggtgctgacg ccctcccggt gcagctgcag  19320
ggtctggtcc ttgtaaatct cggctcggag gtgcgtctcg gccaggcgtc ggcgcagggc  19380
cgcgtgggcg gcatctcggt ccattccgcc accctgcggg cgacccgggg ggtgctctga  19440
```

-continued

```
tagtctcgcg tgcccaaggc ccgtgatcgg ggtacttcgc cgccgcgacc cgccacccgg  19500
tgtgcgcgat gtttggtcag cagctggcgt ccgacgtcca gcagtacctg gagcgcctcg  19560
agaaacagag gcaacttaag gtgggcgcgg acgaggcgtc ggcgggcctc accatgggcg  19620
gcgatgccct acgagtgccc tttttagatt tcgcgaccgc gacccccaag cgccaccaga  19680
ccgtggtccc tggcgtcggg acgctccacg actgctgcga gcactcgccg ctcttctcgg  19740
ccgtggcgcg gcggctgctg tttaatagcc tggtgccggc gcaactaaag gggcgtgatt  19800
tcgggggcga ccacacggcc aagctggaat tcctggcccc cgagttggta cgggcggtgg  19860
cgcgactgcg gtttaaggag tgcgcgccgg cggacgtggt gcctcagcgt aacgcctact  19920
atagcgttct gaatacgttt caggccctcc accgctccga agcctttcgc cagctggtgc  19980
actttgtgcg ggactttgcc cagctgctca aaacctcctt ccgggcctcc agcctcacgg  20040
agaccacggg cccccccaaa aaacgggcca aggtggacgt ggccacccac ggccggacgt  20100
acggcacgct ggagctgttc caaaaaatga tccttatgca cgccacctac tttctggccg  20160
ccgtgctcct cggggaccac gcggagcagg tcaacacgtt cctgcgtctc gtgtttgaga  20220
tccccctgtt tagcgacgcg gccgtgcgcc acttccgcca gcgcgccacc gtgtttctcg  20280
tcccccggcg ccacggcaag acctggtttc tggtgcccct catcgcgctg tcgctggcct  20340
cctttcgggg gatcaagatc ggctacacgg cgcacatccg caaggcgacc gagccggtgt  20400
ttgaggagat cgacgcctgc ctgcggggct ggttcggttc ggcccgagtg gaccacgtta  20460
aaggggaaac catctccttc tcgtttccgg acgggtcgcg cagtaccatc gtgtttgcct  20520
ccagccacaa cacaaacgta agtcctcttt tctttcgcat ggctctccca aggggccccg  20580
ggtcgacccg acccacaccc acccacccac atacacacac aaccagacgc gggaggaaag  20640
tctgccccgt gggcactgat tttattcgg gatcgcttga ggaggcccgg gcaacggccc  20700
gggcaacggt ggggcaactc gtagcaaata ggcgactgat gtacgaagag aagacacaca  20760
ggcgccaccc ggcgctggtc ggggggatgt tgtccgcgcc gcaccgtccc ccgacgacct  20820
cttgcagacg gtccgtgatg caaggacggc ggggggcctg cagcagggtg accgtatcca  20880
cgggatggcc aaagagaagc ggacacaggc tagcatcccc ctggaccgcc agggtacact  20940
gggccatctt ggcccacaga cacggggcga cgcagggaca ggactccgtt acgacggagg  21000
agagccacag tgcgttggcg gaatcgatgt ggggcggcgg ggcgcaggac tcgcagcccc  21060
ccgggtggtt ggtgatcctg gccaggagcc atcccagatg gcgggccctg cttcccggtg  21120
gacagagcga ccccaggtcg ctgtccatgg cccagcagta gatctggccg ctggggaggt  21180
gccaccaggc ccccgggccc aaggcgcagc acgcgcccgg ctccgggggg gtcttcgcgg  21240
ggaccagata cgcgccatcc agctcgccga ccactggctc ctccgcgagc tgttcggtgg  21300
ttgggtcggg ggtttcctcc gggggggtgg ccgcccgtat gcgtgcgaac gtgagggtgc  21360
acaggagcgg ggtcaggggg tgcgtcacgc tccggaggtg gacgatcgcg cagtagcggc  21420
gctcgcggtt aaagaaaaag agggcaaaga aggtgttcgg gggcaaccgc agcgccttgg  21480
ggcgcgtcag atacagaaaa atctcgcaga agagggcgcg cccggggtct gggttaggaa  21540
gggccacctg acacagaggc tcggtgagga ccgttagaca ccgaaagatc ttgagccgct  21600
cgtccgcccg aacgacgcgc cacacaaaga cggagttgac aatgcgcgcg atagagtcga  21660
cgtccgtccc caggtcgtcg actctatcgc gcgtgccgcg agctccggcc cgggaatccg  21720
gccggggcaa ggtccccggg ggaccaggcg gcgccagggg ccgccggggt cccagctgcg  21780
ccatgccggg ggcgggggga gggcaaaccc cagaggcggg ggccaacggc gcggggagga  21840
```

gtgggtgggc gaggtggccg ggggaaggcg cccgctagcg agaccggccg ttcccggacg 21900
acaccttgcg acaaaaccta aggacagcgg cccgcgcgac ggggtccgag aggctaaggt 21960
aggccgcgat gttaatggtg aacgcaaagc cgccgggaaa gacaactatg ccacagaggc 22020
ggcgattaaa ccccaggcag aggtaggcgt agctttcccc gggcaggtat tgctcgcaga 22080
ccctgcgtgg ggctgtggag gggacggcct ccatgaagcg acatttactc tgctcgcgtt 22140
tactgacgtc accatccatc gccacggcga ttggacgatt gttaagccgc agcgtgtctc 22200
cgcttgtgct gtagtagtca aaaacgtaat ggccgtcgga gtcggcaaag cgggccggga 22260
ggtcgtcgcc gagcgggacg acccgccgcc cccgaccgcc ccgtcccccc aggtgtgcca 22320
ggacggccag ggcatacgcg gtgtgaaaaa aggcgtcggg ggcggtcccc tcgacggcgc 22380
gcatcaggtt ctcgaggaga atggggaagc gcctggtcac ctcccccaac cacgcgcgtt 22440
ggtcggggcc aaagtcatag cgcaggcgct gtgagattcg cgggccgccc tgaagcgcgg 22500
cccggatggc ctggcccagg gcccggaggc acgccagatg tatgcgcgcg gtaaaggcga 22560
cctcggcggc gatgtcaaag ggcggcagga cggggcgcgg gtggcgcagg ggcacctcga 22620
gcgcgggaaa gcgtagcagc agctccgcct gcccagcggg agacagctgg tgggggcgca 22680
cgacgcgttc tgcggcgcag gcctcggtca gggccgtggc cagcgccgag gacagcagcg 22740
gagggcgggc gcgtcgcccg ccccacgcca cggagttctc gtaggagacg acgacgaagc 22800
gctgcttggt tccgtagtgg tggcgcagga ccacggagat agaacgacgg ctccacagcc 22860
agtccggccg gtcgccgccg gccagggctt cccatccgcg atccaaccac tcgaccagcg 22920
accgcggctt tgcggtacca ggggtaaggg ttagaacgtc gttcaggatg tcctcgcccc 22980
cgggcccgtg gggcgctggg gccacaaagc ggcccccgcc ggggggctcc agacccgcca 23040
gcaccgcatc tgcgtcagcc gcccccatgg cgcccccgct gacggcctgg tgaaccaggg 23100
cgccctggcg tagccccgat gcaacgccac aggccgcacg cccggtccgc gctcggaccg 23160
ggtggcggcg ggtgacgtcc tgcactgccc gctgaaccaa cgcgaggatc tcctcgttct 23220
cctgtgcgat ggacacgtcc tgggccgcgg tcgtgtcgcc gccgggggcc gtcagctgct 23280
cctccgggga gatggggggg tcggacgccc cgacgatggg cgggtctgcg ggcgcccccg 23340
cgtggggccg ggccaagggc tgcggacgcg gggacgcgct ttcccccaga cccatggaca 23400
ggtgggccgc agcctccttc gcggccggcg gggcggcggc gccaagcaga gcgacgtagc 23460
ggcacaaatg ccgacagacg cgcatgatgc gcgtgctgtc ggccgcgtag cgcgtgttgg 23520
gggggacgag ctcgtcgtaa ctaaacagaa tcacgcgggc acagctcgcc cccgagcccc 23580
acgcaaggcg cagcgccgcc acggcgtacg ggtcatagac gccctgcgcg tcacacacca 23640
cgggcaggga gacgaacaac cccccggcgc tggacgcacg cggaaggagg ccagggtgtg 23700
ccggcacgac gggggccaga agctccccca ccgcatccgc gggcacgtag gcggcaaacg 23760
ccgtgcacca cggggtacag tcgccggtgg catgagcccg agtctggatt tcgacctgga 23820
agtttgcggc cgtcccgagt ccggggcggc cgcgcatcag ggcggccaga gggattcccg 23880
cggccgccag gcactcgctg gatatgatga cgtgaaccaa agaccgaggg ccgacccggg 23940
ccgtggccga gatcgtctgg acctcgttgg ccaagtgcgc gttcatggtt cgggggtggg 24000
tgtgggtgtg taggcgatgc gggtcccccg agtccgcggg aagggcgtgg gtttggcgcg 24060
cgtatgcgta ttcgccaacg gaggcgtgcg tgcttatgcg cggcgcgttt cttctgtctc 24120
tagggaatcc gaggccagga ctttaacctg ctctttgtcg acgaggccaa ctttattcgc 24180

```
ccggatgcgg tccagacgat tatgggcttt ctcaaccagg ccaactgcaa gattatcttc  24240
gtgtcgtcca ccaacaccgg gaaggccagt acgagctttt tgtacaacct ccgcggggcc  24300
gcagacgagc ttctcaacgt ggtgacctat atatgcgatg atcacatgcc gagggtggtg  24360
acgcacacaa acgccacggc ctgttcttgt tatatcctca acaagcccgt tttcatcacg  24420
atggacgggg cggttcgccg gaccgccgat ttgtttctgg ccgattcctt catgcaggag  24480
atcatcgggg gccaggccag ggagaccggc gacgaccggc ccgttctgac caagtctgcg  24540
ggggagcggt ttctgttgta ccgcccctcg accaccacca acagcggcct catggccccc  24600
gatttgtacg tgtacgtgga tcccgcgttc acggccaaca cccgagcctc cgggaccggc  24660
gtcgctgtcg tcgggcggta ccgcgacgat tatatcatct tcgccctgga gcactttttt  24720
ctccgcgcgc tcacgggctc ggcccccgcc gacatcgccc gctgcgtcgt ccacagtctg  24780
acgcaggtcc tggccctgca tcccggggcg tttcgcggcg tccgggtggc ggtcgaggga  24840
aatagcagcc aggactcggc cgtcgccatc gccacgcacg tgcacacaga gatgcaccgc  24900
ctactggcct cggagggggc cgacgcgggc tcgggccccg agcttctctt ctaccactgc  24960
gagcctcccg ggagcgcggt gctgtacccc tttttcctgc tcaacaaaca gaagacgccc  25020
gcctttgaac actttattaa aaagtttaac tccgggggcg tcatggcctc ccaggagatc  25080
gtttccgcga cggtgcgcct gcagaccgac ccggtcgagt atctgctcga gcagctaaat  25140
aacctcaccg aaaccgtctc ccccaacact gacgtccgta cgtattccgg aaaacggaac  25200
ggcgcctcgg atgaccttat ggtcgccgtc attatggcca tctacctcgc ggcccaggcc  25260
ggacctccgc acacattcgc tcctatcaca cgcgtctcgt gagcgcccaa taaacacacc  25320
caggtatgct acgcacgacc acggtgtcgt ctgttaaggg ggggggggga agggggtgtt  25380
ggcgggaagc gtgggaacac gggggattct ctcacgaccg gcaccagtac caccccccctg  25440
tgaacacaga aaccccaacc caaatcccat aaacatacga cacacaggca tattttggaa  25500
tttcttaggt ttttatttat ttaggtatgc tggggtttct ccctggatgc ccaccccccac  25560
ccccccgtgg gtctagccgg gccttaggga tagcgtataa cgggggccat gtctccggac  25620
cgcacaacgg ccgcgccgtc aaaggtgcac acccgaacca cgggagccag ggccaaggtg  25680
tctcctagtt ggcccgcgtg ggtcagccag gcgacgagcg cctcgtaaag cggcagcctt  25740
cgctctccat cctgcatcag ggccggggct tcggggtgaa tgagctgggc ggcctcccgc  25800
gtgacactct gcatctgcag tagagcgttc acgtacccgt cctgggcact tagcgcaaag  25860
agccggggga ttagcgtaag gatgatggtg gttccctccg tgatcgagta aaccatgtta  25920
aggaccagcg atcgcagctc ggcgtttacg ggaccgagtt gttggacgtc cgccagcagc  25980
gagaggcgac tcccgttgta gtacagcacg ttgaggtctg gcagccctcc ggggtttctg  26040
gggctggggt tcaggtcccg gatgcccctg gccacgagcc gcgccacgat ttcgcgcgcc  26100
aggggcgatg gaagcggaac gggaaaccgc aacgtgaggt ccagcgaatc caggcgcacg  26160
tccgtcgctt ggccctcgaa cacgggcggg acgaggctga tggggtcccc gttacagaga  26220
tctacggggg aggtgttgcg aaggttaacg gtgccggcgt gggtgaggcc cacgtccagg  26280
gggcaggcga cgattcgcgt gggaagcacc cgggtgatga ccgcggggaa gcgccttcgg  26340
tacgccagca acaaccccaa cgtgtcggga ctgacgcctc cggagacgaa ggattcgtgc  26400
gccacgtcgg ccagcgtcag ttgccggcgg atggtcggca ggaataccac ccgcccttcg  26460
cagcgctgca gcgccgccgc atcggggcgc gagatgcccg agggtatcgc gatgtcagtt  26520
tcaaagccgt ccgccagcat ggcgccgatc cacgcggcag ggagtgcagt ggtggttcgg  26580
```

```
gtggcgggag gagcgcggtg ggggtcagcg gcgtagcaga gacgggcgac caacctcgca  26640
taggacgggg ggtgggtctt agggggttgg gaggcgacag ggaccccaga gcatgcgcgg  26700
ggaggtctgt cgggcccaga cgcaccgaga gcgaatccgt ccgcggagtc ccggcttggg  26760
ttttatgggg cccggccctc ggaatcgcgg cttgtcggcg gggacaaagg gggcggggct  26820
aggggcttgc ggaaacagaa gacgcgtggg ataaaagaat cgcactaccc caaggaaggg  26880
cggggcggtt tattacagag ccagtccctt gagcggggat gcgtcataga cgagatactg  26940
cgcgaagtgg gtctcccgcg cgtgggcttc cccgttgcgg gcactgcgga ggagggcggg  27000
gtcgctggcg caggtgagcg ggtaggcctc ctgaaacagg ccacacgggt cctccacgag  27060
ttcgcggcac cccgggggc gcttaaactg tacgtcgctg gcggcggtgg ccgtggacac  27120
cgccgaaccc gtctccacga tcaggcgctc caggcagcga tgtttggcgg cgatgtcggc  27180
cgacgtaaag aacttaaagc aggggctgag caccggcgag gccccgttga ggtggtaggc  27240
cccgttatag agcaggtccc cgtacgaaaa tcgctgcgac gcccacgggt tggccgtggc  27300
cgcgaaggcc cgggacgggt cgctctggcc gtggtcgtac atgagggcgg tgacatcccc  27360
ctccttgtcc cccgcgtaaa cgcccccggc ggcgcgtccc cgggggttgc agggccggcg  27420
gaagtagttg acgtcggtcg acacgggggt ggcgataaac tcacacacgg cgtcctggcc  27480
gtggtccatc cctgcgcgcc gcggcacctg ggcgcacccg aacacgggga cgggctgggc  27540
cggccccagg cggtttcccg ccacgaccgc gttccgcagg tacacggctg ccgcgttgtc  27600
caggagaggg ggagccccgc ggcccaggta aaagttttgg ggaaggttgc ccatgtcggt  27660
gacggggttg cggacggttg ccgtggccac gacggcggtg tagcccacgc ccaggtccac  27720
gttcgcgcgc ggctgggtga gcgtgaagtt taccccccg ccagtttcgt gccgggccac  27780
ctggagctgg cccaggaagt acgcctccga cgcgcgctcc gagaacagca cgttctcagt  27840
cacaaagcgg tcctgtcgga cgacggtgaa cccaaacccg ggatggaggc ccgtcttgag  27900
ctgatgatgc aaggccacgg gactgatctt gaagtacccc gccatgagcg cgtaggtcag  27960
cgcgttctcc ccggccgcgc tctcgcggac gtgctgcacg acgggctgtc ggatcgacga  28020
aaagtagttg gcccccagag ccgggggac caggggacc tgccgcgaca ggtcgcgcag  28080
ggccgggggg aaattgggcg cgttcgccac gtggtcggcc ccggcgaaca gcgcgtggac  28140
ggggaggggg taaaaatagt cgccattttg gatggtatgg tccagatgct ggggggccat  28200
cagcaggatt ccggcgtgca acgccccgtc gaatatgcgc atgttggtgg tggacgcggt  28260
gttggcgccc gcgtcgggcg ccgccgagca gagcagcgcc gttgtgcgtt cggccatgtt  28320
gtgggccagc acctgcagcg tgagcatggc gggcccgtcc actaccacgc gcccgttgtg  28380
aaacatggcg ttgaccgtgt tggccaccag attggccggg tgcaggggt gcgcggggtc  28440
cgtcacgggg tcgctggggc actcctcgcc gggggcgatc tccgggacca ccatgttctg  28500
cagggtggcg tatacgcggt cgaagcgaac ccccgcggtg cagcagcggc cccgcgagaa  28560
ggcgggcacc atcacgtagt agtaaatctt gtggtgcacg gtccagtccg cccccggtg  28620
cggccggtca tccgcggcgt ccgcggctcg ggcctgggtg ttgtgcagca gctggccgtc  28680
gttgcggttg aagtccgcgg tcgccacgtt acatgccgcc gcgtacacgg ggtcgtggcc  28740
ccccgcgcta acccggcagt cgcgatggcg gtccagggcc gcgcgccgca tcagggcgtc  28800
acagtcccac acgaggggtg gcagcagcgc cgggtctcgc attaggtgat tcagctcggc  28860
ttgcgcctgc ccgcccagct ccgggccggt cagggtaaag tcatcaacca gctgggccag  28920
```

-continued ggcctcgacg tgcgccacca ggtcccggta cacggccatg cactcctcgg gaaggtctcc 28980
cccgaggtag gtcacgacgt acgagaccag cgagtagtcg ttcacgaacg ccgcgcaccg 29040
cgtgttgttc cagtagctgg tgatgcactg gaccacgagc cgggccaggg cgcagaagac 29100
gtgctcgctg ccgtgtatgg cggcctgcag caggtaaaac accgccgggt agttgcggtc 29160
gtcgaacgcc ccgcgaacgg cggcgatggt ggcgggggcc atggcgtggc gtcccacccc 29220
cagctccagg ccccgggcgt cccggaacgc cgccggacat agcgccaggg gcaagttgcc 29280
gttcaccacg cgccaggtgg cctggatctc ccccgggccg gccgggggaa cgtccccccc 29340
cggcagctcc acgtcggcca cccccacaaa gaagtcgaac gcggggtgca gctcaagagc 29400
caggttggcg ttgtcgggct gcataaactg ctccggggtc atctggcctt ccgcgaccca 29460
tcggacccgc ccgtgggcca ggcgctgccc ccaggcgttc aaaaacagct gctgcatgtc 29520
tgcggcgggg ccggccgggg ccgccacgta cgccccgtac ggattggcgg cttcgacggg 29580
gtcgcggtta aggcccccga ccgccgcgtc aacgttcatc agcgaagggt ggcacacggt 29640
cccgatcgcg tgttccagag acaggcgcag cacctggcgg tccttccccc aaaaaaacag 29700
ctggcggggc gggaaggcgc ggggatccgg gtggccgggg gcggggacta ggtccccggc 29760
gtgcgcggca aaccgttcca tgaccggatt gaacaggccc aggggcagga cgaacgtcag 29820
gtccatggcg cccaccaggg ggtagggaac gttggtggcg gcgtagatgc gcttctccag 29880
ggcctccaga aagaccagct tctcgccgat ggacaccaga tccgcgcgca cgcgcgtcgt 29940 ctgggggggcg ctctcgagct cgtccagcgt ctgccggttc aggtcgagct gctcctcctg 30000
catctccagc aggtggcggc ccacgtcgtc cagacttcgc acggccttgc ccatcacgag 30060
cgccgtgacc aggttggccc cgttcaggac catctcgccg tacgtcaccg gcacgtcggc 30120
ttcggtgtcc tccactttca ggaaggactg caggaggcgc tgtttgatcg gggcggtggt 30180
gacgagcacc ccgtcgaccg gccgcccgcg cgtgtcggca tgcgtcagac ggggcacggc 30240
cacggagggc tgcgtggccg tggtgaggtc cacgagccag gcctcgacgg cctcccggcg 30300
gtggcccgcc ttgcccagga aaaagctcgt ctcgcagaag cttcgcttta gctcggcgac 30360
cagggtcgcc cgggccaccc tggtggccag gcggccgttg tccaggtatc gttgcatcgg 30420
caacaacaaa gccaggggcg gcgccttttc cagcagcacg tgcagcatct ggtcggccgt 30480
gccgcgctca aacgccccga ggacggcctg gacgttgcga gcgagctgtt ggatggcgcg 30540
caactggcga tgcgcgccga tacccgtccc gtccagggcc tcccccgtga gcagggcgat 30600
ggcctcggtg gccaggctga aggcggcgtt cagggcccgg cggtcgataa tcttggtcat 30660
gtaattgtgt gtgggttgct cgatggggtg cgggccgtcg cgggcaatca gcggctggtg 30720
gacctcgaac tgtacgcgcc cctcgttcat gtaggccagc tccggaaact tggtacacac 30780
gcacgccacc gacaacccga gctccagaaa gcgcacgagc gacagggtgt tgcaatacga 30840
ccccagcagg gcgtcgaact cgacgtcgta caggctgttt gcatcggagc gcacgcggga 30900
aaaaaaatca aacaggcgtc gatgcgacgc cacctcgatc gtgctaagga gggacccggt 30960
cggcaccatg gccgcggcat accggtatcc cggagggtcg cggttgggag cggccatggg 31020
gtcgcgtgga gatcggctgt ctctagcgat attggcccgg ggaggctaag atccacccca 31080
acgcccggcc acccgtgtac gtgcccgacg gcccaaggtc caccgaaaga cacgacgggc 31140
ccggacccaa aaaggcgggg gatgctgtgt gagaggccgg gtgccggtcg ggggggaaag 31200
gcaccgggag aaggctgcgg cctcgttcca ggagaaccca gtgtccccaa cagacccggg 31260
gacgtgggat cccaggcctt atataccccc ccccccgccc cacccccgtt agaacgcgac 31320
gggtgcattc aagatggccc tggtccaaaa gcgtgccagg aagaaattgg cagaggcggc 31380
aaagctgtcc gccgccgcca cccacatcga ggccccggcc gcgcaggcta tccccagggc 31440
ccgtgtgcgc aggggatcgg tgggcggcag catttggttg gtggcgataa agtggaaaag 31500
cccgtccgga ctgaaggtct cgtgggcggc ggcgaacaag gcacacaggg ccgtgcctcc 31560
caaaaacacg gacatccccc aaaacacggg cgccgacaac ggcagacgat ccctcttgat 31620
gttaacgtac aggaggagcg cccgcaccgc ccacgtaacg tagtagccga cgatggcggc 31680
caggatacag gccggcgcca ccacccttcc ggtcagcccg taatacatgc ccgctgccac 31740
catctccaac ggcttcagga ccaaaaacga ccaaaggaac agaatcacgc gctttgaaaa 31800
gaccggctgg gtatggggcg gaagacgcga gtatgccgaa ctgacaaaaa aatcagaggt 31860
gccgtacgag gacaatgaaa actgttcctc cagcggcagt tctccctcct cccccccgaa 31920
ggcggcctcg tcgaccagat ctcgatccac cagaggaagg tcatcccgca tggtcatggg 31980
gtgtgcggtg gaggtgggga gaccgaaacc gcaaagggtc gcttacgtca gcaggatccc 32040
gagatcaaag acacccgggt tcttgcacaa acaccacccg ggttgcatcc gcggaggcga 32100
gtgttttgat aaggccgttc cgcgccttga tataaccttt gatgttgacc acaaaacccg 32160
gaatttacgc ctacgcccca atgcccacgc aagatgaggt aggtaacccc cccgtgggtg 32220
tgacgttgcg tttagttcat tggaggccaa ggggaaaaat ggggtgggga ggaaacggaa 32280
aacccagtag gccgtgtcgg gaacacgccc ggggttgtcc tcaaaaggca gggtccatac 32340
tacggaagcc gtcgttgtat tcgagacctg cctgtgcaac gcacgtcggg gttgcctgtg 32400
tccggttcgg cccccaccgc gtgcggcacg cacgaggacg agtccgcgtg ctttattggc 32460
gttccaagcg ttgccctcca gtttctgttg tcggtgttcc cccataccca cgcccacatc 32520
caccgtaggg ggcctctggg ccgtgttacg tcgccgcccg cgatggagct tagctacgcc 32580
accaccatgc actaccggga cgttgtgttt tacgtcacaa cggaccgaaa ccgggcctac 32640
tttgtgtgcg gggggtgtgt ttattccgtg gggcggccgt gtgcctcgca gcccggggag 32700
attgccaagt ttggtctggt cgttcgaggg acaggcccag acgaccgcgt ggtcgccaac 32760
tatgtac 32767

<210> SEQ ID NO 850
<211> LENGTH: 32767
<212> TYPE: DNA
<213> ORGANISM: Artificial Sequence
<220> FEATURE:
<223> OTHER INFORMATION: recombinant viral vector ONCR-158

<400> SEQUENCE: 850
aaaaaagctg aacgagaaac gtaaaatgat ataaatatca atatattaaa ttagattttg 60
cataaaaaac agactacata atactgtaaa acacaacata tccagtcact atgaatcaac 120
tacttagatg gtattagtga cctgtagtcg accgacagcc ttccaaatgt tcttcgggtg 180
atgctgccaa cttagtcgac cgacagcctt ccaaatgttc ttctcaaacg gaatcgtcgt 240
atccagccta ctcgctattg tcctcaatgc cgtattaaat cataaaaaga aataagaaaa 300
agaggtgcga gcctcttttt tgtgtgacaa aataaaaaca tctacctatt catatacgct 360
agtgtcatag tcctgaaaat catctgcatc aagaacaatt tcacaactct tatacttttc 420
tcttacaagt cgttcggctt catctggatt ttcagcctct atacttacta aacgtgataa 480
agtttctgta atttctactg tatcgacctg cagactggct gtgtataagg gagcctgaca 540

-continued

```
tttatattcc ccagaacatc aggttaatgg cgtttttgat gtcattttcg cggtggctga    600
gatcagccac ttcttccccg ataacggaga ccggcacact ggccatatcg gtggtcatca    660
tgcgccagct ttcatccccg atatgcacca ccgggtaaag ttcacgggag actttatctg    720
acagcagacg tgcactggcc aggggggatca ccatccgtcg cccgggcgtg tcaataatat    780
cactctgtac atccacaaac agacgataac ggctctctct tttataggtg taaaccttaa    840
actgcatttc accagcccct gttctcgtca gcaaaagagc cgttcatttc aataaaccgg    900
gcgacctcag ccatcccttc ctgattttcc gctttccagc gttcggcacg cagacgacgg    960
gcttcattct gcatggttgt gcttaccaga ccggagatat tgacatcata tatgccttga   1020
gcaactgata gctgtcgctg tcaactgtca ctgtaatacg ctgcttcata gcatacctct   1080
ttttgacata cttcgggtat acatatcagt atatattctt ataccgcaaa aatcagcgcg   1140
caaatacgca tactgttatc tggcttttag taagccggat ccacgcggcg tttacgcccc   1200
ccctgccact catcgcagta ctgttgtaat tcattaagca ttctgccgac atggaagcca   1260
tcacaaacgg catgatgaac ctgaatcgcc agcggcatca gcaccttgtc gccttgcgta   1320
taatatttgc ccatggtgaa aacgggggcg aagaagttgt ccatattggc cacgtttaaa   1380
aaggccgtaa tatccagctg aacggtctgg ttataggtac attgagcaac tgactgaaat   1440
gcctcaaaat gttctttacg atgccattgg gatatatcaa cggtggtata tccagtgatt   1500
tttttctcca ttttagcttc cttagctcct gaaaatctcg ataactcaaa aaatacgccc   1560
ggtagtgatc ttatttcatt atggtgaaag ttggaacctc ttacgtgccg atcaacgtct   1620
cattttcgcc aaaagttggc ccagggcttc ccggtatcaa cagggacacc aggatttatt   1680
tattctgcga agtgatcttc cgtcacaggt atttattcgg cgcaaagtgc gtcgggtgat   1740
gctgccaact tagtcgacta caggtcacta ataccatcta agtagttgat tcatagtgac   1800
tggatatgtt gtgttttaca gtattatgta gtctgttttt tatgcaaaat ctaatttaat   1860
atattgatat ttatatcatt ttacgtttct cgttcagctt tcttgtacaa agtggtttta   1920
atggaccgcc cgcaaggggg ggggggcatt tcagtgtcgg gtgacgagcg cgatccggcc   1980
gggatcctag gaccccaaaa gtttgtctgc gtattccagg gcggggctca gttgaatctc   2040
ccgcagcacc tctaccagca ggtccgcggt gggctggaga aactcggccg tcccggggca   2100
ggcggttgtc gggggtggag gcgcggcgcc caccccgtgt gccgcgcctg gcgtctcctc   2160
tgggggcgac ccgtaaatgg ttgcagtgat gtaaatggtg tccgcggtcc agaccacggt   2220
caaaatgccg gccgtggcgc tccgggcgct ttcgccgcgc gaggagctga cccaggagtc   2280
gaacggatac gcgtacatat gggcgtccca cccgcgttcg agcttctggt tgctgtcccg   2340
gcctataaag cggtaggcac aaaattcggc gcgacagtcg ataatcacca acagcccaat   2400
gggggtgtgc tggataacaa cgcctccgcg cggcaggcgg tcctggcgct cccggccccg   2460
taccatgatc gcgcgggtgc cgtactcaaa aacatgcacc acctgcgcgg cgtcgggcag   2520
tgcgctggtc agcgaggccc tggcgtggca taggctatac gcgatggtcg tctgtggatt   2580
ggacatctcg cggtgggtag tgagtccccc gggccgggtt cggtggaact gtaaggggac   2640
ggcgggttaa tagacaatga ccacgttcgg atcgcgcaga gccgatagta tgtgctcact   2700
aatgacgtca tcgcgctcgt ggcgctcccg gagcggattt aagttcatgc gaaggaattc   2760
ggaggaggtg gtgcgggaca tggccacgta cgcgctgttg aggcgcaggt tgccgggcgt   2820
aaagcagatg gcgaccttgt ccaggctaag gccctgggag cgcgtgatgg tcatggcaag   2880
cttggagctg atgccgtagt cggcgtttat ggccatggcc agctccgtag agtcaatgga   2940
```

ctcgacaaac tcgctgatgt tggtgttgac gacggacatg aagccgtgtt ggtcccgcaa 3000
gaccacgtaa ggcagggggg cctcttccag taactcggcc acgttggccg tcgcgtgccg 3060
cctccgcagc tcgtccgcaa aggcaaacac ccgtgcgtac gtgtatccca tgagcgtata 3120
attgtccgtc tgcagggcga cggacatcag ccccccgcgc ggcgagccgg tcagcatctc 3180
gcagccccgg aagataacgt tgtccacgta cgtgctaaag gggcgactt caaatgcctc 3240
cccgaagagc tcttggagga ttcggaatct cccgaggaag gcccgcttca gcagcgcaaa 3300
ctgggtgtga acggcggcgg tggtctccgg ttccccgggg gtgtagtggc agtaaaacac 3360
gtcgagctgt tgttcgtcca gccccgcgaa aataacgtcg aggtcgtcgt cgggaaaatc 3420
gtccgggccc ccgtcccgcg gccccagttg cttaaaatca aacgcacgct cgccgggggc 3480
gcctgcgtcg gccattaccg acgcctgcgt cggcaccccc gaagatttgg ggcgcagaga 3540
cagaatctcc gccgttagtt ctcccatgcg ggcgtaggcg agggtcctct gggtcgcatc 3600
caggcccggg cgctgcagaa agttgtaaaa ggagataagc ccgctaaata tgagccgcga 3660
caggaacctg taggcaaact ccaccgaagt ctccccctga gtctttacaa agctgtcgtc 3720
acgcaacact gcctcgaagg cccggaacgt cccactaaac ccaaaaacca gttttcgcag 3780
gcgcgcggtc accgcgatct ggctgttgag gacgtaagtg acgtcgttgc gggccacgac 3840
cagctgctgt ttgctgtgca cctcgcagcg catgtgcccc gcgtcctggt cctggctctg 3900
cgagtagttg gtgatgcggc tggcgttggc cgtgagccac ttttcaatcg tcaggccggg 3960
ctggtgtgtc agccgtcggt attcgtcaaa ctccttgacc gacacgaacg taagcacggg 4020
gagggtgaac acgacgaact ccccctcacg ggtcaccttc aggtaggcgt ggagcttggc 4080
catgtacgcg ctcacctctt tgtgggagga gaacagccgc gtccagccgg ggaggttggc 4140
ggggttggtg atgtagtttt ccgggacgac gaagcgatcc acgaactgca tgtgctcctc 4200
ggtgatgggc aggccgtact ccagcacctt catgaggtta ccgaactcgt gctcgacgca 4260
ccgtttgttg ttaataaaaa tggcccagct atacgagagg cgggcgtact cgcgcagcgt 4320
gcggttgcag atgaggtacg tgagcacgtt ctcgctctgg cggacggaac accgcagttt 4380
ctggtgctcg aaggtcgact ccagggacgc cgtctgcgtc ggcgagccca cacacaccaa 4440
cacgggccgc aggcgggccg cgtactgggg ggtgtggtac agggcgttaa tcatccacca 4500
gcaatacacc acggccgtga ggaggtgacg cccaaggagc ccggcctcgt cgatgacgat 4560
cacgttgctg cgggtaaagg ccggcagcgc cccgtgggtg gccggggcca accgcgtcag 4620
ggcgccctcg gccaacccca gggtccgttc cagggcggcc agggcgcgaa actcgttccg 4680
caactcctcg cccccggagg cggccagggc gcgcttcgtg aggtccaaaa tcacctccca 4740
gtagtacgtc agatctcgtc gctgcaggtc ctccagcgag gcggggttgc tggtcagggt 4800
gtacgggtac tgtcccagtt gggcctggac gtgattcccg cgaaacccaa attcatgaaa 4860
gatggtgttg atgggtcggc tgagaaaggc gcccgagagt ttggcgtaca tgttttgggc 4920
cgcaatgcgc gtggcgcccg tcaccacaca gtccaagacc tcgttgattg tctgcacgca 4980
cgtgctcttt ccggagccag cgttgccggt gataagatac accgcgaacg gaaactccct 5040
gaggggcagg cctgcggggg actctaaggc cgccacgtcc cggaaccact gcagatgggg 5100
cacttgcgct ccgtcgagct gttgttgcga gagctctcgg atgcgcttaa ggattggctg 5160
caccccgtgc atagacgtaa aatttaaaaa ggcctcggcc ctccctggaa cggctggtcg 5220
gtccccgggt tgctgaaggt gcggcgggcc gggtttctgt ccgtctagct ggcgctcccc 5280

-continued gccggccgcc gccatgaccg caccacgctc gcgggccccc actacgcgtg cgcgggggga 5340
cacggaagcg ctgtgctccc ccgaggacgg ctgggtaaag gttcacccca gccccggtac 5400
gatgctgttc cgcgagattc tccacgggca gctggggtat accgagggcc agggggtgta 5460
caacgtcgtc cggtccagcg aggcgaccac ccggcagctg caggcggcga tctttcacgc 5520
gctcctcaac gccaccactt accgggacct cgaggcggac tggctcggcc acgtggcggc 5580
ccgcggtctg cagccccaac ggctggttcg ccggtacagg aacgcccggg aggcggatat 5640
cgccggggtg gccgagcggg tgttcgacac gtggcggaac acgcttagga cgacgctgct 5700
ggactttgcc cacgggttgg tcgcctgctt tgcgccgggc ggcccgagcg gcccgtcaag 5760
cttccccaaa tatatcgact ggctgacgtg cctggggctg gtccccatat tacgcaagcg 5820
acaagaaggg ggtgtgacgc agggtctgag ggcgtttctc aagcagcacc cgctgacccg 5880
ccagctggcc acggtcgcgg aggccgcgga gcgcgccggc cccgggtttt ttgagctggc 5940
gctggccttc gactccacgc gcgtggcgga ctacgaccgc gtgtatatct actacaacca 6000
ccgccggggc gactggctcg tgcgagaccc catcagcggg cagcgcggag aatgtctggt 6060
gctgtggccc cccttgtgga ccggggaccg tctggtcttc gattcgcccg tccagcggct 6120
gtttcccgag atcgtcgcgt gtcactccct ccgggaacac gcgcacgtct gccggctgcg 6180
caataccgcg tccgtcaagg tgctgctggg gcgcaagagc gacagcgagc gcggggtggc 6240
cggtgccgcg cgggtcgtta acaaggtgtt gggggaggac gacgagacca aggccgggtc 6300
ggccgcctcg cgcctcgtgc ggcttatcat caacatgaag ggcatgcgcc acgtaggcga 6360
cattaacgac accgtgcgtt cctacctcga cgaggccggg gggcacctga tagacgcccc 6420
ggccgtcgac ggtaccctcc ctggattcgg caagggcgga aacagccgcg ggtctgcggg 6480
ccaggaccag ggggggcggg cgccgcagct tcgccaggcc ttccgcacgg ccgtggttaa 6540
caacatcaac ggcgtgttgg agggctatat aaataacctg tttggaacca tcgagcgcct 6600
gcgcgagacc aacgcgggcc tggcgaccca attgcaggag cgcgaccgcg agctccggcg 6660
cgcaacagcg ggggccctgg agcgccagca gcgcgcggcc gacctggcgg ccgagtccgt 6720
gaccggtgga tgcggcagcc gccctgcggg ggcggacctg ctccgggccg actatgacat 6780
tatcgacgtc agcaagtcca tggacgacga cacgtacgtc gccaacagct ttcagcaccc 6840
gtacatccct tcgtacgccc aggacctgga gcgcctgtcg cgcctctggg agcacgagct 6900
ggtgcgctgt tttaaaattc tgtgtcaccg caacaaccag ggccaagaga cgtcgatctc 6960
gtactccagc ggggcgatcg ccgcattcgt cgccccctac tttgagtcag tgcttcgggc 7020
cccccgggta ggcgcgccca tcacgggctc cgatgtcatc ctgggggagg aggagttatg 7080
ggatgcggtg tttaagaaaa cccgcctgca aacgtacctg acagacatcg cggccctgtt 7140
cgtcgcggac gtccagcacg cagcgctgcc cccgcccccc tccccggtcg gcgccgattt 7200
ccggcccggc gcgtccccgc ggggccggtc cagatcgcgg tcgcccggaa gaactgcgcg 7260
aggcgcgccg gaccagggcg ggggcatcgg gcaccgggat ggccgccgcg acggccgacg 7320
atgaggggtc ggccgccacc atcctcaagc aggccatcgc cggggaccgc agcctggtcg 7380
aggcggccga ggcgattagc cagcagacgc tgctccgcct ggcctgcgag gtgcgccagg 7440
tcggcgaccg ccagccgcgg tttaccgcca ccagcatcgc gcgcgtcgac gtcgcgcctg 7500
ggtgccggtt gcggttcgtt ctggacggga gtcccgagga cgcctatgtg acgtcggagg 7560
attactttaa gcgctgctgc ggccagtcca gttatcgcgg cttcgcggtg gcggtcctga 7620
cggccaacga ggaccacgtg cacagcctgg ccgtgccccc cctcgttctg ctgcaccggt 7680

```
tctccctgtt caaccccagg gacctcctgg actttgagct tgcctgtctg ctgatgtacc   7740
tggagaactg cccccgaagc cacgccaccc cgtcgacctt tgccaaggtt ctggcgtggc   7800
tcggggtcgc gggtcgccgc acgtccccat tcgaacgcgt tcgctgcctt ttcctccgca   7860
gttgccactg ggtcctaaac acactcatgt tcatggtgta cgtaaaaccg ttcgacgacg   7920
agttcgtcct gccccactgg tacatggccc ggtacctgct ggccaacaac ccgccccccg   7980
ttctctcggc cctgttctgt gccaccccga cgagctcctc attccggctg ccggggccgc   8040
ccccccgctc cgactgcgtg gcctataacc ccgccgggat catggggagc tgctgggcgt   8100
cggaggaggt gcgcgcgcct ctggtctatt ggtggctttc ggagacccca aaacgacaga   8160
cgtcgtcgct gttttatcag ttttgttgaa ttttaggaaa taaacccggt tttgtttctg   8220
tggcctcccg acggatgcgc gtgtccttac tccgtcttgg tgggtgggtg gctgtgtatg   8280
gcgtcccatc tgtgcgggga ggggggcaag tcggcacgta ttcggacaga ctcaagcaca   8340
taagacgaac aaaaggtttg taacttcgta ccgtgagtaa taatgtggac tttattgctt   8400
aagaatacgc gtagagaaat aagacgaaca aaaggtttgt gattttattg cttaagaata   8460
cgcgtagatg gtcgtaccgt gagtaataat gtggttcata agacgaacaa aaggtttgtg   8520
acattattgc ttaagaatac gcgtaggtgg tcgtaccgtg agtaataatg tgtactttat   8580
tgcttaagaa tacgcgtagg ctatcgtacc gtgagtaata atgtgcctta taagacgaac   8640
aaaaggtttg tacacggggg agcgctcttg tctcagggca atgtttttat tggtcaaact   8700
caggcaaaca gaaacgacat cttgtcgtca aagggataca caaacttccc cccctcgccc   8760
catactcccg ccagcacccc ggtaaacacc aactcaatct cgcgcaggat ttcgcgcagg   8820
tgatgagcgc agtccacggg ggggagcaca aggggccgcg ggtatagatc gacggggacg   8880
ccgaccgact ccccgcctcc gggacagaca cgcacgacgc gccgccagta gtgctctgcg   8940
tccagcaagg cgccgccgcg gaaggcagtg gggggcaagg ggtcgctggc ctcaaagggg   9000
gacacccgaa cgctccagta ctccgcgtcc aaccgtttat taaacgcgtc caagataagg   9060
cggtcgcagg cgtcctccat aaggccccgg gccgtgagtg cgtcctcctc cggcacgcat   9120
gccgttgtca ggcccaggac ccgtcgcagc gtgtcgcgta cgacccctgc cgccgtggtg   9180
tacgcgggcc cgcggagagg aaatccccca agatggtcag tgttgtcgcg ggagttccag   9240
aaccacactc ccgcctggct ccaggcgact gcgtgggtgt agacgccctc gagggccagg   9300
cacagtgggt gccgcagccg gacggcgttg gccctaagca cggctcccac ggccgtctcg   9360
atggcccgcc gggcgtcctc gatcaccccg gaagccgcat ccgcgtcttg ggggtccacg   9420
ttaaagacac cccagaacgc acccccatcg cccccgcaga ccgcgaactt caccgagctg   9480
gccgtctcct cgatctgcag gcagacggcg gccattaccc cacccaggag ctgccgcagc   9540
gcagggcagg cgttgcacgt gtccgggacc aggcgctcca agacggcccc ggcccagggc   9600
tctgagggag cggccaccac cagcgcgtcc agtcttgcta ggcccgtccg gccgtggggg   9660
tccgccagcc cgctcccccc gaggtcggcc agggccgcca ggagctgggc gcgaagtccg   9720
gggaagcaaa accgcgccgt ccagacgggc ccgacggccg cgggcgggtc taacagttgg   9780
atgattttag tggcgggatg ccaccgcgcc accgcctccc gcaccgcggg caggaggcat   9840
ccggctgccg ccgaggccac gccgggccag gctcgcgggg ggaggacgac cctggccccc   9900
accgcgggcc aggcccccag gagcgcggcg taagcggccg cggccccgcg caccaggtcc   9960
cgtgccgact cggccgtggc cggcacggtg aacgtgggcc aacccggaaa ccccaggacg  10020
```

-continued gcaaagtacg ggacgggtcc cccccggacc tcaaactcgg gccccagaaa ggcaaagacg 10080
ggggccaggg ccccgggggc ggcgtggacc gtggtatgcc actgccggaa aagggcgacg 10140
agcgccggcg cggagaactt ctcgccggcg cttacaaagt agtcgtaatc gcggggcagc 10200
agcacccgtg ccgtgactcg ttgcgggtgc ccgcgtggcc gcaggcccac ctcgcacacc 10260
tcgaccaggt ccccgaacgc gccctccttc ttgatcggcg gaaacgcaag agtctggtat 10320
tcgcgcgcaa atagcgcggt tccggtggtg atgttaacgg tcagcgaagc ggcggacgcg 10380
cactgggggg tgtcgcgaat ggccgccagg cgcgcccacg ccagccgcgc gtcgggatgc 10440
tcggcaacgc gcgccgccag ggccataggg tcgatgtcaa tgttggcctc cgcgaccagg 10500
agagcggcgc gaggggcggc gggcgggccc cacgacgctc tctcaacttt caccaccagt 10560
cccgtgcgtg ggtccgagcc gatacgcagc ggggcgaaca gggccaccgg cccggtctgg 10620
cgctccaggg ccgccaggac gcacgcgtac agcgcccgcc acagagtcgg gttctccagg 10680
ggctccagcg gggaggcggc cggcgtcgtc gcggcgcggg cggccgccac gacggcctgg 10740
acggagacgt ccgcggagcc gtagaaatcc cgcagctccg tcgcggtgac ggagacctcc 10800
gcaaagcgcg cgcgaccctc ccctgcggcg ttgcgacata caaaatacac cagggcgtgg 10860
aagtactcgc gagcgcgggg gggcagccat accgcgtaaa gggtaatggc gctgacgctc 10920
tcctccaccc acacgatatc tgcggtgtcc atcgcacggc ccctaaggat cacgggcggt 10980
ctgtgggtcc catgctgccg tgcctggccg ggcccggtgg gtcgcggaaa ccggtgacgg 11040
ggggggggcg gtttttgggg ttggggtggg ggtgggaaac ggcccgggtc cgggggccaa 11100
cttggcccct cggtgcgttc cggcaacagc gccgccggtc cgcggacgac cacgtaccga 11160
acgagtgcgg tcccgagact tatagggtgc taaagttcac cgccccctgc atcatgggcc 11220
aggcctcggt ggggagctcc gacagcgccg cctccaggat gatgtcagcg ttggggttgg 11280
cgctggatga gtgcgtgcgc aaacagcgcc cccacgcggg cacgcgtagc ttgaagcgcg 11340
cgcccgcaaa ctcccgcttg tgggccataa gcagggcgta cagctgcctg tgggtccggc 11400
aggcgctgtg gtcgatgtgg tgggcgtcca acaaccccac gattgtctgt ttggtgaggt 11460
ttttaacgcg ccccgccccg ggaaacgtct gcgtgctttt ggccatctgc acgccaaaca 11520
gttcgcccca gattatcttg aacagcgcca ccgcgtggtc cgtctcgcta acggacccgc 11580
gcgggggaca gccgcttagg gcgtcggcga cgcgcttgac ggcttcctcc gagagcagaa 11640
gtccgtcggt tacgttacag tggcccagtt cgaacaccag ctgcatgtag cggtcgtagt 11700
ggggggtcag taggtccagc acgtcatcgg ggccgaaggt cctcccagat cccccggccg 11760
ccgagtccca atgcaggcgc gcggccatgg tgctgcacag gcacaacagc tcccagacgg 11820
gggttacgtt cagggtgggg ggcagggcca cgagctccag ctctccggtg acgttgatcg 11880
tggggatgac gcccgtggcg tagtggtcat agatccgccg aaatatggcg ctgctgcggg 11940
tggccatggg aacgcggaga caggcctcca gcaacgccag gtaaataaac cgcgtgcgtc 12000
ccatcaggct gttgaggttg cgcatgagcg cgacaatttc cgccggcgcg acatcggacc 12060
ggaggtattt ttcgacgaaa agacccacct cctccgtctc ggcggcctgg gccggcagcg 12120
acgcctcggg atcccggcac cgcagctccc gtagatcgcg ctgggccctg agggcgtcga 12180
aatgtacgcc ccgcaaaaac agacagaagt cctttggggt cagggtatcg tcgtgtcccc 12240
agaagcgcac gcgtatgcag tttagggtca gcagcatgtg aaggatgtta aggctgtccg 12300
agagacacgc cagcgtgcat ctctcaaagt agtgtttgta acggaatttg ttgtagatgc 12360
gcgacccccg ccccagcgac gtgtcgcatg ccgacgcgtc acagcgcccc ttgaaccggc 12420

```
gacacagcag gtttgtgacc tgggagaact gcgcgggcca ctggccgcag gaactgacca  12480
cgtgattaag gagcatgggc gtaaagacgg gctccgagcg cgccccggag ccgtccatgt  12540
aaatcagtag ctcccccttg cggagggtgc gcacccgtcc cagggactgg tacacggaca  12600
ccatgtccgg tccgtagttc atgggtttca cgtaggcgaa catgccatca aagtgcaggg  12660
gatcgaagct gaggcccacg gttacgaccg tcgtgtatat aaccacgcgg tattggcccc  12720
acgtggtcac gtccccgagg ggggtgagcg agtgaagcaa cagcacgcgg tccgtaaact  12780
gacggcagaa ccgggccacg atctccgcga aggagaccgt cgacgaaaaa atgcagatgt  12840
tatcgccccc gccaaggcgc gcttccagct ccccaaagaa cgtggccccc cgggcctccg  12900
gagaggcgtc cggagacggg ccgctcggcg gcccgggcgg gcgcagggca gcctgcagga  12960
gctcggtccc cagacgcggg agaaacaggc accggcgcgc cgaaaacccg ggcatggcgt  13020
actcgccgac caccacatgc acgttttttt cgccccggag accgcacagg aagtccacca  13080
actgcgcgtt ggcggttgcg tccatggcga tgatccgagg acagatgcgc agcaggcgta  13140
gcattaacgc atccacgcgg cccagttgct gcatcgttgg cgaatagagc tggcccagcg  13200
tcgacataac ctcgtccaga acgaggacgt cgtagttgtt cagaaggttg gggcccacgc  13260
gatgaaggct ttccacctgg acgataagtc ggtggaaggg gcggtcgttc ataatgtaat  13320
tggtggatga gaagtaggtg acaaagtcga ccaggcctga ctcagcgaac cgcgtcgcta  13380
gggtctgggt aaaactccga cgacaggaga cgacgagcac actcgtgtcc ggagagtgga  13440
tcgcttcccg cagccagcgg atcagcgcgg tagtttttcc cgaccccatt ggcgcgcgga  13500
ccacagtcac gcacctggcc gtcggggcgc tcgcgttggg gaaggtgacg ggtccgtgct  13560
gctgccgctc gatcgttgtt ttcgggtgaa cccggggcac ccattcggcc aaatcccccc  13620
cgtacaacat ccgcgctagc gatacgctcg acgtgtactg ttcgcactcg tcgtccccaa  13680
tgggacgccc ggcccccaga ggatctcccg actccgcgcc ccccacgaaa ggcatgaccg  13740
gggcgcggac ggcgtggtgg gtctggtgtg tgcaggtggc gacgtttgtg gtctctgcgg  13800
tctgcgtcac ggggctcctc gtcctggcct ctgtgttccg ggcacggttt ccctgctttt  13860
acgccacggc gagctcttat gccggggtga actccacggc cgaggtgcgc gggggtgtag  13920
ccgtgcccct caggttggac acgcagagcc ttgtgggcac ttatgtaatc acggccgtgt  13980
tgttgttggc cgtggccgtg tatgccgtgg tcggcgccgt gacctcccgc tacgaccgcg  14040
ccctggacgc gggccgccgt ctggctgcgg cccgcatggc catgccgcac gccacgctga  14100
tcgccggaaa cgtctgctct tggttgctgc agatcaccgt cctgttgctg gcccatcgca  14160
tcagccagct ggcccacctg gtttacgtcc tgcactttgc gtgtctggtg tattttgcgg  14220
cccatttttg caccaggggg gtcctgagcg ggacgtatct gcgtcaggtg cacggcctga  14280
tggagctggc ccccgaccat catcgcgtcg tcggcccggc tcgcgccgtg ctgacaaacg  14340
ccttgctgtt gggcgtcttc ctgtgcacgg ccgacgccgc ggtatccctg aataccatcg  14400
ccgcgttcaa ctttaatttt tcggccccgg gcatgctcat ctgcctgacc gtgctgttcg  14460
ccattctcgt cgtatcgctg ttgttggtgg tcgagggggt gttgtgtcac tacgtgcgcg  14520
tgttggtggg cccccacctg ggggccgtgg ccgccacggg catcgtcggc ctggcctgcg  14580
agcactatta caccaacggc tactacgttg tggagacgca gtggccgggg gctcagacgg  14640
gagtccgcgt cgccctcgcc ctggtcgccg cctttgccct cggcatggcc gtgctccgct  14700
gcacccgcgc ctatctgtat cacaggcggc accacaccaa attttttatg cgcatgcgcg  14760
```

acacgcgaca ccgcgcacat tccgccctca agcgcgtacg cagttccatg cgcggatcgc 14820
gagacggccg ccacaggccc gcacccggca gcccgcccgg gattcccgaa tatgcggaag 14880
acccctacgc gatctcatac ggcggccagc tcgaccggta cggagattcc gacggggagc 14940
cgatttacga cgaggtggcg gacgaccaaa ccgacgtatt gtacgccaag atacaacacc 15000
cgcggcacct gcccgacgac gatcccatct atgacaccgt tggggggtac gaccccgagc 15060
ccgccgagga ccccgtgtac agcaccgtcc gccgttggta gctgtttggt tccgttttaa 15120
taaaccgttt gtgtttaacc cgaccgtggt gtatgtctgg tgtgtggcgt ccgatcccgt 15180
tactatcacc gtcccccccc ccccctcaac cccggcgatt gtgggttttt taaaaacgac 15240
acgcgtgcga ccgtatacag aacattgttt tggtttttat tcgctatcgg acatgggggg 15300
tggaaactgg gtggcggggc aggcgcctcc gggggtccgc cggtgagtgt ggcgcgaggg 15360
ggggtccgat gaacgcaggc gctgtctccc cggggcccgc gtaaccccgc gcatatccgg 15420
gggcacgtag aaattacctt cctcttcgga ctcgatatcc acgacgtcaa agtcgtgggc 15480
ggtcagcgag acgacctccc cgtcgtcggt gatgaggacg ttgtttcggc agcagcaggg 15540
ccgggccccg gagaacgaga ggcccatagc tcggcgagcg tgtcgtcgaa tgccaggcgg 15600
ctgcttcgct ggatggcctt atagatctcc ggatcgatgc ggacgggggt aatgatcagg 15660
gcgatcggaa cggcctggtt cgggagaatg gacgccttgc tgggtcctgc ggccccgaga 15720
gccccggcgc cgtcctccag gcggaacgtt acgccctcct ccgcgctggt gcggtgcctg 15780
ccgataaacg tcaccagatg cgggtggggg gggcagtcgg ggaagtggct gtcgagcacg 15840
tagccctgca ccaagatctg cttaaagttc gggtgacggg ggttcgcgaa gacgggctcg 15900
cggcggacca gatccccgga gctccaggac acgggggaga tggtgtggcg tccgaggtcg 15960
ggggcgccaa acagaagcac ctccgagaca acgccgctat ttaactccac caaggcccga 16020
tccgcggcgg agcaccgcct tttttcgccc gaggcgtggg cctctgacca ggcctggtct 16080
tgcgtgacga gagcctcctc cgggccgggg acgcgcccgg gcgcgaagta tcgcacgctg 16140
ggcttcggga tcgaccggat aaatgcccgg aacgcctccg gggaccggtg tgccatcaag 16200
tcctcgtacg cggaggccgt ggggtcgctg gggtccatgg ggtcgaaagc gtacttggcc 16260
cggcatttga cctcgtaaaa ggccaggggg gtcttgggga ctggggccag gtagccgtga 16320
atgtcccgag gacagacgag aatatccagg gacgccccga ccatccccgt gtgaccgtcc 16380
atgaggaccc cacacgtatg cacgttctct tcggcgaggt cgctgggttc gtggaagata 16440
aagcgccgcg tgtcggcgcc ggcctcgccg ccgtcgtccg cgcggcccac gcagtagcga 16500
aacagcaggc ttcgggccgt cggctcgttc acccgcccga acatcaccgc cgaagactgt 16560
acatccggcc gcaggctggc gttgtgcttc agccactggg gcgagaaaca cggaccctgg 16620
gggccccagc ggagggtgga tgcggtcgtg aggccccgcc ggagcagggc ccatagctgg 16680
cagtcggcct ggttttgcgt ggccgcctcg taaaacccca tgaggggccg gggcgccacg 16740
gcgtccgcgg cggccggggg cccgcggcgc gtcaggcgcc ataggtgccg accgagtccg 16800
cggtccacca tacccgcctc ctcgaggacc acggccaggg aacacagata atccaggcgg 16860
gcccagaggg gaccgatggc cagaggggcg cggacgccgc gcagcaaccc gcgcaggtgg 16920
cgctcgaacg tctcggctag tatatgggag ggcagcgcgt tggggatcac cgacgccgac 16980
cacatagagt caaggtccgg ggagtcggga tcggcgtccg ggtcgcgggc gtgggtgccc 17040
ccaggagata gcggaatgtc tggggtcgga ggccctgagg cgtcagaaag tgccggcgac 17100
gcggcccggg gcttttcgtc tgcggtgtcg gtggcgtgct gatcacgtgg ggggttaacg 17160

-continued

```
ggcgaatggg agctcgggtc cacagctgat gtcgtctggg gtgggggggg caggggacgg  17220
aaggtggttg tcagcggaag actgttaggg cgggggcgct tggggggct gtcggggcca  17280
cgaggggtgt cctcggccag ggcccaggga cgcttagtca cggtgcgtcc cggcggacat  17340
gctgggccta ccgtggactc catttccgag acgacgtggg gggagcggtg gttgagcgcg  17400
ccgccgggtg aacgctgatt ctcacgacag cgcgtgccgc gcgcacgggt tggtgtgaca  17460
caggcgggac accagcacca ggagaggctt aagctcggga ggcagcgcca ccgacgacag  17520
tatcgccttg tgtgtgtgct ggtaatttat acaccgatcc gtaaacgcgc gccgaatctt  17580
gggattgcgg aggtggcgcc ggatgccctc tgggacgtca tacgccaggc cgtgggtgtt  17640
ggtctcggcc gagttgacaa acagggctgg gtgcagcacg cagcgatagg cgagcagggc  17700
cagggcgaag tccggcgaca gctggttgtt aaaatactgg taaccgggaa accgggtcac  17760
gggtacgccc aggctcgggg cgacgtacac gctaaccacc aactccagca gcgtctggcc  17820
cagggcgtac aggtcaaccg ctaacccgac gtcgtgcttc aggcggtggt tggtaaattc  17880
ggcccgttcg ttgttaaggt atttcaccaa cagctccggg ggctggttat acccgtgacc  17940
caccagggtg tgaaagttgg ctgtggttag ggcggtgggc atgccaaaca tccgggggga  18000
cttgaggtcc ggctcctgga ggcaaaactg cccccgggcg atcgtggagt tggagttgag  18060
ggtgacgagg ctaaagtcgg cgaggacggc ccgccggagc gagacggcgt ccgaccgcag  18120
catgacgagg atgttggcgc acttgatatc caggtggctg atcccgcagg tggtgtttaa  18180
aaacacaacg gcgcgggcca gctccgtgaa gcactggtgg agggccgtcg agaccgaggg  18240
gtttgttgtg cgcagggacg ccagttggcc gatatactta ccgaggtcca tgtcgtacgc  18300
ggggaacact atctgtcgtt gttgcagcga gaacccgagg ggcgcgatga agccgcggat  18360
gttgtgggtg cggccggcgc gtagaacgca ctccccgacc aacagggtcg cgatgagctc  18420
aacggcaaac cactcctttt cctttatggt cttaacggca agcttatgtt cgcgaatcag  18480
ttggacgtca ccgtatcccc cagaccccc gaagcttcgg gccccgggga tctcgagggt  18540
cgtgtagtgt agggcggggt tgatggcgaa cacggggctg catagcttgc ggatgcgcgt  18600
gagggtgagg atgtgcgagg gggacgaggg gggtgcggtt aacgccgcct gggatctgcg  18660
caggggcggg cggttcagtt tggccgccgt accgggcgtc tcgggggacg cgcggcgatg  18720
agacgagcgg ctcattcgcc atcgggatag tcccgcgcga agccgctcgc ggaggccgga  18780
tcggtggcgg gacccgtggg aggagcggga gacggcggcg tcctggagag aggggccgct  18840
ggggcgcccg gaggccccgt gggggttgga gtgtacgtag gatgcgagcc aatccttgaa  18900
ggaccgttgg cgtgcacctt gggggctgag gttagctgcc acatgaccag caggtcgctg  18960
tctgcgggac tcatccatcc ttcggccagg tcgccgtctc cccacagaga agcgttggtc  19020
gctgcttcct cgagttgctc ctcctggtcc gcaagacgat cgtccacggc gtccaggcgc  19080
tcaccaagcg ccggatcgag gtaccgtcgg tgtgcggtta gaaagtcacg acgcgccgct  19140
tgctcctcca cgcgaatttt aacacaggtc gcgcgctgtc gcatcatctc taagcgcgcg  19200
cgggacttta gccgcgcctc caattccaag tgggccgcct ttgcagccat aaaggcgcca  19260
acaaaccgag gatcttgggt gctgacgccc tcccggtgca gctgcagggt ctggtccttg  19320
taaatctcgg ctcggaggtg cgtctcggcc aggcgtcggc gcagggccgc gtgggcggca  19380
tctcggtcca ttccgccacc ctgcgggcga cccgggggt gctctgatag tctcgcgtgc  19440
ccaaggcccg tgatcggggt acttcgccgc cgcgacccgc cacccggtgt gcgcgatgtt  19500
```

tggtcagcag ctggcgtccg acgtccagca gtacctggag cgcctcgaga aacagaggca 19560
acttaaggtg ggcgcggacg aggcgtcggc gggcctcacc atgggcggcg atgccctacg 19620
agtgcccttt ttagatttcg cgaccgcgac cccaagcgc caccagaccg tggtccctgg 19680
cgtcgggacg ctccacgact gctgcgagca ctcgccgctc ttctcggccg tggcgcggcg 19740
gctgctgttt aatagcctgg tgccggcgca actaaagggg cgtgatttcg gggcgacca 19800
cacggccaag ctggaattcc tggcccccga gttggtacgg gcggtggcgc gactgcggtt 19860
taaggagtgc gcgccggcgg acgtggtgcc tcagcgtaac gcctactata gcgttctgaa 19920
tacgtttcag gccctccacc gctccgaagc ctttcgccag ctggtgcact ttgtgcggga 19980
ctttgcccag ctgctcaaaa cctccttccg ggcctccagc ctcacggaga ccacgggccc 20040
ccccaaaaaa cgggccaagg tggacgtggc cacccacggc cggacgtacg gcacgctgga 20100
gctgttccaa aaaatgatcc ttatgcacgc cacctacttt ctggccgccg tgctcctcgg 20160
ggaccacgcg gagcaggtca acacgttcct gcgtctcgtg tttgagatcc ccctgtttag 20220
cgacgcggcc gtgcgccact tccgccagcg cgccaccgtg tttctcgtcc cccggcgcca 20280
cggcaagacc tggtttctgg tgcccctcat cgcgctgtcg ctggcctcct ttcgggggat 20340
caagatcggc tacacggcgc acatccgcaa ggcgaccgag ccggtgtttg aggagatcga 20400
cgcctgcctg cggggctggt tcggttcggc ccgagtggac cacgttaaag ggaaaccat 20460
ctccttctcg tttccggacg ggtcgcgcag taccatcgtg tttgcctcca gccacaacac 20520
aaacgtaagt cctcttttct ttcgcatggc tctcccaagg ggccccgggt cgacccgacc 20580
cacacccacc cacccacata cacacacaac cagacgcggg aggaaagtct gccccgtggg 20640
cactgatttt tattcgggat cgcttgagga ggcccgggca acggcccggg caacggtggg 20700
gcaactcgta gcaaataggc gactgatgta cgaagagaag acacacaggc gccacccggc 20760
gctggtcggg gggatgttgt ccgcgccgca ccgtccccg acgacctctt gcagacggtc 20820
cgtgatgcaa ggacggcggg gggcctgcag cagggtgacc gtatccacgg gatggccaaa 20880
gagaagcgga cacaggctag catcccccctg gaccgccagg gtacactggg ccatcttggc 20940
ccacagacac ggggcgacgc agggacagga ctccgttacg acggaggaga gccacagtgc 21000
gttggcggaa tcgatgtggg gcggcggggc gcaggactcg cagcccccg ggtggttggt 21060
gatcctggcc aggagccatc ccagatggcg ggccctgctt cccggtggac agagcgaccc 21120
caggtcgctg tccatggccc agcagtagat ctggccgctg gggaggtgcc accaggcccc 21180
cgggcccaag gcgcagcacg cgcccggctc cgggggggtc ttcgcgggga ccagatacgc 21240
gccatccagc tcgccgacca ctggctcctc cgcgagctgt tcggtggttg ggtcgggggt 21300
ttcctccggg ggggtggccg cccgtatgcg tgcgaacgtg agggtgcaca ggagcggggt 21360
caggggggtgc gtcacgctcc ggaggtggac gatcgcgcag tagcggcgct cgcggttaaa 21420
gaaaaagagg gcaaagaagg tgttcggggg caaccgcagc gccttggggc gcgtcagata 21480
cagaaaaatc tcgcagaaga gggcgcgccc ggggtctggg ttaggaaggg ccacctgaca 21540
cagaggctcg gtgaggaccg ttagacaccg aaagatcttg agccgctcgt ccgcccgaac 21600
gacgcgccac acaaagacgg agttgacaat gcgcgcgata gagtcgacgt ccgtccccag 21660
gtcgtcgact ctatcgcgcg tgccgcgagc tccggcccgg gaatccggcc ggggcaaggt 21720
ccccggggga ccaggcggcg ccaggggccg ccggggtccc agctgcgcca tgccgggggc 21780
ggggggaggg caaaccccag aggcgggggc caacggcgcg gggaggagtg ggtgggcgag 21840
gtggccgggg gaaggcgccc gctagcgaga ccggccgttc ccggacgaca ccttgcgaca 21900

-continued aaacctaagg acagcggccc gcgcgacggg gtccgagagg ctaaggtagg ccgcgatgtt 21960
aatggtgaac gcaaagccgc cgggaaagac aactatgcca cagaggcggc gattaaaccc 22020
caggcagagg taggcgtagc tttccccggg caggtattgc tcgcagaccc tgcgtggggc 22080
tgtggagggg acggcctcca tgaagcgaca tttactctgc tcgcgtttac tgacgtcacc 22140
atccatcgcc acggcgattg gacgattgtt aagccgcagc gtgtctccgc ttgtgctgta 22200
gtagtcaaaa acgtaatggc cgtcggagtc ggcaaagcgg gccgggaggt cgtcgccgag 22260
cgggacgacc cgccgccccc gaccgccccg tccccccagg tgtgccagga cggccagggc 22320
atacgcggtg tgaaaaaagg cgtcgggggc ggtcccctcg acggcgcgca tcaggttctc 22380
gaggagaatg gggaagcgcc tggtcacctc ccccaaccac gcgcgttggt cggggccaaa 22440
gtcatagcgc aggcgctgtg agattcgcgg gccgccctga agcgcggccc ggatggcctg 22500
gcccagggcc cggaggcacg ccagatgtat gcgcgcggta aaggcgacct cggcggcgat 22560
gtcaaagggc ggcaggacgg ggcgcgggtg gcgcaggggc acctcgagcg cgggaaagcg 22620
tagcagcagc tccgcctgcc cagcgggaga cagctggtgg gggcgcacga cgcgttctgc 22680
ggcgcaggcc tcggtcaggg ccgtggccag cgccgaggac agcagcggag ggcgggcgcg 22740
tcgcccgccc cacgccacgg agttctcgta ggagacgacg acgaagcgct gcttggttcc 22800
gtagtggtgg cgcaggacca cggagataga acgacggctc cacagccagt ccggccggtc 22860
gccgccggcc agggcttccc atccgcgatc caaccactcg accagcgacc gcggctttgc 22920
ggtaccaggg gtaagggtta gaacgtcgtt caggatgtcc tcgcccccgg gcccgtgggg 22980
cgctggggcc acaaagcggc ccccgccggg gggctccaga cccgccagca ccgcatctgc 23040
gtcagccgcc cccatggcgc ccccgctgac ggcctggtga accagggcgc cctggcgtag 23100
ccccgatgca acgccacagg ccgcacgccc ggtccgcgct cggaccgggt ggcggcgggt 23160
gacgtcctgc actgcccgct gaaccaacgc gaggatctcc tcgttctcct gtgcgatgga 23220
cacgtcctgg gccgcggtcg tgtcgccgcc gggggccgtc agctgctcct ccggggagat 23280
gggggggtcg gacgccccga cgatgggcgg gtctgcgggc gcccccgcgt ggggccgggc 23340
caagggctgc ggacgcgggg acgcgctttc ccccagaccc atggacaggt gggccgcagc 23400
ctccttcgcg gccggcgggg cggcggcgcc aagcagagcg acgtagcggc acaaatgccg 23460
acagacgcgc atgatgcgcg tgctgtcggc cgcgtagcgc gtgttggggg ggacgagctc 23520
gtcgtaacta aacagaatca cgcgggcaca gctcgccccc gagccccacg caaggcgcag 23580
cgccgccacg gcgtacgggt catagacgcc ctgcgcgtca cacaccacgg gcagggagac 23640
gaacaacccc ccggcgctgg acgcacgcgg aaggaggcca gggtgtgccg gcacgacggg 23700
ggccagaagc tcccccaccg catccgcggg cacgtaggcg gcaaacgccg tgcaccacgg 23760
ggtacagtcg ccggtggcat gagcccgagt ctggatttcg acctggaagt ttgcggccgt 23820
cccgagtccg gggcggccgc gcatcagggc ggccagaggg attcccgcgg ccgccaggca 23880
ctcgctggat atgatgacgt gaaccaaaga ccgagggccg acccgggccg tggccgagat 23940
cgtctggacc tcgttggcca agtgcgcgtt catggttcgg gggtgggtgt gggtgtgtag 24000
gcgatgcggg tcccccgagt ccgcgggaag ggcgtgggtt tggcgcgcgt atgcgtattc 24060
gccaacggag gcgtgcgtgc ttatgcgcgg cgcgtttctt ctgtctctag ggaatccgag 24120
gccaggactt taacctgctc tttgtcgacg aggccaactt tattcgcccg gatgcggtcc 24180
agacgattat gggctttctc aaccaggcca actgcaagat tatcttcgtg tcgtccacca 24240

-continued

```
acaccgggaa ggccagtacg agctttttgt acaacctccg cggggccgca gacgagcttc  24300
tcaacgtggt gacctatata tgcgatgatc acatgccgag ggtggtgacg cacacaaacg  24360
ccacggcctg ttcttgttat atcctcaaca agcccgtttt catcacgatg gacggggcgg  24420
ttcgccggac cgccgatttg tttctggccg attccttcat gcaggagatc atcgggggcc  24480
aggccaggga gaccggcgac gaccggcccg ttctgaccaa gtctgcgggg gagcggtttc  24540
tgttgtaccg cccctcgacc accaccaaca gcggcctcat ggcccccgat ttgtacgtgt  24600
acgtggatcc cgcgttcacg gccaacaccc gagcctccgg gaccggcgtc gctgtcgtcg  24660
ggcggtaccg cgacgattat atcatcttcg ccctggagca ctttttctc cgcgcgctca  24720
cgggctcggc ccccgccgac atcgcccgct gcgtcgtcca cagtctgacg caggtcctgg  24780
ccctgcatcc cggggcgttt cgcggcgtcc gggtggcggt cgagggaaat agcagccagg  24840
actcggccgt cgccatcgcc acgcacgtgc acacagagat gcaccgccta ctggcctcgg  24900
agggggccga cgcgggctcg ggccccgagc ttctcttcta ccactgcgag cctcccggga  24960
gcgcggtgct gtaccccttt ttcctgctca acaaacagaa gacgcccgcc tttgaacact  25020
ttattaaaaa gtttaactcc gggggcgtca tggcctccca ggagatcgtt tccgcgacgg  25080
tgcgcctgca gaccgacccg gtcgagtatc tgctcgagca gctaaataac ctcaccgaaa  25140
ccgtctcccc caacactgac gtccgtacgt attccggaaa acggaacggc gcctcggatg  25200
accttatggt cgccgtcatt atggccatct acctcgcggc ccaggccgga cctccgcaca  25260
cattcgctcc tatcacacgc gtctcgtgag cgcccaataa acacacccag gtatgctacg  25320
cacgaccacg gtgtcgtctg ttaagggggg ggggggaagg gggtgttggc gggaagcgtg  25380
ggaacacggg ggattctctc acgaccggca ccagtaccac ccccctgtga acacagaaac  25440
cccaacccaa atcccataaa catacgacac acaggcatat tttggaattt cttaggtttt  25500
tatttattta ggtatgctgg ggtttctccc tggatgccca ccccccacccc cccgtgggtc  25560
tagccgggcc ttagggatag cgtataacgg gggccatgtc tccggaccgc acaacggccg  25620
cgccgtcaaa ggtgcacacc cgaaccacgg gagccagggc caaggtgtct cctagttggc  25680
ccgcgtgggt cagccaggcg acgagcgcct cgtaaagcgg cagccttcgc tctccatcct  25740
gcatcagggc cggggcttcg gggtgaatga gctgggcggc ctcccgcgtg acactctgca  25800
tctgcagtag agcgttcacg tacccgtcct gggcacttag cgcaaagagc cgggggatta  25860
gcgtaaggat gatggtggtt ccctccgtga tcgagtaaac catgttaagg accagcgatc  25920
gcagctcggc gtttacggga ccgagttgtt ggacgtccgc cagcagcgag aggcgactcc  25980
cgttgtagta cagcacgttg aggtctggca gccctccggg gtttctgggg ctggggttca  26040
ggtcccggat gcccctggcc acgagccgcg ccacgatttc gcgcgccagg ggcgatggaa  26100
gcggaacggg aaaccgcaac gtgaggtcca gcgaatccag gcgcacgtcc gtcgcttggc  26160
cctcgaacac gggcgggacg aggctgatgg ggtccccgtt acagagatct acgggggagg  26220
tgttgcgaag gttaacggtg ccggcgtggg tgaggcccac gtccaggggg caggcgacga  26280
ttcgcgtggg aagcacccgg gtgatgaccg cggggaagcg ccttcggtac gccagcaaca  26340
accccaacgt gtcgggactg acgcctccgg agacgaagga ttcgtgcgcc acgtcggcca  26400
gcgtcagttg ccggcggatg gtcggcagga ataccacccg cccttcgcag cgctgcagcg  26460
ccgccgcatc ggggcgcgag atgcccgagg gtatcgcgat gtcagtttca aagccgtccg  26520
ccagcatggc gccgatccac gcggcaggga gtgcagtggt ggttcgggtg gcgggaggag  26580
cgcggtgggg gtcagcggcg tagcagagac gggcgaccaa cctcgcatag gacggggggt  26640
```

```
gggtcttagg gggttgggag gcgacaggga ccccagagca tgcgcgggga ggtctgtcgg  26700
gcccagacgc accgagagcg aatccgtccg cggagtcccg gcttgggttt tatggggccc  26760
ggccctcgga atcgcggctt gtcggcgggg acaaaggggg cggggctagg ggcttgcgga  26820
aacagaagac gcgtgggata aaagaatcgc actaccccaa ggaagggcgg ggcggtttat  26880
tacagagcca gtcccttgag cggggatgcg tcatagacga gatactgcgc gaagtgggtc  26940
tcccgcgcgt gggcttcccc gttgcgggca ctgcggagga gggcggggtc gctggcgcag  27000
gtgagcgggt aggcctcctg aaacaggcca cacgggtcct ccacgagttc gcggcacccc  27060
ggggggcgct taaactgtac gtcgctggcg gcggtggccg tggacaccgc cgaacccgtc  27120
tccacgatca ggcgctccag gcagcgatgt ttggcggcga tgtcggccga cgtaaagaac  27180
ttaaagcagg ggctgagcac cggcgaggcc ccgttgaggt ggtaggcccc gttatagagc  27240
aggtccccgt acgaaaatcg ctgcgacgcc cacgggttgg ccgtggccgc gaaggcccgg  27300
gacgggtcgc tctggccgtg gtcgtacatg agggcggtga catccccctc cttgtccccc  27360
gcgtaaacgc ccccggcggc gcgtccccgg gggttgcagg gccggcggaa gtagttgacg  27420
tcggtcgaca cgggggtggc gataaactca cacacggcgt cctggccgtg gtccatccct  27480
gcgcgccgcg gcacctgggc gcacccgaac acggggacgg gctgggccgg ccccaggcgg  27540
tttcccgcca cgaccgcgtt ccgcaggtac acggctgccg cgttgtccag gagaggggga  27600
gccccgcggc ccaggtaaaa gttttgggga aggttgccca tgtcggtgac ggggttgcgg  27660
acggttgccg tggccacgac ggcggtgtag cccacgccca ggtccacgtt cgcgcgcggc  27720
tgggtgagcg tgaagtttac ccccccgcca gtttcgtgcc gggccacctg gagctggccc  27780
aggaagtacg cctccgacgc gcgctccgag aacagcacgt tctcagtcac aaagcggtcc  27840
tgtcggacga cggtgaaccc aaacccggga tggaggcccg tcttgagctg atgatgcaag  27900
gccacgggac tgatcttgaa gtaccccgcc atgagcgcgt aggtcagcgc gttctccccg  27960
gccgcgctct cgcggacgtg ctgcacgacg ggctgtcgga tcgacgaaaa gtagttggcc  28020
cccagagccg gggggaccag ggggacctgc cgcgacaggt cgcgcagggc cggggggaaa  28080
ttgggcgcgt tcgccacgtg gtcggccccg gcgaacagcg cgtggacggg gagggggtaa  28140
aaatagtcgc cattttggat ggtatggtcc agatgctggg gggccatcag caggattccg  28200
gcgtgcaacg ccccgtcgaa tatgcgcatg ttggtggtgg acgcggtgtt ggcgcccgcg  28260
tcgggcgccg ccgagcagag cagcgccgtt gtgcgttcgg ccatgttgtg ggccagcacc  28320
tgcagcgtga gcatggcggg cccgtccact accacgcgcc cgttgtgaaa catggcgttg  28380
accgtgttgg ccaccagatt ggccgggtgc agggggtgcg cggggtccgt cacggggtcg  28440
ctggggcact cctcgccggg ggcgatctcc gggaccacca tgttctgcag ggtggcgtat  28500
acgcggtcga agcgaacccc cgcggtgcag cagcggcccc gcgagaaggc gggcaccatc  28560
acgtagtagt aaatcttgtg gtgcacggtc cagtccgccc cccggtgcgg ccggtcatcc  28620
gcggcgtccg cggctcgggc ctgggtgttg tgcagcagct ggccgtcgtt gcggttgaag  28680
tccgcggtcg ccacgttaca tgccgccgcg tacacggggt cgtggccccc cgcgctaacc  28740
cggcagtcgc gatggcggtc cagggccgcg cgccgcatca gggcgtcaca gtcccacacg  28800
aggggtggca gcagcgccgg gtctcgcatt aggtgattca gctcggcttg cgcctgcccg  28860
cccagctccg ggccggtcag ggtaaagtca tcaaccagct gggccagggc ctcgacgtgc  28920
gccaccaggt cccggtacac ggccatgcac tcctcgggaa ggtctccccc gaggtaggtc  28980
```

```
acgacgtacg agaccagcga gtagtcgttc acgaacgccg cgcaccgcgt gttgttccag  29040
tagctggtga tgcactggac cacgagccgg gccagggcgc agaagacgtg ctcgctgccg  29100
tgtatggcgg cctgcagcag gtaaaacacc gccgggtagt tgcggtcgtc gaacgccccg  29160
cgaacggcgg cgatggtggc gggggccatg gcgtggcgtc ccaccccccag ctccaggccc  29220
cgggcgtccc ggaacgccgc cggacatagc gccaggggca agttgccgtt caccacgcgc  29280
caggtggcct ggatctcccc cgggccggcc gggggaacgt cccccccccgg cagctccacg  29340
tcggccaccc ccacaaagaa gtcgaacgcg gggtgcagct caagagccag gttggcgttg  29400
tcgggctgca taaactgctc cggggtcatc tggccttccg cgacccatcg gacccgcccg  29460
tgggccaggc gctgccccca ggcgttcaaa aacagctgct gcatgtctgc ggcggggccg  29520
gccggggccg ccacgtacgc cccgtacgga ttggcggctt cgacggggtc gcggttaagg  29580
cccccgaccg ccgcgtcaac gttcatcagc gaagggtggc acacggtccc gatcgcgtgt  29640
tccagagaca ggcgcagcac ctggcggtcc ttcccccaaa aaaacagctg gcggggcggg  29700
aaggcgcggg gatccgggtg gccgggggcg gggactaggt ccccggcgtg cgcggcaaac  29760
cgttccatga ccggattgaa caggcccagg ggcaggacga acgtcaggtc catggcgccc  29820
accagggggt agggaacgtt ggtggcggcg tagatgcgct tctccagggc ctccagaaag  29880
accagcttct cgccgatgga caccagatcc gcgcgcacgc gcgtcgtctg gggggcgctc  29940
tcgagctcgt ccagcgtctg ccggttcagg tcgagctgct cctcctgcat ctccagcagg  30000
tggcggccca cgtcgtccag acttcgcacg gccttgccca tcacgagcgc cgtgaccagg  30060
ttggccccgt tcaggaccat ctcgccgtac gtcaccggca cgtcggcttc ggtgtcctcc  30120
actttcagga aggactgcag gaggcgctgt ttgatcgggg cggtggtgac gagcaccccg  30180
tcgaccggcc gcccgcgcgt gtcggcatgc gtcagacggg gcacggccac ggagggctgc  30240
gtggccgtgg tgaggtccac gagccaggcc tcgacggcct cccggcggtg gcccgccttg  30300
cccaggaaaa agctcgtctc gcagaagctt cgctttagct cggcgaccag ggtcgcccgg  30360
gccaccctgg tggccaggcg gccgttgtcc aggtatcgtt gcatcggcaa caacaaagcc  30420
aggggcggcg ccttttccag cagcacgtgc agcatctggt cggccgtgcc gcgctcaaac  30480
gccccgagga cggcctggac gttgcgagcg agctgttgga tggcgcgcaa ctggcgatgc  30540
gcgccgatac ccgtcccgtc cagggcctcc cccgtgagca gggcgatggc ctcggtggcc  30600
aggctgaagg cggcgttcag ggcccggcgg tcgataatct tggtcatgta attgtgtgtg  30660
ggttgctcga tggggtgcgg gccgtcgcgg gcaatcagcg gctggtggac ctcgaactgt  30720
acgcgcccct cgttcatgta ggccagctcc ggaaacttgg tacacacgca cgccaccgac  30780
aacccgagct ccagaaagcg cacgagcgac agggtgttgc aatacgaccc cagcagggcg  30840
tcgaactcga cgtcgtacag gctgtttgca tcggagcgca cgcgggaaaa aaaatcaaac  30900
aggcgtcgat gcgacgccac ctcgatcgtg ctaaggaggg acccggtcgg caccatggcc  30960
gcggcatacc ggtatcccgg agggtcgcgg ttgggagcgg ccatggggtc gcgtggagat  31020
cggctgtctc tagcgatatt ggcccgggga ggctaagatc caccccaacg cccggccacc  31080
cgtgtacgtg cccgacggcc caaggtccac cgaaagacac gacgggcccg gacccaaaaa  31140
ggcgggggat gctgtgtgag aggccgggtg ccggtcgggg gggaaaggca ccgggagaag  31200
gctgcggcct cgttccagga gaacccagtg tccccaacag acccggggac gtgggatccc  31260
aggccttata taccccccccc cccgccccac ccccgttaga acgcgacggg tgcattcaag  31320
atggccctgg tccaaaagcg tgccaggaag aaattggcag aggcggcaaa gctgtccgcc  31380
```

gccgccaccc acatcgaggc cccggccgcg caggctatcc ccagggcccg tgtgcgcagg 31440
ggatcggtgg gcggcagcat ttggttggtg gcgataaagt ggaaaagccc gtccggactg 31500
aaggtctcgt gggcggcggc gaacaaggca cacagggccg tgcctcccaa aaacacggac 31560
atcccccaaa acacgggcgc cgacaacggc agacgatccc tcttgatgtt aacgtacagg 31620
aggagcgccc gcaccgccca cgtaacgtag tagccgacga tggcggccag gatacaggcc 31680
ggcgccacca cccttccggt cagcccgtaa tacatgcccg ctgccaccat ctccaacggc 31740
ttcaggacca aaaacgacca aaggaacaga atcacgcgct ttgaaaagac cggctgggta 31800
tggggcggaa gacgcgagta tgccgaactg acaaaaaaat cagaggtgcc gtacgaggac 31860
aatgaaaact gttcctccag cggcagttct ccctcctccc ccccgaaggc ggcctcgtcg 31920
accagatctc gatccaccag aggaaggtca tcccgcatgg tcatggggtg tgcggtggag 31980
gtggggagac cgaaaccgca aagggtcgct tacgtcagca ggatcccgag atcaaagaca 32040
cccgggttct tgcacaaaca ccacccgggt tgcatccgcg gaggcgagtg ttttgataag 32100
gccgttccgc gccttgatat aacctttgat gttgaccaca aaacccggaa tttacgccta 32160
cgccccaatg cccacgcaag atgaggtagg taaccccccc gtgggtgtga cgttgcgttt 32220
agttcattgg aggccaaggg gaaaaatggg gtggggagga aacggaaaac ccagtaggcc 32280
gtgtcgggaa cacgcccggg gttgtcctca aaaggcaggg tccatactac ggaagccgtc 32340
gttgtattcg agacctgcct gtgcaacgca cgtcggggtt gcctgtgtcc ggttcggccc 32400
ccaccgcgtg cggcacgcac gaggacgagt ccgcgtgctt tattggcgtt ccaagcgttg 32460
ccctccagtt tctgttgtcg gtgttccccc atacccacgc ccacatccac cgtagggggc 32520
ctctgggccg tgttacgtcg ccgcccgcga tggagcttag ctacgccacc accatgcact 32580
accgggacgt tgtgttttac gtcacaacgg accgaaaccg ggcctacttt gtgtgcgggg 32640
ggtgtgttta ttccgtgggg cggccgtgtg cctcgcagcc cggggagatt gccaagtttg 32700
gtctggtcgt tcgagggaca ggcccagacg accgcgtggt cgccaactat gtacgaagcg 32760
agctccg 32767

<210> SEQ ID NO 851
<211> LENGTH: 32767
<212> TYPE: DNA
<213> ORGANISM: Artificial Sequence
<220> FEATURE:
<223> OTHER INFORMATION: recombinant viral vector ONCR-159

<400> SEQUENCE: 851
aaaaaagctg aacgagaaac gtaaaatgat ataaatatca atatattaaa ttagattttg 60
cataaaaaac agactacata atactgtaaa acacaacata tccagtcact atgaatcaac 120
tacttagatg gtattagtga cctgtagtcg accgacagcc ttccaaatgt tcttcgggtg 180
atgctgccaa cttagtcgac cgacagcctt ccaaatgttc ttctcaaacg gaatcgtcgt 240
atccagccta ctcgctattg tcctcaatgc cgtattaaat cataaaaaga aataagaaaa 300
agaggtgcga gcctcttttt tgtgtgacaa aataaaaaca tctacctatt catatacgct 360
agtgtcatag tcctgaaaat catctgcatc aagaacaatt tcacaactct tatacttttc 420
tcttacaagt cgttcggctt catctggatt ttcagcctct atacttacta aacgtgataa 480
agtttctgta atttctactg tatcgacctg cagactggct gtgtataagg gagcctgaca 540
tttatattcc ccagaacatc aggttaatgg cgtttttgat gtcattttcg cggtggctga 600

-continued

```
gatcagccac ttcttccccg ataacggaga ccggcacact ggccatatcg gtggtcatca    660
tgcgccagct ttcatccccg atatgcacca ccgggtaaag ttcacgggag actttatctg    720
acagcagacg tgcactggcc aggggatca ccatccgtcg cccgggcgtg tcaataatat    780
cactctgtac atccacaaac agacgataac ggctctctct tttataggtg taaaccttaa    840
actgcatttc accagcccct gttctcgtca gcaaaagagc cgttcatttc aataaaccgg    900
gcgacctcag ccatcccttc ctgattttcc gctttccagc gttcggcacg cagacgacgg    960
gcttcattct gcatggttgt gcttaccaga ccggagatat tgacatcata tatgccttga   1020
gcaactgata gctgtcgctg tcaactgtca ctgtaatacg ctgcttcata gcatacctct   1080
ttttgacata cttcgggtat acatatcagt atatattctt ataccgcaaa aatcagcgcg   1140
caaatacgca tactgttatc tggcttttag taagccggat ccacgcggcg tttacgcccc   1200
ccctgccact catcgcagta ctgttgtaat tcattaagca ttctgccgac atggaagcca   1260
tcacaaacgg catgatgaac ctgaatcgcc agcggcatca gcaccttgtc gccttgcgta   1320
taatatttgc ccatggtgaa aacgggggcg aagaagttgt ccatattggc cacgtttaaa   1380
aaggccgtaa tatccagctg aacggtctgg ttataggtac attgagcaac tgactgaaat   1440
gcctcaaaat gttctttacg atgccattgg gatatatcaa cggtggtata tccagtgatt   1500
tttttctcca ttttagcttc cttagctcct gaaaatctcg ataactcaaa aaatacgccc   1560
ggtagtgatc ttatttcatt atggtgaaag ttggaacctc ttacgtgccg atcaacgtct   1620
cattttcgcc aaaagttggc ccagggcttc ccggtatcaa cagggacacc aggatttatt   1680
tattctgcga agtgatcttc cgtcacaggt atttattcgg cgcaaagtgc gtcgggtgat   1740
gctgccaact tagtcgacta caggtcacta ataccatcta agtagttgat tcatagtgac   1800
tggatatgtt gtgttttaca gtattatgta gtctgttttt tatgcaaaat ctaatttaat   1860
atattgatat ttatatcatt ttacgtttct cgttcagctt tcttgtacaa agtggtttta   1920
atggaccgcc cgcaaggggg ggggggcatt tcagtgtcgg gtgacgagcg cgatccggcc   1980
gggatcctag gaccccaaaa gtttgtctgc gtattccagg gcggggctca gttgaatctc   2040
ccgcagcacc tctaccagca ggtccgcggt gggctggaga aactcggccg tcccggggca   2100
ggcggttgtc gggggtggag gcgcggcgcc caccccgtgt gccgcgcctg gcgtctcctc   2160
tgggggcgac ccgtaaatgg ttgcagtgat gtaaatggtg tccgcggtcc agaccacggt   2220
caaaatgccg gccgtggcgc tccgggcgct ttcgccgcgc gaggagctga cccaggagtc   2280
gaacggatac gcgtacatat gggcgtccca cccgcgttcg agcttctggt tgctgtcccg   2340
gcctataaag cggtaggcac aaaattcggc gcgacagtcg ataatcacca acagcccaat   2400
gggggtgtgc tggataacaa cgcctccgcg cggcaggcgg tcctggcgct cccggccccg   2460
taccatgatc gcgcgggtgc cgtactcaaa aacatgcacc acctgcgcgg cgtcgggcag   2520
tgcgctggtc agcgaggccc tggcgtggca taggctatac gcgatggtcg tctgtggatt   2580
ggacatctcg cggtgggtag tgagtccccc gggccgggtt cggtggaact gtaaggggac   2640
ggcgggttaa tagacaatga ccacgttcgg atcgcgcaga gccgatagta tgtgctcact   2700
aatgacgtca tcgcgctcgt ggcgctcccg gagcggattt aagttcatgc gaaggaattc   2760
ggaggaggtg gtgcgggaca tggccacgta cgcgctgttg aggcgcaggt tgccgggcgt   2820
aaagcagatg gcgaccttgt ccaggctaag gccctgggag cgcgtgatgg tcatggcaag   2880
cttggagctg atgccgtagt cggcgtttat ggccatggcc agctccgtag agtcaatgga   2940
ctcgacaaac tcgctgatgt tggtgttgac gacggacatg aagccgtgtt ggtcccgcaa   3000
```

```
gaccacgtaa ggcagggggg cctcttccag taactcggcc acgttggccg tcgcgtgccg   3060
cctccgcagc tcgtccgcaa aggcaaacac ccgtgcgtac gtgtatccca tgagcgtata   3120
attgtccgtc tgcagggcga cggacatcag ccccccgcgc ggcgagccgg tcagcatctc   3180
gcagccccgg aagataacgt tgtccacgta cgtgctaaag gggcgactt caaatgcctc    3240
cccgaagagc tcttggagga ttcggaatct cccgaggaag gcccgcttca gcagcgcaaa   3300
ctgggtgtga acggcggcgg tggtctccgg ttccccgggg gtgtagtggc agtaaaacac   3360
gtcgagctgt tgttcgtcca gccccgcgaa aataacgtcg aggtcgtcgt cgggaaaatc   3420
gtccgggccc ccgtcccgcg gccccagttg cttaaaatca aacgcacgct cgccgggggc   3480
gcctgcgtcg gccattaccg acgcctgcgt cggcaccccc gaagatttgg ggcgcagaga   3540
cagaatctcc gccgttagtt ctcccatgcg ggcgtaggcg agggtcctct gggtcgcatc   3600
caggcccggg cgctgcagaa agttgtaaaa ggagataagc ccgctaaata tgagccgcga   3660
caggaacctg taggcaaact ccaccgaagt ctccccctga gtctttacaa agctgtcgtc   3720
acgcaacact gcctcgaagg cccggaacgt cccactaaac ccaaaaacca gttttcgcag   3780
gcgcgcggtc accgcgatct ggctgttgag gacgtaagtg acgtcgttgc gggccacgac   3840
cagctgctgt ttgctgtgca cctcgcagcg catgtgcccc gcgtcctggt cctggctctg   3900
cgagtagttg gtgatgcggc tggcgttggc cgtgagccac ttttcaatcg tcaggccggg   3960
ctggtgtgtc agccgtcggt attcgtcaaa ctccttgacc gacacgaacg taagcacggg   4020
gagggtgaac acgacgaact ccccctcacg ggtcaccttc aggtaggcgt ggagcttggc   4080
catgtacgcg ctcacctctt tgtgggagga gaacagccgc gtccagccgg ggaggttggc   4140
ggggttggtg atgtagtttt ccgggacgac gaagcgatcc acgaactgca tgtgctcctc   4200
ggtgatgggc aggccgtact ccagcacctt catgaggtta ccgaactcgt gctcgacgca   4260
ccgtttgttg ttaataaaaa tggcccagct atacgagagg cgggcgtact cgcgcagcgt   4320
gcggttgcag atgaggtacg tgagcacgtt ctcgctctgg cggacggaac accgcagttt   4380
ctggtgctcg aaggtcgact ccagggacgc cgtctgcgtc ggcgagccca cacacaccaa   4440
cacgggccgc aggcgggccg cgtactgggg ggtgtggtac agggcgttaa tcatccacca   4500
gcaatacacc acggccgtga ggaggtgacg cccaaggagc ccggcctcgt cgatgacgat   4560
cacgttgctg cgggtaaagg ccggcagcgc cccgtgggtg gccggggcca accgcgtcag   4620
ggcgccctcg gccaacccca gggtccgttc cagggcggcc agggcgcgaa actcgttccg   4680
caactcctcg cccccggagg cggccagggc gcgcttcgtg aggtccaaaa tcacctccca   4740
gtagtacgtc agatctcgtc gctgcaggtc ctccagcgag gcggggttgc tggtcagggt   4800
gtacgggtac tgtcccagtt gggcctggac gtgattcccg cgaaacccaa attcatgaaa   4860
gatggtgttg atgggtcggc tgagaaaggc gcccgagagt ttggcgtaca tgttttgggc   4920
cgcaatgcgc gtggcgcccg tcaccacaca gtccaagacc tcgttgattg tctgcacgca   4980
cgtgctcttt ccggagccag cgttgccggt gataagatac accgcgaacg gaaactccct   5040
gaggggcagg cctgcggggg actctaaggc cgccacgtcc cggaaccact gcagatgggg   5100
cacttgcgct ccgtcgagct gttgttgcga gagctctcgg atgcgcttaa ggattggctg   5160
caccccgtgc atagacgtaa aatttaaaaa ggcctcggcc ctccctggaa cggctggtcg   5220
gtccccgggt tgctgaaggt gcggcgggcc gggtttctgt ccgtctagct ggcgctcccc   5280
gccggccgcc gccatgaccg caccacgctc gcgggccccc actacgcgtg cgcgggggga   5340
```

-continued

```
cacggaagcg ctgtgctccc ccgaggacgg ctgggtaaag gttcacccca gccccggtac   5400
gatgctgttc cgcgagattc tccacgggca gctggggtat accgagggcc agggggtgta   5460
caacgtcgtc cggtccagcg aggcgaccac ccggcagctg caggcggcga tctttcacgc   5520
gctcctcaac gccaccactt accgggacct cgaggcggac tggctcggcc acgtggcggc   5580
ccgcggtctg cagccccaac ggctggttcg ccggtacagg aacgcccggg aggcggatat   5640
cgccggggtg gccgagcggg tgttcgacac gtggcggaac acgcttagga cgacgctgct   5700
ggactttgcc cacgggttgg tcgcctgctt tgcgccgggc ggcccgagcg gcccgtcaag   5760
cttccccaaa tatatcgact ggctgacgtg cctggggctg gtccccatat tacgcaagcg   5820
acaagaaggg ggtgtgacgc agggtctgag ggcgtttctc aagcagcacc cgctgacccg   5880
ccagctggcc acggtcgcgg aggccgcgga gcgcgccggc cccgggtttt ttgagctggc   5940
gctggccttc gactccacgc gcgtggcgga ctacgaccgc gtgtatatct actacaacca   6000
ccgccggggc gactggctcg tgcgagaccc catcagcggg cagcgcggag aatgtctggt   6060
gctgtggccc cccttgtgga ccggggaccg tctggtcttc gattcgcccg tccagcggct   6120
gtttcccgag atcgtcgcgt gtcactccct ccgggaacac gcgcacgtct gccggctgcg   6180
caataccgcg tccgtcaagg tgctgctggg gcgcaagagc gacagcgagc gcggggtggc   6240
cggtgccgcg cgggtcgtta acaaggtgtt gggggaggac gacgagacca aggccgggtc   6300
ggccgcctcg cgcctcgtgc ggcttatcat caacatgaag ggcatgcgcc acgtaggcga   6360
cattaacgac accgtgcgtt cctacctcga cgaggccggg gggcacctga tagacgcccc   6420
ggccgtcgac ggtaccctcc ctggattcgg caagggcgga aacagccgcg ggtctgcggg   6480
ccaggaccag ggggggcggg cgccgcagct tcgccaggcc ttccgcacgg ccgtggttaa   6540
caacatcaac ggcgtgttgg agggctatat aaataacctg tttggaacca tcgagcgcct   6600
gcgcgagacc aacgcgggcc tggcgaccca attgcaggag cgcgaccgcg agctccggcg   6660
cgcaacagcg ggggccctgg agcgccagca gcgcgcggcc gacctggcgg ccgagtccgt   6720
gaccggtgga tgcggcagcc gccctgcggg ggcggacctg ctccgggccg actatgacat   6780
tatcgacgtc agcaagtcca tggacgacga cacgtacgtc gccaacagct ttcagcaccc   6840
gtacatccct tcgtacgccc aggacctgga gcgcctgtcg cgcctctggg agcacgagct   6900
ggtgcgctgt tttaaaattc tgtgtcaccg caacaaccag ggccaagaga cgtcgatctc   6960
gtactccagc ggggcgatcg ccgcattcgt cgccccctac tttgagtcag tgcttcgggc   7020
cccccgggta ggcgcgccca tcacgggctc cgatgtcatc ctgggggagg aggagttatg   7080
ggatgcggtg tttaagaaaa cccgcctgca aacgtacctg acagacatcg cggccctgtt   7140
cgtcgcggac gtccagcacg cagcgctgcc cccgcccccc tccccggtcg gcgccgattt   7200
ccggcccggc gcgtccccgc ggggccggtc cagatcgcgg tcgcccggaa gaactgcgcg   7260
aggcgcgccg gaccagggcg ggggcatcgg gcaccgggat ggccgccgcg acggccgacg   7320
atgaggggtc ggccgccacc atcctcaagc aggccatcgc cggggaccgc agcctggtcg   7380
aggcggccga ggcgattagc cagcagacgc tgctccgcct ggcctgcgag gtgcgccagg   7440
tcggcgaccg ccagccgcgg tttaccgcca ccagcatcgc gcgcgtcgac gtcgcgcctg   7500
ggtgccggtt gcggttcgtt ctggacggga gtcccgagga cgcctatgtg acgtcggagg   7560
attactttaa gcgctgctgc ggccagtcca gttatcgcgg cttcgcggtg gcggtcctga   7620
cggccaacga ggaccacgtg cacagcctgg ccgtgccccc cctcgttctg ctgcaccggt   7680
tctccctgtt caaccccagg gacctcctgg actttgagct tgcctgtctg ctgatgtacc   7740
```

-continued

```
tggagaactg cccccgaagc cacgccaccc cgtcgacctt tgccaaggtt ctggcgtggc   7800
tcggggtcgc gggtcgccgc acgtccccat tcgaacgcgt tcgctgcctt ttcctccgca   7860
gttgccactg ggtcctaaac acactcatgt tcatggtgta cgtaaaaccg ttcgacgacg   7920
agttcgtcct gccccactgg tacatggccc ggtacctgct ggccaacaac ccgccccccg   7980
ttctctcggc cctgttctgt gccaccccga cgagctcctc attccggctg ccggggccgc   8040
ccccccgctc cgactgcgtg gcctataacc ccgccgggat catggggagc tgctgggcgt   8100
cggaggaggt gcgcgcgcct ctggtctatt ggtggctttc ggagacccca aaacgacaga   8160
cgtcgtcgct gttttatcag ttttgttgaa ttttaggaaa taaacccggt tttgtttctg   8220
tggcctcccg acggatgcgc gtgtccttcc tccgtcttgg tgggtgggtg tctgtgtatc   8280
gcgtcccatc tgtgcggaga ggggggcat gtcggcacgt attcggacag actcaagcac   8340
acacggggga gcgctcttgt ctcagggcaa tgtttttatt ggtcaaactt ggttattgct   8400
taagaatacg cgtagttgat cgtaccgtga gtaataatgt gactgtactg catcaggaac   8460
tgattggaat tctcgtaccg tgagtaataa tgtgggggta ctgcatcagg aactgattgg   8520
aatagttatt gcttaagaat acgcgtagta attactgcat caggaactga ttggatttat   8580
cgtaccgtga gtaataatgt ggcggttatt gcttaagaat acgcgtaggc tttcgtaccg   8640
tgagtaataa tgtggtcgta ctgcatcagg aactgattgg aagtcttatt gcttaagaat   8700
acgcgtagca tatcaggcaa acagaaacga catcttgtcg tcaaagggat acacaaactt   8760
cccccctct ccccatactc ccgccagcac cccggtaaac accaactcaa tctcgcgcag   8820
gatttcgcgc aggtgatgag cgcagtccac gggggggagc acaaggggcc gcgggtatag   8880
atcgacgggg acgccgaccg actccccgcc tccgggacag acacgcacga cgcgccgcca   8940
gtagtgctct gcgtccagca aggcgccgcc gcggaaggca gtggggggca aggggtcgct   9000
ggcctcaaag ggggacaccc gaacgctcca gtactccgcg tccaaccgtt tattaaacgc   9060
gtccaagata aggcggtcgc aggcgtcctc cataaggccc cgggccgtga gtgcgtcctc   9120
ctccggcacg catgccgttg tcaggcccag gacccgtcgc agcgtgtcgc gtacgacccc   9180
tgccgccgtg gtgtacgcgg gcccgcggag aggaaatccc ccaagatggt cagtgttgtc   9240
gcgggagttc cagaaccaca ctcccgcctg gctccaggcg actgcgtggg tgtagacgcc   9300
ctcgagggcc aggcacagtg ggtgccgcag ccggacggcg ttggccctaa gcacggctcc   9360
cacggccgtc tcgatggccc gccgggcgtc ctcgatcacc ccggaagccg catccgcgtc   9420
ttgggggtcc acgttaaaga caccccagaa cgcaccccca tcgcccccgc agaccgcgaa   9480
cttcaccgag ctggccgtct cctcgatctg caggcagacg gcggccatta ccccacccag   9540
gagctgccgc agcgcagggc aggcgttgca cgtgtccggg accaggcgct ccaagacggc   9600
cccggcccag ggctctgagg gagcggccac caccagcgcg tccagtcttg ctaggcccgt   9660
ccggccgtgg gggtccgcca gcccgctccc cccgaggtcg gccagggccg ccaggagctg   9720
ggcgcgaagt ccggggaagc aaaaccgcgc cgtccagacg ggcccgacgg ccgcgggcgg   9780
gtctaacagt tggatgattt tagtggcggg atgccaccgc gccaccgcct cccgcaccgc   9840
gggcaggagg catccggctg ccgccgaggc cacgccgggc caggctcgcg gggggaggac   9900
gaccctggcc cccaccgcgg gccaggcccc caggagcgcg gcgtaagcgg ccgcggcccc   9960
gcgcaccagg tcccgtgccg actcggccgt ggccggcacg gtgaacgtgg gccaacccgg  10020
aaaccccagg acggcaaagt acgggacggg tcccccccgg acctcaaact cgggccccag  10080
```

-continued

```
aaaggcaaag acgggggcca gggccccggg ggcggcgtgg accgtggtat gccactgccg  10140
gaaaagggcg acgagcgccg gcgcggagaa cttctcgccg gcgcttacaa agtagtcgta  10200
atcgcggggc agcagcaccc gtgccgtgac tcgttgcggg tgcccgcgtg gccgcaggcc  10260
cacctcgcac acctcgacca ggtccccgaa cgcgccctcc ttcttgatcg gcggaaacgc  10320
aagagtctgg tattcgcgcg caaatagcgc ggttccggtg gtgatgttaa cggtcagcga  10380
agcggcggac gcgcactggg gggtgtcgcg aatggccgcc aggcgcgccc acgccagccg  10440
cgcgtcggga tgctcggcaa cgcgcgccgc cagggccata gggtcgatgt caatgttggc  10500
ctccgcgacc aggagagcgg cgcgaggggc ggcgggcggg ccccacgacg ctctctcaac  10560
tttcaccacc agtcccgtgc gtgggtccga gccgatacgc agcggggcga acagggccac  10620
cggcccggtc tggcgctcca gggccgccag gacgcacgcg tacagcgccc gccacagagt  10680
cgggttctcc aggggctcca gcggggaggc ggccggcgtc gtcgcggcgc gggcggccgc  10740
cacgacggcc tggacggaga cgtccgcgga gccgtagaaa tcccgcagct ccgtcgcggt  10800
gacggagacc tccgcaaagc gcgcgcgacc ctcccctgcg gcgttgcgac atacaaaata  10860
caccagggcg tggaagtact cgcgagcgcg ggggggcagc cataccgcgt aaagggtaat  10920
ggcgctgacg ctctcctcca cccacacgat atctgcggtg tccatcgcac ggcccctaag  10980
gatcacgggc ggtctgtggg tcccatgctg ccgtgcctgg ccgggcccgg tgggtcgcgg  11040
aaaccggtga cggggggggg gcggtttttg gggttggggt gggggtggga aacggcccgg  11100
gtccgggggc caacttggcc cctcggtgcg ttccggcaac agcgccgccg gtccgcggac  11160
gaccacgtac cgaacgagtg cggtcccgag acttataggg tgctaaagtt caccgccccc  11220
tgcatcatgg gccaggcctc ggtggggagc tccgacagcg ccgcctccag gatgatgtca  11280
gcgttggggt tggcgctgga tgagtgcgtg cgcaaacagc gcccccacgc gggcacgcgt  11340
agcttgaagc gcgcgcccgc aaactcccgc ttgtgggcca taagcagggc gtacagctgc  11400
ctgtgggtcc ggcaggcgct gtggtcgatg tggtgggcgt ccaacaaccc cacgattgtc  11460
tgtttggtga ggtttttaac gcgccccgcc ccgggaaacg tctgcgtgct tttggccatc  11520
tgcacgccaa acagttcgcc ccagattatc ttgaacagcg ccaccgcgtg gtccgtctcg  11580
ctaacggacc cgcgcggggg acagccgctt agggcgtcgg cgacgcgctt gacggcttcc  11640
tccgagagca gaagtccgtc ggttacgtta cagtggccca gttcgaacac cagctgcatg  11700
tagcggtcgt agtgggggt cagtaggtcc agcacgtcat cggggccgaa ggtcctccca  11760
gatcccccgg ccgccgagtc ccaatgcagg cgcgcggcca tggtgctgca caggcacaac  11820
agctcccaga cgggggttac gttcagggtg gggggcaggg ccacgagctc cagctctccg  11880
gtgacgttga tcgtggggat gacgcccgtg gcgtagtggt catagatccg ccgaaatatg  11940
gcgctgctgc gggtggccat gggaacgcgg agacaggcct ccagcaacgc caggtaaata  12000
aaccgcgtgc gtcccatcag gctgttgagg ttgcgcatga gcgcgacaat ttccgccggc  12060
gcgacatcgg accggaggta tttttcgacg aaaagaccca cctcctccgt ctcggcggcc  12120
tgggccggca gcgacgcctc gggatcccgg caccgcagct cccgtagatc gcgctgggcc  12180
ctgagggcgt cgaaatgtac gccccgcaaa aacagacaga agtcctttgg ggtcagggta  12240
tcgtcgtgtc cccagaagcg cacgcgtatg cagtttaggg tcagcagcat gtgaaggatg  12300
ttaaggctgt ccgagagaca cgccagcgtg catctctcaa agtagtgttt gtaacggaat  12360
ttgttgtaga tgcgcgaccc ccgccccagc gacgtgtcgc atgccgacgc gtcacagcgc  12420
cccttgaacc ggcgacacag caggtttgtg acctgggaga actgcgcggg ccactggccg  12480
```

-continued caggaactga ccacgtgatt aaggagcatg ggcgtaaaga cgggctccga gcgcgccccg 12540
gagccgtcca tgtaaatcag tagctccccc ttgcggaggg tgcgcacccg tcccagggac 12600
tggtacacgg acaccatgtc cggtccgtag ttcatgggtt tcacgtaggc gaacatgcca 12660
tcaaagtgca ggggatcgaa gctgaggccc acggttacga ccgtcgtgta tataaccacg 12720
cggtattggc cccacgtggt cacgtccccg aggggggtga gcgagtgaag caacagcacg 12780
cggtccgtaa actgacggca gaaccgggcc acgatctccg cgaaggagac cgtcgacgaa 12840
aaaatgcaga tgttatcgcc cccgccaagg cgcgcttcca gctccccaaa gaacgtggcc 12900
ccccgggcct ccggagaggc gtccggagac gggccgctcg gcggcccggg cgggcgcagg 12960
gcagcctgca ggagctcggt ccccagacgc gggagaaaca ggcaccggcg cgccgaaaac 13020
ccgggcatgg cgtactcgcc gaccaccaca tgcacgtttt tttcgccccg gagaccgcac 13080
aggaagtcca ccaactgcgc gttggcggtt gcgtccatgg cgatgatccg aggacagatg 13140
cgcagcaggc gtagcattaa cgcatccacg cggcccagtt gctgcatcgt tggcgaatag 13200
agctggccca gcgtcgacat aacctcgtcc agaacgagga cgtcgtagtt gttcagaagg 13260
ttggggccca cgcgatgaag gctttccacc tggacgataa gtcggtggaa ggggcggtcg 13320
ttcataatgt aattggtgga tgagaagtag gtgacaaagt cgaccaggcc tgactcagcg 13380
aaccgcgtcg ctagggtctg ggtaaaactc cgacgacagg agacgacgag cacactcgtg 13440
tccggagagt ggatcgcttc ccgcagccag cggatcagcg cggtagtttt tcccgacccc 13500
attggcgcgc ggaccacagt cacgcacctg gccgtcgggg cgctcgcgtt ggggaaggtg 13560
acgggtccgt gctgctgccg ctcgatcgtt gttttcgggt gaacccgggg cacccattcg 13620
gccaaatccc ccccgtacaa catccgcgct agcgatacgc tcgacgtgta ctgttcgcac 13680
tcgtcgtccc caatgggacg cccggccccc agaggatctc ccgactccgc gccccccacg 13740
aaaggcatga ccggggcgcg gacggcgtgg tgggtctggt gtgtgcaggt ggcgacgttt 13800
gtggtctctg cggtctgcgt cacggggctc ctcgtcctgg cctctgtgtt ccgggcacgg 13860
tttccctgct tttacgccac ggcgagctct tatgccgggg tgaactccac ggccgaggtg 13920
cgcgggggtg tagccgtgcc cctcaggttg gacacgcaga gccttgtggg cacttatgta 13980
atcacggccg tgttgttgtt ggccgtggcc gtgtatgccg tggtcggcgc cgtgacctcc 14040
cgctacgacc gcgccctgga cgcgggccgc cgtctggctg cggcccgcat ggccatgccg 14100
cacgccacgc tgatcgccgg aaacgtctgc tcttggttgc tgcagatcac cgtcctgttg 14160
ctggcccatc gcatcagcca gctggcccac ctggtttacg tcctgcactt tgcgtgtctg 14220
gtgtattttg cggcccattt ttgcaccagg ggggtcctga gcgggacgta tctgcgtcag 14280
gtgcacggcc tgatggagct ggccccgacc catcatcgcg tcgtcggccc ggctcgcgcc 14340
gtgctgacaa acgccttgct gttgggcgtc ttcctgtgca cggccgacgc cgcggtatcc 14400
ctgaatacca tcgccgcgtt caactttaat ttttcggccc cgggcatgct catctgcctg 14460
accgtgctgt tcgccattct cgtcgtatcg ctgttgttgg tggtcgaggg ggtgttgtgt 14520
cactacgtgc gcgtgttggt gggcccccac ctgggggccg tggccgccac gggcatcgtc 14580
ggcctggcct gcgagcacta ttacaccaac ggctactacg ttgtggagac gcagtggccg 14640
ggggctcaga cgggagtccg cgtcgccctc gccctggtcg ccgcctttgc cctcggcatg 14700
gccgtgctcc gctgcacccg cgcctatctg tatcacaggc ggcaccacac caaatttttt 14760
atgcgcatgc gcgacacgcg acaccgcgca cattccgccc tcaagcgcgt acgcagttcc 14820

```
atgcgcggat cgcgagacgg ccgccacagg cccgcacccg gcagcccgcc cgggattccc  14880
gaatatgcgg aagaccccta cgcgatctca tacggcggcc agctcgaccg gtacggagat  14940
tccgacgggg agccgattta cgacgaggtg gcggacgacc aaaccgacgt attgtacgcc  15000
aagatacaac acccgcggca cctgcccgac gacgatccca tctatgacac cgttgggggg  15060
tacgaccccg agcccgccga ggaccccgtg tacagcaccg tccgccgttg gtagctgttt  15120
ggttccgttt taataaaccg tttgtgttta acccgaccgt ggtgtatgtc tggtgtgtgg  15180
cgtccgatcc cgttactatc accgtccccc cccccccctc aaccccggcg attgtgggtt  15240
ttttaaaaac gacacgcgtg cgaccgtata cagaacattg ttttggtttt tattcgctat  15300
cggacatggg gggtggaaac tgggtggcgg ggcaggcgcc tccgggggtc cgccggtgag  15360
tgtggcgcga ggggggggtcc gatgaacgca ggcgctgtct ccccggggcc cgcgtaaccc  15420
cgcgcatatc cgggggcacg tagaaattac cttcctcttc ggactcgata tccacgacgt  15480
caaagtcgtg ggcggtcagc gagacgacct ccccgtcgtc ggtgatgagg acgttgtttc  15540
ggcagcagca gggccgggcc ccggagaacg agaggcccat agctcggcga gcgtgtcgtc  15600
gaatgccagg cggctgcttc gctggatggc cttatagatc tccggatcga tgcggacggg  15660
ggtaatgatc agggcgatcg gaacggcctg gttcgggaga atggacgcct tgctgggtcc  15720
tgcggccccg agagccccgg cgccgtcctc caggcggaac gttacgccct cctccgcgct  15780
ggtgcggtgc ctgccgataa acgtcaccag atgcgggtgg ggggggcagt cggggaagtg  15840
gctgtcgagc acgtagccct gcaccaagat ctgcttaaag ttcgggtgac gggggttcgc  15900
gaagacgggc tcgcggcgga ccagatcccc ggagctccag gacacggggg agatggtgtg  15960
gcgtccgagg tcgggggcgc caaacagaag cacctccgag acaacgccgc tatttaactc  16020
caccaaggcc cgatccgcgg cggagcaccg cctttttttcg cccgaggcgt gggcctctga  16080
ccaggcctgg tcttgcgtga cgagagcctc ctccgggccg gggacgcgcc cgggcgcgaa  16140
gtatcgcacg ctgggcttcg ggatcgaccg gataaatgcc cggaacgcct ccggggaccg  16200
gtgtgccatc aagtcctcgt acgcggaggc cgtggggtcg ctggggtcca tggggtcgaa  16260
agcgtacttg gcccggcatt tgacctcgta aaaggccagg ggggtcttgg ggactggggc  16320
caggtagccg tgaatgtccc gaggacagac gagaatatcc agggacgccc cgaccatccc  16380
cgtgtgaccg tccatgagga ccccacacgt atgcacgttc tcttcggcga ggtcgctggg  16440
ttcgtggaag ataaagcgcc gcgtgtcggc gccggcctcg ccgccgtcgt ccgcgcggcc  16500
cacgcagtag cgaaacagca ggcttcgggc cgtcggctcg ttcacccgcc cgaacatcac  16560
cgccgaagac tgtacatccg gccgcaggct ggcgttgtgc ttcagccact ggggcgagaa  16620
acacggaccc tgggggcccc agcggagggt ggatgcggtc gtgaggcccc gccggagcag  16680
ggcccatagc tggcagtcgg cctggttttg cgtggccgcc tcgtaaaacc ccatgagggg  16740
ccggggcgcc acggcgtccg cggcggccgg gggcccgcgg cgcgtcaggc gccataggtg  16800
ccgaccgagt ccgcggtcca ccatacccgc ctcctcgagg accacggcca gggaacacag  16860
ataatccagg cgggcccaga ggggaccgat ggccagaggg gcgcggacgc cgcgcagcaa  16920
cccgcgcagg tggcgctcga acgtctcggc tagtatatgg gagggcagcg cgttggggat  16980
caccgacgcc gaccacatag agtcaaggtc cggggagtcg ggatcggcgt ccgggtcgcg  17040
ggcgtgggtg cccccaggag atagcggaat gtctggggtc ggaggccctg aggcgtcaga  17100
aagtgccggc gacgcggccc ggggcttttc gtctgcggtg tcggtggcgt gctgatcacg  17160
tggggggtta acgggcgaat gggagctcgg gtccacagct gatgtcgtct ggggtggggg  17220
```

gggcagggga cggaaggtgg ttgtcagcgg aagactgtta gggcgggggc gcttgggggg 17280
gctgtcgggg ccacgagggg tgtcctcggc cagggcccag ggacgcttag tcacggtgcg 17340
tcccggcgga catgctgggc ctaccgtgga ctccatttcc gagacgacgt ggggggagcg 17400
gtggttgagc gcgccgccgg gtgaacgctg attctcacga cagcgcgtgc cgcgcgcacg 17460
ggttggtgtg acacaggcgg gacaccagca ccaggagagg cttaagctcg ggaggcagcg 17520
ccaccgacga cagtatcgcc ttgtgtgtgt gctggtaatt tatacaccga tccgtaaacg 17580
cgcgccgaat cttgggattg cggaggtggc gccggatgcc ctctgggacg tcatacgcca 17640
ggccgtgggt gttggtctcg gccgagttga caaacagggc tgggtgcagc acgcagcgat 17700
aggcgagcag ggccagggcg aagtccggcg acagctggtt gttaaaatac tggtaaccgg 17760
gaaaccgggt cacgggtacg cccaggctcg gggcgacgta cacgctaacc accaactcca 17820
gcagcgtctg gcccagggcg tacaggtcaa ccgctaaccc gacgtcgtgc ttcaggcggt 17880
ggttggtaaa ttcggcccgt tcgttgttaa ggtatttcac caacagctcc gggggctggt 17940
tatacccgtg acccaccagg gtgtgaaagt tggctgtggt tagggcggtg ggcatgccaa 18000
acatccgggg ggacttgagg tccggctcct ggaggcaaaa ctgcccccgg gcgatcgtgg 18060
agttggagtt gagggtgacg aggctaaagt cggcgaggac ggcccgccgg agcgagacgg 18120
cgtccgaccg cagcatgacg aggatgttgg cgcacttgat atccaggtgg ctgatcccgc 18180
aggtggtgtt taaaaacaca acggcgcggg ccagctccgt gaagcactgg tggagggccg 18240
tcgagaccga ggggtttgtt gtgcgcaggg acgccagttg gccgatatac ttaccgaggt 18300
ccatgtcgta cgcggggaac actatctgtc gttgttgcag cgagaacccg aggggcgcga 18360
tgaagccgcg gatgttgtgg gtgcggccgg cgcgtagaac gcactccccg accaacaggg 18420
tcgcgatgag ctcaacggca aaccactcct tttcctttat ggtcttaacg gcaagcttat 18480
gttcgcgaat cagttggacg tcaccgtatc cccagaccc cccgaagctt cgggccccgg 18540
ggatctcgag ggtcgtgtag tgtagggcgg ggttgatggc gaacacgggg ctgcatagct 18600
tgcggatgcg cgtgagggtg aggatgtgcg agggggacga ggggggtgcg gttaacgccg 18660
cctgggatct gcgcaggggc gggcggttca gtttggccgc cgtaccgggc gtctcggggg 18720
acgcgcggcg atgagacgag cggctcattc gccatcggga tagtcccgcg cgaagccgct 18780
cgcggaggcc ggatcggtgg cgggacccgt gggaggagcg ggagacggcg gcgtcctgga 18840
gagaggggcc gctggggcgc ccggaggccc cgtgggggtt ggagtgtacg taggatgcga 18900
gccaatcctt gaaggaccgt tggcgtgcac cttgggggct gaggttagct gccacatgac 18960
cagcaggtcg ctgtctgcgg gactcatcca tccttcggcc aggtcgccgt ctccccacag 19020
agaagcgttg gtcgctgctt cctcgagttg ctcctcctgg tccgcaagac gatcgtccac 19080
ggcgtccagg cgctcaccaa gcgccggatc gaggtaccgt cggtgtgcgg ttagaaagtc 19140
acgacgcgcc gcttgctcct ccacgcgaat tttaacacag gtcgcgcgct gtcgcatcat 19200
ctctaagcgc gcgcgggact ttagccgcgc ctccaattcc aagtgggccg cctttgcagc 19260
cataaaggcg ccaacaaacc gaggatcttg ggtgctgacg ccctcccggt gcagctgcag 19320
ggtctggtcc ttgtaaatct cggctcggag gtgcgtctcg gccaggcgtc ggcgcagggc 19380
cgcgtgggcg gcatctcggt ccattccgcc accctgcggg cgacccgggg ggtgctctga 19440
tagtctcgcg tgcccaaggc ccgtgatcgg ggtacttcgc cgccgcgacc cgccacccgg 19500
tgtgcgcgat gtttggtcag cagctggcgt ccgacgtcca gcagtacctg gagcgcctcg 19560

```
agaaacagag gcaacttaag gtgggcgcgg acgaggcgtc ggcgggcctc accatgggcg  19620
gcgatgccct acgagtgccc tttttagatt tcgcgaccgc gacccccaag cgccaccaga  19680
ccgtggtccc tggcgtcggg acgctccacg actgctgcga gcactcgccg ctcttctcgg  19740
ccgtggcgcg gcggctgctg tttaatagcc tggtgccggc gcaactaaag gggcgtgatt  19800
tcgggggcga ccacacggcc aagctggaat tcctggcccc cgagttggta cgggcggtgg  19860
cgcgactgcg gtttaaggag tgcgcgccgg cggacgtggt gcctcagcgt aacgcctact  19920
atagcgttct gaatacgttt caggccctcc accgctccga agcctttcgc cagctggtgc  19980
actttgtgcg ggactttgcc cagctgctca aaacctcctt ccgggcctcc agcctcacgg  20040
agaccacggg cccccccaaa aaacgggcca aggtggacgt ggccacccac ggccggacgt  20100
acggcacgct ggagctgttc caaaaaatga tccttatgca cgccacctac tttctggccg  20160
ccgtgctcct cggggaccac gcggagcagg tcaacacgtt cctgcgtctc gtgtttgaga  20220
tccccctgtt tagcgacgcg gccgtgcgcc acttccgcca gcgcgccacc gtgtttctcg  20280
tcccccggcg ccacggcaag acctggtttc tggtgcccct catcgcgctg tcgctggcct  20340
cctttcgggg gatcaagatc ggctacacgg cgcacatccg caaggcgacc gagccggtgt  20400
ttgaggagat cgacgcctgc ctgcggggct ggttcggttc ggcccgagtg gaccacgtta  20460
aaggggaaac catctccttc tcgtttccgg acgggtcgcg cagtaccatc gtgtttgcct  20520
ccagccacaa cacaaacgta agtcctcttt tctttcgcat ggctctccca aggggccccg  20580
ggtcgacccg acccacaccc acccacccac atacacacac aaccagacgc gggaggaaag  20640
tctgccccgt gggcactgat tttattcgg gatcgcttga ggaggcccgg gcaacggccc  20700
gggcaacggt ggggcaactc gtagcaaata ggcgactgat gtacgaagag aagacacaca  20760
ggcgccaccc ggcgctggtc ggggggatgt tgtccgcgcc gcaccgtccc ccgacgacct  20820
cttgcagacg gtccgtgatg caaggacggc ggggggcctg cagcagggtg accgtatcca  20880
cgggatggcc aaagagaagc ggacacaggc tagcatcccc ctggaccgcc agggtacact  20940
gggccatctt ggcccacaga cacggggcga cgcagggaca ggactccgtt acgacggagg  21000
agagccacag tgcgttggcg gaatcgatgt ggggcggcgg ggcgcaggac tcgcagcccc  21060
ccgggtggtt ggtgatcctg gccaggagcc atcccagatg gcgggccctg cttcccggtg  21120
gacagagcga ccccaggtcg ctgtccatgg cccagcagta gatctggccg ctggggaggt  21180
gccaccaggc ccccgggccc aaggcgcagc acgcgcccgg ctccgggggg gtcttcgcgg  21240
ggaccagata cgcgccatcc agctcgccga ccactggctc ctccgcgagc tgttcggtgg  21300
ttgggtcggg ggtttcctcc ggggggtgg ccgcccgtat gcgtgcgaac gtgagggtgc  21360
acaggagcgg ggtcaggggg tgcgtcacgc tccggaggtg gacgatcgcg cagtagcggc  21420
gctcgcggtt aaagaaaaag agggcaaaga aggtgttcgg gggcaaccgc agcgccttgg  21480
ggcgcgtcag atacagaaaa atctcgcaga agagggcgcg cccggggtct gggttaggaa  21540
gggccacctg acacagaggc tcggtgagga ccgttagaca ccgaaagatc ttgagccgct  21600
cgtccgcccg aacgacgcgc cacacaaaga cggagttgac aatgcgcgcg atagagtcga  21660
cgtccgtccc caggtcgtcg actctatcgc gcgtgccgcg agctccggcc cgggaatccg  21720
gccggggcaa ggtccccggg ggaccaggcg gcgccagggg ccgccggggt cccagctgcg  21780
ccatgccggg ggcgggggga gggcaaaccc cagaggcggg ggccaacggc gcggggagga  21840
gtgggtgggc gaggtggccg ggggaaggcg cccgctagcg agaccggccg ttcccggacg  21900
acaccttgcg acaaaaccta aggacagcgg cccgcgcgac ggggtccgag aggctaaggt  21960
```

```
aggccgcgat gttaatggtg aacgcaaagc cgccgggaaa gacaactatg ccacagaggc  22020
ggcgattaaa ccccaggcag aggtaggcgt agctttcccc gggcaggtat tgctcgcaga  22080
ccctgcgtgg ggctgtggag gggacggcct ccatgaagcg acatttactc tgctcgcgtt  22140
tactgacgtc accatccatc gccacggcga ttggacgatt gttaagccgc agcgtgtctc  22200
cgcttgtgct gtagtagtca aaaacgtaat ggccgtcgga gtcggcaaag cgggccggga  22260
ggtcgtcgcc gagcgggacg acccgccgcc cccgaccgcc ccgtccccc aggtgtgcca  22320
ggacggccag ggcatacgcg gtgtgaaaaa aggcgtcggg ggcggtcccc tcgacggcgc  22380
gcatcaggtt ctcgaggaga atggggaagc gcctggtcac ctcccccaac cacgcgcgtt  22440
ggtcggggcc aaagtcatag cgcaggcgct gtgagattcg cgggccgccc tgaagcgcgg  22500
cccggatggc ctggcccagg gcccggaggc acgccagatg tatgcgcgcg gtaaaggcga  22560
cctcggcggc gatgtcaaag ggcggcagga cggggcgcgg gtggcgcagg ggcacctcga  22620
gcgcgggaaa gcgtagcagc agctccgcct gcccagcggg agacagctgg tgggggcgca  22680
cgacgcgttc tgcggcgcag gcctcggtca gggccgtggc cagcgccgag gacagcagcg  22740
gagggcgggc gcgtcgcccg ccccacgcca cggagttctc gtaggagacg acgacgaagc  22800
gctgcttggt tccgtagtgg tggcgcagga ccacggagat agaacgacgg ctccacagcc  22860
agtccggccg gtcgccgccg gccagggctt cccatccgcg atccaaccac tcgaccagcg  22920
accgcggctt tgcggtacca ggggtaaggg ttagaacgtc gttcaggatg tcctcgcccc  22980
cgggcccgtg gggcgctggg gccacaaagc ggcccccgcc ggggggctcc agacccgcca  23040
gcaccgcatc tgcgtcagcc gcccccatgg cgcccccgct gacggcctgg tgaaccaggg  23100
cgccctggcg tagccccgat gcaacgccac aggccgcacg cccggtccgc gctcggaccg  23160
ggtggcggcg ggtgacgtcc tgcactgccc gctgaaccaa cgcgaggatc tcctcgttct  23220
cctgtgcgat ggacacgtcc tgggccgcgg tcgtgtcgcc gccgggggcc gtcagctgct  23280
cctccgggga gatggggggg tcggacgccc cgacgatggg cgggtctgcg ggcgcccccg  23340
cgtggggccg ggccaagggc tgcggacgcg gggacgcgct ttcccccaga cccatggaca  23400
ggtgggccgc agcctccttc gcggccggcg gggcggcggc gccaagcaga gcgacgtagc  23460
ggcacaaatg ccgacagacg cgcatgatgc gcgtgctgtc ggccgcgtag cgcgtgttgg  23520
gggggacgag ctcgtcgtaa ctaaacagaa tcacgcgggc acagctcgcc cccgagcccc  23580
acgcaaggcg cagcgccgcc acggcgtacg ggtcatagac gccctgcgcg tcacacacca  23640
cgggcaggga gacgaacaac cccccggcgc tggacgcacg cggaaggagg ccagggtgtg  23700
ccggcacgac gggggccaga agctccccca ccgcatccgc gggcacgtag gcggcaaacg  23760
ccgtgcacca cggggtacag tcgccggtgg catgagcccg agtctggatt tcgacctgga  23820
agtttgcggc cgtcccgagt ccggggcggc cgcgcatcag ggcggccaga gggattcccg  23880
cggccgccag gcactcgctg gatatgatga cgtgaaccaa agaccgaggg ccgacccggg  23940
ccgtggccga gatcgtctgg acctcgttgg ccaagtgcgc gttcatggtt cgggggtggg  24000
tgtgggtgtg taggcgatgc gggtcccccg agtccgcggg aagggcgtgg gtttggcgcg  24060
cgtatgcgta ttcgccaacg gaggcgtgcg tgcttatgcg cggcgcgttt cttctgtctc  24120
tagggaatcc gaggccagga ctttaacctg ctctttgtcg acgaggccaa ctttattcgc  24180
ccggatgcgg tccagacgat tatgggcttt ctcaaccagg ccaactgcaa gattatcttc  24240
gtgtcgtcca ccaacaccgg gaaggccagt acgagctttt tgtacaacct ccgcggggcc  24300
```

gcagacgagc ttctcaacgt ggtgacctat atatgcgatg atcacatgcc gagggtggtg 24360
acgcacacaa acgccacggc ctgttcttgt tatatcctca acaagcccgt tttcatcacg 24420
atggacgggg cggttcgccg gaccgccgat ttgtttctgg ccgattcctt catgcaggag 24480
atcatcgggg gccaggccag ggagaccggc gacgaccggc ccgttctgac caagtctgcg 24540
ggggagcggt ttctgttgta ccgcccctcg accaccacca acagcggcct catggccccc 24600
gatttgtacg tgtacgtgga tcccgcgttc acggccaaca cccgagcctc cgggaccggc 24660
gtcgctgtcg tcgggcggta ccgcgacgat tatatcatct tcgccctgga gcactttttt 24720
ctccgcgcgc tcacgggctc ggcccccgcc gacatcgccc gctgcgtcgt ccacagtctg 24780
acgcaggtcc tggccctgca tcccggggcg tttcgcggcg tccgggtggc ggtcgaggga 24840
aatagcagcc aggactcggc cgtcgccatc gccacgcacg tgcacacaga gatgcaccgc 24900
ctactggcct cggagggggc cgacgcgggc tcgggccccg agcttctctt ctaccactgc 24960
gagcctcccg ggagcgcggt gctgtacccc tttttcctgc tcaacaaaca gaagacgccc 25020
gcctttgaac actttattaa aaagtttaac tccgggggcg tcatggcctc ccaggagatc 25080
gtttccgcga cggtgcgcct gcagaccgac ccggtcgagt atctgctcga gcagctaaat 25140
aacctcaccg aaaccgtctc ccccaacact gacgtccgta cgtattccgg aaaacggaac 25200
ggcgcctcgg atgaccttat ggtcgccgtc attatggcca tctacctcgc ggcccaggcc 25260
ggacctccgc acacattcgc tcctatcaca cgcgtctcgt gagcgcccaa taaacacacc 25320
caggtatgct acgcacgacc acggtgtcgt ctgttaaggg ggggggggga agggggtgtt 25380
ggcgggaagc gtgggaacac gggggattct ctcacgaccg gcaccagtac cacccccctg 25440
tgaacacaga aaccccaacc caaatcccat aaacatacga cacacaggca tattttggaa 25500
tttcttaggt ttttatttat ttaggtatgc tggggtttct ccctggatgc ccacccccac 25560
ccccccgtgg gtctagccgg gccttaggga tagcgtataa cgggggccat gtctccggac 25620
cgcacaacgg ccgcgccgtc aaaggtgcac acccgaacca cgggagccag ggccaaggtg 25680
tctcctagtt ggcccgcgtg ggtcagccag gcgacgagcg cctcgtaaag cggcagcctt 25740
cgctctccat cctgcatcag ggccggggct tcggggtgaa tgagctgggc ggcctcccgc 25800
gtgacactct gcatctgcag tagagcgttc acgtacccgt cctgggcact tagcgcaaag 25860
agccggggga ttagcgtaag gatgatggtg gttccctccg tgatcgagta aaccatgtta 25920
aggaccagcg atcgcagctc ggcgtttacg ggaccgagtt gttggacgtc cgccagcagc 25980
gagaggcgac tcccgttgta gtacagcacg ttgaggtctg gcagccctcc ggggtttctg 26040
gggctggggt tcaggtcccg gatgcccctg gccacgagcc gcgccacgat ttcgcgcgcc 26100
aggggcgatg gaagcggaac gggaaaccgc aacgtgaggt ccagcgaatc caggcgcacg 26160
tccgtcgctt ggccctcgaa cacgggcggg acgaggctga tggggtcccc gttacagaga 26220
tctacggggg aggtgttgcg aaggttaacg gtgccggcgt gggtgaggcc cacgtccagg 26280
gggcaggcga cgattcgcgt gggaagcacc cgggtgatga ccgcggggaa gcgccttcgg 26340
tacgccagca acaaccccaa cgtgtcggga ctgacgcctc cggagacgaa ggattcgtgc 26400
gccacgtcgg ccagcgtcag ttgccggcgg atggtcggca ggaataccac ccgcccttcg 26460
cagcgctgca gcgccgccgc atcggggcgc gagatgcccg agggtatcgc gatgtcagtt 26520
tcaaagccgt ccgccagcat ggcgccgatc cacgcggcag ggagtgcagt ggtggttcgg 26580
gtggcgggag gagcgcggtg ggggtcagcg gcgtagcaga gacgggcgac caacctcgca 26640
taggacgggg ggtgggtctt agggggttgg gaggcgacag ggaccccaga gcatgcgcgg 26700

```
ggaggtctgt cgggcccaga cgcaccgaga gcgaatccgt ccgcggagtc ccggcttggg  26760
ttttatgggg cccggccctc ggaatcgcgg cttgtcggcg gggacaaagg gggcggggct  26820
aggggcttgc ggaaacagaa gacgcgtggg ataaaagaat cgcactaccc caaggaaggg  26880
cggggcggtt tattacagag ccagtccctt gagcggggat gcgtcataga cgagatactg  26940
cgcgaagtgg gtctcccgcg cgtgggcttc cccgttgcgg gcactgcgga ggagggcggg  27000
gtcgctggcg caggtgagcg ggtaggcctc ctgaaacagg ccacacgggt cctccacgag  27060
ttcgcggcac cccggggggc gcttaaactg tacgtcgctg gcggcggtgg ccgtggacac  27120
cgccgaaccc gtctccacga tcaggcgctc caggcagcga tgtttggcgg cgatgtcggc  27180
cgacgtaaag aacttaaagc aggggctgag caccggcgag gccccgttga ggtggtaggc  27240
cccgttatag agcaggtccc cgtacgaaaa tcgctgcgac gcccacgggt tggccgtggc  27300
cgcgaaggcc cgggacgggt cgctctggcc gtggtcgtac atgagggcgg tgacatcccc  27360
ctccttgtcc cccgcgtaaa cgcccccggc ggcgcgtccc cgggggttgc agggccggcg  27420
gaagtagttg acgtcggtcg acacgggggt ggcgataaac tcacacacgg cgtcctggcc  27480
gtggtccatc cctgcgcgcc gcggcacctg ggcgcacccg aacacgggga cgggctgggc  27540
cggccccagg cggtttcccg ccacgaccgc gttccgcagg tacacggctg ccgcgttgtc  27600
caggagaggg ggagccccgc ggcccaggta aaagttttgg ggaaggttgc ccatgtcggt  27660
gacggggttg cggacggttg ccgtggccac gacggcggtg tagcccacgc ccaggtccac  27720
gttcgcgcgc ggctgggtga gcgtgaagtt taccccccg ccagtttcgt gccgggccac  27780
ctggagctgg cccaggaagt acgcctccga cgcgcgctcc gagaacagca cgttctcagt  27840
cacaaagcgg tcctgtcgga cgacggtgaa cccaaacccg ggatggaggc ccgtcttgag  27900
ctgatgatgc aaggccacgg gactgatctt gaagtacccc gccatgagcg cgtaggtcag  27960
cgcgttctcc ccggccgcgc tctcgcggac gtgctgcacg acgggctgtc ggatcgacga  28020
aaagtagttg gcccccagag ccggggggac caggggggacc tgccgcgaca ggtcgcgcag  28080
ggccgggggg aaattgggcg cgttcgccac gtggtcggcc ccggcgaaca gcgcgtggac  28140
ggggaggggg taaaaatagt cgccattttg gatggtatgg tccagatgct ggggggccat  28200
cagcaggatt ccggcgtgca acgccccgtc gaatatgcgc atgttggtgg tggacgcggt  28260
gttggcgccc gcgtcgggcg ccgccgagca gagcagcgcc gttgtgcgtt cggccatgtt  28320
gtgggccagc acctgcagcg tgagcatggc gggcccgtcc actaccacgc gcccgttgtg  28380
aaacatggcg ttgaccgtgt tggccaccag attggccggg tgcagggggt gcgcggggtc  28440
cgtcacgggg tcgctggggc actcctcgcc gggggcgatc tccgggacca ccatgttctg  28500
cagggtggcg tatacgcggt cgaagcgaac ccccgcggtg cagcagcggc cccgcgagaa  28560
ggcgggcacc atcacgtagt agtaaatctt gtggtgcacg gtccagtccg ccccccggtg  28620
cggccggtca tccgcggcgt ccgcggctcg ggcctgggtg ttgtgcagca gctggccgtc  28680
gttgcggttg aagtccgcgg tcgccacgtt acatgccgcc gcgtacacgg ggtcgtggcc  28740
ccccgcgcta acccggcagt cgcgatggcg gtccagggcc gcgcgccgca tcagggcgtc  28800
acagtcccac acgaggggtg gcagcagcgc cgggtctcgc attaggtgat tcagctcggc  28860
ttgcgcctgc ccgcccagct ccgggccggt cagggtaaag tcatcaacca gctgggccag  28920
ggcctcgacg tgcgccacca ggtcccggta cacggccatg cactcctcgg gaaggtctcc  28980
cccgaggtag gtcacgacgt acgagaccag cgagtagtcg ttcacgaacg ccgcgcaccg  29040
```

-continued

```
cgtgttgttc cagtagctgg tgatgcactg gaccacgagc cgggccaggg cgcagaagac  29100
gtgctcgctg ccgtgtatgg cggcctgcag caggtaaaac accgccgggt agttgcggtc  29160
gtcgaacgcc ccgcgaacgg cggcgatggt ggcgggggcc atggcgtggc gtcccacccc  29220
cagctccagg ccccgggcgt cccggaacgc cgccggacat agcgccaggg gcaagttgcc  29280
gttcaccacg cgccaggtgg cctggatctc ccccgggccg gccgggggaa cgtccccccc  29340
cggcagctcc acgtcggcca cccccacaaa gaagtcgaac gcggggtgca gctcaagagc  29400
caggttggcg ttgtcgggct gcataaactg ctccggggtc atctggcctt ccgcgaccca  29460
tcggacccgc ccgtgggcca ggcgctgccc ccaggcgttc aaaaacagct gctgcatgtc  29520
tgcggcgggg ccggccgggg ccgccacgta cgccccgtac ggattggcgg cttcgacggg  29580
gtcgcggtta aggcccccga ccgccgcgtc aacgttcatc agcgaagggt ggcacacggt  29640
cccgatcgcg tgttccagag acaggcgcag cacctggcgg tccttccccc aaaaaaacag  29700
ctggcggggc gggaaggcgc ggggatccgg gtggccgggg gcggggacta ggtccccggc  29760
gtgcgcggca aaccgttcca tgaccggatt gaacaggccc aggggcagga cgaacgtcag  29820
gtccatggcg cccaccaggg ggtagggaac gttggtggcg gcgtagatgc gcttctccag  29880
ggcctccaga aagaccagct tctcgccgat ggacaccaga tccgcgcgca cgcgcgtcgt  29940
ctgggggcg ctctcgagct cgtccagcgt ctgccggttc aggtcgagct gctcctcctg  30000
catctccagc aggtggcggc ccacgtcgtc cagacttcgc acggccttgc ccatcacgag  30060
cgccgtgacc aggttggccc cgttcaggac catctcgccg tacgtcaccg gcacgtcggc  30120
ttcggtgtcc tccactttca ggaaggactg caggaggcgc tgtttgatcg gggcggtggt  30180
gacgagcacc ccgtcgaccg gccgcccgcg cgtgtcggca tgcgtcagac ggggcacggc  30240
cacggagggc tgcgtggccg tggtgaggtc cacgagccag gcctcgacgg cctcccggcg  30300
gtggcccgcc ttgcccagga aaaagctcgt ctcgcagaag cttcgcttta gctcggcgac  30360
cagggtcgcc cgggccaccc tggtggccag gcggccgttg tccaggtatc gttgcatcgg  30420
caacaacaaa gccaggggcg gcgccttttc cagcagcacg tgcagcatct ggtcggccgt  30480
gccgcgctca aacgccccga ggacggcctg gacgttgcga gcgagctgtt ggatggcgcg  30540
caactggcga tgcgcgccga tacccgtccc gtccagggcc tcccccgtga gcagggcgat  30600
ggcctcggtg gccaggctga aggcggcgtt cagggcccgg cggtcgataa tcttggtcat  30660
gtaattgtgt gtgggttgct cgatggggtg cgggccgtcg cgggcaatca gcggctggtg  30720
gacctcgaac tgtacgcgcc cctcgttcat gtaggccagc tccggaaact tggtacacac  30780
gcacgccacc gacaacccga gctccagaaa gcgcacgagc gacagggtgt tgcaatacga  30840
ccccagcagg gcgtcgaact cgacgtcgta caggctgttt gcatcggagc gcacgcggga  30900
aaaaaaatca aacaggcgtc gatgcgacgc cacctcgatc gtgctaagga gggacccggt  30960
cggcaccatg gccgcggcat accggtatcc cggagggtcg cggttgggag cggccatggg  31020
gtcgcgtgga gatcggctgt ctctagcgat attggcccgg ggaggctaag atccacccca  31080
acgcccggcc acccgtgtac gtgcccgacg gcccaaggtc caccgaaaga cacgacgggc  31140
ccggacccaa aaaggcgggg gatgctgtgt gagaggccgg gtgccggtcg gggggaaag  31200
gcaccgggag aaggctgcgg cctcgttcca ggagaaccca gtgtccccaa cagacccggg  31260
gacgtgggat cccaggcctt atatacccc cccccgccc cacccccgtt agaacgcgac  31320
gggtgcattc aagatggccc tggtccaaaa gcgtgccagg aagaaattgg cagaggcggc  31380
aaagctgtcc gccgccgcca cccacatcga ggccccggcc gcgcaggcta tccccagggc  31440
```

ccgtgtgcgc aggggatcgg tgggcggcag catttggttg gtggcgataa agtggaaaag 31500
cccgtccgga ctgaaggtct cgtgggcggc ggcgaacaag gcacacaggg ccgtgcctcc 31560
caaaaacacg gacatccccc aaaacacggg cgccgacaac ggcagacgat ccctcttgat 31620
gttaacgtac aggaggagcg cccgcaccgc ccacgtaacg tagtagccga cgatggcggc 31680
caggatacag gccggcgcca ccacccttcc ggtcagcccg taatacatgc ccgctgccac 31740
catctccaac ggcttcagga ccaaaaacga ccaaaggaac agaatcacgc gctttgaaaa 31800
gaccggctgg gtatggggcg gaagacgcga gtatgccgaa ctgacaaaaa aatcagaggt 31860
gccgtacgag gacaatgaaa actgttcctc cagcggcagt tctccctcct cccccccgaa 31920
ggcggcctcg tcgaccagat ctcgatccac cagaggaagg tcatcccgca tggtcatggg 31980
gtgtgcggtg gaggtgggga gaccgaaacc gcaaagggtc gcttacgtca gcaggatccc 32040
gagatcaaag acacccgggt tcttgcacaa acaccacccg ggttgcatcc gcggaggcga 32100
gtgttttgat aaggccgttc cgcgccttga tataaccttt gatgttgacc acaaaacccg 32160
gaatttacgc ctacgcccca atgcccacgc aagatgaggt aggtaacccc cccgtgggtg 32220
tgacgttgcg tttagttcat tggaggccaa ggggaaaaat ggggtgggga ggaaacggaa 32280
aacccagtag gccgtgtcgg gaacacgccc ggggttgtcc tcaaaaggca gggtccatac 32340
tacggaagcc gtcgttgtat tcgagacctg cctgtgcaac gcacgtcggg gttgcctgtg 32400
tccggttcgg cccccaccgc gtgcggcacg cacgaggacg agtccgcgtg ctttattggc 32460
gttccaagcg ttgccctcca gtttctgttg tcggtgttcc cccataccca cgcccacatc 32520
caccgtaggg ggcctctggg ccgtgttacg tcgccgcccg cgatggagct tagctacgcc 32580
accaccatgc actaccggga cgttgtgttt tacgtcacaa cggaccgaaa ccgggcctac 32640
tttgtgtgcg gggggtgtgt ttattccgtg gggcggccgt gtgcctcgca gcccggggag 32700
attgccaagt ttggtctggt cgttcgaggg acaggcccag acgaccgcgt ggtcgccaac 32760
tatgtac 32767

<210> SEQ ID NO 852
<211> LENGTH: 208
<212> TYPE: DNA
<213> ORGANISM: Artificial Sequence
<220> FEATURE:
<223> OTHER INFORMATION: miRT-1-143_1736

<400> SEQUENCE: 852
ccatatacat acttctttac attccatcct gagctacagt gcttcatctc attgcataca 60
tacttcttta cattccaacg tgagctacag tgcttcatct catccgatac atacttcttt 120
acattccacg gcgagctaca gtgcttcatc tcaccttata catacttctt tacattccaa 180
aaagagctac agtgcttcat ctcaccat 208

<210> SEQ ID NO 853
<211> LENGTH: 308
<212> TYPE: DNA
<213> ORGANISM: Artificial Sequence
<220> FEATURE:
<223> OTHER INFORMATION: miRT-128m-122-219_6793

<400> SEQUENCE: 853
cacgagaatt gcgtttggac aatcagacac aaacaccatt gtcacactcc atcttaaaga 60
gaccggttca ctgtggatgt caaacaccat tgtcacactc caacttagaa ttgcgtttgg 120

```
acaatcaagg gaaagagacc ggttcactgt ggccagcaaa caccattgtc acactccaaa      180

acaaagagac cggttcactg tggtacgaga attgcgtttg gacaatcaga aaaaagagac      240

cggttcactg tggaatacaa acaccattgt cacactccaa caaagaattg cgtttggaca      300

atcaggtt                                                              308

<210> SEQ ID NO 854
<211> LENGTH: 308
<212> TYPE: DNA
<213> ORGANISM: Artificial Sequence
<220> FEATURE:
<223> OTHER INFORMATION: miRT-128m-204-219_9304

<400> SEQUENCE: 854

aagtaaagag accggttcac tgtggaataa gaattgcgtt tggacaatca aggtaggcat       60

aggatgacaa agggaacagc aaagagaccg gttcactgtg gggctagaat tgcgtttgga      120

caatcacgta aggcatagga tgacaaaggg aacgagaaag agaccggttc actgtggggg      180

aagaattgcg tttggacaat catactaggc ataggatgac aaagggaatt agaaagagac      240

cggttcactg tggatttaga attgcgtttg gacaatcata gaaggcatag gatgacaaag      300

ggaattgt                                                              308

<210> SEQ ID NO 855
<211> LENGTH: 324
<212> TYPE: DNA
<213> ORGANISM: Artificial Sequence
<220> FEATURE:
<223> OTHER INFORMATION: miRT-217-137-126m_3163

<400> SEQUENCE: 855

tatgctacgc gtattcttaa gcaataagac ttccaatcag ttcctgatgc agtacgacca       60

cattattact cacggtacga aagcctacgc gtattcttaa gcaataaccg ccacattatt      120

actcacggta cgataaatcc aatcagttcc tgatgcagta attactacgc gtattcttaa      180

gcaataacta ttccaatcag ttcctgatgc agtaccccca cattattact cacggtacga      240

gaattccaat cagttcctga tgcagtacag tcacattatt actcacggta cgatcaacta      300

cgcgtattct taagcaataa ccaa                                            324
```